US012674002B2

(12) United States Patent
Vogelstein et al.

(10) Patent No.: US 12,674,002 B2
(45) Date of Patent: Jul. 7, 2026

(54) MANABODIES TARGETING TUMOR ANTIGENS AND METHODS OF USING

(71) Applicant: The Johns Hopkins University, Baltimore, MD (US)

(72) Inventors: Bert Vogelstein, Baltimore, MD (US); Kenneth W. Kinzler, Frankford, DE (US); Emily Han-Chung Hsiue, Baltimore, MD (US); Jacqueline Douglass, Baltimore, MD (US); Michael S. Hwang, Seattle, WA (US); Alexander H. Pearlman, Baltimore, MD (US); Nickolas Papadopoulos, Towson, MD (US); Shibin Zhou, Owings Mills, MD (US); Brian J. Mog, Baltimore, MD (US); Katharine M. Wright, Baltimore, MD (US); Sandra B. Gabelli, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 1056 days.

(21) Appl. No.: 17/783,506

(22) PCT Filed: Dec. 17, 2020

(86) PCT No.: PCT/US2020/065617
§ 371 (c)(1),
(2) Date: Jun. 8, 2022

(87) PCT Pub. No.: WO2021/127184
PCT Pub. Date: Jun. 24, 2021

(65) Prior Publication Data
US 2023/0051847 A1      Feb. 16, 2023

Related U.S. Application Data

(60) Provisional application No. 62/949,220, filed on Dec. 17, 2019, provisional application No. 63/059,638, filed on Jul. 31, 2020.

(51) Int. Cl.
| | |
|---|---|
| *C07K 16/28* | (2006.01) |
| *A61K 39/395* | (2006.01) |
| *A61P 35/00* | (2006.01) |
| *C07K 16/30* | (2006.01) |
| *A61K 39/00* | (2006.01) |

(52) U.S. Cl.
CPC .............. *C07K 16/30* (2013.01); *A61P 35/00* (2018.01); *C07K 16/2809* (2013.01); *A61K 39/395* (2013.01); *A61K 2039/505* (2013.01); *C07K 2317/24* (2013.01); *C07K 2317/622* (2013.01)

(58) Field of Classification Search
CPC ............ C07K 16/2809; C07K 16/2833; C07K 16/30; C07K 16/32; C07K 16/468; C07K 2317/24; C07K 2317/32; C07K 2317/33; C07K 2317/34; C07K 2317/622; C07K 2317/52; C07K 2317/569; A61K 2239/27; A61K 40/00; A61K 2039/505; A61K 2039/545; A61P 35/00; A61P 35/02
See application file for complete search history.

(56) References Cited

U.S. PATENT DOCUMENTS

| | | | |
|---|---|---|---|
| 6,750,325 | B1 | 6/2004 | Jolliffe et al. |
| 7,655,751 | B2 | 2/2010 | Itoh et al. |
| 9,718,893 | B2 | 8/2017 | Jung et al. |
| 10,118,964 | B2 | 11/2018 | Zhou et al. |
| 11,111,299 | B2 | 9/2021 | Huang et al. |
| 11,401,332 | B2 | 8/2022 | Lim et al. |
| 11,807,662 | B2 | 11/2023 | Hsiue et al. |
| 2003/0022244 | A1 | 1/2003 | Solomon et al. |
| 2005/0042218 | A1 | 2/2005 | Zauderer |
| 2006/0177896 | A1 | 8/2006 | Mach et al. |
| 2007/0065437 | A1 | 3/2007 | Elson et al. |
| 2008/0044413 | A1 | 2/2008 | Hammond et al. |
| 2013/0287748 | A1 | 10/2013 | June et al. |
| 2018/0086832 | A1 | 3/2018 | Vogelstein et al. |
| 2019/0248879 | A1 | 8/2019 | Sabapathy et al. |
| 2020/0079854 | A1 | 3/2020 | Hsiue |
| 2020/0368337 | A1 | 11/2020 | Fritsch et al. |
| 2021/0147572 | A1 | 5/2021 | Weidanz |
| 2024/0165155 | A1 | 5/2024 | Smith et al. |
| 2024/0166751 | A1 | 5/2024 | Vogelstein et al. |
| 2024/0294648 | A1 | 9/2024 | Hsiue et al. |

(Continued)

FOREIGN PATENT DOCUMENTS

| | | |
|---|---|---|
| CN | 101228187 A | 8/2008 |
| CN | 102675462 | 9/2012 |
| CN | 103635486 | 3/2014 |

(Continued)

OTHER PUBLICATIONS

Padlan, Advances in Protein Chemistry, 1996, 49:57-133).*
Berglund, Berglund et al., Protein Science, 2008, 17:606-613.*
Herold et al., Determinants of the assembly and function of antibody variable domains, Scientific Reports, 7:12276, doi:10.1038/s41598-017-12519-9, Sep. 2017.
Kranz et al., Restricted reassociation of heavy and light chains from hapten-specific monoclonal antibodies, Proc. Natl. Acad. Sci., USA, 78(9):5807-5811, 1981.
Ladner, R.C., Mapping the Epitopes of Antibodies, Biotechnol. Genet. Eng. Rev. 24:1-30, 2007.

(Continued)

*Primary Examiner* — Hong Sang
(74) *Attorney, Agent, or Firm* — Fish & Richardson P.C.

(57) ABSTRACT

This document provides methods and materials for assessing a mammal having or suspected of having cancer and/or for treating a mammal having cancer. For example, molecules including one or more antigen-binding domains (e.g., a single-chain variable fragment (scFv)) that can bind to a modified peptide (e.g., a tumor antigen), as well as method for using such molecules, are provided.

14 Claims, 108 Drawing Sheets

Specification includes a Sequence Listing.

(56) References Cited

U.S. PATENT DOCUMENTS

2025/0034252 A1     1/2025 Vogelstein et al.

FOREIGN PATENT DOCUMENTS

| CN | 108250301 A | 7/2018 | |
| CN | 110382550 A | 10/2019 | |
| JP | 2004187676 | 7/2004 | |
| JP | 2008533986 | 8/2008 | |
| JP | 2020534839 A | 12/2020 | |
| WO | WO 2003070752 | 8/2003 | |
| WO | WO 2005116072 | 12/2005 | |
| WO | WO 2006100681 | 9/2006 | |
| WO | WO 2012162067 | 11/2012 | |
| WO | WO 2014134165 | 9/2014 | |
| WO | WO 2015142675 | 9/2015 | |
| WO | WO 2015150526 | 10/2015 | |
| WO | WO 2016085904 | 6/2016 | |
| WO | WO 2016154047 | 9/2016 | |
| WO | WO 2016154246 | 9/2016 | |
| WO | WO 2016166139 | 10/2016 | |
| WO | WO 2016187508 | 11/2016 | |
| WO | WO 2016199141 | 12/2016 | |
| WO | WO 2016201124 | 12/2016 | |
| WO | WO 2017021527 | 2/2017 | |
| WO | WO 2017048593 | 3/2017 | |
| WO | WO 2017134134 | 8/2017 | |
| WO | WO 2017134158 | 8/2017 | |
| WO | WO 2018071796 | 4/2018 | |
| WO | WO-2018074978 A1 * | 4/2018 | .............. A61P 35/00 |
| WO | WO 2018213467 | 11/2018 | |
| WO | WO 2019067242 | 4/2019 | |
| WO | WO 2019112941 | 6/2019 | |
| WO | WO 2019164451 A1 | 8/2019 | |
| WO | WO 2021127184 | 6/2021 | |
| WO | WO 2021127814 | 7/2021 | |

OTHER PUBLICATIONS

ClinicalTrials.gov [online], "Neoadjuvant Nivolumab, or Nivolumab in Combination With Ipilimumab, in Resectable NSCLC (NA_00092076)," NCT0225962, last updated Nov. 3, 2023, retrieved on Jan. 11, 2024, retrieved from URL<https://clinicaltrials.gov/study/NCT02259621>, 42 pages.

Danilova et al., "The Mutation-Associated Neoantigen Functional Expansion of Specific T Cells (MANAFEST) Assay: A Sensitive Platform for Monitoring Antitumor Immunity," Cancer Immunology Research, Jun. 12, 2018, 6(8):888-899.

International Search Report and Written Opinion in International Appln. No. PCT/US2022/053065, mailed on Mar. 20, 2023, 9 pages.

PCT International Preliminary Report on Patentability in International Appln. No. PCT/US2022/022791, mailed on Oct. 12, 2023, 13 pages.

Smith et al, "Persistent mutant oncogene specific T cells in two patients benefitting from anti-PD-1," Journal for ImmunoTherapy of Cancer, Feb. 11, 2019, 7(1):40, 10 pages.

Castle et al., "Mutation-Derived Neoantigens for Cancer Immunotherapy," Frontiers in Immunology, Aug. 7, 2019, 10:1856, 7 pages.

Extended Search Report in European Appln. No. 20902329.0, mailed on Jan. 26, 2024, 7 pages.

International Preliminary Report on Patentability in International Appln. No. PCT/US2022/053065, mailed on Jun. 27, 2024, 6 pages.

[No Author Listed], "The problem with neoantigen prediction," Nature Biotechnology, 2017, 35(2):97.

Abelin et al., "Mass spectrometry profiling of HLA-associated peptidomes in mono-allelic cells enables more accurate epitope prediction," Immunity, 2017, 46(2):315-26.

Abrams et al., "Generation of stable CD4+ and CD8+ T cell lines from patients immunized with ras oncogene-derived peptides reflecting codon 12 mutations," Cell Immunol, Dec. 1997, 182(2):137-151.

Abrams et al., "Mutant ras epitopes as targets for cancer vaccines," Feb. 1996, Semin Oncol, 23(1):118-134 (Abstract only).

Adair et al., "Humanization of the murine anti-human CD3 monoclonal antibody OKT3," Human Antibodies, 1994, 5(1-2):41-7.

Adderley et al., "KRAS-mutant non-small cell lung cancer: Converging small molecules and immune checkpoint inhibition," EBioMedicine, 2019, 41:711-6.

Aldoss et al., "Correlates of resistance and relapse during blinatumomab therapy for relapsed/refractory acute lymphoblastic leukemia," American journal of hematology, 2017, 92(9):858-65.

Anagnostou et al.,.. "Evolution of Neoantigen Landscape during Immune Checkpoint Blockade in Non-Small Cell Lung Cancer", Cancer Discovery, 2017, 7(3):264-276.

Anderson et al., "Intracellular transport of class I MHC molecules in antigen processing mutant cell lines," Oct. 1993, J. Immunology, 151(7):3407-3419.

Andreatta et al., "Gapped sequence alignment using artificial neural networks: application to the MHC class I system," Bioinformatics, 2016, 32(4):511-7.

Apps et al., "A critical look at HLA-G," Trends in Immunol, Jul. 2008, 29(7):313-321.

Asano et al., "Rearranging the domain order of a diabody-based IgG-like bispecific antibody enhances its antitumor activity and improves its degradation resistance and pharmacokinetics," InMAbs, 2014, 6(5):1243-1254.

Asano et al., "Structural considerations for functional anti-EGFR$^X$ anti-CD3 bispecific diabodies in light of domain order and binding affinity," Oncotarget, 2018, 9(17):13884.

Ataie et al., "Structure of a TCR-mimic antibody with target predicts pharmacogenetics," Journal of molecular biology. 2016 , 428(1):194-205.

Ayriss et al., "High-throughput screening of single-chain antibodies using multiplexed flow cytometry," Jan. 2007, Journal of Proteome Research, 6(3):1072-1082, 11 pages.

Azriel-Rosenfeld et al., "A Human Synthetic Combinatorial Library of Arrayable Single-chain antibodies based on Shuffling in Vivo Formed CDRs into General Framework Regions," J. Mol. Biol, 2004, 335:177-192.

Baker et al., "Chromosome 17 deletions and p53 gene mutations in colorectal carcinomas," Science, Apr. 1989, 244(4901):217-21.

Bargou et al., "Tumor regression in cancer patients by very low doses of a T cell-engaging antibody," Science, 2008, 321(5891):974-7.

Barretina et al., "The Cancer Cell Line Encyclopedia enables predictive modelling of anticancer drug sensitivity," Nature, 2012, 483(7391):603-7.

Bedard et al., "Small molecules, big impact: 20 years of targeted therapy in oncology," The Lancet, 2020, 395(10229):1078-88.

Bernal et al., "Implication of the β2-microglobulin gene in the generation of tumor escape phenotypes," Sep. 2012, Cancer Immunol Immunother, 61(9):1359-71.

Beverley et al., "Distinctive functional characteristics of human „T lymphocytes defined by E rosetting or a monoclonal anti-T cell antibody," European Journal of Immunology, 1981, 11(4):329-34.

Bluemel et al., "Epitope distance to the target cell membrane and antigen size determine the potency of T cell-mediated lysis by BiTE antibodies specific for a large melanoma surface antigen," Cancer immunology, immunotherapy, 2010, 59(8):1197-209.

Bondgaard et al., "High specificity but low sensitivity of mutation-specific antibodies against EGFR mutations in non-small-cell cancer," Dec. 2014, Mod Pathol, 27(12):1590-1598, 9 pages.

Borg et al., "A novel interaction between Rab7b and actomyosin reveals a dual role in intracellular transport and cell migration," Journal of Cell Science, 2014, 127(22):4927-39.

Bossi et al., "Examining the presentation of tumor-associated antigens on peptide-pulsed T2 cells," Oncoimmunology, 2013, 2(11):e26840.

Bostrom et al., "Chapter 2: Design and construction of synthetic phage-displayed fab libraries," May 2009, Methods in Molecular Biology, 562:17-35, 19 pages.

(56) References Cited

OTHER PUBLICATIONS

Bouvier et al., "Crystal structures of HLA-A*0201 complexed with antigenic peptides with either the amino- or carboxyl-terminal group substituted by a methyl group," May 1998, Proteins, 33(3):97-106, 10 pages.

Bradbury et al., "Beyond natural antibodies: the power of in vitro display technologies," Nat Biotechnol, Mar. 2011, 29(3):245-254, 28 pages.

Brickner et al., "The PANE1 gene encodes a novel human minor histocompatibility antigen that is selectively expressed in B-lymphoid cells and B-CLL," May 1, 2006, Blood, 107(9):3779-3786, 24 pages.

Brinkmann et al., "The making of bispecific antibodies," InMAbs, 2017, 9(2):182-212.

Brischwein et al., "MT110: A novel bispecific single-chain antibody construct with high efficacy in eradicating established tumors," Mol Immunol., 2006, 43:1129-43.

Buhrman et al., "Analysis of binding site hot spots on the surface of Ras GTPase," Journal of Molecular Biology, 2011, 413(4):773-89.

Cameron et al., "Identification of a Titin-derived HLA-A1-presented peptide as a cross-reactive target for engineered MAGE A3-directed T cells," Science Translational Medicine, 2013, 5(197):197ra103.

Canon et al., "The clinical KRAS (G12C) inhibitor AMG 510 drives anti-tumour immunity," Nature, 2019, 575(7781):217-23.

Carosella et al., "Beyond the increasing complexity of the immunomodulatory HLA-G molecule," Blood, May 2008, 111(10):4862-4870.

Carter et al., "Humanization of an anti-p185HER2 antibody for human cancer therapy," May 1992, Proc. Natl. Acad. Sci., 89(10):4285-4289, 5 pages.

Castle et al., "Exploiting the mutanome for tumor vaccination," Mar. 1, 2012, Cancer Res, 72(5):1081-1091, 12 pages.

Caushi et al., "Transcriptional programs of neoantigen-specific TIL in anti-PD-1-treated lung cancers," Nature, Jul. 21, 2021, 596(7870):126-132.

Chang et al., "A therapeutic T cell receptor mimic antibody targets tumor-associated PRAME peptide/HLA-I antigens," The Journal of Clinical Investigation, 2017, 127(7):2705-18.

Chapuis et al., "T cell receptor gene therapy targeting WT1 prevents acute myeloid leukemia relapse post-transplant," Nature Medicine, 2019, 25(7):1064-72.

Chen et al., "A comprehensive survey of genomic alterations in gastric cancer reveals recurrent neoantigens as potential therapeutic targets," BioMed Research International, 2019.

Choudhuri et al., "T-cell receptor triggering is critically dependent on the dimensions of its peptide-MHC ligand," Nature, 2005, 436(7050):578-82.

Coles et al., "TCRs with distinct specificity profiles use different binding modes to engage an identical peptide-HLA complex," The Journal of Immunology, 2020, 204(7):1943-53.

Coordinators, "Database resources of the national center for biotechnology information," Nucleic acids research, 2018, 46(Database issue):D8.

Cottrell et al., "Pathologic features of response to neoadjuvant anti-PD-1 in resected non-small-cell lung carcinoma: a proposal for quantitative immune-related pathologic response criteria (irPRC)," Ann. Oncol., Aug. 1, 2018, 29(8):1853-1860.

Curran et al., "Chimeric antigen receptors for T cell immunotherapy: current understanding and future directions," Gene Med, 2012, 14(6):405-415.

D'Angelo et al., "Incidence of EGFR Exon 19 Deletions and L858R in Tumor Specimens From Men and Cigarette Smokers with Lung Adenocarcinomas," May 20, 2011, J. Clin. Oncol., 29(15):2066-2070, 5 pages.

Dao et al., "Approaching untargetable tumor-associated antigens with antibodies," Jul. 2013, OncoImmunology, 2(7):e24678, 2 pages.

Dao et al., "Targeting the intracellular WT1 oncogene product with a therapeutic human antibody," Mar. 2013, Science Translational Medicine, 5(176):176ra33, 22 pages.

Dao et al., "Therapeutic bispecific T-cell engager antibody targeting the intracellular oncoprotein WT1," Nat. Biotechnol, Oct. 2015, 33:1079-1086.

De Castro et al., "ScanProsite: detection of PROSITE signature matches and ProRule-associated functional and structural residues in proteins," Nucleic Acids Research, 2006, 34(suppl_2):W362-5.

De Verteuil et al., "Origin and plasticity of MHC I-associated self peptides," Jul. 2012, Autoimmunity Reviews, 11(9):627-635.

Denkberg et al., "Modification of a tumor-derived peptide at an HLA-A2 anchor residue can alter the conformation of the MHC-peptide complex: probing with TCR-like recombinant antibodies," J. Immunol, 2002, 169:4399-4407.

Digiusto et al., "Preparing clinical grade Ag-specific T cells for adoptive immunotherapy trials," Cytotherapy, 2007, 9(&):613-29.

Dufner et al., "Harnessing phage and ribosome display for antibody optimisation," Trends in Biotechnology, Nov. 2006, 24(11):523-529.

Efremova et al., "Neoantigens Generated by Individual Mutations and Their Role in Cancer Immunity and Immunotherapy," Frontiers in Immunology, 2017, 8(Article 1679):1-8.

Eigenbrot et al., "X-ray structures of the antigen-binding domains from three variants of humanized anti-p185HER2 antibody 4D5 and comparison with molecular modeling," Feb. 1993, J. Mol. Biol., 229(4):969-995.

Ellis et al., "Frequencies of HLA-A2 alleles in five U.S. population groups: Predominance of A*02011 and identification of HLA-A*0231," Mar. 2000, Human Immunology, 61(3):334-340.

Eshhar et al., "Specific activation and targeting of cytotoxic lymphocytes through chimeric single chains consisting of antibody-binding domains and the gamma or zeta subunits of the immunoglobulin and T-cell receptors," Proc. Natl. Acad. Sci. USA, 1993, 90(2):720-724.

Extended European Search Report in European Application No. 18802867.4, mailed Mar. 15, 2021, 16 pages.

Extended European Search Report in European Application No. 16769561.8, dated Jul. 6, 2018, 9 pages.

Extended European Search Report in European Application No. 18802867.4, dated Dec. 11, 2020, 21 pages.

Faroudi et al., "Cutting edge: T lymphocyte activation by repeated immunological synapse formation and intermittent signaling," The Journal of Immunology, 2003, 171(3):1128-32.

Fearon et al., "A Genetic Model for Colorectal Tumorigenesis," Cell Press, Jun. 1, 1990, 61(5):759-767, 9 pages.

Fellhouse et al., "High-throughput generation of synthetic antibodies from highly functional minimalist phage-displayed libraries," Aug. 2007, J. Mol. Biol., 373(4):924-940, 17 pages.

Forde et al., "Neoadjuvant PD-1 Blockade in Resectable Lung Cancer," N. Engl. J. Med., May 24, 2018, 378(21):1976-1986.

Gejman et al., "Identification of the Targets of T-cell Receptor Therapeutic Agents and Cells by Use of a High-Throughput Genetic Platform Identifying T-cell Targets Using a High-Throughput Method," Cancer Immunology Research, 2020, 8(5):672-84.

GenBank Accession No. AAH03596.1, "Tumor protein p53 [*Homo sapiens*]," dated Jun. 9, 2008, 2 pages.

Gerstung et al., "The evolutionary history of 2,658 cancers," Nature, 2020, 578(7793):122-8.

Gomez-Eerland et al., "Manufacture of gene-modified human T-cells with a memory stem/central memory phenotype," Human gene therapy methods, 2014, 25(5):277-87.

Gonzalez-Galarza, et al., "Allele frequency net 2015 update: new features for HLA epitopes, KIR and disease and HLA adverse drug reaction associations," Nucleic Acids Research, 2015, 43(D1):D784-8.

Grossman et al., "Toward a shared vision for cancer genomic data," New England Journal of Medicine, 2016, 375(12):1109-12.

Gubin et al., "Checkpoint Blockade Cancer Immunotherapy Targets Tumour-Specific Mutant Antigens," Nov. 27, 2014, Nature, 515(7528):577-581, 32 pages.

Halilovic et al., "Therapeutic strategies for inhibiting oncogenic BRAF signaling," Curr Opin Pharmacol, Aug. 2008, 8(4):419-426.

Ham et al., "TP53gain-of-function mutation promotes inflammation in glioblastoma," Cell Death & Differentiation, May 2018, 26(3):409-425.

(56)　　　　　References Cited

OTHER PUBLICATIONS

Hammond et al., "Selective targeting and potent control of tumor growth using an EphA2/CD3-Bispecific single-chain antibody construct," Cancer research, 2007, 67(8):3927-35.

Harndahl et al., "Peptide binding to HLA class I molecules: homogenous, high-throughput screening, and affinity assays," J. Biomol. Screen, Feb. 2009, 14(2):173-180.

Harper et al., "An approved in vitro approach to preclinical safety and efficacy evaluation of engineered T cell receptor anti-CD3 bispecific (ImmTAC) molecules," PLoS One, 2018, 13(10):e0205491.

Hexham et al., "Influence of relative binding affinity on efficacy in a panel of anti-CD3 scFv immunotoxins," Molecular immunology, 2001, 38(5):397-408.

hla.alleles.org [online], "HLA Nomenclature," retrieved on Mar. 17, 2015, retrieved from URL<http://hla.alleles.org/nomenclature/stat. html>, 2 pages.

Hobbs et al., "RAS isoforms and mutations in cancer at a glance," Journal of Cell Science, 2016, 129(7):1287-92.

Holliger et al., ". . . "Diabodies": small bivalent and bispecific antibody fragments," Proceedings of the National Academy of Sciences, 1993, 90(14):6444-8.

Hoof et al., "Proteome sampling by the HLA class I antigen processing pathway," May 2012, Plos Computational Biology, 8(5):e1002517, 9 pages.

Houghton, et al., "Immune recognition of self in immunity against cancer," J. Clin. Invest., 2004, 114(4):468-471.

Hsiue et al., "Targeting a neoantigen derived from a common TP53 mutation," Science, Mar. 1, 2021, 371(6533): eabc8697.

Huang et al., "CD-HIT Suite: a web server for clustering and comparing biological sequences," Bioinformatics, 2010, 26(5):680-2.

Huehls et al., "Bispecific T-cell engagers for cancer immunotherapy," Immunology and cell biology, 2015, 93(3):290-6.

International Preliminary Report on Patentability in International Application No. PCT/US2016/023673, dated Sep. 26, 2017, 8 pages (with English translation).

International Preliminary Report on Patentability in International Application No. PCT/US2020/06561, dated May 17, 2022, 6 pages.

International Search Report and Written Opinion in International Application No. PCT/US2016/023673, dated Jul. 25, 2016, 13 pages.

International Search Report and Written Opinion in International Application No. PCT/US2020/065617, mailed on Apr. 1, 2021, 8 pages.

Janes et al., "Targeting KRAS mutant cancers with a covalent G12C-specific inhibitor," Cell, 2018, 172(3):578-89.

Jena et al., "Redirecting T-cell specificity by introducing a tumor-specific chimeric antigen receptor," Aug. 2010, Blood, 116(7):1035-1044, 17 pages.

Johnson et al., "Effector cell recruitment with novel Fv-based dual-affinity re-targeting protein leads to potent tumor cytolysis and in vivo B-cell depletion. Journal of molecular biology," 2010, 399(3):436-49.

Jones et al., "Core signaling pathways in human pancreatic cancers revealed by global genomic analyses," Science, 2008, 321(5897):1801-6.

Junttila et al., "Antitumor Efficacy of a Bispecific Antibody That Targets HER2 and Activates T Cells," Cancer research, 2014, 74(19):5561-71.

Kato et al., "A monoclonal antibody IMab-1 specifically recognizes IDH1R132H, the most common glioma-derived mutation," Biochemical and Biophysical Research Communications, 2009, 390(3):547-51.

Kato et al., "Effective screening of T cells recognizing neoantigens and construction of T-cell receptor-engineered T cells," Oncotarget, 2018, 9(13):11009.

Kato et al., "Understanding the function-structure and function-mutation relationships of p53 tumor suppressor protein by high-resolution missense mutation analysis," Proceedings of the National Academy of Sciences, 2003, 100(14): 8424-9.

Kershaw et al., "Clinical application of genetically modified T cells in cancer therapy," Apr. 2014, Clinical & Translational Immunology, 3(5):e16, 7 pages.

Kershaw et al.,.. "Supernatural T cells: genetic modification of T cells for cancer therapy," Nature Reviews Immunol., 2005, 5(12):928-940.

Kim et al., "TCR mechanobiology: torques and tunable structures linked to early T cell signaling," Frontiers in immunology, 2012, 3(76):1-8.

Kim et al., "The αβ T cell receptor is an anisotropic mechanosensor," Journal of Biological Chemistry, 2009, 284(45):31028-37.

Kinde et al., "Detection and quantification of rare mutations with massively parallel sequencing," Proceedings of the National Academy of Sciences, 2011, 108(23):9530-5.

Kipriyanov et al., "Effect of domain order on the activity of bacterially produced bispecific single-chain Fv antibodies," Journal of molecular biology, 2003, 330(1):99-111.

Koide et al., "The importance of being tyrosine: lessons in molecular recognition from minimalist synthetic binding proteins," May 2009, ACS Chem. Biol., 4(5):325-334, 16 pages.

Kraemer et al., " HLA-E: Presentation of a broader peptide repertoire impacts the cellular immune response-implications on HSCT outcome," Stem Cells Inter, 2015, article ID 346714, pp. 1-12.

Krissinel et al., "Inference of macromolecular assemblies from crystalline state," Journal of Molecular Biology, 2007, 372(3):774-97.

Kula et al., "T-Scan: a genome-wide method for the systematic discovery of T cell epitopes," Cell, 2019, 178(4):1016-28.

Kunik et al., "Structural consensus among antibodies defines the antigen binding site," Feb. 2012, PLoS Computational Biology, 8(2):e1002388, 12 pages.

Kuroda et al., "Structural classification of CDR-H3 revisited: a lesson in antibody modeling," Nov. 2008, Proteins, 73(3):608-620.

Labrijn et al., "Bispecific antibodies: a mechanistic review of the pipeline," Nature reviews Drug discovery, 2019, 18(8):585-608.

Le et al., "Mismatch repair deficiency predicts response of solid tumors to PD-1 blockade," Science, Jul. 2017, 357(6349):409-413.

Li et al., "A model for RAS mutation patterns in cancers: finding the sweet spot," Nature Reviews Cancer, 2018, 18(12):767-77.

Li et al., "Construction and characterization of a humanized anti-human CD3 monoclonal antibody 12F6 with effective immunoregulation functions," Immunology, 2005, 116(4):487-98.

Liddy et al., "Monoclonal TCR-redirected tumor cell killing," Nature Medicine, 2012, 18(6):980-7.

Lin et al., "Enhanced homology-directed human genome engineering by controlled timing of CRISPR/Cas9 delivery," eLife, 2014, 3:e04766.

Link et al., "Anti-CD3-based bispecific antibody designed for therapy of human B-cell malignancy can induce T-cell activation by antigen-dependent and antigen-independent mechanisms," Jul. 1998, Int. J. Cancer, 77(2):251-256, 7 pages.

Low et al., "Immunologic recognition of a shared p53 mutated neoantigen in a patient with metastatic colorectal cancer," Cancer Immunology Research, 2019, 7(4):534-43.

Low et al., "Targeting mutant p53-expressing tumours with a T cell receptor-like antibody specific for a wild-type antigen," Nature Communications, 2019, 10(1):1-4.

Lowe et al., "TCR-like antibody drug conjugates mediate killing of tumor cells with low peptide/HLA targets," MAbs 2017, 9(4):603-614.

Lu et al., "The effect of variable domain orientation and arrangement on the antigen-binding activity of a recombinant human bispecific diabody," Biochemical and biophysical research communications, 2004, 318(2):507-13.

Luft et al., "Exogenous peptides presented by transporter associated with antigen processing (TAP)-Deficient and TAP-Competent cells: Intracellular loading and kinetics of presentation," Sep. 1, 2017, J. Immunol., 167(5):2529-2537, 10 pages.

Lundegaard et al., "Accurate approximation method for prediction of class I MHC affinities for peptides of length 8, 10 and 11 using prediction tools trained on 9mers," Apr. 2008, Bioinformatics, 24(11):1397-1398, 2 pages.

(56) References Cited

OTHER PUBLICATIONS

Lundegaard et al., "NetMHC-3.0: accurate web accessible predictions of human, mouse and monkey MHC class I affinities for peptides of length 8-11," May 7, 2008, Nucleic Acids Research, 36:W509-512, 4 pages.

Maiers et al., "High-resolution HLA alleles and haplotypes in the United States population," Human Immunology, 2007, 68(9):779-88.

Malekzadeh et al., "Neoantigen screening identifies broad TP53 mutant immunogenicity in patients with epithelial cancers," The Journal of Clinical Investigation, 2019, 129(3): 1109-1114.

Martayan et al., "Class I HLA folding and antigen presentation in beta 2-microglobulin-defective Daudi cells," Mar. 2009, The Journal of Immunology, 2009, 182:3609-3617.

Marubashi et al., "Rab7B/42 is functionally involved in protein degradation on melanosomes in keratinocytes," Cell structure and function, 2020, 19039.

Maruyama et al., "Increasing the efficiency of precise genome editing with CRISPR-Cas9 by inhibition of nonhomologous end joining," Nature biotechnology, 2015, 33(5):538-42.

Maude et al., "Chimeric antigen receptor T cells for sustained remissions in leukemia," New England Journal of Medicine, 2014, 371(16):1507-17.

McConnell et al., "An integrated approach to extreme thermostablilization and affinity maturation of an antibody," Feb. 2013, PEDS, 26(2):151-163, 13 pages.

Merchant et al., "An efficient route to human bispecific IgG," Nature biotechnology, 1998, 16(7):677-81.

Miller et al., "A human monoclonal antibody neutralizes diverse HIV-1 isolates by binding a critical gp41 epitope," Oct. 11, 2005, Proc. Natl. Acad. Sci., 102(41):14759-14764, 6 pages.

Miller et al., "An engineered antibody fragment targeting mutant β-catenin via major histocompatibility complex I neoantigen presentation," Journal of Biological Chemistry, 2019, 294(50):19322-34.

Miller et al., "High somatic mutation and neoantigen burden are correlated with decreased progression-free survival in multiple myeloma," Blood Cancer Journal, 2017, 7:e612, 1-11.

Miller et al., "T Cell Receptor-Like Recognition of Tumor In Vivo by Synthetic Antibody Fragment," Aug. 2012, PLoS One, 7(8):e43746, 14 pages.

Moore et al., "Application of dual affinity retargeting molecules to achieve optimal redirected T-cell killing of B-cell lymphoma," Blood, The Journal of the American Society of Hematology, 2011, 117(17):4542-51.

Morgan et al., "Cancer regression and neurological toxicity following anti-MAGE-A3 TCR gene therapy," Journal of Immunotherapy, 2013, 36(2):133-51.

Muzumdar et al., "Survival of pancreatic cancer cells lacking KRAS function," Nature communications, 2017, 8(1):1-9.

Myszka, "Improving biosensor analysis" 1999, J. Mol. Recognit, 12:279-284.

NCBI.gov [Online], "HLA-F major histocompatibility complex, class I F [Homo sapiens(humans)], " Sep. 4, 2016, retrieved on Sep. 29, 2016, retrieved from URL,http://www.ncbi.nlm.nih.gov/gene/3134> 14 pages.

Nielsen et al., "Reliable prediction of T-cell epitopes using neural networks with novel sequence representations," Feb. 2003, Protein Science, 12(5):1007-1017, 11 pages.

Nolan et al., "Flow cytometry: a versatile tool for all phases of drug discovery," Apr. 1999, Drug Discov Today, 4(4):173-180, 8 pages.

Novak et al., "Selective antibody-mediated targeting of class I MHC to EGFR-expressing tumor cells induces potent antitumor CTL activity in vitro and in vivo," Oct. 2006, International Journal of Cancer, 120:329-336, 8 pages.

Ostrem et al., "K-Ras (G12C) inhibitors allosterically control GTP affinity and effector interactions," Nature, 2013, 503(7477):548-51.

Paix et al., "Precision genome editing using synthesis-dependent repair of Cas9-induced DNA breaks," Proceedings of the National Academy of Sciences, 2017, 114(50):E10745-54.

Park et al., "Long-term follow-up of CD19 CAR therapy in acute lymphoblastic leukemia," New England Journal of Medicine, 2018, 378(5):449-59.

Parkhurst et al., "Unique Neoantigens Arise from Somatic Mutations in Patients with Gastrointestinal Cancers Neoantigens in Patients with Gastrointestinal Cancers," Cancer discovery, 2019, 9(8):1022-35.

PCT International Preliminary Report on Patentability in International Appln. No. PCT/US2018/032996, dated Nov. 19, 2019, 5 pages.

PCT International Search Report and Written Opinion in International Application No. PCT/US2018/032996, mailed on Aug. 27, 2018, 20 pages.

PCT International search Report and Written Opinion in International Appln. No. PCT/US2022/022791, mailed on Nov. 17, 2022, 21 pages.

Petryszak et al., "Expression Atlas update—an integrated database of gene and protein expression in humans, animals and plants," Nucleic acids research, 2016, 44(D1):D746-52.

Porgador et al., "Localization, quantitation, and in situ detection of specific peptide-MHC class I complexes using a monoclonal antibody," Jun. 1997, Immunity, 6(6):715-726, 12 pages.

Prior et al., "A comprehensive survey of Ras mutations in cancer," Cancer Research, 2012, 72(10):2457-67.

Prior et al., "The Frequency of Ras Mutations in Cancer," Cancer Research, 2020, 80(14):2969-74.

Purbhoo et al., "T cell killing does not require the formation of a stable mature immunological synapse," Nature Immunology, 2004, 5(5):524-30.

Puri et al., "Highly efficient selection of epitope specific antibody through competitive yeast display library sorting," Aug. 2013, mAbs, 5(4):533-539, 7 pages.

Rafiq et al., "Engineering strategies to overcome the current roadblocks in CAR T cell therapy," Nature Reviews Clinical Oncology, 2020, 17(3):147-67.

Rafiq et al., "Optimized T-cell receptor-mimic chimeric antigen receptor T cells directed toward the intracellular Wilms Tumor 1 antigen," Leukemia, 2017, 31(8):1788-97.

Rahma et al., "The immunological and clinical effects of mutated ras peptide vaccine in combination with IL-2, GM-CSF, or both in patients with solid tumors," Feb. 2014, Journal of Translational Medicine, 12:55, 12 pages.

Raman et al., "Direct molecular mimicry enables off-target cardiovascular toxicity by an enhanced affinity TCR designed for cancer immunotherapy," Scientific Reports, 2016, 6(1):1-0.

Richardson et al., "Enhancing homology-directed genome editing by catalytically active and inactive CRISPR-Cas9 using asymmetric donor DNA," Nature biotechnology, 2016, 34(3):339-44.

Rizvi et al., "Cancer immunology. Mutational landscape determines sensitivity to PD-1 blockade in non-small cell lung cancer," Science, Apr. 3, 2015, 348(6230):124-128.

Robbins et al., "Mining exomic sequencing data to identify mutated antigens recognized by adoptively transferred tumor-reactive T cells," Jun. 2013, Nat Med, 19(6):747-752, 14 pages.

Roblek et al., "Monoclonal antibodies specific for disease-associated point-mutants: Lamin A/C R453W and R482W," May 2010, PloS One, 5(5):e10604, 14 pages.

Rodrigues et al., "Engineering a humanized bispecific F(ab) 2 fragment for improved binding to T cells, " International Journal of Cancer, 1992, 7:45-50.

Rosenberg et al., "Adoptive cell transfer as personalized immunotherapy for human cancer," Science, 2015, 348(6230):62-8.

Rosenberg et al., "Use of tumor-infiltrating lymphocytes and interleukin-2 in the immunotherapy of patients with metastatic melanoma," New England Journal of Medicine, 1988, 319(25):1676-80.

Sadelain et al., "The promise and potential pitfalls of chimeric antigen receptors," Curr. Opin. Immunol., 2009, 21(2):215-223.

Salter et al., "Genes regulating HLA class I antigen expression in T-B lymphoblast hybrids," Mar. 1985, Immunogenetics, 21(3):235-246.

(56) References Cited

OTHER PUBLICATIONS

Schmidt et al., "In silico and cell-based analyses reveal strong divergence between prediction and observation of T-cell-recognized tumor antigen T-cell epitopes," Journal of Biological Chemistry, 2017, 292(28):11840-9.

Scholtalbers et al., "TCLP: an online cancer cell line catalogue integrating HLA type, predicted neo-epitopes, virus and gene expression," Genome medicine, 2015, 7(1):1-7.

Schreiber et al., "Cancer Immunoediting: Integrating Immunity's Roles in Cancer Suppression and Promotion," Mar. 2011, Science, 331(6024):1565-1570, 6 pages.

Schumacher et al., "Neoantigens in cancer immunotherapy," Science, 2015, 348(6230):69-74.

Schuster et al., "Tisagenlecleucel in adult relapsed or refractory diffuse large B-cell lymphoma," New England Journal of Medicine, 2019, 380(1):45-56.

Scott et al., "Monoclonal antibodies in cancer therapy," Cancer immunity, 2012, 12:14.

Segal et al., "Epitope landscape in breast and colorectal cancer," Cancer Research, 2008, 68(3):889-92.

Sela-Culang et al., "The structural basis of antibody-antigen recognition," Oct. 2013, Frontiers in Immunology, 4:302, 13 pages.

Sergeeva et al., "An anti-PR1/HLA-A2 T-cell receptor-like antibody mediates complement-dependent cytotoxicity against acute myeloid leukemia progenitor cells," Blood, 2011, 117(160):4262-4272.

Shalaby et al., "Development of humanized bispecific antibodies reactive with cytotoxic lymphocytes and tumor cells overexpressing the HER2 protooncogene," The Journal of Experimental Medicine, 1992, 175(1):217-25.

Sharma et al., "Epidermal growth factor receptor mutations in lung cancer," Mar. 2007, Nat. Rev. Cancer, 7(3):169-181, 13 pages.

Sharma et al., "Recent advances in T-cell engineering for use in immunotherapy," F1000Research, 2016, 5:F1000 Faculty Rev):2344.

Shtraizent et al., "Hot Spot Mutation in TP53 (R248Q) Causes Oncogenic Gain-of-Function Phenotypes in a Breast Cancer Cell Line Derived from an African American Patient," Int. J. Environ. Res. Public Health, 2016, 13(1):22.

Sidhu et al., Phage-displayed Antibody Libraries of Synthetic Heavy Chain Complementarity Determining Regions, Feb. 2004, J. Mol. Biol., 338(2):299-310, 12 pages.

Skora et al., Generation of MANAbodies specific to HLA-restricted epitopes encoded by somatically mutated genes. Proceedings of the National Academy of Science of the USA.2015, Epub Jul. 27, 2015, 112(32):9967-9972.

Sliwkowski et al., "Antibody therapeutics in cancer," Science, Sep. 13, 2013, 341(6151):1192-1198.

Snyder et al., "Genetic basis for clinical response to CTLA-4 blockade in melanoma," N. Engl. J. Med., Dec. 4, 2014, 371(23):2189-2199.

Sondek et al., "A general strategy for random insertion and substitution mutagenesis: substoichiometric coupling of trinucleotide phosphoramidites," Proceedings of the National Academy of Sciences, 1992, 89(8):3581-5.

Steinwand et al., "The influence of antibody fragment format on phage display based affinity maturation of IgG," Nov. 26, 2013, mAbs, 6(1):204-218, 16 pages.

Stewart-Jones et al., "Rational development of high-affinity T-cell receptor-like antibodies," Proceedings of the National Academy of Sciences, 2009, 106(14):5784-8.

Stone et al., "A sensitivity scale for targeting T cells with chimeric antigen receptors (CARs) and bispecific T-cell Engagers (BiTEs)," Oncoimmunology, 2012, 1(16):863-73.

Sugiyama et al., "A semi high-throughput method for screening small bispecific antibodies with high cytotoxicity," Scientific reports, 2017, 7(1):1-2.

Sun et al., "Evolution of CD8+ T Cell Receptor (TCR) Engineered Therapies for the Treatment of Cancer," Cells, Sep. 2021, 10(9):2379.

Sung et al., "Dual-Affinity Re-Targeting proteins direct T cell-mediated cytolysis of latently HIV-infected cells," The Journal of clinical investigation, 2015, 125(11):4077-90.

Taylor et al., "A DNA-based T cell receptor reveals a role for receptor clustering in ligand discrimination," Cell, 2017, 169(1):108-19.

Thakur et al., "Cancer therapy with bispecific antibodies: Clinical experience," Jun. 2010, Curr. Opin. Mol. Ther., 12(3):340-349, 16—pages.

the-scientist.com [online], "Neoantigens Enable Personalized Cancer Immunotherapy," Apr. 2017, [retrieved on May 4, 2018], retrieved from: URL<https://www.the-scientist.com/?articles.view/articleNo/49000/title/Neoantigens-Enable-Personalized-Cancer-Immunotherapy/>, 5 pages.

Thomas et al., "Mesothelin-specific CD8+ T cell responses provide evidence of in vivo cross-priming by antigen-presenting cells in vaccinated pancreatic cancer patients," The Journal of experimental medicine, 2004, 200(3):297-306.

Thomsen et al., "Seq2Logo: a method for construction and visualization of amino acid binding motifs and sequence profiles including sequence weighting, pseudo counts and two-sided representation of amino acid enrichment and depletion," Nucleic acids research, 2012, 40(W1):W281-7.

Tran et al., "Cancer immunotherapy based on mutation-specific CD4+ T cells in a patient with epithelial cancer," Science, 2014, 344(6184):641-5.

Tran et al., "T-cell transfer therapy targeting mutant KRAS in cancer," New England Journal of Medicine, 2016, 375(23):2255-62.

Tsai et al., "Discovery of a selective inhibitor of oncogenic B-Raf kinase with potent antimelanoma activity," PNAS, Feb. 26, 2008, 105(8):3041-3046, 6 pages.

Tsukahara et al., "Specific targeting of a naturally presented osteosarcoma antigen, papillomavirus binding factor peptide, using an artificial monoclonal antibody," Aug. 2014, Journal of Biological Chemistry, 289(32):22035-22047, 14 pages.

Tumeh et al., "PD-1 blockade induces responses by inhibiting adaptive immune resistance," Nature, Nov. 27, 2014, 515(7528):568-571.

Uhlen et al., "Tissue-based map of the human proteome," Science, 2015, 347(6220):1260419.

Van Allen et al., "Genomic correlates of response to CTLA-4 blockade in metastatic melanoma," Science, Oct. 2015, 350(6257):207-211.

Van Wauwe et al., "OKT3: a monoclonal anti-human T lymphocyte antibody with potent mitogenic properties," The Journal of Immunology, 1980, 124(6):2708-13.

Vauquelin et al., "Exploring avidity: understanding the potential gains in functional affinity and target residence time of bivalent and heterobivalent ligands," British journal of pharmacology, 2013, 168(8):1771-85.

Verma et al., "TCR mimic monoclonal antibody targets a specific peptide/HLA class I complex and significantly impedes tumor growth in vivo using breast cancer models," Feb. 2010, J. Immunol., 184(4):2156-2165, 11 pages.

Vita et al., "The immune epitope database (IEDB): 2018 update," Nucleic acids research, 2019, 47(D1):D339-43.

Vogelstein et al., "Cancer genome landscapes," Science, 2013, 339(6127):1546-58.

Vonderheide et al., "Engineering T cells for cancer: our synthetic future," Jan. 2014, Immunol Rev., 257(1):7-13, 10 pages.

Wang et al., "A naturally processed peptide presented by HLA-A*0201 is expressed at low abundance and recognized by an alloreactive CD8+ cytotoxic T cell with apparent high affinity," Jun. 1997, J. Immunol., 158(12):5797-5804, 8 pages.

Wang et al., "Direct Detection and Quantification of Neoantigens," Cancer Immunology Research, 2019, 7 (11):1748-1754.

Wang et al., "Identification of T-cell Receptors Targeting KRAS-Mutated Human Tumors," Cancer Immunol Res, 2016, 4:204-214.

Ward et al., "The Role of Neoantigens in Naturally Occurring and Therapeutically Induced Immune Responses to Cancer," Adv Immunol, 2016, 130:25-74.

Warren et al., "A census of predicted mutational epitopes suitable for immunologic cancer control," Human Immunol., 2010, pp. 245-254.

(56)     References Cited

OTHER PUBLICATIONS

Watanabe et al., "Expanding the therapeutic window for CAR T cell therapy in solid tumors: the knowns and unknowns of CAR T cell biology," Frontiers in Immunology, 2018, 9:2486.

Webb et al., "Functional and structural characteristics of NY-ESO-1-related HLA A2-restricted epitopes and the design of a novel immunogenic analogue," Journal of Biological Chemistry, 2004, 279(22):23438-46.

Weiner et al., "Antibodies and cancer therapy: versatile platforms for cancer immunotherapy," May 2010, Nature Reviews Immunology, 10(5):317-327, 26 pages.

Wu et al., "Kinetic and structural analysis of mutant CD4 receptors that are defective in HIV gp120 binding," Proceedings of the National Academy of Sciences, 1996, 93(26):15030-5.

Wu et al., "T cell engaging bispecific antibody (T-BsAb): from technology to therapeutics," Pharmacology & Therapeutics, 2018, 182:161-75.

Yadav et al., "Predicting immunogenic tumour mutations by combining mass spectrometry and exome sequencing," Nov. 27, 2014, Nature, 515(7528):572-576, 16 pages.

Yang et al., "Rab7b, a novel lysosome-associated small GTPase, is involved in monocytic differentiation of human acute promyelocytic leukemia cells," Biochemical and biophysical research communications, 2004, 318(3):792-9.

Ylera et al., "Off-rate screening for selection of high-affinity anti-drug antibodies," Oct. 2013, Analytical Biochemistry, 441(2):208-213, 6 pages.

Yossef et al., "Enhanced detection of neoantigen-reactive T cells targeting unique and shared oncogenes for personalized cancer immunotherapy," JCI insight, 2018, 3(19):e122467.

Yu et al., "Mutation-specific antibodies for the detection of EGFR mutations in non-small-cell lung cancer," Clinical Cancer Research, 2009, 15(9):3023-8.

Zacharakis et al., "Immune recognition of somatic mutations leading to complete durable regression in metastatic breast cancer," Nature medicine, 2018, 24(6):724-30.

Zhu et al., "Engineering high affinity humanized anti-p185HER2/anti-CD3 bispecific F (ab') 2 for efficient lysis of p185HER2 overexpressing tumor cells," International Journal of Cancer, 1995, 62(3):319-24.

Zhu et al., "Identification of heavy chain residues in a humanized anti-CD3 antibody important for efficient antigen binding and T cell activation," The Journal of Immunology, 1995, 155(4):1903-10.

Zumrut et al., "Integrating ligand-receptor interactions and in vitro evolution for streamlined discovery of artificial nucleic acid ligands," Molecular Therapy—Nucleic Acids, 2019, 17:150-63.

Duan et al., "T-cell receptor mimic antibodies for cancer immunotherapy," Molecular Cancer Therapeutics, 20(9):1533-1541, 2021.

Extended Search Report in European Appln. No. 22908460.3, mailed on Nov. 13, 2025, 7 pages.

* cited by examiner

SEQUENCE LISTING

<160> NUMBER OF SEQ ID NOS: 740

<210> SEQ ID NO 1
<211> LENGTH: 9
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 1

His Met Thr Glu Val Val Arg His Cys
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Leu Asp Thr Ala Gly His Glu Glu Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Leu Asp Thr Ala Gly Leu Glu Glu Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Leu Asp Thr Ala Gly Arg Glu Glu Tyr
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Asp Val Asn Thr Ala
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Tyr Ser Arg Tyr Ser Pro Val Thr Phe
1               5                   10
```

```
<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Gln Ser Ser Thr Pro Val Thr Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Ser Ser Tyr Tyr Pro Asn Thr Phe
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Gln Trp Ser Ser Pro Asp Thr Phe
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Ser Asn Ala Tyr Pro Ile Thr Phe
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Asn Val Tyr Ala Ser Gly Met
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 12

Gly Phe Asn Val Tyr Gln Ser Asp Met
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Asn Leu Tyr Gln Arg Asp Met
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Phe Asn Leu Ser Tyr Tyr Asp Met
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Asn Leu Asn Ser Tyr Tyr Met
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ile Tyr Pro Asp Ser Asp Tyr Thr Tyr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ile Trp Pro Tyr Ser Gly Tyr Thr Tyr
1               5                   10

<210> SEQ ID NO 18
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Leu Leu Tyr Gly Ser Asp His Thr Glu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ile Tyr Tyr Gly Ser Gly Tyr Thr Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Ile Ile Pro Gly Tyr Gly Tyr Thr Asn
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Arg Asp Ser Ser Phe Tyr Tyr Val Tyr Ala Met Asp Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Arg Asp Gly Met Tyr Ala Phe Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Arg Ala Thr Tyr Glu Glu Ala Phe Asp Tyr
```

-continued

```
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Arg Gly Ser Tyr Val Ser Gly Met Asp Tyr
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Arg Ser Tyr Tyr Met Tyr Met Asp Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Val Ile Tyr Tyr Pro Phe Thr Phe
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Gln Tyr Asp Tyr Tyr Pro Phe Thr Phe
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gln Ser Ile Tyr Tyr Pro Phe Thr Phe
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 29

Gln Gln Ser Phe Ser Thr Pro Ile Thr Phe
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Gly Glu Tyr Ser Pro Leu Thr Phe
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Thr Tyr Tyr Thr Pro Val Thr Phe
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Phe Asn Leu Tyr Ser Tyr Ala Ile
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Phe Asn Ile Ser Tyr Glu Ala Met
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Phe Asn Leu Tyr Thr Ser Gln Met
1               5

<210> SEQ ID NO 35

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Phe Asn Val Phe Gly Tyr Ala Ile
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Phe Asn Ile Ser Pro Trp Asp Met
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Asn Ile Ser Glu Tyr Leu Met
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Asn Val Phe Glu Ser Ala Met
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Phe Asn Ile Ser His Tyr Val Met
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

-continued

```
Leu Leu Tyr Pro Asp Tyr Gly Val Thr Ser
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Ile Tyr Pro Asn His Gly Ile Thr Ser
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Val Tyr Pro Gly Tyr Tyr Val Thr Ser
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Val Tyr Pro Gly Tyr Asp Val Thr Ser
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Leu Tyr Pro Ser Ser Gly Tyr Thr Asn
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Leu Pro Pro Gly Leu Ser Tyr Thr Asn
1               5                   10

<210> SEQ ID NO 46
<211> LENGTH: 10
<212> TYPE: PRT
<213> ORGANISM: Artificial Sequence
<220> FEATURE:
```

<223> OTHER INFORMATION: Description of Artificial Sequence: Synthetic
     peptide

<400> SEQUENCE: 46

Trp Val Tyr Gly Ser Tyr Asp Tyr Thr Tyr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 47

Asp Phe Tyr Pro His Ser Asp Ser Thr Tyr
1               5                   10

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 48

Ser Arg Tyr Arg Ser Tyr Glu Tyr Ser Val Ser Ser Tyr Ser Tyr Ser
1               5                   10                  15

Ala Met Asp Tyr
            20

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 49

Ser Arg Tyr Ser Ser Ser Ala Met Asp Tyr
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 50

Ser Arg Gly Ala Tyr Tyr Tyr Ser Ser Ala Met Asp Tyr
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 51

Ser Arg Tyr Ser Trp Ala Gly Ala Phe Asp Tyr

-continued

```
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Arg Ser Val Tyr Trp Ser Leu Asp Tyr
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Arg Tyr Gly Tyr Tyr Ala Phe Asp Tyr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Arg Ser Phe Ala Tyr Phe Gln Ala Met Asp Tyr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Arg Tyr Gln Ser Tyr Ser Phe Asp Tyr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Ala Ser Arg Gln Pro Tyr Thr Phe
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 57

Gln Gln Ala Val Ser Tyr Pro Trp Thr Phe
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 58

Gln Gln Thr Ser Ser Tyr Pro Ile Thr Phe
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 59

Gln Gln Ser Trp Tyr Ser Pro Ser Thr Phe
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 60

Gln Gln Ser Tyr Tyr Ala Pro Ile Thr Phe
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 61

Gln Gln Ser Tyr Tyr Ser Pro Trp Thr Phe
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 62

Gln Gln Ala Tyr Tyr Pro Pro Trp Thr Phe
1               5                   10

<210> SEQ ID NO 63
```

-continued

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Ser Tyr Ser Ser Gly Pro Val Thr Phe
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln Thr Tyr Tyr Tyr Pro Phe Thr Phe
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Ser Tyr Tyr Pro Tyr Tyr Pro Trp Thr Phe
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Tyr Asp Arg Pro Ile Thr Phe
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Asn Phe Ser Glu Ser Gly Met
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68
```

-continued

```
Gly Phe Asn Ile Ser Ser Ser Gly Ile
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Phe Asn Ile Tyr Trp Tyr Gly Met
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Phe Asn Ile Ser Ala Ser Gly Met
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Phe Asn Phe Ser Tyr Tyr Gly Met
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Phe Asn Ile Ser Tyr Ser Asn Ile
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Phe Asn Val Ser Arg Trp Ala Met
1               5

<210> SEQ ID NO 74
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 74

Gly Phe Asn Phe Ser Tyr Gly Gly Ile
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Phe Asn Leu Tyr Ala Trp Gly Met
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Phe Asn Val Ser His Ser Ala Met
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Phe Asn Ile Tyr Tyr Glu Ala Met
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

His Phe Ser Gly Asp Ser Gly Tyr Thr Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Met Val Tyr Gly Gly Ser Gly Tyr Thr Asn
1               5                   10

-continued

```
<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Val Tyr Pro Trp Ser Gly Phe Thr Tyr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Ile Trp Gly Gly Ser Ser Tyr Thr Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Trp Ile Tyr Pro Phe Ser Gly Tyr Thr Asn
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Ile Tyr Gly Thr Arg Gly Gly Thr Tyr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Val Tyr Pro Ser Gly Tyr Leu Thr Tyr
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85
```

-continued

```
Met Ile Tyr Pro Leu Thr Gly Tyr Thr Asn
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Val Tyr Gly Gly Trp Gly Ser Thr Ser
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Val His Pro Asp Trp Gly Asn Thr Tyr
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Ile Tyr Pro Trp Asn Asp Tyr Thr Tyr
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Arg Tyr Met Tyr Tyr Ser Gly Tyr Phe Asp Tyr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Arg Trp Ala His Tyr Ser Ala Tyr Met Asp Tyr
1               5                   10

<210> SEQ ID NO 91
<211> LENGTH: 11
<212> TYPE: PRT
<213> ORGANISM: Artificial Sequence
```

-continued

<220> FEATURE:
<223> OTHER INFORMATION: Description of Artificial Sequence: Synthetic
      peptide

<400> SEQUENCE: 91

Ser Arg Asp Tyr Tyr Ser Tyr Ser Leu Asp Tyr
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Arg Gly Gln Tyr Leu Ser Tyr Met Asp Tyr
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Arg Glu Tyr Tyr Ser Arg Ala Phe Asp Tyr
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Arg Tyr Tyr Ser Tyr Ala Met Asp Tyr
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Arg Asn Met Gln Ser Tyr Met Asp Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Arg Asp Tyr Tyr Tyr Ser Val Asp Val
1               5                   10

```
<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Arg Ala Gly Ser Ser Lys Met Ser Ala Gly Ala Phe Asp Tyr
1               5                   10                  15

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Arg Trp Gln Gln Tyr Tyr Tyr Ser Phe Asp Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Arg Asn Tyr Tyr Ala Ala Thr Met Asp Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gln Ser Tyr Thr Ser Pro Leu Thr Phe
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Tyr Trp Tyr Tyr Tyr Pro Ile Thr Phe
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 102

Gln Gln Tyr Tyr Leu Tyr Gln Pro Ile Thr Phe
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Gln Tyr Ser Asn Tyr Pro Leu Thr Phe
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Gln Tyr Ala Ser Asp Pro Ile Thr Phe
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gln Tyr Ser Tyr Asp Pro Ile Thr Phe
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gln Tyr Ile Tyr Asp Pro Val Thr Phe
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Leu Met Tyr Asp Pro Ile Thr Phe
1               5                   10

<210> SEQ ID NO 108
<211> LENGTH: 9
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 108

Gly Phe Asn Ile Tyr Tyr Gly Val Met
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Phe Asn Ile Tyr Ser Tyr Asp Met
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Phe Asn Val Gln Trp Ser His Met
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Phe Asn Ile Gly Met Tyr Thr Met
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Phe Asn Val Phe Tyr Gly Ser Met
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Phe Asn Leu Asp Tyr Gly Trp Met
1               5
```

```
<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Phe Asn Phe Ser Tyr Ser Ala Met
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Asn Val Asp Trp Ala Trp Met
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Phe Asn Phe Gly Thr Tyr Trp Met
1               5

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Met Ile Tyr Pro Asp Ser Ser Trp Thr Tyr
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ile Ser Pro Gly Gly Ser Tyr Thr Tyr
1               5

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 119

Arg Leu Ser Pro Pro Ser Gly Tyr Thr Asn
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Leu Val Tyr Pro Asp Ser Gly Tyr Thr Asn
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Phe Ile Gly Pro Asp Ser Thr Tyr Thr Tyr
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Trp Val Val Pro Gly Ser Asp Tyr Thr Asp
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Val Val Pro Asp Gly Asp Trp Thr Tyr
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Trp Val Val Gly Gly Ser Asp Tyr Thr Tyr
1               5                   10

<210> SEQ ID NO 125
<211> LENGTH: 10

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Trp Phe Leu Pro Asp Tyr Asp Tyr Thr Leu
1               5                   10

<210> SEQ ID NO 126
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ser Arg Asp Gln Asp Phe His Tyr Met Asn Tyr Tyr Leu Ser Tyr Ala
1               5                   10                  15

Leu Asp Tyr

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Arg Ser Ala Phe Thr Gly Tyr Phe Asp Val
1               5                   10

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Arg Leu Ile Leu Ser Lys Gly Gly Tyr Gly Trp Ala Met Asp Tyr
1               5                   10                  15

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Arg Tyr Thr Trp Gln Ser Met Asp Tyr
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130
```

-continued

```
Ser Arg Asp Leu Gly Ser Ala Tyr Ala Met Asp Tyr
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Arg Phe His Tyr Thr Ala Phe Asp Val
1               5                   10

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Arg Gly Trp Tyr Ala Leu Asp Tyr
1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Arg Ser Tyr Tyr Tyr Ala Phe Asp Tyr
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Arg His Gly Glu Tyr Ala Phe Asp Tyr
1               5                   10

<210> SEQ ID NO 135
<211> LENGTH: 9
<212> TYPE: PRT
<213> ORGANISM: Homo sapiens

<400> SEQUENCE: 135

His Met Thr Glu Val Val Arg Arg Cys
1               5

<210> SEQ ID NO 136
<211> LENGTH: 10
<212> TYPE: PRT
<213> ORGANISM: Homo sapiens

<400> SEQUENCE: 136
```

```
Ile Leu Asp Thr Ala Gly Gln Glu Glu Tyr
1               5                   10

<210> SEQ ID NO 137
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Tyr Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Arg Tyr Ser Pro
                85                  90                  95

Val Thr Phe Gly Gln Gly Thr Lys Val Glu Ile Lys Arg Thr Gly Gly
            100                 105                 110

Gly Ser Gly Gly Gly Gly Ser Gly Gly Gly Ala Ser Glu Val Gln Leu
            115                 120                 125

Val Glu Ser Gly Gly Gly Leu Val Gln Pro Gly Gly Ser Leu Arg Leu
        130                 135                 140

Ser Cys Ala Ala Ser Gly Phe Asn Val Tyr Ala Ser Gly Met His Trp
145                 150                 155                 160

Val Arg Gln Ala Pro Gly Lys Gly Leu Glu Trp Val Ala Lys Ile Tyr
                165                 170                 175

Pro Asp Ser Asp Tyr Thr Tyr Tyr Ala Asp Ser Val Lys Gly Arg Phe
            180                 185                 190

Thr Ile Ser Ala Asp Thr Ser Lys Asn Thr Ala Tyr Leu Gln Met Asn
            195                 200                 205

Ser Leu Arg Ala Glu Asp Thr Ala Val Tyr Tyr Cys Ser Arg Asp Ser
        210                 215                 220

Ser Phe Tyr Tyr Val Tyr Ala Met Asp Tyr Trp Gly Gln Gly Thr Leu
225                 230                 235                 240

Val Thr Val Ser Ser
                245

<210> SEQ ID NO 138
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

-continued

```
Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Ser Ser Thr Pro Val
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Val Tyr Gln Ser Asp Met His Trp Val
145                 150                 155                 160

Arg Gln Ala Pro Gly Lys Gly Leu Glu Trp Val Ala Thr Ile Trp Pro
                165                 170                 175

Tyr Ser Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Asp Gly Met
        210                 215                 220

Tyr Ala Phe Asp Tyr Trp Gly Gln Gly Thr Leu Val Thr Val Ser Ser
225                 230                 235                 240
```

```
<210> SEQ ID NO 139
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139
```

```
Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Tyr Pro Asn
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Leu Tyr Gln Arg Asp Met His Trp Val
145                 150                 155                 160
```

```
Arg Gln Ala Pro Gly Lys Gly Leu Glu Trp Val Ala Gly Leu Leu Tyr
            165             170             175

Gly Ser Asp His Thr Glu Tyr Ala Asp Ser Val Lys Gly Arg Phe Thr
            180             185             190

Ile Ser Ala Asp Thr Ser Lys Asn Thr Ala Tyr Leu Gln Met Asn Ser
        195             200             205

Leu Arg Ala Glu Asp Thr Ala Val Tyr Tyr Cys Ser Arg Ala Thr Tyr
        210             215             220

Glu Glu Ala Phe Asp Tyr Trp Gly Gln Gly Thr Leu Val Thr Val Ser
225             230             235             240

Ser

<210> SEQ ID NO 140
<211> LENGTH: 241
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 140

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Val Asn Thr Ala
            20              25              30

Val Ala Trp Tyr Gln Gln Lys Pro Gly Lys Ala Pro Lys Leu Leu Ile
        35              40              45

Tyr Ser Ala Ser Phe Leu Tyr Ser Gly Val Pro Ser Arg Phe Ser Gly
        50              55              60

Ser Arg Ser Gly Thr Asp Phe Thr Leu Thr Ile Thr Ser Leu Gln Pro
65              70              75              80

Glu Asp Phe Ala Thr Tyr Tyr Cys Gln Gln Gln Trp Ser Ser Pro Asp
            85              90              95

Thr Phe Gly Gln Gly Thr Lys Val Glu Ile Lys Arg Thr Gly Gly Gly
            100             105             110

Ser Gly Gly Gly Gly Ser Gly Gly Gly Ala Ser Glu Val Gln Leu Val
        115             120             125

Glu Ser Gly Gly Gly Leu Val Gln Pro Gly Gly Ser Leu Arg Leu Ser
        130             135             140

Cys Ala Ala Ser Gly Phe Asn Leu Ser Tyr Tyr Asp Met His Trp Val
145             150             155             160

Arg Gln Ala Pro Gly Lys Gly Leu Glu Trp Val Ala Leu Ile Tyr Tyr
            165             170             175

Gly Ser Gly Tyr Thr Tyr Tyr Ala Asp Ser Val Lys Gly Arg Phe Thr
            180             185             190

Ile Ser Ala Asp Thr Ser Lys Asn Thr Ala Tyr Leu Gln Met Asn Ser
        195             200             205

Leu Arg Ala Glu Asp Thr Ala Val Tyr Tyr Cys Ser Arg Gly Ser Tyr
        210             215             220

Val Ser Gly Met Asp Tyr Trp Gly Gln Gly Thr Leu Val Thr Val Ser
225             230             235             240

Ser

<210> SEQ ID NO 141
<211> LENGTH: 240
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ala Tyr Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Leu Asn Ser Tyr Tyr Met His Trp Val
145                 150                 155                 160

Arg Gln Ala Pro Gly Lys Gly Leu Glu Trp Val Ala Met Ile Ile Pro
                165                 170                 175

Gly Tyr Gly Tyr Thr Asn Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Tyr Tyr
    210                 215                 220

Met Tyr Met Asp Tyr Trp Gly Gln Gly Thr Leu Val Thr Val Ser Ser
225                 230                 235                 240

<210> SEQ ID NO 142
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

-continued

Glu Asp Phe Ala Thr Tyr Tyr Cys Gln Gln Val Ile Tyr Tyr Pro Phe
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Leu Tyr Ser Tyr Ala Ile His Trp Val
145                 150                 155                 160

Arg Gln Ala Pro Gly Lys Gly Leu Glu Trp Val Ala Leu Leu Tyr Pro
                165                 170                 175

Asp Tyr Gly Val Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Tyr Arg Ser
    210                 215                 220

Tyr Glu Tyr Ser Val Ser Ser Tyr Ser Tyr Ser Ala Met Asp Tyr Trp
225                 230                 235                 240

Gly Gln Gly Thr Leu Val Thr Val Ser Ser
            245                 250

<210> SEQ ID NO 143
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Tyr Tyr Pro Phe
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Tyr Glu Ala Met His Trp Val
145                 150                 155                 160

Arg Gln Ala Pro Gly Lys Gly Leu Glu Trp Val Ala Leu Ile Tyr Pro
                165                 170                 175

Asn His Gly Ile Thr Ser Tyr Ala Asp Ser Val Lys Gly Arg Phe Thr
            180                 185                 190

```
Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Tyr Ser Ser
    210                 215                 220

Ser Ala Met Asp Tyr Trp Gly Gln Gly Thr Leu Val Thr Val Ser Ser
225                 230                 235                 240

<210> SEQ ID NO 144
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Tyr Tyr Pro Phe
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Leu Tyr Thr Ser Gln Met His Trp Val
145                 150                 155                 160

Arg Gln Ala Pro Gly Lys Gly Leu Glu Trp Val Ala Leu Val Tyr Pro
                165                 170                 175

Gly Tyr Tyr Val Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Ala Tyr
    210                 215                 220

Tyr Tyr Ser Ser Ala Met Asp Tyr Trp Gly Gln Gly Thr Leu Val Thr
225                 230                 235                 240

Val Ser Ser

<210> SEQ ID NO 145
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Tyr Tyr Pro Phe
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Val Phe Gly Tyr Ala Ile His Trp Val
145                 150                 155                 160

Arg Gln Ala Pro Gly Lys Gly Leu Glu Trp Val Ala Glu Val Tyr Pro
                165                 170                 175

Gly Tyr Asp Val Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Tyr Ser Trp
    210                 215                 220

Ala Gly Ala Phe Asp Tyr Trp Gly Gln Gly Thr Leu Val Thr Val Ser
225                 230                 235                 240

Ser
```

```
<210> SEQ ID NO 146
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Pro Trp
                85                  90                  95

Thr Phe Gly Gln Gly Thr Lys Val Glu Ile Lys Arg Thr Gly Gly Gly
            100                 105                 110
```

-continued

```
Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Pro Trp Asp Met His Trp Val
145                 150                 155                 160

Arg Gln Ala Pro Gly Lys Gly Leu Glu Trp Val Ala Gln Leu Tyr Pro
                165                 170                 175

Ser Ser Gly Tyr Thr Asn Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Ser Val Tyr
    210                 215                 220

Trp Ser Leu Asp Tyr Trp Gly Gln Gly Thr Leu Val Thr Val Ser Ser
225                 230                 235                 240
```

<210> SEQ ID NO 147
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Glu Tyr Leu Met His Trp Val
145                 150                 155                 160

Arg Gln Ala Pro Gly Lys Gly Leu Glu Trp Val Ala Leu Leu Pro Pro
                165                 170                 175

Gly Leu Ser Tyr Thr Asn Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Tyr Gly Tyr
    210                 215                 220

Tyr Ala Phe Asp Tyr Trp Gly Gln Gly Thr Leu Val Thr Val Ser Ser
225                 230                 235                 240
```

```
<210> SEQ ID NO 148
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Glu Tyr Ser Pro Leu
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Val Phe Glu Ser Ala Met His Trp Val
145                 150                 155                 160

Arg Gln Ala Pro Gly Lys Gly Leu Glu Trp Val Ala Trp Val Tyr Gly
                165                 170                 175

Ser Tyr Asp Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Phe Ala
    210                 215                 220

Tyr Phe Gln Ala Met Asp Tyr Trp Gly Gln Gly Thr Leu Val Thr Val
225                 230                 235                 240

Ser Ser

<210> SEQ ID NO 149
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

-continued

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Tyr Thr Pro Val
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser His Tyr Val Met His Trp Val
145                 150                 155                 160

Arg Gln Ala Pro Gly Lys Gly Leu Glu Trp Val Ala Asp Phe Tyr Pro
                165                 170                 175

His Ser Asp Ser Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Tyr Gln Ser
    210                 215                 220

Tyr Ser Phe Asp Tyr Trp Gly Gln Gly Thr Leu Val Thr Val Ser Ser
225                 230                 235                 240

<210> SEQ ID NO 150
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Arg Gln Pro Tyr
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Phe Ser Glu Ser Gly Met His Trp Val
145                 150                 155                 160

Arg Gln Ala Pro Gly Lys Gly Leu Glu Trp Val Ala His Phe Ser Gly
                165                 170                 175
```

-continued

```
Asp Ser Gly Tyr Thr Tyr Tyr Ala Asp Ser Val Lys Gly Arg Phe Thr
            180             185             190

Ile Ser Ala Asp Thr Ser Lys Asn Thr Ala Tyr Leu Gln Met Asn Ser
        195             200             205

Leu Arg Ala Glu Asp Thr Ala Val Tyr Tyr Cys Ser Arg Tyr Met Tyr
    210             215             220

Tyr Ser Gly Tyr Phe Asp Tyr Trp Gly Gln Gly Thr Leu Val Thr Val
225             230             235             240

Ser Ser

<210> SEQ ID NO 151
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Val Asn Thr Ala
            20              25              30

Val Ala Trp Tyr Gln Gln Lys Pro Gly Lys Ala Pro Lys Leu Leu Ile
        35              40              45

Tyr Ser Ala Ser Phe Leu Tyr Ser Gly Val Pro Ser Arg Phe Ser Gly
    50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Gln Gln Ala Val Ser Tyr Pro Trp
                85              90              95

Thr Phe Gly Gln Gly Thr Lys Val Glu Ile Lys Arg Thr Gly Gly Gly
            100             105             110

Ser Gly Gly Gly Gly Ser Gly Gly Gly Ala Ser Glu Val Gln Leu Val
        115             120             125

Glu Ser Gly Gly Gly Leu Val Gln Pro Gly Gly Ser Leu Arg Leu Ser
    130             135             140

Cys Ala Ala Ser Gly Phe Asn Ile Ser Ser Ser Gly Ile His Trp Val
145             150             155             160

Arg Gln Ala Pro Gly Lys Gly Leu Glu Trp Val Ala Met Val Tyr Gly
            165             170             175

Gly Ser Gly Tyr Thr Asn Tyr Ala Asp Ser Val Lys Gly Arg Phe Thr
            180             185             190

Ile Ser Ala Asp Thr Ser Lys Asn Thr Ala Tyr Leu Gln Met Asn Ser
        195             200             205

Leu Arg Ala Glu Asp Thr Ala Val Tyr Tyr Cys Ser Arg Trp Ala His
    210             215             220

Tyr Ser Ala Tyr Met Asp Tyr Trp Gly Gln Gly Thr Leu Val Thr Val
225             230             235             240

Ser Ser

<210> SEQ ID NO 152
<211> LENGTH: 241
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Ser Ser Tyr Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Tyr Trp Tyr Gly Met His Trp Val
145                 150                 155                 160

Arg Gln Ala Pro Gly Lys Gly Leu Glu Trp Val Ala Gln Val Tyr Pro
                165                 170                 175

Trp Ser Gly Phe Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Asp Tyr Tyr
    210                 215                 220

Ser Tyr Ser Leu Asp Tyr Trp Gly Gln Gly Thr Leu Val Thr Val Ser
225                 230                 235                 240

Ser

<210> SEQ ID NO 153
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Tyr Ser Pro Ser

-continued

```
                        85                    90                    95

Thr Phe Gly Gln Gly Thr Lys Val Glu Ile Lys Arg Thr Gly Gly Gly
            100                   105                   110

Ser Gly Gly Gly Gly Ser Gly Gly Gly Ala Ser Glu Val Gln Leu Val
            115                   120                   125

Glu Ser Gly Gly Gly Leu Val Gln Pro Gly Gly Ser Leu Arg Leu Ser
    130                   135                   140

Cys Ala Ala Ser Gly Phe Asn Ile Ser Ala Ser Gly Met His Trp Val
145                   150                   155                   160

Arg Gln Ala Pro Gly Lys Gly Leu Glu Trp Val Ala Trp Ile Trp Gly
                165                   170                   175

Gly Ser Ser Tyr Thr Tyr Tyr Ala Asp Ser Val Lys Gly Arg Phe Thr
                180                   185                   190

Ile Ser Ala Asp Thr Ser Lys Asn Thr Ala Tyr Leu Gln Met Asn Ser
            195                   200                   205

Leu Arg Ala Glu Asp Thr Ala Val Tyr Tyr Cys Ser Arg Gly Gln Tyr
    210                   215                   220

Leu Ser Tyr Met Asp Tyr Trp Gly Gln Gly Thr Leu Val Thr Val Ser
225                   230                   235                   240

Ser

<210> SEQ ID NO 154
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Met Thr Gln Ser Pro Ser Ser Leu Ser Ala Ser Val Gly
1                   5                    10                   15

Asp Arg Val Thr Ile Thr Cys Arg Ala Ser Gln Asp Val Asn Thr Ala
            20                   25                    30

Val Ala Trp Tyr Gln Gln Lys Pro Gly Lys Ala Pro Lys Leu Leu Ile
            35                   40                    45

Tyr Ser Ala Ser Phe Leu Tyr Ser Gly Val Pro Ser Arg Phe Ser Gly
    50                   55                    60

Ser Arg Ser Gly Thr Asp Phe Thr Leu Thr Ile Ser Ser Leu Gln Pro
65                   70                    75                   80

Glu Asp Phe Ala Thr Tyr Tyr Cys Gln Gln Ser Tyr Tyr Ala Pro Ile
                85                   90                    95

Thr Phe Gly Gln Gly Thr Lys Val Glu Ile Lys Arg Thr Gly Gly Gly
            100                   105                   110

Ser Gly Gly Gly Gly Ser Gly Gly Gly Ala Ser Glu Val Gln Leu Val
            115                   120                   125

Glu Ser Gly Gly Gly Leu Val Gln Pro Gly Gly Ser Leu Arg Leu Ser
    130                   135                   140

Cys Ala Ala Ser Gly Phe Asn Phe Ser Tyr Tyr Gly Met His Trp Val
145                   150                   155                   160

Arg Gln Ala Pro Gly Lys Gly Leu Glu Trp Val Ala Trp Ile Tyr Pro
                165                   170                   175

Phe Ser Gly Tyr Thr Asn Tyr Ala Asp Ser Val Lys Gly Arg Phe Thr
                180                   185                   190

Ile Ser Ala Asp Thr Ser Lys Asn Thr Ala Tyr Leu Gln Met Asn Ser
```

-continued

```
            195                 200                 205

Leu Arg Ala Glu Asp Thr Ala Val Tyr Tyr Cys Ser Arg Glu Tyr Tyr
    210                 215                 220

Ser Arg Ala Phe Asp Tyr Trp Gly Gln Gly Thr Leu Val Thr Val Ser
225                 230                 235                 240

Ser

<210> SEQ ID NO 155
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Ser Pro Trp
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Tyr Ser Asn Ile His Trp Val
145                 150                 155                 160

Arg Gln Ala Pro Gly Lys Gly Leu Glu Trp Val Ala Met Ile Tyr Gly
            165                 170                 175

Thr Arg Gly Gly Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Tyr Tyr Ser
    210                 215                 220

Tyr Ala Met Asp Tyr Trp Gly Gln Gly Thr Leu Val Thr Val Ser Ser
225                 230                 235                 240

<210> SEQ ID NO 156
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Tyr Pro Pro Trp
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Val Ser Arg Trp Ala Met His Trp Val
145                 150                 155                 160

Arg Gln Ala Pro Gly Lys Gly Leu Glu Trp Val Ala Arg Val Tyr Pro
                165                 170                 175

Ser Gly Tyr Leu Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Asn Met Gln
    210                 215                 220

Ser Tyr Met Asp Tyr Trp Gly Gln Gly Thr Leu Val Thr Val Ser Ser
225                 230                 235                 240
```

```
<210> SEQ ID NO 157
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Gly Pro
                85                  90                  95

Val Thr Phe Gly Gln Gly Thr Lys Val Glu Ile Lys Arg Thr Gly Gly
            100                 105                 110

Gly Ser Gly Gly Gly Gly Ser Gly Gly Gly Ala Ser Glu Val Gln Leu
            115                 120                 125

Val Glu Ser Gly Gly Gly Leu Val Gln Pro Gly Gly Ser Leu Arg Leu
```

-continued

```
              130              135              140

Ser Cys Ala Ala Ser Gly Phe Asn Phe Ser Tyr Gly Gly Ile His Trp
145              150              155              160

Val Arg Gln Ala Pro Gly Lys Gly Leu Glu Trp Val Ala Met Ile Tyr
                 165              170              175

Pro Leu Thr Gly Tyr Thr Asn Tyr Ala Asp Ser Val Lys Gly Arg Phe
                 180              185              190

Thr Ile Ser Ala Asp Thr Ser Lys Asn Thr Ala Tyr Leu Gln Met Asn
             195              200              205

Ser Leu Arg Ala Glu Asp Thr Ala Val Tyr Tyr Cys Ser Arg Asp Tyr
         210              215              220

Tyr Tyr Ser Val Asp Val Trp Gly Gln Gly Thr Leu Val Thr Val Ser
225              230              235              240

Ser
```

<210> SEQ ID NO 158
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Val Asn Thr Ala
             20              25              30

Val Ala Trp Tyr Gln Gln Lys Pro Gly Lys Ala Pro Lys Leu Leu Ile
         35              40              45

Tyr Ser Ala Ser Phe Leu Tyr Ser Gly Val Pro Ser Arg Phe Ser Gly
     50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Gln Gln Thr Tyr Tyr Tyr Pro Phe
                 85              90              95

Thr Phe Gly Gln Gly Thr Lys Val Glu Ile Lys Arg Thr Gly Gly Gly
             100             105             110

Ser Gly Gly Gly Gly Ser Gly Gly Gly Ala Ser Glu Val Gln Leu Val
         115             120             125

Glu Ser Gly Gly Gly Leu Val Gln Pro Gly Gly Ser Leu Arg Leu Ser
         130             135             140

Cys Ala Ala Ser Gly Phe Asn Leu Tyr Ala Trp Gly Met His Trp Val
145             150             155             160

Arg Gln Ala Pro Gly Lys Gly Leu Glu Trp Val Ala Leu Val Tyr Gly
                 165             170             175

Gly Trp Gly Ser Thr Ser Tyr Ala Asp Ser Val Lys Gly Arg Phe Thr
             180             185             190

Ile Ser Ala Asp Thr Ser Lys Asn Thr Ala Tyr Leu Gln Met Asn Ser
         195             200             205

Leu Arg Ala Glu Asp Thr Ala Val Tyr Tyr Cys Ser Arg Ala Gly Ser
         210             215             220

Ser Lys Met Ser Ala Gly Ala Phe Asp Tyr Trp Gly Gln Gly Thr Leu
225             230             235             240

Val Thr Val Ser Ser
```

245

<210> SEQ ID NO 159
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Pro Tyr Tyr
                85                  90                  95

Pro Trp Thr Phe Gly Gln Gly Thr Lys Val Glu Ile Lys Arg Thr Gly
            100                 105                 110

Gly Gly Ser Gly Gly Gly Gly Ser Gly Gly Ala Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Val Ser His Ser Ala Met His
145                 150                 155                 160

Trp Val Arg Gln Ala Pro Gly Lys Gly Leu Glu Trp Val Ala Thr Val
                165                 170                 175

His Pro Asp Trp Gly Asn Thr Tyr Tyr Ala Asp Ser Val Lys Gly Arg
            180                 185                 190

Phe Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Ser Arg Trp
    210                 215                 220

Gln Gln Tyr Tyr Tyr Ser Phe Asp Tyr Trp Gly Gln Gly Thr Leu Val
225                 230                 235                 240

Thr Val Ser Ser

<210> SEQ ID NO 160
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Arg Pro Ile Thr
                85                  90                  95

Phe Gly Gln Gly Thr Lys Val Glu Ile Lys Arg Thr Gly Gly Gly Ser
                100                 105                 110

Gly Gly Gly Gly Ser Gly Gly Gly Ala Ser Glu Val Gln Leu Val Glu
        115                 120                 125

Ser Gly Gly Gly Leu Val Gln Pro Gly Gly Ser Leu Arg Leu Ser Cys
        130                 135                 140

Ala Ala Ser Gly Phe Asn Ile Tyr Tyr Glu Ala Met His Trp Val Arg
145                 150                 155                 160

Gln Ala Pro Gly Lys Gly Leu Glu Trp Val Ala Gln Ile Tyr Pro Trp
                165                 170                 175

Asn Asp Tyr Thr Tyr Tyr Ala Asp Ser Val Lys Gly Arg Phe Thr Ile
                180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Asn Tyr Tyr Ala
    210                 215                 220

Ala Thr Met Asp Tyr Trp Gly Gln Gly Thr Leu Val Thr Val Ser Ser
225                 230                 235                 240

<210> SEQ ID NO 161
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Leu
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
        130                 135                 140

Cys Ala Ala Ser Gly Phe Asn Ile Tyr Tyr Gly Val Met His Trp Val
145                 150                 155                 160

Arg Gln Ala Pro Gly Lys Gly Leu Glu Trp Val Ala Met Ile Tyr Pro

-continued

```
               165                  170                  175

Asp Ser Ser Trp Thr Tyr Tyr Ala Asp Ser Val Lys Gly Arg Phe Thr
            180                  185                  190

Ile Ser Ala Asp Thr Ser Lys Asn Thr Ala Tyr Leu Gln Met Asn Ser
        195                  200                  205

Leu Arg Ala Glu Asp Thr Ala Val Tyr Tyr Cys Ser Arg Asp Gln Asp
    210                  215                  220

Phe His Tyr Met Asn Tyr Tyr Leu Ser Tyr Ala Leu Asp Tyr Trp Gly
225                  230                  235                  240

Gln Gly Thr Leu Val Thr Val Ser Ser
                245

<210> SEQ ID NO 162
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Tyr Tyr Tyr Pro
                85                  90                  95

Ile Thr Phe Gly Gln Gly Thr Lys Val Glu Ile Lys Arg Thr Gly Gly
            100                 105                 110

Gly Ser Gly Gly Gly Gly Ser Gly Gly Gly Ala Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Tyr Ser Tyr Asp Met His Trp
145                 150                 155                 160

Val Arg Gln Ala Pro Gly Lys Gly Leu Glu Trp Val Ala Ile Ser Pro
                165                 170                 175

Gly Gly Ser Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Ala Phe
    210                 215                 220

Thr Gly Tyr Phe Asp Val Trp Gly Gln Gly Thr Leu Val Thr Val Ser
225                 230                 235                 240

Ser

<210> SEQ ID NO 163
<211> LENGTH: 246
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Ala Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Val Gln Trp Ser His Met His Trp Val
145                 150                 155                 160

Arg Gln Ala Pro Gly Lys Gly Leu Glu Trp Val Ala Arg Leu Ser Pro
                165                 170                 175

Pro Ser Gly Tyr Thr Asn Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Leu Ile Leu
        210                 215                 220

Ser Lys Gly Gly Tyr Gly Trp Ala Met Asp Tyr Trp Gly Gln Gly Thr
225                 230                 235                 240

Leu Val Thr Val Ser Ser
                245

<210> SEQ ID NO 164
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro

```
65              70              75              80
Glu Asp Phe Ala Thr Tyr Tyr Cys Gln Gln Tyr Tyr Leu Tyr Gln Pro
                85              90              95

Ile Thr Phe Gly Gln Gly Thr Lys Val Glu Ile Lys Arg Thr Gly Gly
                100             105             110

Gly Ser Gly Gly Gly Gly Ser Gly Gly Gly Ala Ser Glu Val Gln Leu
            115             120             125

Val Glu Ser Gly Gly Gly Leu Val Gln Pro Gly Gly Ser Leu Arg Leu
    130             135             140

Ser Cys Ala Ala Ser Gly Phe Asn Ile Gly Met Tyr Thr Met His Trp
145             150             155             160

Val Arg Gln Ala Pro Gly Lys Gly Leu Glu Trp Val Ala Leu Val Tyr
                165             170             175

Pro Asp Ser Gly Tyr Thr Asn Tyr Ala Asp Ser Val Lys Gly Arg Phe
            180             185             190

Thr Ile Ser Ala Asp Thr Ser Lys Asn Thr Ala Tyr Leu Gln Met Asn
            195             200             205

Ser Leu Arg Ala Glu Asp Thr Ala Val Tyr Tyr Cys Ser Arg Tyr Thr
    210             215             220

Trp Gln Ser Met Asp Tyr Trp Gly Gln Gly Thr Leu Val Thr Val Ser
225             230             235             240

Ser

<210> SEQ ID NO 165
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Val Asn Thr Ala
                20              25              30

Val Ala Trp Tyr Gln Gln Lys Pro Gly Lys Ala Pro Lys Leu Leu Ile
            35              40              45

Tyr Ser Ala Ser Phe Leu Tyr Ser Gly Val Pro Ser Arg Phe Ser Gly
    50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Gln Gln Tyr Ser Asn Tyr Pro Leu
                85              90              95

Thr Phe Gly Gln Gly Thr Lys Val Glu Ile Lys Arg Thr Gly Gly Gly
            100             105             110

Ser Gly Gly Gly Gly Ser Gly Gly Gly Ala Ser Glu Val Gln Leu Val
            115             120             125

Glu Ser Gly Gly Gly Leu Val Gln Pro Gly Gly Ser Leu Arg Leu Ser
    130             135             140

Cys Ala Ala Ser Gly Phe Asn Val Phe Tyr Gly Ser Met His Trp Val
145             150             155             160

Arg Gln Ala Pro Gly Lys Gly Leu Glu Trp Val Ala Phe Ile Gly Pro
                165             170             175

Asp Ser Thr Tyr Thr Tyr Tyr Ala Asp Ser Val Lys Gly Arg Phe Thr
```

```
                180                 185                 190

Ile Ser Ala Asp Thr Ser Lys Asn Thr Ala Tyr Leu Gln Met Asn Ser
           195                 200                 205

Leu Arg Ala Glu Asp Thr Ala Val Tyr Tyr Cys Ser Arg Asp Leu Gly
       210                 215                 220

Ser Ala Tyr Ala Met Asp Tyr Trp Gly Gln Gly Thr Leu Val Thr Val
225                 230                 235                 240

Ser Ser
```

```
<210> SEQ ID NO 166
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
           20                  25                  30

Val Ala Trp Tyr Gln Gln Lys Pro Gly Lys Ala Pro Lys Leu Leu Ile
       35                  40                  45

Tyr Ser Ala Ser Phe Leu Tyr Ser Gly Val Pro Ser Arg Phe Ser Gly
       50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Ser Asp Pro Ile
               85                  90                  95

Thr Phe Gly Gln Gly Thr Lys Val Glu Ile Lys Arg Thr Gly Gly Gly
           100                 105                 110

Ser Gly Gly Gly Gly Ser Gly Gly Gly Ala Ser Glu Val Gln Leu Val
           115                 120                 125

Glu Ser Gly Gly Gly Leu Val Gln Pro Gly Gly Ser Leu Arg Leu Ser
       130                 135                 140

Cys Ala Ala Ser Gly Phe Asn Leu Asp Tyr Gly Trp Met His Trp Val
145                 150                 155                 160

Arg Gln Ala Pro Gly Lys Gly Leu Glu Trp Val Ala Trp Val Val Pro
               165                 170                 175

Gly Ser Asp Tyr Thr Asp Tyr Ala Asp Ser Val Lys Gly Arg Phe Thr
           180                 185                 190

Ile Ser Ala Asp Thr Ser Lys Asn Thr Ala Tyr Leu Gln Met Asn Ser
           195                 200                 205

Leu Arg Ala Glu Asp Thr Ala Val Tyr Tyr Cys Ser Arg Phe His Tyr
       210                 215                 220

Thr Ala Phe Asp Val Trp Gly Gln Gly Thr Leu Val Thr Val Ser Ser
225                 230                 235                 240
```

```
<210> SEQ ID NO 167
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Asp Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Phe Ser Tyr Ser Ala Met His Trp Val
145                 150                 155                 160

Arg Gln Ala Pro Gly Lys Gly Leu Glu Trp Val Ala Asp Val Val Pro
                165                 170                 175

Asp Gly Asp Trp Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Trp Tyr
    210                 215                 220

Ala Leu Asp Tyr Trp Gly Gln Gly Thr Leu Val Thr Val Ser Ser
225                 230                 235
```

```
<210> SEQ ID NO 168
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Asp Pro Val
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
```

US 12,674,002 B2

261

262

-continued

```
            115                 120                 125

Glu Ser Gly Gly Gly Leu Val Gln Pro Gly Gly Ser Leu Arg Leu Ser
    130                 135                 140

Cys Ala Ala Ser Gly Phe Asn Val Asp Trp Ala Trp Met His Trp Val
145                 150                 155                 160

Arg Gln Ala Pro Gly Lys Gly Leu Glu Trp Val Ala Trp Val Val Gly
                165                 170                 175

Gly Ser Asp Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Ser Tyr Tyr
    210                 215                 220

Tyr Ala Phe Asp Tyr Trp Gly Gln Gly Thr Leu Val Thr Val Ser Ser
225                 230                 235                 240

<210> SEQ ID NO 169
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Met Tyr Asp Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Phe Gly Thr Tyr Trp Met His Trp Val
145                 150                 155                 160

Arg Gln Ala Pro Gly Lys Gly Leu Glu Trp Val Ala Trp Phe Leu Pro
                165                 170                 175

Asp Tyr Asp Tyr Thr Leu Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg His Gly Glu
    210                 215                 220

Tyr Ala Phe Asp Tyr Trp Gly Gln Gly Thr Leu Val Thr Val Ser Ser
225                 230                 235                 240
```

```
<210> SEQ ID NO 170
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Tyr Ser Phe Thr Gly Tyr Thr Met Asn Trp Val Arg
145                 150                 155                 160

Gln Ala Pro Gly Lys Gly Leu Glu Trp Val Ala Leu Ile Asn Pro Tyr
                165                 170                 175

Lys Gly Val Ser Thr Tyr Asn Gln Lys Phe Lys Asp Arg Phe Thr Ile
            180                 185                 190

Ser Val Asp Lys Ser Lys Asn Thr Ala Tyr Leu Gln Met Asn Ser Leu
        195                 200                 205

Arg Ala Glu Asp Thr Ala Val Tyr Tyr Cys Ala Arg Ser Gly Tyr Tyr
    210                 215                 220

Gly Asp Ser Asp Trp Tyr Phe Asp Val Trp Gly Gln Gly Thr Leu Val
225                 230                 235                 240

Thr Val Ser Ser

<210> SEQ ID NO 171
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Lys Phe Ser Gly
```

```
       50              55              60

Ser Gly Ser Gly Thr Asp Tyr Ser Leu Thr Ile Ser Asn Leu Glu Gln
65              70              75              80

Glu Asp Ile Ala Thr Tyr Phe Cys Gln Gln Gly Asn Thr Leu Pro Trp
                85              90              95

Thr Phe Ala Gly Gly Thr Lys Leu Glu Ile Lys Gly Gly Gly Gly Ser
            100             105             110

Gly Gly Gly Gly Ser Gly Gly Gly Ser Glu Val Gln Leu Gln Gln
            115             120             125

Ser Gly Pro Glu Leu Val Lys Pro Gly Ala Ser Met Lys Ile Ser Cys
        130             135             140

Lys Ala Ser Gly Tyr Ser Phe Thr Gly Tyr Thr Met Asn Trp Val Lys
145             150             155             160

Gln Ser His Gly Lys Asn Leu Glu Trp Met Gly Leu Ile Asn Pro Tyr
                165             170             175

Lys Gly Val Ser Thr Tyr Asn Gln Lys Phe Lys Asp Lys Ala Thr Leu
            180             185             190

Thr Val Asp Lys Ser Ser Ser Thr Ala Tyr Met Glu Leu Leu Ser Leu
            195             200             205

Thr Ser Glu Asp Ser Ala Val Tyr Tyr Cys Ala Arg Ser Gly Tyr Tyr
        210             215             220

Gly Asp Ser Asp Trp Tyr Phe Asp Val Trp Gly Ala Gly Thr Thr Val
225             230             235             240

Thr Val Ser Ser
```

```
<210> SEQ ID NO 172
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Ser Tyr Met
                20              25              30

Asn Trp Tyr Gln Gln Lys Pro Gly Lys Ala Pro Lys Arg Trp Ile Tyr
            35              40              45

Asp Thr Ser Lys Val Ala Ser Gly Val Pro Ala Arg Phe Ser Gly Ser
        50              55              60

Gly Ser Gly Thr Asp Tyr Ser Leu Thr Ile Asn Ser Leu Glu Ala Glu
65              70              75              80

Asp Ala Ala Thr Tyr Tyr Cys Gln Gln Trp Ser Ser Asn Pro Leu Thr
                85              90              95

Phe Gly Gly Gly Thr Lys Val Glu Ile Lys Gly Gly Gly Gly Ser Gly
            100             105             110

Gly Gly Gly Ser Gly Gly Gly Gly Ser Asp Val Gln Leu Val Gln Ser
            115             120             125

Gly Ala Glu Val Lys Lys Pro Gly Ala Ser Val Lys Val Ser Cys Lys
        130             135             140

Ala Ser Gly Tyr Thr Phe Thr Arg Tyr Thr Met His Trp Val Arg Gln
145             150             155             160

Ala Pro Gly Gln Gly Leu Glu Trp Ile Gly Tyr Ile Asn Pro Ser Arg
```

-continued

```
                165                 170                 175

Gly Tyr Thr Asn Tyr Ala Asp Ser Val Lys Gly Arg Phe Thr Ile Thr
            180                 185                 190

Thr Asp Lys Ser Thr Ser Thr Ala Tyr Met Glu Leu Ser Ser Leu Arg
        195                 200                 205

Ser Glu Asp Thr Ala Thr Tyr Tyr Cys Ala Arg Tyr Tyr Asp Asp His
    210                 215                 220

Tyr Cys Leu Asp Tyr Trp Gly Gln Gly Thr Thr Val Thr Val Ser Ser
225                 230                 235                 240

<210> SEQ ID NO 173
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
            85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
            165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Ser Leu Tyr Leu Gln
        195                 200                 205

Met Asn Ser Leu Lys Thr Glu Asp Thr Ala Val Tyr Tyr Cys Val Arg
    210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser
                245

<210> SEQ ID NO 174
<211> LENGTH: 240
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 174

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Ser Gly
            100                 105                 110

Gly Gly Gly Ser Gly Gly Gly Ser Asp Ile Lys Leu Gln Gln Ser
            115                 120                 125

Gly Ala Glu Leu Ala Arg Pro Gly Ala Ser Val Lys Met Ser Cys Lys
        130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
                180                 185                 190

Thr Asp Lys Ser Ser Ser Thr Ala Tyr Met Gln Leu Ser Ser Leu Thr
            195                 200                 205

Ser Glu Asp Ser Ala Val Tyr Tyr Cys Ala Arg Tyr Tyr Asp Asp His
        210                 215                 220

Tyr Cys Leu Asp Tyr Trp Gly Gln Gly Thr Thr Leu Thr Val Ser Ser
225                 230                 235                 240
```

<210> SEQ ID NO 175
<211> LENGTH: 240
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 175

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95
```

-continued

```
Phe Gly Ser Gly Thr Lys Leu Glu Ile Asn Gly Gly Gly Ser Gly
            100                 105                 110

Gly Gly Gly Ser Gly Gly Gly Ser Gln Val Gln Leu Gln Gln Ser
            115                 120                 125

Gly Ala Glu Leu Ala Arg Pro Gly Ala Ser Val Lys Met Ser Cys Lys
    130                 135                 140

Ala Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
                180                 185                 190

Thr Asp Lys Ser Ser Ser Thr Ala Tyr Met Gln Leu Ser Ser Leu Thr
            195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240
```

```
<210> SEQ ID NO 176
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176
```

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
            115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Lys Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Asn Thr Ala Tyr Leu Gln
            195                 200                 205

Met Asn Asn Leu Lys Thr Glu Asp Thr Ala Val Tyr Tyr Cys Val Arg
    210                 215                 220
```

```
His Gly Asn Phe Gly Asn Ser Tyr Ile Ser Tyr Trp Ala Tyr Trp Gly
225                 230                 235                 240

Gln Gly Thr Leu Val Thr Val Ser Ser
                245

<210> SEQ ID NO 177
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Ile Val Leu Thr Gln Ser Pro Ala Thr Leu Ser Leu Ser Pro Gly
1                 5                 10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
          35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys Gly Gly Gly Gly
          100                 105                 110

Ser Gly Gly Gly Gly Ser Gly Gly Gly Ser Gln Val Gln Leu Val
          115                 120                 125

Glu Ser Gly Gly Gly Val Val Gln Pro Gly Arg Ser Leu Arg Leu Ser
     130                 135                 140

Cys Ala Ala Ser Gly Phe Lys Phe Ser Gly Tyr Gly Met His Trp Val
145                 150                 155                 160

Arg Gln Ala Pro Gly Lys Gly Leu Glu Trp Val Ala Val Ile Trp Tyr
                165                 170                 175

Asp Gly Ser Lys Lys Tyr Tyr Val Asp Ser Val Lys Gly Arg Phe Thr
                180                 185                 190

Ile Ser Arg Asp Asn Ser Lys Asn Thr Leu Tyr Leu Gln Met Asn Ser
          195                 200                 205

Leu Arg Ala Glu Asp Thr Ala Val Tyr Tyr Cys Ala Arg Gln Met Gly
     210                 215                 220

Tyr Trp His Phe Asp Leu Trp Gly Arg Gly Thr Leu Val Thr Val Ser
225                 230                 235                 240

Ser

<210> SEQ ID NO 178
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Ile Val Leu Thr Gln Ser Pro Arg Thr Leu Ser Leu Ser Pro Gly
1                 5                 10                  15
```

Glu Arg Ala Thr Leu Ser Cys Arg Ala Ser Gln Ser Val Ser Ser Ser
          20                  25                  30

Tyr Leu Ala Trp Tyr Gln Gln Lys Pro Gly Gln Ala Pro Arg Leu Leu
          35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Asp
65                  70                  75                  80

Pro Glu Asp Phe Ala Val Tyr Tyr Cys Gln Gln Tyr Gly Ser Ser Pro
                  85                  90                  95

Ile Thr Phe Gly Gln Gly Thr Arg Leu Glu Ile Lys Gly Gly Gly Gly
               100                 105                 110

Ser Gly Gly Gly Gly Ser Gly Gly Gly Ser Gln Val Gln Leu Val
          115                 120                 125

Glu Ser Gly Gly Gly Val Val Gln Pro Gly Arg Ser Leu Arg Leu Ser
     130                 135                 140

Cys Ala Ala Ser Gly Phe Thr Phe Arg Ser Tyr Gly Met His Trp Val
145                 150                 155                 160

Arg Gln Ala Pro Gly Lys Gly Leu Glu Trp Val Ala Ile Ile Trp Tyr
               165                 170                 175

Asp Gly Ser Lys Lys Asn Tyr Ala Asp Ser Val Lys Gly Arg Phe Thr
               180                 185                 190

Ile Ser Arg Asp Asn Ser Lys Asn Thr Leu Tyr Leu Gln Met Asn Ser
          195                 200                 205

Leu Arg Ala Glu Asp Thr Ala Val Tyr Tyr Cys Ala Arg Gly Thr Gly
     210                 215                 220

Tyr Asn Trp Phe Asp Pro Trp Gly Gln Gly Thr Leu Val Thr Val Ser
225                 230                 235                 240

Ser

<210> SEQ ID NO 179
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Ile Leu Met Thr Gln Ser Pro Ser Ser Leu Ser Ala Ser Val Gly
1                   5                   10                  15

Asp Arg Val Thr Ile Thr Cys Arg Ala Ser Gln Gly Ile Ser Ser Ala
          20                  25                  30

Leu Ala Trp Tyr Gln Gln Lys Pro Gly Lys Ala Pro Lys Leu Leu Ile
          35                  40                  45

Tyr Tyr Ala Ser Ser Leu Gln Ser Gly Val Pro Ser Arg Phe Ser Gly
     50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Leu Thr
                  85                  90                  95

Phe Gly Gly Gly Thr Lys Val Glu Ile Lys Gly Gly Gly Gly Ser Gly
               100                 105                 110

Gly Gly Gly Ser Gly Gly Gly Ser Gln Val Gln Leu Val Glu Ser
          115                 120                 125

```
Gly Gly Gly Val Val Gln Pro Gly Arg Ser Leu Arg Leu Ser Cys Ala
    130                 135                 140

Ala Ser Gly Phe Thr Phe Arg Ser Tyr Gly Met His Trp Val Arg Gln
145                 150                 155                 160

Ala Pro Gly Lys Gly Leu Glu Trp Val Ala Ile Ile Trp Tyr Asp Gly
                165                 170                 175

Ser Lys Lys Asn Tyr Ala Asp Ser Val Lys Gly Arg Phe Thr Ile Ser
                180                 185                 190

Arg Asp Asn Ser Lys Asn Thr Leu Tyr Leu Gln Met Asn Ser Leu Arg
                195                 200                 205

Ala Glu Asp Thr Ala Val Tyr Tyr Cys Ala Arg Gly Thr Gly Tyr Asn
    210                 215                 220

Trp Phe Asp Pro Trp Gly Gln Gly Thr Leu Val Thr Val Ser Ser
225                 230                 235
```

```
<210> SEQ ID NO 180
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys Gly Gly Gly Gly
            100                 105                 110

Ser Gly Gly Gly Gly Ser Gly Gly Gly Ser Gln Val Gln Leu Val
            115                 120                 125

Gln Ser Gly Gly Gly Val Val Gln Ser Gly Arg Ser Leu Arg Leu Ser
    130                 135                 140

Cys Ala Ala Ser Gly Phe Lys Phe Ser Gly Tyr Gly Met His Trp Val
145                 150                 155                 160

Arg Gln Ala Pro Gly Lys Gly Leu Glu Trp Val Ala Val Ile Trp Tyr
                165                 170                 175

Asp Gly Ser Lys Lys Tyr Tyr Val Asp Ser Val Lys Gly Arg Phe Thr
                180                 185                 190

Ile Ser Arg Asp Asn Ser Lys Asn Thr Leu Tyr Leu Gln Met Asn Ser
            195                 200                 205

Leu Arg Gly Glu Asp Thr Ala Val Tyr Tyr Cys Ala Arg Gln Met Gly
    210                 215                 220

Tyr Trp His Phe Asp Leu Trp Gly Arg Gly Thr Leu Val Thr Val Ser
225                 230                 235                 240

Ser
```

-continued

<210> SEQ ID NO 181
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gln Val Gln Leu Val Gln
        115                 120                 125

Ser Gly Gly Gly Val Val Gln Pro Gly Arg Ser Leu Arg Leu Ser Cys
    130                 135                 140

Val Ala Ser Gly Phe Thr Phe Ser Ser Tyr Gly Met His Trp Val Arg
145                 150                 155                 160

Gln Ala Pro Gly Lys Gly Leu Glu Trp Val Ala Ala Ile Trp Tyr Asn
                165                 170                 175

Gly Arg Lys Gln Asp Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Thr Arg Gly Thr Gly Tyr
    210                 215                 220

Asn Trp Phe Asp Pro Trp Gly Gln Gly Thr Leu Val Thr Val Ser Ser
225                 230                 235                 240

<210> SEQ ID NO 182
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Gly Gly Gly Gly Ser
                100                 105                 110

Gly Gly Gly Gly Ser Gly Gly Gly Ser Gln Val Gln Leu Val Gln
            115                 120                 125

Ser Gly Gly Gly Val Val Gln Pro Gly Arg Ser Leu Arg Leu Ser Cys
        130                 135                 140

Val Ala Ser Gly Phe Thr Phe Ser Ser Tyr Gly Met His Trp Val Arg
145                 150                 155                 160

Gln Ala Pro Gly Lys Gly Leu Glu Trp Val Ala Ala Ile Trp Tyr Asn
                165                 170                 175

Gly Arg Lys Gln Asp Tyr Ala Asp Ser Val Lys Gly Arg Phe Thr Ile
                180                 185                 190

Ser Arg Asp Asn Ser Lys Asn Thr Leu Tyr Leu Gln Met Asn Ser Leu
            195                 200                 205

Arg Ala Glu Asp Thr Ala Val Tyr Tyr Cys Thr Arg Gly Thr Gly Tyr
        210                 215                 220

Asn Trp Phe Asp Pro Trp Gly Gln Gly Thr Leu Val Thr Val Ser Ser
225                 230                 235                 240
```

```
<210> SEQ ID NO 183
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183
```

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
                35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Thr Lys Arg Gly Gly Gly Gly Ser
                100                 105                 110

Gly Gly Gly Gly Ser Gly Gly Gly Gly Ser Gln Val Gln Leu Gln Gln
            115                 120                 125

Ser Gly Ala Glu Leu Ala Arg Pro Gly Ala Ser Val Lys Met Ser Cys
        130                 135                 140

Lys Ala Ser Gly Tyr Thr Phe Thr Ser Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Ser Gly Tyr Thr Lys Tyr Asn Gln Lys Phe Lys Asp Lys Ala Thr Leu
                180                 185                 190
```

```
Thr Ala Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Trp Gln Asp Tyr
    210                 215                 220

Asp Val Tyr Phe Asp Tyr Trp Gly Gln Gly Thr Thr Leu Thr Val Ser
225                 230                 235                 240

Ser

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln Gln Ser Ser Tyr Ser Pro Trp Thr Phe
1               5                 10

<210> SEQ ID NO 185
<211> LENGTH: 9
<212> TYPE: PRT
<213> ORGANISM: Homo sapiens

<400> SEQUENCE: 185

Pro Leu Thr Glu Ile Ile Arg His Tyr
1               5

<210> SEQ ID NO 186
<211> LENGTH: 9
<212> TYPE: PRT
<213> ORGANISM: Homo sapiens

<400> SEQUENCE: 186

Leu Gln Ser Glu Val Ile Arg His Tyr
1               5

<210> SEQ ID NO 187
<211> LENGTH: 9
<212> TYPE: PRT
<213> ORGANISM: Homo sapiens

<400> SEQUENCE: 187

Gln Asn Ser Glu Ile Ile Arg His Ile
1               5

<210> SEQ ID NO 188
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Ile Glu Leu Thr Gln Ser Pro Ser Ser Leu Ser Ala Ser Val Gly
1               5                 10                  15

Asp Arg Val Thr Ile Thr Cys Arg Ser Asn Thr Gly Thr Val Thr Thr
            20                  25                  30

Ser Asn Tyr Ala Ser Trp Tyr Gln Gln Lys Pro Gly Lys Ala Pro Gly
        35                  40                  45
```

US 12,674,002 B2

285                                                                                          286

-continued

Gly Leu Ile Gly His Thr Asn Asn Arg Ala Pro Gly Val Pro Ser Arg
50                      55                      60

Phe Ser Gly Ser Leu Ser Gly Ala Asp Ala Thr Leu Thr Ile Ser Ser
65                      70                      75                      80

Leu Lys Pro Glu Asp Leu Ala Thr Tyr Tyr Cys Ala Leu Trp Tyr Asn
                        85                      90                      95

His Trp Val Phe Gly Gln Gly Thr Lys Leu Glu Ile Lys Gly Gly Gly
                        100                     105                     110

Gly Ser Gly Gly Gly Gly Ser Gly Gly Gly Gly Ser Glu Val Gln Leu
                        115                     120                     125

Gln Glu Ser Gly Gly Gly Leu Val Gln Pro Gly Asp Ser Leu Arg Leu
        130                     135                     140

Ser Cys Ala Ala Ser Gly Phe Thr Phe Ser Asn Tyr Trp Leu Gly Trp
145                     150                     155                     160

Ile Arg Gln Ala Pro Gly Lys Gly Pro Glu Trp Val Gly Asp Ile Tyr
                        165                     170                     175

Pro Gly Gly Gly Tyr Thr Asn Tyr Asn Glu Lys Phe Lys Gly Arg Phe
                        180                     185                     190

Thr Ile Ser Ala Asp Thr Ser Lys Asn Ile Ala Tyr Leu Gln Val Asn
                        195                     200                     205

Ser Leu Arg Ala Glu Asp Thr Ala Val Tyr Tyr Cys Ala Arg Ser Ala
        210                     215                     220

Ser Trp Tyr Phe Asp Val Trp Gly Gln Gly Thr Leu Val Thr Val Ser
225                     230                     235                     240

Ser

<210> SEQ ID NO 189
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Ser Tyr Val Leu Thr Gln Pro Ser Ser Val Ser Val Ala Pro Gly Gln
1                       5                       10                      15

Thr Ala Thr Ile Ser Cys Gly Gly His Asn Ile Gly Ser Lys Asn Val
                        20                      25                      30

His Trp Tyr Gln Gln Arg Pro Gly Gln Ser Pro Val Leu Val Ile Tyr
        35                      40                      45

Gln Asp Asn Lys Arg Pro Ser Gly Ile Pro Glu Arg Phe Ser Gly Ser
50                      55                      60

Asn Ser Gly Asn Thr Ala Thr Leu Thr Ile Ser Gly Thr Gln Ala Met
65                      70                      75                      80

Asp Glu Ala Asp Tyr Tyr Cys Gln Val Trp Asp Asn Tyr Ser Val Leu
                        85                      90                      95

Phe Gly Gly Gly Thr Lys Leu Thr Val Leu Gly Gly Gly Gly Ser Gly
                        100                     105                     110

Gly Gly Gly Ser Gly Gly Gly Ser Gln Val Gln Leu Val Gln Ser
        115                     120                     125

Gly Ala Glu Val Lys Lys Pro Gly Glu Ser Leu Lys Val Ser Cys Lys
        130                     135                     140

Ala Ser Gly Tyr Thr Phe Thr Ser Tyr Tyr Met His Trp Val Arg Gln
145                     150                     155                     160

Ala Pro Gly Gln Gly Leu Glu Trp Met Gly Ile Ile Asn Pro Ser Gly
                165                 170                 175

Gly Ser Thr Ser Tyr Ala Gln Lys Phe Gln Gly Arg Val Thr Met Thr
            180                 185                 190

Arg Asp Thr Ser Thr Ser Thr Val Tyr Met Glu Leu Ser Ser Leu Arg
        195                 200                 205

Ser Glu Asp Thr Ala Val Tyr Tyr Cys Ala Arg Gly Ser Ala Tyr Tyr
    210                 215                 220

Tyr Asp Phe Ala Asp Tyr Trp Gly Gln Gly Thr Leu Val Thr Val Ser
225                 230                 235                 240

Ser

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Tyr Lys Asp Asp Asp Asp Lys
1               5

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ccccggacga tattgaacaa                                                    20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
cagactgacc gagcgaacct                                                    20

<210> SEQ ID NO 193
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Leu Lys Gly
            100                 105                 110

Gly Gly Gly Ser Gly Gly Gly Gly Ser Gly Gly Gly Gly Ser Gln Val
            115                 120                 125

Thr Leu Lys Glu Ser Gly Pro Gly Ile Leu Gln Pro Ser Gln Thr Leu
        130                 135                 140

Ser Leu Thr Cys Ser Phe Ser Gly Phe Ser Leu Arg Thr Ser Gly Met
145                 150                 155                 160

Gly Val Gly Trp Ile Arg Gln Pro Ser Gly Lys Gly Leu Glu Trp Leu
                165                 170                 175

Ala His Ile Trp Trp Asp Asp Asp Lys Arg Tyr Asn Pro Ala Leu Lys
                180                 185                 190

Ser Arg Leu Thr Ile Ser Lys Asp Thr Ser Ser Asn Gln Val Phe Leu
            195                 200                 205

Lys Ile Ala Ser Val Asp Thr Ala Asp Thr Ala Thr Tyr Tyr Cys Ala
        210                 215                 220

Gln Ile Asn Pro Ala Trp Phe Ala Tyr Trp Gly Gln Gly Thr Leu Val
225                 230                 235                 240

Thr Val Ser Ala

<210> SEQ ID NO 194
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Ile Val Leu Thr Gln Ser Pro Asp Ser Leu Ala Val Ser Leu Gly
1                   5                   10                  15

Glu Arg Ala Thr Ile Asn Cys Lys Ala Ser Gln Ser Val Asp Phe Asp
                20                  25                  30

Gly Asp Ser Phe Met Asn Trp Tyr Gln Gln Lys Pro Gly Gln Pro Pro
            35                  40                  45

Lys Leu Leu Ile Tyr Thr Thr Ser Asn Leu Glu Ser Gly Val Pro Asp
        50                  55                  60

Arg Phe Ser Gly Ser Gly Ser Gly Thr Asp Phe Thr Leu Thr Ile Arg
65                  70                  75                  80

Pro Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gln Val
            115                 120                 125

Thr Leu Lys Glu Ser Gly Pro Ala Leu Val Lys Pro Thr Gln Thr Leu
        130                 135                 140

Thr Leu Thr Cys Thr Phe Ser Gly Phe Ser Leu Ser Thr Ser Gly Met
145                 150                 155                 160

Gly Val Gly Trp Ile Arg Gln Pro Pro Gly Lys Ala Leu Glu Trp Leu
                165                 170                 175

```
Ala His Ile Trp Trp Asp Asp Asp Lys Arg Tyr Asn Pro Ala Leu Lys
            180                 185                 190

Ser Arg Leu Thr Ile Ser Lys Asp Thr Ser Lys Asn Gln Val Val Leu
            195                 200                 205

Thr Met Thr Asn Met Asp Pro Val Asp Thr Ala Thr Tyr Tyr Cys Ala
            210                 215                 220

Gln Ile Asn Pro Ala Trp Phe Ala Tyr Trp Gly Gln Gly Thr Leu Val
225                 230                 235                 240

Thr Val Ser Ser
```

```
<210> SEQ ID NO 195
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195
```

```
Asp Ile Glu Leu Thr Gln Glu Ser Ala Leu Thr Thr Ser Pro Gly Glu
1               5                   10                  15

Thr Val Thr Leu Thr Cys Arg Ser Asn Thr Gly Thr Val Thr Thr Ser
            20                  25                  30

Asn Tyr Ala Asn Trp Val Gln Glu Lys Pro Asp His Leu Phe Thr Gly
            35                  40                  45

Leu Ile Gly His Thr Asn Asn Arg Ala Pro Gly Val Pro Ala Arg Phe
            50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Asn Asn
                85                  90                  95

His Trp Val Phe Gly Gly Gly Thr Lys Leu Glu Ile Lys Gly Gly Gly
            100                 105                 110

Gly Ser Gly Gly Gly Gly Ser Gly Gly Gly Gly Ser Glu Val Gln Leu
            115                 120                 125

Gln Glu Ser Gly Ala Glu Leu Val Arg Pro Gly Thr Ser Val Lys Ile
            130                 135                 140

Ser Cys Lys Ala Ser Gly Tyr Thr Phe Thr Asn Tyr Trp Leu Gly Trp
145                 150                 155                 160

Val Lys Gln Arg Pro Gly His Gly Leu Glu Trp Ile Gly Asp Ile Tyr
                165                 170                 175

Pro Gly Gly Gly Tyr Thr Asn Tyr Asn Glu Lys Phe Lys Gly Lys Ala
            180                 185                 190

Thr Val Thr Ala Asp Thr Ser Ser Arg Thr Ala Tyr Val Gln Val Arg
            195                 200                 205

Ser Leu Thr Ser Glu Asp Ser Ala Val Tyr Phe Cys Ala Arg Ser Ala
            210                 215                 220

Ser Trp Tyr Phe Asp Val Trp Gly Gln Gly Thr Thr Val Thr Val Ser
225                 230                 235                 240

Ser
```

```
<210> SEQ ID NO 196
<211> LENGTH: 10
<212> TYPE: PRT
<213> ORGANISM: Homo sapiens
```

-continued

<400> SEQUENCE: 196

Lys Thr Leu Lys Glu Leu Asn Val Ala His
1               5                   10

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: A, I, L, M, V, N, Q, T, or C
<220> FEATURE:
<221> NAME/KEY: MOD_RES
<222> LOCATION: (3)..(3)
<223> OTHER INFORMATION: S or T
<220> FEATURE:
<221> NAME/KEY: MOD_RES
<222> LOCATION: (4)..(4)
<223> OTHER INFORMATION: D or E
<220> FEATURE:
<221> NAME/KEY: MOD_RES
<222> LOCATION: (5)..(5)
<223> OTHER INFORMATION: I or V
<220> FEATURE:
<221> NAME/KEY: MOD_RES
<222> LOCATION: (6)..(6)
<223> OTHER INFORMATION: I, M, V, S, or T
<220> FEATURE:
<221> NAME/KEY: MOD_RES
<222> LOCATION: (9)..(9)
<223> OTHER INFORMATION: A, I, L, V, G, H, S, T, Y, or C

<400> SEQUENCE: 197

Xaa Xaa Xaa Xaa Xaa Xaa Arg His Xaa
1               5

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ggccatggca gatattcaga                                           20

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
ccgggccttt atcatcatc                                            19

<210> SEQ ID NO 200
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 200

Gly Gly Gly Gly Ser
1               5

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Gly Gly Gly Ser Gly Gly Gly Gly Ser Gly Gly Gly Gly Ser
1               5                   10                  15

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ccccttgccg tcccaagcaa                                              20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
gctgccctgg taggttttct                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
gagacctgtg ggaagcgaaa                                              20

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Val Val Val Gly Ala Val Gly Val Gly Lys
1               5                   10

<210> SEQ ID NO 206
<211> LENGTH: 9
<212> TYPE: PRT
```

-continued

<213> ORGANISM: Artificial Sequence
<220> FEATURE:
<223> OTHER INFORMATION: Description of Artificial Sequence: Synthetic
      peptide

<400> SEQUENCE: 206

Val Val Gly Ala Val Gly Val Gly Lys
1               5

<210> SEQ ID NO 207
<211> LENGTH: 10
<212> TYPE: PRT
<213> ORGANISM: Homo sapiens

<400> SEQUENCE: 207

Val Val Val Gly Ala Gly Gly Val Gly Lys
1               5                   10

<210> SEQ ID NO 208
<211> LENGTH: 9
<212> TYPE: PRT
<213> ORGANISM: Homo sapiens

<400> SEQUENCE: 208

Val Val Gly Ala Gly Gly Val Gly Lys
1               5

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Lys Leu Val Val Val Gly Ala Val Gly Val
1               5                   10

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Val Val Gly Ala Cys Gly Val Gly Lys
1               5

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Val Val Gly Ala Cys Gly Val Gly Lys
1               5                   10

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Val Val Gly Ala Asp Gly Val Gly Lys
1               5

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Val Val Val Gly Ala Asp Gly Val Gly Lys
1               5                   10

<210> SEQ ID NO 214
<211> LENGTH: 9
<212> TYPE: PRT
<213> ORGANISM: Homo sapiens

<400> SEQUENCE: 214

Thr Thr Ala Pro Ser Leu Ser Gly Lys
1               5

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ile Leu Asp Thr Ala Gly Lys Glu Glu Tyr
1               5                   10

<210> SEQ ID NO 216
<211> LENGTH: 11
<212> TYPE: PRT
<213> ORGANISM: Homo sapiens

<400> SEQUENCE: 216

Tyr Ser Glu His Pro Thr Phe Thr Ser Gln Tyr
1               5                   10

<210> SEQ ID NO 217
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

```
Val Asn Thr Ala Val Ala Trp Tyr Gln Gln Lys Pro Gly Lys Ala Pro
    50                  55                  60
Lys Leu Leu Ile Tyr Ser Ala Ser Phe Leu Tyr Ser Gly Val Pro Ser
65                  70                  75                  80
Arg Phe Ser Gly Ser Arg Ser Gly Thr Asp Phe Thr Leu Thr Ile Ser
                85                  90                  95
Ser Leu Gln Pro Glu Asp Phe Ala Thr Tyr Tyr Cys Gln Gln Ser Tyr
            100                 105                 110
Tyr Tyr Phe Arg Pro Ile Thr Phe Gly Gln Gly Thr Lys Val Glu Ile
            115                 120                 125
Lys Gly Gly Gly Gly Ser Glu Val Gln Leu Val Glu Ser Gly Gly Gly
        130                 135                 140
Leu Val Gln Pro Gly Gly Ser Leu Arg Leu Ser Cys Ala Ala Ser Gly
145                 150                 155                 160
Tyr Ser Phe Thr Gly Tyr Thr Met Asn Trp Val Arg Gln Ala Pro Gly
                165                 170                 175
Lys Gly Leu Glu Trp Val Ala Leu Ile Asn Pro Tyr Lys Gly Val Ser
            180                 185                 190
Thr Tyr Asn Gln Lys Phe Lys Asp Arg Phe Thr Ile Ser Val Asp Lys
            195                 200                 205
Ser Lys Asn Thr Ala Tyr Leu Gln Met Asn Ser Leu Arg Ala Glu Asp
    210                 215                 220
Thr Ala Val Tyr Tyr Cys Ala Arg Ser Gly Tyr Tyr Gly Asp Ser Asp
225                 230                 235                 240
Trp Tyr Phe Asp Val Trp Gly Gln Gly Thr Leu Val Thr Val Ser Ser
                245                 250                 255
Gly Gly Gly Gly Ser Gly Gly Gly Gly Ser Gly Gly Gly Gly Ser Asp
            260                 265                 270
Ile Gln Met Thr Gln Ser Pro Ser Ser Leu Ser Ala Ser Val Gly Asp
            275                 280                 285
Arg Val Thr Ile Thr Cys Arg Ala Ser Gln Asp Ile Arg Asn Tyr Leu
    290                 295                 300
Asn Trp Tyr Gln Gln Lys Pro Gly Lys Ala Pro Lys Leu Leu Ile Tyr
305                 310                 315                 320
Tyr Thr Ser Arg Leu Glu Ser Gly Val Pro Ser Arg Phe Ser Gly Ser
                325                 330                 335
Gly Ser Gly Thr Asp Tyr Thr Leu Thr Ile Ser Ser Leu Gln Pro Glu
            340                 345                 350
Asp Phe Ala Thr Tyr Tyr Cys Gln Gln Gly Asn Thr Leu Pro Trp Thr
            355                 360                 365
Phe Gly Gln Gly Thr Lys Val Glu Ile Lys Gly Gly Gly Gly Ser Glu
    370                 375                 380
Val Gln Leu Val Glu Ser Gly Gly Gly Leu Val Gln Pro Gly Gly Ser
385                 390                 395                 400
Leu Arg Leu Ser Cys Ala Ala Ser Gly Phe Asn Leu Ser Tyr Ser Asp
                405                 410                 415
Ile His Trp Val Arg Gln Ala Pro Gly Lys Gly Leu Glu Trp Val Ala
                420                 425                 430
Val Val Met Pro Asp Ser Gly His Thr Asn Tyr Ala Asp Ser Val Lys
            435                 440                 445
Gly Arg Phe Thr Ile Ser Ala Asp Thr Ser Lys Asn Thr Ala Tyr Leu
    450                 455                 460
Gln Met Asn Ser Leu Arg Ala Glu Asp Thr Ala Val Tyr Tyr Cys Ser
```

```
465               470               475               480

Arg Ala Thr Asn Ile Pro Val Tyr Ala Phe Asp Tyr Trp Gly Gln Gly
                485               490               495

Thr Leu Val Thr Val Ser Ser His His His His His His
            500               505
```

<210> SEQ ID NO 218
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Gly Ser Glu Val Gln Leu Gln Gln Ser Gly Pro Glu
    130                 135                 140

Leu Val Lys Pro Gly Ala Ser Met Lys Ile Ser Cys Lys Ala Ser Gly
145                 150                 155                 160

Tyr Ser Phe Thr Gly Tyr Thr Met Asn Trp Val Lys Gln Ser His Gly
                165                 170                 175

Lys Asn Leu Glu Trp Met Gly Leu Ile Asn Pro Tyr Lys Gly Val Ser
            180                 185                 190

Thr Tyr Asn Gln Lys Phe Lys Asp Lys Ala Thr Leu Thr Val Asp Lys
            195                 200                 205

Ser Ser Ser Thr Ala Tyr Met Glu Leu Leu Ser Leu Thr Ser Glu Asp
    210                 215                 220

Ser Ala Val Tyr Tyr Cys Ala Arg Ser Gly Tyr Tyr Gly Asp Ser Asp
225                 230                 235                 240

Trp Tyr Phe Asp Val Trp Gly Ala Gly Thr Thr Val Thr Val Ser Ser
                245                 250                 255

Gly Gly Gly Gly Ser Gly Gly Gly Ser Gly Gly Gly Gly Ser Asp
            260                 265                 270

Ile Gln Met Thr Gln Thr Thr Ser Ser Leu Ser Ala Ser Leu Gly Asp
            275                 280                 285

Arg Val Thr Ile Ser Cys Arg Ala Ser Gln Asp Ile Arg Asn Tyr Leu
    290                 295                 300

Asn Trp Tyr Gln Gln Lys Pro Asp Gly Thr Val Lys Leu Leu Ile Tyr
305                 310                 315                 320
```

```
Tyr Thr Ser Arg Leu His Ser Gly Val Pro Ser Lys Phe Ser Gly Ser
                325                 330                 335

Gly Ser Gly Thr Asp Tyr Ser Leu Thr Ile Ser Asn Leu Glu Gln Glu
            340                 345                 350

Asp Ile Ala Thr Tyr Phe Cys Gln Gln Gly Asn Thr Leu Pro Trp Thr
            355                 360                 365

Phe Ala Gly Gly Thr Lys Leu Glu Ile Lys Gly Gly Gly Gly Ser Glu
        370                 375                 380

Val Gln Leu Val Glu Ser Gly Gly Gly Leu Val Gln Pro Gly Gly Ser
385                 390                 395                 400

Leu Arg Leu Ser Cys Ala Ala Ser Gly Phe Asn Leu Ser Tyr Ser Asp
                405                 410                 415

Ile His Trp Val Arg Gln Ala Pro Gly Lys Gly Leu Glu Trp Val Ala
            420                 425                 430

Val Val Met Pro Asp Ser Gly His Thr Asn Tyr Ala Asp Ser Val Lys
            435                 440                 445

Gly Arg Phe Thr Ile Ser Ala Asp Thr Ser Lys Asn Thr Ala Tyr Leu
        450                 455                 460

Gln Met Asn Ser Leu Arg Ala Glu Asp Thr Ala Val Tyr Tyr Cys Ser
465                 470                 475                 480

Arg Ala Thr Asn Ile Pro Val Tyr Ala Phe Asp Tyr Trp Gly Gln Gly
                485                 490                 495

Thr Leu Val Thr Val Ser Ser His His His His His His
            500                 505
```

<210> SEQ ID NO 219
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

```
Met Tyr Arg Met Gln Leu Leu Ser Cys Ile Ala Leu Ser Leu Ala Leu
1                   5                   10                  15

Val Thr Asn Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Arg Asn Tyr Leu Asn Trp Tyr Gln Gln Lys Pro Gly Lys Ala Pro
        50                  55                  60

Lys Leu Leu Ile Tyr Tyr Thr Ser Arg Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Gly Asn
            100                 105                 110

Thr Leu Pro Trp Thr Phe Gly Gln Gly Thr Lys Val Glu Ile Lys Gly
        115                 120                 125

Gly Gly Gly Ser Glu Val Gln Leu Val Glu Ser Gly Gly Gly Leu Val
        130                 135                 140

Gln Pro Gly Gly Ser Leu Arg Leu Ser Cys Ala Ala Ser Gly Phe Asn
145                 150                 155                 160

Leu Ser Tyr Ser Asp Ile His Trp Val Arg Gln Ala Pro Gly Lys Gly
                165                 170                 175
```

-continued

```
Leu Glu Trp Val Ala Val Val Met Pro Asp Ser Gly His Thr Asn Tyr
            180                 185             190

Ala Asp Ser Val Lys Gly Arg Phe Thr Ile Ser Ala Asp Thr Ser Lys
            195                 200             205

Asn Thr Ala Tyr Leu Gln Met Asn Ser Leu Arg Ala Glu Asp Thr Ala
            210                 215             220

Val Tyr Tyr Cys Ser Arg Ala Thr Asn Ile Pro Val Tyr Ala Phe Asp
225                 230             235                 240

Tyr Trp Gly Gln Gly Thr Leu Val Thr Val Ser Ser Gly Gly Gly Gly
                245             250                 255

Ser Gly Gly Gly Gly Ser Gly Gly Gly Gly Ser Asp Ile Gln Met Thr
            260                 265             270

Gln Ser Pro Ser Ser Leu Ser Ala Ser Val Gly Asp Arg Val Thr Ile
            275                 280             285

Thr Cys Arg Ala Ser Gln Asp Val Asn Thr Ala Val Ala Trp Tyr Gln
            290                 295             300

Gln Lys Pro Gly Lys Ala Pro Lys Leu Leu Ile Tyr Ser Ala Ser Phe
305                 310             315                 320

Leu Tyr Ser Gly Val Pro Ser Arg Phe Ser Gly Ser Arg Ser Gly Thr
                325             330                 335

Asp Phe Thr Leu Thr Ile Ser Ser Leu Gln Pro Glu Asp Phe Ala Thr
                340             345                 350

Tyr Tyr Cys Gln Gln Ser Tyr Tyr Tyr Phe Arg Pro Ile Thr Phe Gly
                355             360             365

Gln Gly Thr Lys Val Glu Ile Lys Gly Gly Gly Gly Ser Glu Val Gln
            370                 375             380

Leu Val Glu Ser Gly Gly Gly Leu Val Gln Pro Gly Gly Ser Leu Arg
385                 390             395                 400

Leu Ser Cys Ala Ala Ser Gly Tyr Ser Phe Thr Gly Tyr Thr Met Asn
                405             410             415

Trp Val Arg Gln Ala Pro Gly Lys Gly Leu Glu Trp Val Ala Leu Ile
                420             425             430

Asn Pro Tyr Lys Gly Val Ser Thr Tyr Asn Gln Lys Phe Lys Asp Arg
            435                 440             445

Phe Thr Ile Ser Val Asp Lys Ser Lys Asn Thr Ala Tyr Leu Gln Met
            450                 455             460

Asn Ser Leu Arg Ala Glu Asp Thr Ala Val Tyr Tyr Cys Ala Arg Ser
465                 470             475                 480

Gly Tyr Tyr Gly Asp Ser Asp Trp Tyr Phe Asp Val Trp Gly Gln Gly
                485             490                 495

Thr Leu Val Thr Val Ser Ser His His His His His His
            500                 505
```

```
<210> SEQ ID NO 220
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Met Tyr Arg Met Gln Leu Leu Ser Cys Ile Ala Leu Ser Leu Ala Leu
1               5                   10                  15

Val Thr Asn Ser Asp Ile Gln Met Thr Gln Thr Thr Ser Ser Leu Ser
```

-continued

```
                20              25              30

Ala Ser Leu Gly Asp Arg Val Thr Ile Ser Cys Arg Ala Ser Gln Asp
        35              40              45

Ile Arg Asn Tyr Leu Asn Trp Tyr Gln Gln Lys Pro Asp Gly Thr Val
        50              55              60

Lys Leu Leu Ile Tyr Tyr Thr Ser Arg Leu His Ser Gly Val Pro Ser
65              70              75              80

Lys Phe Ser Gly Ser Gly Ser Gly Thr Asp Tyr Ser Leu Thr Ile Ser
                85              90              95

Asn Leu Glu Gln Glu Asp Ile Ala Thr Tyr Phe Cys Gln Gln Gly Asn
                100             105             110

Thr Leu Pro Trp Thr Phe Ala Gly Gly Thr Lys Leu Glu Ile Lys Gly
        115             120             125

Gly Gly Gly Ser Glu Val Gln Leu Val Glu Ser Gly Gly Gly Leu Val
        130             135             140

Gln Pro Gly Gly Ser Leu Arg Leu Ser Cys Ala Ala Ser Gly Phe Asn
145             150             155             160

Leu Ser Tyr Ser Asp Ile His Trp Val Arg Gln Ala Pro Gly Lys Gly
                165             170             175

Leu Glu Trp Val Ala Val Val Met Pro Asp Ser Gly His Thr Asn Tyr
                180             185             190

Ala Asp Ser Val Lys Gly Arg Phe Thr Ile Ser Ala Asp Thr Ser Lys
        195             200             205

Asn Thr Ala Tyr Leu Gln Met Asn Ser Leu Arg Ala Glu Asp Thr Ala
        210             215             220

Val Tyr Tyr Cys Ser Arg Ala Thr Asn Ile Pro Val Tyr Ala Phe Asp
225             230             235             240

Tyr Trp Gly Gln Gly Thr Leu Val Thr Val Ser Ser Gly Gly Gly Gly
                245             250             255

Ser Gly Gly Gly Gly Ser Gly Gly Gly Gly Ser Asp Ile Gln Met Thr
        260             265             270

Gln Ser Pro Ser Ser Leu Ser Ala Ser Val Gly Asp Arg Val Thr Ile
        275             280             285

Thr Cys Arg Ala Ser Gln Asp Val Asn Thr Ala Val Ala Trp Tyr Gln
        290             295             300

Gln Lys Pro Gly Lys Ala Pro Lys Leu Leu Ile Tyr Ser Ala Ser Phe
305             310             315             320

Leu Tyr Ser Gly Val Pro Ser Arg Phe Ser Gly Ser Arg Ser Gly Thr
                325             330             335

Asp Phe Thr Leu Thr Ile Ser Ser Leu Gln Pro Glu Asp Phe Ala Thr
                340             345             350

Tyr Tyr Cys Gln Gln Ser Tyr Tyr Tyr Phe Arg Pro Ile Thr Phe Gly
        355             360             365

Gln Gly Thr Lys Val Glu Ile Lys Gly Gly Gly Gly Ser Glu Val Gln
        370             375             380

Leu Gln Gln Ser Gly Pro Glu Leu Val Lys Pro Gly Ala Ser Met Lys
385             390             395             400

Ile Ser Cys Lys Ala Ser Gly Tyr Ser Phe Thr Gly Tyr Thr Met Asn
                405             410             415

Trp Val Lys Gln Ser His Gly Lys Asn Leu Glu Trp Met Gly Leu Ile
                420             425             430

Asn Pro Tyr Lys Gly Val Ser Thr Tyr Asn Gln Lys Phe Lys Asp Lys
        435             440             445
```

-continued

```
Ala Thr Leu Thr Val Asp Lys Ser Ser Ser Thr Ala Tyr Met Glu Leu
    450             455             460

Leu Ser Leu Thr Ser Glu Asp Ser Ala Val Tyr Tyr Cys Ala Arg Ser
465             470             475             480

Gly Tyr Tyr Gly Asp Ser Asp Trp Tyr Phe Asp Val Trp Gly Ala Gly
                485             490             495

Thr Thr Val Thr Val Ser Ser His His His His His His
            500             505

<210> SEQ ID NO 221
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Met Tyr Arg Met Gln Leu Leu Ser Cys Ile Ala Leu Ser Leu Ala Leu
1               5               10              15

Val Thr Asn Ser Glu Val Gln Leu Val Glu Ser Gly Gly Gly Leu Val
            20              25              30

Gln Pro Gly Gly Ser Leu Arg Leu Ser Cys Ala Ala Ser Gly Phe Asn
        35              40              45

Leu Ser Tyr Ser Asp Ile His Trp Val Arg Gln Ala Pro Gly Lys Gly
    50              55              60

Leu Glu Trp Val Ala Val Val Met Pro Asp Ser Gly His Thr Asn Tyr
65              70              75              80

Ala Asp Ser Val Lys Gly Arg Phe Thr Ile Ser Ala Asp Thr Ser Lys
                85              90              95

Asn Thr Ala Tyr Leu Gln Met Asn Ser Leu Arg Ala Glu Asp Thr Ala
            100             105             110

Val Tyr Tyr Cys Ser Arg Ala Thr Asn Ile Pro Val Tyr Ala Phe Asp
            115             120             125

Tyr Trp Gly Gln Gly Thr Leu Val Thr Val Ser Ser Gly Gly Gly Gly
    130             135             140

Ser Asp Ile Gln Met Thr Gln Ser Pro Ser Ser Leu Ser Ala Ser Val
145             150             155             160

Gly Asp Arg Val Thr Ile Thr Cys Arg Ala Ser Gln Asp Ile Arg Asn
                165             170             175

Tyr Leu Asn Trp Tyr Gln Gln Lys Pro Gly Lys Ala Pro Lys Leu Leu
            180             185             190

Ile Tyr Tyr Thr Ser Arg Leu Glu Ser Gly Val Pro Ser Arg Phe Ser
        195             200             205

Gly Ser Gly Ser Gly Thr Asp Tyr Thr Leu Thr Ile Ser Ser Leu Gln
    210             215             220

Pro Glu Asp Phe Ala Thr Tyr Tyr Cys Gln Gln Gly Asn Thr Leu Pro
225             230             235             240

Trp Thr Phe Gly Gln Gly Thr Lys Val Glu Ile Lys Gly Gly Gly Gly
                245             250             255

Ser Gly Gly Gly Gly Ser Gly Gly Gly Ser Glu Val Gln Leu Val
            260             265             270

Glu Ser Gly Gly Gly Leu Val Gln Pro Gly Gly Ser Leu Arg Leu Ser
    275             280             285

Cys Ala Ala Ser Gly Tyr Ser Phe Thr Gly Tyr Thr Met Asn Trp Val
```

```
       290                295                300
Arg Gln Ala Pro Gly Lys Gly Leu Glu Trp Val Ala Leu Ile Asn Pro
305                     310                 315                320

Tyr Lys Gly Val Ser Thr Tyr Asn Gln Lys Phe Lys Asp Arg Phe Thr
                    325                 330                335

Ile Ser Val Asp Lys Ser Lys Asn Thr Ala Tyr Leu Gln Met Asn Ser
                340                 345                 350

Leu Arg Ala Glu Asp Thr Ala Val Tyr Tyr Cys Ala Arg Ser Gly Tyr
            355                 360                 365

Tyr Gly Asp Ser Asp Trp Tyr Phe Asp Val Trp Gly Gln Gly Thr Leu
        370                 375                 380

Val Thr Val Ser Ser Gly Gly Gly Ser Asp Ile Gln Met Thr Gln
385                     390                 395                400

Ser Pro Ser Ser Leu Ser Ala Ser Val Gly Asp Arg Val Thr Ile Thr
                405                 410                 415

Cys Arg Ala Ser Gln Asp Val Asn Thr Ala Val Ala Trp Tyr Gln Gln
                420                 425                 430

Lys Pro Gly Lys Ala Pro Lys Leu Leu Ile Tyr Ser Ala Ser Phe Leu
                435                 440                 445

Tyr Ser Gly Val Pro Ser Arg Phe Ser Gly Ser Arg Ser Gly Thr Asp
        450                 455                 460

Phe Thr Leu Thr Ile Ser Ser Leu Gln Pro Glu Asp Phe Ala Thr Tyr
465                     470                 475                480

Tyr Cys Gln Gln Ser Tyr Tyr Tyr Phe Arg Pro Ile Thr Phe Gly Gln
                485                 490                 495

Gly Thr Lys Val Glu Ile Lys His His His His His His
                500                 505
```

```
<210> SEQ ID NO 222
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Leu Ser Tyr Ser Asp Ile His Trp Val Arg Gln Ala Pro Gly Lys Gly
        50                  55                  60

Leu Glu Trp Val Ala Val Val Met Pro Asp Ser Gly His Thr Asn Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
                100                 105                 110

Val Tyr Tyr Cys Ser Arg Ala Thr Asn Ile Pro Val Tyr Ala Phe Asp
            115                 120                 125

Tyr Trp Gly Gln Gly Thr Leu Val Thr Val Ser Ser Gly Gly Gly Gly
        130                 135                 140
```

```
Ser Asp Ile Gln Met Thr Gln Thr Thr Ser Ser Leu Ser Ala Ser Leu
145                 150                 155                 160

Gly Asp Arg Val Thr Ile Ser Cys Arg Ala Ser Gln Asp Ile Arg Asn
                165                 170                 175

Tyr Leu Asn Trp Tyr Gln Gln Lys Pro Asp Gly Thr Val Lys Leu Leu
            180                 185                 190

Ile Tyr Tyr Thr Ser Arg Leu His Ser Gly Val Pro Ser Lys Phe Ser
        195                 200                 205

Gly Ser Gly Ser Gly Thr Asp Tyr Ser Leu Thr Ile Ser Asn Leu Glu
    210                 215                 220

Gln Glu Asp Ile Ala Thr Tyr Phe Cys Gln Gln Gly Asn Thr Leu Pro
225                 230                 235                 240

Trp Thr Phe Ala Gly Gly Thr Lys Leu Glu Ile Lys Gly Gly Gly Gly
                245                 250                 255

Ser Gly Gly Gly Gly Ser Gly Gly Gly Gly Ser Glu Val Gln Leu Gln
                260                 265                 270

Gln Ser Gly Pro Glu Leu Val Lys Pro Gly Ala Ser Met Lys Ile Ser
            275                 280                 285

Cys Lys Ala Ser Gly Tyr Ser Phe Thr Gly Tyr Thr Met Asn Trp Val
    290                 295                 300

Lys Gln Ser His Gly Lys Asn Leu Glu Trp Met Gly Leu Ile Asn Pro
305                 310                 315                 320

Tyr Lys Gly Val Ser Thr Tyr Asn Gln Lys Phe Lys Asp Lys Ala Thr
                325                 330                 335

Leu Thr Val Asp Lys Ser Ser Ser Thr Ala Tyr Met Glu Leu Leu Ser
            340                 345                 350

Leu Thr Ser Glu Asp Ser Ala Val Tyr Tyr Cys Ala Arg Ser Gly Tyr
            355                 360                 365

Tyr Gly Asp Ser Asp Trp Tyr Phe Asp Val Trp Gly Ala Gly Thr Thr
    370                 375                 380

Val Thr Val Ser Ser Gly Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Arg Ala Ser Gln Asp Val Asn Thr Ala Val Ala Trp Tyr Gln Gln
                420                 425                 430

Lys Pro Gly Lys Ala Pro Lys Leu Leu Ile Tyr Ser Ala Ser Phe Leu
            435                 440                 445

Tyr Ser Gly Val Pro Ser Arg Phe Ser Gly Ser Arg Ser Gly Thr Asp
    450                 455                 460

Phe Thr Leu Thr Ile Ser Ser Leu Gln Pro Glu Asp Phe Ala Thr Tyr
465                 470                 475                 480

Tyr Cys Gln Gln Ser Tyr Tyr Tyr Phe Arg Pro Ile Thr Phe Gly Gln
                485                 490                 495

Gly Thr Lys Val Glu Ile Lys His His His His His
            500                 505
```

<210> SEQ ID NO 223
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

-continued

```
Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Pro Gly Gly Ser Leu Arg Leu Ser Cys Ala Ala Ser Gly Tyr Ser
        35                  40                  45

Phe Thr Gly Tyr Thr Met Asn Trp Val Arg Gln Ala Pro Gly Lys Gly
    50                  55                  60

Leu Glu Trp Val Ala Leu Ile Asn Pro Tyr Lys Gly Val Ser Thr Tyr
65                  70                  75                  80

Asn Gln Lys Phe Lys Asp Arg Phe Thr Ile Ser Val Asp Lys Ser Lys
                85                  90                  95

Asn Thr Ala Tyr Leu Gln Met Asn Ser Leu Arg Ala Glu Asp Thr Ala
            100                 105                 110

Val Tyr Tyr Cys Ala Arg Ser Gly Tyr Tyr Gly Asp Ser Asp Trp Tyr
        115                 120                 125

Phe Asp Val Trp Gly Gln Gly Thr Leu Val Thr Val Ser Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Arg Ala Ser Gln Asp Val
                165                 170                 175

Asn Thr Ala Val Ala Trp Tyr Gln Gln Lys Pro Gly Lys Ala Pro Lys
            180                 185                 190

Leu Leu Ile Tyr Ser Ala Ser Phe Leu Tyr Ser Gly Val Pro Ser Arg
            195                 200                 205

Phe Ser Gly Ser Arg Ser Gly Thr Asp Phe Thr Leu Thr Ile Ser Ser
    210                 215                 220

Leu Gln Pro Glu Asp Phe Ala Thr Tyr Tyr Cys Gln Gln Ser Tyr Tyr
225                 230                 235                 240

Tyr Phe Arg Pro Ile Thr Phe Gly Gln Gly Thr Lys Val Glu Ile Lys
                245                 250                 255

Gly Gly Gly Gly Ser Gly Gly Gly Gly Ser Gly Gly Gly Gly Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Phe Asn Leu Ser Tyr Ser Asp
    290                 295                 300

Ile His Trp Val Arg Gln Ala Pro Gly Lys Gly Leu Glu Trp Val Ala
305                 310                 315                 320

Val Val Met Pro Asp Ser Gly His Thr Asn Tyr Ala Asp Ser Val Lys
                325                 330                 335

Gly Arg Phe Thr Ile Ser Ala Asp Thr Ser Lys Asn Thr Ala Tyr Leu
            340                 345                 350

Gln Met Asn Ser Leu Arg Ala Glu Asp Thr Ala Val Tyr Tyr Cys Ser
        355                 360                 365

Arg Ala Thr Asn Ile Pro Val Tyr Ala Phe Asp Tyr Trp Gly Gln Gly
    370                 375                 380

Thr Leu Val Thr Val Ser Ser Gly Gly Gly Gly Ser Asp Ile Gln Met
385                 390                 395                 400

Thr Gln Ser Pro Ser Ser Leu Ser Ala Ser Val Gly Asp Arg Val Thr
                405                 410                 415
```

Ile Thr Cys Arg Ala Ser Gln Asp Ile Arg Asn Tyr Leu Asn Trp Tyr
420 425 430

Gln Gln Lys Pro Gly Lys Ala Pro Lys Leu Leu Ile Tyr Tyr Thr Ser
435 440 445

Arg Leu Glu Ser Gly Val Pro Ser Arg Phe Ser Gly Ser Gly Ser Gly
450 455 460

Thr Asp Tyr Thr Leu Thr Ile Ser Ser Leu Gln Pro Glu Asp Phe Ala
465 470 475 480

Thr Tyr Tyr Cys Gln Gln Gly Asn Thr Leu Pro Trp Thr Phe Gly Gln
485 490 495

Gly Thr Lys Val Glu Ile Lys His His His His His His
500 505

<210> SEQ ID NO 224
<211> LENGTH: 509
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 224

Met Tyr Arg Met Gln Leu Leu Ser Cys Ile Ala Leu Ser Leu Ala Leu
1               5                   10                  15

Val Thr Asn Ser Glu Val Gln Leu Gln Gln Ser Gly Pro Glu Leu Val
            20                  25                  30

Lys Pro Gly Ala Ser Met Lys Ile Ser Cys Lys Ala Ser Gly Tyr Ser
        35                  40                  45

Phe Thr Gly Tyr Thr Met Asn Trp Val Lys Gln Ser His Gly Lys Asn
    50                  55                  60

Leu Glu Trp Met Gly Leu Ile Asn Pro Tyr Lys Gly Val Ser Thr Tyr
65                  70                  75                  80

Asn Gln Lys Phe Lys Asp Lys Ala Thr Leu Thr Val Asp Lys Ser Ser
            85                  90                  95

Ser Thr Ala Tyr Met Glu Leu Leu Ser Leu Thr Ser Glu Asp Ser Ala
            100                 105                 110

Val Tyr Tyr Cys Ala Arg Ser Gly Tyr Tyr Gly Asp Ser Asp Trp Tyr
        115                 120                 125

Phe Asp Val Trp Gly Ala Gly Thr Thr Val Thr Val Ser Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Arg Ala Ser Gln Asp Val
            165                 170                 175

Asn Thr Ala Val Ala Trp Tyr Gln Gln Lys Pro Gly Lys Ala Pro Lys
            180                 185                 190

Leu Leu Ile Tyr Ser Ala Ser Phe Leu Tyr Ser Gly Val Pro Ser Arg
        195                 200                 205

Phe Ser Gly Ser Arg Ser Gly Thr Asp Phe Thr Leu Thr Ile Ser Ser
    210                 215                 220

Leu Gln Pro Glu Asp Phe Ala Thr Tyr Tyr Cys Gln Gln Ser Tyr Tyr
225                 230                 235                 240

Tyr Phe Arg Pro Ile Thr Phe Gly Gln Gly Thr Lys Val Glu Ile Lys
            245                 250                 255

Gly Gly Gly Gly Ser Gly Gly Gly Gly Ser Gly Gly Gly Gly Ser Glu
            260                 265                 270

-continued

```
Val Gln Leu Val Glu Ser Gly Gly Gly Leu Val Gln Pro Gly Gly Ser
        275                 280                 285

Leu Arg Leu Ser Cys Ala Ala Ser Gly Phe Asn Leu Ser Tyr Ser Asp
        290                 295                 300

Ile His Trp Val Arg Gln Ala Pro Gly Lys Gly Leu Glu Trp Val Ala
305                 310                 315                 320

Val Val Met Pro Asp Ser Gly His Thr Asn Tyr Ala Asp Ser Val Lys
                325                 330                 335

Gly Arg Phe Thr Ile Ser Ala Asp Thr Ser Lys Asn Thr Ala Tyr Leu
                340                 345                 350

Gln Met Asn Ser Leu Arg Ala Glu Asp Thr Ala Val Tyr Tyr Cys Ser
        355                 360                 365

Arg Ala Thr Asn Ile Pro Val Tyr Ala Phe Asp Tyr Trp Gly Gln Gly
        370                 375                 380

Thr Leu Val Thr Val Ser Ser Gly Gly Gly Ser Asp Ile Gln Met
385                 390                 395                 400

Thr Gln Thr Thr Ser Ser Leu Ser Ala Ser Leu Gly Asp Arg Val Thr
                405                 410                 415

Ile Ser Cys Arg Ala Ser Gln Asp Ile Arg Asn Tyr Leu Asn Trp Tyr
                420                 425                 430

Gln Gln Lys Pro Asp Gly Thr Val Lys Leu Leu Ile Tyr Tyr Thr Ser
        435                 440                 445

Arg Leu His Ser Gly Val Pro Ser Lys Phe Ser Gly Ser Gly Ser Gly
        450                 455                 460

Thr Asp Tyr Ser Leu Thr Ile Ser Asn Leu Glu Gln Glu Asp Ile Ala
465                 470                 475                 480

Thr Tyr Phe Cys Gln Gln Gly Asn Thr Leu Pro Trp Thr Phe Ala Gly
                485                 490                 495

Gly Thr Lys Leu Glu Ile Lys His His His His His His
            500                 505
```

```
<210> SEQ ID NO 225
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225
```

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
        50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
```

-continued

```
            115                 120                 125
Lys Gly Gly Gly Ser Asp Val Gln Leu Val Gln Ser Gly Ala Glu
    130                 135                 140
Val Lys Lys Pro Gly Ala Ser Val Lys Val Ser Cys Lys Ala Ser Gly
145                 150                 155                 160
Tyr Thr Phe Thr Arg Tyr Thr Met His Trp Val Arg Gln Ala Pro Gly
                165                 170                 175
Gln Gly Leu Glu Trp Ile Gly Tyr Ile Asn Pro Ser Arg Gly Tyr Thr
                180                 185                 190
Asn Tyr Ala Asp Ser Val Lys Gly Arg Phe Thr Ile Thr Thr Asp Lys
    195                 200                 205
Ser Thr Ser Thr Ala Tyr Met Glu Leu Ser Ser Leu Arg Ser Glu Asp
    210                 215                 220
Thr Ala Thr Tyr Tyr Cys Ala Arg Tyr Tyr Asp Asp His Tyr Cys Leu
225                 230                 235                 240
Asp Tyr Trp Gly Gln Gly Thr Thr Val Thr Val Ser Ser Gly Gly Gly
                245                 250                 255
Gly Ser Gly Gly Gly Gly Ser Gly Gly Gly Gly Ser Asp Ile Val Leu
                260                 265                 270
Thr Gln Ser Pro Ala Thr Leu Ser Leu Ser Pro Gly Glu Arg Ala Thr
                275                 280                 285
Leu Ser Cys Arg Ala Ser Gln Ser Val Ser Tyr Met Asn Trp Tyr Gln
    290                 295                 300
Gln Lys Pro Gly Lys Ala Pro Lys Arg Trp Ile Tyr Asp Thr Ser Lys
305                 310                 315                 320
Val Ala Ser Gly Val Pro Ala Arg Phe Ser Gly Ser Gly Ser Gly Thr
                325                 330                 335
Asp Tyr Ser Leu Thr Ile Asn Ser Leu Glu Ala Glu Asp Ala Ala Thr
                340                 345                 350
Tyr Tyr Cys Gln Gln Trp Ser Ser Asn Pro Leu Thr Phe Gly Gly Gly
                355                 360                 365
Thr Lys Val Glu Ile Lys Gly Gly Gly Gly Ser Glu Val Gln Leu Val
    370                 375                 380
Glu Ser Gly Gly Gly Leu Val Gln Pro Gly Gly Ser Leu Arg Leu Ser
385                 390                 395                 400
Cys Ala Ala Ser Gly Phe Asn Leu Ser Tyr Ser Asp Ile His Trp Val
                405                 410                 415
Arg Gln Ala Pro Gly Lys Gly Leu Glu Trp Val Ala Val Val Met Pro
                420                 425                 430
Asp Ser Gly His Thr Asn Tyr Ala Asp Ser Val Lys Gly Arg Phe Thr
    435                 440                 445
Ile Ser Ala Asp Thr Ser Lys Asn Thr Ala Tyr Leu Gln Met Asn Ser
    450                 455                 460
Leu Arg Ala Glu Asp Thr Ala Val Tyr Tyr Cys Ser Arg Ala Thr Asn
465                 470                 475                 480
Ile Pro Val Tyr Ala Phe Asp Tyr Trp Gly Gln Gly Thr Leu Val Thr
                485                 490                 495
Val Ser Ser His His His His His His
            500                 505
```

```
<210> SEQ ID NO 226
<211> LENGTH: 514
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 226

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
        50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Thr Phe Asn Thr Tyr Ala Met Asn Trp Val Arg Gln Ala Pro Gly
                165                 170                 175

Lys Gly Leu Glu Trp Val Ala Arg Ile Arg Ser Lys Tyr Asn Asn Tyr
            180                 185                 190

Ala Thr Tyr Tyr Ala Asp Ser Val Lys Asp Arg Phe Thr Ile Ser Arg
        195                 200                 205

Asp Asp Ser Lys Asn Ser Leu Tyr Leu Gln Met Asn Ser Leu Lys Thr
    210                 215                 220

Glu Asp Thr Ala Val Tyr Tyr Cys Val Arg His Gly Asn Phe Gly Asn
225                 230                 235                 240

Ser Tyr Val Ser Trp Phe Ala Tyr Trp Gly Gln Gly Thr Leu Val Thr
                245                 250                 255

Val Ser Ser Gly Gly Gly Gly Ser Gly Gly Gly Ser Gly Gly Gly
            260                 265                 270

Gly Ser Gln Ala Val Val Thr Gln Glu Pro Ser Leu Thr Val Ser Pro
        275                 280                 285

Gly Gly Thr Val Thr Leu Thr Cys Arg Ser Ser Thr Gly Ala Val Thr
    290                 295                 300

Thr Ser Asn Tyr Ala Asn Trp Val Gln Gln Lys Pro Gly Gln Ala Pro
305                 310                 315                 320

Arg Gly Leu Ile Gly Gly Thr Asn Lys Arg Ala Pro Trp Thr Pro Ala
                325                 330                 335

Arg Phe Ser Gly Ser Leu Leu Gly Gly Lys Ala Ala Leu Thr Ile Thr
            340                 345                 350

Gly Ala Gln Ala Glu Asp Glu Ala Asp Tyr Tyr Cys Ala Leu Trp Tyr
        355                 360                 365

Ser Asn Leu Trp Val Phe Gly Gly Gly Thr Lys Leu Thr Val Leu Gly
    370                 375                 380

Gly Gly Gly Ser Glu Val Gln Leu Val Glu Ser Gly Gly Gly Leu Val

-continued

```
385            390            395            400

Gln Pro Gly Gly Ser Leu Arg Leu Ser Cys Ala Ala Ser Gly Phe Asn
               405            410            415

Leu Ser Tyr Ser Asp Ile His Trp Val Arg Gln Ala Pro Gly Lys Gly
               420            425            430

Leu Glu Trp Val Ala Val Val Met Pro Asp Ser Gly His Thr Asn Tyr
               435            440            445

Ala Asp Ser Val Lys Gly Arg Phe Thr Ile Ser Ala Asp Thr Ser Lys
    450            455            460

Asn Thr Ala Tyr Leu Gln Met Asn Ser Leu Arg Ala Glu Asp Thr Ala
465            470            475            480

Val Tyr Tyr Cys Ser Arg Ala Thr Asn Ile Pro Val Tyr Ala Phe Asp
               485            490            495

Tyr Trp Gly Gln Gly Thr Leu Val Thr Val Ser Ser His His His His
               500            505            510

His His
```

```
<210> SEQ ID NO 227
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Met Tyr Arg Met Gln Leu Leu Ser Cys Ile Ala Leu Ser Leu Ala Leu
1              5              10             15

Val Thr Asn Ser Asp Ile Gln Met Thr Gln Ser Pro Ser Ser Leu Ser
               20             25             30

Ala Ser Val Gly Asp Arg Val Thr Ile Thr Cys Arg Ala Ser Gln Asp
               35             40             45

Val Asn Thr Ala Val Ala Trp Tyr Gln Gln Lys Pro Gly Lys Ala Pro
    50             55             60

Lys Leu Leu Ile Tyr Ser Ala Ser Phe Leu Tyr Ser Gly Val Pro Ser
65             70             75             80

Arg Phe Ser Gly Ser Arg Ser Gly Thr Asp Phe Thr Leu Thr Ile Ser
               85             90             95

Ser Leu Gln Pro Glu Asp Phe Ala Thr Tyr Tyr Cys Gln Gln Ser Tyr
               100            105            110

Tyr Tyr Phe Arg Pro Ile Thr Phe Gly Gln Gly Thr Lys Val Glu Ile
               115            120            125

Lys Gly Gly Gly Gly Ser Asp Ile Lys Leu Gln Gln Ser Gly Ala Glu
    130            135            140

Leu Ala Arg Pro Gly Ala Ser Val Lys Met Ser Cys Lys Thr Ser Gly
145            150            155            160

Tyr Thr Phe Thr Arg Tyr Thr Met His Trp Val Lys Gln Arg Pro Gly
               165            170            175

Gln Gly Leu Glu Trp Ile Gly Tyr Ile Asn Pro Ser Arg Gly Tyr Thr
               180            185            190

Asn Tyr Asn Gln Lys Phe Lys Asp Lys Ala Thr Leu Thr Thr Asp Lys
               195            200            205

Ser Ser Ser Thr Ala Tyr Met Gln Leu Ser Ser Leu Thr Ser Glu Asp
    210            215            220

Ser Ala Val Tyr Tyr Cys Ala Arg Tyr Tyr Asp Asp His Tyr Cys Leu
```

-continued

```
225                 230                 235                 240

Asp Tyr Trp Gly Gln Gly Thr Thr Leu Thr Val Ser Ser Gly Gly Gly
            245                 250                 255

Gly Ser Gly Gly Gly Gly Ser Gly Gly Gly Gly Ser Asp Ile Gln Leu
            260                 265                 270

Thr Gln Ser Pro Ala Ile Met Ser Ala Ser Pro Gly Glu Lys Val Thr
            275                 280                 285

Met Thr Cys Arg Ala Ser Ser Ser Val Ser Tyr Met Asn Trp Tyr Gln
    290                 295                 300

Gln Lys Ser Gly Thr Ser Pro Lys Arg Trp Ile Tyr Asp Thr Ser Lys
305                 310                 315                 320

Val Ala Ser Gly Val Pro Tyr Arg Phe Ser Gly Ser Gly Ser Gly Thr
            325                 330                 335

Ser Tyr Ser Leu Thr Ile Ser Ser Met Glu Ala Glu Asp Ala Ala Thr
            340                 345                 350

Tyr Tyr Cys Gln Gln Trp Ser Ser Asn Pro Leu Thr Phe Gly Ala Gly
            355                 360                 365

Thr Lys Leu Glu Leu Lys Gly Gly Gly Ser Glu Val Gln Leu Val
    370                 375                 380

Glu Ser Gly Gly Gly Leu Val Gln Pro Gly Gly Ser Leu Arg Leu Ser
385                 390                 395                 400

Cys Ala Ala Ser Gly Phe Asn Leu Ser Tyr Ser Asp Ile His Trp Val
            405                 410                 415

Arg Gln Ala Pro Gly Lys Gly Leu Glu Trp Val Ala Val Met Pro
            420                 425                 430

Asp Ser Gly His Thr Asn Tyr Ala Asp Ser Val Lys Gly Arg Phe Thr
            435                 440                 445

Ile Ser Ala Asp Thr Ser Lys Asn Thr Ala Tyr Leu Gln Met Asn Ser
    450                 455                 460

Leu Arg Ala Glu Asp Thr Ala Val Tyr Tyr Cys Ser Arg Ala Thr Asn
465                 470                 475                 480

Ile Pro Val Tyr Ala Phe Asp Tyr Trp Gly Gln Gly Thr Leu Val Thr
            485                 490                 495

Val Ser Ser His His His His His His
            500                 505
```

```
<210> SEQ ID NO 228
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80
```

-continued

```
Arg Phe Ser Gly Ser Arg Ser Gly Thr Asp Phe Thr Leu Thr Ile Ser
            85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Gly Ser Gln Val Gln Leu Gln Gln Ser Gly Ala Glu
    130                 135                 140

Leu Ala Arg Pro Gly Ala Ser Val Lys Met Ser Cys Lys Ala Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
            180                 185                 190

Asn Tyr Asn Gln Lys Phe Lys Asp Lys Ala Thr Leu Thr Thr Asp Lys
            195                 200                 205

Ser Ser Ser Thr Ala Tyr Met Gln Leu Ser Ser Leu Thr Ser Glu Asp
    210                 215                 220

Ser Ala Val Tyr Tyr Cys Ala Arg Tyr Tyr Asp Asp His Tyr Cys Leu
225                 230                 235                 240

Asp Tyr Trp Gly Gln Gly Thr Thr Leu Thr Val Ser Ser Gly Gly Gly
            245                 250                 255

Gly Ser Gly Gly Gly Gly Ser Gly Gly Gly Gly Ser Gln Ile Val Leu
            260                 265                 270

Thr Gln Ser Pro Ala Ile Met Ser Ala Ser Pro Gly Glu Lys Val Thr
            275                 280                 285

Met Thr Cys Ser Ala Ser Ser Ser Val Ser Tyr Met Asn Trp Tyr Gln
    290                 295                 300

Gln Lys Ser Gly Thr Ser Pro Lys Arg Trp Ile Tyr Asp Thr Ser Lys
305                 310                 315                 320

Leu Ala Ser Gly Val Pro Ala His Phe Arg Gly Ser Gly Ser Gly Thr
            325                 330                 335

Ser Tyr Ser Leu Thr Ile Ser Gly Met Glu Ala Glu Asp Ala Ala Thr
            340                 345                 350

Tyr Tyr Cys Gln Gln Trp Ser Ser Asn Pro Phe Thr Phe Gly Ser Gly
            355                 360                 365

Thr Lys Leu Glu Ile Asn Gly Gly Gly Gly Ser Glu Val Gln Leu Val
    370                 375                 380

Glu Ser Gly Gly Gly Leu Val Gln Pro Gly Gly Ser Leu Arg Leu Ser
385                 390                 395                 400

Cys Ala Ala Ser Gly Phe Asn Leu Ser Tyr Ser Asp Ile His Trp Val
            405                 410                 415

Arg Gln Ala Pro Gly Lys Gly Leu Glu Trp Val Ala Val Val Met Pro
            420                 425                 430

Asp Ser Gly His Thr Asn Tyr Ala Asp Ser Val Lys Gly Arg Phe Thr
            435                 440                 445

Ile Ser Ala Asp Thr Ser Lys Asn Thr Ala Tyr Leu Gln Met Asn Ser
    450                 455                 460

Leu Arg Ala Glu Asp Thr Ala Val Tyr Tyr Cys Ser Arg Ala Thr Asn
465                 470                 475                 480

Ile Pro Val Tyr Ala Phe Asp Tyr Trp Gly Gln Gly Thr Leu Val Thr
            485                 490                 495

Val Ser Ser His His His His His His
```

-continued

<210> SEQ ID NO 229
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Gln Val Gln Leu Val Glu Ser Gly Gly Gly
    130                 135                 140

Val Val Gln Pro Gly Arg Ser Leu Arg Leu Ser Cys Ala Ala Ser Gly
145                 150                 155                 160

Phe Lys Phe Ser Gly Tyr Gly Met His Trp Val Arg Gln Ala Pro Gly
                165                 170                 175

Lys Gly Leu Glu Trp Val Ala Val Ile Trp Tyr Asp Gly Ser Lys Lys
            180                 185                 190

Tyr Tyr Val Asp Ser Val Lys Gly Arg Phe Thr Ile Ser Arg Asp Asn
        195                 200                 205

Ser Lys Asn Thr Leu Tyr Leu Gln Met Asn Ser Leu Arg Ala Glu Asp
    210                 215                 220

Thr Ala Val Tyr Tyr Cys Ala Arg Gln Met Gly Tyr Trp His Phe Asp
225                 230                 235                 240

Leu Trp Gly Arg Gly Thr Leu Val Thr Val Ser Ser Gly Gly Gly Gly
                245                 250                 255

Ser Gly Gly Gly Gly Ser Gly Gly Gly Gly Ser Glu Ile Val Leu Thr
            260                 265                 270

Gln Ser Pro Ala Thr Leu Ser Leu Ser Pro Gly Glu Arg Ala Thr Leu
        275                 280                 285

Ser Cys Arg Ala Ser Gln Ser Val Ser Ser Tyr Leu Ala Trp Tyr Gln
    290                 295                 300

Gln Lys Pro Gly Gln Ala Pro Arg Leu Leu Ile Tyr Asp Ala Ser Asn
305                 310                 315                 320

Arg Ala Thr Gly Ile Pro Ala Arg Phe Ser Gly Ser Gly Ser Gly Thr
                325                 330                 335

Asp Phe Thr Leu Thr Ile Ser Ser Leu Glu Pro Glu Asp Phe Ala Val
            340                 345                 350

-continued

```
Tyr Tyr Cys Gln Gln Arg Ser Asn Trp Pro Pro Leu Thr Phe Gly Gly
        355             360             365

Gly Thr Lys Val Glu Ile Lys Gly Gly Gly Ser Glu Val Gln Leu
    370             375             380

Val Glu Ser Gly Gly Gly Leu Val Gln Pro Gly Gly Ser Leu Arg Leu
385             390             395             400

Ser Cys Ala Ala Ser Gly Phe Asn Leu Ser Tyr Ser Asp Ile His Trp
            405             410             415

Val Arg Gln Ala Pro Gly Lys Gly Leu Glu Trp Val Ala Val Val Met
            420             425             430

Pro Asp Ser Gly His Thr Asn Tyr Ala Asp Ser Val Lys Gly Arg Phe
            435             440             445

Thr Ile Ser Ala Asp Thr Ser Lys Asn Thr Ala Tyr Leu Gln Met Asn
    450             455             460

Ser Leu Arg Ala Glu Asp Thr Ala Val Tyr Tyr Cys Ser Arg Ala Thr
465             470             475             480

Asn Ile Pro Val Tyr Ala Phe Asp Tyr Trp Gly Gln Gly Thr Leu Val
            485             490             495

Thr Val Ser Ser His His His His His His
            500             505
```

```
<210> SEQ ID NO 230
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230
```

```
Met Tyr Arg Met Gln Leu Leu Ser Cys Ile Ala Leu Ser Leu Ala Leu
1               5               10              15

Val Thr Asn Ser Asp Ile Gln Met Thr Gln Ser Pro Ser Ser Leu Ser
            20              25              30

Ala Ser Val Gly Asp Arg Val Thr Ile Thr Cys Arg Ala Ser Gln Asp
        35              40              45

Val Asn Thr Ala Val Ala Trp Tyr Gln Gln Lys Pro Gly Lys Ala Pro
    50              55              60

Lys Leu Leu Ile Tyr Ser Ala Ser Phe Leu Tyr Ser Gly Val Pro Ser
65              70              75              80

Arg Phe Ser Gly Ser Arg Ser Gly Thr Asp Phe Thr Leu Thr Ile Ser
            85              90              95

Ser Leu Gln Pro Glu Asp Phe Ala Thr Tyr Tyr Cys Gln Gln Ser Tyr
            100             105             110

Tyr Tyr Phe Arg Pro Ile Thr Phe Gly Gln Gly Thr Lys Val Glu Ile
        115             120             125

Lys Gly Gly Gly Gly Ser Gln Val Gln Leu Val Glu Ser Gly Gly Gly
    130             135             140

Val Val Gln Pro Gly Arg Ser Leu Arg Leu Ser Cys Ala Ala Ser Gly
145             150             155             160

Phe Thr Phe Arg Ser Tyr Gly Met His Trp Val Arg Gln Ala Pro Gly
            165             170             175

Lys Gly Leu Glu Trp Val Ala Ile Ile Trp Tyr Asp Gly Ser Lys Lys
            180             185             190

Asn Tyr Ala Asp Ser Val Lys Gly Arg Phe Thr Ile Ser Arg Asp Asn
        195             200             205
```

-continued

```
Ser Lys Asn Thr Leu Tyr Leu Gln Met Asn Ser Leu Arg Ala Glu Asp
    210             215             220

Thr Ala Val Tyr Tyr Cys Ala Arg Gly Thr Gly Tyr Asn Trp Phe Asp
225             230             235             240

Pro Trp Gly Gln Gly Thr Leu Val Thr Val Ser Ser Gly Gly Gly Gly
            245             250             255

Ser Gly Gly Gly Gly Ser Gly Gly Gly Gly Ser Glu Ile Val Leu Thr
            260             265             270

Gln Ser Pro Arg Thr Leu Ser Leu Ser Pro Gly Glu Arg Ala Thr Leu
            275             280             285

Ser Cys Arg Ala Ser Gln Ser Val Ser Ser Ser Tyr Leu Ala Trp Tyr
    290             295             300

Gln Gln Lys Pro Gly Gln Ala Pro Arg Leu Leu Ile Tyr Gly Ala Ser
305             310             315             320

Ser Arg Ala Thr Gly Ile Pro Asp Arg Phe Ser Gly Ser Gly Ser Gly
            325             330             335

Thr Asp Phe Thr Leu Thr Ile Ser Arg Leu Asp Pro Glu Asp Phe Ala
            340             345             350

Val Tyr Tyr Cys Gln Gln Tyr Gly Ser Ser Pro Ile Thr Phe Gly Gln
            355             360             365

Gly Thr Arg Leu Glu Ile Lys Gly Gly Gly Gly Ser Glu Val Gln Leu
    370             375             380

Val Glu Ser Gly Gly Gly Leu Val Gln Pro Gly Gly Ser Leu Arg Leu
385             390             395             400

Ser Cys Ala Ala Ser Gly Phe Asn Leu Ser Tyr Ser Asp Ile His Trp
            405             410             415

Val Arg Gln Ala Pro Gly Lys Gly Leu Glu Trp Val Ala Val Val Met
            420             425             430

Pro Asp Ser Gly His Thr Asn Tyr Ala Asp Ser Val Lys Gly Arg Phe
            435             440             445

Thr Ile Ser Ala Asp Thr Ser Lys Asn Thr Ala Tyr Leu Gln Met Asn
    450             455             460

Ser Leu Arg Ala Glu Asp Thr Ala Val Tyr Tyr Cys Ser Arg Ala Thr
465             470             475             480

Asn Ile Pro Val Tyr Ala Phe Asp Tyr Trp Gly Gln Gly Thr Leu Val
            485             490             495

Thr Val Ser Ser His His His His His His
            500             505
```

```
<210> SEQ ID NO 231
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Met Tyr Arg Met Gln Leu Leu Ser Cys Ile Ala Leu Ser Leu Ala Leu
1               5               10              15

Val Thr Asn Ser Asp Ile Gln Met Thr Gln Ser Pro Ser Ser Leu Ser
            20              25              30

Ala Ser Val Gly Asp Arg Val Thr Ile Thr Cys Arg Ala Ser Gln Asp
        35              40              45

Val Asn Thr Ala Val Ala Trp Tyr Gln Gln Lys Pro Gly Lys Ala Pro
```

-continued

```
            50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Gly Ser Gln Val Gln Leu Val Gln Ser Gly Gly Gly
        130                 135                 140

Val Val Gln Ser Gly Arg Ser Leu Arg Leu Ser Cys Ala Ala Ser Gly
145                 150                 155                 160

Phe Lys Phe Ser Gly Tyr Gly Met His Trp Val Arg Gln Ala Pro Gly
                165                 170                 175

Lys Gly Leu Glu Trp Val Ala Val Ile Trp Tyr Asp Gly Ser Lys Lys
            180                 185                 190

Tyr Tyr Val Asp Ser Val Lys Gly Arg Phe Thr Ile Ser Arg Asp Asn
            195                 200                 205

Ser Lys Asn Thr Leu Tyr Leu Gln Met Asn Ser Leu Arg Gly Glu Asp
        210                 215                 220

Thr Ala Val Tyr Tyr Cys Ala Arg Gln Met Gly Tyr Trp His Phe Asp
225                 230                 235                 240

Leu Trp Gly Arg Gly Thr Leu Val Thr Val Ser Ser Gly Gly Gly Gly
                245                 250                 255

Ser Gly Gly Gly Gly Ser Gly Gly Gly Ser Glu Ile Val Leu Thr
            260                 265                 270

Gln Ser Pro Ala Thr Leu Ser Leu Ser Pro Gly Glu Arg Ala Thr Leu
            275                 280                 285

Ser Cys Arg Ala Ser Gln Ser Val Ser Ser Tyr Leu Ala Trp Tyr Gln
        290                 295                 300

Gln Lys Pro Gly Gln Ala Pro Arg Leu Leu Ile Tyr Asp Ala Ser Asn
305                 310                 315                 320

Arg Ala Thr Gly Ile Pro Ala Arg Phe Ser Gly Ser Gly Ser Gly Thr
                325                 330                 335

Asp Phe Thr Leu Thr Ile Ser Ser Leu Glu Pro Glu Asp Phe Ala Val
            340                 345                 350

Tyr Tyr Cys Gln Gln Arg Ser Asn Trp Pro Pro Leu Thr Phe Gly Gly
            355                 360                 365

Gly Thr Lys Val Glu Ile Lys Gly Gly Gly Gly Ser Glu Val Gln Leu
            370                 375                 380

Val Glu Ser Gly Gly Gly Leu Val Gln Pro Gly Gly Ser Leu Arg Leu
385                 390                 395                 400

Ser Cys Ala Ala Ser Gly Phe Asn Leu Ser Tyr Ser Asp Ile His Trp
                405                 410                 415

Val Arg Gln Ala Pro Gly Lys Gly Leu Glu Trp Val Ala Val Val Met
            420                 425                 430

Pro Asp Ser Gly His Thr Asn Tyr Ala Asp Ser Val Lys Gly Arg Phe
            435                 440                 445

Thr Ile Ser Ala Asp Thr Ser Lys Asn Thr Ala Tyr Leu Gln Met Asn
        450                 455                 460

Ser Leu Arg Ala Glu Asp Thr Ala Val Tyr Tyr Cys Ser Arg Ala Thr
465                 470                 475                 480
```

Asn Ile Pro Val Tyr Ala Phe Asp Tyr Trp Gly Gln Gly Thr Leu Val
            485                 490                 495

Thr Val Ser Ser His His His His His His
        500                 505

<210> SEQ ID NO 232
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Gln Val Gln Leu Val Gln Ser Gly Gly Gly
    130                 135                 140

Val Val Gln Pro Gly Arg Ser Leu Arg Leu Ser Cys Val Ala Ser Gly
145                 150                 155                 160

Phe Thr Phe Ser Ser Tyr Gly Met His Trp Val Arg Gln Ala Pro Gly
                165                 170                 175

Lys Gly Leu Glu Trp Val Ala Ala Ile Trp Tyr Asn Gly Arg Lys Gln
            180                 185                 190

Asp Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Ala Glu Asp
    210                 215                 220

Thr Ala Val Tyr Tyr Cys Thr Arg Gly Thr Gly Tyr Asn Trp Phe Asp
225                 230                 235                 240

Pro Trp Gly Gln Gly Thr Leu Val Thr Val Ser Ser Gly Gly Gly Gly
                245                 250                 255

Ser Gly Gly Gly Gly Ser Gly Gly Gly Ser Glu Ile Val Leu Thr
            260                 265                 270

Gln Ser Pro Ala Thr Leu Ser Leu Ser Pro Gly Glu Arg Ala Thr Leu
        275                 280                 285

Ser Cys Arg Ala Ser Gln Ser Val Ser Ser Tyr Leu Ala Trp Tyr Gln
    290                 295                 300

Gln Lys Pro Gly Gln Ala Pro Arg Leu Leu Ile Tyr Asp Ala Ser Asn
305                 310                 315                 320

Arg Ala Thr Gly Ile Pro Ala Arg Phe Ser Gly Ser Gly Ser Gly Thr

-continued

```
                       325                 330                 335

Asp Phe Thr Leu Thr Ile Ser Ser Leu Glu Pro Glu Asp Phe Ala Val
        340                 345                 350

Tyr Tyr Cys Gln Gln Arg Ser Asn Trp Pro Trp Thr Phe Gly Gln Gly
            355                 360                 365

Thr Lys Val Glu Ile Lys Gly Gly Gly Ser Glu Val Gln Leu Val
        370                 375                 380

Glu Ser Gly Gly Gly Leu Val Gln Pro Gly Gly Ser Leu Arg Leu Ser
385                 390                 395                 400

Cys Ala Ala Ser Gly Phe Asn Leu Ser Tyr Ser Asp Ile His Trp Val
            405                 410                 415

Arg Gln Ala Pro Gly Lys Gly Leu Glu Trp Val Ala Val Val Met Pro
            420                 425                 430

Asp Ser Gly His Thr Asn Tyr Ala Asp Ser Val Lys Gly Arg Phe Thr
            435                 440                 445

Ile Ser Ala Asp Thr Ser Lys Asn Thr Ala Tyr Leu Gln Met Asn Ser
        450                 455                 460

Leu Arg Ala Glu Asp Thr Ala Val Tyr Tyr Cys Ser Arg Ala Thr Asn
465                 470                 475                 480

Ile Pro Val Tyr Ala Phe Asp Tyr Trp Gly Gln Gly Thr Leu Val Thr
            485                 490                 495

Val Ser Ser His His His His His His
        500                 505

<210> SEQ ID NO 233
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
            85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Gln Val Gln Leu Val Gln Ser Gly Gly Gly
    130                 135                 140

Val Val Gln Pro Gly Arg Ser Leu Arg Leu Ser Cys Val Ala Ser Gly
145                 150                 155                 160

Phe Thr Phe Ser Ser Tyr Gly Met His Trp Val Arg Gln Ala Pro Gly
            165                 170                 175
```

-continued

```
Lys Gly Leu Glu Trp Val Ala Ala Ile Trp Tyr Asn Gly Arg Lys Gln
            180                 185                 190

Asp Tyr Ala Asp Ser Val Lys Gly Arg Phe Thr Ile Ser Arg Asp Asn
            195                 200                 205

Ser Lys Asn Thr Leu Tyr Leu Gln Met Asn Ser Leu Arg Ala Glu Asp
        210                 215                 220

Thr Ala Val Tyr Tyr Cys Thr Arg Gly Thr Gly Tyr Asn Trp Phe Asp
225                 230                 235                 240

Pro Trp Gly Gln Gly Thr Leu Val Thr Val Ser Ser Gly Gly Gly Gly
                245                 250                 255

Ser Gly Gly Gly Gly Ser Gly Gly Gly Gly Ser Ala Ile Gln Leu Thr
            260                 265                 270

Gln Ser Pro Ser Ser Leu Ser Ala Ser Val Gly Asp Arg Val Thr Ile
            275                 280                 285

Thr Cys Arg Ala Ser Gln Gly Ile Ser Ser Ala Leu Ala Trp Tyr Gln
        290                 295                 300

Gln Lys Pro Gly Lys Ala Pro Lys Leu Leu Ile Tyr Asp Ala Ser Ser
305                 310                 315                 320

Leu Glu Ser Gly Val Pro Ser Arg Phe Ser Gly Ser Gly Ser Gly Thr
                325                 330                 335

Asp Phe Thr Leu Thr Ile Ser Ser Leu Gln Pro Glu Asp Phe Ala Thr
            340                 345                 350

Tyr Tyr Cys Gln Gln Phe Asn Ser Tyr Pro Ile Thr Phe Gly Gln Gly
            355                 360                 365

Thr Arg Leu Glu Ile Lys Gly Gly Gly Gly Ser Glu Val Gln Leu Val
        370                 375                 380

Glu Ser Gly Gly Gly Leu Val Gln Pro Gly Gly Ser Leu Arg Leu Ser
385                 390                 395                 400

Cys Ala Ala Ser Gly Phe Asn Leu Ser Tyr Ser Asp Ile His Trp Val
                405                 410                 415

Arg Gln Ala Pro Gly Lys Gly Leu Glu Trp Val Ala Val Val Met Pro
            420                 425                 430

Asp Ser Gly His Thr Asn Tyr Ala Asp Ser Val Lys Gly Arg Phe Thr
        435                 440                 445

Ile Ser Ala Asp Thr Ser Lys Asn Thr Ala Tyr Leu Gln Met Asn Ser
    450                 455                 460

Leu Arg Ala Glu Asp Thr Ala Val Tyr Tyr Cys Ser Arg Ala Thr Asn
465                 470                 475                 480

Ile Pro Val Tyr Ala Phe Asp Tyr Trp Gly Gln Gly Thr Leu Val Thr
                485                 490                 495

Val Ser Ser His His His His His His
            500                 505
```

```
<210> SEQ ID NO 234
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30
```

-continued

```
Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Gly Ser Gln Val Gln Leu Gln Gln Ser Gly Ala Glu
        130                 135                 140

Leu Ala Arg Pro Gly Ala Ser Val Lys Met Ser Cys Lys Ala Ser Gly
145                 150                 155                 160

Tyr Thr Phe Thr Ser Tyr Thr Met His Trp Val Lys Gln Arg Pro Gly
                165                 170                 175

Gln Gly Leu Glu Trp Ile Gly Tyr Ile Asn Pro Ser Ser Gly Tyr Thr
            180                 185                 190

Lys Tyr Asn Gln Lys Phe Lys Asp Lys Ala Thr Leu Thr Ala Asp Lys
            195                 200                 205

Ser Ser Ser Thr Ala Tyr Met Gln Leu Ser Ser Leu Thr Ser Glu Asp
    210                 215                 220

Ser Ala Val Tyr Tyr Cys Ala Arg Trp Gln Asp Tyr Asp Val Tyr Phe
225                 230                 235                 240

Asp Tyr Trp Gly Gln Gly Thr Thr Leu Thr Val Ser Ser Gly Gly Gly
            245                 250                 255

Gly Ser Gly Gly Gly Gly Ser Gly Gly Gly Gly Ser Gln Ile Val Leu
        260                 265                 270

Ser Gln Ser Pro Ala Ile Leu Ser Ala Ser Pro Gly Glu Lys Val Thr
    275                 280                 285

Met Thr Cys Arg Ala Ser Ser Ser Val Ser Tyr Met His Trp Tyr Gln
    290                 295                 300

Gln Lys Pro Gly Ser Ser Pro Lys Pro Trp Ile Tyr Ala Thr Ser Asn
305                 310                 315                 320

Leu Ala Ser Gly Val Pro Ala Arg Phe Ser Gly Ser Gly Ser Gly Thr
            325                 330                 335

Ser Tyr Ser Leu Thr Ile Ser Arg Val Glu Ala Glu Asp Ala Ala Thr
            340                 345                 350

Tyr Tyr Cys Gln Gln Trp Ser Ser Asn Pro Pro Thr Phe Gly Gly Gly
            355                 360                 365

Thr Lys Leu Glu Thr Lys Arg Gly Gly Gly Gly Ser Glu Val Gln Leu
    370                 375                 380

Val Glu Ser Gly Gly Gly Leu Val Gln Pro Gly Gly Ser Leu Arg Leu
385                 390                 395                 400

Ser Cys Ala Ala Ser Gly Phe Asn Leu Ser Tyr Ser Asp Ile His Trp
            405                 410                 415

Val Arg Gln Ala Pro Gly Lys Gly Leu Glu Trp Val Ala Val Val Met
            420                 425                 430

Pro Asp Ser Gly His Thr Asn Tyr Ala Asp Ser Val Lys Gly Arg Phe
            435                 440                 445
```

-continued

```
Thr Ile Ser Ala Asp Thr Ser Lys Asn Thr Ala Tyr Leu Gln Met Asn
    450                 455                 460

Ser Leu Arg Ala Glu Asp Thr Ala Val Tyr Tyr Cys Ser Arg Ala Thr
465                 470                 475                 480

Asn Ile Pro Val Tyr Ala Phe Asp Tyr Trp Gly Gln Gly Thr Leu Val
                485                 490                 495

Thr Val Ser Ser His His His His His His
            500                 505
```

```
<210> SEQ ID NO 235
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Met Tyr Arg Met Gln Leu Leu Ser Cys Ile Ala Leu Ser Leu Ala Leu
1                   5                   10                  15

Val Thr Asn Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
                100                 105                 110

Tyr Tyr Phe Arg Pro Ile Thr Phe Gly Gln Gly Thr Lys Val Glu Ile
            115                 120                 125

Lys Gly Gly Gly Gly Ser Gly Gly Gly Gly Ser Gly Gly Gly Gly Ser
    130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Asn Leu Ser Tyr Ser
                165                 170                 175

Asp Ile His Trp Val Arg Gln Ala Pro Gly Lys Gly Leu Glu Trp Val
            180                 185                 190

Ala Val Val Met Pro Asp Ser Gly His Thr Asn Tyr Ala Asp Ser Val
            195                 200                 205

Lys Gly Arg Phe Thr Ile Ser Ala Asp Thr Ser Lys Asn Thr Ala Tyr
    210                 215                 220

Leu Gln Met Asn Ser Leu Arg Ala Glu Asp Thr Ala Val Tyr Tyr Cys
225                 230                 235                 240

Ser Arg Ala Thr Asn Ile Pro Val Tyr Ala Phe Asp Tyr Trp Gly Gln
                245                 250                 255

Gly Thr Leu Val Thr Val Ser Ser Gly Gly Gly Gly Ser Glu Val Gln
            260                 265                 270

Leu Val Glu Ser Gly Gly Gly Leu Val Gln Pro Gly Gly Ser Leu Arg
            275                 280                 285

Leu Ser Cys Ala Ala Ser Gly Tyr Ser Phe Thr Gly Tyr Thr Met Asn
    290                 295                 300
```

-continued

```
Trp Val Arg Gln Ala Pro Gly Lys Gly Leu Glu Trp Val Ala Leu Ile
305                 310                 315                 320

Asn Pro Tyr Lys Gly Val Ser Thr Tyr Asn Gln Lys Phe Lys Asp Arg
                325                 330                 335

Phe Thr Ile Ser Val Asp Lys Ser Lys Asn Thr Ala Tyr Leu Gln Met
            340                 345                 350

Asn Ser Leu Arg Ala Glu Asp Thr Ala Val Tyr Tyr Cys Ala Arg Ser
        355                 360                 365

Gly Tyr Tyr Gly Asp Ser Asp Trp Tyr Phe Asp Val Trp Gly Gln Gly
    370                 375                 380

Thr Leu Val Thr Val Ser Ser Gly Gly Gly Ser Gly Gly Gly Gly
385                 390                 395                 400

Ser Gly Gly Gly Gly Ser Asp Ile Gln Met Thr Gln Ser Pro Ser Ser
                405                 410                 415

Leu Ser Ala Ser Val Gly Asp Arg Val Thr Ile Thr Cys Arg Ala Ser
            420                 425                 430

Gln Asp Ile Arg Asn Tyr Leu Asn Trp Tyr Gln Gln Lys Pro Gly Lys
        435                 440                 445

Ala Pro Lys Leu Leu Ile Tyr Tyr Thr Ser Arg Leu Glu Ser Gly Val
    450                 455                 460

Pro Ser Arg Phe Ser Gly Ser Gly Ser Gly Thr Asp Tyr Thr Leu Thr
465                 470                 475                 480

Ile Ser Ser Leu Gln Pro Glu Asp Phe Ala Thr Tyr Tyr Cys Gln Gln
                485                 490                 495

Gly Asn Thr Leu Pro Trp Thr Phe Gly Gln Gly Thr Lys Val Glu Ile
                500                 505                 510

Lys His His His His His His
        515
```

```
<210> SEQ ID NO 236
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236
```

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Gly Gly Gly Gly Ser Gly Gly Gly Gly Ser
```

-continued

```
       130                    135                    140

Glu Val Gln Leu Val Glu Ser Gly Gly Gly Leu Val Gln Pro Gly Gly
145                    150                    155                    160

Ser Leu Arg Leu Ser Cys Ala Ala Ser Gly Phe Asn Leu Ser Tyr Ser
                   165                    170                    175

Asp Ile His Trp Val Arg Gln Ala Pro Gly Lys Gly Leu Glu Trp Val
               180                    185                    190

Ala Val Val Met Pro Asp Ser Gly His Thr Asn Tyr Ala Asp Ser Val
           195                    200                    205

Lys Gly Arg Phe Thr Ile Ser Ala Asp Thr Ser Lys Asn Thr Ala Tyr
       210                    215                    220

Leu Gln Met Asn Ser Leu Arg Ala Glu Asp Thr Ala Val Tyr Tyr Cys
225                    230                    235                    240

Ser Arg Ala Thr Asn Ile Pro Val Tyr Ala Phe Asp Tyr Trp Gly Gln
                   245                    250                    255

Gly Thr Leu Val Thr Val Ser Ser Gly Gly Gly Ser Glu Val Gln
               260                    265                    270

Leu Gln Gln Ser Gly Pro Glu Leu Val Lys Pro Gly Ala Ser Met Lys
           275                    280                    285

Ile Ser Cys Lys Ala Ser Gly Tyr Ser Phe Thr Gly Tyr Thr Met Asn
       290                    295                    300

Trp Val Lys Gln Ser His Gly Lys Asn Leu Glu Trp Met Gly Leu Ile
305                    310                    315                    320

Asn Pro Tyr Lys Gly Val Ser Thr Tyr Asn Gln Lys Phe Lys Asp Lys
                   325                    330                    335

Ala Thr Leu Thr Val Asp Lys Ser Ser Ser Thr Ala Tyr Met Glu Leu
               340                    345                    350

Leu Ser Leu Thr Ser Glu Asp Ser Ala Val Tyr Tyr Cys Ala Arg Ser
           355                    360                    365

Gly Tyr Tyr Gly Asp Ser Asp Trp Tyr Phe Asp Val Trp Gly Ala Gly
       370                    375                    380

Thr Thr Val Thr Val Ser Ser Gly Gly Gly Gly Ser Gly Gly Gly Gly
385                    390                    395                    400

Ser Gly Gly Gly Gly Ser Asp Ile Gln Met Thr Gln Thr Thr Ser Ser
                   405                    410                    415

Leu Ser Ala Ser Leu Gly Asp Arg Val Thr Ile Ser Cys Arg Ala Ser
               420                    425                    430

Gln Asp Ile Arg Asn Tyr Leu Asn Trp Tyr Gln Gln Lys Pro Asp Gly
           435                    440                    445

Thr Val Lys Leu Leu Ile Tyr Tyr Thr Ser Arg Leu His Ser Gly Val
       450                    455                    460

Pro Ser Lys Phe Ser Gly Ser Gly Ser Gly Thr Asp Tyr Ser Leu Thr
465                    470                    475                    480

Ile Ser Asn Leu Glu Gln Glu Asp Ile Ala Thr Tyr Phe Cys Gln Gln
                   485                    490                    495

Gly Asn Thr Leu Pro Trp Thr Phe Ala Gly Gly Thr Lys Leu Glu Ile
               500                    505                    510

Lys His His His His His His
           515

<210> SEQ ID NO 237
<211> LENGTH: 515
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 237

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Gly Ser Gly Gly Gly Gly Ser Gly Gly Gly Gly Ser
    130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Asn Leu Ser Tyr Ser
                165                 170                 175

Asp Ile His Trp Val Arg Gln Ala Pro Gly Lys Gly Leu Glu Trp Val
            180                 185                 190

Ala Val Val Met Pro Asp Ser Gly His Thr Asn Tyr Ala Asp Ser Val
            195                 200                 205

Lys Gly Arg Phe Thr Ile Ser Ala Asp Thr Ser Lys Asn Thr Ala Tyr
    210                 215                 220

Leu Gln Met Asn Ser Leu Arg Ala Glu Asp Thr Ala Val Tyr Tyr Cys
225                 230                 235                 240

Ser Arg Ala Thr Asn Ile Pro Val Tyr Ala Phe Asp Tyr Trp Gly Gln
                245                 250                 255

Gly Thr Leu Val Thr Val Ser Ser Gly Gly Gly Ser Asp Val Gln
            260                 265                 270

Leu Val Gln Ser Gly Ala Glu Val Lys Lys Pro Gly Ala Ser Val Lys
            275                 280                 285

Val Ser Cys Lys Ala Ser Gly Tyr Thr Phe Thr Arg Tyr Thr Met His
    290                 295                 300

Trp Val Arg Gln Ala Pro Gly Gln Gly Leu Glu Trp Ile Gly Tyr Ile
305                 310                 315                 320

Asn Pro Ser Arg Gly Tyr Thr Asn Tyr Ala Asp Ser Val Lys Gly Arg
                325                 330                 335

Phe Thr Ile Thr Thr Asp Lys Ser Thr Ser Thr Ala Tyr Met Glu Leu
            340                 345                 350

Ser Ser Leu Arg Ser Glu Asp Thr Ala Thr Tyr Tyr Cys Ala Arg Tyr
            355                 360                 365

Tyr Asp Asp His Tyr Cys Leu Asp Tyr Trp Gly Gln Gly Thr Thr Val
    370                 375                 380

Thr Val Ser Ser Gly Gly Gly Gly Ser Gly Gly Gly Gly Ser Gly Gly
```

385                 390                 395                 400

Gly Gly Ser Asp Ile Val Leu Thr Gln Ser Pro Ala Thr Leu Ser Leu
                405                 410                 415

Ser Pro Gly Glu Arg Ala Thr Leu Ser Cys Arg Ala Ser Gln Ser Val
                420                 425                 430

Ser Tyr Met Asn Trp Tyr Gln Gln Lys Pro Gly Lys Ala Pro Lys Arg
                435                 440                 445

Trp Ile Tyr Asp Thr Ser Lys Val Ala Ser Gly Val Pro Ala Arg Phe
        450                 455                 460

Ser Gly Ser Gly Ser Gly Thr Asp Tyr Ser Leu Thr Ile Asn Ser Leu
465                 470                 475                 480

Glu Ala Glu Asp Ala Ala Thr Tyr Tyr Cys Gln Gln Trp Ser Ser Asn
                485                 490                 495

Pro Leu Thr Phe Gly Gly Gly Thr Lys Val Glu Ile Lys His His His
                500                 505                 510

His His His
        515

<210> SEQ ID NO 238
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Met Tyr Arg Met Gln Leu Leu Ser Cys Ile Ala Leu Ser Leu Ala Leu
1                   5                   10                  15

Val Thr Asn Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
                100                 105                 110

Tyr Tyr Phe Arg Pro Ile Thr Phe Gly Gln Gly Thr Lys Val Glu Ile
            115                 120                 125

Lys Gly Gly Gly Gly Ser Gly Gly Gly Gly Ser Gly Gly Gly Gly Ser
        130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Asn Leu Ser Tyr Ser
                165                 170                 175

Asp Ile His Trp Val Arg Gln Ala Pro Gly Lys Gly Leu Glu Trp Val
            180                 185                 190

Ala Val Val Met Pro Asp Ser Gly His Thr Asn Tyr Ala Asp Ser Val
            195                 200                 205

Lys Gly Arg Phe Thr Ile Ser Ala Asp Thr Ser Lys Asn Thr Ala Tyr
        210                 215                 220

-continued

```
Leu Gln Met Asn Ser Leu Arg Ala Glu Asp Thr Ala Val Tyr Tyr Cys
225                 230                 235                 240

Ser Arg Ala Thr Asn Ile Pro Val Tyr Ala Phe Asp Tyr Trp Gly Gln
                245                 250                 255

Gly Thr Leu Val Thr Val Ser Ser Gly Gly Gly Ser Glu Val Gln
                260                 265                 270

Leu Val Glu Ser Gly Gly Gly Leu Val Gln Pro Gly Gly Ser Leu Arg
                275                 280                 285

Leu Ser Cys Ala Ala Ser Gly Phe Thr Phe Asn Thr Tyr Ala Met Asn
                290                 295                 300

Trp Val Arg Gln Ala Pro Gly Lys Gly Leu Glu Trp Val Ala Arg Ile
305                 310                 315                 320

Arg Ser Lys Tyr Asn Asn Tyr Ala Thr Tyr Tyr Ala Asp Ser Val Lys
                325                 330                 335

Asp Arg Phe Thr Ile Ser Arg Asp Asp Ser Lys Asn Ser Leu Tyr Leu
                340                 345                 350

Gln Met Asn Ser Leu Lys Thr Glu Asp Thr Ala Val Tyr Tyr Cys Val
                355                 360                 365

Arg His Gly Asn Phe Gly Asn Ser Tyr Val Ser Trp Phe Ala Tyr Trp
        370                 375                 380

Gly Gln Gly Thr Leu Val Thr Val Ser Ser Gly Gly Gly Gly Ser Gly
385                 390                 395                 400

Gly Gly Gly Ser Gly Gly Gly Gly Ser Gln Ala Val Val Thr Gln Glu
                405                 410                 415

Pro Ser Leu Thr Val Ser Pro Gly Gly Thr Val Thr Leu Thr Cys Arg
                420                 425                 430

Ser Ser Thr Gly Ala Val Thr Thr Ser Asn Tyr Ala Asn Trp Val Gln
                435                 440                 445

Gln Lys Pro Gly Gln Ala Pro Arg Gly Leu Ile Gly Gly Thr Asn Lys
        450                 455                 460

Arg Ala Pro Trp Thr Pro Ala Arg Phe Ser Gly Ser Leu Leu Gly Gly
465                 470                 475                 480

Lys Ala Ala Leu Thr Ile Thr Gly Ala Gln Ala Glu Asp Glu Ala Asp
                485                 490                 495

Tyr Tyr Cys Ala Leu Trp Tyr Ser Asn Leu Trp Val Phe Gly Gly Gly
                500                 505                 510

Thr Lys Leu Thr Val Leu His His His His His
        515                 520
```

<210> SEQ ID NO 239
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
        50                  55                  60
```

-continued

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Ser Gly Gly Gly Ser Gly Gly Gly Gly Ser
        130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Asn Leu Ser Tyr Ser
                165                 170                 175

Asp Ile His Trp Val Arg Gln Ala Pro Gly Lys Gly Leu Glu Trp Val
            180                 185                 190

Ala Val Val Met Pro Asp Ser Gly His Thr Asn Tyr Ala Asp Ser Val
            195                 200                 205

Lys Gly Arg Phe Thr Ile Ser Ala Asp Thr Ser Lys Asn Thr Ala Tyr
        210                 215                 220

Leu Gln Met Asn Ser Leu Arg Ala Glu Asp Thr Ala Val Tyr Tyr Cys
225                 230                 235                 240

Ser Arg Ala Thr Asn Ile Pro Val Tyr Ala Phe Asp Tyr Trp Gly Gln
                245                 250                 255

Gly Thr Leu Val Thr Val Ser Ser Gly Gly Gly Gly Ser Gln Val Gln
            260                 265                 270

Leu Gln Gln Ser Gly Ala Glu Leu Ala Arg Pro Gly Ala Ser Val Lys
            275                 280                 285

Met Ser Cys Lys Ala Ser Gly Tyr Thr Phe Thr Arg Tyr Thr Met His
    290                 295                 300

Trp Val Lys Gln Arg Pro Gly Gln Gly Leu Glu Trp Ile Gly Tyr Ile
305                 310                 315                 320

Asn Pro Ser Arg Gly Tyr Thr Asn Tyr Asn Gln Lys Phe Lys Asp Lys
                325                 330                 335

Ala Thr Leu Thr Thr Asp Lys Ser Ser Ser Thr Ala Tyr Met Gln Leu
            340                 345                 350

Ser Ser Leu Thr Ser Glu Asp Ser Ala Val Tyr Tyr Cys Ala Arg Tyr
            355                 360                 365

Tyr Asp Asp His Tyr Cys Leu Asp Tyr Trp Gly Gln Gly Thr Thr Leu
    370                 375                 380

Thr Val Ser Ser Gly Gly Gly Gly Ser Gly Gly Gly Gly Ser Gly Gly
385                 390                 395                 400

Gly Gly Ser Gln Ile Val Leu Thr Gln Ser Pro Ala Ile Met Ser Ala
            405                 410                 415

Ser Pro Gly Glu Lys Val Thr Met Thr Cys Ser Ala Ser Ser Ser Val
            420                 425                 430

Ser Tyr Met Asn Trp Tyr Gln Gln Lys Ser Gly Thr Ser Pro Lys Arg
            435                 440                 445

Trp Ile Tyr Asp Thr Ser Lys Leu Ala Ser Gly Val Pro Ala His Phe
    450                 455                 460

Arg Gly Ser Gly Ser Gly Thr Ser Tyr Ser Leu Thr Ile Ser Gly Met
465                 470                 475                 480

```
Glu Ala Glu Asp Ala Ala Thr Tyr Tyr Cys Gln Gln Trp Ser Ser Asn
            485                 490                 495

Pro Phe Thr Phe Gly Ser Gly Thr Lys Leu Glu Ile Asn His His His
            500                 505                 510

His His His
        515

<210> SEQ ID NO 240
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
            85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Gly Ser Gly Gly Gly Gly Ser Gly Gly Gly Gly Ser
    130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Asn Leu Ser Tyr Ser
            165                 170                 175

Asp Ile His Trp Val Arg Gln Ala Pro Gly Lys Gly Leu Glu Trp Val
            180                 185                 190

Ala Val Val Met Pro Asp Ser Gly His Thr Asn Tyr Ala Asp Ser Val
            195                 200                 205

Lys Gly Arg Phe Thr Ile Ser Ala Asp Thr Ser Lys Asn Thr Ala Tyr
    210                 215                 220

Leu Gln Met Asn Ser Leu Arg Ala Glu Asp Thr Ala Val Tyr Tyr Cys
225                 230                 235                 240

Ser Arg Ala Thr Asn Ile Pro Val Tyr Ala Phe Asp Tyr Trp Gly Gln
            245                 250                 255

Gly Thr Leu Val Thr Val Ser Ser Gly Gly Gly Ser Asp Ile Gln
            260                 265                 270

Met Thr Gln Ser Pro Ser Ser Leu Ser Ala Ser Val Gly Asp Arg Val
            275                 280                 285

Thr Ile Thr Cys Arg Ala Ser Gln Asp Ile Arg Asn Tyr Leu Asn Trp
    290                 295                 300

Tyr Gln Gln Lys Pro Gly Lys Ala Pro Lys Leu Leu Ile Tyr Tyr Thr
305                 310                 315                 320
```

-continued

```
Ser Arg Leu Glu Ser Gly Val Pro Ser Arg Phe Ser Gly Ser Gly Ser
            325                 330                 335

Gly Thr Asp Tyr Thr Leu Thr Ile Ser Ser Leu Gln Pro Glu Asp Phe
            340                 345                 350

Ala Thr Tyr Tyr Cys Gln Gln Gly Asn Thr Leu Pro Trp Thr Phe Gly
            355                 360                 365

Gln Gly Thr Lys Val Glu Ile Lys Gly Gly Gly Ser Gly Gly Gly
            370                 375                 380

Gly Ser Gly Gly Gly Gly Ser Glu Val Gln Leu Val Glu Ser Gly Gly
385                 390                 395                 400

Gly Leu Val Gln Pro Gly Gly Ser Leu Arg Leu Ser Cys Ala Ala Ser
            405                 410                 415

Gly Tyr Ser Phe Thr Gly Tyr Thr Met Asn Trp Val Arg Gln Ala Pro
            420                 425                 430

Gly Lys Gly Leu Glu Trp Val Ala Leu Ile Asn Pro Tyr Lys Gly Val
            435                 440                 445

Ser Thr Tyr Asn Gln Lys Phe Lys Asp Arg Phe Thr Ile Ser Val Asp
            450                 455                 460

Lys Ser Lys Asn Thr Ala Tyr Leu Gln Met Asn Ser Leu Arg Ala Glu
465                 470                 475                 480

Asp Thr Ala Val Tyr Tyr Cys Ala Arg Ser Gly Tyr Tyr Gly Asp Ser
            485                 490                 495

Asp Trp Tyr Phe Asp Val Trp Gly Gln Gly Thr Leu Val Thr Val Ser
            500                 505                 510

Ser His His His His His His
        515
```

```
<210> SEQ ID NO 241
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241
```

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
        50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
            85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Gly Ser Gly Gly Gly Gly Ser Gly Gly Gly Gly Ser
        130                 135                 140

Glu Val Gln Leu Val Glu Ser Gly Gly Gly Leu Val Gln Pro Gly Gly
```

-continued

```
145                 150                 155                 160

Ser Leu Arg Leu Ser Cys Ala Ala Ser Gly Phe Asn Leu Ser Tyr Ser
                165                 170                 175

Asp Ile His Trp Val Arg Gln Ala Pro Gly Lys Gly Leu Glu Trp Val
            180                 185                 190

Ala Val Val Met Pro Asp Ser Gly His Thr Asn Tyr Ala Asp Ser Val
            195                 200                 205

Lys Gly Arg Phe Thr Ile Ser Ala Asp Thr Ser Lys Asn Thr Ala Tyr
        210                 215                 220

Leu Gln Met Asn Ser Leu Arg Ala Glu Asp Thr Ala Val Tyr Tyr Cys
225                 230                 235                 240

Ser Arg Ala Thr Asn Ile Pro Val Tyr Ala Phe Asp Tyr Trp Gly Gln
                245                 250                 255

Gly Thr Leu Val Thr Val Ser Ser Gly Gly Gly Ser Asp Ile Gln
            260                 265                 270

Met Thr Gln Thr Thr Ser Ser Leu Ser Ala Ser Leu Gly Asp Arg Val
            275                 280                 285

Thr Ile Ser Cys Arg Ala Ser Gln Asp Ile Arg Asn Tyr Leu Asn Trp
        290                 295                 300

Tyr Gln Gln Lys Pro Asp Gly Thr Val Lys Leu Leu Ile Tyr Tyr Thr
305                 310                 315                 320

Ser Arg Leu His Ser Gly Val Pro Ser Lys Phe Ser Gly Ser Gly Ser
                325                 330                 335

Gly Thr Asp Tyr Ser Leu Thr Ile Ser Asn Leu Glu Gln Glu Asp Ile
            340                 345                 350

Ala Thr Tyr Phe Cys Gln Gln Gly Asn Thr Leu Pro Trp Thr Phe Ala
            355                 360                 365

Gly Gly Thr Lys Leu Glu Ile Lys Gly Gly Gly Gly Ser Gly Gly Gly
        370                 375                 380

Gly Ser Gly Gly Gly Gly Ser Glu Val Gln Leu Gln Gln Ser Gly Pro
385                 390                 395                 400

Glu Leu Val Lys Pro Gly Ala Ser Met Lys Ile Ser Cys Lys Ala Ser
                405                 410                 415

Gly Tyr Ser Phe Thr Gly Tyr Thr Met Asn Trp Val Lys Gln Ser His
            420                 425                 430

Gly Lys Asn Leu Glu Trp Met Gly Leu Ile Asn Pro Tyr Lys Gly Val
            435                 440                 445

Ser Thr Tyr Asn Gln Lys Phe Lys Asp Lys Ala Thr Leu Thr Val Asp
        450                 455                 460

Lys Ser Ser Ser Thr Ala Tyr Met Glu Leu Leu Ser Leu Thr Ser Glu
465                 470                 475                 480

Asp Ser Ala Val Tyr Tyr Cys Ala Arg Ser Gly Tyr Tyr Gly Asp Ser
                485                 490                 495

Asp Trp Tyr Phe Asp Val Trp Gly Ala Gly Thr Thr Val Thr Val Ser
            500                 505                 510

Ser His His His His His His
        515
```

```
<210> SEQ ID NO 242
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 242

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
            85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Gly Gly Gly Gly Ser Gly Gly Gly Gly Ser
    130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Asn Leu Ser Tyr Ser
            165                 170                 175

Asp Ile His Trp Val Arg Gln Ala Pro Gly Lys Gly Leu Glu Trp Val
            180                 185                 190

Ala Val Val Met Pro Asp Ser Gly His Thr Asn Tyr Ala Asp Ser Val
            195                 200                 205

Lys Gly Arg Phe Thr Ile Ser Ala Asp Thr Ser Lys Asn Thr Ala Tyr
    210                 215                 220

Leu Gln Met Asn Ser Leu Arg Ala Glu Asp Thr Ala Val Tyr Tyr Cys
225                 230                 235                 240

Ser Arg Ala Thr Asn Ile Pro Val Tyr Ala Phe Asp Tyr Trp Gly Gln
            245                 250                 255

Gly Thr Leu Val Thr Val Ser Ser Gly Gly Gly Ser Asp Ile Val
            260                 265                 270

Leu Thr Gln Ser Pro Ala Thr Leu Ser Leu Ser Pro Gly Glu Arg Ala
            275                 280                 285

Thr Leu Ser Cys Arg Ala Ser Gln Ser Val Ser Tyr Met Asn Trp Tyr
    290                 295                 300

Gln Gln Lys Pro Gly Lys Ala Pro Lys Arg Trp Ile Tyr Asp Thr Ser
305                 310                 315                 320

Lys Val Ala Ser Gly Val Pro Ala Arg Phe Ser Gly Ser Gly Ser Gly
            325                 330                 335

Thr Asp Tyr Ser Leu Thr Ile Asn Ser Leu Glu Ala Glu Asp Ala Ala
            340                 345                 350

Thr Tyr Tyr Cys Gln Gln Trp Ser Ser Asn Pro Leu Thr Phe Gly Gly
        355                 360                 365

Gly Thr Lys Val Glu Ile Lys Gly Gly Gly Gly Ser Gly Gly Gly Gly
    370                 375                 380

Ser Gly Gly Gly Gly Ser Asp Val Gln Leu Val Gln Ser Gly Ala Glu
385                 390                 395                 400

Val Lys Lys Pro Gly Ala Ser Val Lys Val Ser Cys Lys Ala Ser Gly
```

-continued

```
                    405                410                415
Tyr Thr Phe Thr Arg Tyr Thr Met His Trp Val Arg Gln Ala Pro Gly
            420                425                430

Gln Gly Leu Glu Trp Ile Gly Tyr Ile Asn Pro Ser Arg Gly Tyr Thr
            435                440                445

Asn Tyr Ala Asp Ser Val Lys Gly Arg Phe Thr Ile Thr Thr Asp Lys
            450                455                460

Ser Thr Ser Thr Ala Tyr Met Glu Leu Ser Ser Leu Arg Ser Glu Asp
465                470                475                480

Thr Ala Thr Tyr Tyr Cys Ala Arg Tyr Tyr Asp Asp His Tyr Cys Leu
                485                490                495

Asp Tyr Trp Gly Gln Gly Thr Thr Val Thr Val Ser Ser His His His
            500                505                510

His His His
        515
```

<210> SEQ ID NO 243
<211> LENGTH: 524
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 243

```
Met Tyr Arg Met Gln Leu Leu Ser Cys Ile Ala Leu Ser Leu Ala Leu
1                5                10                15

Val Thr Asn Ser Asp Ile Gln Met Thr Gln Ser Pro Ser Ser Leu Ser
            20                25                30

Ala Ser Val Gly Asp Arg Val Thr Ile Thr Cys Arg Ala Ser Gln Asp
            35                40                45

Val Asn Thr Ala Val Ala Trp Tyr Gln Gln Lys Pro Gly Lys Ala Pro
            50                55                60

Lys Leu Leu Ile Tyr Ser Ala Ser Phe Leu Tyr Ser Gly Val Pro Ser
65                70                75                80

Arg Phe Ser Gly Ser Arg Ser Gly Thr Asp Phe Thr Leu Thr Ile Ser
                85                90                95

Ser Leu Gln Pro Glu Asp Phe Ala Thr Tyr Tyr Cys Gln Gln Ser Tyr
            100                105                110

Tyr Tyr Phe Arg Pro Ile Thr Phe Gly Gln Gly Thr Lys Val Glu Ile
            115                120                125

Lys Gly Gly Gly Gly Ser Gly Gly Gly Gly Ser Gly Gly Gly Gly Ser
            130                135                140

Glu Val Gln Leu Val Glu Ser Gly Gly Gly Leu Val Gln Pro Gly Gly
145                150                155                160

Ser Leu Arg Leu Ser Cys Ala Ala Ser Gly Phe Asn Leu Ser Tyr Ser
                165                170                175

Asp Ile His Trp Val Arg Gln Ala Pro Gly Lys Gly Leu Glu Trp Val
            180                185                190

Ala Val Val Met Pro Asp Ser Gly His Thr Asn Tyr Ala Asp Ser Val
            195                200                205

Lys Gly Arg Phe Thr Ile Ser Ala Asp Thr Ser Lys Asn Thr Ala Tyr
            210                215                220

Leu Gln Met Asn Ser Leu Arg Ala Glu Asp Thr Ala Val Tyr Tyr Cys
225                230                235                240
```

-continued

```
Ser Arg Ala Thr Asn Ile Pro Val Tyr Ala Phe Asp Tyr Trp Gly Gln
            245                 250                 255

Gly Thr Leu Val Thr Val Ser Ser Gly Gly Gly Ser Gln Ala Val
            260                 265                 270

Val Thr Gln Glu Pro Ser Leu Thr Val Ser Pro Gly Gly Thr Val Thr
            275                 280                 285

Leu Thr Cys Arg Ser Ser Thr Gly Ala Val Thr Thr Ser Asn Tyr Ala
    290                 295                 300

Asn Trp Val Gln Gln Lys Pro Gly Gln Ala Pro Arg Gly Leu Ile Gly
305                 310                 315                 320

Gly Thr Asn Lys Arg Ala Pro Trp Thr Pro Ala Arg Phe Ser Gly Ser
            325                 330                 335

Leu Leu Gly Gly Lys Ala Ala Leu Thr Ile Thr Gly Ala Gln Ala Glu
            340                 345                 350

Asp Glu Ala Asp Tyr Tyr Cys Ala Leu Trp Tyr Ser Asn Leu Trp Val
            355                 360                 365

Phe Gly Gly Gly Thr Lys Leu Thr Val Leu Gly Gly Gly Gly Ser Gly
    370                 375                 380

Gly Gly Gly Ser Gly Gly Gly Gly Ser Glu Val Gln Leu Val Glu Ser
385                 390                 395                 400

Gly Gly Gly Leu Val Gln Pro Gly Gly Ser Leu Arg Leu Ser Cys Ala
            405                 410                 415

Ala Ser Gly Phe Thr Phe Asn Thr Tyr Ala Met Asn Trp Val Arg Gln
            420                 425                 430

Ala Pro Gly Lys Gly Leu Glu Trp Val Ala Arg Ile Arg Ser Lys Tyr
            435                 440                 445

Asn Asn Tyr Ala Thr Tyr Tyr Ala Asp Ser Val Lys Asp Arg Phe Thr
    450                 455                 460

Ile Ser Arg Asp Asp Ser Lys Asn Ser Leu Tyr Leu Gln Met Asn Ser
465                 470                 475                 480

Leu Lys Thr Glu Asp Thr Ala Val Tyr Tyr Cys Val Arg His Gly Asn
            485                 490                 495

Phe Gly Asn Ser Tyr Val Ser Trp Phe Ala Tyr Trp Gly Gln Gly Thr
            500                 505                 510

Leu Val Thr Val Ser Ser His His His His His His
        515                 520
```

```
<210> SEQ ID NO 244
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80
```

-continued

```
Arg Phe Ser Gly Ser Arg Ser Gly Thr Asp Phe Thr Leu Thr Ile Ser
            85              90              95

Ser Leu Gln Pro Glu Asp Phe Ala Thr Tyr Tyr Cys Gln Gln Ser Tyr
            100             105             110

Tyr Tyr Phe Arg Pro Ile Thr Phe Gly Gln Gly Thr Lys Val Glu Ile
            115             120             125

Lys Gly Gly Gly Gly Ser Gly Gly Gly Ser Gly Gly Gly Gly Ser
    130             135             140

Glu Val Gln Leu Val Glu Ser Gly Gly Gly Leu Val Gln Pro Gly Gly
145             150             155             160

Ser Leu Arg Leu Ser Cys Ala Ala Ser Gly Phe Asn Leu Ser Tyr Ser
            165             170             175

Asp Ile His Trp Val Arg Gln Ala Pro Gly Lys Gly Leu Glu Trp Val
            180             185             190

Ala Val Val Met Pro Asp Ser Gly His Thr Asn Tyr Ala Asp Ser Val
            195             200             205

Lys Gly Arg Phe Thr Ile Ser Ala Asp Thr Ser Lys Asn Thr Ala Tyr
    210             215             220

Leu Gln Met Asn Ser Leu Arg Ala Glu Asp Thr Ala Val Tyr Tyr Cys
225             230             235             240

Ser Arg Ala Thr Asn Ile Pro Val Tyr Ala Phe Asp Tyr Trp Gly Gln
            245             250             255

Gly Thr Leu Val Thr Val Ser Ser Gly Gly Gly Ser Gln Ile Val
            260             265             270

Leu Thr Gln Ser Pro Ala Ile Met Ser Ala Ser Pro Gly Glu Lys Val
            275             280             285

Thr Met Thr Cys Ser Ala Ser Ser Ser Val Ser Tyr Met Asn Trp Tyr
    290             295             300

Gln Gln Lys Ser Gly Thr Ser Pro Lys Arg Trp Ile Tyr Asp Thr Ser
305             310             315             320

Lys Leu Ala Ser Gly Val Pro Ala His Phe Arg Gly Ser Gly Ser Gly
            325             330             335

Thr Ser Tyr Ser Leu Thr Ile Ser Gly Met Glu Ala Glu Asp Ala Ala
            340             345             350

Thr Tyr Tyr Cys Gln Gln Trp Ser Ser Asn Pro Phe Thr Phe Gly Ser
            355             360             365

Gly Thr Lys Leu Glu Ile Asn Gly Gly Gly Ser Gly Gly Gly Gly
    370             375             380

Ser Gly Gly Gly Gly Ser Gln Val Gln Leu Gln Gln Ser Gly Ala Glu
385             390             395             400

Leu Ala Arg Pro Gly Ala Ser Val Lys Met Ser Cys Lys Ala Ser Gly
            405             410             415

Tyr Thr Phe Thr Arg Tyr Thr Met His Trp Val Lys Gln Arg Pro Gly
            420             425             430

Gln Gly Leu Glu Trp Ile Gly Tyr Ile Asn Pro Ser Arg Gly Tyr Thr
            435             440             445

Asn Tyr Asn Gln Lys Phe Lys Asp Lys Ala Thr Leu Thr Thr Asp Lys
    450             455             460

Ser Ser Ser Thr Ala Tyr Met Gln Leu Ser Ser Leu Thr Ser Glu Asp
465             470             475             480

Ser Ala Val Tyr Tyr Cys Ala Arg Tyr Tyr Asp Asp His Tyr Cys Leu
            485             490             495
```

-continued

Asp Tyr Trp Gly Gln Gly Thr Thr Leu Thr Val Ser Ser His His His
        500                 505                 510

His His His
        515

<210> SEQ ID NO 245
<211> LENGTH: 606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Ser Gly Gly Gly Gly Glu Val Gln Leu Val Glu Ser
        130                 135                 140

Gly Gly Gly Leu Val Gln Pro Gly Gly Ser Leu Arg Leu Ser Cys Ala
145                 150                 155                 160

Ala Ser Gly Tyr Ser Phe Thr Gly Tyr Thr Met Asn Trp Val Arg Gln
                165                 170                 175

Ala Pro Gly Lys Gly Leu Glu Trp Val Ala Leu Ile Asn Pro Tyr Lys
            180                 185                 190

Gly Val Ser Thr Tyr Asn Gln Lys Phe Lys Asp Arg Phe Thr Ile Ser
            195                 200                 205

Val Asp Lys Ser Lys Asn Thr Ala Tyr Leu Gln Met Asn Ser Leu Arg
    210                 215                 220

Ala Glu Asp Thr Ala Val Tyr Tyr Cys Ala Arg Ser Gly Tyr Tyr Gly
225                 230                 235                 240

Asp Ser Asp Trp Tyr Phe Asp Val Trp Gly Gln Gly Thr Leu Val Thr
                245                 250                 255

Val Ser Ser Gly Gly Cys Gly Gly Gly Glu Val Ala Ala Leu Glu Lys
            260                 265                 270

Glu Val Ala Ala Leu Glu Lys Glu Val Ala Ala Leu Glu Lys Glu Val
        275                 280                 285

Ala Ala Leu Glu Lys Glu Gly Arg Gly Ser Leu Leu Thr Cys Gly Asp
    290                 295                 300

Val Glu Glu Asn Pro Gly Pro Met Tyr Arg Met Gln Leu Leu Ser Cys
305                 310                 315                 320

Ile Ala Leu Ser Leu Ala Leu Val Thr Asn Ser Asp Ile Gln Met Thr
                325                 330                 335

-continued

```
Gln Ser Pro Ser Ser Leu Ser Ala Ser Val Gly Asp Arg Val Thr Ile
            340                 345                 350

Thr Cys Arg Ala Ser Gln Asp Ile Arg Asn Tyr Leu Asn Trp Tyr Gln
            355                 360                 365

Gln Lys Pro Gly Lys Ala Pro Lys Leu Leu Ile Tyr Tyr Thr Ser Arg
            370                 375                 380

Leu Glu Ser Gly Val Pro Ser Arg Phe Ser Gly Ser Gly Ser Gly Thr
385                 390                 395                 400

Asp Tyr Thr Leu Thr Ile Ser Ser Leu Gln Pro Glu Asp Phe Ala Thr
                405                 410                 415

Tyr Tyr Cys Gln Gln Gly Asn Thr Leu Pro Trp Thr Phe Gly Gln Gly
            420                 425                 430

Thr Lys Val Glu Ile Lys Gly Gly Gly Ser Gly Gly Gly Gly Glu Val
            435                 440                 445

Gln Leu Val Glu Ser Gly Gly Gly Leu Val Gln Pro Gly Gly Ser Leu
    450                 455                 460

Arg Leu Ser Cys Ala Ala Ser Gly Phe Asn Leu Ser Tyr Ser Asp Ile
465                 470                 475                 480

His Trp Val Arg Gln Ala Pro Gly Lys Gly Leu Glu Trp Val Ala Val
                485                 490                 495

Val Met Pro Asp Ser Gly His Thr Asn Tyr Ala Asp Ser Val Lys Gly
            500                 505                 510

Arg Phe Thr Ile Ser Ala Asp Thr Ser Lys Asn Thr Ala Tyr Leu Gln
            515                 520                 525

Met Asn Ser Leu Arg Ala Glu Asp Thr Ala Val Tyr Tyr Cys Ser Arg
            530                 535                 540

Ala Thr Asn Ile Pro Val Tyr Ala Phe Asp Tyr Trp Gly Gln Gly Thr
545                 550                 555                 560

Leu Val Thr Val Ser Ser Gly Gly Cys Gly Gly Gly Lys Val Ala Ala
                565                 570                 575

Leu Lys Glu Lys Val Ala Ala Leu Lys Glu Lys Val Ala Ala Leu Lys
            580                 585                 590

Glu Lys Val Ala Ala Leu Lys Glu His His His His His His
            595                 600                 605
```

```
<210> SEQ ID NO 246
<211> LENGTH: 606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Met Tyr Arg Met Gln Leu Leu Ser Cys Ile Ala Leu Ser Leu Ala Leu
1                 5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
```

-continued

```
                    85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Ser Gly Gly Gly Glu Val Gln Leu Gln Gln Ser
    130                 135                 140

Gly Pro Glu Leu Val Lys Pro Gly Ala Ser Met Lys Ile Ser Cys Lys
145                 150                 155                 160

Ala Ser Gly Tyr Ser Phe Thr Gly Tyr Thr Met Asn Trp Val Lys Gln
                165                 170                 175

Ser His Gly Lys Asn Leu Glu Trp Met Gly Leu Ile Asn Pro Tyr Lys
            180                 185                 190

Gly Val Ser Thr Tyr Asn Gln Lys Phe Lys Asp Lys Ala Thr Leu Thr
            195                 200                 205

Val Asp Lys Ser Ser Ser Thr Ala Tyr Met Glu Leu Leu Ser Leu Thr
    210                 215                 220

Ser Glu Asp Ser Ala Val Tyr Tyr Cys Ala Arg Ser Gly Tyr Tyr Gly
225                 230                 235                 240

Asp Ser Asp Trp Tyr Phe Asp Val Trp Gly Ala Gly Thr Thr Val Thr
                245                 250                 255

Val Ser Ser Gly Gly Cys Gly Gly Gly Glu Val Ala Ala Leu Glu Lys
            260                 265                 270

Glu Val Ala Ala Leu Glu Lys Glu Val Ala Ala Leu Glu Lys Glu Val
            275                 280                 285

Ala Ala Leu Glu Lys Glu Gly Arg Gly Ser Leu Leu Thr Cys Gly Asp
    290                 295                 300

Val Glu Glu Asn Pro Gly Pro Met Tyr Arg Met Gln Leu Leu Ser Cys
305                 310                 315                 320

Ile Ala Leu Ser Leu Ala Leu Val Thr Asn Ser Asp Ile Gln Met Thr
                325                 330                 335

Gln Thr Thr Ser Ser Leu Ser Ala Ser Leu Gly Asp Arg Val Thr Ile
            340                 345                 350

Ser Cys Arg Ala Ser Gln Asp Ile Arg Asn Tyr Leu Asn Trp Tyr Gln
            355                 360                 365

Gln Lys Pro Asp Gly Thr Val Lys Leu Leu Ile Tyr Tyr Thr Ser Arg
    370                 375                 380

Leu His Ser Gly Val Pro Ser Lys Phe Ser Gly Ser Gly Ser Gly Thr
385                 390                 395                 400

Asp Tyr Ser Leu Thr Ile Ser Asn Leu Glu Gln Glu Asp Ile Ala Thr
                405                 410                 415

Tyr Phe Cys Gln Gln Gly Asn Thr Leu Pro Trp Thr Phe Ala Gly Gly
            420                 425                 430

Thr Lys Leu Glu Ile Lys Gly Gly Gly Ser Gly Gly Gly Glu Val
            435                 440                 445

Gln Leu Val Glu Ser Gly Gly Gly Leu Val Gln Pro Gly Gly Ser Leu
    450                 455                 460

Arg Leu Ser Cys Ala Ala Ser Gly Phe Asn Leu Ser Tyr Ser Asp Ile
465                 470                 475                 480

His Trp Val Arg Gln Ala Pro Gly Lys Gly Leu Glu Trp Val Ala Val
                485                 490                 495

Val Met Pro Asp Ser Gly His Thr Asn Tyr Ala Asp Ser Val Lys Gly
            500                 505                 510
```

-continued

```
Arg Phe Thr Ile Ser Ala Asp Thr Ser Lys Asn Thr Ala Tyr Leu Gln
        515                 520                 525

Met Asn Ser Leu Arg Ala Glu Asp Thr Ala Val Tyr Tyr Cys Ser Arg
    530                 535                 540

Ala Thr Asn Ile Pro Val Tyr Ala Phe Asp Tyr Trp Gly Gln Gly Thr
545                 550                 555                 560

Leu Val Thr Val Ser Ser Gly Gly Cys Gly Gly Gly Lys Val Ala Ala
                565                 570                 575

Leu Lys Glu Lys Val Ala Ala Leu Lys Glu Lys Val Ala Ala Leu Lys
            580                 585                 590

Glu Lys Val Ala Ala Leu Lys Glu His His His His His His
        595                 600                 605

<210> SEQ ID NO 247
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Ser Gly Gly Gly Gly Asp Val Gln Leu Val Gln Ser
    130                 135                 140

Gly Ala Glu Val Lys Lys Pro Gly Ala Ser Val Lys Val Ser Cys Lys
145                 150                 155                 160

Ala Ser Gly Tyr Thr Phe Thr Arg Tyr Thr Met His Trp Val Arg Gln
                165                 170                 175

Ala Pro Gly Gln Gly Leu Glu Trp Ile Gly Tyr Ile Asn Pro Ser Arg
            180                 185                 190

Gly Tyr Thr Asn Tyr Ala Asp Ser Val Lys Gly Arg Phe Thr Ile Thr
        195                 200                 205

Thr Asp Lys Ser Thr Ser Thr Ala Tyr Met Glu Leu Ser Ser Leu Arg
    210                 215                 220

Ser Glu Asp Thr Ala Thr Tyr Tyr Cys Ala Arg Tyr Tyr Asp Asp His
225                 230                 235                 240

Tyr Cys Leu Asp Tyr Trp Gly Gln Gly Thr Thr Val Thr Val Ser Ser
                245                 250                 255

Gly Gly Cys Gly Gly Gly Glu Val Ala Ala Leu Glu Lys Glu Val Ala
```

-continued

```
            260               265               270

Ala Leu Glu Lys Glu Val Ala Ala Leu Glu Lys Glu Val Ala Ala Leu
        275               280               285

Glu Lys Glu Gly Arg Gly Ser Leu Leu Thr Cys Gly Asp Val Glu Glu
        290               295               300

Asn Pro Gly Pro Met Tyr Arg Met Gln Leu Leu Ser Cys Ile Ala Leu
305               310               315               320

Ser Leu Ala Leu Val Thr Asn Ser Asp Ile Val Leu Thr Gln Ser Pro
                325               330               335

Ala Thr Leu Ser Leu Ser Pro Gly Glu Arg Ala Thr Leu Ser Cys Arg
                340               345               350

Ala Ser Gln Ser Val Ser Tyr Met Asn Trp Tyr Gln Gln Lys Pro Gly
                355               360               365

Lys Ala Pro Lys Arg Trp Ile Tyr Asp Thr Ser Lys Val Ala Ser Gly
        370               375               380

Val Pro Ala Arg Phe Ser Gly Ser Gly Ser Gly Thr Asp Tyr Ser Leu
385               390               395               400

Thr Ile Asn Ser Leu Glu Ala Glu Asp Ala Ala Thr Tyr Tyr Cys Gln
                405               410               415

Gln Trp Ser Ser Asn Pro Leu Thr Phe Gly Gly Gly Thr Lys Val Glu
                420               425               430

Ile Lys Gly Gly Gly Ser Gly Gly Gly Gly Glu Val Gln Leu Val Glu
                435               440               445

Ser Gly Gly Gly Leu Val Gln Pro Gly Gly Ser Leu Arg Leu Ser Cys
        450               455               460

Ala Ala Ser Gly Phe Asn Leu Ser Tyr Ser Asp Ile His Trp Val Arg
465               470               475               480

Gln Ala Pro Gly Lys Gly Leu Glu Trp Val Ala Val Val Met Pro Asp
                485               490               495

Ser Gly His Thr Asn Tyr Ala Asp Ser Val Lys Gly Arg Phe Thr Ile
                500               505               510

Ser Ala Asp Thr Ser Lys Asn Thr Ala Tyr Leu Gln Met Asn Ser Leu
                515               520               525

Arg Ala Glu Asp Thr Ala Val Tyr Tyr Cys Ser Arg Ala Thr Asn Ile
        530               535               540

Pro Val Tyr Ala Phe Asp Tyr Trp Gly Gln Gly Thr Leu Val Thr Val
545               550               555               560

Ser Ser Gly Gly Cys Gly Gly Gly Lys Val Ala Ala Leu Lys Glu Lys
                565               570               575

Val Ala Ala Leu Lys Glu Lys Val Ala Ala Leu Lys Glu Lys Val Ala
                580               585               590

Ala Leu Lys Glu His His His His His His
        595               600
```

```
<210> SEQ ID NO 248
<211> LENGTH: 611
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248
```

```
Met Tyr Arg Met Gln Leu Leu Ser Cys Ile Ala Leu Ser Leu Ala Leu
1               5               10              15
```

-continued

```
Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Ser Gly Gly Gly Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Thr Phe Asn Thr Tyr Ala Met Asn Trp Val Arg Gln
            165                 170                 175

Ala Pro Gly Lys Gly Leu Glu Trp Val Ala Arg Ile Arg Ser Lys Tyr
        180                 185                 190

Asn Asn Tyr Ala Thr Tyr Tyr Ala Asp Ser Val Lys Asp Arg Phe Thr
        195                 200                 205

Ile Ser Arg Asp Asp Ser Lys Asn Ser Leu Tyr Leu Gln Met Asn Ser
    210                 215                 220

Leu Lys Thr Glu Asp Thr Ala Val Tyr Tyr Cys Val Arg His Gly Asn
225                 230                 235                 240

Phe Gly Asn Ser Tyr Val Ser Trp Phe Ala Tyr Trp Gly Gln Gly Thr
                245                 250                 255

Leu Val Thr Val Ser Ser Gly Gly Cys Gly Gly Gly Glu Val Ala Ala
            260                 265                 270

Leu Glu Lys Glu Val Ala Ala Leu Glu Lys Glu Val Ala Ala Leu Glu
        275                 280                 285

Lys Glu Val Ala Ala Leu Glu Lys Glu Gly Arg Gly Ser Leu Leu Thr
    290                 295                 300

Cys Gly Asp Val Glu Glu Asn Pro Gly Pro Met Tyr Arg Met Gln Leu
305                 310                 315                 320

Leu Ser Cys Ile Ala Leu Ser Leu Ala Leu Val Thr Asn Ser Gln Ala
            325                 330                 335

Val Val Thr Gln Glu Pro Ser Leu Thr Val Ser Pro Gly Gly Thr Val
            340                 345                 350

Thr Leu Thr Cys Arg Ser Ser Thr Gly Ala Val Thr Thr Ser Asn Tyr
        355                 360                 365

Ala Asn Trp Val Gln Gln Lys Pro Gly Gln Ala Pro Arg Gly Leu Ile
    370                 375                 380

Gly Gly Thr Asn Lys Arg Ala Pro Trp Thr Pro Ala Arg Phe Ser Gly
385                 390                 395                 400

Ser Leu Leu Gly Gly Lys Ala Ala Leu Thr Ile Thr Gly Ala Gln Ala
                405                 410                 415

Glu Asp Glu Ala Asp Tyr Tyr Cys Ala Leu Trp Tyr Ser Asn Leu Trp
            420                 425                 430

Val Phe Gly Gly Gly Thr Lys Leu Thr Val Leu Gly Gly Gly Ser Gly
```

-continued

```
              435                    440                    445

Gly Gly Gly Glu Val Gln Leu Val Glu Ser Gly Gly Gly Leu Val Gln
    450                    455                    460

Pro Gly Gly Ser Leu Arg Leu Ser Cys Ala Ala Ser Gly Phe Asn Leu
465                    470                    475                    480

Ser Tyr Ser Asp Ile His Trp Val Arg Gln Ala Pro Gly Lys Gly Leu
                    485                    490                    495

Glu Trp Val Ala Val Val Met Pro Asp Ser Gly His Thr Asn Tyr Ala
                500                    505                    510

Asp Ser Val Lys Gly Arg Phe Thr Ile Ser Ala Asp Thr Ser Lys Asn
                515                    520                    525

Thr Ala Tyr Leu Gln Met Asn Ser Leu Arg Ala Glu Asp Thr Ala Val
    530                    535                    540

Tyr Tyr Cys Ser Arg Ala Thr Asn Ile Pro Val Tyr Ala Phe Asp Tyr
545                    550                    555                    560

Trp Gly Gln Gly Thr Leu Val Thr Val Ser Ser Gly Gly Cys Gly Gly
                565                    570                    575

Gly Lys Val Ala Ala Leu Lys Glu Lys Val Ala Ala Leu Lys Glu Lys
                580                    585                    590

Val Ala Ala Leu Lys Glu Lys Val Ala Ala Leu Lys Glu His His His
    595                    600                    605

His His His
    610
```

```
<210> SEQ ID NO 249
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Met Tyr Arg Met Gln Leu Leu Ser Cys Ile Ala Leu Ser Leu Ala Leu
1                   5                   10                  15

Val Thr Asn Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Ser Gly Gly Gly Gly Gln Val Gln Leu Gln Gln Ser
    130                 135                 140

Gly Ala Glu Leu Ala Arg Pro Gly Ala Ser Val Lys Met Ser Cys Lys
145                 150                 155                 160

Ala Ser Gly Tyr Thr Phe Thr Arg Tyr Thr Met His Trp Val Lys Gln
                165                 170                 175
```

-continued

Arg Pro Gly Gln Gly Leu Glu Trp Ile Gly Tyr Ile Asn Pro Ser Arg
180                185                190

Gly Tyr Thr Asn Tyr Asn Gln Lys Phe Lys Asp Lys Ala Thr Leu Thr
195                200                205

Thr Asp Lys Ser Ser Ser Thr Ala Tyr Met Gln Leu Ser Ser Leu Thr
210                215                220

Ser Glu Asp Ser Ala Val Tyr Tyr Cys Ala Arg Tyr Tyr Asp Asp His
225                230                235                240

Tyr Cys Leu Asp Tyr Trp Gly Gln Gly Thr Thr Leu Thr Val Ser Ser
245                250                255

Gly Gly Cys Gly Gly Gly Glu Val Ala Ala Leu Glu Lys Glu Val Ala
260                265                270

Ala Leu Glu Lys Glu Val Ala Ala Leu Glu Lys Glu Val Ala Ala Leu
275                280                285

Glu Lys Glu Gly Arg Gly Ser Leu Leu Thr Cys Gly Asp Val Glu Glu
290                295                300

Asn Pro Gly Pro Met Tyr Arg Met Gln Leu Leu Ser Cys Ile Ala Leu
305                310                315                320

Ser Leu Ala Leu Val Thr Asn Ser Gln Ile Val Leu Thr Gln Ser Pro
325                330                335

Ala Ile Met Ser Ala Ser Pro Gly Glu Lys Val Thr Met Thr Cys Ser
340                345                350

Ala Ser Ser Ser Val Ser Tyr Met Asn Trp Tyr Gln Gln Lys Ser Gly
355                360                365

Thr Ser Pro Lys Arg Trp Ile Tyr Asp Thr Ser Lys Leu Ala Ser Gly
370                375                380

Val Pro Ala His Phe Arg Gly Ser Gly Ser Gly Thr Ser Tyr Ser Leu
385                390                395                400

Thr Ile Ser Gly Met Glu Ala Glu Asp Ala Ala Thr Tyr Tyr Cys Gln
405                410                415

Gln Trp Ser Ser Asn Pro Phe Thr Phe Gly Ser Gly Thr Lys Leu Glu
420                425                430

Ile Asn Gly Gly Gly Ser Gly Gly Gly Gly Glu Val Gln Leu Val Glu
435                440                445

Ser Gly Gly Gly Leu Val Gln Pro Gly Gly Ser Leu Arg Leu Ser Cys
450                455                460

Ala Ala Ser Gly Phe Asn Leu Ser Tyr Ser Asp Ile His Trp Val Arg
465                470                475                480

Gln Ala Pro Gly Lys Gly Leu Glu Trp Val Ala Val Val Met Pro Asp
485                490                495

Ser Gly His Thr Asn Tyr Ala Asp Ser Val Lys Gly Arg Phe Thr Ile
500                505                510

Ser Ala Asp Thr Ser Lys Asn Thr Ala Tyr Leu Gln Met Asn Ser Leu
515                520                525

Arg Ala Glu Asp Thr Ala Val Tyr Tyr Cys Ser Arg Ala Thr Asn Ile
530                535                540

Pro Val Tyr Ala Phe Asp Tyr Trp Gly Gln Gly Thr Leu Val Thr Val
545                550                555                560

Ser Ser Gly Gly Cys Gly Gly Gly Lys Val Ala Ala Leu Lys Glu Lys
565                570                575

Val Ala Ala Leu Lys Glu Lys Val Ala Ala Leu Lys Glu Lys Val Ala
580                585                590

Ala Leu Lys Glu His His His His His His

```
            595                  600

<210> SEQ ID NO 250
<211> LENGTH: 532
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Tyr Ser Phe Thr Gly Tyr Thr Met Asn Trp Val Arg Gln Ala Pro Gly
                165                 170                 175

Lys Gly Leu Glu Trp Val Ala Leu Ile Asn Pro Tyr Lys Gly Val Ser
            180                 185                 190

Thr Tyr Asn Gln Lys Phe Lys Asp Arg Phe Thr Ile Ser Val Asp Lys
        195                 200                 205

Ser Lys Asn Thr Ala Tyr Leu Gln Met Asn Ser Leu Arg Ala Glu Asp
    210                 215                 220

Thr Ala Val Tyr Tyr Cys Ala Arg Ser Gly Tyr Tyr Gly Asp Ser Asp
225                 230                 235                 240

Trp Tyr Phe Asp Val Trp Gly Gln Gly Thr Leu Val Thr Val Ser Ser
                245                 250                 255

Glu Gly Arg Gly Ser Leu Leu Thr Cys Gly Asp Val Glu Glu Asn Pro
            260                 265                 270

Gly Pro Met Tyr Arg Met Gln Leu Leu Ser Cys Ile Ala Leu Ser Leu
        275                 280                 285

Ala Leu Val Thr Asn Ser Asp Ile Gln Met Thr Gln Ser Pro Ser Ser
    290                 295                 300

Leu Ser Ala Ser Val Gly Asp Arg Val Thr Ile Thr Cys Arg Ala Ser
305                 310                 315                 320

Gln Asp Ile Arg Asn Tyr Leu Asn Trp Tyr Gln Gln Lys Pro Gly Lys
                325                 330                 335

Ala Pro Lys Leu Leu Ile Tyr Tyr Thr Ser Arg Leu Glu Ser Gly Val
            340                 345                 350
```

-continued

```
Pro Ser Arg Phe Ser Gly Ser Gly Ser Gly Thr Asp Tyr Thr Leu Thr
        355             360             365

Ile Ser Ser Leu Gln Pro Glu Asp Phe Ala Thr Tyr Tyr Cys Gln Gln
    370             375             380

Gly Asn Thr Leu Pro Trp Thr Phe Gly Gln Gly Thr Lys Val Glu Ile
385             390             395             400

Lys Gly Gly Gly Gly Ser Glu Val Gln Leu Val Glu Ser Gly Gly Gly
                405             410             415

Leu Val Gln Pro Gly Gly Ser Leu Arg Leu Ser Cys Ala Ala Ser Gly
            420             425             430

Phe Asn Leu Ser Tyr Ser Asp Ile His Trp Val Arg Gln Ala Pro Gly
            435             440             445

Lys Gly Leu Glu Trp Val Ala Val Val Met Pro Asp Ser Gly His Thr
        450             455             460

Asn Tyr Ala Asp Ser Val Lys Gly Arg Phe Thr Ile Ser Ala Asp Thr
465             470             475             480

Ser Lys Asn Thr Ala Tyr Leu Gln Met Asn Ser Leu Arg Ala Glu Asp
            485             490             495

Thr Ala Val Tyr Tyr Cys Ser Arg Ala Thr Asn Ile Pro Val Tyr Ala
            500             505             510

Phe Asp Tyr Trp Gly Gln Gly Thr Leu Val Thr Val Ser Ser His His
            515             520             525

His His His His
    530
```

<210> SEQ ID NO 251
<211> LENGTH: 532
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

```
Met Tyr Arg Met Gln Leu Leu Ser Cys Ile Ala Leu Ser Leu Ala Leu
1               5               10              15

Val Thr Asn Ser Asp Ile Gln Met Thr Gln Ser Pro Ser Ser Leu Ser
            20              25              30

Ala Ser Val Gly Asp Arg Val Thr Ile Thr Cys Arg Ala Ser Gln Asp
            35              40              45

Val Asn Thr Ala Val Ala Trp Tyr Gln Gln Lys Pro Gly Lys Ala Pro
    50              55              60

Lys Leu Leu Ile Tyr Ser Ala Ser Phe Leu Tyr Ser Gly Val Pro Ser
65              70              75              80

Arg Phe Ser Gly Ser Arg Ser Gly Thr Asp Phe Thr Leu Thr Ile Ser
            85              90              95

Ser Leu Gln Pro Glu Asp Phe Ala Thr Tyr Tyr Cys Gln Gln Ser Tyr
            100             105             110

Tyr Tyr Phe Arg Pro Ile Thr Phe Gly Gln Gly Thr Lys Val Glu Ile
            115             120             125

Lys Gly Gly Gly Gly Ser Glu Val Gln Leu Gln Gln Ser Gly Pro Glu
        130             135             140

Leu Val Lys Pro Gly Ala Ser Met Lys Ile Ser Cys Lys Ala Ser Gly
145             150             155             160

Tyr Ser Phe Thr Gly Tyr Thr Met Asn Trp Val Lys Gln Ser His Gly
            165             170             175
```

-continued

```
Lys Asn Leu Glu Trp Met Gly Leu Ile Asn Pro Tyr Lys Gly Val Ser
            180                 185                 190

Thr Tyr Asn Gln Lys Phe Lys Asp Lys Ala Thr Leu Thr Val Asp Lys
            195                 200                 205

Ser Ser Ser Thr Ala Tyr Met Glu Leu Leu Ser Leu Thr Ser Glu Asp
            210                 215                 220

Ser Ala Val Tyr Tyr Cys Ala Arg Ser Gly Tyr Tyr Gly Asp Ser Asp
225                 230                 235                 240

Trp Tyr Phe Asp Val Trp Gly Ala Gly Thr Thr Val Thr Val Ser Ser
                245                 250                 255

Glu Gly Arg Gly Ser Leu Leu Thr Cys Gly Asp Val Glu Glu Asn Pro
            260                 265                 270

Gly Pro Met Tyr Arg Met Gln Leu Leu Ser Cys Ile Ala Leu Ser Leu
            275                 280                 285

Ala Leu Val Thr Asn Ser Asp Ile Gln Met Thr Gln Thr Thr Ser Ser
            290                 295                 300

Leu Ser Ala Ser Leu Gly Asp Arg Val Thr Ile Ser Cys Arg Ala Ser
305                 310                 315                 320

Gln Asp Ile Arg Asn Tyr Leu Asn Trp Tyr Gln Gln Lys Pro Asp Gly
                325                 330                 335

Thr Val Lys Leu Leu Ile Tyr Tyr Thr Ser Arg Leu His Ser Gly Val
            340                 345                 350

Pro Ser Lys Phe Ser Gly Ser Gly Ser Gly Thr Asp Tyr Ser Leu Thr
            355                 360                 365

Ile Ser Asn Leu Glu Gln Glu Asp Ile Ala Thr Tyr Phe Cys Gln Gln
            370                 375                 380

Gly Asn Thr Leu Pro Trp Thr Phe Ala Gly Gly Thr Lys Leu Glu Ile
385                 390                 395                 400

Lys Gly Gly Gly Gly Ser Glu Val Gln Leu Val Glu Ser Gly Gly Gly
                405                 410                 415

Leu Val Gln Pro Gly Gly Ser Leu Arg Leu Ser Cys Ala Ala Ser Gly
            420                 425                 430

Phe Asn Leu Ser Tyr Ser Asp Ile His Trp Val Arg Gln Ala Pro Gly
            435                 440                 445

Lys Gly Leu Glu Trp Val Ala Val Val Met Pro Asp Ser Gly His Thr
            450                 455                 460

Asn Tyr Ala Asp Ser Val Lys Gly Arg Phe Thr Ile Ser Ala Asp Thr
465                 470                 475                 480

Ser Lys Asn Thr Ala Tyr Leu Gln Met Asn Ser Leu Arg Ala Glu Asp
                485                 490                 495

Thr Ala Val Tyr Tyr Cys Ser Arg Ala Thr Asn Ile Pro Val Tyr Ala
                500                 505                 510

Phe Asp Tyr Trp Gly Gln Gly Thr Leu Val Thr Val Ser Ser His His
            515                 520                 525

His His His His
        530
```

```
<210> SEQ ID NO 252
<211> LENGTH: 528
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 252

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Asp Val Gln Leu Val Gln Ser Gly Ala Glu
    130                 135                 140

Val Lys Lys Pro Gly Ala Ser Val Lys Val Ser Cys Lys Ala Ser Gly
145                 150                 155                 160

Tyr Thr Phe Thr Arg Tyr Thr Met His Trp Val Arg Gln Ala Pro Gly
                165                 170                 175

Gln Gly Leu Glu Trp Ile Gly Tyr Ile Asn Pro Ser Arg Gly Tyr Thr
            180                 185                 190

Asn Tyr Ala Asp Ser Val Lys Gly Arg Phe Thr Ile Thr Thr Asp Lys
        195                 200                 205

Ser Thr Ser Thr Ala Tyr Met Glu Leu Ser Ser Leu Arg Ser Glu Asp
    210                 215                 220

Thr Ala Thr Tyr Tyr Cys Ala Arg Tyr Tyr Asp Asp His Tyr Cys Leu
225                 230                 235                 240

Asp Tyr Trp Gly Gln Gly Thr Thr Val Thr Val Ser Ser Glu Gly Arg
                245                 250                 255

Gly Ser Leu Leu Thr Cys Gly Asp Val Glu Glu Asn Pro Gly Pro Met
            260                 265                 270

Tyr Arg Met Gln Leu Leu Ser Cys Ile Ala Leu Ser Leu Ala Leu Val
        275                 280                 285

Thr Asn Ser Asp Ile Val Leu Thr Gln Ser Pro Ala Thr Leu Ser Leu
    290                 295                 300

Ser Pro Gly Glu Arg Ala Thr Leu Ser Cys Arg Ala Ser Gln Ser Val
305                 310                 315                 320

Ser Tyr Met Asn Trp Tyr Gln Gln Lys Pro Gly Lys Ala Pro Lys Arg
                325                 330                 335

Trp Ile Tyr Asp Thr Ser Lys Val Ala Ser Gly Val Pro Ala Arg Phe
            340                 345                 350

Ser Gly Ser Gly Ser Gly Thr Asp Tyr Ser Leu Thr Ile Asn Ser Leu
        355                 360                 365

Glu Ala Glu Asp Ala Ala Thr Tyr Tyr Cys Gln Gln Trp Ser Ser Asn
    370                 375                 380

Pro Leu Thr Phe Gly Gly Gly Thr Lys Val Glu Ile Lys Gly Gly Gly
385                 390                 395                 400

Gly Ser Glu Val Gln Leu Val Glu Ser Gly Gly Gly Leu Val Gln Pro
                405                 410                 415
```

-continued

```
Gly Gly Ser Leu Arg Leu Ser Cys Ala Ala Ser Gly Phe Asn Leu Ser
        420                 425                 430

Tyr Ser Asp Ile His Trp Val Arg Gln Ala Pro Gly Lys Gly Leu Glu
        435                 440                 445

Trp Val Ala Val Val Met Pro Asp Ser Gly His Thr Asn Tyr Ala Asp
    450                 455                 460

Ser Val Lys Gly Arg Phe Thr Ile Ser Ala Asp Thr Ser Lys Asn Thr
465                 470                 475                 480

Ala Tyr Leu Gln Met Asn Ser Leu Arg Ala Glu Asp Thr Ala Val Tyr
                485                 490                 495

Tyr Cys Ser Arg Ala Thr Asn Ile Pro Val Tyr Ala Phe Asp Tyr Trp
            500                 505                 510

Gly Gln Gly Thr Leu Val Thr Val Ser Ser His His His His His His
        515                 520                 525
```

<210> SEQ ID NO 253
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Glu Val Gln Leu Val Glu Ser Gly Gly Gly
        130                 135                 140

Leu Val Gln Pro Gly Gly Ser Leu Arg Leu Ser Cys Ala Ala Ser Gly
145                 150                 155                 160

Phe Thr Phe Asn Thr Tyr Ala Met Asn Trp Val Arg Gln Ala Pro Gly
                165                 170                 175

Lys Gly Leu Glu Trp Val Ala Arg Ile Arg Ser Lys Tyr Asn Asn Tyr
            180                 185                 190

Ala Thr Tyr Tyr Ala Asp Ser Val Lys Asp Arg Phe Thr Ile Ser Arg
        195                 200                 205

Asp Asp Ser Lys Asn Ser Leu Tyr Leu Gln Met Asn Ser Leu Lys Thr
        210                 215                 220

Glu Asp Thr Ala Val Tyr Tyr Cys Val Arg His Gly Asn Phe Gly Asn
225                 230                 235                 240

Ser Tyr Val Ser Trp Phe Ala Tyr Trp Gly Gln Gly Thr Leu Val Thr
```

-continued

```
                    245              250               255

Val Ser Ser Glu Gly Arg Gly Ser Leu Leu Thr Cys Gly Asp Val Glu
                260               265               270

Glu Asn Pro Gly Pro Met Tyr Arg Met Gln Leu Leu Ser Cys Ile Ala
            275               280               285

Leu Ser Leu Ala Leu Val Thr Asn Ser Gln Ala Val Val Thr Gln Glu
        290               295               300

Pro Ser Leu Thr Val Ser Pro Gly Gly Thr Val Thr Leu Thr Cys Arg
    305               310               315               320

Ser Ser Thr Gly Ala Val Thr Thr Ser Asn Tyr Ala Asn Trp Val Gln
                325               330               335

Gln Lys Pro Gly Gln Ala Pro Arg Gly Leu Ile Gly Gly Thr Asn Lys
            340               345               350

Arg Ala Pro Trp Thr Pro Ala Arg Phe Ser Gly Ser Leu Leu Gly Gly
            355               360               365

Lys Ala Ala Leu Thr Ile Thr Gly Ala Gln Ala Glu Asp Glu Ala Asp
        370               375               380

Tyr Tyr Cys Ala Leu Trp Tyr Ser Asn Leu Trp Val Phe Gly Gly Gly
    385               390               395               400

Thr Lys Leu Thr Val Leu Gly Gly Gly Gly Ser Glu Val Gln Leu Val
                405               410               415

Glu Ser Gly Gly Gly Leu Val Gln Pro Gly Gly Ser Leu Arg Leu Ser
            420               425               430

Cys Ala Ala Ser Gly Phe Asn Leu Ser Tyr Ser Asp Ile His Trp Val
            435               440               445

Arg Gln Ala Pro Gly Lys Gly Leu Glu Trp Val Ala Val Val Met Pro
        450               455               460

Asp Ser Gly His Thr Asn Tyr Ala Asp Ser Val Lys Gly Arg Phe Thr
    465               470               475               480

Ile Ser Ala Asp Thr Ser Lys Asn Thr Ala Tyr Leu Gln Met Asn Ser
                485               490               495

Leu Arg Ala Glu Asp Thr Ala Val Tyr Tyr Cys Ser Arg Ala Thr Asn
            500               505               510

Ile Pro Val Tyr Ala Phe Asp Tyr Trp Gly Gln Gly Thr Leu Val Thr
            515               520               525

Val Ser Ser His His His His His His
    530               535
```

<210> SEQ ID NO 254
<211> LENGTH: 528
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60
```

-continued

```
Lys Leu Leu Ile Tyr Ser Ala Ser Phe Leu Tyr Ser Gly Val Pro Ser
65              70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
            115                 120                 125

Lys Gly Gly Gly Gly Ser Gln Val Gln Leu Gln Gln Ser Gly Ala Glu
    130                 135                 140

Leu Ala Arg Pro Gly Ala Ser Val Lys Met Ser Cys Lys Ala Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
            180                 185                 190

Asn Tyr Asn Gln Lys Phe Lys Asp Lys Ala Thr Leu Thr Thr Asp Lys
            195                 200                 205

Ser Ser Ser Thr Ala Tyr Met Gln Leu Ser Ser Leu Thr Ser Glu Asp
    210                 215                 220

Ser Ala Val Tyr Tyr Cys Ala Arg Tyr Tyr Asp Asp His Tyr Cys Leu
225                 230                 235                 240

Asp Tyr Trp Gly Gln Gly Thr Thr Leu Thr Val Ser Ser Glu Gly Arg
            245                 250                 255

Gly Ser Leu Leu Thr Cys Gly Asp Val Glu Glu Asn Pro Gly Pro Met
            260                 265                 270

Tyr Arg Met Gln Leu Leu Ser Cys Ile Ala Leu Ser Leu Ala Leu Val
    275                 280                 285

Thr Asn Ser Gln Ile Val Leu Thr Gln Ser Pro Ala Ile Met Ser Ala
    290                 295                 300

Ser Pro Gly Glu Lys Val Thr Met Thr Cys Ser Ala Ser Ser Ser Val
305                 310                 315                 320

Ser Tyr Met Asn Trp Tyr Gln Gln Lys Ser Gly Thr Ser Pro Lys Arg
                325                 330                 335

Trp Ile Tyr Asp Thr Ser Lys Leu Ala Ser Gly Val Pro Ala His Phe
            340                 345                 350

Arg Gly Ser Gly Ser Gly Thr Ser Tyr Ser Leu Thr Ile Ser Gly Met
            355                 360                 365

Glu Ala Glu Asp Ala Ala Thr Tyr Tyr Cys Gln Gln Trp Ser Ser Asn
    370                 375                 380

Pro Phe Thr Phe Gly Ser Gly Thr Lys Leu Glu Ile Asn Gly Gly Gly
385                 390                 395                 400

Gly Ser Glu Val Gln Leu Val Glu Ser Gly Gly Gly Leu Val Gln Pro
            405                 410                 415

Gly Gly Ser Leu Arg Leu Ser Cys Ala Ala Ser Gly Phe Asn Leu Ser
            420                 425                 430

Tyr Ser Asp Ile His Trp Val Arg Gln Ala Pro Gly Lys Gly Leu Glu
            435                 440                 445

Trp Val Ala Val Val Met Pro Asp Ser Gly His Thr Asn Tyr Ala Asp
    450                 455                 460

Ser Val Lys Gly Arg Phe Thr Ile Ser Ala Asp Thr Ser Lys Asn Thr
465                 470                 475                 480

Ala Tyr Leu Gln Met Asn Ser Leu Arg Ala Glu Asp Thr Ala Val Tyr
```

```
              485             490             495
Tyr Cys Ser Arg Ala Thr Asn Ile Pro Val Tyr Ala Phe Asp Tyr Trp
        500             505             510
Gly Gln Gly Thr Leu Val Thr Val Ser Ser His His His His His His
        515             520             525
```

<210> SEQ ID NO 255
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

```
Met Tyr Arg Met Gln Leu Leu Ser Cys Ile Ala Leu Ser Leu Ala Leu
1               5               10              15
Val Thr Asn Ser Asp Ile Gln Met Thr Gln Ser Pro Ser Ser Leu Ser
            20              25              30
Ala Ser Val Gly Asp Arg Val Thr Ile Thr Cys Arg Ala Ser Gln Asp
        35              40              45
Val Asn Thr Ala Val Ala Trp Tyr Gln Gln Lys Pro Gly Lys Ala Pro
    50              55              60
Lys Leu Leu Ile Tyr Ser Ala Ser Phe Leu Tyr Ser Gly Val Pro Ser
65              70              75              80
Arg Phe Ser Gly Ser Arg Ser Gly Thr Asp Phe Thr Leu Thr Ile Ser
            85              90              95
Ser Leu Gln Pro Glu Asp Phe Ala Thr Tyr Tyr Cys Gln Gln Ser Tyr
            100             105             110
Tyr Tyr Phe Arg Pro Ile Thr Phe Gly Gln Gly Thr Lys Val Glu Ile
        115             120             125
Lys Gly Gly Gly Gly Ser Gly Gly Gly Gly Ser Gly Gly Gly Gly Ser
    130             135             140
Glu Val Gln Leu Val Glu Ser Gly Gly Gly Leu Val Gln Pro Gly Gly
145             150             155             160
Ser Leu Arg Leu Ser Cys Ala Ala Ser Gly Phe Asn Leu Ser Tyr Ser
            165             170             175
Asp Ile His Trp Val Arg Gln Ala Pro Gly Lys Gly Leu Glu Trp Val
            180             185             190
Ala Val Val Met Pro Asp Ser Gly His Thr Asn Tyr Ala Asp Ser Val
        195             200             205
Lys Gly Arg Phe Thr Ile Ser Ala Asp Thr Ser Lys Asn Thr Ala Tyr
    210             215             220
Leu Gln Met Asn Ser Leu Arg Ala Glu Asp Thr Ala Val Tyr Tyr Cys
225             230             235             240
Ser Arg Ala Thr Asn Ile Pro Val Tyr Ala Phe Asp Tyr Trp Gly Gln
            245             250             255
Gly Thr Leu Val Thr Val Ser Ser Gly Gly Gly Ser Glu Pro Lys
            260             265             270
Ser Ser Asp Lys Thr His Thr Cys Pro Pro Cys Pro Ala Pro Glu Leu
            275             280             285
Leu Gly Gly Pro Ser Val Phe Leu Phe Pro Pro Lys Pro Lys Asp Thr
    290             295             300
Leu Met Ile Ser Arg Thr Pro Glu Val Thr Cys Val Val Val Asp Val
305             310             315             320
```

-continued

```
Ser His Glu Asp Pro Glu Val Lys Phe Asn Trp Tyr Val Asp Gly Val
            325                 330                 335

Glu Val His Asn Ala Lys Thr Lys Pro Arg Glu Glu Gln Tyr Ala Ser
            340                 345                 350

Thr Tyr Arg Val Val Ser Val Leu Thr Val Leu His Gln Asp Trp Leu
            355                 360                 365

Asn Gly Lys Glu Tyr Lys Cys Lys Val Ser Asn Lys Ala Leu Pro Ala
        370                 375                 380

Pro Ile Ala Lys Thr Ile Ser Lys Ala Lys Gly Gln Pro Arg Glu Pro
385                 390                 395                 400

Gln Val Cys Thr Leu Pro Pro Ser Arg Glu Glu Met Thr Lys Asn Gln
                405                 410                 415

Val Ser Leu Ser Cys Ala Val Lys Gly Phe Tyr Pro Ser Asp Ile Ala
            420                 425                 430

Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Val Ser Lys Leu
        450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys His His His His His
            500                 505
```

<210> SEQ ID NO 256
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Arg Asn Tyr Leu Asn Trp Tyr Gln Gln Lys Pro Gly Lys Ala Pro
        50                  55                  60

Lys Leu Leu Ile Tyr Tyr Thr Ser Arg Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Gly Asn
            100                 105                 110

Thr Leu Pro Trp Thr Phe Gly Gln Gly Thr Lys Val Glu Ile Lys Gly
            115                 120                 125

Gly Gly Gly Ser Gly Gly Gly Gly Ser Gly Gly Gly Gly Ser Glu Val
        130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Tyr Ser Phe Thr Gly Tyr Thr Met
                165                 170                 175
```

-continued

```
Asn Trp Val Arg Gln Ala Pro Gly Lys Gly Leu Glu Trp Val Ala Leu
        180                 185                 190

Ile Asn Pro Tyr Lys Gly Val Ser Thr Tyr Asn Gln Lys Phe Lys Asp
        195                 200                 205

Arg Phe Thr Ile Ser Val Asp Lys Ser Lys Asn Thr Ala Tyr Leu Gln
        210                 215                 220

Met Asn Ser Leu Arg Ala Glu Asp Thr Ala Val Tyr Tyr Cys Ala Arg
225                 230                 235                 240

Ser Gly Tyr Tyr Gly Asp Ser Asp Trp Tyr Phe Asp Val Trp Gly Gln
                245                 250                 255

Gly Thr Leu Val Thr Val Ser Ser Gly Gly Gly Gly Ser Glu Pro Lys
        260                 265                 270

Ser Ser Asp Lys Thr His Thr Cys Pro Pro Cys Pro Ala Pro Glu Leu
        275                 280                 285

Leu Gly Gly Pro Ser Val Phe Leu Phe Pro Pro Lys Pro Lys Asp Thr
        290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Ala Ser
                340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
        370                 375                 380

Pro Ile Ala Lys Thr Ile Ser Lys Ala Lys Gly Gln Pro Arg Glu Pro
385                 390                 395                 400

Gln Val Tyr Thr Leu Pro Pro Cys Arg Glu Glu Met Thr Lys Asn Gln
                405                 410                 415

Val Ser Leu Trp Cys Leu Val Lys Gly Phe Tyr Pro Ser Asp Ile Ala
                420                 425                 430

Val Glu Trp Glu Ser Asn Gly Gln Pro Glu Asn Asn Tyr Lys Thr Thr
                435                 440                 445

Pro Pro Val Leu Asp Ser Asp Gly Ser Phe Phe Leu Tyr Ser Lys Leu
        450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
                500
```

```
<210> SEQ ID NO 257
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Met Tyr Arg Met Gln Leu Leu Ser Cys Ile Ala Leu Ser Leu Ala Leu
1               5                   10                  15

Val Thr Asn Ser Asp Ile Gln Met Thr Gln Thr Thr Ser Ser Leu Ser
```

-continued

```
            20              25              30
Ala Ser Leu Gly Asp Arg Val Thr Ile Ser Cys Arg Ala Ser Gln Asp
            35              40              45
Ile Arg Asn Tyr Leu Asn Trp Tyr Gln Gln Lys Pro Asp Gly Thr Val
        50              55              60
Lys Leu Leu Ile Tyr Tyr Thr Ser Arg Leu His Ser Gly Val Pro Ser
65              70              75              80
Lys Phe Ser Gly Ser Gly Ser Gly Thr Asp Tyr Ser Leu Thr Ile Ser
                85              90              95
Asn Leu Glu Gln Glu Asp Ile Ala Thr Tyr Phe Cys Gln Gln Gly Asn
                100             105             110
Thr Leu Pro Trp Thr Phe Ala Gly Gly Thr Lys Leu Glu Ile Lys Gly
            115             120             125
Gly Gly Gly Ser Gly Gly Gly Gly Ser Gly Gly Gly Ser Glu Val
            130             135             140
Gln Leu Gln Gln Ser Gly Pro Glu Leu Val Lys Pro Gly Ala Ser Met
145             150             155             160
Lys Ile Ser Cys Lys Ala Ser Gly Tyr Ser Phe Thr Gly Tyr Thr Met
                165             170             175
Asn Trp Val Lys Gln Ser His Gly Lys Asn Leu Glu Trp Met Gly Leu
            180             185             190
Ile Asn Pro Tyr Lys Gly Val Ser Thr Tyr Asn Gln Lys Phe Lys Asp
            195             200             205
Lys Ala Thr Leu Thr Val Asp Lys Ser Ser Ser Thr Ala Tyr Met Glu
        210             215             220
Leu Leu Ser Leu Thr Ser Glu Asp Ser Ala Val Tyr Tyr Cys Ala Arg
225             230             235             240
Ser Gly Tyr Tyr Gly Asp Ser Asp Trp Tyr Phe Asp Val Trp Gly Ala
                245             250             255
Gly Thr Thr Val Thr Val Ser Ser Gly Gly Gly Ser Glu Pro Lys
            260             265             270
Ser Ser Asp Lys Thr His Thr Cys Pro Pro Cys Pro Ala Pro Glu Leu
            275             280             285
Leu Gly Gly Pro Ser Val Phe Leu Phe Pro Pro Lys Pro Lys Asp Thr
        290             295             300
Leu Met Ile Ser Arg Thr Pro Glu Val Thr Cys Val Val Val Asp Val
305             310             315             320
Ser His Glu Asp Pro Glu Val Lys Phe Asn Trp Tyr Val Asp Gly Val
                325             330             335
Glu Val His Asn Ala Lys Thr Lys Pro Arg Glu Glu Gln Tyr Ala Ser
            340             345             350
Thr Tyr Arg Val Val Ser Val Leu Thr Val Leu His Gln Asp Trp Leu
            355             360             365
Asn Gly Lys Glu Tyr Lys Cys Lys Val Ser Asn Lys Ala Leu Pro Ala
        370             375             380
Pro Ile Ala Lys Thr Ile Ser Lys Ala Lys Gly Gln Pro Arg Glu Pro
385             390             395             400
Gln Val Tyr Thr Leu Pro Pro Cys Arg Glu Glu Met Thr Lys Asn Gln
                405             410             415
Val Ser Leu Trp Cys Leu Val Lys Gly Phe Tyr Pro Ser Asp Ile Ala
            420             425             430
Val Glu Trp Glu Ser Asn Gly Gln Pro Glu Asn Asn Tyr Lys Thr Thr
            435             440             445
```

```
Pro Pro Val Leu Asp Ser Asp Gly Ser Phe Phe Leu Tyr Ser Lys Leu
    450             455             460

Thr Val Asp Lys Ser Arg Trp Gln Gln Gly Asn Val Phe Ser Cys Ser
465             470             475             480

Val Met His Glu Ala Leu His Asn His Tyr Thr Gln Lys Ser Leu Ser
            485             490             495

Leu Ser Pro Gly Lys
            500

<210> SEQ ID NO 258
<211> LENGTH: 755
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Met Tyr Arg Met Gln Leu Leu Ser Cys Ile Ala Leu Ser Leu Ala Leu
1               5               10              15

Val Thr Asn Ser Asp Ile Gln Met Thr Gln Ser Pro Ser Ser Leu Ser
            20              25              30

Ala Ser Val Gly Asp Arg Val Thr Ile Thr Cys Arg Ala Ser Gln Asp
            35              40              45

Val Asn Thr Ala Val Ala Trp Tyr Gln Gln Lys Pro Gly Lys Ala Pro
    50              55              60

Lys Leu Leu Ile Tyr Ser Ala Ser Phe Leu Tyr Ser Gly Val Pro Ser
65              70              75              80

Arg Phe Ser Gly Ser Arg Ser Gly Thr Asp Phe Thr Leu Thr Ile Ser
            85              90              95

Ser Leu Gln Pro Glu Asp Phe Ala Thr Tyr Tyr Cys Gln Gln Ser Tyr
            100             105             110

Tyr Tyr Phe Arg Pro Ile Thr Phe Gly Gln Gly Thr Lys Val Glu Ile
            115             120             125

Lys Gly Gly Gly Gly Ser Gly Gly Gly Gly Ser Gly Gly Gly Gly Ser
    130             135             140

Glu Val Gln Leu Val Glu Ser Gly Gly Gly Leu Val Gln Pro Gly Gly
145             150             155             160

Ser Leu Arg Leu Ser Cys Ala Ala Ser Gly Phe Asn Leu Ser Tyr Ser
            165             170             175

Asp Ile His Trp Val Arg Gln Ala Pro Gly Lys Gly Leu Glu Trp Val
            180             185             190

Ala Val Val Met Pro Asp Ser Gly His Thr Asn Tyr Ala Asp Ser Val
            195             200             205

Lys Gly Arg Phe Thr Ile Ser Ala Asp Thr Ser Lys Asn Thr Ala Tyr
    210             215             220

Leu Gln Met Asn Ser Leu Arg Ala Glu Asp Thr Ala Val Tyr Tyr Cys
225             230             235             240

Ser Arg Ala Thr Asn Ile Pro Val Tyr Ala Phe Asp Tyr Trp Gly Gln
            245             250             255

Gly Thr Leu Val Thr Val Ser Ser Gly Gly Gly Ser Glu Pro Lys
            260             265             270

Ser Ser Asp Lys Thr His Thr Cys Pro Pro Cys Pro Ala Pro Glu Leu
            275             280             285

Leu Gly Gly Pro Ser Val Phe Leu Phe Pro Pro Lys Pro Lys Asp Thr
```

-continued

```
        290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Ala Ser
                340                 345                 350

Thr Tyr Arg Val Val Ser Val Leu Thr Val Leu His Gln Asp Trp Leu
            355                 360                 365

Asn Gly Lys Glu Tyr Lys Cys Lys Val Ser Asn Lys Ala Leu Pro Ala
            370                 375                 380

Pro Ile Ala Lys Thr Ile Ser Lys Ala Lys Gly Gln Pro Arg Glu Pro
385                 390                 395                 400

Gln Val Tyr Thr Leu Pro Pro Cys Arg Glu Glu Met Thr Lys Asn Gln
                405                 410                 415

Val Ser Leu Trp Cys Leu Val Lys Gly Phe Tyr Pro Ser Asp Ile Ala
                420                 425                 430

Val Glu Trp Glu Ser Asn Gly Gln Pro Glu Asn Asn Tyr Lys Thr Thr
                435                 440                 445

Pro Pro Val Leu Asp Ser Asp Gly Ser Phe Phe Leu Tyr Ser Lys Leu
    450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys Ala Ser Gly Gly Gly Ser Gly Gly Gly Ser Glu
                500                 505                 510

Val Gln Leu Val Glu Ser Gly Gly Gly Leu Val Gln Pro Gly Gly Ser
                515                 520                 525

Leu Arg Leu Ser Cys Ala Ala Ser Gly Tyr Ser Phe Thr Gly Tyr Thr
    530                 535                 540

Met Asn Trp Val Arg Gln Ala Pro Gly Lys Gly Leu Glu Trp Val Ala
545                 550                 555                 560

Leu Ile Asn Pro Tyr Lys Gly Val Ser Thr Tyr Asn Gln Lys Phe Lys
                565                 570                 575

Asp Arg Phe Thr Ile Ser Val Asp Lys Ser Lys Asn Thr Ala Tyr Leu
                580                 585                 590

Gln Met Asn Ser Leu Arg Ala Glu Asp Thr Ala Val Tyr Tyr Cys Ala
            595                 600                 605

Arg Ser Gly Tyr Tyr Gly Asp Ser Asp Trp Tyr Phe Asp Val Trp Gly
    610                 615                 620

Gln Gly Thr Leu Val Thr Val Ser Ser Gly Gly Gly Ser Gly Gly
625                 630                 635                 640

Gly Gly Ser Gly Gly Gly Gly Ser Asp Ile Gln Met Thr Gln Ser Pro
                645                 650                 655

Ser Ser Leu Ser Ala Ser Val Gly Asp Arg Val Thr Ile Thr Cys Arg
            660                 665                 670

Ala Ser Gln Asp Ile Arg Asn Tyr Leu Asn Trp Tyr Gln Gln Lys Pro
            675                 680                 685

Gly Lys Ala Pro Lys Leu Leu Ile Tyr Tyr Thr Ser Arg Leu Glu Ser
    690                 695                 700

Gly Val Pro Ser Arg Phe Ser Gly Ser Gly Ser Gly Thr Asp Tyr Thr
705                 710                 715                 720
```

-continued

```
Leu Thr Ile Ser Ser Leu Gln Pro Glu Asp Phe Ala Thr Tyr Tyr Cys
            725                 730                 735

Gln Gln Gly Asn Thr Leu Pro Trp Thr Phe Gly Gln Gly Thr Lys Val
            740                 745                 750

Glu Ile Lys
        755

<210> SEQ ID NO 259
<211> LENGTH: 755
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
            85                  90                  95

Ser Leu Gln Pro Glu Asp Phe Ala Thr Tyr Tyr Cys Gln Gln Ser Tyr
            100                 105                 110

Tyr Tyr Phe Arg Pro Ile Thr Phe Gly Gln Gly Thr Lys Val Glu Ile
        115                 120                 125

Lys Gly Gly Gly Gly Ser Gly Gly Gly Gly Ser Gly Gly Gly Gly Ser
        130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Asn Leu Ser Tyr Ser
            165                 170                 175

Asp Ile His Trp Val Arg Gln Ala Pro Gly Lys Gly Leu Glu Trp Val
            180                 185                 190

Ala Val Val Met Pro Asp Ser Gly His Thr Asn Tyr Ala Asp Ser Val
        195                 200                 205

Lys Gly Arg Phe Thr Ile Ser Ala Asp Thr Ser Lys Asn Thr Ala Tyr
    210                 215                 220

Leu Gln Met Asn Ser Leu Arg Ala Glu Asp Thr Ala Val Tyr Tyr Cys
225                 230                 235                 240

Ser Arg Ala Thr Asn Ile Pro Val Tyr Ala Phe Asp Tyr Trp Gly Gln
            245                 250                 255

Gly Thr Leu Val Thr Val Ser Ser Gly Gly Gly Ser Glu Pro Lys
            260                 265                 270

Ser Ser Asp Lys Thr His Thr Cys Pro Pro Cys Pro Ala Pro Glu Leu
            275                 280                 285

Leu Gly Gly Pro Ser Val Phe Leu Phe Pro Pro Lys Pro Lys Asp Thr
    290                 295                 300

Leu Met Ile Ser Arg Thr Pro Glu Val Thr Cys Val Val Val Asp Val
```

-continued

```
305                310                315                320

Ser His Glu Asp Pro Glu Val Lys Phe Asn Trp Tyr Val Asp Gly Val
             325                330                335

Glu Val His Asn Ala Lys Thr Lys Pro Arg Glu Glu Gln Tyr Ala Ser
             340                345                350

Thr Tyr Arg Val Val Ser Val Leu Thr Val Leu His Gln Asp Trp Leu
             355                360                365

Asn Gly Lys Glu Tyr Lys Cys Lys Val Ser Asn Lys Ala Leu Pro Ala
             370                375                380

Pro Ile Ala Lys Thr Ile Ser Lys Ala Lys Gly Gln Pro Arg Glu Pro
385                390                395                400

Gln Val Tyr Thr Leu Pro Pro Cys Arg Glu Glu Met Thr Lys Asn Gln
                 405                410                415

Val Ser Leu Trp Cys Leu Val Lys Gly Phe Tyr Pro Ser Asp Ile Ala
             420                425                430

Val Glu Trp Glu Ser Asn Gly Gln Pro Glu Asn Asn Tyr Lys Thr Thr
             435                440                445

Pro Pro Val Leu Asp Ser Asp Gly Ser Phe Phe Leu Tyr Ser Lys Leu
             450                455                460

Thr Val Asp Lys Ser Arg Trp Gln Gln Gly Asn Val Phe Ser Cys Ser
465                470                475                480

Val Met His Glu Ala Leu His Asn His Tyr Thr Gln Lys Ser Leu Ser
                 485                490                495

Leu Ser Pro Gly Lys Ala Ser Gly Gly Gly Ser Gly Gly Gly Ser Glu
             500                505                510

Val Gln Leu Gln Gln Ser Gly Pro Glu Leu Val Lys Pro Gly Ala Ser
             515                520                525

Met Lys Ile Ser Cys Lys Ala Ser Gly Tyr Ser Phe Thr Gly Tyr Thr
             530                535                540

Met Asn Trp Val Lys Gln Ser His Gly Lys Asn Leu Glu Trp Met Gly
545                550                555                560

Leu Ile Asn Pro Tyr Lys Gly Val Ser Thr Tyr Asn Gln Lys Phe Lys
                 565                570                575

Asp Lys Ala Thr Leu Thr Val Asp Lys Ser Ser Ser Thr Ala Tyr Met
                 580                585                590

Glu Leu Leu Ser Leu Thr Ser Glu Asp Ser Ala Val Tyr Tyr Cys Ala
                 595                600                605

Arg Ser Gly Tyr Tyr Gly Asp Ser Asp Trp Tyr Phe Asp Val Trp Gly
             610                615                620

Ala Gly Thr Thr Val Thr Val Ser Ser Gly Gly Gly Ser Gly Gly
625                630                635                640

Gly Gly Ser Gly Gly Gly Gly Ser Asp Ile Gln Met Thr Gln Thr Thr
                 645                650                655

Ser Ser Leu Ser Ala Ser Leu Gly Asp Arg Val Thr Ile Ser Cys Arg
             660                665                670

Ala Ser Gln Asp Ile Arg Asn Tyr Leu Asn Trp Tyr Gln Gln Lys Pro
             675                680                685

Asp Gly Thr Val Lys Leu Leu Ile Tyr Tyr Thr Ser Arg Leu His Ser
             690                695                700

Gly Val Pro Ser Lys Phe Ser Gly Ser Gly Ser Gly Thr Asp Tyr Ser
705                710                715                720

Leu Thr Ile Ser Asn Leu Glu Gln Glu Asp Ile Ala Thr Tyr Phe Cys
                 725                730                735
```

```
Gln Gln Gly Asn Thr Leu Pro Trp Thr Phe Ala Gly Gly Thr Lys Leu
            740                 745                 750

Glu Ile Lys
        755

<210> SEQ ID NO 260
<211> LENGTH: 10
<212> TYPE: PRT
<213> ORGANISM: Homo sapiens

<400> SEQUENCE: 260

Ile Ile Val Gly Ala Ile Gly Val Gly Lys
1               5               10

<210> SEQ ID NO 261
<211> LENGTH: 12
<212> TYPE: PRT
<213> ORGANISM: Homo sapiens

<400> SEQUENCE: 261

Leu Ile Ile Val Gly Ala Ile Gly Val Gly Lys Thr
1               5               10

<210> SEQ ID NO 262
<211> LENGTH: 9
<212> TYPE: PRT
<213> ORGANISM: Homo sapiens

<400> SEQUENCE: 262

Ile Val Gly Ala Ile Gly Val Gly Lys
1               5

<210> SEQ ID NO 263
<211> LENGTH: 11
<212> TYPE: PRT
<213> ORGANISM: Homo sapiens

<400> SEQUENCE: 263

Leu Ala Val Val Gly Pro Val Gly Ala Gly Lys
1               5               10

<210> SEQ ID NO 264
<211> LENGTH: 9
<212> TYPE: PRT
<213> ORGANISM: Homo sapiens

<400> SEQUENCE: 264

Val Val Gly Pro Val Gly Ala Gly Lys
1               5

<210> SEQ ID NO 265
<211> LENGTH: 10
<212> TYPE: PRT
<213> ORGANISM: Homo sapiens

<400> SEQUENCE: 265

Ala Val Val Gly Pro Val Gly Ala Gly Lys
1               5               10

<210> SEQ ID NO 266
<211> LENGTH: 10
<212> TYPE: PRT
<213> ORGANISM: Homo sapiens
```

-continued

```
<400> SEQUENCE: 266

Val Val Val Gly Asn Val Gly Phe Gly Lys
1               5                   10

<210> SEQ ID NO 267
<211> LENGTH: 9
<212> TYPE: PRT
<213> ORGANISM: Homo sapiens

<400> SEQUENCE: 267

Val Val Gly Asn Val Gly Phe Gly Lys
1               5

<210> SEQ ID NO 268
<211> LENGTH: 10
<212> TYPE: PRT
<213> ORGANISM: Homo sapiens

<400> SEQUENCE: 268

Val Val Val Gly Ala Ser Gly Val Gly Lys
1               5                   10

<210> SEQ ID NO 269
<211> LENGTH: 9
<212> TYPE: PRT
<213> ORGANISM: Homo sapiens

<400> SEQUENCE: 269

Val Val Gly Ala Ser Gly Val Gly Lys
1               5

<210> SEQ ID NO 270
<211> LENGTH: 10
<212> TYPE: PRT
<213> ORGANISM: Homo sapiens

<400> SEQUENCE: 270

Lys Val Val Gly Ala Arg Gly Val Gly Lys
1               5                   10

<210> SEQ ID NO 271
<211> LENGTH: 9
<212> TYPE: PRT
<213> ORGANISM: Homo sapiens

<400> SEQUENCE: 271

Val Val Gly Ala Arg Gly Val Gly Lys
1               5

<210> SEQ ID NO 272
<211> LENGTH: 15
<212> TYPE: PRT
<213> ORGANISM: Homo sapiens

<400> SEQUENCE: 272

Leu Gly Ser Val Gln Leu Cys Gly Val Gly Lys Phe Pro Ser Leu
1               5                   10                  15

<210> SEQ ID NO 273
<211> LENGTH: 9
<212> TYPE: PRT
<213> ORGANISM: Homo sapiens

<400> SEQUENCE: 273
```

```
Ser Val Gln Leu Cys Gly Val Gly Lys
1               5

<210> SEQ ID NO 274
<211> LENGTH: 14
<212> TYPE: PRT
<213> ORGANISM: Homo sapiens

<400> SEQUENCE: 274

Ser Arg Asn Val Val Ile Ala Ala Asp Gly Val Leu Lys Ile
1               5                   10

<210> SEQ ID NO 275
<211> LENGTH: 9
<212> TYPE: PRT
<213> ORGANISM: Homo sapiens

<400> SEQUENCE: 275

Val Ile Ala Ala Asp Gly Val Leu Lys
1               5

<210> SEQ ID NO 276
<211> LENGTH: 10
<212> TYPE: PRT
<213> ORGANISM: Homo sapiens

<400> SEQUENCE: 276

Val Val Ile Ala Ala Asp Gly Val Leu Lys
1               5                   10

<210> SEQ ID NO 277
<211> LENGTH: 10
<212> TYPE: PRT
<213> ORGANISM: Homo sapiens

<400> SEQUENCE: 277

Val Val Val Gly Asp Gly Gly Val Gly Lys
1               5                   10

<210> SEQ ID NO 278
<211> LENGTH: 13
<212> TYPE: PRT
<213> ORGANISM: Homo sapiens

<400> SEQUENCE: 278

Trp Ala Val Val Ser Gly Ala Thr Asp Gly Ile Gly Lys
1               5                   10

<210> SEQ ID NO 279
<211> LENGTH: 10
<212> TYPE: PRT
<213> ORGANISM: Homo sapiens

<400> SEQUENCE: 279

Val Ser Gly Ala Thr Asp Gly Ile Gly Lys
1               5                   10

<210> SEQ ID NO 280
<211> LENGTH: 13
<212> TYPE: PRT
<213> ORGANISM: Homo sapiens

<400> SEQUENCE: 280

Lys Cys Phe Ile Val Gly Ala Asp Asn Val Gly Ser Lys
1               5                   10
```

-continued

```
<210> SEQ ID NO 281
<211> LENGTH: 10
<212> TYPE: PRT
<213> ORGANISM: Homo sapiens

<400> SEQUENCE: 281

Ile Val Gly Ala Asp Asn Val Gly Ser Lys
1               5               10

<210> SEQ ID NO 282
<211> LENGTH: 13
<212> TYPE: PRT
<213> ORGANISM: Homo sapiens

<400> SEQUENCE: 282

Lys Cys Val Val Val Gly Asp Gly Ala Val Gly Lys Thr
1               5               10

<210> SEQ ID NO 283
<211> LENGTH: 10
<212> TYPE: PRT
<213> ORGANISM: Homo sapiens

<400> SEQUENCE: 283

Val Val Val Gly Asp Gly Ala Val Gly Lys
1               5               10

<210> SEQ ID NO 284
<211> LENGTH: 12
<212> TYPE: PRT
<213> ORGANISM: Homo sapiens

<400> SEQUENCE: 284

Val Val Val Gly Val Gly Gly Ala Val Gly Val Gly
1               5               10

<210> SEQ ID NO 285
<211> LENGTH: 12
<212> TYPE: PRT
<213> ORGANISM: Homo sapiens

<400> SEQUENCE: 285

Val Val Val Gly Val Val Gly Met Gly His Val Pro
1               5               10

<210> SEQ ID NO 286
<211> LENGTH: 14
<212> TYPE: PRT
<213> ORGANISM: Homo sapiens

<400> SEQUENCE: 286

Ala Gly Glu Lys Val Gly Ile Val Gly Arg Thr Gly Ala Gly
1               5               10

<210> SEQ ID NO 287
<211> LENGTH: 15
<212> TYPE: PRT
<213> ORGANISM: Homo sapiens

<400> SEQUENCE: 287

Leu Gln Val Val Gly Val Val Ser Val Ala Val Ala Val Ile Pro
1               5               10              15
```

-continued

```
<210> SEQ ID NO 288
<211> LENGTH: 15
<212> TYPE: PRT
<213> ORGANISM: Homo sapiens

<400> SEQUENCE: 288

Arg Leu Val Val Leu Val Gly Pro Val Gly Val Gly Leu Asn Glu
1               5               10              15

<210> SEQ ID NO 289
<211> LENGTH: 13
<212> TYPE: PRT
<213> ORGANISM: Homo sapiens

<400> SEQUENCE: 289

Leu Arg Val Ile Gly Ala Val Gly Ile Gly Ile Ala Cys
1               5               10

<210> SEQ ID NO 290
<211> LENGTH: 13
<212> TYPE: PRT
<213> ORGANISM: Homo sapiens

<400> SEQUENCE: 290

Ala Glu Asn Arg Gly Ala Val Val Val Gly Asn Val Gly
1               5               10

<210> SEQ ID NO 291
<211> LENGTH: 12
<212> TYPE: PRT
<213> ORGANISM: Homo sapiens

<400> SEQUENCE: 291

Asp Val Val Val Asp Ala Phe Cys Gly Val Gly Gly
1               5               10

<210> SEQ ID NO 292
<211> LENGTH: 14
<212> TYPE: PRT
<213> ORGANISM: Homo sapiens

<400> SEQUENCE: 292

Val Ser Leu Ala Gly Ala Cys Gly Val Gly Gly Tyr Gly Ser
1               5               10

<210> SEQ ID NO 293
<211> LENGTH: 14
<212> TYPE: PRT
<213> ORGANISM: Homo sapiens

<400> SEQUENCE: 293

His Ser Leu Pro Gly Ala Cys Gly Val Gly Pro Pro Arg Ala
1               5               10

<210> SEQ ID NO 294
<211> LENGTH: 13
<212> TYPE: PRT
<213> ORGANISM: Homo sapiens

<400> SEQUENCE: 294

Glu Thr Glu Val Gly Pro Cys Gly Val Gly Glu Ala Ser
1               5               10

<210> SEQ ID NO 295
<211> LENGTH: 13
```

<210> TYPE: PRT
<213> ORGANISM: Homo sapiens

<400> SEQUENCE: 295

Thr Leu Gly Leu Val Gly Pro Cys Gly Val Gly Gly Ala
1               5                   10

<210> SEQ ID NO 296
<211> LENGTH: 13
<212> TYPE: PRT
<213> ORGANISM: Homo sapiens

<400> SEQUENCE: 296

Leu Gln His Val Val Leu Ala Ala Cys Ala Leu Leu Cys
1               5                   10

<210> SEQ ID NO 297
<211> LENGTH: 12
<212> TYPE: PRT
<213> ORGANISM: Homo sapiens

<400> SEQUENCE: 297

Glu Lys Asp Lys Gly Asn Cys Gly Val Gly Lys Ser
1               5                   10

<210> SEQ ID NO 298
<211> LENGTH: 14
<212> TYPE: PRT
<213> ORGANISM: Homo sapiens

<400> SEQUENCE: 298

Trp Ser Leu Val Val Gly Ala Tyr Val Cys Gly Val Ser Gly
1               5                   10

<210> SEQ ID NO 299
<211> LENGTH: 13
<212> TYPE: PRT
<213> ORGANISM: Homo sapiens

<400> SEQUENCE: 299

Lys Val Val Val Gly Ser Cys Asn Arg Thr Ile Gln Asn
1               5                   10

<210> SEQ ID NO 300
<211> LENGTH: 14
<212> TYPE: PRT
<213> ORGANISM: Homo sapiens

<400> SEQUENCE: 300

Ser Asp Ser Gly Ala Leu Leu Cys Gly Val Gly Lys Asp His
1               5                   10

<210> SEQ ID NO 301
<211> LENGTH: 13
<212> TYPE: PRT
<213> ORGANISM: Homo sapiens

<400> SEQUENCE: 301

Val Val Val Val Gly Ser Cys Met Thr Asp Leu Val Ser
1               5                   10

<210> SEQ ID NO 302
<211> LENGTH: 14
<212> TYPE: PRT
<213> ORGANISM: Homo sapiens

<400> SEQUENCE: 302

Gln Gln Val Val Gly Ala Cys Lys Pro Cys Ser Asp Pro Asn
1               5                   10

<210> SEQ ID NO 303
<211> LENGTH: 15
<212> TYPE: PRT
<213> ORGANISM: Homo sapiens

<400> SEQUENCE: 303

Gly Val Asp Ala Gly Val Gly Ala Asp Val Gly Thr Gly Val Asp
1               5                   10                  15

<210> SEQ ID NO 304
<211> LENGTH: 14
<212> TYPE: PRT
<213> ORGANISM: Homo sapiens

<400> SEQUENCE: 304

Asp Leu Val Ile Val Gly Ala Glu Gly Val Val Glu Asn Gly
1               5                   10

<210> SEQ ID NO 305
<211> LENGTH: 14
<212> TYPE: PRT
<213> ORGANISM: Homo sapiens

<400> SEQUENCE: 305

Leu Cys Glu Val Gly Thr Asp Gly Leu Leu Ala Thr Ser Leu
1               5                   10

<210> SEQ ID NO 306
<211> LENGTH: 13
<212> TYPE: PRT
<213> ORGANISM: Homo sapiens

<400> SEQUENCE: 306

Ala Val Val Val Gly Ala Asp Arg Val Val Ala Asn Gly
1               5                   10

<210> SEQ ID NO 307
<211> LENGTH: 15
<212> TYPE: PRT
<213> ORGANISM: Homo sapiens

<400> SEQUENCE: 307

Lys Gly Glu Val Gly Ala Asp Gly Val Pro Gly Phe Pro Gly Leu
1               5                   10                  15

<210> SEQ ID NO 308
<211> LENGTH: 14
<212> TYPE: PRT
<213> ORGANISM: Homo sapiens

<400> SEQUENCE: 308

Gly Asp Pro Gly Lys Asp Gly Val Gly Gln Pro Gly Leu Pro
1               5                   10

<210> SEQ ID NO 309
<211> LENGTH: 13
<212> TYPE: PRT
<213> ORGANISM: Homo sapiens

<400> SEQUENCE: 309

```
Ser His Phe Val Gly Ala Asp Gly Val Arg Ala Phe Leu
1               5                   10

<210> SEQ ID NO 310
<211> LENGTH: 10
<212> TYPE: PRT
<213> ORGANISM: Homo sapiens

<400> SEQUENCE: 310

Asp Thr Glu Leu Gln Gly Met Asn Glu Tyr
1               5                   10

<210> SEQ ID NO 311
<211> LENGTH: 10
<212> TYPE: PRT
<213> ORGANISM: Homo sapiens

<400> SEQUENCE: 311

Ala Cys Asp Ser Thr Leu Gly Pro Ala Tyr
1               5                   10

<210> SEQ ID NO 312
<211> LENGTH: 10
<212> TYPE: PRT
<213> ORGANISM: Homo sapiens

<400> SEQUENCE: 312

Ala Leu Gly Arg Leu Leu Gly Val Ala His
1               5                   10

<210> SEQ ID NO 313
<211> LENGTH: 10
<212> TYPE: PRT
<213> ORGANISM: Homo sapiens

<400> SEQUENCE: 313

Ala Leu His Asn Ser Leu Ser Pro Ala Tyr
1               5                   10

<210> SEQ ID NO 314
<211> LENGTH: 10
<212> TYPE: PRT
<213> ORGANISM: Homo sapiens

<400> SEQUENCE: 314

Ala Leu Lys Glu Asp Val Gly Pro Gly Lys
1               5                   10

<210> SEQ ID NO 315
<211> LENGTH: 10
<212> TYPE: PRT
<213> ORGANISM: Homo sapiens

<400> SEQUENCE: 315

Ala Leu Met Arg Pro Leu Ser Pro Gly Lys
1               5                   10

<210> SEQ ID NO 316
<211> LENGTH: 10
<212> TYPE: PRT
<213> ORGANISM: Homo sapiens

<400> SEQUENCE: 316

Ala Leu Val Ser Phe Leu Asn Val Ala His
```

-continued

```
1               5               10

<210> SEQ ID NO 317
<211> LENGTH: 10
<212> TYPE: PRT
<213> ORGANISM: Homo sapiens

<400> SEQUENCE: 317

Ala Leu Tyr Lys Gly Leu Gly Pro Ala Tyr
1               5               10

<210> SEQ ID NO 318
<211> LENGTH: 10
<212> TYPE: PRT
<213> ORGANISM: Homo sapiens

<400> SEQUENCE: 318

Ala Met Gly Ser Phe Leu Ser Val Ala Lys
1               5               10

<210> SEQ ID NO 319
<211> LENGTH: 10
<212> TYPE: PRT
<213> ORGANISM: Homo sapiens

<400> SEQUENCE: 319

Ala Thr Ser Gly Ala Leu Ser Pro Ala Lys
1               5               10

<210> SEQ ID NO 320
<211> LENGTH: 10
<212> TYPE: PRT
<213> ORGANISM: Homo sapiens

<400> SEQUENCE: 320

Ala Thr Val Thr Gln Leu Ser Pro Gly His
1               5               10

<210> SEQ ID NO 321
<211> LENGTH: 10
<212> TYPE: PRT
<213> ORGANISM: Homo sapiens

<400> SEQUENCE: 321

Ala Val Ile Asn Val Leu Asn Val Ala His
1               5               10

<210> SEQ ID NO 322
<211> LENGTH: 10
<212> TYPE: PRT
<213> ORGANISM: Homo sapiens

<400> SEQUENCE: 322

Ala Val Lys Tyr Ala Leu Ser Val Gly Tyr
1               5               10

<210> SEQ ID NO 323
<211> LENGTH: 10
<212> TYPE: PRT
<213> ORGANISM: Homo sapiens

<400> SEQUENCE: 323

Ala Val Leu Phe Phe Leu Thr Pro Ala Lys
1               5               10
```

<210> SEQ ID NO 324
<211> LENGTH: 10
<212> TYPE: PRT
<213> ORGANISM: Homo sapiens

<400> SEQUENCE: 324

Cys Leu Leu Pro Lys Leu Ser Pro Gly Lys
1               5                   10

<210> SEQ ID NO 325
<211> LENGTH: 10
<212> TYPE: PRT
<213> ORGANISM: Homo sapiens

<400> SEQUENCE: 325

Cys Leu Asn Met Leu Ile Gly Val Gly Lys
1               5                   10

<210> SEQ ID NO 326
<211> LENGTH: 10
<212> TYPE: PRT
<213> ORGANISM: Homo sapiens

<400> SEQUENCE: 326

Glu Cys Gly Arg Phe Ile Thr Pro Ala His
1               5                   10

<210> SEQ ID NO 327
<211> LENGTH: 10
<212> TYPE: PRT
<213> ORGANISM: Homo sapiens

<400> SEQUENCE: 327

Glu Leu Leu Phe Asp Leu Gly Val Ala Tyr
1               5                   10

<210> SEQ ID NO 328
<211> LENGTH: 10
<212> TYPE: PRT
<213> ORGANISM: Homo sapiens

<400> SEQUENCE: 328

Glu Leu Met Gly Cys Leu Gly Val Ala Lys
1               5                   10

<210> SEQ ID NO 329
<211> LENGTH: 10
<212> TYPE: PRT
<213> ORGANISM: Homo sapiens

<400> SEQUENCE: 329

Glu Leu Pro Cys Arg Ile Ser Pro Gly Lys
1               5                   10

<210> SEQ ID NO 330
<211> LENGTH: 10
<212> TYPE: PRT
<213> ORGANISM: Homo sapiens

<400> SEQUENCE: 330

Glu Leu Pro Glu Asp Val Asn Pro Ala Lys
1               5                   10

<210> SEQ ID NO 331

-continued

```
<211> LENGTH: 10
<212> TYPE: PRT
<213> ORGANISM: Homo sapiens

<400> SEQUENCE: 331

Glu Leu Pro Gln Ser Val Gly Pro Gly Lys
1               5                   10

<210> SEQ ID NO 332
<211> LENGTH: 10
<212> TYPE: PRT
<213> ORGANISM: Homo sapiens

<400> SEQUENCE: 332

Glu Leu Ser Glu Glu Ile Asn Val Ala His
1               5                   10

<210> SEQ ID NO 333
<211> LENGTH: 10
<212> TYPE: PRT
<213> ORGANISM: Homo sapiens

<400> SEQUENCE: 333

Glu Met Gly Arg Val Val Ser Val Ala Tyr
1               5                   10

<210> SEQ ID NO 334
<211> LENGTH: 10
<212> TYPE: PRT
<213> ORGANISM: Homo sapiens

<400> SEQUENCE: 334

Glu Thr Leu Gln Arg Leu Ser Pro Ala His
1               5                   10

<210> SEQ ID NO 335
<211> LENGTH: 10
<212> TYPE: PRT
<213> ORGANISM: Homo sapiens

<400> SEQUENCE: 335

Glu Thr Met Ser Ser Leu Ser Pro Gly Lys
1               5                   10

<210> SEQ ID NO 336
<211> LENGTH: 10
<212> TYPE: PRT
<213> ORGANISM: Homo sapiens

<400> SEQUENCE: 336

Glu Thr Ser Pro Phe Ile Thr Pro Gly Lys
1               5                   10

<210> SEQ ID NO 337
<211> LENGTH: 10
<212> TYPE: PRT
<213> ORGANISM: Homo sapiens

<400> SEQUENCE: 337

Glu Thr Val Gly Gly Ile Ser Pro Gly Lys
1               5                   10

<210> SEQ ID NO 338
<211> LENGTH: 10
<212> TYPE: PRT
```

-continued

```
<213> ORGANISM: Homo sapiens

<400> SEQUENCE: 338

Glu Thr Tyr Ser Ala Leu Ser Pro Gly Lys
1               5                   10

<210> SEQ ID NO 339
<211> LENGTH: 10
<212> TYPE: PRT
<213> ORGANISM: Homo sapiens

<400> SEQUENCE: 339

Glu Val Pro Asn Gly Val Ser Pro Gly His
1               5                   10

<210> SEQ ID NO 340
<211> LENGTH: 10
<212> TYPE: PRT
<213> ORGANISM: Homo sapiens

<400> SEQUENCE: 340

Gly Cys Gly Gly Leu Val Thr Val Ala His
1               5                   10

<210> SEQ ID NO 341
<211> LENGTH: 10
<212> TYPE: PRT
<213> ORGANISM: Homo sapiens

<400> SEQUENCE: 341

Gly Cys Leu Trp Ala Leu Asn Pro Ala Lys
1               5                   10

<210> SEQ ID NO 342
<211> LENGTH: 10
<212> TYPE: PRT
<213> ORGANISM: Homo sapiens

<400> SEQUENCE: 342

Gly Cys Thr Glu Leu Leu Asn Val Ala His
1               5                   10

<210> SEQ ID NO 343
<211> LENGTH: 10
<212> TYPE: PRT
<213> ORGANISM: Homo sapiens

<400> SEQUENCE: 343

Gly Cys Tyr Thr Met Val Ser Val Ala Tyr
1               5                   10

<210> SEQ ID NO 344
<211> LENGTH: 10
<212> TYPE: PRT
<213> ORGANISM: Homo sapiens

<400> SEQUENCE: 344

Gly Leu Leu His Tyr Ile Asn Pro Ala His
1               5                   10

<210> SEQ ID NO 345
<211> LENGTH: 10
<212> TYPE: PRT
<213> ORGANISM: Homo sapiens
```

<400> SEQUENCE: 345

Gly Leu Met Gly Ala Val Asn Val Ala Lys
1               5                   10

<210> SEQ ID NO 346
<211> LENGTH: 10
<212> TYPE: PRT
<213> ORGANISM: Homo sapiens

<400> SEQUENCE: 346

Gly Leu Thr Gly Ala Val Asn Val Ala Lys
1               5                   10

<210> SEQ ID NO 347
<211> LENGTH: 10
<212> TYPE: PRT
<213> ORGANISM: Homo sapiens

<400> SEQUENCE: 347

Gly Leu Val Gly Ala Val Asn Val Ala Lys
1               5                   10

<210> SEQ ID NO 348
<211> LENGTH: 10
<212> TYPE: PRT
<213> ORGANISM: Homo sapiens

<400> SEQUENCE: 348

Gly Thr Pro Thr Pro Val Ser Val Ala His
1               5                   10

<210> SEQ ID NO 349
<211> LENGTH: 10
<212> TYPE: PRT
<213> ORGANISM: Homo sapiens

<400> SEQUENCE: 349

Gly Val Ala Ala Glu Val Ser Pro Ala Lys
1               5                   10

<210> SEQ ID NO 350
<211> LENGTH: 10
<212> TYPE: PRT
<213> ORGANISM: Homo sapiens

<400> SEQUENCE: 350

Gly Val Pro Glu Phe Ile Ser Val Gly Tyr
1               5                   10

<210> SEQ ID NO 351
<211> LENGTH: 10
<212> TYPE: PRT
<213> ORGANISM: Homo sapiens

<400> SEQUENCE: 351

Gly Val Thr Gly Ala Val Asn Val Ala Lys
1               5                   10

<210> SEQ ID NO 352
<211> LENGTH: 10
<212> TYPE: PRT
<213> ORGANISM: Homo sapiens

<400> SEQUENCE: 352

Gly Val Thr Ser Ala Val Asn Val Ala Lys
1               5                   10

<210> SEQ ID NO 353
<211> LENGTH: 10
<212> TYPE: PRT
<213> ORGANISM: Homo sapiens

<400> SEQUENCE: 353

His Cys Lys Lys Leu Val Asn Pro Ala Lys
1               5                   10

<210> SEQ ID NO 354
<211> LENGTH: 10
<212> TYPE: PRT
<213> ORGANISM: Homo sapiens

<400> SEQUENCE: 354

His Ile Gln Glu Gly Leu Asn Pro Gly His
1               5                   10

<210> SEQ ID NO 355
<211> LENGTH: 10
<212> TYPE: PRT
<213> ORGANISM: Homo sapiens

<400> SEQUENCE: 355

His Leu Met Pro Ile Ile Thr Pro Ala Tyr
1               5                   10

<210> SEQ ID NO 356
<211> LENGTH: 10
<212> TYPE: PRT
<213> ORGANISM: Homo sapiens

<400> SEQUENCE: 356

His Thr His Asp Glu Leu Gly Val Ala His
1               5                   10

<210> SEQ ID NO 357
<211> LENGTH: 10
<212> TYPE: PRT
<213> ORGANISM: Homo sapiens

<400> SEQUENCE: 357

His Val Cys Gly Glu Val Gly Val Gly Tyr
1               5                   10

<210> SEQ ID NO 358
<211> LENGTH: 10
<212> TYPE: PRT
<213> ORGANISM: Homo sapiens

<400> SEQUENCE: 358

Ile Ile Phe Asp Leu Leu Ser Val Gly Lys
1               5                   10

<210> SEQ ID NO 359
<211> LENGTH: 10
<212> TYPE: PRT
<213> ORGANISM: Homo sapiens

<400> SEQUENCE: 359

Ile Leu Met Gly Pro Val Thr Pro Ala His
1               5                   10

-continued

```
<210> SEQ ID NO 360
<211> LENGTH: 10
<212> TYPE: PRT
<213> ORGANISM: Homo sapiens

<400> SEQUENCE: 360

Ile Leu Ser Ser Glu Val Ser Pro Gly His
1               5                   10

<210> SEQ ID NO 361
<211> LENGTH: 10
<212> TYPE: PRT
<213> ORGANISM: Homo sapiens

<400> SEQUENCE: 361

Ile Met Gly Ser Tyr Leu Gly Val Ala His
1               5                   10

<210> SEQ ID NO 362
<211> LENGTH: 10
<212> TYPE: PRT
<213> ORGANISM: Homo sapiens

<400> SEQUENCE: 362

Ile Met Leu Thr Pro Val Thr Val Ala Tyr
1               5                   10

<210> SEQ ID NO 363
<211> LENGTH: 10
<212> TYPE: PRT
<213> ORGANISM: Homo sapiens

<400> SEQUENCE: 363

Ile Met Met Gln Leu Val Ser Val Ala Lys
1               5                   10

<210> SEQ ID NO 364
<211> LENGTH: 10
<212> TYPE: PRT
<213> ORGANISM: Homo sapiens

<400> SEQUENCE: 364

Ile Met Val Ala Thr Val Ser Pro Ala His
1               5                   10

<210> SEQ ID NO 365
<211> LENGTH: 10
<212> TYPE: PRT
<213> ORGANISM: Homo sapiens

<400> SEQUENCE: 365

Ile Thr Ile Phe Ala Val Gly Val Gly Lys
1               5                   10

<210> SEQ ID NO 366
<211> LENGTH: 10
<212> TYPE: PRT
<213> ORGANISM: Homo sapiens

<400> SEQUENCE: 366

Ile Thr Ile Gln Asp Ile Gly Val Gly Lys
1               5                   10
```

-continued

```
<210> SEQ ID NO 367
<211> LENGTH: 10
<212> TYPE: PRT
<213> ORGANISM: Homo sapiens

<400> SEQUENCE: 367

Ile Thr Met Tyr Ala Val Gly Val Gly Lys
1               5                   10

<210> SEQ ID NO 368
<211> LENGTH: 10
<212> TYPE: PRT
<213> ORGANISM: Homo sapiens

<400> SEQUENCE: 368

Arg Thr Gly Lys Asp Leu Gly Pro Ala Tyr
1               5                   10

<210> SEQ ID NO 369
<211> LENGTH: 10
<212> TYPE: PRT
<213> ORGANISM: Homo sapiens

<400> SEQUENCE: 369

Ile Val Val Gly Asp Leu Ser Val Gly Lys
1               5                   10

<210> SEQ ID NO 370
<211> LENGTH: 10
<212> TYPE: PRT
<213> ORGANISM: Homo sapiens

<400> SEQUENCE: 370

Ile Val Val Pro Ser Leu Asn Val Ala Lys
1               5                   10

<210> SEQ ID NO 371
<211> LENGTH: 10
<212> TYPE: PRT
<213> ORGANISM: Homo sapiens

<400> SEQUENCE: 371

Lys Ile Cys Asn Tyr Val Gly Pro Ala Lys
1               5                   10

<210> SEQ ID NO 372
<211> LENGTH: 10
<212> TYPE: PRT
<213> ORGANISM: Homo sapiens

<400> SEQUENCE: 372

Lys Ile Phe Gly Val Ile Gly Val Gly His
1               5                   10

<210> SEQ ID NO 373
<211> LENGTH: 10
<212> TYPE: PRT
<213> ORGANISM: Homo sapiens

<400> SEQUENCE: 373

Lys Ile Leu Gln Met Val Asn Val Ala Lys
1               5                   10

<210> SEQ ID NO 374
<211> LENGTH: 10
```

<212> TYPE: PRT
<213> ORGANISM: Homo sapiens

<400> SEQUENCE: 374

Lys Leu Lys Lys Gln Leu Gly Pro Gly Lys
1               5                   10

<210> SEQ ID NO 375
<211> LENGTH: 10
<212> TYPE: PRT
<213> ORGANISM: Homo sapiens

<400> SEQUENCE: 375

Lys Leu Lys Thr Pro Leu Asn Pro Ala Lys
1               5                   10

<210> SEQ ID NO 376
<211> LENGTH: 10
<212> TYPE: PRT
<213> ORGANISM: Homo sapiens

<400> SEQUENCE: 376

Lys Leu Leu Thr Asp Val Gly Pro Ala Lys
1               5                   10

<210> SEQ ID NO 377
<211> LENGTH: 10
<212> TYPE: PRT
<213> ORGANISM: Homo sapiens

<400> SEQUENCE: 377

Lys Met Val Trp Arg Ile Asn Pro Ala His
1               5                   10

<210> SEQ ID NO 378
<211> LENGTH: 10
<212> TYPE: PRT
<213> ORGANISM: Homo sapiens

<400> SEQUENCE: 378

Ile Val Met Tyr Ala Val Gly Val Gly Lys
1               5                   10

<210> SEQ ID NO 379
<211> LENGTH: 10
<212> TYPE: PRT
<213> ORGANISM: Homo sapiens

<400> SEQUENCE: 379

Lys Val Thr His Ile Leu Asn Val Ala Tyr
1               5                   10

<210> SEQ ID NO 380
<211> LENGTH: 10
<212> TYPE: PRT
<213> ORGANISM: Homo sapiens

<400> SEQUENCE: 380

Leu Leu Asp Asp Leu Ile Thr Pro Ala Lys
1               5                   10

<210> SEQ ID NO 381
<211> LENGTH: 10
<212> TYPE: PRT
<213> ORGANISM: Homo sapiens

<400> SEQUENCE: 381

Leu Leu Gly Ala Thr Ile Gly Val Ala Lys
1               5                   10

<210> SEQ ID NO 382
<211> LENGTH: 10
<212> TYPE: PRT
<213> ORGANISM: Homo sapiens

<400> SEQUENCE: 382

Leu Leu Leu Ala Phe Leu Thr Val Ala Tyr
1               5                   10

<210> SEQ ID NO 383
<211> LENGTH: 10
<212> TYPE: PRT
<213> ORGANISM: Homo sapiens

<400> SEQUENCE: 383

Leu Leu Leu Pro Ala Val Gly Pro Gly His
1               5                   10

<210> SEQ ID NO 384
<211> LENGTH: 10
<212> TYPE: PRT
<213> ORGANISM: Homo sapiens

<400> SEQUENCE: 384

Leu Leu Leu Gln Val Leu Ser Val Gly Lys
1               5                   10

<210> SEQ ID NO 385
<211> LENGTH: 10
<212> TYPE: PRT
<213> ORGANISM: Homo sapiens

<400> SEQUENCE: 385

Leu Leu Leu Ser Gly Val Gly Pro Ala His
1               5                   10

<210> SEQ ID NO 386
<211> LENGTH: 10
<212> TYPE: PRT
<213> ORGANISM: Homo sapiens

<400> SEQUENCE: 386

Leu Leu Asn Ala Val Leu Ser Pro Gly His
1               5                   10

<210> SEQ ID NO 387
<211> LENGTH: 10
<212> TYPE: PRT
<213> ORGANISM: Homo sapiens

<400> SEQUENCE: 387

Leu Leu Gln Gln Lys Leu Asn Val Gly Lys
1               5                   10

<210> SEQ ID NO 388
<211> LENGTH: 10
<212> TYPE: PRT
<213> ORGANISM: Homo sapiens

<400> SEQUENCE: 388

Leu Leu Ser Glu Glu Ile Asn Val Ala Lys
1               5                   10

<210> SEQ ID NO 389
<211> LENGTH: 10
<212> TYPE: PRT
<213> ORGANISM: Homo sapiens

<400> SEQUENCE: 389

Leu Leu Val Gly Asp Val Thr Val Gly Tyr
1               5                   10

<210> SEQ ID NO 390
<211> LENGTH: 10
<212> TYPE: PRT
<213> ORGANISM: Homo sapiens

<400> SEQUENCE: 390

Leu Leu Val His Ile Leu Ser Pro Ala His
1               5                   10

<210> SEQ ID NO 391
<211> LENGTH: 10
<212> TYPE: PRT
<213> ORGANISM: Homo sapiens

<400> SEQUENCE: 391

Leu Thr Asp Ala Ala Ile Gly Pro Ala Tyr
1               5                   10

<210> SEQ ID NO 392
<211> LENGTH: 10
<212> TYPE: PRT
<213> ORGANISM: Homo sapiens

<400> SEQUENCE: 392

Leu Thr Val Glu Val Leu Ser Val Gly Lys
1               5                   10

<210> SEQ ID NO 393
<211> LENGTH: 10
<212> TYPE: PRT
<213> ORGANISM: Homo sapiens

<400> SEQUENCE: 393

Leu Val Ile Gly Asp Leu Gly Val Gly Lys
1               5                   10

<210> SEQ ID NO 394
<211> LENGTH: 10
<212> TYPE: PRT
<213> ORGANISM: Homo sapiens

<400> SEQUENCE: 394

Leu Val Ile Gly Glu Leu Gly Val Gly Lys
1               5                   10

<210> SEQ ID NO 395
<211> LENGTH: 10
<212> TYPE: PRT
<213> ORGANISM: Homo sapiens

<400> SEQUENCE: 395

Leu Val Pro Trp Ser Val Gly Val Gly His

```
1               5                    10
```

```
<210> SEQ ID NO 396
<211> LENGTH: 10
<212> TYPE: PRT
<213> ORGANISM: Homo sapiens

<400> SEQUENCE: 396

Met Leu Leu Ala Asn Ile Ser Val Ala Lys
1               5                    10

<210> SEQ ID NO 397
<211> LENGTH: 10
<212> TYPE: PRT
<213> ORGANISM: Homo sapiens

<400> SEQUENCE: 397

Met Leu Ser Arg Tyr Ile Asn Pro Ala Lys
1               5                    10

<210> SEQ ID NO 398
<211> LENGTH: 10
<212> TYPE: PRT
<213> ORGANISM: Homo sapiens

<400> SEQUENCE: 398

Met Leu Trp Met Thr Ile Ser Val Gly Tyr
1               5                    10

<210> SEQ ID NO 399
<211> LENGTH: 10
<212> TYPE: PRT
<213> ORGANISM: Homo sapiens

<400> SEQUENCE: 399

Met Thr Asp Lys Leu Val Thr Pro Gly Lys
1               5                    10

<210> SEQ ID NO 400
<211> LENGTH: 10
<212> TYPE: PRT
<213> ORGANISM: Homo sapiens

<400> SEQUENCE: 400

Asn Leu Met Asn Val Leu Ser Val Gly Lys
1               5                    10

<210> SEQ ID NO 401
<211> LENGTH: 10
<212> TYPE: PRT
<213> ORGANISM: Homo sapiens

<400> SEQUENCE: 401

Asn Leu Gln Thr Ala Ile Thr Val Ala Lys
1               5                    10

<210> SEQ ID NO 402
<211> LENGTH: 10
<212> TYPE: PRT
<213> ORGANISM: Homo sapiens

<400> SEQUENCE: 402

Asn Thr Leu Met Ser Leu Ser Val Gly Lys
1               5                    10
```

<210> SEQ ID NO 403
<211> LENGTH: 10
<212> TYPE: PRT
<213> ORGANISM: Homo sapiens

<400> SEQUENCE: 403

Asn Val Gly Gly Leu Leu Gly Pro Ala Lys
1               5                   10

<210> SEQ ID NO 404
<211> LENGTH: 10
<212> TYPE: PRT
<213> ORGANISM: Homo sapiens

<400> SEQUENCE: 404

Asn Val Gly Arg Leu Ile Thr Pro Ala Lys
1               5                   10

<210> SEQ ID NO 405
<211> LENGTH: 10
<212> TYPE: PRT
<213> ORGANISM: Homo sapiens

<400> SEQUENCE: 405

Asn Val Asn Gln Cys Leu Gly Pro Gly Lys
1               5                   10

<210> SEQ ID NO 406
<211> LENGTH: 10
<212> TYPE: PRT
<213> ORGANISM: Homo sapiens

<400> SEQUENCE: 406

Asn Val Ser Phe Ser Leu Ser Pro Gly Lys
1               5                   10

<210> SEQ ID NO 407
<211> LENGTH: 10
<212> TYPE: PRT
<213> ORGANISM: Homo sapiens

<400> SEQUENCE: 407

Pro Leu Ser Phe Lys Val Gly Val Gly Lys
1               5                   10

<210> SEQ ID NO 408
<211> LENGTH: 10
<212> TYPE: PRT
<213> ORGANISM: Homo sapiens

<400> SEQUENCE: 408

Pro Thr Cys Ala Leu Ile Thr Val Gly His
1               5                   10

<210> SEQ ID NO 409
<211> LENGTH: 10
<212> TYPE: PRT
<213> ORGANISM: Homo sapiens

<400> SEQUENCE: 409

Pro Thr Thr Thr Ser Leu Gly Pro Ala Lys
1               5                   10

<210> SEQ ID NO 410

```
<211> LENGTH: 10
<212> TYPE: PRT
<213> ORGANISM: Homo sapiens

<400> SEQUENCE: 410

Gln Ile Gln Ala Glu Leu Ser Pro Ala His
1               5                   10

<210> SEQ ID NO 411
<211> LENGTH: 10
<212> TYPE: PRT
<213> ORGANISM: Homo sapiens

<400> SEQUENCE: 411

Gln Leu His Pro His Leu Thr Val Ala Lys
1               5                   10

<210> SEQ ID NO 412
<211> LENGTH: 10
<212> TYPE: PRT
<213> ORGANISM: Homo sapiens

<400> SEQUENCE: 412

Gln Met Leu Arg Thr Ile Gly Val Gly Lys
1               5                   10

<210> SEQ ID NO 413
<211> LENGTH: 10
<212> TYPE: PRT
<213> ORGANISM: Homo sapiens

<400> SEQUENCE: 413

Gln Thr Gln Lys Thr Val Thr Pro Ala Tyr
1               5                   10

<210> SEQ ID NO 414
<211> LENGTH: 10
<212> TYPE: PRT
<213> ORGANISM: Homo sapiens

<400> SEQUENCE: 414

Gln Val Gln Ala Leu Leu Gly Val Ala Lys
1               5                   10

<210> SEQ ID NO 415
<211> LENGTH: 10
<212> TYPE: PRT
<213> ORGANISM: Homo sapiens

<400> SEQUENCE: 415

Arg Leu Ala Arg Ala Leu Asn Pro Ala Lys
1               5                   10

<210> SEQ ID NO 416
<211> LENGTH: 10
<212> TYPE: PRT
<213> ORGANISM: Homo sapiens

<400> SEQUENCE: 416

Arg Leu Gly Gly Ile Val Gly Pro Ala Tyr
1               5                   10

<210> SEQ ID NO 417
<211> LENGTH: 10
<212> TYPE: PRT
```

-continued

```
<213> ORGANISM: Homo sapiens

<400> SEQUENCE: 417

Arg Leu Thr Pro Ser Val Thr Pro Ala Tyr
1               5                   10

<210> SEQ ID NO 418
<211> LENGTH: 10
<212> TYPE: PRT
<213> ORGANISM: Homo sapiens

<400> SEQUENCE: 418

Arg Leu Val Lys Trp Val Thr Val Ala His
1               5                   10

<210> SEQ ID NO 419

<400> SEQUENCE: 419

000

<210> SEQ ID NO 420
<211> LENGTH: 10
<212> TYPE: PRT
<213> ORGANISM: Homo sapiens

<400> SEQUENCE: 420

Ser Ile Ala Gly Met Ile Thr Val Ala Tyr
1               5                   10

<210> SEQ ID NO 421
<211> LENGTH: 10
<212> TYPE: PRT
<213> ORGANISM: Homo sapiens

<400> SEQUENCE: 421

Ser Leu Ile Gln Glu Leu Ser Val Ala Tyr
1               5                   10

<210> SEQ ID NO 422
<211> LENGTH: 10
<212> TYPE: PRT
<213> ORGANISM: Homo sapiens

<400> SEQUENCE: 422

Ser Leu Lys Asn Asp Leu Gly Val Gly Tyr
1               5                   10

<210> SEQ ID NO 423
<211> LENGTH: 10
<212> TYPE: PRT
<213> ORGANISM: Homo sapiens

<400> SEQUENCE: 423

Ser Leu Leu Asp Thr Leu Ser Pro Ala Tyr
1               5                   10

<210> SEQ ID NO 424
<211> LENGTH: 10
<212> TYPE: PRT
<213> ORGANISM: Homo sapiens

<400> SEQUENCE: 424

Ser Leu Leu Pro Val Leu Gly Val Ala Lys
1               5                   10
```

<210> SEQ ID NO 425
<211> LENGTH: 10
<212> TYPE: PRT
<213> ORGANISM: Homo sapiens

<400> SEQUENCE: 425

Ser Leu Leu Gln Leu Leu Thr Pro Ala Tyr
1               5                   10

<210> SEQ ID NO 426
<211> LENGTH: 10
<212> TYPE: PRT
<213> ORGANISM: Homo sapiens

<400> SEQUENCE: 426

Ser Leu Gln Phe Phe Ile Ser Pro Gly Lys
1               5                   10

<210> SEQ ID NO 427
<211> LENGTH: 10
<212> TYPE: PRT
<213> ORGANISM: Homo sapiens

<400> SEQUENCE: 427

Ser Leu Gln Thr Met Leu Ser Val Gly Tyr
1               5                   10

<210> SEQ ID NO 428
<211> LENGTH: 10
<212> TYPE: PRT
<213> ORGANISM: Homo sapiens

<400> SEQUENCE: 428

Ser Thr Ala Asn Leu Ile Gly Pro Gly His
1               5                   10

<210> SEQ ID NO 429
<211> LENGTH: 10
<212> TYPE: PRT
<213> ORGANISM: Homo sapiens

<400> SEQUENCE: 429

Ser Thr Tyr Ala His Leu Ser Pro Ala Lys
1               5                   10

<210> SEQ ID NO 430
<211> LENGTH: 10
<212> TYPE: PRT
<213> ORGANISM: Homo sapiens

<400> SEQUENCE: 430

Ser Val Lys Thr Asn Leu Gly Val Gly Lys
1               5                   10

<210> SEQ ID NO 431
<211> LENGTH: 10
<212> TYPE: PRT
<213> ORGANISM: Homo sapiens

<400> SEQUENCE: 431

Ser Val Leu Ser Ser Leu Thr Pro Ala Lys
1               5                   10

```
<210> SEQ ID NO 432
<211> LENGTH: 10
<212> TYPE: PRT
<213> ORGANISM: Homo sapiens

<400> SEQUENCE: 432

Ser Val Asn Pro Ser Ile Ser Pro Ala His
1               5                   10

<210> SEQ ID NO 433

<400> SEQUENCE: 433

000

<210> SEQ ID NO 434
<211> LENGTH: 10
<212> TYPE: PRT
<213> ORGANISM: Homo sapiens

<400> SEQUENCE: 434

Ser Val Ser Glu Leu Leu Thr Pro Ala Lys
1               5                   10

<210> SEQ ID NO 435
<211> LENGTH: 10
<212> TYPE: PRT
<213> ORGANISM: Homo sapiens

<400> SEQUENCE: 435

Ser Val Thr Gly Ala Ile Thr Val Ala Lys
1               5                   10

<210> SEQ ID NO 436
<211> LENGTH: 10
<212> TYPE: PRT
<213> ORGANISM: Homo sapiens

<400> SEQUENCE: 436

Thr Cys Pro Lys Gly Leu Asn Pro Gly Lys
1               5                   10

<210> SEQ ID NO 437
<211> LENGTH: 10
<212> TYPE: PRT
<213> ORGANISM: Homo sapiens

<400> SEQUENCE: 437

Thr Ile Lys Thr Leu Ile Thr Val Ala His
1               5                   10

<210> SEQ ID NO 438
<211> LENGTH: 10
<212> TYPE: PRT
<213> ORGANISM: Homo sapiens

<400> SEQUENCE: 438

Thr Leu Ala Asn Asn Val Thr Pro Ala Lys
1               5                   10

<210> SEQ ID NO 439
<211> LENGTH: 10
<212> TYPE: PRT
<213> ORGANISM: Homo sapiens

<400> SEQUENCE: 439
```

```
Thr Leu Ala Arg Gly Leu Ser Pro Ala Tyr
1               5               10

<210> SEQ ID NO 440
<211> LENGTH: 10
<212> TYPE: PRT
<213> ORGANISM: Homo sapiens

<400> SEQUENCE: 440

Thr Leu Lys Gly Glu Ile Ser Pro Gly Lys
1               5               10

<210> SEQ ID NO 441
<211> LENGTH: 10
<212> TYPE: PRT
<213> ORGANISM: Homo sapiens

<400> SEQUENCE: 441

Thr Met Ile Met Gly Ile Ser Pro Ala Tyr
1               5               10

<210> SEQ ID NO 442
<211> LENGTH: 10
<212> TYPE: PRT
<213> ORGANISM: Homo sapiens

<400> SEQUENCE: 442

Thr Thr Cys Ser Pro Leu Ser Pro Gly Lys
1               5               10

<210> SEQ ID NO 443
<211> LENGTH: 10
<212> TYPE: PRT
<213> ORGANISM: Homo sapiens

<400> SEQUENCE: 443

Thr Val His Pro Gln Leu Thr Val Gly Lys
1               5               10

<210> SEQ ID NO 444
<211> LENGTH: 10
<212> TYPE: PRT
<213> ORGANISM: Homo sapiens

<400> SEQUENCE: 444

Thr Val Ile Lys Glu Ile Ser Val Ala Lys
1               5               10

<210> SEQ ID NO 445
<211> LENGTH: 10
<212> TYPE: PRT
<213> ORGANISM: Homo sapiens

<400> SEQUENCE: 445

Thr Val Leu Ser Ala Ile Asn Val Gly Lys
1               5               10

<210> SEQ ID NO 446
<211> LENGTH: 10
<212> TYPE: PRT
<213> ORGANISM: Homo sapiens

<400> SEQUENCE: 446

Thr Val Asn Pro Ala Leu Thr Pro Ala Lys
```

-continued

```
1               5                  10

<210> SEQ ID NO 447
<211> LENGTH: 10
<212> TYPE: PRT
<213> ORGANISM: Homo sapiens

<400> SEQUENCE: 447

Thr Val Pro Pro Cys Ile Gly Val Ala Lys
1               5                  10

<210> SEQ ID NO 448
<211> LENGTH: 10
<212> TYPE: PRT
<213> ORGANISM: Homo sapiens

<400> SEQUENCE: 448

Thr Val Val Ala Asp Ile Ser Val Ala Lys
1               5                  10

<210> SEQ ID NO 449
<211> LENGTH: 10
<212> TYPE: PRT
<213> ORGANISM: Homo sapiens

<400> SEQUENCE: 449

Val Cys Ala Ala Asp Ile Ser Pro Gly His
1               5                  10

<210> SEQ ID NO 450
<211> LENGTH: 10
<212> TYPE: PRT
<213> ORGANISM: Homo sapiens

<400> SEQUENCE: 450

Val Ile Thr Lys Phe Ile Asn Val Ala Lys
1               5                  10

<210> SEQ ID NO 451
<211> LENGTH: 10
<212> TYPE: PRT
<213> ORGANISM: Homo sapiens

<400> SEQUENCE: 451

Val Leu Cys Gly Asp Leu Asn Val Ala His
1               5                  10

<210> SEQ ID NO 452
<211> LENGTH: 10
<212> TYPE: PRT
<213> ORGANISM: Homo sapiens

<400> SEQUENCE: 452

Val Leu Ser Arg Arg Val Ser Pro Gly Tyr
1               5                  10

<210> SEQ ID NO 453
<211> LENGTH: 10
<212> TYPE: PRT
<213> ORGANISM: Homo sapiens

<400> SEQUENCE: 453

Val Leu Thr Pro Glu Leu Ser Pro Gly Lys
1               5                  10
```

<210> SEQ ID NO 454
<211> LENGTH: 10
<212> TYPE: PRT
<213> ORGANISM: Homo sapiens

<400> SEQUENCE: 454

Val Met Lys Arg Ser Leu Gly Val Gly Tyr
1               5                   10

<210> SEQ ID NO 455
<211> LENGTH: 10
<212> TYPE: PRT
<213> ORGANISM: Homo sapiens

<400> SEQUENCE: 455

Val Thr Lys Asp Gly Val Thr Val Ala Lys
1               5                   10

<210> SEQ ID NO 456
<211> LENGTH: 10
<212> TYPE: PRT
<213> ORGANISM: Homo sapiens

<400> SEQUENCE: 456

Val Thr Gln Pro Ser Leu Gly Val Gly Tyr
1               5                   10

<210> SEQ ID NO 457
<211> LENGTH: 10
<212> TYPE: PRT
<213> ORGANISM: Homo sapiens

<400> SEQUENCE: 457

Val Thr Val Gln Ser Leu Ser Pro Ala Lys
1               5                   10

<210> SEQ ID NO 458
<211> LENGTH: 10
<212> TYPE: PRT
<213> ORGANISM: Homo sapiens

<400> SEQUENCE: 458

Val Val Ala Ala Val Val Ser Val Ala Tyr
1               5                   10

<210> SEQ ID NO 459
<211> LENGTH: 10
<212> TYPE: PRT
<213> ORGANISM: Homo sapiens

<400> SEQUENCE: 459

Val Val Cys Gly Leu Leu Ser Val Gly Lys
1               5                   10

<210> SEQ ID NO 460
<211> LENGTH: 10
<212> TYPE: PRT
<213> ORGANISM: Homo sapiens

<400> SEQUENCE: 460

Val Val Ile Asp Gly Leu Asn Val Ala Lys
1               5                   10

<210> SEQ ID NO 461

```
<211> LENGTH: 10
<212> TYPE: PRT
<213> ORGANISM: Homo sapiens

<400> SEQUENCE: 461

Val Val Leu Asp Asp Ile Ser Pro Gly Lys
1               5                   10

<210> SEQ ID NO 462
<211> LENGTH: 10
<212> TYPE: PRT
<213> ORGANISM: Homo sapiens

<400> SEQUENCE: 462

Ala Ala Glu Gln Ala Gly Ile Ile Glu Ala
1               5                   10

<210> SEQ ID NO 463
<211> LENGTH: 10
<212> TYPE: PRT
<213> ORGANISM: Homo sapiens

<400> SEQUENCE: 463

Ala Cys Asp Asn His Ala Leu Gln Glu Ala
1               5                   10

<210> SEQ ID NO 464
<211> LENGTH: 10
<212> TYPE: PRT
<213> ORGANISM: Homo sapiens

<400> SEQUENCE: 464

Ala Phe Pro Trp Ala Ala Leu Arg Asp Ala
1               5                   10

<210> SEQ ID NO 465
<211> LENGTH: 10
<212> TYPE: PRT
<213> ORGANISM: Homo sapiens

<400> SEQUENCE: 465

Ala Gly Glu Cys Cys Ala Leu Gln Glu Tyr
1               5                   10

<210> SEQ ID NO 466
<211> LENGTH: 10
<212> TYPE: PRT
<213> ORGANISM: Homo sapiens

<400> SEQUENCE: 466

Ala Gly Pro His Pro Gly Met Gly Asp Ala
1               5                   10

<210> SEQ ID NO 467
<211> LENGTH: 10
<212> TYPE: PRT
<213> ORGANISM: Homo sapiens

<400> SEQUENCE: 467

Ala Lys Ala Lys Met Ala Leu Ala Glu Ala
1               5                   10

<210> SEQ ID NO 468
<211> LENGTH: 10
<212> TYPE: PRT
```

<213> ORGANISM: Homo sapiens

<400> SEQUENCE: 468

Ala Leu Ala Ile Ala Ala Leu Ala Glu Ala
1               5                   10

<210> SEQ ID NO 469
<211> LENGTH: 10
<212> TYPE: PRT
<213> ORGANISM: Homo sapiens

<400> SEQUENCE: 469

Ala Met Arg Ala Ser Ala Leu Gln Glu Ala
1               5                   10

<210> SEQ ID NO 470
<211> LENGTH: 10
<212> TYPE: PRT
<213> ORGANISM: Homo sapiens

<400> SEQUENCE: 470

Ala Gln Ser Gly Pro Ala Leu Gly Glu Ala
1               5                   10

<210> SEQ ID NO 471
<211> LENGTH: 10
<212> TYPE: PRT
<213> ORGANISM: Homo sapiens

<400> SEQUENCE: 471

Ala Ser Pro Leu Thr Gly Ile Ala Asp Ala
1               5                   10

<210> SEQ ID NO 472
<211> LENGTH: 10
<212> TYPE: PRT
<213> ORGANISM: Homo sapiens

<400> SEQUENCE: 472

Ala Ser Pro Thr Ala Gly Leu Gln Glu Ala
1               5                   10

<210> SEQ ID NO 473
<211> LENGTH: 10
<212> TYPE: PRT
<213> ORGANISM: Homo sapiens

<400> SEQUENCE: 473

Ala Thr Cys His Phe Ala Leu Gly Glu Tyr
1               5                   10

<210> SEQ ID NO 474
<211> LENGTH: 10
<212> TYPE: PRT
<213> ORGANISM: Homo sapiens

<400> SEQUENCE: 474

Cys Cys Ala Lys His Gly Leu Ala Glu Ala
1               5                   10

<210> SEQ ID NO 475
<211> LENGTH: 10
<212> TYPE: PRT
<213> ORGANISM: Homo sapiens -continued

```
<400> SEQUENCE: 475

Cys Gly Arg Leu Tyr Gly Leu Gln Glu Ala
1               5                   10

<210> SEQ ID NO 476
<211> LENGTH: 10
<212> TYPE: PRT
<213> ORGANISM: Homo sapiens

<400> SEQUENCE: 476

Cys Ser Ala Leu Asp Ala Ile Arg Glu Ala
1               5                   10

<210> SEQ ID NO 477
<211> LENGTH: 10
<212> TYPE: PRT
<213> ORGANISM: Homo sapiens

<400> SEQUENCE: 477

Cys Val Ala Leu Gln Ala Leu Ala Glu Tyr
1               5                   10

<210> SEQ ID NO 478
<211> LENGTH: 10
<212> TYPE: PRT
<213> ORGANISM: Homo sapiens

<400> SEQUENCE: 478

Asp Ala Ala Ser Ala Ala Leu Ala Asp Ala
1               5                   10

<210> SEQ ID NO 479
<211> LENGTH: 10
<212> TYPE: PRT
<213> ORGANISM: Homo sapiens

<400> SEQUENCE: 479

Asp Ala Asp Arg Asp Gly Ile Gly Asp Ala
1               5                   10

<210> SEQ ID NO 480
<211> LENGTH: 10
<212> TYPE: PRT
<213> ORGANISM: Homo sapiens

<400> SEQUENCE: 480

Asp Ala Arg Lys Gln Ala Ile Arg Asp Ala
1               5                   10

<210> SEQ ID NO 481
<211> LENGTH: 10
<212> TYPE: PRT
<213> ORGANISM: Homo sapiens

<400> SEQUENCE: 481

Asp Ala Ser Gly His Gly Leu Asn Glu Ala
1               5                   10

<210> SEQ ID NO 482
<211> LENGTH: 10
<212> TYPE: PRT
<213> ORGANISM: Homo sapiens

<400> SEQUENCE: 482
```

-continued

```
Asp Phe Asp Lys Asp Gly Ile Gly Asp Ala
1               5                   10

<210> SEQ ID NO 483
<211> LENGTH: 10
<212> TYPE: PRT
<213> ORGANISM: Homo sapiens

<400> SEQUENCE: 483

Asp Ile Ser Gly Asn Ala Met Gly Asp Ala
1               5                   10

<210> SEQ ID NO 484
<211> LENGTH: 10
<212> TYPE: PRT
<213> ORGANISM: Homo sapiens

<400> SEQUENCE: 484

Asp Lys Asp Lys Gln Ala Ile Asn Glu Tyr
1               5                   10

<210> SEQ ID NO 485
<211> LENGTH: 10
<212> TYPE: PRT
<213> ORGANISM: Homo sapiens

<400> SEQUENCE: 485

Asp Lys Glu Phe Phe Gly Leu Arg Asp Tyr
1               5                   10

<210> SEQ ID NO 486
<211> LENGTH: 10
<212> TYPE: PRT
<213> ORGANISM: Homo sapiens

<400> SEQUENCE: 486

Asp Lys Glu Leu Thr Gly Leu Asn Glu Ala
1               5                   10

<210> SEQ ID NO 487
<211> LENGTH: 10
<212> TYPE: PRT
<213> ORGANISM: Homo sapiens

<400> SEQUENCE: 487

Asp Leu Pro His Thr Ala Ile Gln Glu Ala
1               5                   10

<210> SEQ ID NO 488
<211> LENGTH: 10
<212> TYPE: PRT
<213> ORGANISM: Homo sapiens

<400> SEQUENCE: 488

Asp Gln Ala Gly Ala Ala Met Glu Glu Ala
1               5                   10

<210> SEQ ID NO 489
<211> LENGTH: 10
<212> TYPE: PRT
<213> ORGANISM: Homo sapiens

<400> SEQUENCE: 489

Asp Ser Asp Gly Asp Gly Ile Gly Asp Ala
1               5                   10
```

-continued

```
<210> SEQ ID NO 490
<211> LENGTH: 10
<212> TYPE: PRT
<213> ORGANISM: Homo sapiens

<400> SEQUENCE: 490

Asp Ser Ser Ala Ala Ala Ile Ile Asp Ala
1               5                   10

<210> SEQ ID NO 491
<211> LENGTH: 10
<212> TYPE: PRT
<213> ORGANISM: Homo sapiens

<400> SEQUENCE: 491

Asp Thr Pro Pro Ser Ala Leu Gln Glu Ala
1               5                   10

<210> SEQ ID NO 492
<211> LENGTH: 10
<212> TYPE: PRT
<213> ORGANISM: Homo sapiens

<400> SEQUENCE: 492

Asp Thr Arg Pro Ala Gly Leu Glu Glu Ala
1               5                   10

<210> SEQ ID NO 493
<211> LENGTH: 10
<212> TYPE: PRT
<213> ORGANISM: Homo sapiens

<400> SEQUENCE: 493

Asp Val Asp Arg Asp Gly Ile Gly Asp Ala
1               5                   10

<210> SEQ ID NO 494
<211> LENGTH: 10
<212> TYPE: PRT
<213> ORGANISM: Homo sapiens

<400> SEQUENCE: 494

Asp Val Glu Pro Gln Ala Leu Asn Glu Ala
1               5                   10

<210> SEQ ID NO 495
<211> LENGTH: 10
<212> TYPE: PRT
<213> ORGANISM: Homo sapiens

<400> SEQUENCE: 495

Glu Ala Ala Ala Ser Ala Leu Ala Asp Ala
1               5                   10

<210> SEQ ID NO 496
<211> LENGTH: 10
<212> TYPE: PRT
<213> ORGANISM: Homo sapiens

<400> SEQUENCE: 496

Glu Ala Ala Lys Pro Ala Leu Glu Glu Ala
1               5                   10
```

```
<210> SEQ ID NO 497
<211> LENGTH: 10
<212> TYPE: PRT
<213> ORGANISM: Homo sapiens

<400> SEQUENCE: 497

Glu Ala Gln Asn Asn Gly Leu Ile Asp Ala
1               5                   10

<210> SEQ ID NO 498
<211> LENGTH: 10
<212> TYPE: PRT
<213> ORGANISM: Homo sapiens

<400> SEQUENCE: 498

Glu Ala Arg Leu Gln Ala Leu Gln Glu Ala
1               5                   10

<210> SEQ ID NO 499
<211> LENGTH: 10
<212> TYPE: PRT
<213> ORGANISM: Homo sapiens

<400> SEQUENCE: 499

Glu Phe Arg Arg Ser Gly Leu Glu Glu Ala
1               5                   10

<210> SEQ ID NO 500
<211> LENGTH: 10
<212> TYPE: PRT
<213> ORGANISM: Homo sapiens

<400> SEQUENCE: 500

Glu Gly Ala Cys His Ala Leu Glu Glu Tyr
1               5                   10

<210> SEQ ID NO 501
<211> LENGTH: 10
<212> TYPE: PRT
<213> ORGANISM: Homo sapiens

<400> SEQUENCE: 501

Glu Gly Cys Asn Gly Gly Leu Met Asp Tyr
1               5                   10

<210> SEQ ID NO 502
<211> LENGTH: 10
<212> TYPE: PRT
<213> ORGANISM: Homo sapiens

<400> SEQUENCE: 502

Glu Gly Ser Lys Tyr Gly Ile Asp Glu Tyr
1               5                   10

<210> SEQ ID NO 503
<211> LENGTH: 10
<212> TYPE: PRT
<213> ORGANISM: Homo sapiens

<400> SEQUENCE: 503

Glu Ile Ser Pro Ala Ala Ile Ala Asp Ala
1               5                   10

<210> SEQ ID NO 504
<211> LENGTH: 10
```

-continued

```
<212> TYPE: PRT
<213> ORGANISM: Homo sapiens

<400> SEQUENCE: 504

Glu Lys Gln Lys Asn Ala Leu Gly Glu Ala
1               5               10

<210> SEQ ID NO 505
<211> LENGTH: 10
<212> TYPE: PRT
<213> ORGANISM: Homo sapiens

<400> SEQUENCE: 505

Glu Lys Arg Lys His Ala Ile Glu Glu Ala
1               5               10

<210> SEQ ID NO 506
<211> LENGTH: 10
<212> TYPE: PRT
<213> ORGANISM: Homo sapiens

<400> SEQUENCE: 506

Glu Lys Ser Gln Cys Ala Leu Glu Glu Tyr
1               5               10

<210> SEQ ID NO 507
<211> LENGTH: 10
<212> TYPE: PRT
<213> ORGANISM: Homo sapiens

<400> SEQUENCE: 507

Glu Gln Ala Asn Asn Ala Ile Gly Asp Tyr
1               5               10

<210> SEQ ID NO 508
<211> LENGTH: 10
<212> TYPE: PRT
<213> ORGANISM: Homo sapiens

<400> SEQUENCE: 508

Glu Gln Glu Gln Gln Gly Leu Gln Glu Ala
1               5               10

<210> SEQ ID NO 509
<211> LENGTH: 10
<212> TYPE: PRT
<213> ORGANISM: Homo sapiens

<400> SEQUENCE: 509

Glu Ser Ser Val Gln Ala Leu Ile Asp Ala
1               5               10

<210> SEQ ID NO 510
<211> LENGTH: 10
<212> TYPE: PRT
<213> ORGANISM: Homo sapiens

<400> SEQUENCE: 510

Glu Thr Asp Gly His Gly Leu Ala Glu Ala
1               5               10

<210> SEQ ID NO 511
<211> LENGTH: 10
<212> TYPE: PRT
<213> ORGANISM: Homo sapiens
```

<400> SEQUENCE: 511

Glu Thr Arg Gly Ser Ala Leu Asp Asp Ala
1               5                   10

<210> SEQ ID NO 512
<211> LENGTH: 10
<212> TYPE: PRT
<213> ORGANISM: Homo sapiens

<400> SEQUENCE: 512

Phe Ala Asp Gly Phe Ala Leu Glu Glu Ala
1               5                   10

<210> SEQ ID NO 513
<211> LENGTH: 10
<212> TYPE: PRT
<213> ORGANISM: Homo sapiens

<400> SEQUENCE: 513

Phe Ala Glu Val Gln Gly Met Gln Glu Ala
1               5                   10

<210> SEQ ID NO 514
<211> LENGTH: 10
<212> TYPE: PRT
<213> ORGANISM: Homo sapiens

<400> SEQUENCE: 514

Phe Gly Gln Leu Asn Gly Ile Asp Glu Tyr
1               5                   10

<210> SEQ ID NO 515
<211> LENGTH: 10
<212> TYPE: PRT
<213> ORGANISM: Homo sapiens

<400> SEQUENCE: 515

Phe Gly Ser Pro Gly Gly Leu Arg Glu Ala
1               5                   10

<210> SEQ ID NO 516
<211> LENGTH: 10
<212> TYPE: PRT
<213> ORGANISM: Homo sapiens

<400> SEQUENCE: 516

Phe Lys Glu Gly Met Ala Leu Glu Asp Tyr
1               5                   10

<210> SEQ ID NO 517
<211> LENGTH: 10
<212> TYPE: PRT
<213> ORGANISM: Homo sapiens

<400> SEQUENCE: 517

Phe Lys Glu Leu Asp Gly Leu Arg Glu Ala
1               5                   10

<210> SEQ ID NO 518
<211> LENGTH: 10
<212> TYPE: PRT
<213> ORGANISM: Homo sapiens

<400> SEQUENCE: 518

-continued

```
Phe Leu Gln Gln Ala Ala Leu Glu Glu Tyr
1               5                   10

<210> SEQ ID NO 519
<211> LENGTH: 10
<212> TYPE: PRT
<213> ORGANISM: Homo sapiens

<400> SEQUENCE: 519

Phe Gln Ala Ala Thr Ala Ile Met Glu Ala
1               5                   10

<210> SEQ ID NO 520
<211> LENGTH: 10
<212> TYPE: PRT
<213> ORGANISM: Homo sapiens

<400> SEQUENCE: 520

Gly Ala Ala Arg Gln Ala Leu Ala Asp Ala
1               5                   10

<210> SEQ ID NO 521
<211> LENGTH: 10
<212> TYPE: PRT
<213> ORGANISM: Homo sapiens

<400> SEQUENCE: 521

Gly Ala Asp Val Asn Ala Ile Asn Glu Ala
1               5                   10

<210> SEQ ID NO 522
<211> LENGTH: 10
<212> TYPE: PRT
<213> ORGANISM: Homo sapiens

<400> SEQUENCE: 522

Gly Ala Pro Ala Pro Ala Leu Ala Asp Tyr
1               5                   10

<210> SEQ ID NO 523
<211> LENGTH: 10
<212> TYPE: PRT
<213> ORGANISM: Homo sapiens

<400> SEQUENCE: 523

Gly Ala Pro Lys Ala Gly Leu Glu Glu Ala
1               5                   10

<210> SEQ ID NO 524
<211> LENGTH: 10
<212> TYPE: PRT
<213> ORGANISM: Homo sapiens

<400> SEQUENCE: 524

Gly Cys Asp Pro Ser Gly Leu Gly Glu Ala
1               5                   10

<210> SEQ ID NO 525
<211> LENGTH: 10
<212> TYPE: PRT
<213> ORGANISM: Homo sapiens

<400> SEQUENCE: 525

Gly Gly Arg Ala Ser Gly Leu Gly Glu Ala
```

-continued

```
1               5               10

<210> SEQ ID NO 526
<211> LENGTH: 10
<212> TYPE: PRT
<213> ORGANISM: Homo sapiens

<400> SEQUENCE: 526

Gly Lys Cys Lys Asp Gly Leu Gly Glu Tyr
1               5               10

<210> SEQ ID NO 527
<211> LENGTH: 10
<212> TYPE: PRT
<213> ORGANISM: Homo sapiens

<400> SEQUENCE: 527

Gly Leu Asp Ala Ala Gly Ile Glu Glu Ala
1               5               10

<210> SEQ ID NO 528
<211> LENGTH: 10
<212> TYPE: PRT
<213> ORGANISM: Homo sapiens

<400> SEQUENCE: 528

Gly Asn Asp Ala Ala Ala Ile Arg Asp Ala
1               5               10

<210> SEQ ID NO 529
<211> LENGTH: 10
<212> TYPE: PRT
<213> ORGANISM: Homo sapiens

<400> SEQUENCE: 529

Gly Asn Ser Arg Ser Ala Leu Gln Glu Ala
1               5               10

<210> SEQ ID NO 530
<211> LENGTH: 10
<212> TYPE: PRT
<213> ORGANISM: Homo sapiens

<400> SEQUENCE: 530

Gly Gln Glu Pro Gly Gly Met Glu Asp Ala
1               5               10

<210> SEQ ID NO 531
<211> LENGTH: 10
<212> TYPE: PRT
<213> ORGANISM: Homo sapiens

<400> SEQUENCE: 531

Gly Gln Arg Val Pro Ala Leu Glu Glu Ala
1               5               10

<210> SEQ ID NO 532
<211> LENGTH: 10
<212> TYPE: PRT
<213> ORGANISM: Homo sapiens

<400> SEQUENCE: 532

Gly Ser Ala Leu Ala Ala Leu Arg Asp Ala
1               5               10
```

<210> SEQ ID NO 533
<211> LENGTH: 10
<212> TYPE: PRT
<213> ORGANISM: Homo sapiens

<400> SEQUENCE: 533

Gly Thr Pro Phe Thr Ala Ile Arg Glu Ala
1               5                   10

<210> SEQ ID NO 534
<211> LENGTH: 10
<212> TYPE: PRT
<213> ORGANISM: Homo sapiens

<400> SEQUENCE: 534

Gly Thr Pro Thr Pro Ala Leu Gly Asp Ala
1               5                   10

<210> SEQ ID NO 535
<211> LENGTH: 10
<212> TYPE: PRT
<213> ORGANISM: Homo sapiens

<400> SEQUENCE: 535

Gly Thr Gln Pro Pro Gly Met Gly Glu Ala
1               5                   10

<210> SEQ ID NO 536
<211> LENGTH: 10
<212> TYPE: PRT
<213> ORGANISM: Homo sapiens

<400> SEQUENCE: 536

Gly Val Pro Phe Thr Ala Ile Arg Glu Ala
1               5                   10

<210> SEQ ID NO 537
<211> LENGTH: 10
<212> TYPE: PRT
<213> ORGANISM: Homo sapiens

<400> SEQUENCE: 537

His Lys Ser Lys Gln Ala Leu Arg Asp Tyr
1               5                   10

<210> SEQ ID NO 538
<211> LENGTH: 10
<212> TYPE: PRT
<213> ORGANISM: Homo sapiens

<400> SEQUENCE: 538

His Leu Pro Asn Ala Ala Leu Ala Glu Ala
1               5                   10

<210> SEQ ID NO 539
<211> LENGTH: 10
<212> TYPE: PRT
<213> ORGANISM: Homo sapiens

<400> SEQUENCE: 539

His Ser Glu Arg Gly Ala Leu Gln Asp Ala
1               5                   10

<210> SEQ ID NO 540

```
<211> LENGTH: 10
<212> TYPE: PRT
<213> ORGANISM: Homo sapiens

<400> SEQUENCE: 540

His Thr Ser Ser Gly Gly Leu Gly Asp Ala
1               5                   10

<210> SEQ ID NO 541
<211> LENGTH: 10
<212> TYPE: PRT
<213> ORGANISM: Homo sapiens

<400> SEQUENCE: 541

Ile Ala Asp Asn Gly Gly Leu Arg Glu Ala
1               5                   10

<210> SEQ ID NO 542
<211> LENGTH: 10
<212> TYPE: PRT
<213> ORGANISM: Homo sapiens

<400> SEQUENCE: 542

Ile Leu Glu Gly Ala Ala Leu Asp Glu Ala
1               5                   10

<210> SEQ ID NO 543
<211> LENGTH: 10
<212> TYPE: PRT
<213> ORGANISM: Homo sapiens

<400> SEQUENCE: 543

Ile Leu Arg Ser Met Gly Met Glu Asp Ala
1               5                   10

<210> SEQ ID NO 544
<211> LENGTH: 10
<212> TYPE: PRT
<213> ORGANISM: Homo sapiens

<400> SEQUENCE: 544

Ile Asn Arg Val Ser Ala Met Arg Asp Tyr
1               5                   10

<210> SEQ ID NO 545
<211> LENGTH: 10
<212> TYPE: PRT
<213> ORGANISM: Homo sapiens

<400> SEQUENCE: 545

Ile Gln Gln His Thr Ala Met Asn Asp Ala
1               5                   10

<210> SEQ ID NO 546
<211> LENGTH: 10
<212> TYPE: PRT
<213> ORGANISM: Homo sapiens

<400> SEQUENCE: 546

Ile Gln Ser Lys Gly Gly Leu Asp Glu Ala
1               5                   10

<210> SEQ ID NO 547
<211> LENGTH: 10
<212> TYPE: PRT
```

<213> ORGANISM: Homo sapiens

<400> SEQUENCE: 547

Lys Ala Glu Ser Gly Ala Leu Ile Glu Ala
1               5                   10

<210> SEQ ID NO 548
<211> LENGTH: 10
<212> TYPE: PRT
<213> ORGANISM: Homo sapiens

<400> SEQUENCE: 548

Lys Phe Ser Arg Ser Ala Leu Arg Asp Ala
1               5                   10

<210> SEQ ID NO 549
<211> LENGTH: 10
<212> TYPE: PRT
<213> ORGANISM: Homo sapiens

<400> SEQUENCE: 549

Lys Ile Gln Cys Gln Ala Ile Arg Glu Ala
1               5                   10

<210> SEQ ID NO 550
<211> LENGTH: 10
<212> TYPE: PRT
<213> ORGANISM: Homo sapiens

<400> SEQUENCE: 550

Lys Lys Gln Ser Asp Gly Met Glu Glu Tyr
1               5                   10

<210> SEQ ID NO 551
<211> LENGTH: 10
<212> TYPE: PRT
<213> ORGANISM: Homo sapiens

<400> SEQUENCE: 551

Lys Asn Ser Trp Ser Gly Ile Glu Asp Tyr
1               5                   10

<210> SEQ ID NO 552
<211> LENGTH: 10
<212> TYPE: PRT
<213> ORGANISM: Homo sapiens

<400> SEQUENCE: 552

Lys Gln Ala Leu Ser Ala Leu Glu Glu Ala
1               5                   10

<210> SEQ ID NO 553
<211> LENGTH: 10
<212> TYPE: PRT
<213> ORGANISM: Homo sapiens

<400> SEQUENCE: 553

Lys Ser Ser Trp Phe Gly Leu Arg Glu Ala
1               5                   10

<210> SEQ ID NO 554
<211> LENGTH: 10
<212> TYPE: PRT
<213> ORGANISM: Homo sapiens -continued

```
<400> SEQUENCE: 554

Lys Val Pro Lys Ser Ala Leu Asp Glu Tyr
1               5                   10

<210> SEQ ID NO 555
<211> LENGTH: 10
<212> TYPE: PRT
<213> ORGANISM: Homo sapiens

<400> SEQUENCE: 555

Leu Ala Ala Leu Gln Ala Leu Gly Glu Ala
1               5                   10

<210> SEQ ID NO 556
<211> LENGTH: 10
<212> TYPE: PRT
<213> ORGANISM: Homo sapiens

<400> SEQUENCE: 556

Leu Ala Arg Pro Pro Gly Leu Glu Glu Ala
1               5                   10

<210> SEQ ID NO 557
<211> LENGTH: 10
<212> TYPE: PRT
<213> ORGANISM: Homo sapiens

<400> SEQUENCE: 557

Leu Cys Glu Leu Gln Gly Leu Gln Asp Ala
1               5                   10

<210> SEQ ID NO 558
<211> LENGTH: 10
<212> TYPE: PRT
<213> ORGANISM: Homo sapiens

<400> SEQUENCE: 558

Leu Phe Ser Leu His Gly Leu Ile Glu Tyr
1               5                   10

<210> SEQ ID NO 559
<211> LENGTH: 10
<212> TYPE: PRT
<213> ORGANISM: Homo sapiens

<400> SEQUENCE: 559

Leu Gly Cys Val Phe Ala Ile Ala Asp Tyr
1               5                   10

<210> SEQ ID NO 560
<211> LENGTH: 10
<212> TYPE: PRT
<213> ORGANISM: Homo sapiens

<400> SEQUENCE: 560

Leu Gly Glu Arg Gly Ala Leu Arg Glu Ala
1               5                   10

<210> SEQ ID NO 561
<211> LENGTH: 10
<212> TYPE: PRT
<213> ORGANISM: Homo sapiens

<400> SEQUENCE: 561
```

```
Leu Gly Ser Met Asp Ala Ile Ile Asp Ala
1               5               10

<210> SEQ ID NO 562
<211> LENGTH: 10
<212> TYPE: PRT
<213> ORGANISM: Homo sapiens

<400> SEQUENCE: 562

Leu Gly Ser Pro Gln Ala Ile Glu Glu Ala
1               5               10

<210> SEQ ID NO 563
<211> LENGTH: 10
<212> TYPE: PRT
<213> ORGANISM: Homo sapiens

<400> SEQUENCE: 563

Leu Gly Ser Thr Asp Gly Ile Ile Asp Ala
1               5               10

<210> SEQ ID NO 564
<211> LENGTH: 10
<212> TYPE: PRT
<213> ORGANISM: Homo sapiens

<400> SEQUENCE: 564

Leu Lys Ala Ser Ala Ala Leu Gly Glu Ala
1               5               10

<210> SEQ ID NO 565
<211> LENGTH: 10
<212> TYPE: PRT
<213> ORGANISM: Homo sapiens

<400> SEQUENCE: 565

Leu Leu Ala Ala Ala Gly Leu Ala Asp Ala
1               5               10

<210> SEQ ID NO 566
<211> LENGTH: 10
<212> TYPE: PRT
<213> ORGANISM: Homo sapiens

<400> SEQUENCE: 566

Leu Leu Ala Leu Asp Gly Leu Arg Glu Ala
1               5               10

<210> SEQ ID NO 567
<211> LENGTH: 10
<212> TYPE: PRT
<213> ORGANISM: Homo sapiens

<400> SEQUENCE: 567

Leu Leu Cys Ser Tyr Gly Met Asp Asp Tyr
1               5               10

<210> SEQ ID NO 568
<211> LENGTH: 10
<212> TYPE: PRT
<213> ORGANISM: Homo sapiens

<400> SEQUENCE: 568

Leu Leu Arg Pro Pro Gly Leu Gly Glu Ala
1               5               10
```

<210> SEQ ID NO 569
<211> LENGTH: 10
<212> TYPE: PRT
<213> ORGANISM: Homo sapiens

<400> SEQUENCE: 569

Leu Leu Ser Ser Ser Gly Leu Asn Glu Tyr
1               5                   10

<210> SEQ ID NO 570
<211> LENGTH: 10
<212> TYPE: PRT
<213> ORGANISM: Homo sapiens

<400> SEQUENCE: 570

Leu Asn Glu Leu Gln Ala Leu Ile Glu Ala
1               5                   10

<210> SEQ ID NO 571
<211> LENGTH: 10
<212> TYPE: PRT
<213> ORGANISM: Homo sapiens

<400> SEQUENCE: 571

Leu Asn Pro Lys Thr Gly Leu Ile Asp Tyr
1               5                   10

<210> SEQ ID NO 572
<211> LENGTH: 10
<212> TYPE: PRT
<213> ORGANISM: Homo sapiens

<400> SEQUENCE: 572

Leu Ser Asp Leu Ser Ala Met Glu Asp Ala
1               5                   10

<210> SEQ ID NO 573
<211> LENGTH: 10
<212> TYPE: PRT
<213> ORGANISM: Homo sapiens

<400> SEQUENCE: 573

Leu Ser Gln Leu Phe Ala Met Ile Glu Ala
1               5                   10

<210> SEQ ID NO 574
<211> LENGTH: 10
<212> TYPE: PRT
<213> ORGANISM: Homo sapiens

<400> SEQUENCE: 574

Leu Ser Ser Thr Ser Ala Ile Ile Asp Tyr
1               5                   10

<210> SEQ ID NO 575
<211> LENGTH: 10
<212> TYPE: PRT
<213> ORGANISM: Homo sapiens

<400> SEQUENCE: 575

Leu Val Cys Leu Gly Ala Leu Ala Glu Ala
1               5                   10

-continued

```
<210> SEQ ID NO 576
<211> LENGTH: 10
<212> TYPE: PRT
<213> ORGANISM: Homo sapiens

<400> SEQUENCE: 576

Leu Val Glu Ser Gly Ala Leu Ile Asp Ala
1               5                   10

<210> SEQ ID NO 577
<211> LENGTH: 10
<212> TYPE: PRT
<213> ORGANISM: Homo sapiens

<400> SEQUENCE: 577

Met Ala Ala Ala Ser Ala Met Ala Glu Ala
1               5                   10

<210> SEQ ID NO 578
<211> LENGTH: 10
<212> TYPE: PRT
<213> ORGANISM: Homo sapiens

<400> SEQUENCE: 578

Met Gly Ser Leu Thr Gly Ile Ala Asp Ala
1               5                   10

<210> SEQ ID NO 579
<211> LENGTH: 10
<212> TYPE: PRT
<213> ORGANISM: Homo sapiens

<400> SEQUENCE: 579

Met Leu Arg Arg Pro Ala Leu Glu Asp Tyr
1               5                   10

<210> SEQ ID NO 580
<211> LENGTH: 10
<212> TYPE: PRT
<213> ORGANISM: Homo sapiens

<400> SEQUENCE: 580

Met Asn Glu Tyr Asn Ala Leu Asn Glu Ala
1               5                   10

<210> SEQ ID NO 581
<211> LENGTH: 10
<212> TYPE: PRT
<213> ORGANISM: Homo sapiens

<400> SEQUENCE: 581

Met Ser Ala Phe Pro Gly Ile Asp Glu Ala
1               5                   10

<210> SEQ ID NO 582
<211> LENGTH: 10
<212> TYPE: PRT
<213> ORGANISM: Homo sapiens

<400> SEQUENCE: 582

Met Val Asp Phe Ala Ala Met Arg Glu Ala
1               5                   10

<210> SEQ ID NO 583
<211> LENGTH: 10
```

<212> TYPE: PRT
<213> ORGANISM: Homo sapiens

<400> SEQUENCE: 583

Met Val Arg Asn Gln Ala Met Ala Asp Ala
1               5               10

<210> SEQ ID NO 584
<211> LENGTH: 10
<212> TYPE: PRT
<213> ORGANISM: Homo sapiens

<400> SEQUENCE: 584

Asn Ala Ser Arg Gln Gly Ile Glu Asp Ala
1               5               10

<210> SEQ ID NO 585
<211> LENGTH: 10
<212> TYPE: PRT
<213> ORGANISM: Homo sapiens

<400> SEQUENCE: 585

Asn Phe Arg Ile Ser Ala Ile Asn Asp Ala
1               5               10

<210> SEQ ID NO 586
<211> LENGTH: 10
<212> TYPE: PRT
<213> ORGANISM: Homo sapiens

<400> SEQUENCE: 586

Asn Lys Asp Ile Ser Ala Ile Glu Glu Ala
1               5               10

<210> SEQ ID NO 587
<211> LENGTH: 10
<212> TYPE: PRT
<213> ORGANISM: Homo sapiens

<400> SEQUENCE: 587

Asn Lys Ser Gln Gln Ala Leu Ala Asp Ala
1               5               10

<210> SEQ ID NO 588
<211> LENGTH: 10
<212> TYPE: PRT
<213> ORGANISM: Homo sapiens

<400> SEQUENCE: 588

Asn Gln Pro Ile Tyr Ala Leu Gln Glu Ala
1               5               10

<210> SEQ ID NO 589
<211> LENGTH: 10
<212> TYPE: PRT
<213> ORGANISM: Homo sapiens

<400> SEQUENCE: 589

Asn Ser Cys Val Ser Ala Met Gln Glu Tyr
1               5               10

<210> SEQ ID NO 590
<211> LENGTH: 10
<212> TYPE: PRT
<213> ORGANISM: Homo sapiens -continued

<400> SEQUENCE: 590

Pro Phe Ala Ala Ala Ala Ile Asn Glu Ala
1               5                   10

<210> SEQ ID NO 591
<211> LENGTH: 10
<212> TYPE: PRT
<213> ORGANISM: Homo sapiens

<400> SEQUENCE: 591

Pro Gly Ala Pro Gln Ala Leu Gly Asp Ala
1               5                   10

<210> SEQ ID NO 592
<211> LENGTH: 10
<212> TYPE: PRT
<213> ORGANISM: Homo sapiens

<400> SEQUENCE: 592

Pro Gly Glu Gly Ala Ala Leu Ala Asp Ala
1               5                   10

<210> SEQ ID NO 593
<211> LENGTH: 10
<212> TYPE: PRT
<213> ORGANISM: Homo sapiens

<400> SEQUENCE: 593

Pro Gly Glu Gly Ala Ala Met Ala Glu Tyr
1               5                   10

<210> SEQ ID NO 594
<211> LENGTH: 10
<212> TYPE: PRT
<213> ORGANISM: Homo sapiens

<400> SEQUENCE: 594

Pro Gly Pro Gly Gly Gly Leu Glu Asp Ala
1               5                   10

<210> SEQ ID NO 595
<211> LENGTH: 10
<212> TYPE: PRT
<213> ORGANISM: Homo sapiens

<400> SEQUENCE: 595

Pro Gly Gln Ala Gln Ala Leu Glu Glu Ala
1               5                   10

<210> SEQ ID NO 596
<211> LENGTH: 10
<212> TYPE: PRT
<213> ORGANISM: Homo sapiens

<400> SEQUENCE: 596

Pro Gly Arg Lys Gly Ala Met Gly Asp Ala
1               5                   10

<210> SEQ ID NO 597
<211> LENGTH: 10
<212> TYPE: PRT
<213> ORGANISM: Homo sapiens

<400> SEQUENCE: 597

```
Pro Ile Cys Leu Met Ala Leu Arg Glu Ala
1               5                   10

<210> SEQ ID NO 598
<211> LENGTH: 10
<212> TYPE: PRT
<213> ORGANISM: Homo sapiens

<400> SEQUENCE: 598

Pro Leu Glu Phe Ala Ala Ile Gly Asp Tyr
1               5                   10

<210> SEQ ID NO 599
<211> LENGTH: 10
<212> TYPE: PRT
<213> ORGANISM: Homo sapiens

<400> SEQUENCE: 599

Pro Leu Gln Ala Gln Ala Leu Gly Glu Ala
1               5                   10

<210> SEQ ID NO 600
<211> LENGTH: 10
<212> TYPE: PRT
<213> ORGANISM: Homo sapiens

<400> SEQUENCE: 600

Pro Asn Arg Leu Ser Ala Met Arg Glu Ala
1               5                   10

<210> SEQ ID NO 601
<211> LENGTH: 10
<212> TYPE: PRT
<213> ORGANISM: Homo sapiens

<400> SEQUENCE: 601

Pro Ser Ser Arg Thr Ala Leu Ala Glu Ala
1               5                   10

<210> SEQ ID NO 602
<211> LENGTH: 10
<212> TYPE: PRT
<213> ORGANISM: Homo sapiens

<400> SEQUENCE: 602

Pro Thr Ala Gly Ala Gly Ile Glu Asp Ala
1               5                   10

<210> SEQ ID NO 603
<211> LENGTH: 10
<212> TYPE: PRT
<213> ORGANISM: Homo sapiens

<400> SEQUENCE: 603

Pro Thr Pro Pro Pro Ala Leu Arg Glu Ala
1               5                   10

<210> SEQ ID NO 604
<211> LENGTH: 10
<212> TYPE: PRT
<213> ORGANISM: Homo sapiens

<400> SEQUENCE: 604

Pro Thr Arg Leu Pro Ala Leu Gly Glu Ala
```

```
1               5               10
```

<210> SEQ ID NO 605
<211> LENGTH: 10
<212> TYPE: PRT
<213> ORGANISM: Homo sapiens

<400> SEQUENCE: 605

```
Gln Ala Ala Lys Gln Ala Leu Ala Glu Ala
1               5               10
```

<210> SEQ ID NO 606
<211> LENGTH: 10
<212> TYPE: PRT
<213> ORGANISM: Homo sapiens

<400> SEQUENCE: 606

```
Gln Ala Glu Ala Asp Ala Leu Ala Asp Ala
1               5               10
```

<210> SEQ ID NO 607
<211> LENGTH: 10
<212> TYPE: PRT
<213> ORGANISM: Homo sapiens

<400> SEQUENCE: 607

```
Gln Phe Gln Gln Ser Ala Leu Ala Asp Tyr
1               5               10
```

<210> SEQ ID NO 608
<211> LENGTH: 10
<212> TYPE: PRT
<213> ORGANISM: Homo sapiens

<400> SEQUENCE: 608

```
Gln Gly Arg Gly Gln Gly Leu Glu Glu Ala
1               5               10
```

<210> SEQ ID NO 609
<211> LENGTH: 10
<212> TYPE: PRT
<213> ORGANISM: Homo sapiens

<400> SEQUENCE: 609

```
Gln Gly Ser Leu Ala Ala Leu Gly Glu Ala
1               5               10
```

<210> SEQ ID NO 610
<211> LENGTH: 10
<212> TYPE: PRT
<213> ORGANISM: Homo sapiens

<400> SEQUENCE: 610

```
Gln Lys Gln Lys Ser Ala Leu Asp Glu Ala
1               5               10
```

<210> SEQ ID NO 611
<211> LENGTH: 10
<212> TYPE: PRT
<213> ORGANISM: Homo sapiens

<400> SEQUENCE: 611

```
Gln Leu Pro Pro Ala Gly Met Glu Glu Ala
1               5               10
```

<210> SEQ ID NO 612
<211> LENGTH: 10
<212> TYPE: PRT
<213> ORGANISM: Homo sapiens

<400> SEQUENCE: 612

Gln Leu Gln His Ala Gly Leu Arg Glu Ala
1               5                   10

<210> SEQ ID NO 613
<211> LENGTH: 10
<212> TYPE: PRT
<213> ORGANISM: Homo sapiens

<400> SEQUENCE: 613

Gln Leu Arg Thr Ser Ala Leu Met Glu Ala
1               5                   10

<210> SEQ ID NO 614
<211> LENGTH: 10
<212> TYPE: PRT
<213> ORGANISM: Homo sapiens

<400> SEQUENCE: 614

Gln Met Glu Lys Cys Ala Leu Met Glu Ala
1               5                   10

<210> SEQ ID NO 615
<211> LENGTH: 10
<212> TYPE: PRT
<213> ORGANISM: Homo sapiens

<400> SEQUENCE: 615

Gln Ser Ala Trp Ala Gly Leu Arg Glu Ala
1               5                   10

<210> SEQ ID NO 616
<211> LENGTH: 10
<212> TYPE: PRT
<213> ORGANISM: Homo sapiens

<400> SEQUENCE: 616

Gln Val Gln Asn Asn Gly Leu Ile Asp Ala
1               5                   10

<210> SEQ ID NO 617
<211> LENGTH: 10
<212> TYPE: PRT
<213> ORGANISM: Homo sapiens

<400> SEQUENCE: 617

Gln Val Arg Lys Ala Gly Met Asn Asp Ala
1               5                   10

<210> SEQ ID NO 618
<211> LENGTH: 10
<212> TYPE: PRT
<213> ORGANISM: Homo sapiens

<400> SEQUENCE: 618

Arg Ala Ala Leu Thr Gly Leu Ala Asp Ala
1               5                   10

<210> SEQ ID NO 619

```
<211> LENGTH: 10
<212> TYPE: PRT
<213> ORGANISM: Homo sapiens

<400> SEQUENCE: 619

Arg Ala Pro Gly Pro Ala Leu Gly Glu Ala
1               5                   10

<210> SEQ ID NO 620
<211> LENGTH: 10
<212> TYPE: PRT
<213> ORGANISM: Homo sapiens

<400> SEQUENCE: 620

Arg Ala Ser Trp Gly Gly Leu Arg Glu Ala
1               5                   10

<210> SEQ ID NO 621
<211> LENGTH: 10
<212> TYPE: PRT
<213> ORGANISM: Homo sapiens

<400> SEQUENCE: 621

Arg Cys Ser Asn Gln Gly Ile Glu Asp Tyr
1               5                   10

<210> SEQ ID NO 622
<211> LENGTH: 10
<212> TYPE: PRT
<213> ORGANISM: Homo sapiens

<400> SEQUENCE: 622

Arg Phe Arg Leu Pro Gly Leu Gly Glu Ala
1               5                   10

<210> SEQ ID NO 623
<211> LENGTH: 10
<212> TYPE: PRT
<213> ORGANISM: Homo sapiens

<400> SEQUENCE: 623

Arg Gly Ala Gln Gly Gly Ile Ala Glu Ala
1               5                   10

<210> SEQ ID NO 624
<211> LENGTH: 10
<212> TYPE: PRT
<213> ORGANISM: Homo sapiens

<400> SEQUENCE: 624

Arg Gly Gln Leu Tyr Gly Leu Arg Asp Ala
1               5                   10

<210> SEQ ID NO 625
<211> LENGTH: 10
<212> TYPE: PRT
<213> ORGANISM: Homo sapiens

<400> SEQUENCE: 625

Arg Lys Ser Lys Gln Ala Leu Arg Asp Tyr
1               5                   10

<210> SEQ ID NO 626
<211> LENGTH: 10
<212> TYPE: PRT
```

<213> ORGANISM: Homo sapiens

<400> SEQUENCE: 626

Arg Leu Ala Cys Cys Ala Leu Gln Asp Ala
1               5                   10

<210> SEQ ID NO 627
<211> LENGTH: 10
<212> TYPE: PRT
<213> ORGANISM: Homo sapiens

<400> SEQUENCE: 627

Arg Leu Cys Lys Ala Ala Ile Ala Asp Tyr
1               5                   10

<210> SEQ ID NO 628
<211> LENGTH: 10
<212> TYPE: PRT
<213> ORGANISM: Homo sapiens

<400> SEQUENCE: 628

Arg Met Glu Asn Gln Ala Leu Gln Glu Ala
1               5                   10

<210> SEQ ID NO 629
<211> LENGTH: 10
<212> TYPE: PRT
<213> ORGANISM: Homo sapiens

<400> SEQUENCE: 629

Arg Met Pro Thr Thr Gly Ile Asn Glu Tyr
1               5                   10

<210> SEQ ID NO 630
<211> LENGTH: 10
<212> TYPE: PRT
<213> ORGANISM: Homo sapiens

<400> SEQUENCE: 630

Arg Asn Arg Met His Gly Leu Asn Asp Ala
1               5                   10

<210> SEQ ID NO 631
<211> LENGTH: 10
<212> TYPE: PRT
<213> ORGANISM: Homo sapiens

<400> SEQUENCE: 631

Arg Ser Ser Ser Met Gly Leu Gln Glu Tyr
1               5                   10

<210> SEQ ID NO 632
<211> LENGTH: 10
<212> TYPE: PRT
<213> ORGANISM: Homo sapiens

<400> SEQUENCE: 632

Arg Thr Arg Met His Gly Leu Asn Asp Ala
1               5                   10

<210> SEQ ID NO 633
<211> LENGTH: 10
<212> TYPE: PRT
<213> ORGANISM: Homo sapiens

<400> SEQUENCE: 633

Arg Val Pro Ser Pro Gly Met Glu Glu Ala
1               5               10

<210> SEQ ID NO 634
<211> LENGTH: 10
<212> TYPE: PRT
<213> ORGANISM: Homo sapiens

<400> SEQUENCE: 634

Arg Val Pro Thr Thr Gly Ile Ile Glu Tyr
1               5               10

<210> SEQ ID NO 635
<211> LENGTH: 10
<212> TYPE: PRT
<213> ORGANISM: Homo sapiens

<400> SEQUENCE: 635

Ser Ala Ala Ile Gly Ala Leu Gln Glu Ala
1               5               10

<210> SEQ ID NO 636
<211> LENGTH: 10
<212> TYPE: PRT
<213> ORGANISM: Homo sapiens

<400> SEQUENCE: 636

Ser Ala Ala Val Gly Ala Leu Gln Glu Ala
1               5               10

<210> SEQ ID NO 637
<211> LENGTH: 10
<212> TYPE: PRT
<213> ORGANISM: Homo sapiens

<400> SEQUENCE: 637

Ser Ala Ser Ala Thr Ala Leu Ala Asp Ala
1               5               10

<210> SEQ ID NO 638
<211> LENGTH: 10
<212> TYPE: PRT
<213> ORGANISM: Homo sapiens

<400> SEQUENCE: 638

Ser Ala Ser His Ser Ala Leu Gln Asp Ala
1               5               10

<210> SEQ ID NO 639
<211> LENGTH: 10
<212> TYPE: PRT
<213> ORGANISM: Homo sapiens

<400> SEQUENCE: 639

Ser Phe Asp Val Phe Ala Leu Asn Glu Ala
1               5               10

<210> SEQ ID NO 640
<211> LENGTH: 10
<212> TYPE: PRT
<213> ORGANISM: Homo sapiens

<400> SEQUENCE: 640

```
Ser Phe Ser Leu Ser Ala Leu Arg Glu Ala
1               5                   10

<210> SEQ ID NO 641
<211> LENGTH: 10
<212> TYPE: PRT
<213> ORGANISM: Homo sapiens

<400> SEQUENCE: 641

Ser Gly Glu Thr Ser Gly Leu Gln Glu Ala
1               5                   10

<210> SEQ ID NO 642
<211> LENGTH: 10
<212> TYPE: PRT
<213> ORGANISM: Homo sapiens

<400> SEQUENCE: 642

Ser Lys Asp Thr Asp Ala Leu Ile Asp Ala
1               5                   10

<210> SEQ ID NO 643
<211> LENGTH: 10
<212> TYPE: PRT
<213> ORGANISM: Homo sapiens

<400> SEQUENCE: 643

Ser Leu Ala Pro Ala Gly Ile Ala Asp Ala
1               5                   10

<210> SEQ ID NO 644
<211> LENGTH: 10
<212> TYPE: PRT
<213> ORGANISM: Homo sapiens

<400> SEQUENCE: 644

Ser Leu Arg Gln Pro Gly Leu Ala Glu Ala
1               5                   10

<210> SEQ ID NO 645
<211> LENGTH: 10
<212> TYPE: PRT
<213> ORGANISM: Homo sapiens

<400> SEQUENCE: 645

Ser Asn Cys Ser Asp Gly Met Met Asp Tyr
1               5                   10

<210> SEQ ID NO 646
<211> LENGTH: 10
<212> TYPE: PRT
<213> ORGANISM: Homo sapiens

<400> SEQUENCE: 646

Ser Ser Ala Val Met Ala Leu Gln Glu Ala
1               5                   10

<210> SEQ ID NO 647
<211> LENGTH: 10
<212> TYPE: PRT
<213> ORGANISM: Homo sapiens

<400> SEQUENCE: 647

Ser Ser Asp Gly Ala Gly Ile Gln Glu Ala
1               5                   10
```

```
<210> SEQ ID NO 648
<211> LENGTH: 10
<212> TYPE: PRT
<213> ORGANISM: Homo sapiens

<400> SEQUENCE: 648

Ser Ser Asp Lys Ser Gly Met Ile Glu Tyr
1               5                   10

<210> SEQ ID NO 649
<211> LENGTH: 10
<212> TYPE: PRT
<213> ORGANISM: Homo sapiens

<400> SEQUENCE: 649

Ser Ser Pro Ser Gln Ala Met Gln Glu Tyr
1               5                   10

<210> SEQ ID NO 650
<211> LENGTH: 10
<212> TYPE: PRT
<213> ORGANISM: Homo sapiens

<400> SEQUENCE: 650

Ser Thr Ser Ala Ala Ala Leu Gln Glu Ala
1               5                   10

<210> SEQ ID NO 651
<211> LENGTH: 10
<212> TYPE: PRT
<213> ORGANISM: Homo sapiens

<400> SEQUENCE: 651

Ser Val Asp Tyr Asp Gly Ile Asn Asp Ala
1               5                   10

<210> SEQ ID NO 652
<211> LENGTH: 10
<212> TYPE: PRT
<213> ORGANISM: Homo sapiens

<400> SEQUENCE: 652

Thr Ala Ala Pro Thr Ala Leu Gly Glu Ala
1               5                   10

<210> SEQ ID NO 653
<211> LENGTH: 10
<212> TYPE: PRT
<213> ORGANISM: Homo sapiens

<400> SEQUENCE: 653

Thr Ala Pro Ala His Gly Met Glu Asp Tyr
1               5                   10

<210> SEQ ID NO 654
<211> LENGTH: 10
<212> TYPE: PRT
<213> ORGANISM: Homo sapiens

<400> SEQUENCE: 654

Thr Gly Asp Phe His Ala Ile Asp Glu Tyr
1               5                   10
```

```
<210> SEQ ID NO 655
<211> LENGTH: 10
<212> TYPE: PRT
<213> ORGANISM: Homo sapiens

<400> SEQUENCE: 655

Thr Gly Gln Leu Ser Gly Ile Ala Glu Ala
1               5               10

<210> SEQ ID NO 656
<211> LENGTH: 10
<212> TYPE: PRT
<213> ORGANISM: Homo sapiens

<400> SEQUENCE: 656

Thr Gln Glu Lys Phe Ala Leu Glu Glu Ala
1               5               10

<210> SEQ ID NO 657
<211> LENGTH: 10
<212> TYPE: PRT
<213> ORGANISM: Homo sapiens

<400> SEQUENCE: 657

Thr Gln Glu Leu Ser Ala Leu Arg Glu Ala
1               5               10

<210> SEQ ID NO 658
<211> LENGTH: 10
<212> TYPE: PRT
<213> ORGANISM: Homo sapiens

<400> SEQUENCE: 658

Thr Ser Arg Pro Ala Ala Leu Asp Glu Ala
1               5               10

<210> SEQ ID NO 659
<211> LENGTH: 10
<212> TYPE: PRT
<213> ORGANISM: Homo sapiens

<400> SEQUENCE: 659

Thr Thr Ser Phe Pro Ala Leu Glu Glu Ala
1               5               10

<210> SEQ ID NO 660
<211> LENGTH: 10
<212> TYPE: PRT
<213> ORGANISM: Homo sapiens

<400> SEQUENCE: 660

Val Ala Ala Ala Ala Gly Leu Glu Glu Ala
1               5               10

<210> SEQ ID NO 661
<211> LENGTH: 10
<212> TYPE: PRT
<213> ORGANISM: Homo sapiens

<400> SEQUENCE: 661

Val Ala Ala Gln Ala Ala Leu Glu Asp Ala
1               5               10

<210> SEQ ID NO 662
<211> LENGTH: 10
```

<212> TYPE: PRT
<213> ORGANISM: Homo sapiens

<400> SEQUENCE: 662

Val Ala Glu Gln Phe Ala Ile Ala Glu Ala
1               5                   10

<210> SEQ ID NO 663
<211> LENGTH: 10
<212> TYPE: PRT
<213> ORGANISM: Homo sapiens

<400> SEQUENCE: 663

Val Ala Gln Cys Asp Ala Leu Ile Asp Ala
1               5                   10

<210> SEQ ID NO 664
<211> LENGTH: 10
<212> TYPE: PRT
<213> ORGANISM: Homo sapiens

<400> SEQUENCE: 664

Val Gly Asp Val Ala Gly Leu Ala Glu Ala
1               5                   10

<210> SEQ ID NO 665
<211> LENGTH: 10
<212> TYPE: PRT
<213> ORGANISM: Homo sapiens

<400> SEQUENCE: 665

Val Gly Ser Gly Ala Ala Leu Ala Asp Ala
1               5                   10

<210> SEQ ID NO 666
<211> LENGTH: 10
<212> TYPE: PRT
<213> ORGANISM: Homo sapiens

<400> SEQUENCE: 666

Val Lys Ala Leu Tyr Gly Leu Glu Glu Tyr
1               5                   10

<210> SEQ ID NO 667
<211> LENGTH: 10
<212> TYPE: PRT
<213> ORGANISM: Homo sapiens

<400> SEQUENCE: 667

Val Lys Gln Ala Asn Ala Ile Ile Asp Tyr
1               5                   10

<210> SEQ ID NO 668
<211> LENGTH: 10
<212> TYPE: PRT
<213> ORGANISM: Homo sapiens

<400> SEQUENCE: 668

Val Leu Ala Ala Met Gly Met Gly Asp Ala
1               5                   10

<210> SEQ ID NO 669
<211> LENGTH: 10
<212> TYPE: PRT
<213> ORGANISM: Homo sapiens -continued

<400> SEQUENCE: 669

Val Leu Glu Ser Asn Gly Met Ile Asp Ala
1               5                   10

<210> SEQ ID NO 670
<211> LENGTH: 10
<212> TYPE: PRT
<213> ORGANISM: Homo sapiens

<400> SEQUENCE: 670

Val Leu Arg Thr Pro Gly Leu Arg Asp Ala
1               5                   10

<210> SEQ ID NO 671
<211> LENGTH: 10
<212> TYPE: PRT
<213> ORGANISM: Homo sapiens

<400> SEQUENCE: 671

Val Gln Cys Leu His Ala Leu Glu Glu Tyr
1               5                   10

<210> SEQ ID NO 672
<211> LENGTH: 10
<212> TYPE: PRT
<213> ORGANISM: Homo sapiens

<400> SEQUENCE: 672

Val Ser Arg Val Asp Gly Met Asp Asp Ala
1               5                   10

<210> SEQ ID NO 673
<211> LENGTH: 10
<212> TYPE: PRT
<213> ORGANISM: Homo sapiens

<400> SEQUENCE: 673

Val Val Ala Val Ala Ala Met Gly Asp Ala
1               5                   10

<210> SEQ ID NO 674
<211> LENGTH: 10
<212> TYPE: PRT
<213> ORGANISM: Homo sapiens

<400> SEQUENCE: 674

Val Val Asp Phe Ala Ala Met Arg Asp Ala
1               5                   10

<210> SEQ ID NO 675
<211> LENGTH: 10
<212> TYPE: PRT
<213> ORGANISM: Homo sapiens

<400> SEQUENCE: 675

Trp Gln Ala Asn Gln Ala Leu Gln Glu Tyr
1               5                   10

<210> SEQ ID NO 676
<211> LENGTH: 10
<212> TYPE: PRT
<213> ORGANISM: Homo sapiens

<400> SEQUENCE: 676

-continued

```
Trp Thr Glu Phe Asn Gly Ile Arg Asp Tyr
1               5                   10

<210> SEQ ID NO 677

<400> SEQUENCE: 677

000

<210> SEQ ID NO 678
<211> LENGTH: 10
<212> TYPE: PRT
<213> ORGANISM: Homo sapiens

<400> SEQUENCE: 678

Trp Thr Glu Val Pro Ala Met Arg Glu Ala
1               5                   10

<210> SEQ ID NO 679
<211> LENGTH: 10
<212> TYPE: PRT
<213> ORGANISM: Homo sapiens

<400> SEQUENCE: 679

Tyr Gln Glu Ile Pro Gly Leu Glu Glu Tyr
1               5                   10

<210> SEQ ID NO 680
<211> LENGTH: 10
<212> TYPE: PRT
<213> ORGANISM: Homo sapiens

<400> SEQUENCE: 680

Tyr Ser Pro His Thr Gly Ile Gln Glu Tyr
1               5                   10

<210> SEQ ID NO 681
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, g, unknown or other

<400> SEQUENCE: 681
cgacgtaaaa cgacggccag tnnnnnnnnn nnnnncgtgc agaggataca gcagtg          56

<210> SEQ ID NO 682
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 682
cacacaggaa acagctatga ccatgctaac ggtaaccagg gtgccctg                   48

<210> SEQ ID NO 683
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, W, D, or Y
<220> FEATURE:
<221> NAME/KEY: MOD_RES
<222> LOCATION: (2)..(2)
<223> OTHER INFORMATION: I, L, M, V, T, or C
<220> FEATURE:
<221> NAME/KEY: MOD_RES
<222> LOCATION: (3)..(3)
<223> OTHER INFORMATION: R or E
<220> FEATURE:
<221> NAME/KEY: MOD_RES
<222> LOCATION: (4)..(4)
<223> OTHER INFORMATION: I, L, or V
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: I, L, or V
<220> FEATURE:
<221> NAME/KEY: MOD_RES
<222> LOCATION: (7)..(7)
<223> OTHER INFORMATION: G, N, S, or T
<220> FEATURE:
<221> NAME/KEY: MOD_RES
<222> LOCATION: (8)..(8)
<223> OTHER INFORMATION: V or P
<220> FEATURE:
<221> NAME/KEY: MOD_RES
<222> LOCATION: (9)..(9)
<223> OTHER INFORMATION: A or G
<220> FEATURE:
<221> NAME/KEY: MOD_RES
<222> LOCATION: (10)..(10)
<223> OTHER INFORMATION: H, K, or Y

<400> SEQUENCE: 683

Xaa Xaa Xaa Xaa Xaa Xaa Xaa Xaa Xaa Xaa
1               5                   10

<210> SEQ ID NO 684
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: P, W, R, H, D, E, or Y
<220> FEATURE:
<221> NAME/KEY: MOD_RES
<222> LOCATION: (3)..(3)
<223> OTHER INFORMATION: A, P, R, D, E, Q, S, or C
<220> FEATURE:
<221> NAME/KEY: MOD_RES
<222> LOCATION: (4)..(4)
<223> OTHER INFORMATION: D or E
<220> FEATURE:
<221> NAME/KEY: MOD_RES
<222> LOCATION: (5)..(5)
<223> OTHER INFORMATION: A, M, F, P, G, H, D, N, Q, S, T, Y, or C
<220> FEATURE:
<221> NAME/KEY: MOD_RES
```

```
<222> LOCATION: (6)..(6)
<223> OTHER INFORMATION: A or G
<220> FEATURE:
<221> NAME/KEY: MOD_RES
<222> LOCATION: (7)..(7)
<223> OTHER INFORMATION: I, L or M
<220> FEATURE:
<221> NAME/KEY: MOD_RES
<222> LOCATION: (8)..(8)
<223> OTHER INFORMATION: A, I, M, G, R ,D, E, N, or Q
<220> FEATURE:
<221> NAME/KEY: MOD_RES
<222> LOCATION: (9)..(9)
<223> OTHER INFORMATION: D or E
<220> FEATURE:
<221> NAME/KEY: MOD_RES
<222> LOCATION: (10)..(10)
<223> OTHER INFORMATION: A or Y

<400> SEQUENCE: 684

Xaa Xaa Xaa Xaa Xaa Xaa Xaa Xaa Xaa Xaa
1               5                   10

<210> SEQ ID NO 685
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
gctgcgacgt ggggtcggac                                                20

<210> SEQ ID NO 686
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
cagactgacc gagcgaacct g                                              21

<210> SEQ ID NO 687
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
attagctgta tcgtcaaggc actcttgcct acgccaacgg cgccgacaac gacgagttta      60
tattcagtca ttttcagcag gccttataa                                       89

<210> SEQ ID NO 688
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
aatgactgaa tataaacttg                                                20
```

-continued

```
<210> SEQ ID NO 689
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 689
aacaagattt acctctattg ttggatcata ttcgtccaca aaatgattct gaattagctg      60
tatcgtcaag gcactcttgc ctacgtcacc agctccaact accacaagtt tatattcagt     120
cattttc                                                              127

<210> SEQ ID NO 690
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
cttgtggtag ttggagctgt                                                 20

<210> SEQ ID NO 691
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
cctcatgtat tggtctctca tgg                                             23

<210> SEQ ID NO 692
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
aaacctgttt gttggacata ctggatacag ctggacatga ggaatattct gcaatgagag      60
accaatacat gaggacaggc gaaggcttcc t                                    91

<210> SEQ ID NO 693
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
aaacctgttt gttggacata ctggatacag ctggaagaga ggaatattct gcaatgagag      60
accaatacat gaggacaggc gaaggcttcc t                                    91

<210> SEQ ID NO 694
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 694

Gly Gly Gly Gly Ser Gly Gly Gly Gly Ser
1               5                   10

<210> SEQ ID NO 695
<211> LENGTH: 65
<212> TYPE: DNA
<213> ORGANISM: Unknown
<220> FEATURE:
<223> OTHER INFORMATION: Description of Unknown:
      KRAS sequence

<400> SEQUENCE: 695
tatcgtcaag gcactcttgc ctacgccacc agctccaact accacaagtt tatattcagt    60
cattt                                                                65

<210> SEQ ID NO 696
<211> LENGTH: 64
<212> TYPE: DNA
<213> ORGANISM: Unknown
<220> FEATURE:
<223> OTHER INFORMATION: Description of Unknown:
      KRAS sequence

<400> SEQUENCE: 696
tatcgtcaag gcactcttgc ctacgccacc agctccaact accacaagtt tatattcagt    60
catt                                                                 64

<210> SEQ ID NO 697
<211> LENGTH: 66
<212> TYPE: DNA
<213> ORGANISM: Unknown
<220> FEATURE:
<223> OTHER INFORMATION: Description of Unknown:
      NRAS sequence

<400> SEQUENCE: 697
tttgttggac atactggata cagctggaca agaagagtac agtgccatga gagaccaata    60
catgag                                                               66

<210> SEQ ID NO 698
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

Gly Gly Gly Ser Gly Gly Gly Gly Ser Gly Gly Gly Ala Ser
1               5                   10

<210> SEQ ID NO 699
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 699

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Tyr Phe Arg
                85                  90                  95

Pro Ile Thr Phe Gly Gln Gly Thr Lys Val Glu Ile Lys
            100                 105
```

<210> SEQ ID NO 700
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 700

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Ser
            20                  25                  30

Asp Ile His Trp Val Arg Gln Ala Pro Gly Lys Gly Leu Glu Trp Val
            35                  40                  45

Ala Val Val Met Pro Asp Ser Gly His Thr Asn Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Ala Thr Asn Ile Pro Val Tyr Ala Phe Asp Tyr Trp Gly Gln
            100                 105                 110

Gly Thr Leu Val Thr Val Ser Ser
        115                 120
```

<210> SEQ ID NO 701
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 701

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80
```

-continued

Glu Asp Phe Ala Thr Tyr Tyr Cys Gln Gln Val Ile Tyr Tyr Pro Phe
                85                  90                  95

Thr Phe Gly Gln Gly Thr Lys Val Glu Ile Lys
            100                 105

<210> SEQ ID NO 702
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Tyr
            20                  25                  30

Ala Ile His Trp Val Arg Gln Ala Pro Gly Lys Gly Leu Glu Trp Val
        35                  40                  45

Ala Leu Leu Tyr Pro Asp Tyr Gly Val Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Tyr Arg Ser Tyr Glu Tyr Ser Val Ser Ser Tyr Ser Tyr Ser
            100                 105                 110

Ala Met Asp Tyr Trp Gly Gln Gly Thr Leu Val Thr Val Ser Ser
        115                 120                 125

<210> SEQ ID NO 703
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Ser Tyr Pro Trp
                85                  90                  95

Thr Phe Gly Gln Gly Thr Lys Val Glu Ile Lys
            100                 105

<210> SEQ ID NO 704
<211> LENGTH: 119
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 704

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Gly Ile His Trp Val Arg Gln Ala Pro Gly Lys Gly Leu Glu Trp Val
        35                  40                  45

Ala Met Val Tyr Gly Gly Ser Gly Tyr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Ala His Tyr Ser Ala Tyr Met Asp Tyr Trp Gly Gln Gly
            100                 105                 110

Thr Leu Val Thr Val Ser Ser
        115

<210> SEQ ID NO 705
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 705

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asn Tyr Pro Leu
            85                  90                  95

Thr Phe Gly Gln Gly Thr Lys Val Glu Ile Lys
            100                 105

<210> SEQ ID NO 706
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 706

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Phe Tyr Gly
            20                  25                  30
```

```
Ser Met His Trp Val Arg Gln Ala Pro Gly Lys Gly Leu Glu Trp Val
        35                  40                  45

Ala Phe Ile Gly Pro Asp Ser Thr Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Asp Leu Gly Ser Ala Tyr Ala Met Asp Tyr Trp Gly Gln Gly
                100                 105                 110

Thr Leu Val Thr Val Ser Ser
        115

<210> SEQ ID NO 707
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
                20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Lys Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Ala Gly Gly Thr Lys Leu Glu Ile Lys
                100                 105

<210> SEQ ID NO 708
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 708

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Met
        35                  40                  45

Gly Leu Ile Asn Pro Tyr Lys Gly Val Ser Thr Tyr Asn Gln Lys Phe
        50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95
```

Ala Arg Ser Gly Tyr Tyr Gly Asp Ser Asp Trp Tyr Phe Asp Val Trp
        100                 105                 110

Gly Ala Gly Thr Thr Val Thr Val Ser Ser
        115                 120

<210> SEQ ID NO 709
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 709

Asp Ile Gln Met Thr Gln Ser Pro Ser Ser Leu Ser Ala Ser Val Gly
1                 5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 710
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 710

Glu Val Gln Leu Val Glu Ser Gly Gly Gly Leu Val Gln Pro Gly Gly
1                 5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 711
<211> LENGTH: 106
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 711

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105
```

<210> SEQ ID NO 712
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 712

```
Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115
```

<210> SEQ ID NO 713
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 713

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
```

```
              35                40                45
Leu Ile Gly Gly Thr Asn Lys Arg Ala Pro Trp Thr Pro Ala Arg Phe
    50                55                60
Ser Gly Ser Leu Leu Gly Gly Lys Ala Ala Leu Thr Ile Thr Gly Ala
65                70                75                80
Gln Ala Glu Asp Glu Ala Asp Tyr Tyr Cys Ala Leu Trp Tyr Ser Asn
                85                90                95
Leu Trp Val Phe Gly Gly Gly Thr Lys Leu Thr Val Leu
            100               105
```

```
<210> SEQ ID NO 714
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 714

Glu Val Gln Leu Val Glu Ser Gly Gly Gly Leu Val Gln Pro Gly Gly
1                 5                 10                15
Ser Leu Arg Leu Ser Cys Ala Ala Ser Gly Phe Thr Phe Asn Thr Tyr
            20                25                30
Ala Met Asn Trp Val Arg Gln Ala Pro Gly Lys Gly Leu Glu Trp Val
        35                40                45
Ala Arg Ile Arg Ser Lys Tyr Asn Asn Tyr Ala Thr Tyr Tyr Ala Asp
    50                55                60
Ser Val Lys Asp Arg Phe Thr Ile Ser Arg Asp Asp Ser Lys Asn Ser
65                70                75                80
Leu Tyr Leu Gln Met Asn Ser Leu Lys Thr Glu Asp Thr Ala Val Tyr
                85                90                95
Tyr Cys Val Arg His Gly Asn Phe Gly Asn Ser Tyr Val Ser Trp Phe
            100               105               110
Ala Tyr Trp Gly Gln Gly Thr Leu Val Thr Val Ser Ser
        115               120               125
```

```
<210> SEQ ID NO 715
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 715

Asp Ile Gln Leu Thr Gln Ser Pro Ala Ile Met Ser Ala Ser Pro Gly
1                 5                 10                15
Glu Lys Val Thr Met Thr Cys Arg Ala Ser Ser Ser Val Ser Tyr Met
            20                25                30
Asn Trp Tyr Gln Gln Lys Ser Gly Thr Ser Pro Lys Arg Trp Ile Tyr
        35                40                45
Asp Thr Ser Lys Val Ala Ser Gly Val Pro Tyr Arg Phe Ser Gly Ser
    50                55                60
Gly Ser Gly Thr Ser Tyr Ser Leu Thr Ile Ser Ser Met Glu Ala Glu
65                70                75                80
Asp Ala Ala Thr Tyr Tyr Cys Gln Gln Trp Ser Ser Asn Pro Leu Thr
                85                90                95
Phe Gly Ala Gly Thr Lys Leu Glu Leu Lys
```

-continued

```
                100             105

<210> SEQ ID NO 716
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 716

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 717
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 717

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 718
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 718
```

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115
```

```
<210> SEQ ID NO 719
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 719

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105
```

```
<210> SEQ ID NO 720
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 720

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
        115

<210> SEQ ID NO 721
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 721

Glu Ile Val Leu Thr Gln Ser Pro Arg Thr Leu Ser Leu Ser Pro Gly
1                   5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Asp
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 722
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 722

Gln Val Gln Leu Val Glu Ser Gly Gly Gly Val Val Gln Pro Gly Arg
1                   5                   10                  15

Ser Leu Arg Leu Ser Cys Ala Ala Ser Gly Phe Thr Phe Arg Ser Tyr
                20                  25                  30

Gly Met His Trp Val Arg Gln Ala Pro Gly Lys Gly Leu Glu Trp Val
            35                  40                  45

Ala Ile Ile Trp Tyr Asp Gly Ser Lys Lys Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Tyr Asn Trp Phe Asp Pro Trp Gly Gln Gly Thr
            100                 105                 110

Leu Val Thr Val Ser Ser
        115
```

-continued

<210> SEQ ID NO 723
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 723

Gln Val Gln Leu Val Gln Ser Gly Gly Gly Val Val Gln Ser Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
        115

<210> SEQ ID NO 724
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 724

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 725
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 725

```
Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ala Ile Trp Tyr Asn Gly Arg Lys Gln Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
                100                 105                 110

Leu Val Thr Val Ser Ser
            115
```

<210> SEQ ID NO 726
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 726

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
                100                 105
```

<210> SEQ ID NO 727
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 727

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
        50                  55                  60
```

```
Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Thr Lys Arg
            100                 105

<210> SEQ ID NO 728
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 728

Gln Val Gln Leu Gln Gln Ser Gly Ala Glu Leu Ala Arg Pro Gly Ala
1                   5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Ser Ser Gly Tyr Thr Lys Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gln Asp Tyr Asp Val Tyr Phe Asp Tyr Trp Gly Gln Gly
            100                 105                 110

Thr Thr Leu Thr Val Ser Ser
        115

<210> SEQ ID NO 729
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 729

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Tyr Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Arg Tyr Ser Pro
                85                  90                  95

Val Thr Phe Gly Gln Gly Thr Lys Val Glu Ile Lys
            100                 105

<210> SEQ ID NO 730
<211> LENGTH: 121
```

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 730

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Tyr Ala Ser
            20                  25                  30

Gly Met His Trp Val Arg Gln Ala Pro Gly Lys Gly Leu Glu Trp Val
        35                  40                  45

Ala Lys Ile Tyr Pro Asp Ser Asp Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Asp Ser Ser Phe Tyr Tyr Val Tyr Ala Met Asp Tyr Trp Gly
            100                 105                 110

Gln Gly Thr Leu Val Thr Val Ser Ser
        115                 120

<210> SEQ ID NO 731
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 731

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ala Tyr Pro Ile
                85                  90                  95

Thr Phe Gly Gln Gly Thr Lys Val Glu Ile Lys
            100                 105

<210> SEQ ID NO 732
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 732

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Asn Ser Tyr
```

-continued

```
                20                  25                  30

Tyr Met His Trp Val Arg Gln Ala Pro Gly Lys Gly Leu Glu Trp Val
            35                  40                  45

Ala Met Ile Ile Pro Gly Tyr Gly Tyr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Ser Tyr Tyr Met Tyr Met Asp Tyr Trp Gly Gln Gly Thr Leu
                100                 105                 110

Val Thr Val Ser Ser
            115
```

<210> SEQ ID NO 733
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 733

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Tyr Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Arg Tyr Ser Pro
                85                  90                  95

Val Thr Phe Gly Gln Gly Thr Lys Val Glu Ile Lys Gly Gly Gly Gly
                100                 105                 110

Ser Glu Val Gln Leu Gln Gln Ser Gly Pro Glu Leu Val Lys Pro Gly
            115                 120                 125

Ala Ser Met Lys Ile Ser Cys Lys Ala Ser Gly Tyr Ser Phe Thr Gly
    130                 135                 140

Tyr Thr Met Asn Trp Val Lys Gln Ser His Gly Lys Asn Leu Glu Trp
145                 150                 155                 160

Met Gly Leu Ile Asn Pro Tyr Lys Gly Val Ser Thr Tyr Asn Gln Lys
                165                 170                 175

Phe Lys Asp Lys Ala Thr Leu Thr Val Asp Lys Ser Ser Ser Thr Ala
                180                 185                 190

Tyr Met Glu Leu Leu Ser Leu Thr Ser Glu Asp Ser Ala Val Tyr Tyr
            195                 200                 205

Cys Ala Arg Ser Gly Tyr Tyr Gly Asp Ser Asp Trp Tyr Phe Asp Val
    210                 215                 220

Trp Gly Ala Gly Thr Thr Val Thr Val Ser Ser Gly Gly Gly Gly Ser
225                 230                 235                 240

Gly Gly Gly Gly Ser Gly Gly Gly Ser Asp Ile Gln Met Thr Gln
            245                 250                 255
```

Thr Thr Ser Ser Leu Ser Ala Ser Leu Gly Asp Arg Val Thr Ile Ser
        260             265             270

Cys Arg Ala Ser Gln Asp Ile Arg Asn Tyr Leu Asn Trp Tyr Gln Gln
        275             280             285

Lys Pro Asp Gly Thr Val Lys Leu Leu Ile Tyr Tyr Thr Ser Arg Leu
        290             295             300

His Ser Gly Val Pro Ser Lys Phe Ser Gly Ser Gly Ser Gly Thr Asp
305             310             315             320

Tyr Ser Leu Thr Ile Ser Asn Leu Glu Gln Glu Asp Ile Ala Thr Tyr
            325             330             335

Phe Cys Gln Gln Gly Asn Thr Leu Pro Trp Thr Phe Ala Gly Gly Thr
            340             345             350

Lys Leu Glu Ile Lys Gly Gly Gly Ser Glu Val Gln Leu Val Glu
        355             360             365

Ser Gly Gly Gly Leu Val Gln Pro Gly Gly Ser Leu Arg Leu Ser Cys
    370             375             380

Ala Ala Ser Gly Phe Asn Val Tyr Ala Ser Gly Met His Trp Val Arg
385             390             395             400

Gln Ala Pro Gly Lys Gly Leu Glu Trp Val Ala Lys Ile Tyr Pro Asp
            405             410             415

Ser Asp Tyr Thr Tyr Tyr Ala Asp Ser Val Lys Gly Arg Phe Thr Ile
            420             425             430

Ser Ala Asp Thr Ser Lys Asn Thr Ala Tyr Leu Gln Met Asn Ser Leu
        435             440             445

Arg Ala Glu Asp Thr Ala Val Tyr Tyr Cys Ser Arg Asp Ser Ser Phe
    450             455             460

Tyr Tyr Val Tyr Ala Met Asp Tyr Trp Gly Gln Gly Thr Leu Val Thr
465             470             475             480

Val Ser Ser

<210> SEQ ID NO 734
<211> LENGTH: 478
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 734

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Val Asn Thr Ala
            20              25              30

Val Ala Trp Tyr Gln Gln Lys Pro Gly Lys Ala Pro Lys Leu Leu Ile
            35              40              45

Tyr Ser Ala Ser Phe Leu Tyr Ser Gly Val Pro Ser Arg Phe Ser Gly
    50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Gln Gln Ser Asn Ala Tyr Pro Ile
            85              90              95

Thr Phe Gly Gln Gly Thr Lys Val Glu Ile Lys Gly Gly Gly Gly Ser
        100             105             110

Glu Val Gln Leu Gln Gln Ser Gly Pro Glu Leu Val Lys Pro Gly Ala
        115             120             125

```
Ser Met Lys Ile Ser Cys Lys Ala Ser Gly Tyr Ser Phe Thr Gly Tyr
    130                 135                 140

Thr Met Asn Trp Val Lys Gln Ser His Gly Lys Asn Leu Glu Trp Met
145                 150                 155                 160

Gly Leu Ile Asn Pro Tyr Lys Gly Val Ser Thr Tyr Asn Gln Lys Phe
                165                 170                 175

Lys Asp Lys Ala Thr Leu Thr Val Asp Lys Ser Ser Ser Thr Ala Tyr
            180                 185                 190

Met Glu Leu Leu Ser Leu Thr Ser Glu Asp Ser Ala Val Tyr Tyr Cys
        195                 200                 205

Ala Arg Ser Gly Tyr Tyr Gly Asp Ser Asp Trp Tyr Phe Asp Val Trp
    210                 215                 220

Gly Ala Gly Thr Thr Val Thr Val Ser Ser Gly Gly Gly Ser Gly
225                 230                 235                 240

Gly Gly Gly Ser Gly Gly Gly Ser Asp Ile Gln Met Thr Gln Thr
                245                 250                 255

Thr Ser Ser Leu Ser Ala Ser Leu Gly Asp Arg Val Thr Ile Ser Cys
        260                 265                 270

Arg Ala Ser Gln Asp Ile Arg Asn Tyr Leu Asn Trp Tyr Gln Gln Lys
    275                 280                 285

Pro Asp Gly Thr Val Lys Leu Leu Ile Tyr Tyr Thr Ser Arg Leu His
    290                 295                 300

Ser Gly Val Pro Ser Lys Phe Ser Gly Ser Gly Ser Gly Thr Asp Tyr
305                 310                 315                 320

Ser Leu Thr Ile Ser Asn Leu Glu Gln Glu Asp Ile Ala Thr Tyr Phe
                325                 330                 335

Cys Gln Gln Gly Asn Thr Leu Pro Trp Thr Phe Ala Gly Gly Thr Lys
            340                 345                 350

Leu Glu Ile Lys Gly Gly Gly Gly Ser Glu Val Gln Leu Val Glu Ser
        355                 360                 365

Gly Gly Gly Leu Val Gln Pro Gly Gly Ser Leu Arg Leu Ser Cys Ala
    370                 375                 380

Ala Ser Gly Phe Asn Leu Asn Ser Tyr Tyr Met His Trp Val Arg Gln
385                 390                 395                 400

Ala Pro Gly Lys Gly Leu Glu Trp Val Ala Met Ile Ile Pro Gly Tyr
                405                 410                 415

Gly Tyr Thr Asn Tyr Ala Asp Ser Val Lys Gly Arg Phe Thr Ile Ser
            420                 425                 430

Ala Asp Thr Ser Lys Asn Thr Ala Tyr Leu Gln Met Asn Ser Leu Arg
        435                 440                 445

Ala Glu Asp Thr Ala Val Tyr Tyr Cys Ser Arg Ser Tyr Tyr Met Tyr
    450                 455                 460

Met Asp Tyr Trp Gly Gln Gly Thr Leu Val Thr Val Ser Ser
465                 470                 475
```

```
<210> SEQ ID NO 735
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 735

Asp Ile Gln Met Thr Gln Ser Pro Ser Ser Leu Ser Ala Ser Val Gly
1                   5                   10                  15
```

-continued

```
Asp Arg Val Thr Ile Thr Cys Arg Ala Ser Gln Asp Val Asn Thr Ala
        20                  25                  30

Val Ala Trp Tyr Gln Gln Lys Pro Gly Lys Ala Pro Lys Leu Leu Ile
        35                  40                  45

Tyr Ser Ala Tyr Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Arg Tyr Ser Pro
                85                  90                  95

Val Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Val Tyr Ala Ser Gly Met His Trp Val
145                 150                 155                 160

Arg Gln Ala Pro Gly Lys Gly Leu Glu Trp Val Ala Lys Ile Tyr Pro
                165                 170                 175

Asp Ser Asp Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Asp Ser Ser
    210                 215                 220

Phe Tyr Tyr Val Tyr Ala Met Asp Tyr Trp Gly Gln Gly Thr Leu Val
225                 230                 235                 240

Thr Val Ser Ser Gly Gly Gly Gly Ser Glu Val Gln Leu Gln Gln Ser
            245                 250                 255

Gly Pro Glu Leu Val Lys Pro Gly Ala Ser Met Lys Ile Ser Cys Lys
            260                 265                 270

Ala Ser Gly Tyr Ser Phe Thr Gly Tyr Thr Met Asn Trp Val Lys Gln
            275                 280                 285

Ser His Gly Lys Asn Leu Glu Trp Met Gly Leu Ile Asn Pro Tyr Lys
    290                 295                 300

Gly Val Ser Thr Tyr Asn Gln Lys Phe Lys Asp Lys Ala Thr Leu Thr
305                 310                 315                 320

Val Asp Lys Ser Ser Ser Thr Ala Tyr Met Glu Leu Leu Ser Leu Thr
            325                 330                 335

Ser Glu Asp Ser Ala Val Tyr Tyr Cys Ala Arg Ser Gly Tyr Tyr Gly
            340                 345                 350

Asp Ser Asp Trp Tyr Phe Asp Val Trp Gly Ala Gly Thr Thr Val Thr
            355                 360                 365

Val Ser Ser Gly Gly Gly Gly Ser Gly Gly Gly Gly Ser Gly Gly Gly
    370                 375                 380

Gly Ser Asp Ile Gln Met Thr Gln Thr Thr Ser Ser Leu Ser Ala Ser
385                 390                 395                 400

Leu Gly Asp Arg Val Thr Ile Ser Cys Arg Ala Ser Gln Asp Ile Arg
                405                 410                 415

Asn Tyr Leu Asn Trp Tyr Gln Gln Lys Pro Asp Gly Thr Val Lys Leu
            420                 425                 430
```

```
Leu Ile Tyr Tyr Thr Ser Arg Leu His Ser Gly Val Pro Ser Lys Phe
        435                 440                 445

Ser Gly Ser Gly Ser Gly Thr Asp Tyr Ser Leu Thr Ile Ser Asn Leu
    450                 455                 460

Glu Gln Glu Asp Ile Ala Thr Tyr Phe Cys Gln Gln Gly Asn Thr Leu
465                 470                 475                 480

Pro Trp Thr Phe Ala Gly Gly Thr Lys Leu Glu Ile Lys
                485                 490

<210> SEQ ID NO 736
<211> LENGTH: 971
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 736

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Tyr Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Arg Tyr Ser Pro
                85                  90                  95

Val Thr Phe Gly Gln Gly Thr Lys Val Glu Ile Lys Gly Gly Gly Gly
            100                 105                 110

Ser Glu Val Gln Leu Gln Gln Ser Gly Pro Glu Leu Val Lys Pro Gly
        115                 120                 125

Ala Ser Met Lys Ile Ser Cys Lys Ala Ser Gly Tyr Ser Phe Thr Gly
    130                 135                 140

Tyr Thr Met Asn Trp Val Lys Gln Ser His Gly Lys Asn Leu Glu Trp
145                 150                 155                 160

Met Gly Leu Ile Asn Pro Tyr Lys Gly Val Ser Thr Tyr Asn Gln Lys
                165                 170                 175

Phe Lys Asp Lys Ala Thr Leu Thr Val Asp Lys Ser Ser Ser Thr Ala
            180                 185                 190

Tyr Met Glu Leu Leu Ser Leu Thr Ser Glu Asp Ser Ala Val Tyr Tyr
        195                 200                 205

Cys Ala Arg Ser Gly Tyr Tyr Gly Asp Ser Asp Trp Tyr Phe Asp Val
    210                 215                 220

Trp Gly Ala Gly Thr Thr Val Thr Val Ser Ser Gly Gly Gly Gly Ser
225                 230                 235                 240

Gly Gly Gly Gly Ser Gly Gly Gly Ser Asp Ile Gln Met Thr Gln
                245                 250                 255

Thr Thr Ser Ser Leu Ser Ala Ser Leu Gly Asp Arg Val Thr Ile Ser
            260                 265                 270

Cys Arg Ala Ser Gln Asp Ile Arg Asn Tyr Leu Asn Trp Tyr Gln Gln
        275                 280                 285

Lys Pro Asp Gly Thr Val Lys Leu Leu Ile Tyr Tyr Thr Ser Arg Leu
    290                 295                 300
```

-continued

```
His Ser Gly Val Pro Ser Lys Phe Ser Gly Ser Gly Ser Gly Thr Asp
305                 310                 315                 320

Tyr Ser Leu Thr Ile Ser Asn Leu Glu Gln Glu Asp Ile Ala Thr Tyr
                325                 330                 335

Phe Cys Gln Gln Gly Asn Thr Leu Pro Trp Thr Phe Ala Gly Gly Thr
            340                 345                 350

Lys Leu Glu Ile Lys Gly Gly Gly Ser Glu Val Gln Leu Val Glu
        355                 360                 365

Ser Gly Gly Gly Leu Val Gln Pro Gly Gly Ser Leu Arg Leu Ser Cys
    370                 375                 380

Ala Ala Ser Gly Phe Asn Val Tyr Ala Ser Gly Met His Trp Val Arg
385                 390                 395                 400

Gln Ala Pro Gly Lys Gly Leu Glu Trp Val Ala Lys Ile Tyr Pro Asp
                405                 410                 415

Ser Asp Tyr Thr Tyr Tyr Ala Asp Ser Val Lys Gly Arg Phe Thr Ile
            420                 425                 430

Ser Ala Asp Thr Ser Lys Asn Thr Ala Tyr Leu Gln Met Asn Ser Leu
        435                 440                 445

Arg Ala Glu Asp Thr Ala Val Tyr Tyr Cys Ser Arg Asp Ser Ser Phe
    450                 455                 460

Tyr Tyr Val Tyr Ala Met Asp Tyr Trp Gly Gln Gly Thr Leu Val Thr
465                 470                 475                 480

Val Ser Ser Gly Gly Gly Gly Asp Lys Thr His Thr Cys Pro Pro Cys
            485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Cys Glu
545                 550                 555                 560

Glu Gln Tyr Gly Ser Thr Tyr Arg Cys Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Lys Gly Gly Gly Ser Gly
705                 710                 715                 720
```

-continued

```
Gly Gly Gly Ser Gly Gly Gly Gly Ser Gly Gly Gly Gly Ser Gly Gly
            725             730             735

Gly Gly Ser Gly Gly Gly Gly Ser Asp Lys Thr His Thr Cys Pro Pro
            740             745             750

Cys Pro Ala Pro Glu Leu Leu Gly Gly Pro Ser Val Phe Leu Phe Pro
            755             760             765

Pro Lys Pro Lys Asp Thr Leu Met Ile Ser Arg Thr Pro Glu Val Thr
    770             775             780

Cys Val Val Val Asp Val Ser His Glu Asp Pro Glu Val Lys Phe Asn
785             790             795             800

Trp Tyr Val Asp Gly Val Glu Val His Asn Ala Lys Thr Lys Pro Cys
            805             810             815

Glu Glu Gln Tyr Gly Ser Thr Tyr Arg Cys Val Ser Val Leu Thr Val
            820             825             830

Leu His Gln Asp Trp Leu Asn Gly Lys Glu Tyr Lys Cys Lys Val Ser
            835             840             845

Asn Lys Ala Leu Pro Ala Pro Ile Glu Lys Thr Ile Ser Lys Ala Lys
    850             855             860

Gly Gln Pro Arg Glu Pro Gln Val Tyr Thr Leu Pro Pro Ser Arg Glu
865             870             875             880

Glu Met Thr Lys Asn Gln Val Ser Leu Thr Cys Leu Val Lys Gly Phe
            885             890             895

Tyr Pro Ser Asp Ile Ala Val Glu Trp Glu Ser Asn Gly Gln Pro Glu
            900             905             910

Asn Asn Tyr Lys Thr Thr Pro Pro Val Leu Asp Ser Asp Gly Ser Phe
            915             920             925

Phe Leu Tyr Ser Lys Leu Thr Val Asp Lys Ser Arg Trp Gln Gln Gly
    930             935             940

Asn Val Phe Ser Cys Ser Val Met His Glu Ala Leu His Asn His Tyr
945             950             955             960

Thr Gln Lys Ser Leu Ser Leu Ser Pro Gly Lys
            965             970
```

<210> SEQ ID NO 737
<211> LENGTH: 981
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 737

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Val Asn Thr Ala
            20              25              30

Val Ala Trp Tyr Gln Gln Lys Pro Gly Lys Ala Pro Lys Leu Leu Ile
            35              40              45

Tyr Ser Ala Tyr Phe Leu Tyr Ser Gly Val Pro Ser Arg Phe Ser Gly
    50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Gln Gln Tyr Ser Arg Tyr Ser Pro
            85              90              95

Val Thr Phe Gly Gln Gly Thr Lys Val Glu Ile Lys Gly Gly Gly Gly
            100             105             110
```

```
Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Val Tyr Ala Ser Gly Met His Trp Val
145                 150                 155                 160

Arg Gln Ala Pro Gly Lys Gly Leu Glu Trp Val Ala Lys Ile Tyr Pro
                165                 170                 175

Asp Ser Asp Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Asp Ser Ser
    210                 215                 220

Phe Tyr Tyr Val Tyr Ala Met Asp Tyr Trp Gly Gln Gly Thr Leu Val
225                 230                 235                 240

Thr Val Ser Ser Gly Gly Gly Gly Ser Glu Val Gln Leu Gln Gln Ser
            245                 250                 255

Gly Pro Glu Leu Val Lys Pro Gly Ala Ser Met Lys Ile Ser Cys Lys
            260                 265                 270

Ala Ser Gly Tyr Ser Phe Thr Gly Tyr Thr Met Asn Trp Val Lys Gln
        275                 280                 285

Ser His Gly Lys Asn Leu Glu Trp Met Gly Leu Ile Asn Pro Tyr Lys
    290                 295                 300

Gly Val Ser Thr Tyr Asn Gln Lys Phe Lys Asp Lys Ala Thr Leu Thr
305                 310                 315                 320

Val Asp Lys Ser Ser Ser Thr Ala Tyr Met Glu Leu Leu Ser Leu Thr
            325                 330                 335

Ser Glu Asp Ser Ala Val Tyr Tyr Cys Ala Arg Ser Gly Tyr Tyr Gly
            340                 345                 350

Asp Ser Asp Trp Tyr Phe Asp Val Trp Gly Ala Gly Thr Thr Val Thr
        355                 360                 365

Val Ser Ser Gly Gly Gly Gly Ser Gly Gly Gly Ser Gly Gly Gly
    370                 375                 380

Gly Ser Asp Ile Gln Met Thr Gln Thr Thr Ser Ser Leu Ser Ala Ser
385                 390                 395                 400

Leu Gly Asp Arg Val Thr Ile Ser Cys Arg Ala Ser Gln Asp Ile Arg
                405                 410                 415

Asn Tyr Leu Asn Trp Tyr Gln Gln Lys Pro Asp Gly Thr Val Lys Leu
            420                 425                 430

Leu Ile Tyr Tyr Thr Ser Arg Leu His Ser Gly Val Pro Ser Lys Phe
        435                 440                 445

Ser Gly Ser Gly Ser Gly Thr Asp Tyr Ser Leu Thr Ile Ser Asn Leu
    450                 455                 460

Glu Gln Glu Asp Ile Ala Thr Tyr Phe Cys Gln Gln Gly Asn Thr Leu
465                 470                 475                 480

Pro Trp Thr Phe Ala Gly Gly Thr Lys Leu Glu Ile Lys Gly Gly Gly
                485                 490                 495

Gly Asp Lys Thr His Thr Cys Pro Pro Cys Pro Ala Pro Glu Leu Leu
            500                 505                 510

Gly Gly Pro Ser Val Phe Leu Phe Pro Pro Lys Pro Lys Asp Thr Leu
    515                 520                 525
```

```
Met Ile Ser Arg Thr Pro Glu Val Thr Cys Val Val Val Asp Val Ser
    530                 535                 540

His Glu Asp Pro Glu Val Lys Phe Asn Trp Tyr Val Asp Gly Val Glu
545                 550                 555                 560

Val His Asn Ala Lys Thr Lys Pro Cys Glu Glu Gln Tyr Gly Ser Thr
                565                 570                 575

Tyr Arg Cys Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
        595                 600                 605

Ile Glu Lys Thr Ile Ser Lys Ala Lys Gly Gln Pro Arg Glu Pro Gln
    610                 615                 620

Val Tyr Thr Leu Pro Pro Ser Arg Glu Glu Met Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Phe Leu Tyr Ser Lys Leu Thr
            675                 680                 685

Val Asp Lys Ser Arg Trp Gln Gln Gly Asn Val Phe Ser Cys Ser Val
    690                 695                 700

Met His Glu Ala Leu His Asn His Tyr Thr Gln Lys Ser Leu Ser Leu
705                 710                 715                 720

Ser Pro Gly Lys Gly Gly Gly Ser Gly Gly Gly Ser Gly Gly
                725                 730                 735

Gly Gly Ser Gly Gly Gly Gly Ser Gly Gly Gly Ser Gly Gly Gly
            740                 745                 750

Gly Ser Asp Lys Thr His Thr Cys Pro Pro Cys Pro Ala Pro Glu Leu
        755                 760                 765

Leu Gly Gly Pro Ser Val Phe Leu Phe Pro Pro Lys Pro Lys Asp Thr
    770                 775                 780

Leu Met Ile Ser Arg Thr Pro Glu Val Thr Cys Val Val Val Asp Val
785                 790                 795                 800

Ser His Glu Asp Pro Glu Val Lys Phe Asn Trp Tyr Val Asp Gly Val
                805                 810                 815

Glu Val His Asn Ala Lys Thr Lys Pro Cys Glu Glu Gln Tyr Gly Ser
            820                 825                 830

Thr Tyr Arg Cys Val Ser Val Leu Thr Val Leu His Gln Asp Trp Leu
        835                 840                 845

Asn Gly Lys Glu Tyr Lys Cys Lys Val Ser Asn Lys Ala Leu Pro Ala
    850                 855                 860

Pro Ile Glu Lys Thr Ile Ser Lys Ala Lys Gly Gln Pro Arg Glu Pro
865                 870                 875                 880

Gln Val Tyr Thr Leu Pro Pro Ser Arg Glu Glu Met Thr Lys Asn Gln
                885                 890                 895

Val Ser Leu Thr Cys Leu Val Lys Gly Phe Tyr Pro Ser Asp Ile Ala
            900                 905                 910

Val Glu Trp Glu Ser Asn Gly Gln Pro Glu Asn Asn Tyr Lys Thr Thr
        915                 920                 925

Pro Pro Val Leu Asp Ser Asp Gly Ser Phe Phe Leu Tyr Ser Lys Leu
    930                 935                 940

Thr Val Asp Lys Ser Arg Trp Gln Gln Gly Asn Val Phe Ser Cys Ser
```

-continued

```
945                 950                 955                 960

Val Met His Glu Ala Leu His Asn His Tyr Thr Gln Lys Ser Leu Ser
                    965                 970                 975

Leu Ser Pro Gly Lys
            980

<210> SEQ ID NO 738
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 738

His His His His His His
1               5

<210> SEQ ID NO 739
<211> LENGTH: 21
<212> TYPE: PRT
<213> ORGANISM: Unknown
<220> FEATURE:
<223> OTHER INFORMATION: Description of Unknown:
      KRAS sequence

<400> SEQUENCE: 739

Met Thr Glu Tyr Lys Leu Val Val Val Gly Ala Gly Gly Val Gly Lys
1               5                   10                  15

Ser Ala Leu Thr Ile
            20

<210> SEQ ID NO 740
<211> LENGTH: 21
<212> TYPE: PRT
<213> ORGANISM: Unknown
<220> FEATURE:
<223> OTHER INFORMATION: Description of Unknown:
      NRAS sequence

<400> SEQUENCE: 740

Leu Leu Asp Ile Leu Asp Thr Ala Gly Gln Glu Glu Tyr Ser Ala Met
1               5                   10                  15

Arg Asp Gln Tyr Met
            20
```

MANABODIES TARGETING TUMOR ANTIGENS AND METHODS OF USING

CROSS-REFERENCE TO RELATED APPLICATIONS

This application is a National Stage application under 35 U.S.C. § 371 of International Application No. PCT/US2020/065617 having an International Filing Date of Dec. 17, 2020, which claims the benefit of U.S. Patent Application Ser. No. 62/949,220, filed on Dec. 17, 2019 and U.S. Patent Application Ser. No. 63/059,638, filed on Jul. 31, 2020. The disclosure of the prior applications are considered part of (and are incorporated by reference in) the disclosure of this application.

STATEMENT REGARDING FEDERAL FUNDING

This invention was made with government support under grant CA062924 awarded by the National Institutes of Health. The government has certain rights in the invention.

SEQUENCE LISTING

This document contains a sequence listing that has been submitted electronically as an ASCII text file. The ASCII text file, created on Jun. 8, 2022, is 484 kilobytes in size. The material in the ASCII text file is hereby incorporated by reference in its entirety.

BACKGROUND

1. Technical Field

This document relates to methods and materials for assessing a mammal having or suspected of having cancer and/or for treating a mammal having cancer. For example, this document provides methods and materials for using a molecule including one or more antigen-binding domains (e.g., a single-chain variable fragment (scFv)) that can bind to a modified peptide (e.g., a tumor antigen) to treat a mammal having a cancer.

2. Background Information

Somatic mutations in cancer are ideal targets for cancer therapy as they are expressed only in tumor cells and not in normal cells. Targeting driver gene proteins (broadly subdivided into oncogene proteins and tumor suppressor proteins) have added benefits. First, these mutations typically occur early during the development of the tumor, thus essentially all daughter cancer cells will contain the mutation. Second, the tumor's dependence on their oncogenic-endowing capacity makes resistance less likely. Finally, driver gene proteins tend to have hotspot mutations shared among many patients, thus a therapy targeting a single mutation could be applied to a broad patient population.

Most mutant proteins, including most mutant driver gene proteins, are intracellular. While small molecules can target intracellular proteins, developing small molecules that can specifically inhibit the activity of a mutant driver gene and not its wild-type (WT) counterpart has remained out of reach for the majority of such driver gene proteins. Antibodies, which can have the capacity to distinguish a single amino acid mutation, can typically only target extracellular epitopes.

The immune system samples the intracellular contents of cells through antigen processing and presentation. Following protein proteolysis, a fraction of the resulting peptides are loaded onto a human leukocyte antigen (HLA) and sent to the cell surface where they serve as a way for T cells, via their T cell receptor (TCR), to distinguish self from non-self peptides. For example, a virally-infected cell will present viral peptides in its HLA, triggering T cells to kill that cell. Similarly, in cancer, mutant peptides can be presented in an HLA on the cancer cell surface, referred to as MANAs, for Mutation-Associated NeoAntigens. In some cases, and to varying degrees, patients may mount an anti-cancer T cell response against these mutant-peptide-HLA neoantigens, and checkpoint blockade antibodies can further augment this response. However, many patients, particularly those with a low mutational burden, cannot mount a sufficient anti-cancer T cell response. A therapy or diagnostic specifically targeting MANAs could therefore provide a truly tumor-specific method to diagnose or treat cancer.

HLA class I proteins are present on all nucleated cells. There are three classical HLA class I genes, A, B, and C, each of which are highly polymorphic. Each HLA allele has a particular peptide-binding motif, and as a result, only certain peptides will bind to certain HLA alleles.

There is a continuing need in the art to develop new methods to diagnose, monitor, and effectively treat cancers.

SUMMARY

Identification of therapeutic targets highly specific to cancer cells is one of the greatest challenges for developing an effective cancer therapy.

This document provides methods and materials for treating a mammal having cancer. For example, this document provides methods and materials for using one or more molecules including one or more antigen-binding domains (e.g., scFvs) that can bind to a modified peptide (e.g., a modified peptide present in a peptide-HLA-beta-2 microglobulin (b2M or β2M) complex) to treat a mammal having a cancer (e.g., a cancer expressing the modified peptide). In some cases, one or more molecules including one or more antigen-binding domains (e.g., scFvs) that can bind to a modified peptide (e.g., a modified peptide present in a peptide-HLA-β2M complex) can be administered to a mammal having a cancer (e.g., a cancer expressing the modified peptide) to treat the mammal.

As demonstrated herein, scFvs were identified that target (e.g., bind to) numerous MANAs present in HLA-restricted MANAs derived from common cancer driver mutations, including RAS Q61H/L/R and p53 R175H. Also as demonstrated herein, the scFvs were used to design bispecific antibodies capable of inducing MANA-dependent T cell activation that can lead to recognition and killing of cells (e.g., cancer cells) expressing MANAs.

MANAs can be used as highly specific cancer targets because they are not present in normal tissue(s). The ability to specifically target MANAs provides a tumor-specific method to diagnose and/or treat cancer. For example, scFvs specifically targeting MANAs can be used in full-length antibodies or fragments thereof, antibody drug conjugates (ADCs), antibody radionuclide conjugates, T cells expressing a chimeric antigen receptor (CARTs), or bispecific antibodies to diagnose and/or treat a mammal having cancer. Further, an antibody that can bind to a MANA (a MANA-body), or a fragment thereof capable of binding to a MANA, have the potential of becoming widely applicable and genetically predictable off-the-shelf targeted cancer immunotherapy.

In general, one aspect of this document features molecules having an antigen-binding domain that can bind to a peptide-HLA-β2M complex, where the peptide can be derived from a modified p53 polypeptide. The modified p53 polypeptide can include from 7 amino acids to 25 amino acids (e.g., the modified p53 polypeptide can include 9 amino acids). The modified p53 polypeptide can include the amino acid sequence set forth in SEQ ID NO:1. The antigen binding domain can include an amino acid sequence set forth in any one of SEQ ID NO:137, SEQ ID NO:138, SEQ ID NO:139, SEQ ID NO:140, and SEQ ID NO:141. The molecule can be any one of an antibody, an antibody fragment, a single chain variable fragment (scFv), a chimeric antigen receptor (CAR), a T cell receptor (TCR), a TCR mimic, a tandem scFv, a bispecific T cell engager, a diabody, a single-chain diabody (scDb), an scFv-Fc, a bispecific antibody, and a dual-affinity re-targeting antibody (DART). The molecule also can include an antigen-binding domain that can bind to an effector cell receptor selected from any one of CD3, CD28, CD4, CD8, CD16a, NKG2D, PD-1, CTLA-4, 4-1BB, OX40, ICOS, CD27, and an Fc receptor. In some cases, the antigen-binding domain that can bind to an effector cell can bind to CD3, and the antigen-binding domain can include an amino acid sequence set forth in any one of SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, and SEQ ID NO:183.

In another aspect, this document features molecules that have an antigen-binding domain that can bind to a peptide-HLA-β2M complex, where the peptide can be derived from a modified RAS polypeptide. The modified RAS peptide can include from 7 amino acids to 25 amino acids (e.g., the modified RAS peptide can include 10 amino acids). The modified RAS peptide can include an amino acid sequence set forth in any one of SEQ ID NO:2, SEQ ID NO:3, and SEQ ID NO:4. In some cases, the modified RAS peptide can include the amino acid set forth in SEQ ID NO:2, and the antigen binding domain can include an amino acid sequence set forth in any one of SEQ ID NO:142, SEQ ID NO:143, SEQ ID NO:144, SEQ ID NO:145, SEQ ID NO:146, SEQ ID NO:147, SEQ ID NO:148, and SEQ ID NO:149. In some cases, the modified RAS peptide can include the amino acid sequence set forth in SEQ ID NO:3, and the antigen binding domain can include an amino acid sequence set forth in any one of SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, and SEQ ID NO:160. In some cases, the modified RAS peptide can include the amino acid sequence set forth in SEQ ID NO:4, and the antigen binding domain can include an amino acid sequence set forth in any one of SEQ ID NO:161, SEQ ID NO:162, SEQ ID NO:163, SEQ ID NO:164, SEQ ID NO:165, SEQ ID NO:166, SEQ ID NO:167, SEQ ID NO:168, and SEQ ID NO:169. The molecule can be any one of an antibody, an antibody fragment, a scFv, a CAR, a TCR, a TCR mimic, a tandem scFv, a bispecific T cell engager, a diabody, a scDb, an scFv-Fc, a bispecific antibody, and a DART. The molecule also can include an antigen-binding domain that can bind to an effector cell receptor selected from any one of CD3, CD28, CD4, CD8, CD16a, NKG2D, PD-1, CTLA-4, 4-1BB, OX40, ICOS, CD27, and an Fc receptor. In some cases, the antigen-binding domain that can bind to an effector cell can bind to CD3, and the antigen-binding domain can include an amino acid sequence set forth in any one of SEQ ID NO:170, SEQ ID NO:171, SEQ ID NO:172, SEQ ID NO:173, SEQ ID NO:174, SEQ ID NO:175, SEQ ID NO: 176, SEQ ID NO:177, SEQ ID NO:178, SEQ ID NO:179, SEQ ID NO:180, SEQ ID NO:181, SEQ ID NO:182, and SEQ ID NO:183.

In another aspect, this document features methods for treating a mammal having a cancer. The methods can include, or consist essentially of, administering to a mammal having cancer one or more molecules described herein (e.g., a molecule having an antigen-binding domain that can bind to a peptide-HLA-β2M complex, where the peptide can be derived from a modified p53 polypeptide or a modified RAS polypeptide), where the cancer includes cancer cells expressing the modified peptide. The mammal can be a human. The cancer can be any one of Hodgkin's lymphoma, non-Hodgkin's lymphoma, acute myeloid leukemia, acute lymphoblastic leukemia, multiple myeloma, a myelodysplastic syndrome (MDS), a myeloproliferative disease, lung cancer, pancreatic cancer, gastric cancer, colorectal cancer, ovarian cancer, endometrial cancer, biliary tract cancer, liver cancer, breast cancer, prostate cancer, esophageal cancer, stomach cancer, kidney cancer, bone cancer, soft tissue cancer, head and neck cancer, glioblastoma multiforme, astrocytoma, thyroid cancer, germ cell tumor, and melanoma.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 9A H/K/N RAS mutant Q61H(55-64)-A1 cl.1 scDb was incubated at the specified concentrations with T cells and COS-7 cells co-transfected with plasmids encoding various combinations of HLA-A1, H/K/N RAS(WT), H/K/N RAS(Q61H), H/K/N RAS(Q61K), H/K/N RAS(Q61L), and H/K/N RAS (Q61R) and for 20 hours at 37° C. Following co-culture, conditioned media was collected and assayed for secreted IFNγ by ELISA. FIG. 9B H/K/N RAS mutant Q61L(55-64)-A1 cl.2 scDb was incubated at the specified concentrations with T cells and COS-7 cells co-transfected with plasmids encoding various combinations of HLA-A1, H/K/N RAS(WT), H/K/N RAS(Q61H), H/K/N RAS (Q61K), H/K/N RAS(Q61L), and H/K/N RAS(Q61R) and for 20 hours at 37° C. Following co-culture, conditioned media was collected and assayed for secreted IFNγ by ELISA. FIG. 9C H/K/N RAS mutant Q61R(55-64)-A1 cl.6 scDb was incubated at the specified concentrations with T cells and COS-7 cells co-transfected with plasmids encoding various combinations of HLA-A1, H/K/N RAS(WT), H/K/N RAS(Q61H), H/K/N RAS(Q61K), H/K/N RAS (Q61L), and H/K/N RAS(Q61R) and for 20 hours at 37° C. Following co-culture, conditioned media was collected and assayed for secreted IFNγ by ELISA.

Figure 15:
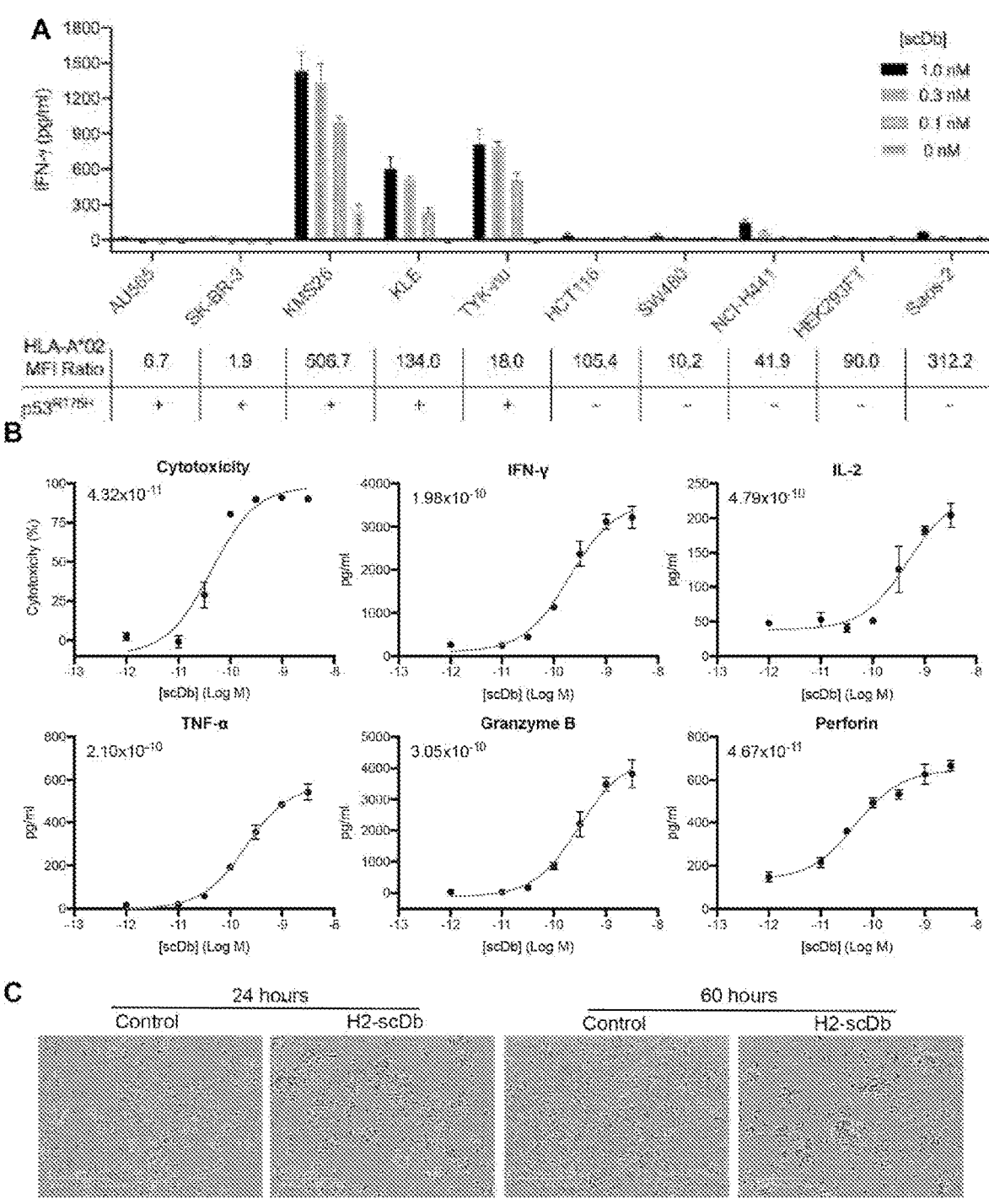

FIGS. 15A-15C show that H2-scDb activates T cells in the presence of tumor cells presenting $p53^{R175H}$ (A) HLA-A*02:01 positive tumor cell lines with different HLA expression levels and $p53^{R175H}$ status were co-incubated with H2-scDb and T cells at an E:T ratio of 2:1. IFN-γ release was measured by ELISA. Data indicate mean±SD of 6 technical replicates and are representative of two independent experiments. The HLA-A*02 median fluorescence intensity (MFI) ratio is defined as MFI (anti-HLA-A*02)/ MFI (isotype control). (B) Polyfunctional T-cell activation mediated by H2-scDb in response to KMS26 at an E:T ratio of 2:1 was assessed by luminescence cytotoxicity and antibody-based assays (see Supplementary Materials). $EC_{50}$ (M) for each assay is shown in the corresponding graphs. Data indicate mean±SD of three technical replicates and are representative of two independent experiments. (C) Real-time live-cell imaging of T cells with CellTracker Green CMFDA-labelled TYK-nu at an E:T ratio of 5:1 with or without H2-scDb. Representative phase contrast and green fluorescence images taken at 24 hours (left) and 60 hours (right) after mixing cells are shown.

FIGS. 16A-16D show a determination of H2-scDb specificity using isogenic target cell lines. (A) HEK293FT and Saos-2 cell lines that were transfected with full-length $p53^{WT}$ full-length $p53^{R175H}$ or were not transfected were co-incubated with T cells at an E:T ratio of 2:1 in the presence of increasing amounts of H2-scDb. IFN-γ release was measured by ELISA. Data indicate mean±SD of three technical replicates. (B) Cell lines expressing $p53^{R175H}$ and transduced or not transduced with HLA-A*02:01 were co-incubated with T-cells and H2-scDb. IFN-γ release was measured by ELISA. Experiments were performed at an E:T ratio of 2:1 in duplicate (AU565) or triplicate (other 3 lines). (B) Cell lines expressing $p53^{R175H}$ were transduced with HLA-A*02:01. Recognition of these cell lines by H2-scDb was assessed by IFN-γ release. Experiments were performed at an E:T ratio of 2:1 in duplicate (AU565) or triplicate (other 3 lines). Data indicate mean±SD. (C) IFN-γ release mediated by H2-scDb in response to parental tumor cell lines and their TP53 KO counterparts at an E:T ratio of 2:1 (KMS26, TYK-nu) or 5:1 (KLE) was measured by ELISA. Data indicate mean±SD of two (TYK-nu) or three (KMS26, KLE) technical replicates and are representative of two independent experiments. (D) Growth of parental (left) or TP53 KO (right) TYK-nu cells co-incubated with H2-scDb and T cells at an E:T ratio of 5:1 was measured by well confluence using real-time live-cell imaging. Data indicate mean±SD of three technical replicates. One-way ANOVA with Tukey's multiple comparison was used to evaluate statistical significance, *denotes P<0.0001.

FIGS. 17A-17H show that H2 binds to the HLA-A*02:01 and the C-terminus of the $p53^{R175H}$ neoantigen. (A) Overall structure of $p53^{R175H}$/HLA-A*02:01 bound to the H2-Fab fragment (PDB: 6W51). The HLA-A*02:01, β2 microglobulin (β2M), $p53^{R175H}$ peptide, and the light and heavy chain of the H2-Fab are labeled accordingly. The $p53^{R175H}$ nine amino acid peptide is between helices α1 and α2 of the HLA. (B) Structure of H2-Fab-$p53^{R175H}$/HLA-A*02:01 at 90° to that shown in (A). (C) Electron density map (2mFo-DFc) of the $p53^{R175H}$ neoantigen. (D) Electron density map (2mFo-DFc) of a selected area of the H2-Fab at CDR-L3 from residues 95 to 99. (E) Zoom in of the interaction of H2-Fab to $p53^{R175H}$/HLA-A*02:01 with CDRs labeled in order from left to right: H2, H1, L3, H3, L1, L2. (F) Bird's-eye view of surface representation of the HLA-A*02:01, $p53^{R175H}$ peptide, and the contacting residues labeled according to CDRs of the H2-Fab. (G) Schematic representation of (F). (H) Diagram of the orientation angle of the H2-Fab. The angle of the orientation was calculated from two vectors: one from N and C termini of the peptide and the other between the intermolecular disulfide bonds of the $V_L$ and $V_H$ domains. The arrowed lines indicate the direction of the vectors.

FIGS. 18A-18F show a structural basis of H2 specificity and identification of putative cross-reactive peptides. (A) Detailed interactions of the $p53^{R175H}$ neoantigen with HLA-A*02:01. The peptide (green) and the side chains (grey) of interacting residues of HLA-A*02:01 are represented as sticks. Hydrogen bonds are shown as dashed lines. (B) Perpendicular view of the $p53^{R175H}$ peptide binding cleft. (C) C-terminus of the p53 peptide (aa Val6-Cys9) with Arg7 and His8 surrounded by the interacting residues of CDR-H1, -H2, -H3, and -L3 shown as sticks. Hydrogen bonds are shown as dashed lines. (D) T2 cells were loaded with 10 μM of HMTEVVRHC (SEQ ID NO:1) peptide variants from the positional scanning library and co-incubated with 1 nM H2-scDb and T cells at an E:T ratio of 2:1. IFN-γ release was measured by cytometric bead array and the mean of triplicate wells was used to plot the heatmap. Black boxes represent the parental $p53^{R175H}$ peptide. (E) Illustration of the binding pattern of H2-scDb as Seq2Logo graph (SEQ ID NO:184), calculated by dividing the IFN-γ value by $10^4$ and using the PSSM-Logo algorithm. (F) T2 cells were loaded with 10 μM of $p53^{R175H}$ (SEQ ID NO:1), $p53^{WT}$ (SEQ ID NO:135), STAT2 (SEQ ID NO:185), VP13A (SEQ ID NO:186), or ZFP3 (SEQ ID NO:187) peptide and co-incubated with 1 nM H2-scDb and T cells at an E:T ratio of 2:1. IFN-γ secretion was measured by ELISA. Data indicate mean±SD of three technical replicates.

Figure 19:
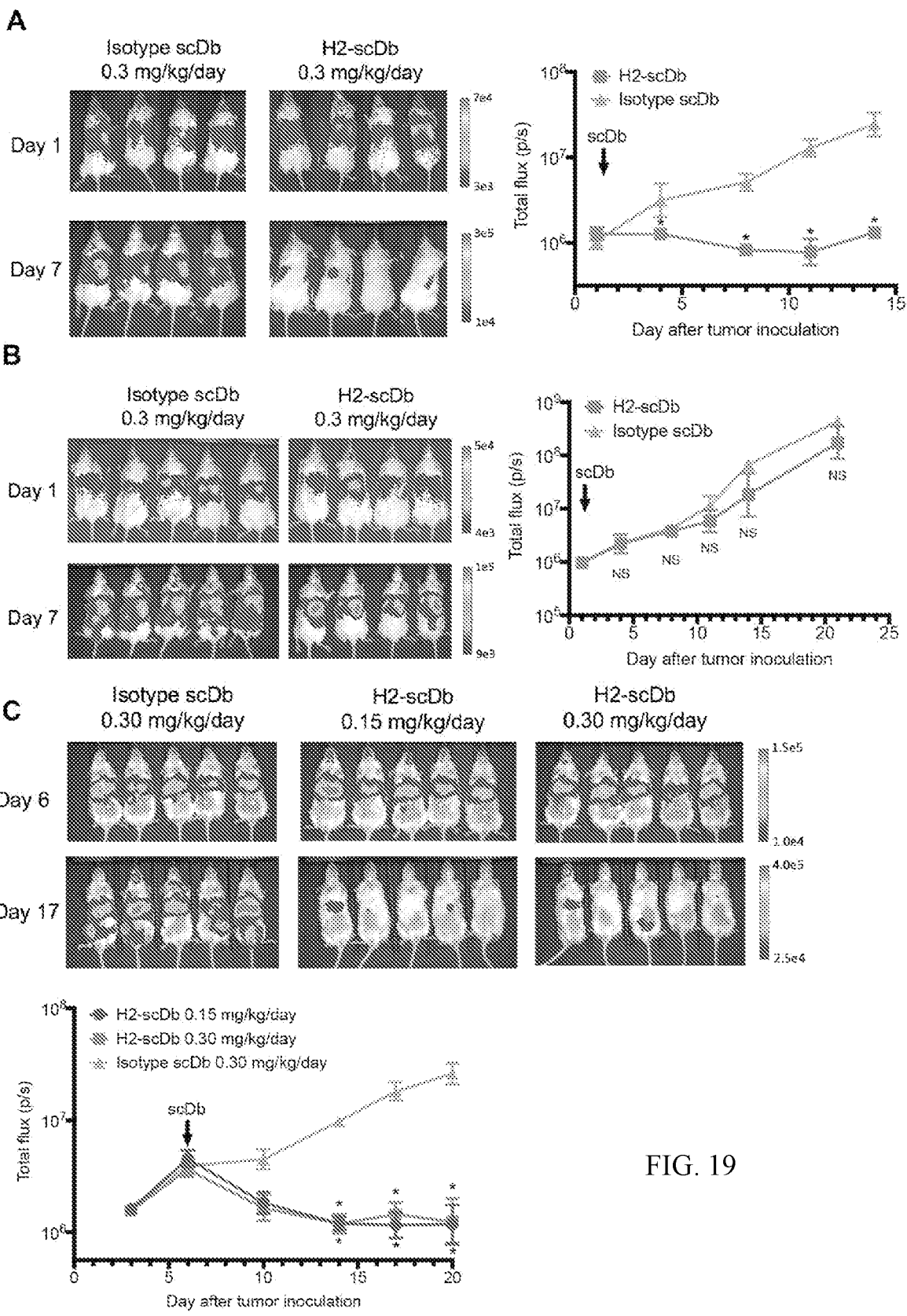

FIGS. 19A-19C show in vivo antitumor efficacy of H2-scDb. In the early treatment model, NSG mice were engrafted with $1×10^7$ human T cells and either $1×10^6$ parental KMS26 (A) or $1×10^6$ TP53 KO KMS26 (B) on day 0. On day 1, intraperitoneal infusion pumps were placed to administer H2-scDb or isotype control scDb. (C) In the established tumor model, mice were engrafted with $1×10^7$ human T cells and $3.5×10^5$ parental KMS26 on day 0, followed by administration of H2-scDb or isotype scDb at the specified dose on day 6. Tumor growth was monitored by bioluminescent imaging. N=4 or 5 mice per group. Color bars denote the radiance (p/sec/cm²/sr) scale at each time point. Plotted data indicate mean SD. * denotes P<0.05 and NS denotes no statistical significance compared to isotype control by multiple t-test with Holm-Šidák correction.

Figure 20:
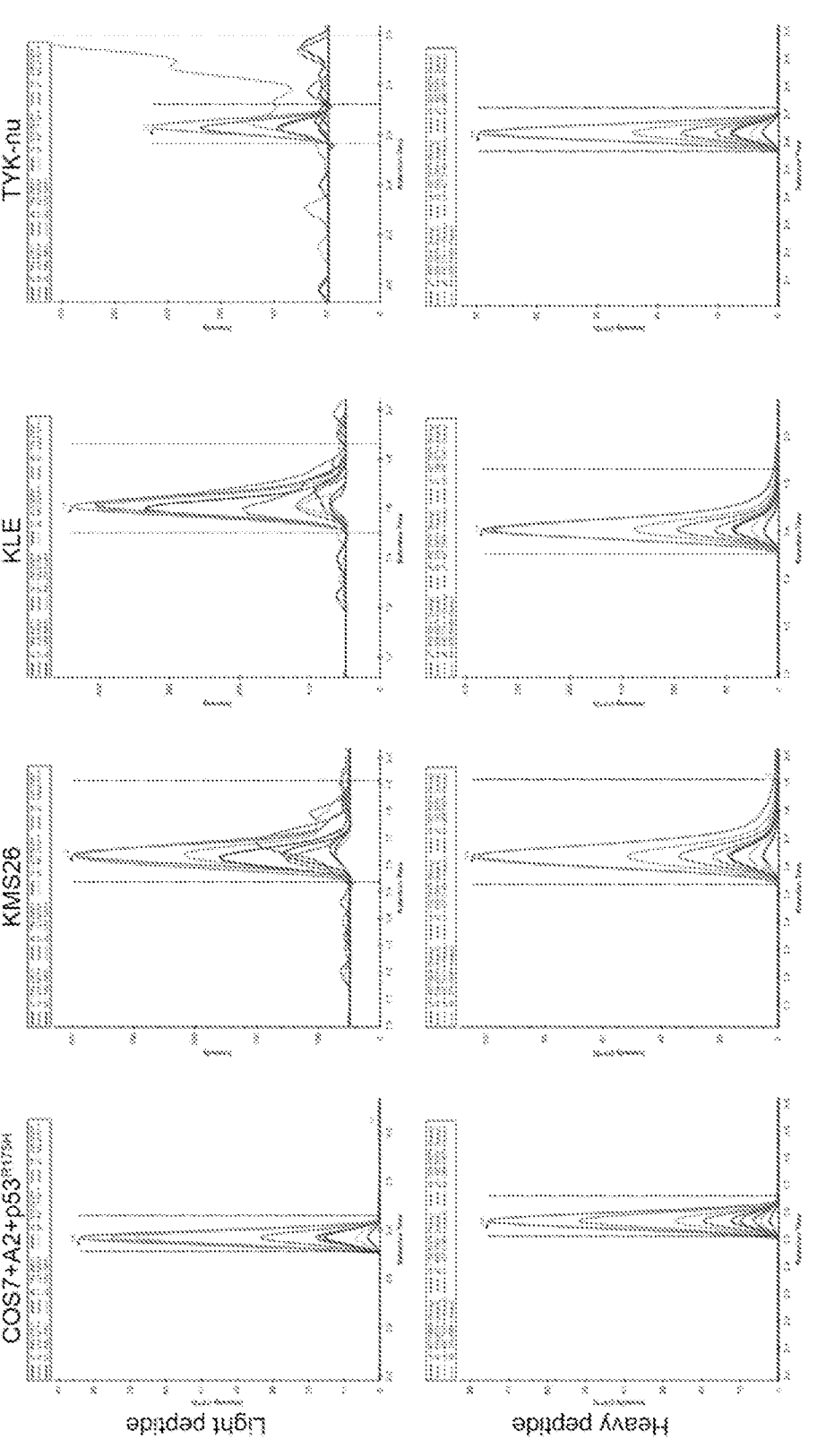

FIG. 20 shows the detection and quantification of $p53^{R175H}$ neoantigen peptide in cells. COS-7 cells transfected with constructs expressing HLA-A*02:01 and $p53^{R175H}$ as well as cells lines with endogenous HLA-A*02:01 and $p53^{R175H}$ expression, were analyzed for the presentation of $p53^{R175H}$ neoantigen peptide HMTEVVRHC (SEQ ID NO:1; upper panel). Heavy isotope labeled $p53^{R175H}$ neoantigen peptide was spiked into the assay and served as standards for absolute copy number quantification (lower panel).

Figure 21:
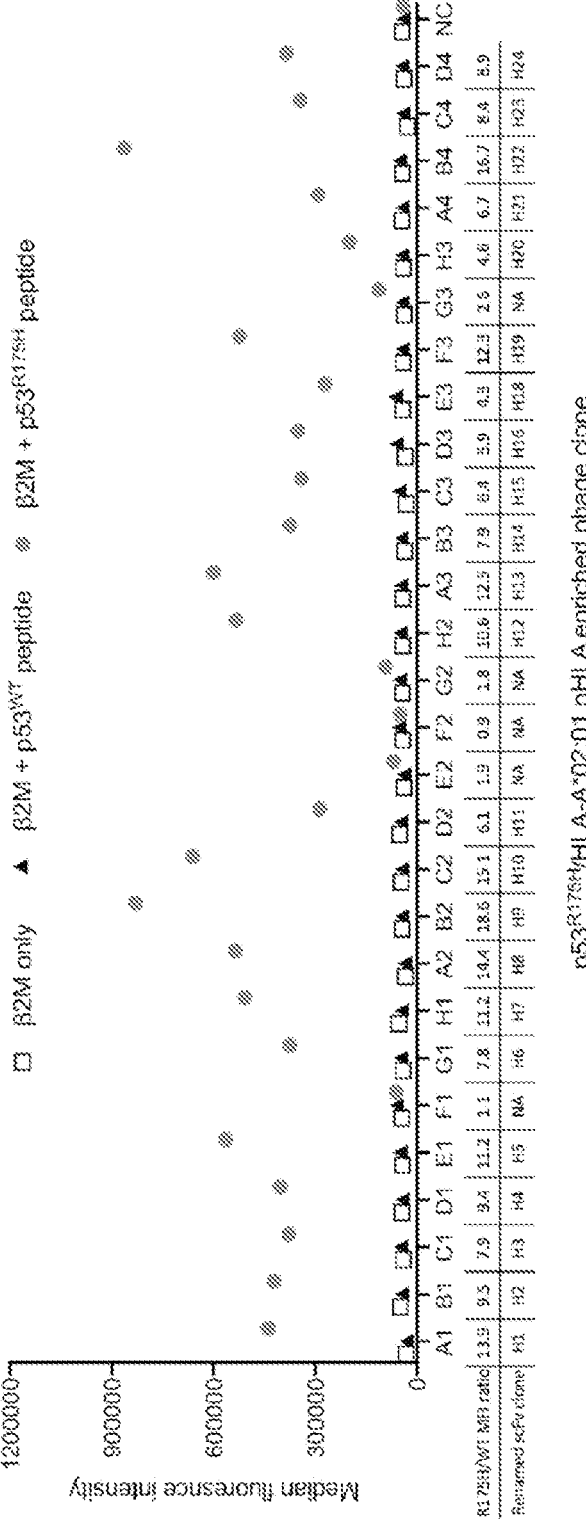

FIG. 21 shows a flow cytometric screening of phage clones enriched by panning. After 5 rounds of panning, phage clones from the enriched phage pool were isolated by limiting dilution and grown in deep 96-well plates. Supernatants containing individual phage clones were used to assess binding to T2 cells loaded with 32 macroglobulin ($\beta$2M) only, $\beta$2M plus p53$^{WT}$ peptide, or $\beta$2M plus p53$^{R175H}$ peptide via flow cytometry. The median fluorescence intensity (MFI) ratio was defined as MFI (R175H peptide)/MFI (WT peptide). NC, no phage control.

Figure 22:
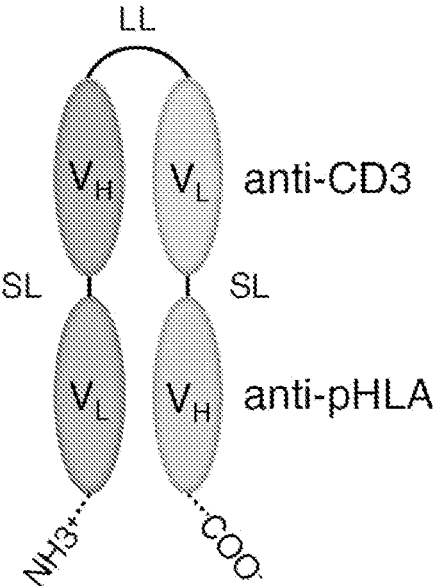

FIG. 22 contains a schematic representation of the structure of the T cell-engaging bispecific single-chain diabody (scDb) used in our experiments. V$_L$, variable light domain; V$_H$, variable heavy domain; pHLA, peptide-HLA complex; LL, long linker; SL, short linker.

Figure 23:
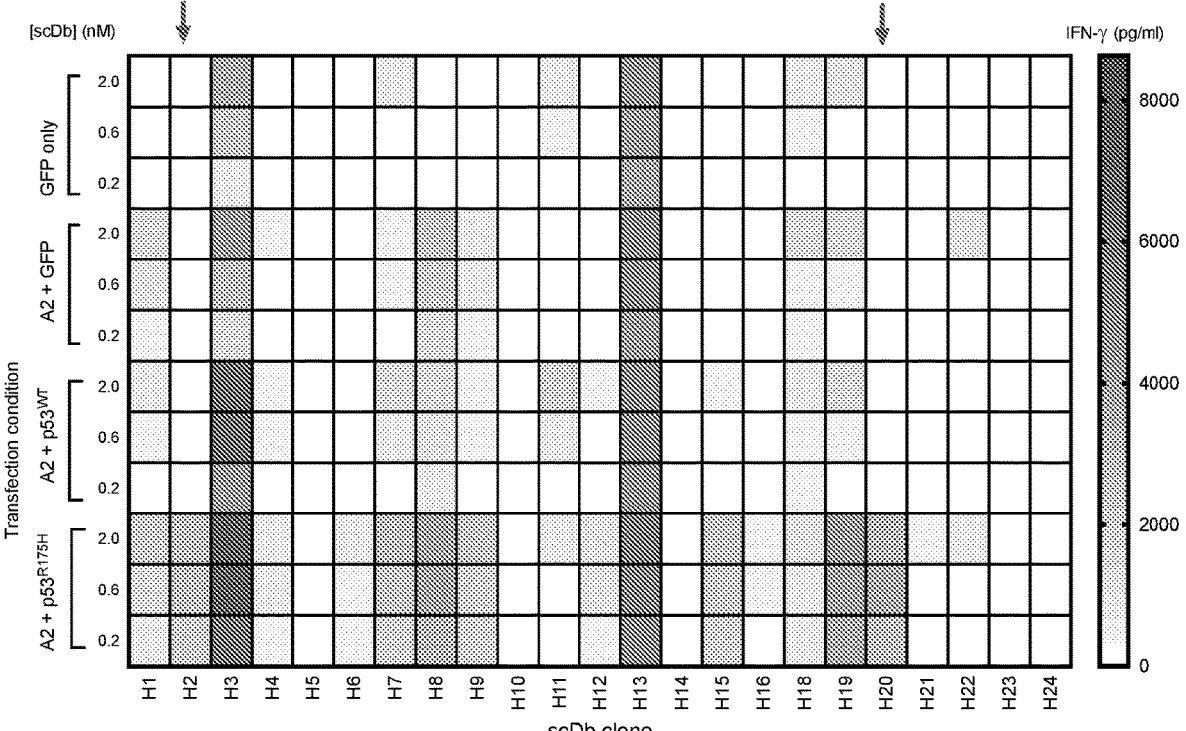

FIG. 23 shows a screening of scDb clones via IFN-$\gamma$ stimulation by p53-expressing cells. scDbs generated by linking each anti-p53$^{R175H}$/HLA-A*02:01 pHLA scFv clone with an anti-CD3 scFv (UCHT1) were coincubated with T cells and COS-7 cells transfected with GFP, HLA-A*02:01+GFP, HLA-A*02:01+p53$^{WT}$, or HLA-A*02:01+p53$^{R175H}$ plasmids at an effector:target (E:T) ratio of 1:1. After a 20-hour coincubation, the supernatant was harvested for IFN-$\gamma$ detection by ELISA. Arrows indicate clones H2 and H20. A2, HLA-A*02:01.

Figure 24:
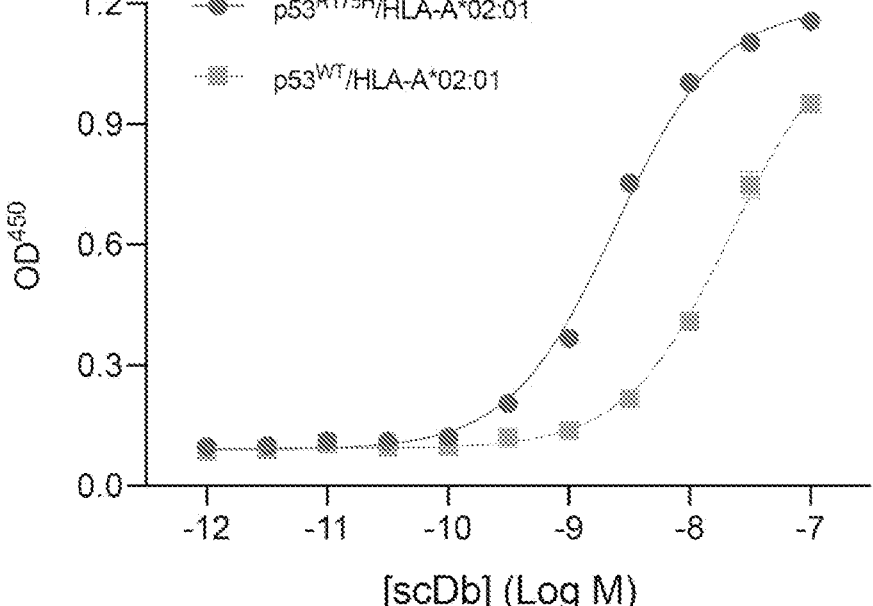

FIG. 24 shows a characterization of H20-scDb. H20-scDb was incubated with biotinylated p53$^{R175H}$/HLA-A*02:01 (red) and p53$^{WT}$/HLA-A*02:01 (gray) pHLA monomers coated on streptavidin microplates at the specified concentrations, then binding detected with protein L and anti-protein L HRP. Data indicate mean±SD of three technical replicates.

Figure 25:
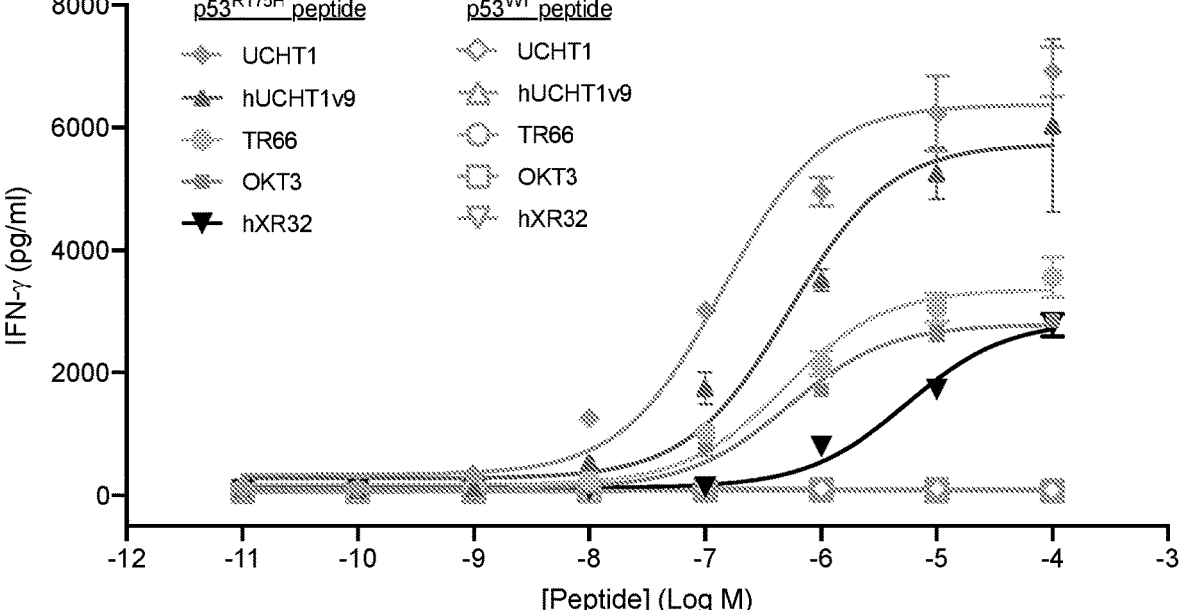

FIG. 25 contains a comparison of scDbs generate with different anti-CD3 scFvs. H2 was linked with different anti-CD3 scFvs in the scDb format and co-incubated with T cells and T2 cells pulsed with titrated concentrations of p53$^{R175H}$ or p53$^{WT}$ peptide at an E:T ratio of 2:1. IFN-$\gamma$ release was measured by ELISA. Data indicate mean±SD of three technical replicates.

Figure 26:
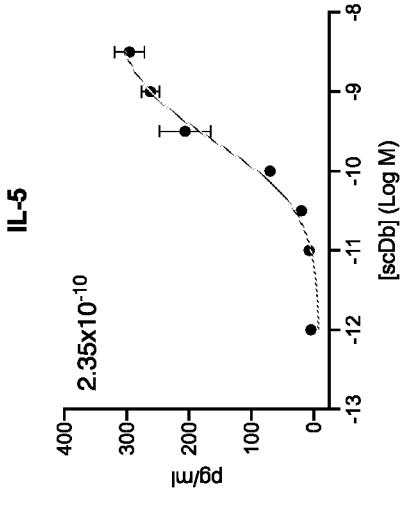
Figure 26:
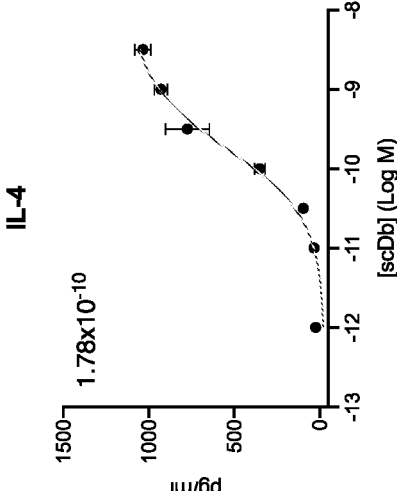
Figure 26:
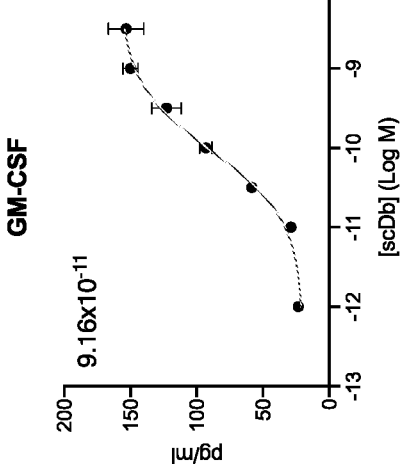
Figure 26:
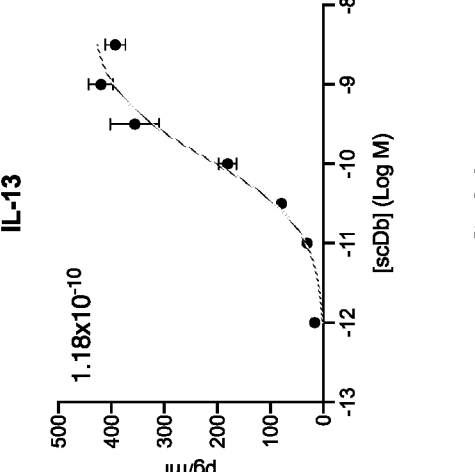
Figure 26:
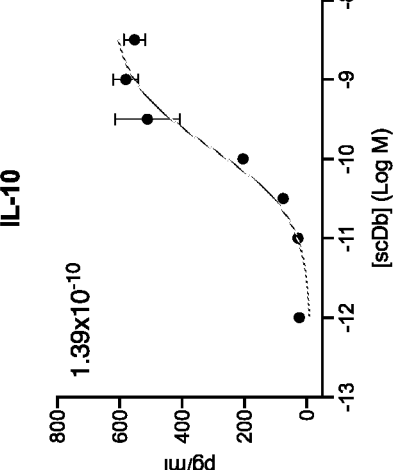

FIG. 26 shows a H2-scDb-induced polyfunctional T-cell response. T-cell cytokine release mediated by H2-scDb in response to KMS26 cell line at an E:T ratio of 2:1 was assessed by antibody-based assays. EC$_{50}$ (M) for each analyte is shown in the corresponding graphs. Data indicate mean±SD of three technical replicates.

Figure 27:
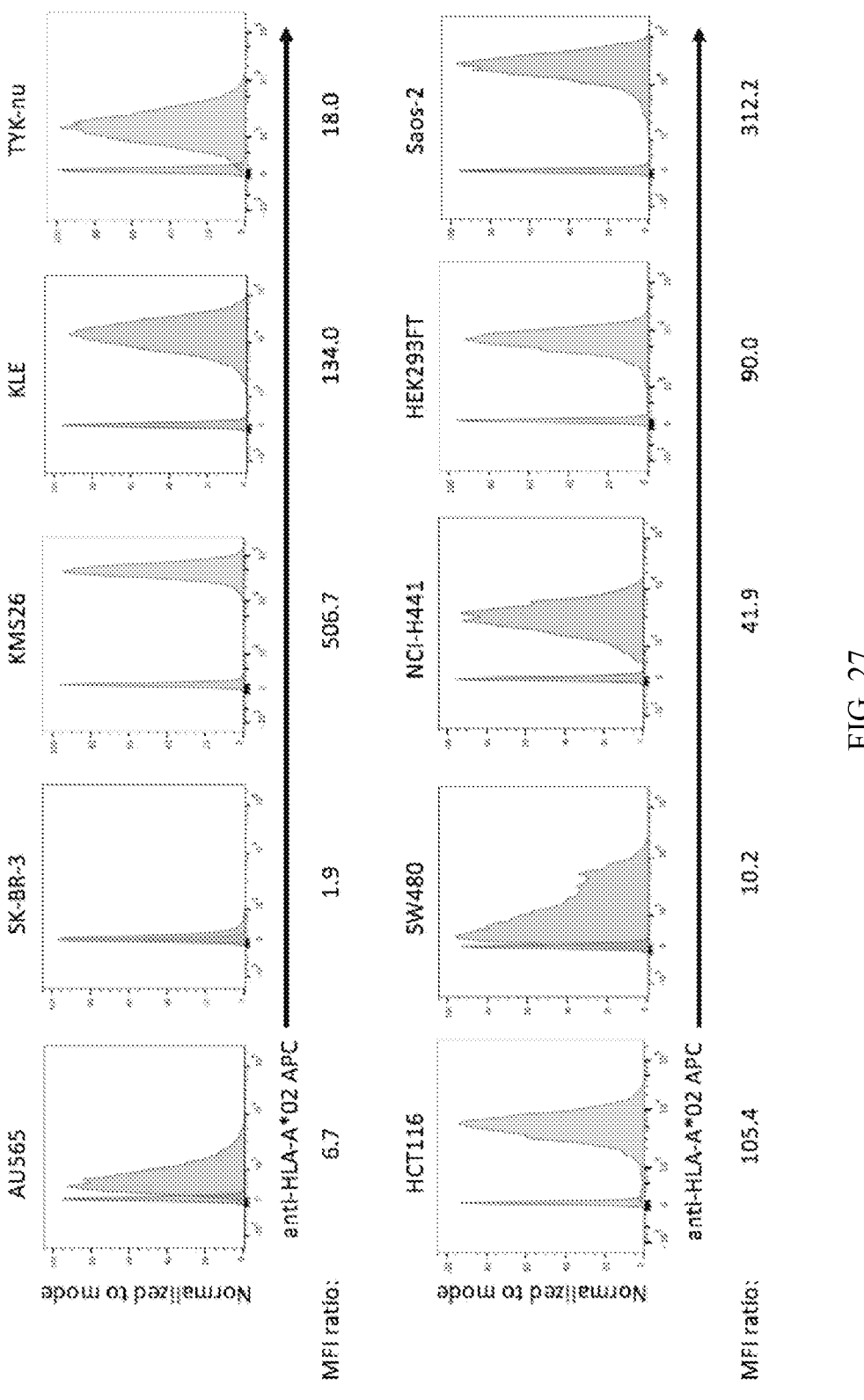

FIG. 27 shows a flow cytometric evaluation of HLA-A*02 expression on tumor cell lines. Expression of HLA-A*02 on tumor cell lines was evaluated by flow cytometry. The red histogram represents staining with anti-HLA-A*02 (clone BB7.2), and the gray histogram represents staining with an isotype control. The median fluorescence intensity (MFI) ratio is defined as MFI (anti-HLA-A*02)/MFI (isotype control).

Figure 28:
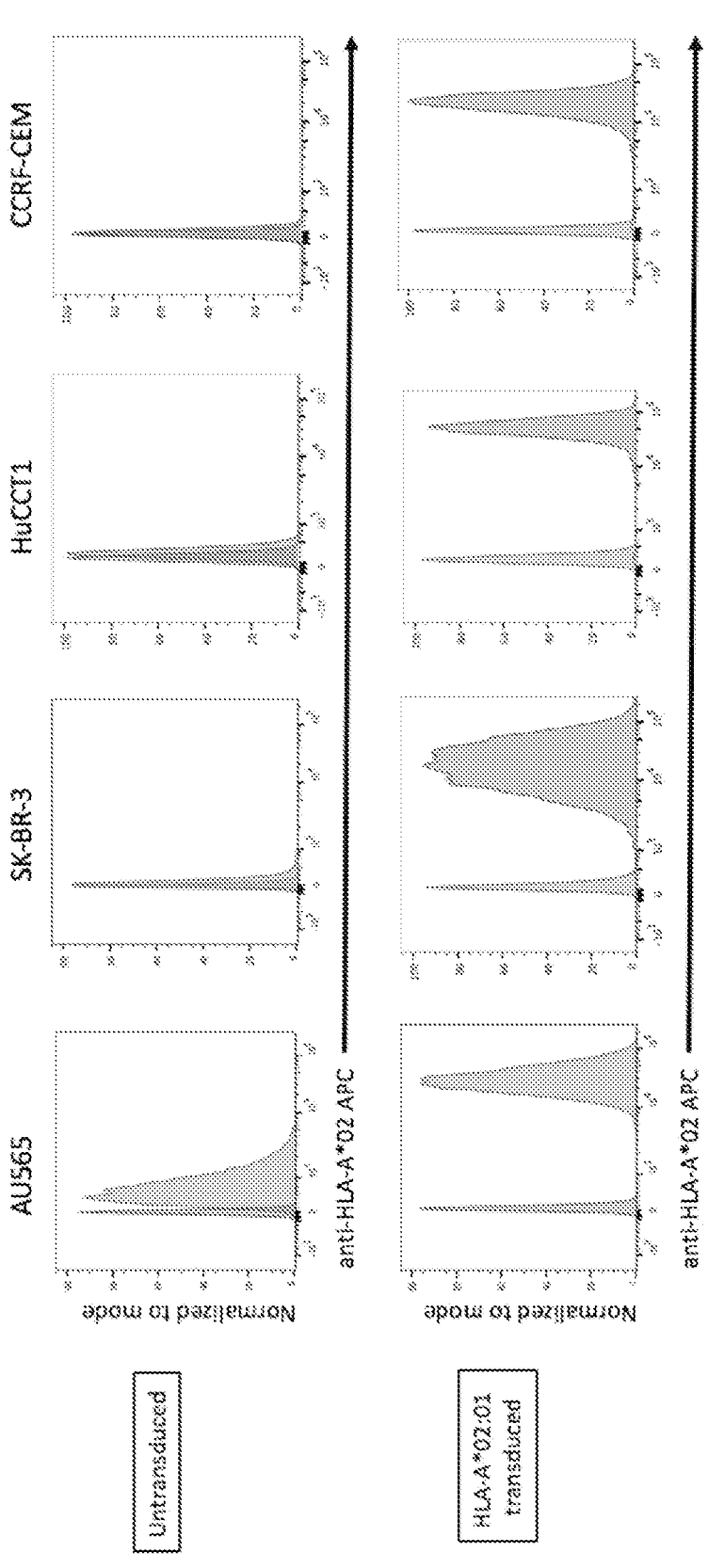

FIG. 28 shows a flow cytometric evaluation of tumor cell lines transduced with HLA-A*02:01-encoding retrovirus. HLA-A*02:01-encoding retrovirus was transduced into cell lines that weakly (AU565, SK-BR-3) or do not detectably (HuCCT1, CCRF-CEM) express HLA-A*02:01. Expression of HLA-A*02:01 in the parental and transduced and sorted cell lines was evaluated by flow cytometry. The red histogram represents staining with anti-HLA-A*02 (clone BB7.2) and the gray histogram represents staining with an isotype control.

Figure 29:
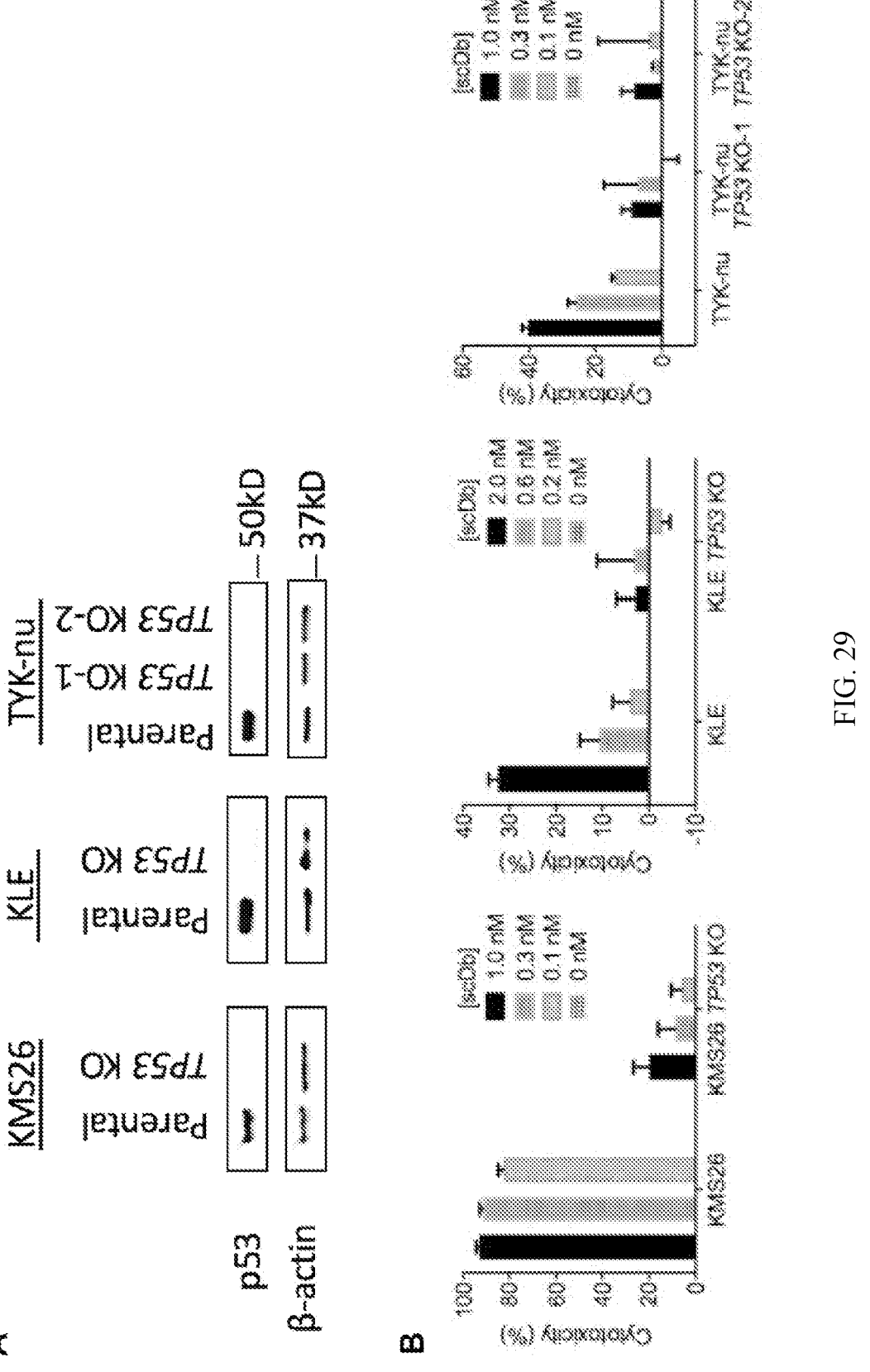

FIGS. 29A-29B show a determination of H2-scDb specificity using CRISPR-edited isogenic cell lines. (A) Expression of p53 protein in the parental and TP53 KO clones of KMS26, KLE, and TYK-nu was assessed by Western blot staining with anti-p53 antibody (clone DO-1). (B) Cytotoxicity mediated by H2-scDb in response to parental tumor cell lines and their TP53 KO counterparts at an E:T ratio of 2:1 (KMS26, TYK-nu) or 5:1 (KLE) was measured by the Bio-Glo (KMS-26) or CellTiter-Glo (TYK-nu, KLE) assay. Data indicate mean±SD of two (TYK-nu) or three (KMS26, KLE) technical replicates and are representative of two independent experiments.

Figure 30:
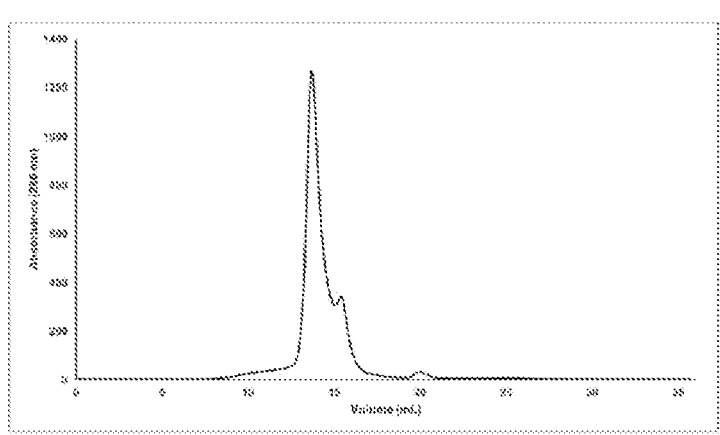
Figure 30:
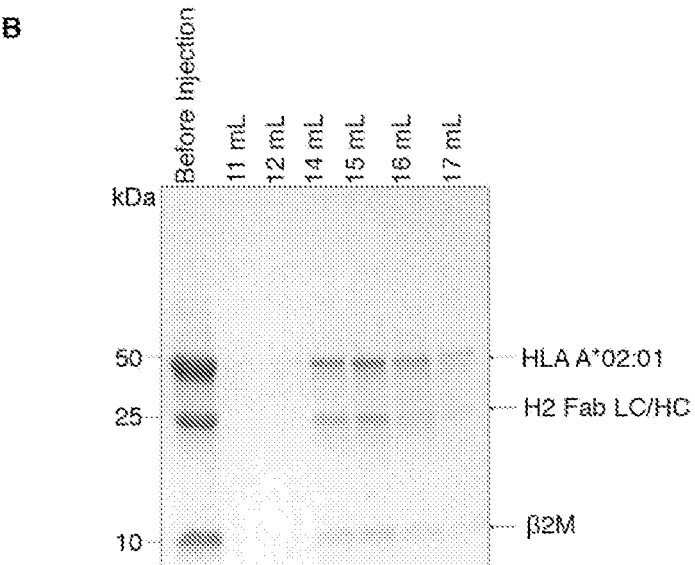

FIGS. 30A-30B shows a H2-Fab-p53$^{R175H}$/HLA-A*02:01 complex. (A) Size-exclusion chromatogram of the pHLA-A*02:01 in complex with the H2-Fab. Protein was monitored by A280 nm with a major peak (~100 kDa). (B) Coomassie-stained gradient SDS-PAGE gel of the eluted fractions at 11-17 mL from (A).

FIGS. 31A-31D show that the neoantigen p53$^{R175H}$ binds to HLA-A*02:01 in a canonical fashion. (A) Bird's-eye view of the p53$^{R175H}$ neoantigen interactions with HLA-A*02:01. The p53 peptide and the side chains of interacting residues of HLA-A*02:01 are represented as sticks. Hydrogen bonds are shown as dashed lines. The N-terminal His1 is anchored by three tyrosine residues of HLA-A*02:01, one at the base of the cleft (Tyr7, not shown) and two on $\alpha$2 (Tyr159, 171), while its side chain is within hydrogen bonding distance of Lys66 ($\alpha$1) and Thr163 ($\alpha$2). Glu63 of HLA-A*02:01 al forms a hydrogen bond with the backbone amino of Met169 at P2, an anchor residue of p53$^{R175H}$ that is situated within the hydrophobic B pocket of the HLA. The main chain of Thr3 is stabilized by a hydrogen bond to Tyr99, located at the base of the cleft while the side chain of Glu4 forms a salt-bridge with the side chain of Arg65. Positions 5-8 (Val172, Val173, Arg174, His175) of the p53$^{R175H}$ neoantigen are stabilized by multiple hydrophobic and aliphatic residues with no direct hydrogen bonding contacts to the HLA-A*02:01. Towards the C-terminus of the neoantigen, the carboxyl group of Cys176 at P9, another anchor residue that lies within the F pocket, is secured by Tyr84 ($\alpha$1) and Lys146 ($\alpha$2), while the side chain sulfhydryl is near Thr143 on $\alpha$2. (B) Surface representation of the HLA-A*02:01 with the p53$^{R175H}$ neoantigen shown as sticks. Anchor pockets B and F are circled in black. (C) Structural alignment of the following HLA-A*02:01-bound peptides in the binding pocket: p53$^{R175H}$ (PDB ID 6W51), p1049 (PDB ID 2JCC), NY-ESO-1 (PDB ID 3HAE), and WT1 (PDB ID 4WUU). (D) Zoomed in view of (B) with helix al transparent and residues at position 7 (P7, Arg174) and 8 (P8, His175) shown as sticks.

Figure 32:
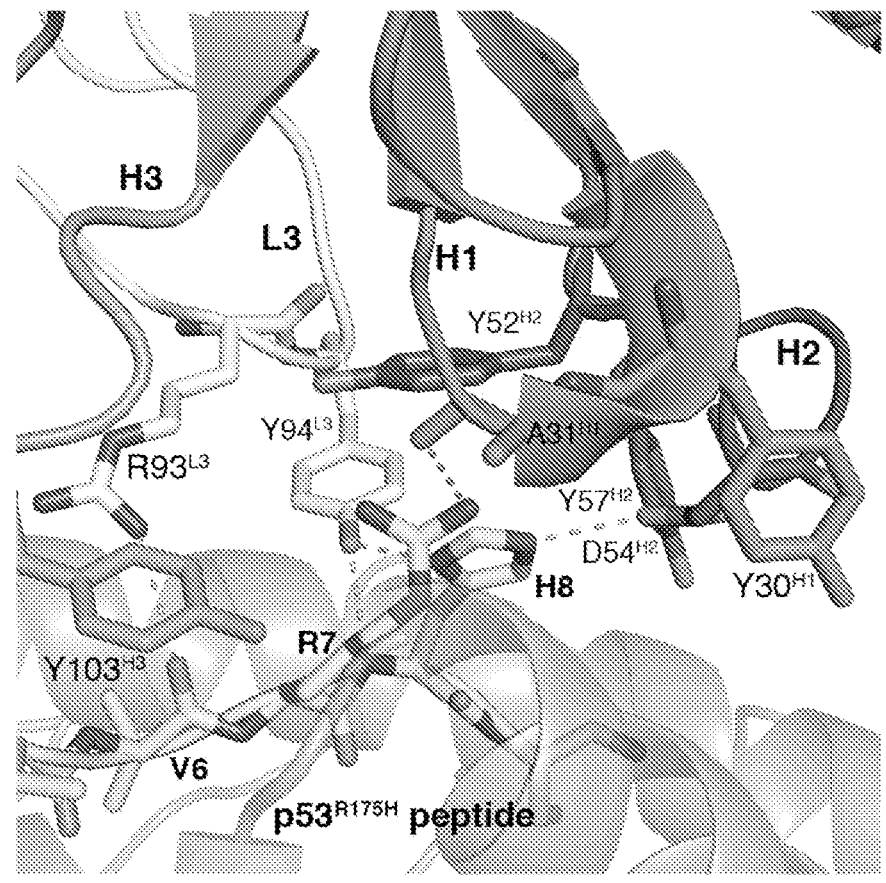

FIG. 32 shows a hydrogen bonding pattern of the H2-Fab cage-like configuration. The imidazole ring of His175 at P8 was at the center of the cage-like structure. The guanidinium group of Arg7 was at hydrogen bonding distance to the backbone carbonyl of Ala31 (CDR-H1). Another neoantigen-antibody direct contact involves the backbone carbonyl of Val6 hydrogen bonding with the side chain of Arg93 (CDR-L3).

FIGS. 33A-33P show a comparison of binding orientations among TCRm-pHLA and TCR-pHLA complexes. (A) Close depiction of binding of the H2-Fab to p53$^{R175H}$/HLA-A*02:01 with CDRs labeled as in FIG. 17. (B) Binding of a TCR to melanoma-associated antigen 3 (MAGE-A3) and HLA-A*01:01 (PDB 5BRZ). Same orientation as (A). The MAGE-A3 TCR displays the canonical, diagonal binding motif to that of most known TCR topologies. (C) Recognition of the 3M4E4 Fab for the NY-ESO-1$_{157-165}$/HLA-A*02:01 complex (PDB 3HAE). Same orientation as (A). (D) Binding of the ESK1 Fab to Wilms tumor 1 peptide and HLA-A*02:01 (PDB 4WUU). Same orientation as (A). (E, F, G and H) Bird's-eye view of surface representation of the HLA-A*02:01/*01:01 with the contacting residues of H2-Fab, MAGE-A3 TCR, 3M4E4 Fab, and ESK1 Fab, respectively, labeled and indicated with arrows. (I, J, K and L) Schematic representation of E, F, G, and H, respectively. H2-Fab-p53$^{R175H}$/HLA-A*02:01 shows a different mode of antibody recognition compared with other Fab/TCR-pHLA complexes. (M, N, O and P) Schematic representation of Fab/TCR orientation angle.

Figure 34:
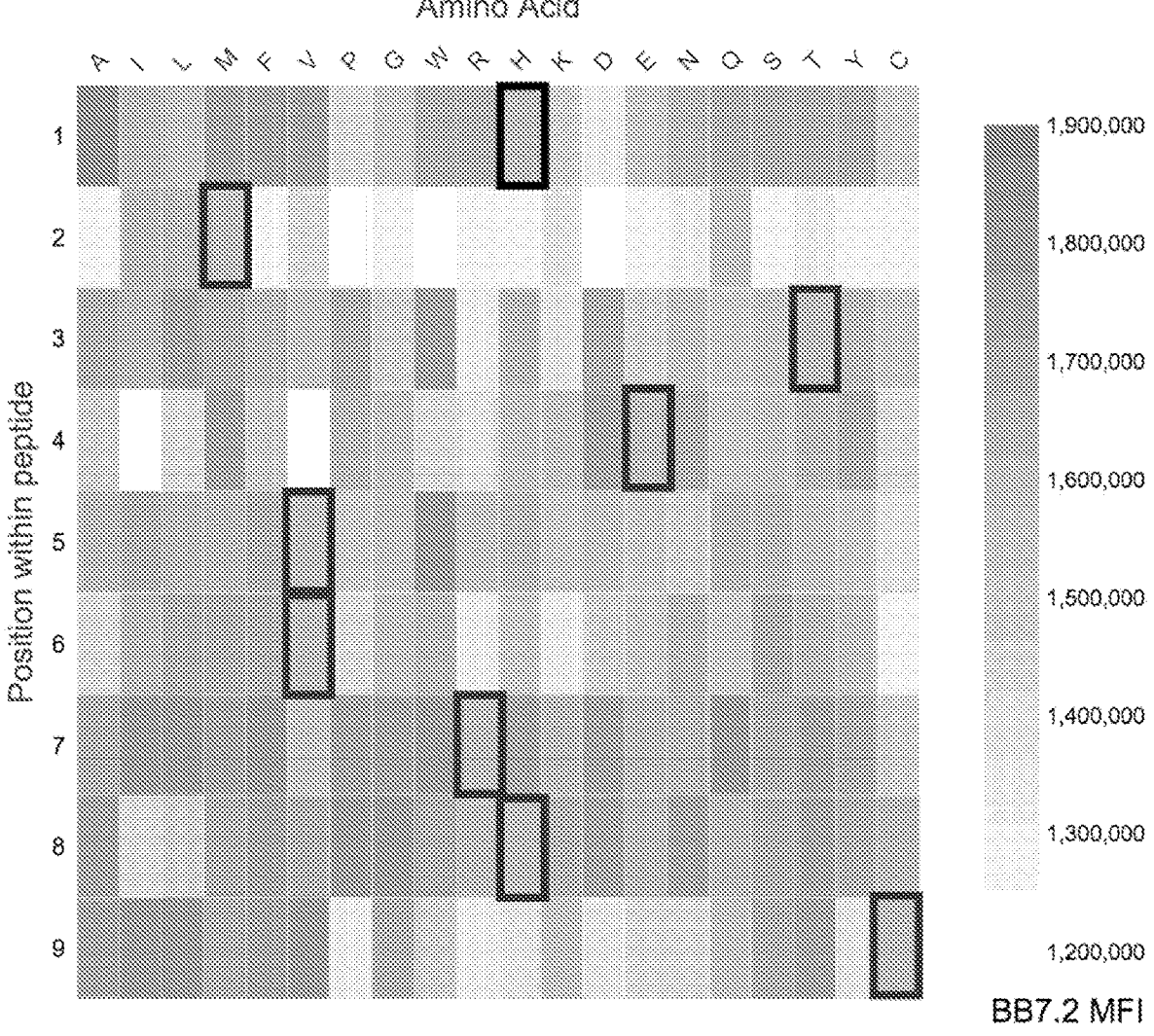

FIG. 34 shows binding of p53$^{R175H}$ positional scanning library peptides to HLA-A*02:01. A peptide library was generated by systemically substituting the amino acid at each position of the target peptide (HMTEVVRHC; SEQ ID NO:1) with each of the remaining 19 common amino acids. T2 cells were loaded with each of the variant peptides at 100 uM in the presence of 10 μg/ml β2M and anti-HLA-A*02 antibody (clone BB7.2). Peptide binding was evaluated by flow cytometry. Black boxes represent the parental peptide. MFI, median fluorescence intensity.

Figure 35:
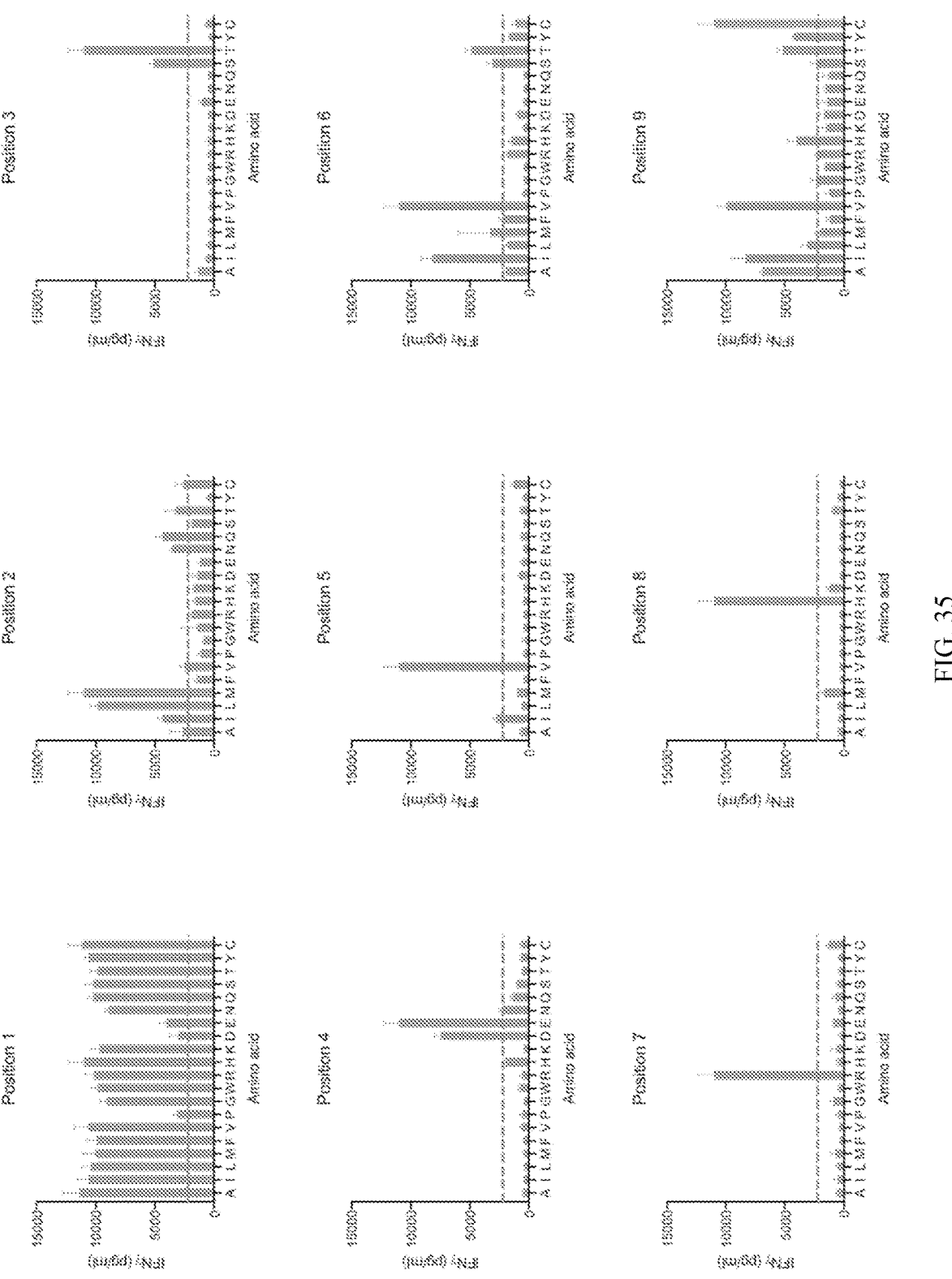

FIG. 35 shows recognition of the p53$^{R175H}$ positional scanning library peptides by H2-scDb. T2 cells loaded with variant peptides in the positional scanning library was incubated with 1 nM H2-scDb and T cells at an E:T ratio of 2:1. IFN-γ release was measured by ELISA. Dotted lines represent 20% of parental peptide IFN-γ value. Peptides for Positions 1-9 are SEQ ID NOs:188-196, respectively. The binding motif established by the 20% reactivity cutoff, expressed in PROSITE pattern, was x-[AILMVNQTC]-[ST]-[DE]-[IV]-[IMVST]-R-H-[AILVGHSTYC] (SEQ ID NO:197). Data indicate mean±SD of three technical replicates.

FIGS. 36A-36B contain an assessment of H2-scDb cross-reactivity H2-scDb was co-incubated with T cells and COS-7 cells transfected with HLA-A*02:01 and full-length p53$^{R175H}$ STAT2, or ZFP3 at an E:T ratio of 5:1. (A) Expression of target proteins by COS-7 cells was assessed by Western blot staining. (B) IFN-γ secretion was measured by ELISA. The signals for all of the transfectants except for p53$^{R175H}$ were indistinguishable and are clustered near the x-axis. Data indicate mean±SD of three technical replicates.

Figure 37:
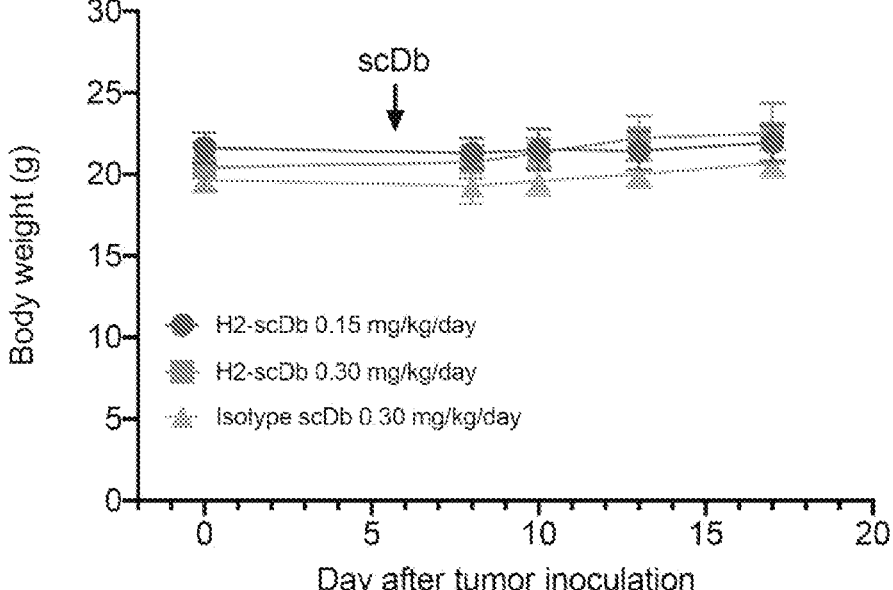

FIG. 37 shows the body weight of NSG mice in the established tumor model. NSG mice were engrafted with $1 \times 10^7$ human T cells and $3.5 \times 10^5$ parental KMS26 on day 0, followed by administration of the specified scDb on day 6. Body weight of the mice were serially monitored. N=5 mice per group. Data shown represent mean±SD.

FIGS. 38A-38H. ELISA and flow cytometry characterization of RAS MANA scFvs. scFvs against RAS MANAs were characterized using ELISA, flow cytometry, and SPR. (A,D-F) Biotinylated G12V or G12WT pHLA-A3 (A) or Q61WT, Q61H, Q61L, or Q61R pHLA-A1 (D-F) were coated on a streptavidin plate at the specified concentrations. Recombinant RAS G12V clone V2 (A), Q61H clone H1 (D), Q61L clone L2 (E), or Q61R clone R6 (F) scFvs were incubated in the wells at 1 μg/mL, followed by detection with protein L and horseradish peroxidase (HRP)-conjugated anti-protein L. All ELISAs were performed in triplicate. (B,G) T2A3 or SigM5 cells were pulsed with the specified peptides at 50 μM, followed by flow cytometric analysis. (B) T2A3 cells were stained with V2 scFv pre-conjugated to anti-FLAG-phycoerythrin (PE), with mean fluorescence intensities (MFI) plotted. (G) SigM5 cells were stained with clone H1, L2, or R6 phage, then detected with rabbit anti-M13 phage and PE-conjugated anti-rabbit antibodies. Phage background-subtracted PE MFI are plotted. (C,H) V2 scFv and L2 single chain diabody (scDb) binding were evaluated by single-cycle kinetics using SPR. (C) The V2 scFv bound to G12V pHLA-A3 with one-to-one binding kinetics and a $K_D$ of 8.7 nM, with negligible binding to G12WT pHLA-A3. (H) The L2-U scDb bound to the Q61L pHLA-A1 with one-to-one binding kinetics and a $K_D$ of 65 nM, with negligible binding to Q61WT pHLA-A1.

FIGS. 39A-39E. Schematic and ELISA characterization of MANA scDbs. (A) Schematic showing the optimal bispecific format, an scDb with variable light (VL) and variable heavy (VH) domains arranged in the following order: VL$_{V2}$-VH$_{UCHT1}$-VL$_{UCHT1}$-VH$_{V2}$. SL, short linker (GGGGS; SEQ ID NO:200); LL, long linker (GGGGS)$_3$ (SEQ ID NO:201). (B-E) anti-MANA/anti-CD3 scDbs were characterized via ELISA. Biotinylated pHLA-A3, pHLA-A1 or recombinant CD3ε/δ protein were coated on a streptavidin plate. Recombinant V2-U (B), H1-U (C), L2-U (D), or R6-U (E) scDbs were incubated at the specified concentrations then detected with protein L and anti-protein L HRP. All ELISAs were performed in triplicate.

FIGS. 40A-40D. Co-cultures with peptide-pulsed cells. (A,B) T2A3 cells were pulsed with either the G12V or G12WT peptides at the specified concentrations. (C,D) SigM5 cells were pulsed with either the Q61L or Q61WT peptides at the specified concentrations. $5 \times 10^4$ (T2A3) or $2.5 \times 10^4$ (SigM5) peptide-pulsed cells were combined with $5 \times 10^4$ human T cells (effector:target ratio or E:T=1:1 or 2:1) and V2-U (A,B), V2-U2 scDb (A,B), or L2-U (C,D) at 1 nM. Plates were incubated for 24 hours and the supernatants assayed for IFNγ (A,C). Target cell cytotoxicity was assayed using CellTiter-Glo (B,D). Percent cytotoxicity was determined by subtracting the T cell signal and normalizing to the no peptide condition. All experiments were performed in triplicate.

FIGS. 41A-41D. Co-culture with transfected COS-7 cells. COS-7 cells were transfected with a 1:1 ratio of plasmids encoding HLA-A3 ("A3") or HLA-A1 ("A1") and RAS variants or other negative controls. 24 hours later, $1 \times 10^4$ COS-7 cells were combined with $5 \times 10^4$ human T cells (E:T=5:1) and V2-U (A), H1-U (B), L2-U (C), or R6-U (D) scDb at the specific concentrations. Plates were incubated for 24 hours and supernatants assayed for IFNγ. All experiments were performed in triplicate.

FIGS. 42A-42F. Effects of V2-U scDb on co-cultures of human T cells with cancer cells. $2 \times 10^4$ target cells from parental NCI-H441 (A,B), NCI-H441 isogenic variants (C,D) or NCI-H358 isogenic variants (E,F) were combined with $6 \times 10^4$ human T cells (E:T=3:1) and V2-U scDbs at the specified concentrations. Cells were incubated for 24 hours and assayed for IFNγ release (A,C,E) and target cell cytotoxicity using CellTiter-Glo (B,D,F). Cytotoxicity was calculated by subtracting the T cell alone signal and normalizing to the no scDb condition (considered as 0% cytotoxicity). All experiments were performed in triplicate. For KRAS genotypes: V/A, G12V/frameshift (also see FIG. 55).

FIGS. 43A-43E. Effects of L2-U scDb on co-cultures of human T cells with cancer cells. $2.5 \times 10^4$ target cells from different cancer cell lines expressing HLA-A1, RAS Q61L, or both (A), parental HL-60 cells (B-C), or HL-60 isogenic variants expressing different RAS Q61 mutations or with HLA-A1 knocked out (KO) (D-E) were combined with $5 \times 10^4$ human T cells (E:T=2:1) and L2-U scDb at the specified concentrations. Cells were incubated for 24 hours and assayed for IFNγ release by ELISA (A,B,D) and target cell cytotoxicity was assessed via CellTiter-Glo (C,E). Cytotoxicity was calculated by subtracting the T cell alone signal and normalizing to the no scDb condition (considered as 0% cytotoxicity). All experiments were performed in triplicate. (For HL-60 NRAS genotypes, also see FIG. 55).

FIGS. 44A-44D. Peptide scanning to assess V2-U and L2-U scDb cross-reactivity. Each amino acid position of the G12V and Q61L 10-mer peptides were systematically changed to the other 19 amino acids, thereby generating libraries of variant peptides each differing from the original peptide by a single amino acid. T2A3 cells were pulsed with 10 M of the G12V peptide scanning library (A,C) and SigM5 cell cells were pulsed with 10 M of the Q61L peptide scanning library (B,D). $2.5 \times 10^4$ peptide-pulsed target cells were combined with $5 \times 10^4$ human T cells (E:T=2:1) and either the V2-U (A,C) or L2-U scDb (B,D) at 1 nM. (A,B) Plates were incubated for 24 hour and assayed for IFNγ release, with the mean of three technical replicates plotted as a heat map. Black boxes indicate amino acids in the parental peptides. (C,D) Illustration of the binding pattern of V2-U and L2-U scDb as Seq2Logo graph (SEQ ID NOs:683 and 684, respectively), calculated by dividing the IFNγ value by $10^3$ and using the PSSM-Logo algorithm.

FIGS. 45A-45C. KRAS neoantigen transitions detected through MANA-SRM. (A-C) COS-7 cells transfected with constructs expressing HLA-A*03:01 and KRAS G12V (A), as well as cells lines NCI-H441 (B) and CFPAC-1 (C) with endogenous HLA-A*03:01 and KRAS G12V expression, were analyzed for the presentation of G12V[7-16] VVVGAVGVGK (SEQ ID NO:205; left) and G12V[8-16] VVGAVGVGK (SEQ ID NO:206; right) peptides (lower panels). The presence or absence of these peptides is denoted with a red arrow or "X," respectively. Heavy isotope labeled RAS G12V peptides were spiked into the assay and served as standards for absolute copy number quantification (upper panels). Transition details for each peptide in each sample were shown on the right side of each individual plot after zooming in on the retention time (x-axis). Peptide quantification was performed based on the plots as previously described.

FIGS. 46A-46C. Design and sequencing of CDR-H3 of the phage library. (A) Expected amino acid diversity at variable codons of CDR-H3, using Kabat numbering. (B) Expected percent of clones with a given codon present in CDR-H3. (C) Expected vs. actual amino acid diversity at variable codons in CDR H3. The actual amino acid diversity was determined by MiSeq next-generation sequencing (NGS) of a portion of the library and subsequent analysis of the top 100,000 most frequent reads. T, theoretical distribution; M, MiSeq NGS analysis.

FIGS. 47A-47E. Characterization of the V2 scFv. (A) ELISA with monoclonal phage. After 4, 5, or 6 rounds of selection, monoclonal phage were amplified in bacteria in a 96-well plate format. Well H12 was not inoculated and thus served as a no phage control. Monoclonal phage were incubated in G12V pHLA-A3 or G12WT pHLA-A3 coated streptavidin ELISA plate. Plates were washed and phage were detected using rabbit anti-M13 and HRP-conjugated anti-rabbit antibodies. Phage clone V2 was identified in the four wells designated by the red arrows. (B) Flow cytometry. T2A3 cells pulsed or not pulsed with the indicated peptides were incubated with the top four candidate phage clones selected for their ability to bind G12V pHLA-A3. The binding was assessed by rabbit anti-phage M13 and PE-conjugated anti-rabbit antibodies. MFI are plotted. (C) ELISA with V2 phage after dilution. Biotinylated pHLA-A3 were coated on a streptavidin plate. V2 phage were incubated at the specified dilutions and detected as in (A). (D) ELISAs with V2 scFv. Similar to (C), except that recombinant V2 scFv was used instead of phage, and detection employed protein L and RP-conjugated anti-protein L. All ELISAs were performed in triplicate. (E) Peptide pulsing of T2A3 cells. T2A3 cells were pulsed with the specified peptides at 50 μM. Cells were stained with anti-HLA-A3 monoclonal antibody GAP.A3 conjugated to PE. MFI are plotted.

FIGS. 48A-48F. Characterization of the RAS Q61H, Q61L, and Q61R scFvs. (A) Flow cytometry. After 5 rounds of selection, monoclonal phage were amplified in bacteria in 96-well plate format. Monoclonal phage were sequenced and clustered to unique phage clones. (A,C,E) SigM5 cells pulsed with the specified peptides were incubated with phage clones from Q61H, Q61L, and Q61R selections, respectively and assessed by rabbit anti-phage M13 and PE-conjugated anti-rabbit antibodies. Mean fluorescence intensities (MFI) are plotted. The top candidates are indicated with arrows. (B,D,F) COS-7 cells were transfected with a 1:1 ratio of plasmids encoding HLA-A1 ("A1") and KRAS Q61 variants (or other negative controls). 24 hours later, $5 \times 10^4$ COS-7 cells were combined with $5 \times 10^4$ human T cells (effector:target ratio or E:T=1:1) and single chain diabody (scDb) proteins generated from the top flow cytometry candidates at the specified concentrations. Plates were incubated for 24 hours and assayed for secreted IFNγ. Black arrows denote the single most specific and reactive clone for each target pHLA complex selected for further investigation.

FIGS. 49A-49D. Bispecific antibody formats and format comparison. (A) Cartoon depictions of the six bispecific formats tested with the RAS G12V pHLA-A3 targeting V2 scFv. (B) Schematic showing the tested orientations of the variable light (VL) and variable heavy (VH) domains of the V2 scFv with different anti-CD3 scFv clones. SL, short linker (GGGGS; SEQ ID NO:200); ML, medium linker $(GGGGS)_2$ (SEQ ID NO:694); LL, long linker $(GGGGS)_3$ (SEQ ID NO:201). (C) ELISAs of V2-bispecific antibody formats to assess binding to G12V pHLA-A3 and recombinant CD3ε/δ protein. Biotinylated G12V pHLA-A3 or CD3ε/δ protein was coated on a streptavidin plate. Different bispecific antibody formats were incubated in wells at specified concentrations followed by detection with protein L and HRP-conjugated anti-protein L. (D) Testing of V2 bispecific formats in co-cultures of T cells and peptide-pulsed T2A3s. T2A3 cells were pulsed with either the G12V or G12WT peptide at the specified concentrations. $2.5 \times 10^4$ peptide-pulsed T2A3 cells were combined with $5 \times 10^4$ T cells (E:T=2:1) and V2 bispecific formats at either 1 nM or 0.2 nM bispecific antibody concentration. Plates were incubated for 24 hours and assayed for IFNγ release. Note that the scFv-Fc format is a heterodimer of an FcKnob and an FcHole protein, with the bivalent scFv-Fc containing one V2 moiety and one anti-CD3 moiety, and the trivalent scFv-Fc containing two V2 moieties and one anti-CD3 moiety.

FIGS. 50A-50D. V2 scDbs made with various anti-CD3 clones. Twelve different anti-CD3 clones were tested in the $VL_{V2}$-$VH_{CD3}$-$VL_{CD3}$-$VH_{V2}$ format. (A) scDbs (all bearing C-terminal 6×HIS tags) were expressed in 293FT cells and purified identically. See Table 12 for sequences of the anti-CD3 clones. The Western blot shows the purified scDbs detected with anti-6×HIS and HRP-conjugated anti-rabbit antibodies. (B) Biotinylated recombinant CD3ε/δ protein was coated on a streptavidin plate. V2 scDbs were added to the plate at 2 g/ml and detected with protein L and HRP-conjugated anti-protein L. (C) COS-7 cells were transfected with a 1:1 ratio of plasmids encoding HLA-A3 and KRAS G12V. 24 hours later, $1 \times 10^4$ COS-7 cells were combined with $5 \times 10^4$ human T cells (E:T=5:1) and V2 scDbs at the indicated concentrations. Cells were incubated for 24 hours and assayed for secreted IFNγ. (D) $2 \times 10^4$ NCI-H441 target cells were combined with $6 \times 10^4$ human T cells (E:T=3:1) and V2 scDb proteins at the indicated concentrations. Cells were incubated for 24 hours and assayed for secreted IFNγ.

FIGS. 51A-51E. Specificity of scDbs. (A) Biotinylated pHLA-A3 or biotinylated recombinant CD3ε/δ protein were coated on a streptavidin plate. V2-U2 scDb was added to the plate at the indicated concentrations and detected with protein L and HRP-conjugated anti-protein L. Each ELISA was performed in triplicate. (B) Biotinylated pHLA-A3 were coated on a streptavidin plate. ScDb was incubated with pHLA at the indicated concentrations, then incubated with recombinant CD3ε/δ containing a human Fc tag and detected with an HRP-conjugated anti-human Fc antibody. (C-E) Biotinylated RAS Q61 pHLA-A1 (Q61WT, Q61H, Q61L, or Q61R) were coated on streptavidin plates at the indicated concentrations. Recombinant H1-U (C), L2-U (D), or R6-U (E) scDb was added to the wells at 10 nM and detected with protein L and HRP-conjugated anti-protein L.

FIGS. 52A-52N. Additional peptide-pulsing data. (A) T2A3 cells were pulsed with the RAS G12V or G12WT peptides at the indicated concentrations. $5 \times 10^4$ T2A3 peptide-pulsed cells were co-cultured with $5 \times 10^4$ human T cells (E:T=1:1) in the presence of either V2-U or V2-U2 scDb at 1 nM. Cells were incubated for 24 hours and TNFα secretion measured. (B) Quantification of G12V peptide on the surface of T2A3 cells. T2A3 cells were pulsed with the G12V peptide at the specified concentrations. G12V pHLA complexes on the cell surface were quantified using the V2 scFv and Quantibrite- and Quifikit-based methods. (C,D) G12 peptide-pulsed dendritic cells. HLA-A3+ immature dendritic cells (iDCs) were pulsed with either the G12V or G12WT peptide at the specified concentrations. $1 \times 10^4$ peptide-pulsed iDCs cells were combined with $5 \times 10^4$ human T cells (E:T=5:1) and either V2-U or V2-U2 scDb at 1 nM. Plates were incubated for 24 hours and assayed for secreted IFNγ (C) and TNFα (D). (E-H) Q61 peptide-pulsed SigM5 cells. SigM5 cells were pulsed with the RAS Q61H, Q61R, or Q61WT peptide at the indicated concentrations. $2.5 \times 10^4$ peptide-pulsed SigM5 cells were combined with $5 \times 10^4$ human T cells (E:T=2:1) and either H1-U (E,F) or R6-U (G,H) scDb at 1 nM. Cells were incubated for 24 hours and assayed for secreted IFNγ (E,G). Target cell cytotoxicity was assayed using CellTiter-Glo (F,H). (I-N) Q61 peptide-pulsed dendritic cells. HLA-A1+iDCs were pulsed with either the Q61H, Q61L, Q61R, or Q61WT peptide at the indicated concentrations. $1 \times 10^4$ peptide-pulsed iDCs cells were combined with $5 \times 10^4$ human T cells (E:T=5:1) and H1-U (I,L), L2-U (J,M), or R6-U (K,N) scDb at 1 nM. Cells were incubated for 24 hours and assayed for secreted IFNγ (I-K) or TNFα (L-N). All experiments were performed in triplicate.

FIGS. 53A-53D. Western blots and co-cultures with transfected COS-7 cells. COS-7 cells were transfected with a 1:1 ratio of plasmids encoding HLA-A3 ("A3") and KRAS variants (or other negative controls). 24 hours later, cells were harvested for western blots (A) or co-cultures (B-D). (A) Western blots for KRAS and HLA-A3 in transfected COS-7. Cells were pelleted and snap frozen and analyzed via western for KRAS, HLA-A3, and 0-actin protein expression. (B-D) $1 \times 10^4$ COS-7 cells were combined with $5 \times 10^4$ human T cells (E:T=5:1) and V2-U (B) or V2-U2 scDb (C,D) at the indicated concentrations. Cells were incubated for 24 hours and supernatant assayed for secreted IFNγ (C) or TNFα (B,D). All ELISAs were performed in triplicate.

Figure 54:
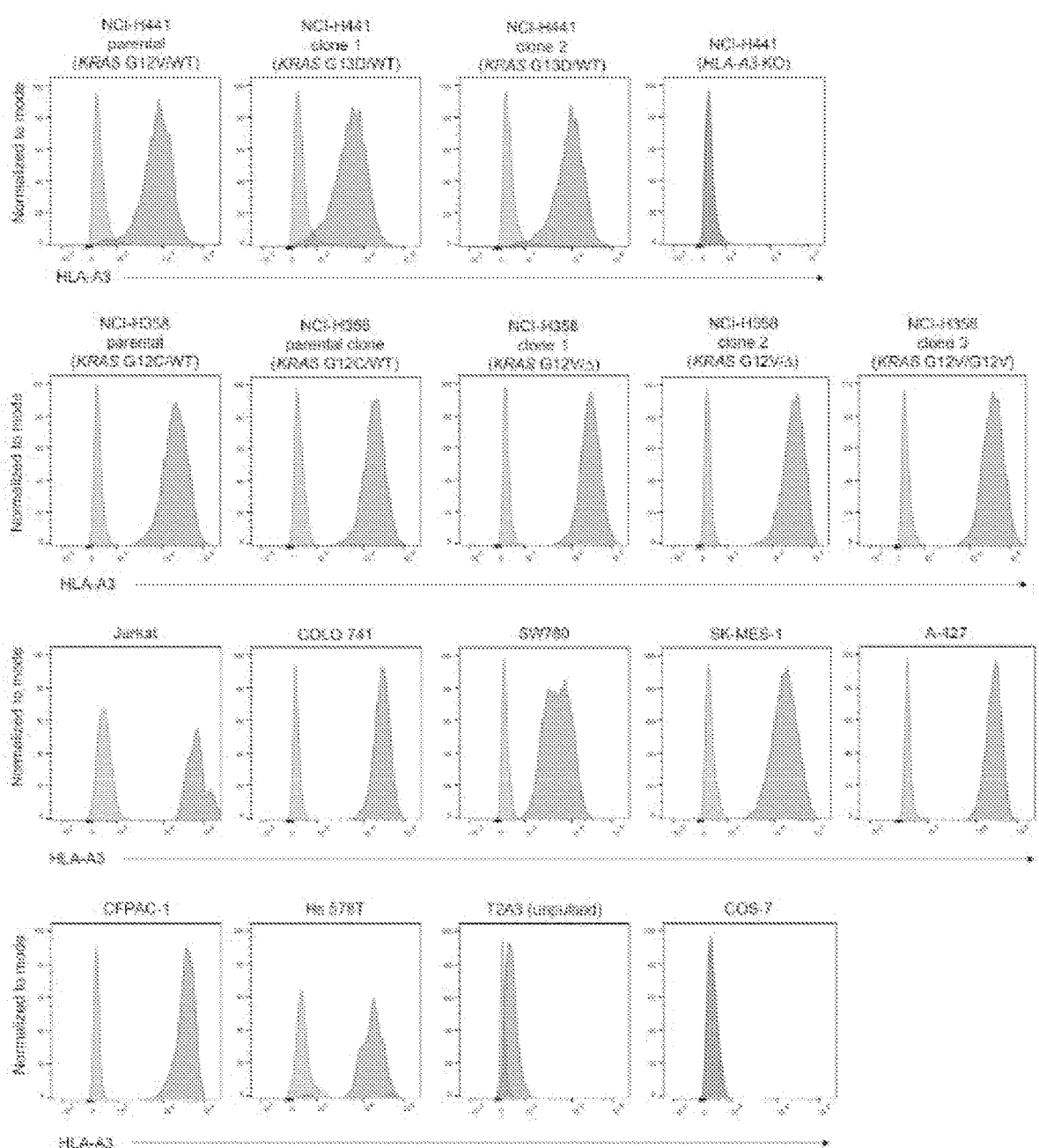

FIG. 54. HLA-A3 expression in target cell lines. $5 \times 10^5$ target cells were stained with PE-conjugated anti-HLA-A3 clone GAP.A3 (shaded red) or PE-conjugated mouse isotype IgG2a control (shaded gray). Histograms show PE intensities of viable cells.

Figure 55:
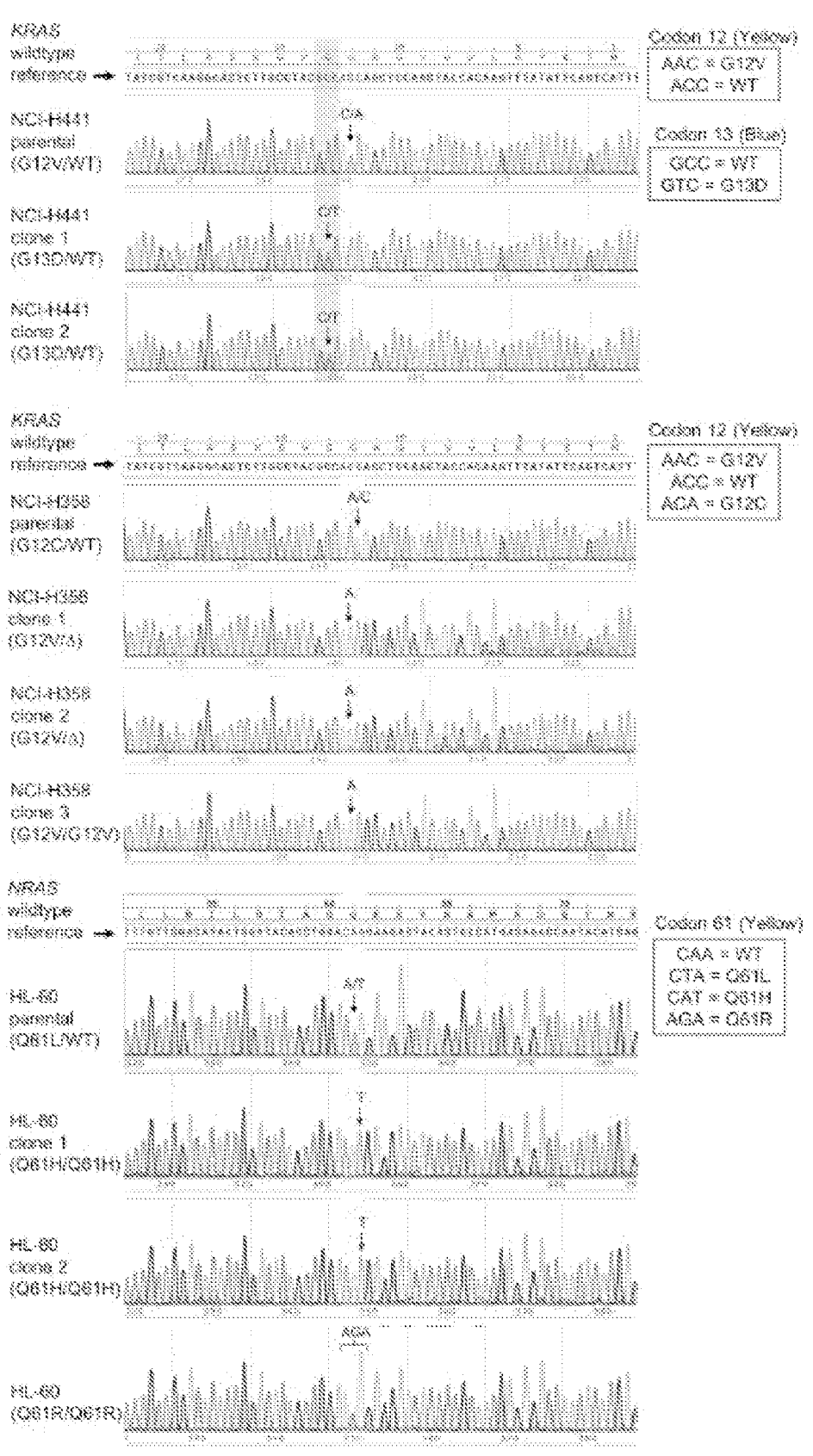

FIG. 55. Sanger sequencing of RAS alleles in CRISPR-modified cell lines. Sanger sequencing of genomic DNA from the KRAS locus of NCI-H441 parental and G13D-KI clones (SEQ ID NO:695), from the KRAS locus of NCI-H358 parental and G12V-KI clones (SEQ ID NO:696), and from the NRAS locus of HL-60 parental, Q61H-KI, and Q61R-KI clones (SEQ ID NO:697). Note that KRAS codons are shown in the antisense orientation.

FIGS. 56A-56B. Effects of V2-U2 scDb on co-culture of T cells with NCI-H441 isogenic cell lines. $2 \times 10^4$ parental NCI-H441 cells or its isogenic clones were combined with $6 \times 10^4$ human T cells (E:T=3:1) and V2-U2 scDb at the indicated concentrations. Cells were incubated for 24 hours and assayed for IFNγ release (A) or target cell cytotoxicity with CellTiter-Glo (B). All experiments were performed in triplicate.

Figure 57:
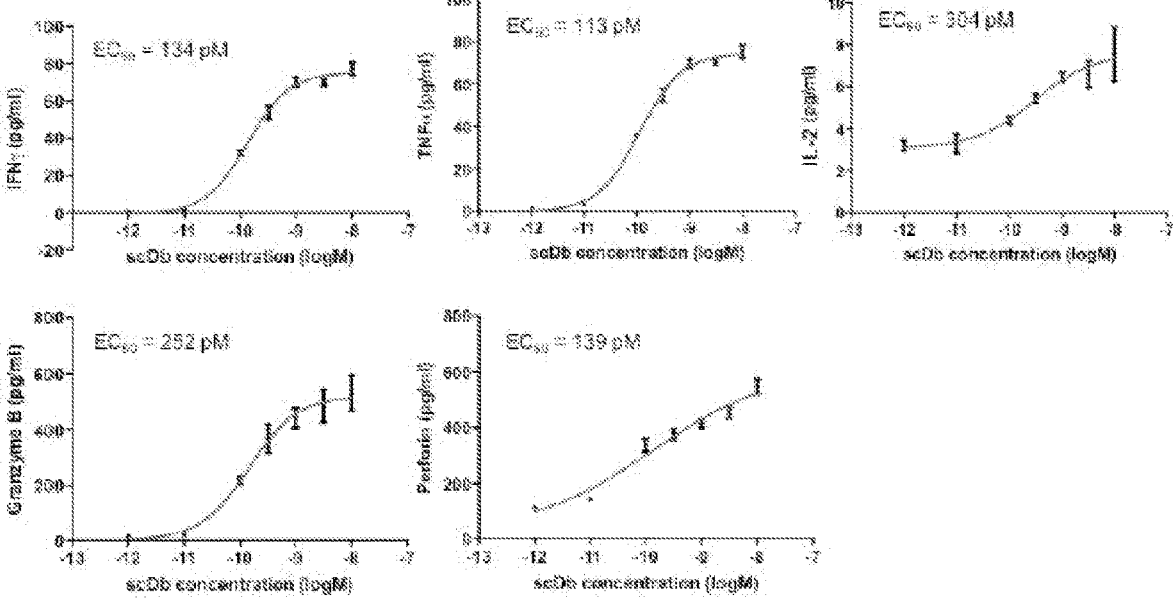

FIG. 57. Poly-functional immune response elicited by V2-U scDb. V2-U scDb at the indicated concentrations was incubated with $2.5 \times 10^4$ NCI-441 cells and $5 \times 10^4$ human T cells (E:T=2:1). Cells were incubated for 24 hours and assayed for secreted IFNγ, TNFα, IL-2, granzyme B, and perforin using Luminex beads. All experiments were performed in triplicate.

FIGS. 58A-58B. Effects of V2-U2 scDb on co-culture of T cells with NCI-H358 isogenic cell lines. $2 \times 10^4$ parental NCI-H358 cells or its isogenic clones were combined with $6 \times 10^4$ human T cells (E:T=3:1) and V2-U2 scDb at the indicated concentrations. Cells were incubated for 24 hours and assayed for IFNγ release (A) or target cell cytotoxicity with CellTiter-Glo (B). All experiments were performed in triplicate.

FIGS. 59A-59B. Effects of V2 scDbs on IFNγ secretion from T cells in co-cultures with HLA-A3+ cell lines. $2 \times 10^4$ target cells were combined with $6 \times 10^4$ human T cells (E:T=3:1) and V2-U (A) or V2-U2 (B) scDb at the indicated concentrations. The cells were incubated for 24 hours and assayed for IFNγ release. All experiments were performed in triplicate. *** denotes P<0.001 and NS denotes no statistical significance between CFPAC-1 and each of the other cell lines without the RAS G12V mutation, as analyzed by two-way ANOVA collapsed across different scDb concentrations for a given cell line, with Tukey's correction for multiple comparisons.

Figure 60:
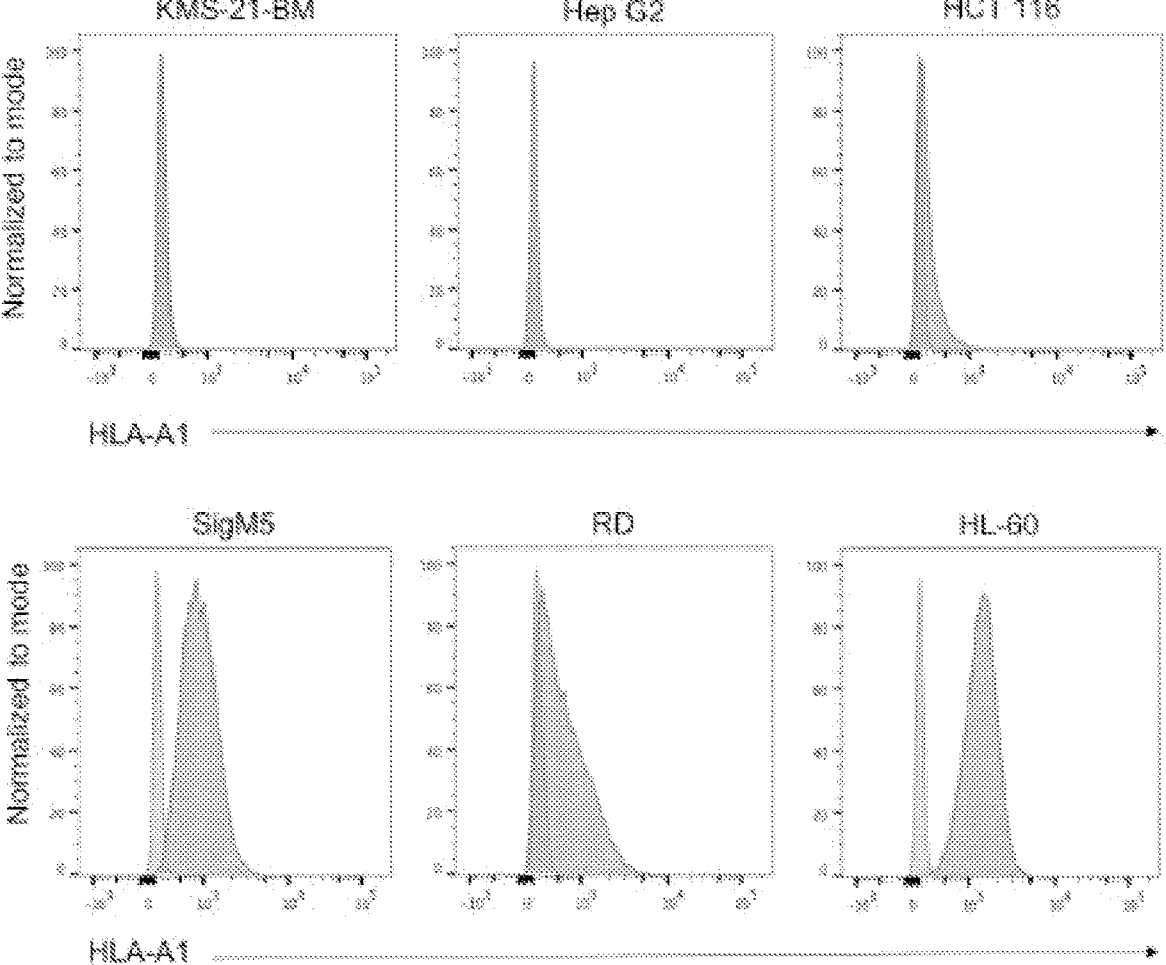

FIG. 60. HLA-A1 expression in target cell lines. $5 \times 10^5$ target cells were incubated with anti-HLA-A1/A11/A26 clone 8.L.101 (shaded red) or mouse IgM isotype control (shaded gray), then stained with a PE-conjugated anti-mouse antibody. Histograms show PE intensities of viable cells.

Figure 61:
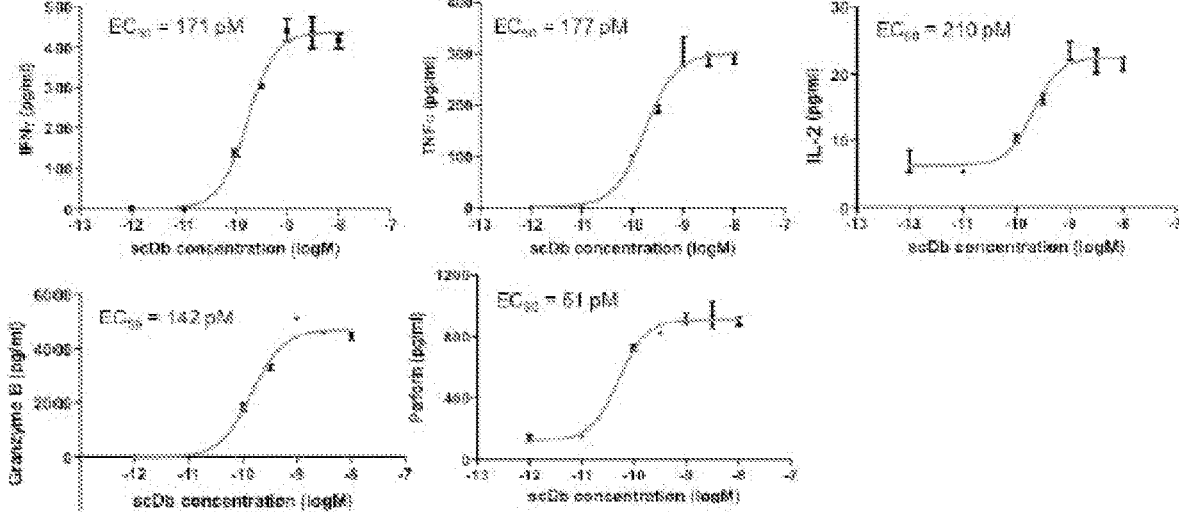

FIG. 61. Poly-functional immune response elicited by L2-U scDb. L2-U scDb at the indicated concentrations was incubated with $2.5 \times 10^4$ HL-60 cells and $5 \times 10^4$ human T cells (E:T=2:1). Cells were incubated for 24 hour and assayed for secreted IFNγ, TNFα, IL-2, granzyme B, and perforin using Luminex beads. All experiments were performed in triplicate.

FIGS. 62A-62F. Testing potential cross-reactive peptides. (A) T2A3 cells were pulsed with 50 μM of the indicated peptides. Pulsed cells were incubated with V2 phage, followed by staining with rabbit anti-M13 phage and PE-conjugated anti-rabbit antibodies or incubated with the PE-conjugated anti-HLA-A3 monoclonal antibody GAP.A3. PE MFI are plotted. (B) Western blot showing endogenous Rab-7b expression in PBMCs, monocytes (Mono), immature DCs (iDC), mature DCs (mDC), and Hs 695T cells, and overexpression of Rab-7b in HLA-A3 and RAB7B co-transfected COS-7 and HCT 116 versus HLA-A3 and GFP co-transfected controls. (C) $1 \times 10^4$ NCI-H441 cells or $5 \times 10^4$ PBMCs, Mono, iDC, or mDC, with or without pulsing with the G12V peptide, were combined with $5 \times 10^4$ human T cells (E:T=5:1 or 1:1) and the V2-U scDb at 1 nM. Cells were incubated for 24 hours and assayed for secreted IFNγ. Normal human cells were derived from an HLA-A3+ donor. (D) Hs 695T were transfected with HLA-A3 or HLA-A2 (negative control) encoding plasmids to assess for endogenous presentation and V2-U scDb recognition of the Rab-7b peptide. As a positive control, HLA-A3-transfected cells were pulsed with the G12V peptide or dimethylformamide (DMF, solvent) only. Parental NCI-H441 cells were included as a positive control and NCI-H441 HLA-A3-KO (A3-KO) and NCI-H441 (KRAS G13D/WT) clone 1 (G13D-KI) were included as negative controls. In each well, $2 \times 10^4$ target cells were combined with $5 \times 10^4$ human T cells (E:T=5:2) and V2-U scDb at the indicated concentrations. Plates were incubated for 24 hours and assayed for secreted IFNγ. (E,F) COS-7 (E) and HCT 116 (F) cells were transfected with either vector only (GFP) or a 1:1 ratio of plasmids encoding HLA-A3 and vector only (GFP), full length KRAS WT, KRAS G12V, or Rab-7b. In each well, $2 \times 10^4$ target cells were combined with $5 \times 10^4$ human T cells (E:T=5:2) and V2-U scDb at the indicated concentrations. Cells were incubated for 24 hour and assayed for secreted IFNγ.

FIGS. 63A-63C. Positional scanning of target peptides that could potentially react with V2 or L2 scDb. (A) Each amino acid of the G12V peptide was systematically changed to the other 19 amino acids. T2A3 cells were pulsed with 10 μM of the G12V peptide library. $2.5 \times 10^4$ peptide-pulsed T2A3 cells were combined with $5 \times 10^4$ human T cells (E:T=2:1) and V2-U scDb at 1 nM. Cells were incubated for 24 hour and assayed for secreted IFNγ. (B) Each amino acid of the Q61L peptide was systematically changed to the other 19 amino acids. SigM5 cells were pulsed with 10 μM of the Q61L peptide library. $2.5 \times 10^4$ peptide-pulsed SigM5 cells were combined with $5 \times 10^4$ human T cells (E:T=2:1) and L2-U scDb at 1 nM. Cells were incubated for 24 hours and assayed for secreted IFNγ. (C) SigM5 cells were pulsed with the Q61L, Q61WT, or CHD4 peptide. $2.5 \times 10^4$ peptide-pulsed SigM5 cells were combined with $5 \times 10^4$ human T cells (E:T=2:1) and L2-U scDb at 1 nM. Cells were incubated for 24 hours and assayed for secreted IFNγ.

Figure 64:
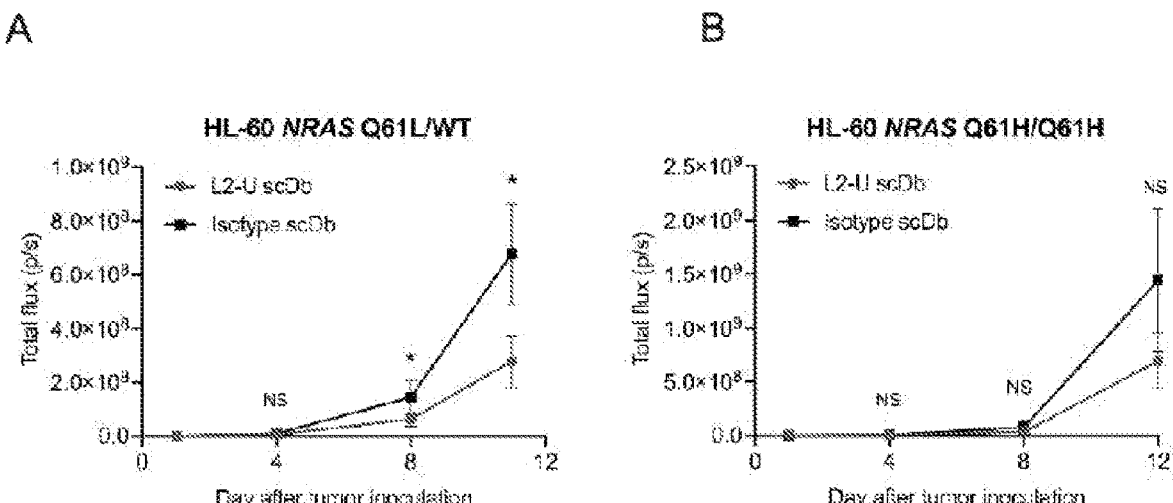

FIGS. 64A-64B. L2-U effects on tumor growth in mouse model systems. (A, B) Mice were engrafted with $1 \times 10^7$ human T cells and $5 \times 10^5$ luciferase-expressing parental HL-60 (A) or CRISPR-edited HL-60 (B) on day 0. One day later, after tumor engraftment was established by bioluminescent imaging, mice were randomized with respect to tumor burden and intravenously injected with $1 \times 10^7$ human T cells. They were then immediately implanted with osmotic pumps delivering L2-U or isotype scDb (V2-U scDb) at 0.42 g/kg/day. Tumor growth was monitored by bioluminescent imaging. N=7 mice per group. Plotted data represent mean±SD. * denotes P<0.05 and NS denotes no statistical significance compared to isotype control according to multiple t-tests with Bonferroni-Dunn correction.

FIGS. 65A-65B. Body weights of NSG mice treated with scDbs. (A,B) NSG mice were implanted with tumors and treated as described in FIG. 64. Body weights of the mice were serially monitored. Data shown represent mean±SD.

Figure 66:

FIG. 66. Diagram of scFv phage library phagemid. Oligonucleotides encoding the scFv and synthesized using TRIM technology were incorporated into a pADL-10b phagemid. This phagemid contains an F1 origin, a transcriptional repressor to limit un-induced expression, a lac operator, and a lac repressor. The scFv was synthesized with a pelB periplasmic secretion signal and was subcloned downstream of the lac operator. A linker (GGGSGGGGSGGGAS; SEQ ID NO:698) connects the variable light and heavy chains of the scFv. A FLAG (DYKDDDDK; SEQ ID NO:190) epitope tag was placed immediately downstream of the variable heavy chain, which was followed in frame by the full-length M13 pIII coat protein sequence.

Figure 67:
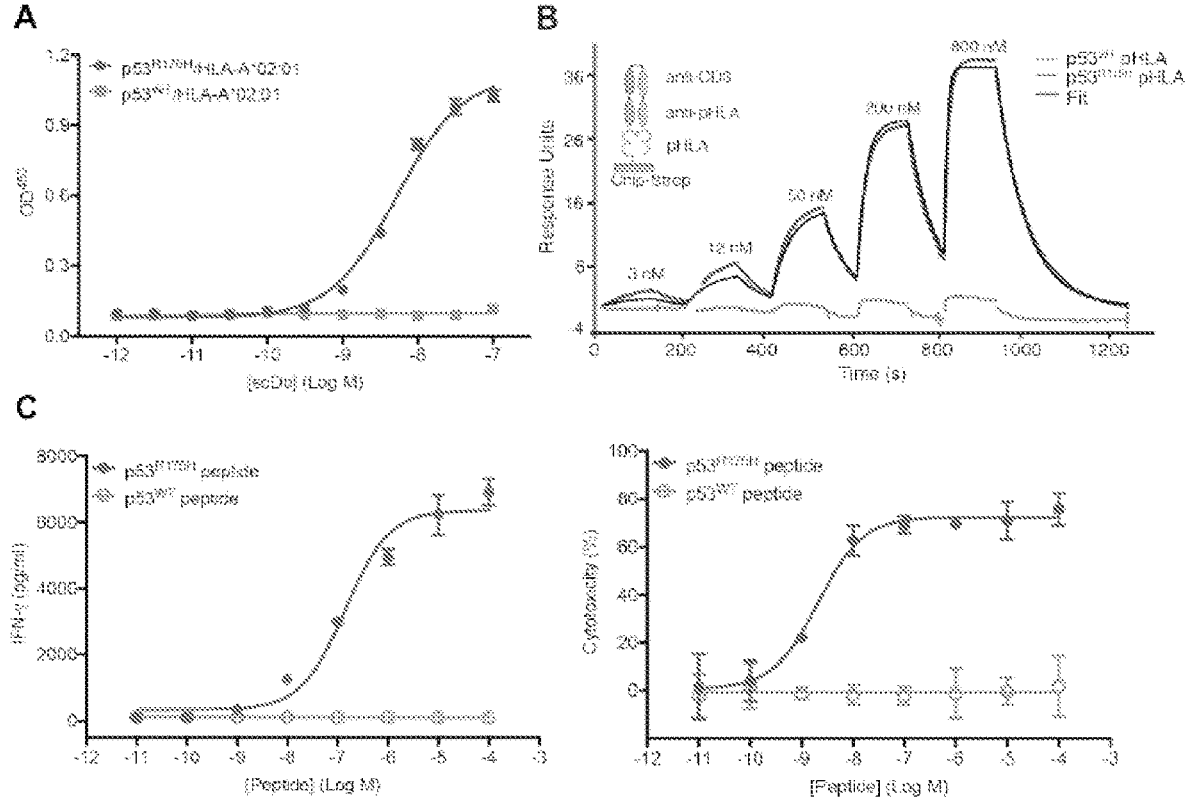

FIGS. 67A-67C. Biological and biophysical characteristics of scFv clone H2. (A) H2-scDb binding to immobilized $p53^{R175H}$/HLA-A*02:01 (red) or $p53^{WT}$/HLA-A*02:01 (gray) pHLA was assessed by ELISA. Data shown represent mean±SD of three technical replicates. (B) H2-scDb binding to $p53^{R175H}$/HLA-A*02:01 was measured by single-cycle kinetics using SPR. H2-scDb was loaded at increasing concentrations, from 3, 12, 50, 200 to 800 nM. The blank- and reference-subtracted binding is shown for $p53^{R175H}$/HLA-A*02:01 (red) and $p53^{WT}$/HLA-A*02:01 (gray). H2-scDb binds to the $p53^{R175H}$/HLA-A*02:01 pHLA with a one-to-one binding kinetics at a $K_D$ of 86 nM (fitted line in black). There was negligible $p53^{WT}$/HLA-A*02:01 binding. (C) T2 cells pulsed with $p53^{R175H}$ or $p53^{WT}$ peptide were co-incubated with H2-scDb and T cells at an effector:target (E:T) ratio of 2:1. IFN-γ release was measured by ELISA (left) and cell lysis was evaluated by the CellTiter-Glo assay (right). Data indicate mean±SD of three technical replicates and are representative of three independent experiments.

FIGS. 68A-68D. H2-scDb activates T cells in the presence of tumor cells presenting $p53^{R175H}$ (A) Illustration depicting the mechanism of action of H2-scDb. (B) HLA-A*02:01 positive tumor cell lines with different HLA expression levels and $p53^{R175H}$ status were co-incubated with H2-scDb and T cells at an E:T ratio of 2:1. IFN-γ release was measured by ELISA. Data indicate mean±SD of six technical replicates and are representative of two independent experiments. The HLA-A*02 median fluorescence intensity (MFI) ratio is defined as MFI (anti-HLA-A*02)/ MFI (isotype control). (C) Polyfunctional T-cell activation mediated by H2-scDb in response to KMS26 at an E:T ratio of 2:1 was assessed by luminescent cytotoxicity and antibody-based assays (see Supplementary Materials). $EC_{50}$ (M) for each assay is shown in the corresponding graphs. Data indicate mean±SD of three technical replicates and are representative of two independent experiments. (D) Real-time live-cell imaging of T cells with GFP-labelled TYK-nu at an E:T ratio of 5:1 with or without H2-scDb. Representative phase contrast and green fluorescence images taken at 24 hours (top) and 96 hours (bottom) after mixing cells are shown.

FIGS. 69A-69E. Determination of H2-scDb specificity using isogenic target cell lines. (A) Methods of the generating of isogenic cell line pairs in cells with different HLA and p53 backgrounds. (B) HEK293FT and Saos-2 cell lines that were transfected with full-length $p53^{WT}$, full-length $p53^{R175H}$ or were not transfected were co-incubated with T cells at an E:T ratio of 2:1 in the presence of increasing amounts of H2-scDb. IFN-γ release was measured by ELISA. Data indicate mean±SD of two technical replicates. (C) Cell lines expressing $p53^{R175H}$ and transduced or not transduced with HLA-A*02:01 were co-incubated with T-cells and H2-scDb. IFN-γ release was measured by ELISA. Experiments were performed at an E:T ratio of 2:1 in three technical replicates. (D) IFN-γ release mediated by H2-scDb in response to parental tumor cell lines and their TP53 KO counterparts at an E:T ratio of 2:1 (KMS26, TYK-nu) or 5:1 (KLE) was measured by ELISA. Data indicate mean SD of two (TYK-nu) or three (KMS26, KLE) technical replicates and are representative of two independent experiments. * P<0.05, P<0.01, *P<0.001 by two-tailed t-test. (E) Parental (left) or TP53 KO (right) TYK-nu cells labeled with nuclear GFP were co-incubated with H2-scDb and T cells at an E:T ratio of 2:1 was measured by real-time live-cell imaging. Data indicate mean±SEM of twelve technical replicates. One-way ANOVA with Tukey's multiple comparison was used to evaluate statistical significance, ****denotes P<0.0001.

FIGS. 70A-70H. H2-Fab binds to the HLA-A*02:01 and the C-terminus of the $p53^{R175H}$ neoantigen. (A) Overall structure of $p53^{R175H}$/HLA-A*02:01 bound to the H2-Fab fragment (PDB ID 6W51). HLA-A*02:01 and β2 microglobulin (β2M) are colored in gray and gold, respectively. The H2-Fab is colored according to the heavy (blue) and light (cyan) chains of the Fab fragment. The $p53^{R175H}$ nine amino acid peptide is shown in light green between helices α1 and α2 of the HLA. (B) Structure of H2-Fab-$p53^{R175H}$/HLA-A*02:01 at 90° to that shown in (A). (C) Electron density map (2mFo-DFc) of the $p53^{R175H}$ neoantigen contour at 16. (D) Electron density map (2mFo-DFc) of a selected area of the H2-Fab at CDR-L3 from residues 95 to 99 contoured at 16. (E) Zoom in of the interaction of H2-Fab to $p53^{R175H}$/HLA-A*02:01 with CDRs colored as in (A). The CDRs are labeled and colored in order from left to right: H2 (purple), H1 (magenta), L3 (yellow), H3 (orange), L1 (red), L2 (dark green). (F) Bird's-eye view of surface representation of the HLA-A*02:01 shown in grey, $p53^{R175H}$ peptide shown in light green, and the contacting residues colored according to CDRs of the H2-Fab. (G) Schematic representation of (F). (H) Diagram of the orientation angle of the H2-Fab to $p53^{R175H}$/HLA-A*02:01. The docking angle of the orientation was calculated from the web server TCR3d which was based on the $C^{alpha}$ of Cys88 of the disulfide bond of the $V_L$ domain and the $C^{alpha}$ of Cys96 of the disulfide bond of the $V_H$ domain of the H2-Fab (red). The arrowed line indicates the direction of orientation with the angle between them.

FIGS. 71A-71F. Structural basis of H2 specificity and identification of putative cross-reactive peptides. (A) Detailed interactions of the $p53^{R175H}$ neoantigen with HLA-A*02:01. The peptide (green) and the side chains (grey) of interacting residues of HLA-A*02:01 are represented as sticks. Hydrogen bonds are shown as dashed lines. (B) Perpendicular view of the $p53^{R175H}$ peptide binding cleft. (C) C-terminus of the peptide (aa Val173-Cys176) with Arg174 and His175 surrounded by the interacting residues of CDR-H1 (magenta), -H2 (purple), -H3 (orange) and -L3 (yellow) shown as sticks. Hydrogen bonds are shown as dashed lines. (D) T2 cells were loaded with 10 μM of HMTEVVRHC (SEQ ID NO:1) peptide variants from the positional scanning library and co-incubated with 1 nM H2-scDb and T cells at an E:T ratio of 2:1. IFN-γ release was measured by cytometric bead array (see Supplementary Materials) and the mean of triplicate wells was used to plot the heatmap. Black boxes represent the parental $p53^{R175H}$ peptide. (E) Illustration of the binding pattern of H2-scDb as Seq2Logo graph, calculated by dividing the IFN-γ value by $10^4$ and using the PSSM-Logo algorithm. (F) T2 cells were loaded with 10 μM of $p53^{R175}$H $p53^{WT}$, STAT2, VPS13A, or ZFP3 peptide and co-incubated with 1 nM H2-scDb and T cells at an E:T ratio of 2:1. IFN-γ secretion was measured by ELISA. Data indicate mean±SD of three technical replicates.

Figure 72:
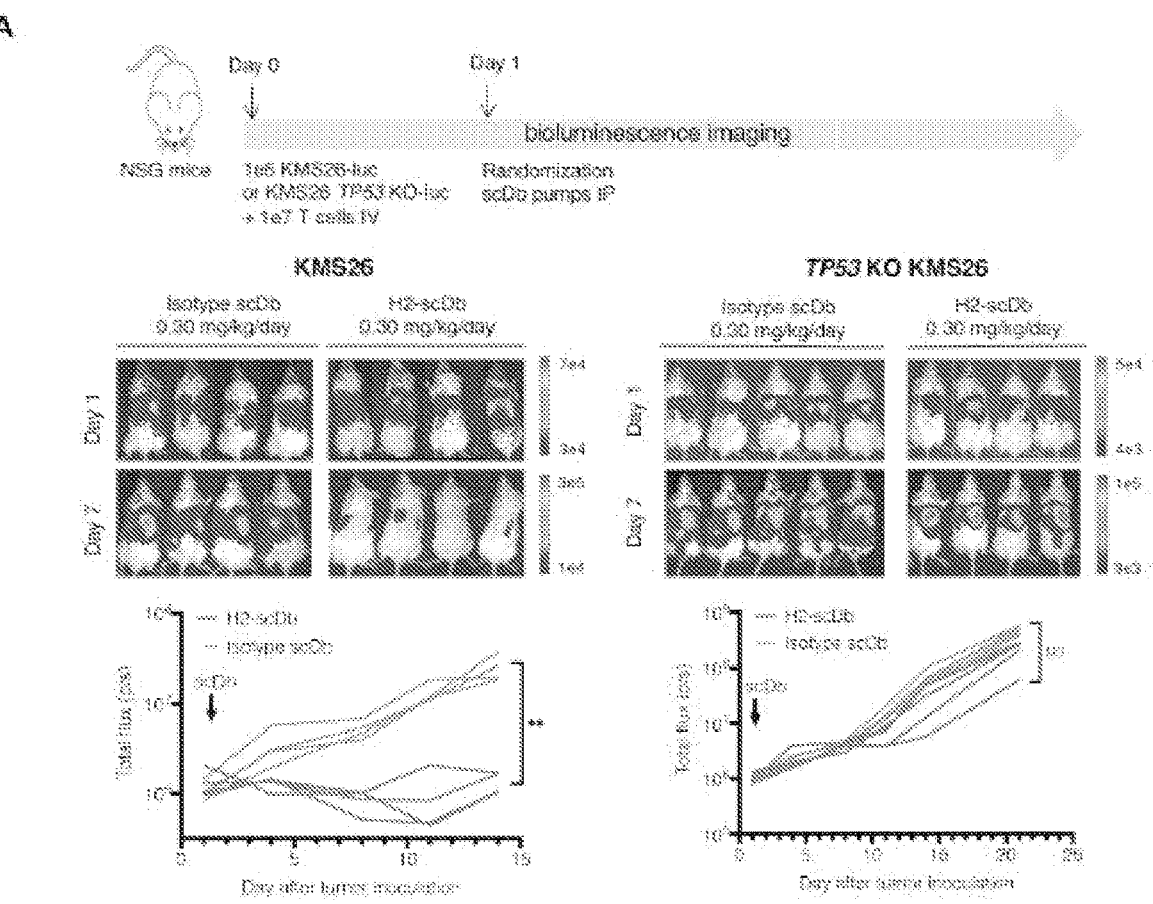
Figure 72:
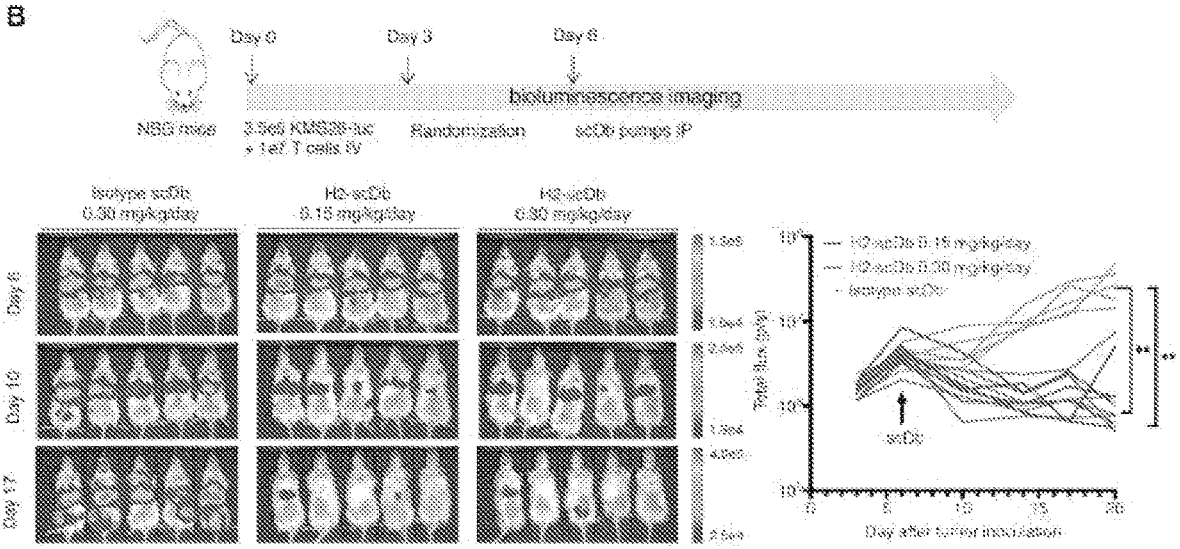

FIGS. 72A-72B. In vivo antitumor efficacy of H2-scDb. In the early treatment model, NSG mice were engrafted with $1×10^7$ human T cells and either $1×10^6$ parental KMS26 (A) or $1×10^6$ TP53 KO KMS26 (B) on day 0. On day 1, intraperitoneal infusion pumps were placed to administer H2-scDb or isotype control scDb. (C) In the established tumor model, mice were engrafted with $1×10^7$ human T cells and $3.5×10^5$ parental KMS26 on day 0, followed by administration of H2-scDb or isotype scDb at the specified doses on day 6. Tumor growth was monitored by bioluminescence imaging. N=4 or 5 mice per group. Color bars denote the radiance (p/sec/cm²/sr) scale at each time point. Plotted data indicate mean±SD. **P<0.01 and NS denotes no statistical significance compared to isotype control by multiple t-test with Holm-Šidák correction.

Figure 73:
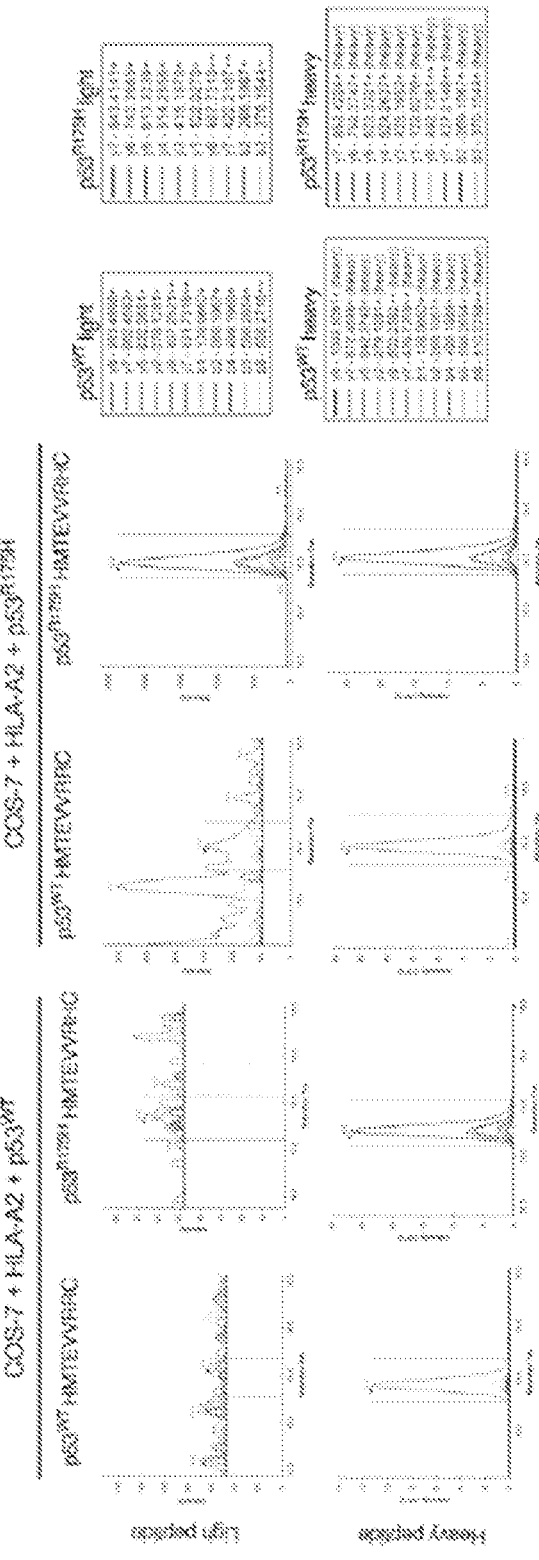
Figure 73:
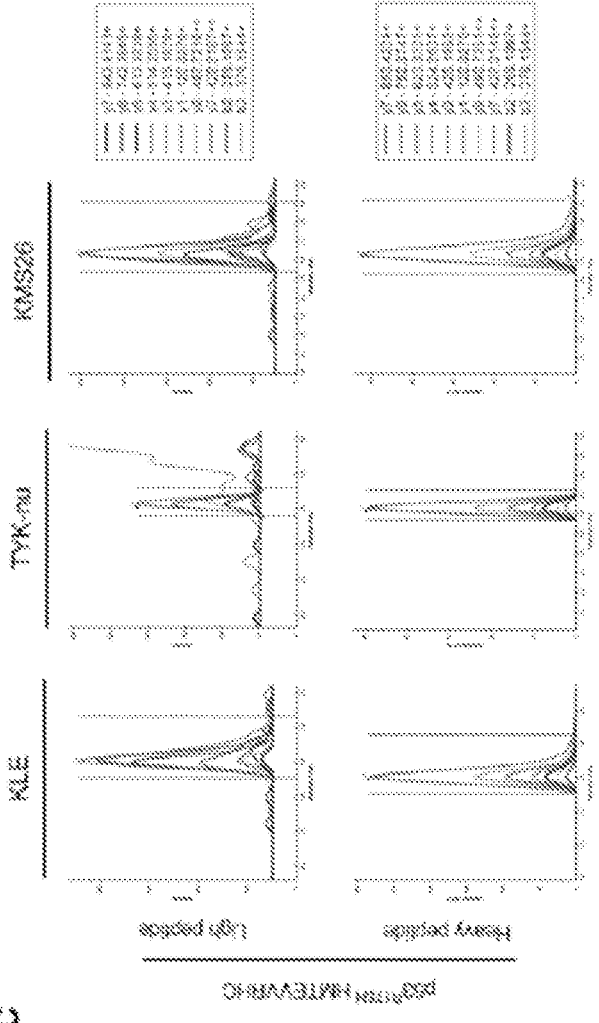
Figure 73:
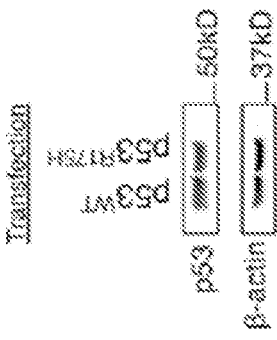

FIGS. 73A-73C. Detection and quantification of $p53^{R175H}$ neoantigen peptide in cells. (A) COS-7 cells transfected with constructs expressing HLA-A*02:01 and $p53^{WT}$ or $p53^{R175H}$ were analyzed for the presentation of the $p53^{WT}$ HMTEVVRRC (SEQ ID NO:135) or the $p53^{R175H}$ HMTEVVRHC (SEQ ID NO:1) peptide. Isotope labeled peptides were spiked into the assay and served as standards for absolute copy number quantification. Multiple ions (indicated by different colors) fragmented from the target peptide in each sample were measured through mass spectrometer as different SRM transitions and their m/Z values were listed in the figure legend. (B) Expression of p53 protein in COS-7 cells transfected with either the full-length $p53^{WT}$ or $p53^{R175H}$ was assessed by Western blotting with anti-p53 antibody (clone DO-1). (C) Cells lines with endogenous HLA-A*02:01 and $p53^{R175H}$ expression were analyzed for the presentation of $p53^{R175H}$ neoantigen peptide as described in (A).

FIGS. 74A-74D. Selection of $p53^{R175H}$/HLA-A*02:01 reactive antibodies and their conversion into T cell-retargeting scDb. (A) Flow cytometric screening of phage clones enriched by panning. After 5 rounds of panning, phage clones from the enriched phage pool were isolated by limiting dilution and grown in deep 96-well plates. Supernatants containing individual phage clones were used to assess binding to T2 cells loaded with 32 microglobulin (β2M) only, β2M plus $p53^{WT}$ peptide (HMTEVVRRC; SEQ ID NO:135), or β2M plus $p53^{R175H}$ peptide (HMTE-VVRHC; SEQ ID NO:1) via flow cytometry. The median fluorescence intensity (MFI) ratio was defined as MFI ($p53^{R175}$ peptide)/MFI ($p53^{WT}$ peptide). NC, no phage control. (B) Schematic representation of the structure of the T cell-engaging bispecific single-chain diabody (scDb) used in our experiments. $V_L$, variable light domain; $V_H$, variable heavy domain; pHLA, peptide-HLA complex; SL, short linker; LL, long linker. The graph was created with BioRender.com. (C) Screening of scDb clones via IFN-γ stimulation by p53-expressing cells. scDbs generated by linking each anti-$p53^{R175H}$/HLA-A*02:01 pHLA scFv clone with an anti-CD3 scFv (UCHT1) were co-incubated with T cells and COS-7 cells transfected with GFP, HLA-A*02:01+GFP, HLA-A*02:01+$p53^{WT}$, or HLA-A*02:01+$p53^{R175H}$ plasmids at an effector:target (E:T) ratio of 1:1. After a 20-hr coincubation, the supernatant was harvested for IFN-γ detection by ELISA. Arrows indicate clones H2 and H20. A2, HLA-A*02:01. (D) Characterization of H20-scDb. H20-scDb was incubated with biotinylated $p53^{R175H}$/HILA-A*02:01 (red) and $p53^{WT}$/HLA-A*02:01 (gray) pHLA monomers coated on streptavidin microplates at the specified concentrations, then binding detected with protein L and anti-protein L HRP. Data indicate mean±SD of three technical replicates.

FIGS. 75A-75E. Characteristics of scDbs generated by linking H2-scFv with anti-CD3 ε scFvs. (A) Expression of scDbs composed of linking H2-scFv with different anti-CD3E scFvs was assessed by anti-6x-His tag Western blotting. (B) Binding of the scDbs to the $CD3_{\epsilon/\delta}$ heterodimer and CDε was compared using ELISA. (C) The scDbs were co-incubated with T cells and T2 cells pulsed with titrated concentrations of $p53^{R175H}$ or $p53^{WT}$ peptide at an E:T ratio of 2:1. IFN-γ release was measured by ELISA. Data indicate mean±SD of three technical replicates. (D) Analytical chromatogram of the purified H2-UCHT1-scDb (H2-scDb) showing absorbance at 280 nm. The retention time of the H2-scDb was marked above the peak. (E) DSF analysis of the negative derivative (RFU vs. temperature) of the H2-scDb. The melting temperature $T_m$ at 69° C. corresponds to the peak/maximum of the first derivative of the curve and the notion of one transition state.

FIGS. 76A-76F. Reactivity of H2-scDb against $p53^{R175H}$/HLA-A*02:01-expressing tumor cells. (A) TYK-nu and its cisplatin resistant subline TYK-nu.CP-r (75) were cultured with H2-scDb and T cells at an E:T ratio of 2:1. IFN-γ release was measured by ELISA. Data indicate mean±SD of six technical replicates and are representative of two independent experiments. (B, C) KMS26 cells were cultured with H2-scDb or an isotype scDb (scFv against an irrelevant pHLA linked with UCHT1 scFv) in the absence or presence of T cells at an E:T ratio of 2:1. IFN-γ release was measured by ELISA (B), and cytotoxicity was assessed by luciferase assay (C). Data indicate mean±SD of three technical replicates.  P<0.01, * P<0.001 by two tailed t-test. (D-F) H2-scDb-induced polyfunctional T-cell response. T-cell cytotoxicity and cytokine release mediated by H2-scDb in response to (D) KMS26 (cytotoxicity and other effector proteins shown in main text), (E) KLE, and (F) TYK-nu cell line at an E:T ratio of 2:1 was assessed by antibody-based assays (see Methods). $EC_{50}$ (M) for each analyte is shown in the corresponding graphs. Data indicate mean±SD of three technical replicates.

Figure 77:
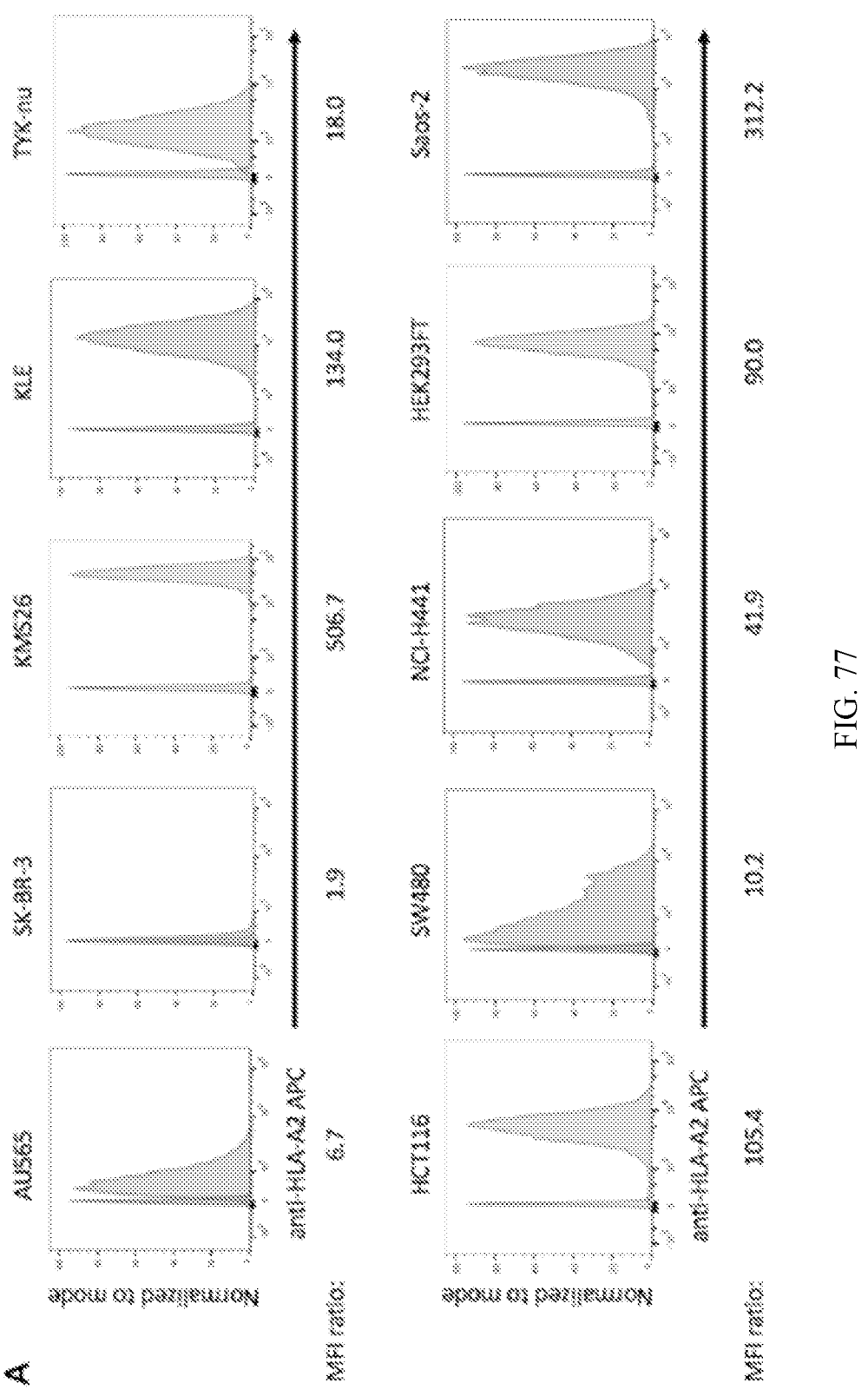
Figure 77:
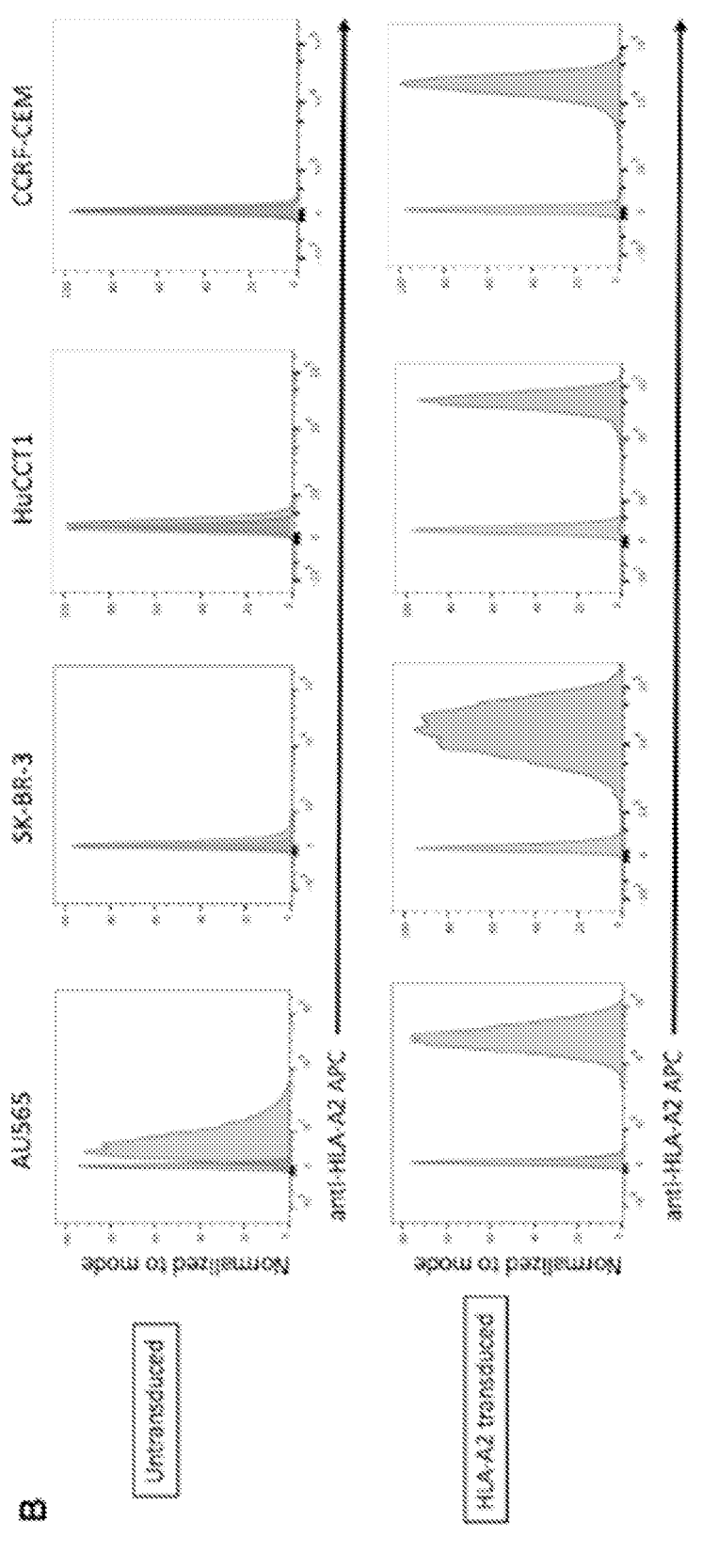

FIGS. 77A-77B. Flow cytometric evaluation of HLA-A*02 expression. (A) Expression of HLA-A*02 on tumor cell lines was evaluated by flow cytometry. The red histogram represents staining with anti-HLA-A*02 (clone BB7.2), and the gray histogram represents staining with an isotype control. The median fluorescence intensity (MFI) ratio is defined as MFI (anti-HLA-A*02)/MFI (isotype control). (B) HLA-A*02:01-encoding retrovirus was transduced into cell lines that weakly (AU565, SK-BR-3) or do not detectably (HuCCT1, CCRF-CEM) express HLA-A*02:01. Expression of HLA-A*02:01 in the parental and transduced and sorted cell lines was evaluated by flow cytometry. The red histogram represents staining with anti-HLA-A*02 (clone BB7.2) and the gray histogram represents staining with an isotype control.

Figure 78:
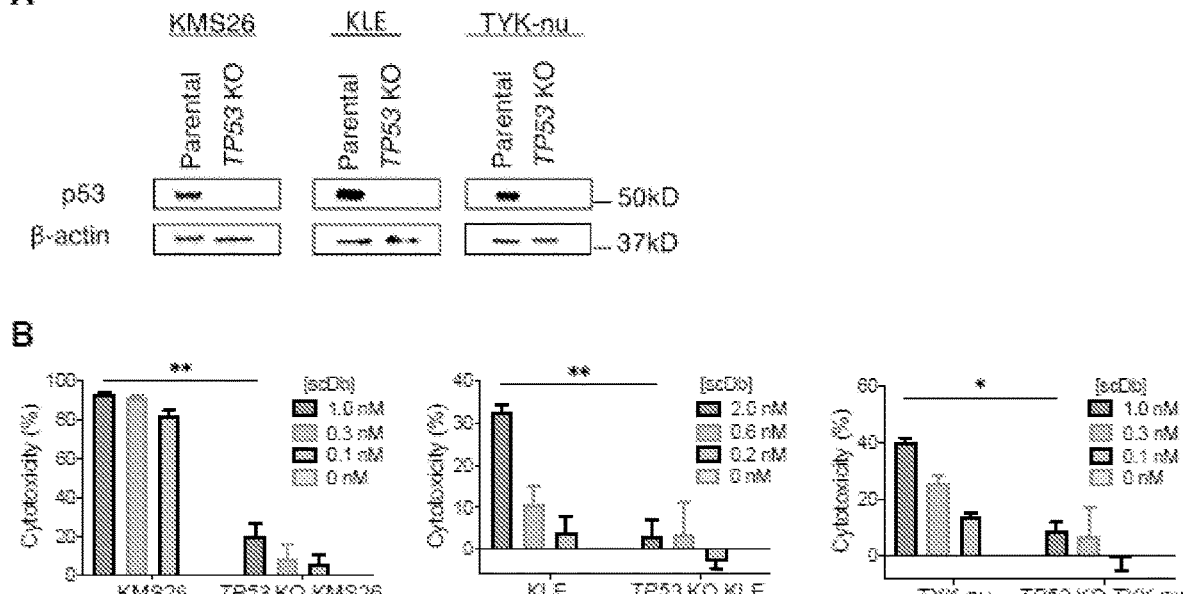

FIGS. 78A-78B. Determination of H2-scDb specificity using CRISPR-edited isogenic cell lines. (A) Expression of p53 protein in the parental and TP53 KO clones of KMS26, KLE, and TYK-nu was assessed by Western blot with anti-p53 antibody (clone DO-1). (B) Cytotoxicity mediated by H2-scDb in response to parental tumor cell lines and their TP53 KO counterparts at an E:T ratio of 2:1 (KMS26, TYK-nu) or 5:1 (KLE) was measured by the Bio-Glo (KMS-26) or CellTiter-Glo (TYK-nu, KLE) assay. Data indicate mean±SD of two (TYK-nu) or three (KMS26, KLE) technical replicates and are representative of two independent experiments.

FIGS. 79A-79D. The H2-Fab-$p53^{R175H}$/HLA-A*02:01 complex. (A) H2-scFv was converted into full-length IgG (H2-IgG) and incubated with biotinylated $p53^{R175H}$/HLA-A*02:01 (red) and $p53^{WT}$/HLA-A*02:01 (gray) pHLA monomers coated on streptavidin microplates at the specified concentrations followed by detection with anti-human IgG HRP. Data indicate mean±SD of three technical replicates. (B) Illustration depicting the generation of H2-Fab from H2-IgG. (C) Size-exclusion chromatogram of the pHLA-A*02:01 in complex with the H2-Fab. Protein was monitored by A280 nm with a major peak (~100 kDa). (D) Coomassie-stained gradient SDS-PAGE gel of the eluted fractions at 11-17 mL from (C).

FIGS. 80A-80D. The neoantigen $p53^{R175H}$ binds to HLA-A*02:01 in a canonical fashion. (A) Bird's-eye view of the $p53^{R175H}$ neoantigen interactions with HLA-A*02:01. The peptide (green) and the side chains (grey) of interacting residues of HLA-A*02:01 are represented as sticks. Hydrogen bonds are shown as dashed lines. The N-terminal His168 is anchored by three tyrosine residues of HLA-A*02:01, one at the base of the cleft (Tyr7, not shown) and two on α2 (Tyr159, 171), while its side chain is within hydrogen bonding distance of Lys66 (α1) and Thr163 (α2, not shown). Glu63 of HLA-A*02:01 al forms a hydrogen bond with the backbone amino of Met169, an anchor residue of $p53^{R175H}$ that is situated within the hydrophobic B pocket of the HLA. The main chain of Thr170 is stabilized by a hydrogen bond to Tyr99 (not shown), located at the base of the cleft while the side chain of Glu4 forms a salt-bridge with the side chain of Arg65. Positions 5-8 (Val172, Val173, Arg174, His175) of the $p53^{R175H}$ neoantigen are stabilized by multiple hydrophobic and aliphatic residues with no direct hydrogen bonding contacts to the HLA-A*02:01. Towards the C-terminus of the neoantigen, the carboxyl group of Cys176, another anchor residue that lies within the F pocket, is secured by Tyr84 (α1) and Lys146 (α2), while the side chain sulfhydryl is near Thr143 on α2. (B) Surface representation of the HLA-A*02:01 (grey) with the $p53^{R175H}$ neoantigen shown in green as sticks. Anchor pockets B and F are circled in orange. (C) Structural alignment of the following HLA-A*02:01-bound peptides in the binding pocket: green (this work, PDB ID 6W51), cyan (p1049, PDB ID 2JCC), magenta (NY-ESO-1, PDB ID 3HAE), and light purple (WT1, PDB ID 4WUU). (D) Zoomed in view of (B) with helix α1 transparent and residues at positions 7 (P7) and 8 (P8) shown as sticks.

Figure 81:
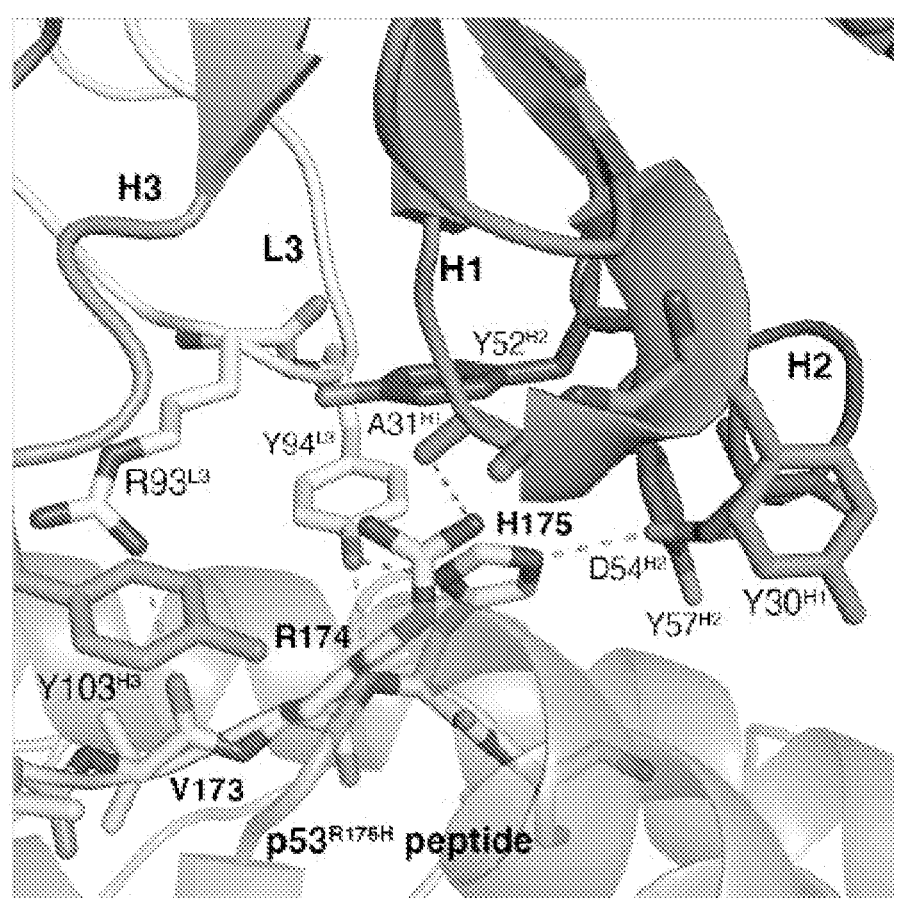

FIG. 81. Hydrogen bonding pattern of the H2-Fab cage-like configuration. The imidazole ring of His175 was at the center of the cage-like structure. The guanidinium group of Arg174 was at hydrogen bonding distance to the backbone carbonyl of Ala31 (CDR-H1). Another neoantigen-antibody direct contact involves the backbone carbonyl of Val173 hydrogen bonding with the side chain of Arg93 (CDR-L3).

FIGS. 82A-82P. Comparison of the binding orientations among TCRm-pHLA and TCR-pHLA complexes. (A) Close depiction of binding of the H2-Fab to $p53^{R175H}$/HLA-A*02:01 with CDRs colored as in FIG. 4. (B) Binding of a TCR to melanoma-associated antigen 3 (MAGE-A3) and HLA-A*01:01 (PDB ID 5BRZ). Same orientation as (A). The MAGE-A3 TCR displays the canonical, diagonal binding motif to that of most known TCR topologies. (C) Recognition of the 3M4E4 Fab for the NY-ESO-$1_{157-165}$/HLA-A*02:01 complex (PDB ID 3HAE). Same orientation as (A). (D) Binding of the ESK1 Fab to Wilms tumor 1 peptide and HLA-A*02:01 (PDB ID 4WUU). Same orientation as (A). (E, F, G and H) Bird's-eye view of surface representation of the HLA-A*02:01/*01:01 colored in grey with the contacting residues of H2-Fab, MAGE-A3 TCR, 3M4E4 Fab, and ESK1 Fab, respectively, colored according to CDRs. (I, J, K and L) Schematic representation of E, F, G, and H, respectively. H2-Fab-p53$^{R175H}$/HLA-A*02:01 shows a different mode of antibody recognition compared with other Fab/TCR-pHLA complexes. Schematic representation of Fab/TCR docking angle. The docking angle was calculated from the web server TCR3d which was based on the C$^{alpha}$ of Cys88 (or equivalent) of the disulfide bond of the V$_L$/α domain and the C$^{alpha}$ of Cys96 (or equivalent) of the disulfide bond of the V$_H$/β domain of each antibody and TCR. The arrowed line indicates the direction of orientation with the angle between them.

FIGS. 83A-83D. Assessment of H2-scDb cross-reactivity. (A) A peptide library was generated by systemically substituting the amino acid at each position of the target peptide (HMTEVVRHC; SEQ ID NO:1) with each of the remaining 19 common amino acids. T2 cells were loaded with each of the variant peptides at 100 μM in the presence of 10 μg/ml β2M and anti-HLA-A*02 antibody (clone BB7.2). HLA-A*02:01 stabilized by peptide binding and was evaluated by flow cytometry (77). Black boxes represent the parental peptide. MFI, median fluorescence intensity. (B) Recognition of the p53$^{R175H}$ positional scanning library peptides by H2-scDb. T2 cells loaded with variant peptides in the positional scanning library were incubated with 1 nM H2-scDb and T cells at an E:T ratio of 2:1. IFN-γ release was measured by ELISA. Dotted lines represent 20% of parental peptide IFN-γ value. The binding motif established by the 20% reactivity cutoff, expressed in PROSITE pattern, was x-[AILMVNQTC]-[ST]-[DE]-[IV]-[IMVST]-R-H-[AIL-VGHSTYC] (SEQ ID NO:197). Data indicate mean±SD of three technical replicates. (C-D) H2-scDb was co-incubated with T cells and COS-7 cells transfected with HLA-A*02:01 and full-length p53$^{R175H}$ STAT2, or ZFP3 at an E:T ratio of 5:1. (C) Expression of target proteins by COS-7 cells was assessed by Western blot staining. (D) IFN-γ secretion was measured by ELISA. The signals for all of the transfectants except for p53$^{R175H}$ were indistinguishable and are clustered near the x-axis. Data indicate mean±SD of three technical replicates and are representative of two independent experiments.

FIGS. 84A-84D. Assessing in vivo efficacy of scDb in NSG mice. (A) Three days after the injection of KMS26 cells and human T cells, peripheral blood of mice was obtained to assess human T cell engraftment by flow cytometry. Plots shown were gated on live cells. (B) Plasma of mice was collected 3 days before and 3 and 10 days after the implantation of intraperitoneal pumps. Plasma concentration of H2-scDb was measured by ELISA. N=9 mice. Data shown represent mean±SEM (C) Serial monitoring of body weight of the mice in the established KMS26 model presented in FIG. 6B. N=5 mice per group. Data shown represent mean±SD. (D) To verify the action of H2-scDb is T cell-dependent, NSG mice were engrafted with 5×10$^5$ parental KMS26 cells on day 0 with and without 1×10$^7$ human T cells, followed by administration of the specified scDb or vehicle via intraperitoneal pumps on day 6. Tumor growth was monitored by bioluminescence imaging. N=4 or 5 mice per group. Data shown represent mean±SD.

DETAILED DESCRIPTION

This document provides methods and materials for assessing a mammal having cancer or suspected of having cancer and/or treating a mammal having cancer. For example, one or more molecules including one or more antigen-binding domains (e.g., scFvs) that can target (e.g., bind to) one or more modified peptides (e.g., peptides present in a peptide-HLA complex such as a peptide-HLA-β2M complex) can be used to assess a mammal having cancer or suspected of having cancer and/or to treat a mammal having a cancer (e.g., a cancer expressing one or more modified peptides). In some cases, one or more molecules includes one or more antigen-binding domains that can bind to a modified peptide can be used to detect the presence or absence of one or more modified peptides in a sample obtained from a mammal having cancer or suspected of having cancer. In some cases, one or more molecules including one or more antigen-binding domains that can bind to a modified peptide can be administered to a mammal having a cancer (e.g., a cancer expressing the modified peptide) to treat the mammal.

As used herein, a modified peptide is a peptide derived from a modified polypeptide. A modified polypeptide can be any appropriate modified polypeptide (e.g., a polypeptide having a disease-causing mutation such as a mutation in an oncogenic or a mutation in a tumor suppressor gene). A modified peptide can have one or more amino acid modifications (e.g., substitutions) relative to a WT peptide (e.g., a peptide derived from a WT polypeptide from which the modified polypeptide is derived). A modified peptide also can be referred to as a mutant peptide. In some cases, a modified peptide can be a tumor antigen. Examples of tumor antigens include, without limitation, MANAs, tumor-associated antigens, and tumor-specific antigens. A modified peptide can be any appropriate length. In some cases, a modified peptide can be from about 7 amino acids to about 25 amino acids (e.g., from about 8 amino acids to about 25 amino acids, from about 9 amino acids to about 25 amino acids, from about 10 amino acids to about 25 amino acids, from about 11 amino acids to about 25 amino acids, from about 12 amino acids to about 25 amino acids, from about 13 amino acids to about 25 amino acids, from about 15 amino acids to about 25 amino acids, from about 18 amino acids to about 25 amino acids, from about 20 amino acids to about 25 amino acids, from about 7 amino acids to about 22 amino acids, from about 7 amino acids to about 20 amino acids, from about 7 amino acids to about 18 amino acids, from about 7 amino acids to about 15 amino acids, from about 7 amino acids to about 12 amino acids, from about 7 amino acids to about 10 amino acids, from about 7 amino acids to about 9 amino acids, from about 8 amino acids to about 22 amino acids, from about 10 amino acids to about 18 amino acids, from about 12 amino acids to about 15 amino acids, from about 8 amino acids to about 12 amino acids, from about 12 amino acids to about 18 amino acids, from about 18 amino acids to about 22 amino acids, or from about 9 amino acids to about 10 amino acids) in length. For example, a modified peptide can be about 9 amino acids in length. For example, a modified peptide can be about 10 amino acids in length. A modified peptide can be derived from any modified polypeptide. Examples of modified polypeptides from which modified peptides described herein can be derived include, without limitation, p53 and RAS (e.g., KRAS, HRAS, and NRAS). A modified peptide can include any appropriate modification. In some cases, modified peptides described herein can include one or more modifications (e.g., mutations) shown in Table 1.

TABLE 1

Modified peptides.

| Protein of origin | Mutation | Mutant Peptide | SEQ ID NO: | WT peptide | SEQ ID NO: | Peptide Codons | HLA Allele |
|---|---|---|---|---|---|---|---|
| p53 | R175H | HMTEVVRHC | 1 | HMTEVVRRC | 135 | 168-176 | A*02:01 |
| H/K/NRAS | Q61H | ILDTAGHEEY | 2 | ILDTAGQEEY | 136 | 55-64 | A*01:01 |
| H/K/NRAS | Q61L | ILDTAGLEEY | 3 | ILDTAGQEEY | 136 | 55-64 | A*01:01 |
| H/K/NRAS | Q61R | ILDTAGREEY | 4 | ILDTAGQEEY | 136 | 55-64 | A*01:01 |

A modified peptide described herein (e.g., a modified peptide including an amino acid sequence set forth in any one of SEQ ID NO:1, SEQ ID NO:2, SEQ ID NO:3, and SEQ ID NO:4) can be in a complex with any appropriate HLA. An HLA can be any appropriate HLA allele. In some cases, an HLA can be a class I HLA (e.g., HLA-A, HLA-B, and HLA-C) allele. In some cases, an HLA can be a class II HLA (e.g., HLA-DP, HLA-DM, HLA-DOA, HLA-DOB, HLA-DQ, and HLA-DR) allele. Examples of HLA alleles that a modified peptide described herein can complex with include, without limitation, HLA-A1 and HLA-A2. Exemplary HLA alleles for particular modified peptides are shown in Table 1. For example, a modified peptide derived from a modified p53 polypeptide (e.g., HMTEVVRHC (SEQ ID NO:1)) can be in a complex with HLA-A2 and β2M. For example a modified peptide derived from a modified H/K/N RAS polypeptide (e.g., ILDTAGHEEY (SEQ ID NO:2), ILDTAGLEEY (SEQ ID NO:3), and ILDTAGREEY (SEQ ID NO:4)) can be in a complex with HLA-A1 (e.g., can be in a complex with HLA-A1 and β2M).

This document provides molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4). In some cases, a molecule including one or more antigen-binding domains that can bind to a modified peptide described herein does not target (e.g., does not bind to) an uncomplexed modified peptide described herein (e.g., a modified peptide described herein that is not present in a complex (e.g., a peptide-HLA-β2M complex)). In some cases, a molecule including one or more antigen-binding domains that can bind to a modified peptide described herein does not target (e.g., does not bind to) a WT peptide (e.g., a peptide derived from a WT polypeptide from which the modified polypeptide is derived).

A molecule including one or more antigen-binding domains (e.g., scFvs) that can bind to a modified peptide described herein can be any appropriate type of molecule. In some cases, a molecule can be a monovalent molecule (e.g., containing a single antigen-binding domain). In some cases, a molecule can be a multivalent molecule (e.g., containing two or more antigen-binding domains and simultaneously targeting two or more antigens). For example, a bispecific molecule can include two antigen-binding domains, a trispecific molecule can include three antigen-binding domains, a quadruspecific molecule can include four antigen-binding domains, etc. Examples of molecules that contain antigen-binding domains include, without limitation, antibodies, antibody fragments, scFvs, chimeric antigen receptors (CARs), T cell receptors (TCRs), TCR mimics, tandem scFvs, bispecific T cell engagers, diabodies, scDbs, scFv-Fcs, bispecific antibodies, bispecific single-chain Fcs, dual-affinity re-targeting antibodies (DARTs), and any other molecule that includes at least one variable heavy chain (VH) and at least one variable light chain (VL). Any of these molecules can be used in accordance with materials and methods described herein. In some cases, an antigen-binding domain can be a scFv. For example, a molecule including one or more antigen-binding domains (e.g., one or more scFvs) that can bind to a modified peptide described herein can be a CAR. For example, a molecule including two scFvs that can bind to a modified peptide described herein can be a single-chain diabody (scDb).

In some cases, when a molecule including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4) is a multivalent molecule (e.g., a bispecific molecule), a first antigen-binding domain can bind to a modified peptide described herein and a second antigen-binding domain can bind to an effector cell (e.g., an antigen present on an effector cell). Examples of effector cells include, without limitation, T cells, natural killer (NK) cells, natural killer T (NKT) cells, B cells, plasma cells, macrophages, monocytes, microglia, dendritic cells, neutrophils, fibroblasts, and mast cells. Examples of antigens present on effector cells include, without limitation, CD3, CD4, CD8, CD28, NKG2D, PD-1, CTLA-4, 4-1BB, OX40, ICOS, CD27, Fc receptors (e.g., CD16a), and any other effector cell surface receptors. In some cases, a molecule described herein can include a first antigen-binding domain that can bind to a modified peptide described herein and a second antigen-binding domain that can bind to an antigen present on a T cell (e.g., CD3). In some cases, sequences (e.g., scFv sequences) that can bind to CD3 can be as shown in Table 4. In some cases, sequences (e.g., scFv sequences) that can bind to CD3 can be as described elsewhere (see, e.g., Rodrigues et al., 1992 *Int J Cancer Suppl.* 7:45-50; Shalaby et al., 1992 *J Exp Med.* 175:217-25; Brischwein et al., 2006 *Mol Immunol.* 43:1129-43; Li et al., 2005 *Immunology.* 116:487-98; WO2012162067; US20070065437; US20070065437; US20070065437; US20070065437; US20070065437; and US20070065437). In some cases, a molecule described herein can include a first antigen-binding domain that can bind to a modified peptide described herein and a second antigen-binding domain that can bind to an antigen present on a NK cell (e.g., CD16a or NKG2D). In some cases, sequences (e.g., scFv sequences) that can bind to CD16a can be as shown in Table 5. By binding both the modified peptide and the effector cell, the multivalent molecule can bring the cell expressing the modified peptide (e.g., as part of the HLA complex) into proximity with the effector cell, permitting the effector cell to act on the cell expressing the modified peptide.

In some cases, when a molecule including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4) is a multivalent molecule (e.g., a bispecific molecule), a molecule can be in any appropriate format which includes at least one VH and at least one VL. For example, a VH and a VL can be in any appropriate orientation. In some cases, a VH can be N-terminal to the VL. In some cases, a VH can be C-terminal to the VL. In some cases, a linker amino acid sequence can be positioned between the VH and VL.

In some cases, when a bispecific molecule includes tandem scFvs, the tandem scFvs can be in any appropriate orientation. Examples of tandem scFv orientations including scFv-A and scFv-B include, without limitation, VLA-LL-VHA-SL-VLB-LL-VHB, VLA-LL-VHA-SL-VHB-LL-VLB, VHA-LL-VLA-SL-VLB-LL-VHB, VHA-LL-VLA-SL-VHB-LL-VLB, VLB-LL-VHB-SL-VLA-LL-VHA, VLB-LL-VHB-SL-VHA-LL-VLA, VHB-LL-VLB-SL-VLA-LL-VHA, and VHB-LL-VLB-SL-VHA-LL-VLA, where SL is a short linker and LL is a long linker. A short linker can be from about 3 amino acids to about 10 amino acids in length. A short linker can include any appropriate amino acids (e.g., glycines and serines) in any appropriate combination. A long linker can be from about 10 amino acids to about 25 amino acids in length. A long linker can include any appropriate amino acids (e.g., glycines and serines) in any appropriate combination.

In some cases, when a bispecific molecule is a diabody, the diabody can be in any appropriate orientation. Examples of diabody orientations including scFv-A and scFv-B include, without limitation, VLA-SL-VHB and VLB-SL-VHA, VLA-SL-VLB and VHB-SL-VHA, VHA-SL-VLB and VHB-SL-VLA, VLB-SL-VHA and VLA-SL-VHB, VLB-SL-VLA and VHA-SL-VHB, and VHB-SL-VLA and VHA-SL-VLB, where SL is a short linker. A short linker can be from about 3 amino acids to about 10 amino acids in length. A short linker can include any appropriate amino acids (e.g., glycines and serines) in any appropriate combination.

In some cases, when a bispecific molecule is a scDb, the scDb can be in any appropriate orientation. Examples of scDb orientations including scFv-A and scFv-B include, without limitation, VLA-SL-VHB-LL-VLB-SL-VHA, VHA-SL-VLB-LL-VHB-SL-VLA, VLA-SL-VLB-LL-VHB-SL-VHA, VHA-SL-VHB-LL-VLB-SL-VLA, VLB-SL-VHA-LL-VLA-SL-VHB, VHB-SL-VLA-LL-VHA-SL-VLB, VLB-SL-VLA-LL-VHA-SL-VHB, and VHB-SL-VHA-LL-VLA-SL-VLB, where SL is a short linker and LL is a long linker. A short linker can be from about 3 amino acids to about 10 amino acids in length. A short linker can include any appropriate amino acids (e.g., glycines and serines) in any appropriate combination. A long linker can be from about 10 amino acids to about 25 amino acids in length. A long linker can include any appropriate amino acids (e.g., glycines and serines) in any appropriate combination.

In some cases, when a bispecific molecule is a scFv-Fc, the scFv-Fc can be in any appropriate orientation. Examples of scFv-Fc orientations including scFv-Fc-A, scFv-Fc-B, and an Fc domain include, without limitation, VLA-LL-VHA-hinge-Fc and VLB-LL-VHB-hinge-Fc, VHA-LL-VLA-hinge-Fc and VHB-LL-VLB-hinge-Fc, VLA-LL-VHA-hinge-Fc and VHB-LL-VLB-hinge-Fc, VHA-LL-VLA-hinge-Fc and VLB-LL-VHB-hinge-Fc, where LL is a long linker. A long linker can be from about 10 amino acids to about 25 amino acids in length. A long linker can include any appropriate amino acids (e.g., glycines and serines) in any appropriate combination. In some cases, an Fc domain in a scFv-Fc can include one or more modifications to increase heterodimerization and/or to decrease homodimerization of the scFv-Fc. In some cases, an Fc domain in a scFv-Fc can exclude a hinge domain. In some cases, an Fc domain in a scFv-Fc can be at the N-terminus of the scFv.

In some cases, when a bispecific molecule is a bispecific single-chain Fc, the bispecific single-chain Fc can be in any appropriate orientation. Examples of bispecific single-chain Fc orientations include, without limitation, VLA-LL-VHA-SL-VHB-LL-VLB-SL-hinge-CH2-CH3-LL-hinge-CH2-CH3, VLA-LL-VHA-SL-VLB-LL-VHB-SL-hinge-CH2-CH3-LL-hinge-CH2-CH3, VHA-LL-VLA-SL-VLB-LL-VHB-SL-hinge-CH2-CH3-LL-hinge-CH2-CH3, VHA-LL-VLA-SL-VHB-LL-VLB-SL-hinge-CH2-CH3-LL-hinge-CH2-CH3, and VLA-SL-VHB-LL-VLB-VHA-SL-hinge-CH2-CH3-LL-hinge-CH2-CH3, where SL is a short linker and LL is a long linker. A short linker can be from about 3 amino acids to about 8 amino acids in length. A short linker can include any appropriate amino acids (e.g., glycines and serines) in any appropriate combination. A long linker can be from about 10 amino acids to about 25 amino acids in length. A long linker can include any appropriate amino acids (e.g., glycines and serines) in any appropriate combination. Any appropriate Fc domain can be used in a bispecific single-chain Fc. In some cases, an Fc domain can include an amino acid sequence derived from an IgG (e.g., a natural IgG). In some cases, an Fc domain can include an amino acid sequence that includes one or more modifications (e.g., one or more modifications to increase stability of the molecule and/or to increase or decrease binding to one or more Fc receptors). In some cases, an Fc domain that can be used in a bispecific single-chain Fc can exclude a hinge domain. In some cases, an Fc domain that can be used in a bispecific single-chain Fc can be at the N-terminus of the scFvs. In some cases, an Fc domain that can be used in a bispecific single-chain Fc can be as described elsewhere (see, e.g., International Patent Application Publication No. WO 2017/134134 A1 at, for example, SEQ ID NOs:25-32; and International Patent Application Publication No. WO 2017/134158 A1 at, for example, Table 38; and SEQ ID NOs:25-32).

A molecule including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4) can include any appropriate complementarity determining regions (CDRs). For example, a molecule including one or more antigen-binding domains that can bind to a modified peptide described herein can include a variable heavy chain (VH) having three VH complementarity determining regions (CDR-VHs) and a variable light chain (VL) having three VL CDRs (CDR-VLs). For example, a molecule that can bind to a modified peptide derived from a modified p53 polypeptide (e.g., HMTEVVRHC (SEQ ID NO:1)) can include one of each of the CDRs set forth below:

```
CDR-VL1:
                                    (SEQ ID NO: 5)
QDVNTA;

CDR-VL2:
SAS and SAY;
```

-continued

```
CDR-VL3:
                             (SEQ ID NO: 6)
QQYSRYSPVTF, (SEQ ID NO: 7)
QQQSSTPVTF, (SEQ ID NO: 8)
QQSSYYPNTF, (SEQ ID NO: 9)
QQQWSSPDTF, (SEQ ID NO: 10)
QQSNAYPITF;

CDR-VH1:
                             (SEQ ID NO: 11)
GFNVYASGM, (SEQ ID NO: 12)
GFNVYQSDM, (SEQ ID NO: 13)
GFNLYQRDM, (SEQ ID NO: 14)
GFNLSYYDM, (SEQ ID NO: 15)
GFNLNSYYM;

CDR-VH2:
                             (SEQ ID NO: 16)
KIYPDSDYTY, (SEQ ID NO: 17)
TIWPYSGYTY, (SEQ ID NO: 18)
GLLYGSDHTE, (SEQ ID NO: 19)
LIYYGSGYTY, (SEQ ID NO: 20)
MIIPGYGYTN;
and

CDR-VH3:
                             (SEQ ID NO: 21)
SRDSSFYYVYAMDY, (SEQ ID NO: 22)
SRDGMYAFDY, (SEQ ID NO: 23)
SRATYEEAFDY, (SEQ ID NO: 24)
SRGSYVSGMDY, (SEQ ID NO: 25)
SRSYYMYMDY.
```

For example, a molecule that can bind to a modified peptide derived from a modified H/K/N RAS polypeptide Q61H (e.g., ILDTAGHEEY (SEQ ID NO:2)) can include one of each of the CDRs set forth below:

```
CDR-VL1:
                             (SEQ ID NO: 5)
QDVNTA;

CDR-VL2:
SAS;
```

-continued

```
CDR-VL3:
                             (SEQ ID NO: 26)
QQVIYYPFTF, (SEQ ID NO: 27)
QQYDYYPFTF, (SEQ ID NO: 28)
QQSIYYPFTF, (SEQ ID NO: 184)
QQSSYSPWTF, (SEQ ID NO: 29)
QQSFSTPITF, (SEQ ID NO: 30)
QQGEYSPLTF, (SEQ ID NO: 31)
QQTYYTPVTF,;

CDR-VH1:
                             (SEQ ID NO: 32)
GFNLYSYAI, (SEQ ID NO: 33)
GFNISYEAM, (SEQ ID NO: 34)
GFNLYTSQM, (SEQ ID NO: 35)
GFNVFGYAI, (SEQ ID NO: 36)
GFNISPWDM, (SEQ ID NO: 37)
GFNISEYLM, (SEQ ID NO: 38)
GFNVFESAM, (SEQ ID NO: 39)
GFNISHYVM;

CDR-VH2:
                             (SEQ ID NO: 40)
LLYPDYGVTS, (SEQ ID NO: 41)
LIYPNHGITS, (SEQ ID NO: 42)
LVYPGYYVTS, (SEQ ID NO: 43)
EVYPGYDVTS, (SEQ ID NO: 44)
QLYPSSGYTN, (SEQ ID NO: 45)
LLPPGLSYTN, (SEQ ID NO: 46)
WVYGSYDYTY, (SEQ ID NO: 47)
DFYPHSDSTY;
and

CDR-VH3:
                             (SEQ ID NO: 48)
SRYRSYEYSVSSYSYSAMDY, (SEQ ID NO: 49)
SRYSSSAMDY,
```

-continued (SEQ ID NO: 50)
SRGAYYYSSAMDY, (SEQ ID NO 51)
SRYSWAGAFDY, (SEQ ID NO: 52)
SRSVYWSLDY, (SEQ ID NO: 53)
SRYGYYAFDY, (SEQ ID NO: 54)
SRSFAYFQAMDY, (SEQ ID NO: 55)
SRYQSYSFDY.

For example, a molecule that can bind to a modified peptide derived from a modified H/K/N RAS polypeptide Q61L (e.g., ILDTAGLEEY (SEQ ID NO:3) can include one of each of the CDRs set forth below:

CDR-VL1:
(SEQ ID NO: 5)
QDVNTA;

CDR-VL2:
SAS;

CDR-VL3:
(SEQ ID NO: 56)
QQASRQPYTF, (SEQ ID NO: 57)
QQAVSYPWTF, (SEQ ID NO: 58)
QQTSSYPITF, (SEQ ID NO: 59)
QQSWYSPSTF, (SEQ ID NO: 60)
QQSYYAPITF, (SEQ ID NO: 61)
QQSYYSPWTF, (SEQ ID NO: 62)
QQAYYPPWTF, (SEQ ID NO: 63)
QQSYSSGPVTF, (SEQ ID NO: 64)
QQTYYYPFTF, (SEQ ID NO: 65)
QQSYYPYYPWTF, (SEQ ID NO: 66)
QQYDRPITF;

CDR-VH1:
(SEQ ID NO: 67)
GFNFSESGM, (SEQ ID NO: 68)
GFNISSSGI, (SEQ ID NO: 69)
GFNIYWYGM, (SEQ ID NO: 70)
GFNISASGM, (SEQ ID NO: 71)
GFNFSYYGM,

-continued (SEQ ID NO: 72)
GFNISYSNI, (SEQ ID NO: 73)
GFNVSRWAM, (SEQ ID NO: 74)
GFNFSYGGI, (SEQ ID NO: 75)
GFNLYAWGM, (SEQ ID NO: 76)
GFNVSHSAM, (SEQ ID NO: 77)
GFNIYYEAM

CDR-VH2:
(SEQ ID NO: 78)
HFSGDSGYTY, (SEQ ID NO: 79)
MVYGGSGYTN, (SEQ ID NO: 80)
QVYPWSGFTY, (SEQ ID NO: 81)
WIWGGSSYTY, (SEQ ID NO: 82)
WIYPFSGYTN,, (SEQ ID NO: 83)
MIYGTRGGTY, (SEQ ID NO: 84)
RVYPSGYLTY, (SEQ ID NO: 85)
MIYPLTGYTN, (SEQ ID NO: 86)
LVYGGWGSTS, (SEQ ID NO: 87)
TVHPDWGNTY, (SEQ ID NO: 88)
QIYPWNDYTY;
and

CDR-VH3:
(SEQ ID NO: 89)
SRYMYYSGYFDY, (SEQ ID NO: 90)
SRWAHYSAYMDY, (SEQ ID NO: 91)
SRDYYSYSLDY, (SEQ ID NO: 92)
SRGQYLSYMDY, (SEQ ID NO: 93)
SREYYSRAFDY, (SEQ ID NO: 94)
SRYYSYAMDY, (SEQ ID NO: 95)
SRNMQSYMDY, (SEQ ID NO: 96)
SRDYYYSVDV, (SEQ ID NO: 97)
SRAGSSKMSAGAFDY,

-continued (SEQ ID NO: 98)
SRWQQYYYSFDY, (SEQ ID NO: 99)
SRNYYAATMDY

For example, a molecule that can bind to a modified peptide derived from a modified H/K/N RAS polypeptide Q61R (e.g., ILDTAGREEY (SEQ ID NO:4) can include one of each of the CDRs set forth below:

CDR-VL1:
(SEQ ID NO: 5)
QDVNTA;

CDR-VL2:
SAS;

CDR-VL3:
(SEQ ID NO: 100)
QQSYTSPLTF,
(SEQ ID NO: 101)
QQYWYYYPITF,
(SEQ ID NO: 60)
QQSYYAPITF,
(SEQ ID NO: 102)
QQYYLYQPITF,
(SEQ ID NO: 103)
QQYSNYPLTF,
(SEQ ID NO: 104)
QQYASDPITF,
(SEQ ID NO: 105)
QQYSYDPITF,
(SEQ ID NO: 106)
QQYIYDPVTF,
(SEQ ID NO: 107)
QQLMYDPITF;

CDR-VH1:
(SEQ ID NO: 108)
GFNIYYGVM,
(SEQ ID NO: 109)
GFNIYSYDM,
(SEQ ID NO: 110)
GFNVQWSHM,
(SEQ ID NO: 111)
GFNIGMYTM,
(SEQ ID NO: 112)

-continued
GFNVFYGSM,
(SEQ ID NO: 113)
GFNLDYGWM,
(SEQ ID NO: 114)
GFNFSYSAM,
(SEQ ID NO: 115)
GFNVDWAWM,
(SEQ ID NO: 116)
GFNFGTYWM;

CDR-VH2:
(SEQ ID NO: 117)
MIYPDSSWTY,
(SEQ ID NO: 118)
ISPGGSYTY,
(SEQ ID NO: 119)
RLSPPSGYTN,
(SEQ ID NO: 120)
LVYPDSGYTN,
(SEQ ID NO: 121)
FIGPDSTYTY,
(SEQ ID NO: 122)
WVVPGSDYTD,
(SEQ ID NO: 123)
DVVPDGDWTY,
(SEQ ID NO: 124)
WVVGGSDYTY,
(SEQ ID NO: 125)
WFLPDYDYTL;
and CDR-VH3:
(SEQ ID NO: 126)
SRDQDFHYMNYYLSYALDY,
(SEQ ID NO: 127)
SRSAFTGYFDV,
(SEQ ID NO: 128)
SRLILSKGGYGWAMDY,
(SEQ ID NO: 129)
SRYTWQSMDY,
(SEQ ID NO: 130)
SRDLGSAYAMDY,
(SEQ ID NO: 131)
SRFHYTAFDV,
(SEQ ID NO: 132)
SRGWYALDY,
(SEQ ID NO: 133)
SRSYYYAFDY,
(SEQ ID NO: 134)
SRHGEYAFDY.

TABLE 2

MANAbody complementarity-determining region (CDR) sequences of light (L) chains and heavy (H) chains.

| Target Peptide(s) | scFv Clone | CDR L1 | CDR L2 | CDR L3 | CDR H1 | CDR H2 | CDR H3 |
|---|---|---|---|---|---|---|---|
| 1) p53 R175H(168-176)-A2 | | | | | | | |
| HMTEV VRHC (SEQ ID NO: 1) | p53_ R175H_ A2_ c12(H2) | QDVN TA (SEQ ID NO: 5) | SAY | QQYSRYS PVTF (SEQ ID NO: 6) | GFNVYAS GM (SEQ ID NO: 11) | KIYPDSD YTY (SEQ ID NO: 16) | SRDSSFY YVYAMDY (SEQ ID NO: 21) |
| HMTEV VRHC (SEQ ID NO: 1) | p53_ R175H_ A2_c16 | QDVN TA (SEQ ID NO: 5) | SAS | QQQSSTP VTF (SEQ ID NO: 7) | GFNVYQS DM (SEQ ID NO: 12) | TIWPYSG YTY (SEQ ID NO: 17) | SRDGMYA FDY (SEQ ID NO: 22) |
| HMTEV VRHC (SEQ ID NO: 1) | p53_ R175H_ A2_c115 | QDV NTA (SEQ ID NO: 5) | SAS | QQSSYYP NTF (SEQ ID NO: 8) | GFNLYQR DM (SEQ ID NO: 13) | GLLYGSD HTE (SEQ ID NO: 18) | SRATYEE AFDY (SEQ ID NO: 23) |

TABLE 2-continued

MANAbody complementarity-determining region (CDR) sequences
of light (L) chains and heavy (H) chains.

| Target Peptide(s) | scFv Clone | CDR L1 | CDR L2 | CDR L3 | CDR H1 | CDR H2 | CDR H3 |
|---|---|---|---|---|---|---|---|
| HMTEV VRHC (SEQ ID NO: 1) | p53_R175H_A2_c116 | QDVNTA (SEQ ID NO: 5) | SAS | QQQWSSPDTF (SEQ ID NO: 9) | GFNLSYYDM (SEQ ID NO: 14) | LIYYGSGYTY (SEQ ID NO: 19) | SRGSYVSGMDY (SEQ ID NO: 24) |
| HMTEV VRHC (SEQ ID NO: 1) | p53_R175H_A2_c120 (H20) | QDVNTA (SEQ ID NO: 5) | SAS | QQSNAYPITF (SEQ ID NO: 10) | GFNLNSYYM (SEQ ID NO: 15) | MIIPGYGYTN (SEQ ID NO: 20) | SRSYYMYMDY (SEQ ID NO: 25) |
| 2) H/K/N RAS Q61H(55-64)-A1 | | | | | | | |
| ILDTAGHEEY (SEQ ID NO: 2) | H/K/N RAS Q61H_A1_c11 | QDVNTA (SEQ ID NO: 5) | SAS | QQVIYYPFTF (SEQ ID NO: 26) | GFNLYSYAI (SEQ ID NO: 32) | LLYPDYGVTS (SEQ ID NO: 40) | SRYRSYEYSVSSYAMDY (SEQ ID NO: 48) |
| ILDTAGHEEY (SEQ ID NO: 2) | H/K/N RAS Q61H_A1_c12 | QDVNTA (SEQ ID NO: 5) | SAS | QQYDYYPFTF (SEQ ID NO: 27) | GFNISYEAM (SEQ ID NO: 33) | LIYPNHGITS (SEQ ID NO: 41) | SRYSSSAMDY (SEQ ID NO: 49) |
| ILDTAGHEEY (SEQ ID NO: 2) | H/K/N RAS Q61H_A1_c13 | QDVNTA (SEQ ID NO: 5) | SAS | QQSIYYPFTF (SEQ ID NO: 28) | GFNLYTSQM (SEQ ID NO: 34) | LVYPGYYVTS (SEQ ID NO: 42) | SRGAYYSSAMDY (SEQ ID NO: 50) |
| ILDTAGHEEY (SEQ ID NO: 2) | H/K/N RAS Q61H_A1_c14 | QDVNTA (SEQ ID NO: 5) | SAS | QQYDYYPFTF (SEQ ID NO: 27) | GFNVFGYAI (SEQ ID NO: 35) | EVYPGYDVTS (SEQ ID NO: 43) | SRYSWAGAFDY (SEQ ID NO: 51) |
| ILDTAGHEEY (SEQ ID NO: 2) | H/K/N RAS Q61H_c15 | QDVNTA (SEQ ID NO: 5) | SAS | QQSSYSPWTF (SEQ ID NO: 184) | GFNISPWDM (SEQ ID NO: 36) | QLYPSSGYTN (SEQ ID NO: 44) | SRSVYWSLDY (SEQ ID NO: 52) |
| ILDTAGHEEY (SEQ ID NO: 2) | H/K/N RAS Q61H_c18 | QDVNTA (SEQ ID NO: 5) | SAS | QQSFSTPITF (SEQ ID NO: 29) | GFNISEYLM (SEQ ID NO: 37) | LLPPGLSYTN (SEQ ID NO: 45) | SRYGYYAFDY (SEQ ID NO: 53) |
| ILDTAGHEEY (SEQ ID NO: 2) | H/K/N RAS Q61H_c19 | QDVNTA (SEQ ID NO: 5) | SAS | QQGEYSPLTF (SEQ ID NO: 30) | GFNVFESAM (SEQ ID NO: 38) | WVYGSYDYTY (SEQ ID NO: 46) | SRSFAYFQAMDY (SEQ ID NO: 54) |
| ILDTAGHEEY (SEQ ID NO: 2) | H/K/N RAS Q61H_c110 | QDVNTA (SEQ ID NO: 5) | SAS | QQTYYTPVTF (SEQ ID NO: 31) | GFNISHYVM (SEQ ID NO: 39) | DFYPHSDSTY (SEQ ID NO: 47) | SRYQSYSFDY (SEQ ID NO: 55) |
| 3) H/K/N RAS Q61L(55-64)-A1 | | | | | | | |
| ILDTAGLEEY (SEQ ID NO: 3) | H/K/N RAS Q61L_c11 | QDVNTA (SEQ ID NO: 5) | SAS | QQASRQPYTF (SEQ ID NO: 56) | GFNFSESGM (SEQ ID NO: 67) | HFSGDSGYTY (SEQ ID NO: 78) | SRYMYYSGYFDY (SEQ ID NO: 89) |
| ILDTAGLEEY (SEQ ID NO: 3) | H/K/N RAS Q61L_ | QDVNTA (SEQ ID | SAS | QQAVSYPWTF (SEQ ID | GFNISSSGI (SEQ ID | MVYGGSGYTN (SEQ ID | SRWAHYSAYMD) (SEQ ID |

TABLE 2-continued

| MANAbody complementarity-determining region (CDR) sequences of light (L) chains and heavy (H) chains. | | | | | | | |
|---|---|---|---|---|---|---|---|
| Target Peptide(s) | scFv Clone | CDR L1 | CDR L2 | CDR L3 | CDR H1 | CDR H2 | CDR H3 |
| NO: 3) | c12 | ID NO: 5) | | NO: 57) | NO: 68) | NO: 79) | NO: 90) |
| ILDTA GLEEY (SEQ ID NO: 3) | H/K/N RAS Q61L_ c13 | QDV NTA (SEQ ID NO: 5) | SAS | QQTSSYP ITF (SEQ ID NO: 58) | GFNIYWY GM (SEQ ID NO: 69) | QVYPWSG FTY (SEQ ID NO: 80) | SRDYYSY SLDY (SEQ ID NO: 91) |
| ILDTA GLEEY (SEQ ID NO: 3) | H/K/N RAS Q61L_ c14 | QDV NTA (SEQ ID NO: 5) | SAS | QQSWYSP STF (SEQ ID NO: 59) | GFNISAS GM (SEQ ID NO: 70) | WIWGGSS YTY (SEQ ID NO: 81) | SRGQYLS YMDY (SEQ ID NO: 92) |
| ILDTA GLEEY (SEQ ID NO: 3) | H/K/N RAS Q61L_ c15 | QDV NTA (SEQ ID NO: 5) | SAS | QQSYYAP ITF (SEQ ID NO: 60) | GFNFSYY GM (SEQ ID NO: 71) | WIYPFSG YTN (SEQ ID NO: 82) | SREYYSR AFDY (SEQ ID NO: 93) |
| ILDTA GLEEY (SEQ ID NO: 3) | H/K/N RAS Q61L_ c16 | QDV NTA (SEQ ID NO: 5) | SAS | QQSYYSP WTF (SEQ ID NO: 61) | GFNISYS NI (SEQ ID NO: 72) | MIYGTRG GTY (SEQ ID NO: 83) | SRYYSYA MDY (SEQ ID NO: 94) |
| ILDTA GLEEY (SEQ ID NO: 3) | H/K/N RAS Q61L_ c17 | QDV NTA (SEQ ID NO: 5) | SAS | QQAYYPP WTF (SEQ ID NO: 62) | GFNVSRW AM (SEQ ID NO: 73) | RVYPSGY LTY (SEQ ID NO: 84) | SRNMQSY MDY (SEQ ID NO: 95) |
| ILDTA GLEEY (SEQ ID NO: 3) | H/K/N RAS Q61L_ c18 | QDV NTA (SEQ ID NO: 5) | SAS | QQSYSSG PVTF (SEQ ID NO: 63) | GFNFSYG GI (SEQ ID NO: 74) | MIYPLTG YTN (SEQ ID NO: 85) | SRDYYYS VDV (SEQ ID NO: 96) |
| ILDTA GLEEY (SEQ ID NO: 3) | H/K/N RAS Q61L_ c19 | QDV NTA (SEQ ID NO: 5) | SAS | QQTYYYP FTF (SEQ ID NO: 64) | GFNLYAW GM (SEQ ID NO: 75) | LVYGGWG STS (SEQ ID NO: 86) | SRAGSSK MSAGA+ (SEQ ID NO: 97) |
| ILDTA GLEEY (SEQ ID NO: 3) | H/K/N RAS Q61L_ C110 | QDV NTA (SEQ ID NO: 5) | SAS | QQSYYPY YPWTF (SEQ ID NO: 65) | GFNVSHS AM (SEQ ID NO: 76) | TVHPDWG NTY (SEQ ID NO: 87) | SRWQQYY YSFDY (SEQ ID NO: 98) |
| ILDTA GLEEY (SEQ ID NO: 3) | H/K/N RAS Q61L_ c111 | QDV NTA (SEQ ID NO: 5) | SAS | QQYDRPI TF (SEQ ID NO: 66) | GFNIYYE AM (SEQ ID NO: 77) | QIYPWND YTY (SEQ ID NO: 88) | SRNYYAA TMDY (SEQ ID NO: 99) |
| 4) H/K/N RAS Q61R(55-64)-A1 | | | | | | | |
| ILDTA GREEY (SEQ ID NO: 4) | H/R/N RAS Q61R_ c11 | QDV NTA (SEQ ID NO: 5) | SAS | QQSYTSP LTF (SEQ ID NO: 100) | GFNIYYG VM (SEQ ID NO: 108) | MIYPDSS WTY (SEQ ID NO: 117) | SRDQDFH YMNYY ALDY (SEQ ID NO: 126) |
| ILDTA GREEY (SEQ ID NO: 4) | H/R/ N RAS Q61R_ c12 | QDV NTA (SEQ ID NO: 5) | SAS | QQYWYYY PITF (SEQ ID NO: 101) | GFNIYSY DM (SEQ ID NO: 109) | ISPGGSY TY (SEQ ID NO: 118) | SRSAFTG YFDV (SEQ ID NO: 127) |
| ILDTA GREEY (SEQ ID | H/R/N RAS Q61R_ | QDV NTA (SEQ ID | SAS | QQSYYAP ITF (SEQ ID | GFNVQWS HM (SEQ ID | RLSPPSG YTN (SEQ ID | SRLILSK GGYGWAM DY |

TABLE 2-continued

| MANAbody complementarity-determining region (CDR) sequences of light (L) chains and heavy (H) chains. | | | | | | | |
|---|---|---|---|---|---|---|---|
| Target Peptide(s) | scFv Clone | CDR L1 | CDR L2 | CDR L3 | CDR H1 | CDR H2 | CDR H3 |
| NO: 4) | c13 | ID NO: 5) | | NO: 60) | NO: 110) | NO: 119) | (SEQ ID NO: 128) |
| ILDTA GREEY (SEQ ID NO: 4) | H/R/N RAS Q61R_ c15 | QDV NTA (SEQ ID NO: 5) | SAS | QQYYLYQ PITF (SEQ ID NO: 102) | GFNIGMY TM (SEQ ID NO: 111) | LVYPDSG YTN (SEQ ID NO: 120) | SRYTWQS MDY (SEQ ID NO: 129) |
| ILDTA GREEY (SEQ ID NO: 4) | H/R/N RAS Q61R_ c16 | QDV NTA (SEQ ID NO: 5) | SAS | QQYSNYP LTF (SEQ ID NO: 103) | GFNVFYG SM (SEQ ID NO: 112) | FIGPDST YTY (SEQ ID NO: 121) | SRDLGSA YAMDY (SEQ ID NO: 130) |
| ILDTA GREEY (SEQ ID NO: 4) | H/R/N RAS Q61R_ c17 | QDV NTA (SEQ ID NO: 5) | SAS | QQYASDP ITF (SEQ ID NO: 104) | GFNLDYG WM (SEQ ID NO: 113) | WVVPGSD YTD (SEQ ID NO: 122) | SRFHYTA FDV (SEQ ID NO: 131) |
| ILDTA GREEY (SEQ ID NO: 4) | H/R/N RAS Q61R_ c113 | QDV NTA (SEQ ID NO: 5) | SAS | QQYSYDP ITF (SEQ ID NO: 105) | GFNFSYS AM (SEQ ID NO: 114) | DVVPDGD WTY (SEQ ID NO: 123) | SRGWYAL DY (SEQ ID NO: 132) |
| ILDTA GREEY (SEQ ID NO: 4) | H/R/N RAS Q61R_ c118 | QDV NTA (SEQ ID NO: 5) | SAS | QQYIYDP VTF (SEQ ID NO: 106) | GFNVDWA WM (SEQ ID NO: 115) | WVVGGSD YTY (SEQ ID NO: 124) | SRSYYYA FDY (SEQ ID NO: 133) |
| ILDTA GREEY (SEQ ID NO: 4) | H/R/N RAS Q61R_ c119 | QDV NTA (SEQ ID NO: 5) | SAS | QQLMYDP ITF (SEQ ID NO: 107) | GFNFGTY WM (SEQ ID NO: 116) | WFLPDYD YTL (SEQ ID NO: 125) | SRHGEYA FDY (SEQ ID NO: 134) |

In some cases, a molecule including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4) can include any appropriate set of CDR sequences (e.g., any of the CDR sequence sets described herein).

A molecule including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4) can include any appropriate sequence. For example, a molecule that can bind to a modified peptide derived from a modified p53 polypeptide (e.g., HMTEVVRHC (SEQ ID NO:1)) can include, without limitation, the scFv sequence set forth in any one of SEQ ID NO:137, SEQ ID NO:138, SEQ ID NO:139, SEQ ID NO:140, or SEQ ID NO:141. For example, a molecule that can bind to a modified peptide derived from a modified H/K/N RAS polypeptide (e.g., ILDTAGHEEY (SEQ ID NO:2), ILDTAGLEEY (SEQ ID NO:3), or ILD-TAGREEY (SEQ ID NO:4)) can include, without limitation, the scFv sequence set forth in any one of SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO: 150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, or SEQ ID NO:169. Examples of sequences (e.g., scFv sequences) that can bind to particular modified peptides are shown in Table 3 and Table 12. In some cases, a molecule including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4) can have a sequence that deviates from a sequence shown in Table 3 and Table 12, sometimes referred to as a variant sequence. For example, a molecule including one or more antigen-binding domains that can bind to a modified peptide described herein can have at least 75% sequence identity (e.g., at least 80% sequence identity, at least 85% sequence identity, at least 90% sequence identity, at least 95% sequence identity, at least 96% sequence identity, at least 97% sequence identity, at least 98% sequence identity, at least 99% sequence identity, or more) to any of the sequences shown in Table 3 and Table 12, provided the variant sequence maintains the ability to bind to a modified peptide described herein. For example, a molecule including one or more antigen-binding domains that can bind to a modified peptide described herein can have one or more (e.g., one, two, three, four, five, six, seven, eight, nine, ten, or more) modifications (e.g., one or more amino acid substitutions) as compared to the sequences shown in Table 3 and Table 12, provided the variant sequence maintains the ability to bind to a modified peptide described herein. In some cases, a molecule including one or more antigen-binding domains that can bind to a modified peptide described herein can include any appropriate set of CDR sequences described herein, and any sequence deviations from a sequence shown in Table 3 and Table 12 can be in the scaffold sequence(s).

A molecule including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4) can be attached (e.g., covalently or non-covalently attached) to a label (e.g., a detectable label). A detectable label can be any appropriate label. In some cases, a label can be used to assist in detecting the presence or absence of one or more modified peptides described herein. For example, a molecule described herein that is labelled can be used in vitro to detect cancer cells (e.g., cancer cells expressing a modified peptide described herein) in a sample obtained from a mammal. In some cases, a label (e.g., a detectable label) can be used to assist in determining the location of one or more modified peptides described herein. For example, molecule described herein that is labelled can be used in vivo to monitor antitumor therapy and/or to detect cancer cells (e.g., cancer cells expressing a modified peptide described herein) in a mammal. Examples of labels that can be attached to a molecule described herein include, without limitation, radionuclides, contrast agents used in magnetic resonance imaging (MRI), computed tomography (CT), ultrasound (US), and other imaging modalities, chromophores, enzymes, and fluorescent molecules (e.g., green fluorescent protein and near-IR fluorescence).

A molecule including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, and SEQ ID NO:4) can be attached (e.g., covalently or non-covalently attached) to a therapeutic agent. A therapeutic agent can be any therapeutic agent. In some cases, a therapeutic agent can be an anti-cancer agent. Examples of therapeutic agents that can be attached to a molecule described herein include, without limitation, anti-cancer agents such as monomethyl auristatin E (MMAE), monomethyl auristatin F (MMAF), maytansine, mertansine/emtansine (DM1), ravtansine/soravtansine (DM4), SN-38, calicheamicin, D6.5, dimeric pyrrolobenzodiazepines (PBDs), α-amantin (AAMT), PNU-159682, ricin, pseudomonas exotoxin A, diphtheria toxin, and gelonin.

This document also provides methods for using one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4). For example, one or more molecules including one or more antigen-binding domains (e.g., scFvs) that can target (e.g., bind to) one or more modified peptides can be used to assess a mammal having cancer or suspected of having cancer and/or to treat a mammal having a cancer (e.g., a cancer expressing one or more modified peptides such as a p53 R175H MANA, a RAS Q61H/L/R MANA, and/or a RAS G12V MANA). In some cases, one or more molecules includes one or more antigen-binding domains that can bind to a modified peptide can be used to detect the presence or absence of one or more modified peptides in a sample obtained from a mammal having cancer or suspected of having cancer. In some cases, one or more molecules including one or more antigen-binding domains that can bind to a modified peptide can be administered to a mammal having a cancer (e.g., a cancer expressing the modified peptide) to treat the mammal. Administration of one or more molecules including one or more antigen-binding domains that can bind to a modified peptide described herein to a mammal (e.g., human) having a cancer can be effective to treat the mammal.

Any type of mammal can be assessed and/or treated as described herein. Examples of mammals that can be assessed and/or treated as described herein include, without limitation, primates (e.g., humans and non-human primates such as chimpanzees, baboons, or monkeys), dogs, cats, pigs, sheep, rabbits, mice, and rats. In some cases, a mammal can be a human.

A mammal can be assessed and/or treated for any appropriate cancer. In some cases, a cancer can express one or more modified peptides (e.g., one or more MANAs) described herein. A cancer can be a primary cancer. A cancer can be a metastatic cancer. A cancer can include one or more solid tumors. A cancer can include one or more non-solid tumors. Examples of cancers that can be assessed as described herein (e.g., based at least in part on the presence of one or more modified peptides described herein) and/or treated as described herein (e.g., by administering one or more molecules including one or more antigen-binding domains (e.g., scFvs) that can bind to a modified peptide described herein) include, without limitation, blood cancers (e.g., Hodgkin's lymphoma, non-Hodgkin's lymphoma, acute myeloid leukemia (AML), acute lymphoblastic leukemia (ALL), multiple myeloma, MDS, and myeloproliferative diseases), lung cancers, pancreatic cancers, gastric cancers, colon cancers (e.g., colorectal cancers), ovarian cancers, endometrial cancers, biliary tract cancers, liver cancers, bone and soft tissue cancers (e.g., sarcomas), breast cancers, prostate cancers, esophageal cancers, stomach cancers, kidney cancers, head and neck cancers, brain cancers (e.g., glioblastoma multiforme and astrocytomas), thyroid cancers, germ cell tumors, and melanomas.

When assessing a mammal having cancer or suspected of having cancer, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be used to assess for the presence or absence of one or more modified peptides described herein. For example, the presence, absence, or level of one or more modified peptides described herein in a sample obtained from a human can be used to determine whether or not the human has a cancer. In some cases, the presence of one or more modified peptides described herein in a sample obtained from a mammal can be used to identify the mammal as having a cancer. For example, a mammal can be identified as having a cancer when a sample obtained from the mammal has one or more modified peptides described herein.

Any appropriate sample obtained from a mammal can be assessed for the presence, absence, or level of one or more modified peptides described herein. For example, biological samples such as tissue samples (e.g., breast tissue, and cervical tissue such as from a Papanicolaou (Pap) test), fluid samples (e.g., blood, serum, plasma, urine, saliva, sputum, and cerebrospinal fluid), and solid samples (e.g. stool) can be obtained from a mammal and assessed for the presence, absence, or level of one or more modified peptides described herein. Any appropriate method can be used to detect the presence, absence, or level of one or more modified peptides described herein. For example, sequencing techniques including, but not limited to, Sanger sequencing, chemical sequencing, nanopore sequencing, sequencing by ligation (SOLiD sequencing), sequencing with mass spectrometry, whole exome sequencing, whole genome sequencing, and/or next-generation sequencing can be used to determine the presence, absence, or level of one or more modified peptides described herein in a sample obtained from a mammal.

When treating a mammal having cancer, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be administered to a mammal having cancer to treat the mammal. In some cases, a mammal can have a cancer expressing one or more modified peptides described herein. For example, one or more molecules including one or more antigen-binding domains that can bind to a modified peptide described herein can be administered to a mammal having a cancer expressing that modified peptide to treat the mammal. For example, one or more molecules including one or more scFvs that can bind to a modified peptide described herein (e.g., one or more scDbs) can be administered to a mammal having a cancer expressing that modified peptide to treat the mammal.

In some cases, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be administered to a mammal (e.g., a mammal having a cancer) once or multiple times over a period of time ranging from days to weeks.

In some cases, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be formulated into a composition (e.g., a pharmaceutically acceptable composition) for administration to a mammal (e.g., a mammal having a cancer). For example, one or more antigen-binding domains that can bind to a modified peptide described herein can be formulated together with one or more pharmaceutically acceptable carriers (additives), excipients, and/or diluents. In some cases, a pharmaceutically acceptable carrier, excipient, or diluent can be a naturally occurring pharmaceutically acceptable carrier, excipient, or diluent. In some cases, a pharmaceutically acceptable carrier, excipient, or diluent can be a non-naturally occurring (e.g., an artificial or synthetic) pharmaceutically acceptable carrier, excipient, or diluent. Examples of pharmaceutically acceptable carriers, excipients, and diluents that can be used in a composition described herein include, without limitation, sucrose, lactose, starch (e.g., starch glycolate), cellulose, cellulose derivatives (e.g., modified celluloses such as microcrystalline cellulose and cellulose ethers like hydroxypropyl cellulose (HIPC) and cellulose ether hydroxypropyl methylcellulose (IPMC)), xylitol, sorbitol, mannitol, gelatin, polymers (e.g., polyvinylpyrrolidone (PVP), polyethylene glycol (PEG), crosslinked polyvinylpyrrolidone (crospovidone), carboxymethyl cellulose, polyethylene-polyoxypropylene-block polymers, and crosslinked sodium carboxymethyl cellulose (croscarmellose sodium)), titanium oxide, azo dyes, silica gel, fumed silica, talc, magnesium carbonate, vegetable stearin, magnesium stearate, aluminum stearate, stearic acid, antioxidants (e.g., vitamin A, vitamin E, vitamin C, retinyl palmitate, and selenium), citric acid, sodium citrate, benzyl alcohol, lysine hydrochloride, trehalose dihydrate, sodium hydroxide, parabens (e.g., methyl paraben and propyl paraben), petrolatum, dimethyl sulfoxide, mineral oil, serum proteins (e.g., human serum albumin), glycine, sorbic acid, potassium sorbate, water, salts or electrolytes (e.g., saline, protamine sulfate, disodium hydrogen phosphate, potassium hydrogen phosphate, sodium chloride, and zinc salts), colloidal silica, magnesium trisilicate, polyacrylates, waxes, wool fat, lecithin, and corn oil. In some cases, a pharmaceutically acceptable carrier, excipient, or diluent can be an antiadherent, a binder, a colorant, a disintegrant, a flavor (e.g., a natural flavor such as a fruit extract or an artificial flavor), a glidant, a lubricant, a preservative, a sorbent, and/or a sweetener.

A composition (e.g., a pharmaceutical composition) containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be formulated into any appropriate dosage form. Examples of dosage forms include solid or liquid forms including, without limitation, gums, capsules, tablets (e.g., chewable tablets, and enteric coated tablets), suppositories, liquids, enemas, suspensions, solutions (e.g., sterile solutions), sustained-release formulations, delayed-release formulations, pills, powders, and granules.

A composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be designed for oral, parenteral (including subcutaneous, intramuscular, intravenous, and intradermal), or intratumoral administration. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

A composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be administered using any appropriate technique and to any appropriate location. A composition including one or more molecules including one or more antigen-binding domains (e.g., scFvs) that can bind to a modified peptide described herein can be administered locally (e.g., intratumorally) or systemically. For example, a composition provided herein can be administered locally by intratumoral administration (e.g., injection into tumors) or by administration into biological spaces infiltrated by tumors (e.g. intraspinal administration, intracerebellar administration, intraperitoneal administration and/or pleural administration). For example, a composition provided herein can be administered systemically by oral administration or by intravenous administration (e.g., injection or infusion) to a mammal (e.g., a human).

Effective doses can vary depending on the risk and/or the severity of the cancer, the route of administration, the age and general health condition of the subject, excipient usage, the possibility of co-usage with other therapeutic treatments such as use of other agents, and the judgment of the treating physician. An effective amount of a composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be any amount that treats a cancer present within the subject without producing significant toxicity to the subject. If a particular subject fails to respond to a particular amount, then the amount of one or more molecules including one or more antigen-binding domains (e.g., scFvs) that can bind to a modified peptide described herein can be increased (e.g., by two-fold, three-fold, four-fold, or more). After receiving this higher amount, the mammal can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be any frequency that effectively treats a mammal having a cancer without producing significant toxicity to the mammal. For example, the frequency of administration of one or more molecules including one or more antigen-binding domains (e.g., scFvs) that can bind to a modified peptide described herein can be from about two to about three times a week to about two to about three times a year. In some cases, a subject having cancer can receive a single administration of one or more antibodies described herein. The frequency of administration of one or more molecules including one or more antigen-binding domains (e.g., scFvs) that can bind to a modified peptide described herein can remain constant or can be variable during the duration of treatment. A course of treatment with a composition containing one or more molecules including one or more antigen-binding domains (e.g., scFvs) that can bind to a modified peptide described herein can include rest periods. For example, a composition containing one or more molecules including one or more antigen-binding domains (e.g., scFvs) that can bind to a modified peptide described herein can be administered every other month over a two-year period followed by a six-month rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be any duration that effectively treats a cancer present within the mammal without producing significant toxicity to the mammal. In some cases, the effective duration can vary from several months to several years. In general, the effective duration for treating a mammal having a cancer can range in duration from about one or two months to five or more years. Multiple factors can influence the actual effective duration used for a particular treatment. For example, an effective duration can vary with the frequency of administration, effective amount, use of multiple treatment agents, route of administration, and severity of the condition being treated.

In certain instances, a cancer within a mammal can be monitored to evaluate the effectiveness of the cancer treatment. Any appropriate method can be used to determine whether or not a mammal having cancer is treated. For example, imaging techniques or laboratory assays can be used to assess the number of cancer cells and/or the size of a tumor present within a mammal. For example, imaging techniques or laboratory assays can be used to assess the location of cancer cells and/or a tumor present within a mammal.

In some cases, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4) can be administered to a mammal having a cancer as a combination therapy with one or more additional cancer treatments (e.g., anti-cancer agents). A cancer treatment can include any appropriate cancer treatments. In some cases, a cancer treatment can include surgery. In some cases, a cancer treatment can include radiation therapy. In some cases, a cancer treatment can include administration of one or more therapeutic agents (e.g., one or more anti-cancer agents). Examples of anti-cancer agents include, without limitation, platinum compounds (e.g., a cisplatin or carboplatin), taxanes (e.g., paclitaxel, docetaxel, or an albumin bound paclitaxel such as nab-paclitaxel), altretamine, capecitabine, cyclophosphamide, etoposide (vp-16), gemcitabine, ifosfamide, irinotecan (cpt-11), liposomal doxorubicin, melphalan, pemetrexed, topotecan, vinorelbine, luteinizing-hormone-releasing hormone (LHRH) agonists (e.g., goserelin and leuprolide), anti-estrogens (e.g., tamoxifen), aromatase inhibitors (e.g., letrozole, anastrozole, and exemestane), angiogenesis inhibitors (e.g., bevacizumab), poly(ADP)-ribose polymerase (PARP) inhibitors (e.g., olaparib, rucaparib, and niraparib), radioactive phosphorus, anti-CTLA-4 antibodies, anti-PD-1 antibodies, anti-PD-L1 antibodies, IL-2 and other cytokines, other bispecific antibodies, and any combinations thereof. In cases where one or more molecules including one or more antigen-binding domains (e.g., scFvs) that can bind to a modified peptide described herein are used in combination with one or more additional cancer treatments, the one or more additional cancer treatments can be administered at the same time or independently. For example, a composition including one or more molecules including one or more antigen-binding domains (e.g., scFvs) that can bind to a modified peptide described herein can be administered first, and the one or more additional cancer treatments administered second, or vice versa.

Also provided herein are kits that include one or more molecules including one or more antigen-binding domains (e.g., scFvs) that can bind to a modified peptide described herein (e.g., a modified peptide including an amino acid sequence set forth in any one of SEQ ID NO:1, SEQ ID NO:2, SEQ ID NO:3, or SEQ ID NO:4). For example, a kit can include a composition (e.g., a pharmaceutically acceptable composition) containing one or more molecules including one or more antigen-binding domains (e.g., scFvs) that can bind to a modified peptide described herein. In some cases, a kit can include instructions for performing any of the methods described herein. In some cases, a kit can include at least one dose of any of the compositions (e.g., pharmaceutical compositions) described herein. In some cases, a kit can provide a means (e.g., a syringe) for administering any of the compositions (e.g., pharmaceutical compositions) described herein.

The invention will be further described in the following examples, which do not limit the scope of the invention described in the claims.

EXAMPLES

Example 1: Identification of MANAbody Clones and Conversion of MANA Body Clones into T Cell-Based Therapeutic Formats In this study, a phage display library was designed and built, which displayed a single chain variable fragment (scFv) on the phage surface. The scFvs present in the library were based on the humanized 4D5 (trastuzumab) framework with amino acid variability introduced at key positions of the scFv's complementarity determining regions (CDRs).

Phage display library was used to identify scFvs that specifically recognized mutation-containing peptides folded into a complex with a recombinant HLA allele alpha chain and beta-2 microglobulin (β2M). These complexes, also referred to herein as monomers, mimic the natural peptide/HLA complexes on a cancer cell surface.

Peptide-HLA targets can include mutant peptides (e.g., MANAs) shown in Table 1. scFvs that can specifically bind to peptide-HLA targets in Table 1 are shown in Table 3. These scFvs can also be referred to as MANAbodies for their ability to bind to MANAs.

TABLE 3

MANAbody scFv sequences.

| Target Peptide(s) | Target HLA Allele | scFv clone name | scFv sequence | SEQ ID NO: |
|---|---|---|---|---|
| 1) p53 R175H(168-176)-A2 | | | | |
| HMTEVVRHC (SEQ ID NO: 1) | HLA-A2 | p53_R175H_A2_cl2 (H2) | DIQMTQSPSSLSASVGDRVTITCRASQDVNTAVAWYQQKPGKAPKLLIYSAYFLYSGVPSRFSGSRSGTDFTLTISSLQPEDFATYYCQQYSRYSPVTFGQGTKVEIKRTGGGSGGGGSGGGASEVQLVESGGGLVQPGGSLRLSCAASGFNVYASGMHWVRQAPGKGLEWVAKIYPDSDYTYYADSVKGRFTISADTSKNTAYLQMNSLRAEDTAVYYCSRDSSFYYVYAMDYWGQGTLVTVSS | 137 |
| HMTEVVRHC (SEQ ID NO: 1) | HLA-A2 | p53_R175H_A2_cl6 | DIQMTQSPSSLSASVGDRVTITCRASQDVNTAVAWYQQKPGKAPKLLIYSASFLYSGVPSRFSGSRSGTDFTLTISSLQPEDFATYYCQQQSSTPVTFGQGTKVEIKRTGGGSGGGGSGGGASEVQLVESGGGLVQPGGSLRLSCAASGFNVYQSDMHWVRQAPGKGLEWVATIWPYSGYTYYADSVKGRFTISADTSKNTAYLQMNSLRAEDTAVYYCSRDGMYAFDYWGQGTLVTVSS | 138 |
| HMTEVVRHC (SEQ ID NO: 1) | HLA-A2 | p53_R175H_A2_cl15 | DIQMTQSPSSLSASVGDRVTITCRASQDVNTAVAWYQQKPGKAPKLLIYSASFLYSGVPSRFSGSRSGTDFTLTISSLQPEDFATYYCQQSSYYPNTFGQGTKVEIKRTGGGSGGGGSGGGASEVQLVESGGGLVQPGGSLRLSCAASGFNLYQRDMHWVRQAPGKGLEWVAGLLYGSDHTEYADSVKGRFTISADTSKNTAYLQMNSLRAEDTAVYYCSRATYEEAFDYWGQGTLVTVSS | 139 |
| HMTEVVRHC (SEQ ID NO: 1) | HLA-A2 | p53_R175H_A2_cl16 | DIQMTQSPSSLSASVGDRVTITCRASQDVNTAVAWYQQKPGKAPKLLIYSASFLYSGVPSRFSGSRSGTDFTLTITSLQPEDFATYYCQQQWSSPDTFGQGTKVEIKRTGGGSGGGGSGGGASEVQLVESGGGLVQPGGSLRLSCAASGFNLSYYDMHWVRQAPGKGLEWVALIYGSGYTYYADSVKGRFTISADTSKN | 140 |

TABLE 3-continued

| | | | | |
|---|---|---|---|---|
| | | | MANAbody scFv sequences. | |
| Target Peptide(s) | Target HLA Allele | scFv clone name | scFv sequence | SEQ ID NO: |
| | | | TAYLQMNSLRAEDTAVYYCSRGSYV SGMDYWGQGTLVTVSS | |
| HMTEVVRHC (SEQ ID NO: 1) | HLA-A2 | p53_R175H_ A2_cl20 (H20) | DIQMTQSPSSLSASVGDRVTITCRA SQDVNTAVAWYQQKPGKAPKLLIYS ASFLYSGVPSRFSGSRSGTDFTLTI SSLQPEDFATYYCQQSNAYPITFGQ GTKVEIKRTGGGSGGGGSGGGASEV QLVESGGGLVQPGGSLRLSCAASGF NLNSYYMHWVRQAPGKGLEWVAMII PGYGYTNYADSVKGRFTISADTSKN TAYLQMNSLRAEDTAVYYCSRSYYM YMDYWGQGTLVTVSS | 141 |
| | | 2) H/K/N RAS Q61H(55-64)-A1 | | |
| ILDTAGHEEY (SEQ ID NO: 2) | HLA-A1 | H/K/N RAS Q61H_A1_ cl1 (H1) | DIQMTQSPSSLSASVGDRVTITCRA SQDVNTAVAWYQQKPGKAPKLLIYS ASFLYSGVPSRFSGSRSGTDFTLTI SSLQPEDFATYYCQQVIYYPFTFGQ GTKVEIKRTGGGSGGGGSGGGASEV QLVESGGGLVQPGGSLRLSCAASGF NLYSYAIHWVRQAPGKGLEWVALLY PDYGVTSYADSVKGRFTISADTSKN TAYLQMNSLRAEDTAVYYCSRYRSY EYSVSSYSYSAMDYWGQGTLVTVSS | 142 |
| ILDTAGHEEY (SEQ ID NO: 2) | HLA-A1 | H/K/N RAS Q61H_A1_cl2 | DIQMTQSPSSLSASVGDRVTITCRA SQDVNTAVAWYQQKPGKAPKLLIYS ASFLYSGVPSRFSGSRSGTDFTLTI SSLQPEDFATYYCQQYDYYPFTFGQ GTKVEIKRTGGGSGGGGSGGGASEV QLVESGGGLVQPGGSLRLSCAASGF NISYEAMHWVRQAPGKGLEWVALIY PNHGITSYADSVKGRFTISADTSKN TAYLQMNSLRAEDTAVYYCSRYSSS AMDYWGQGTLVTVSS | 143 |
| ILDTAGHEEY (SEQ ID NO: 2) | HLA-A1 | H/K/N RAS Q61H_A1_cl3 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSIYYPFTFGQ GTKVEIKRTGGGSGGGGSGGGASEV QLVESGGGLVQPGGSLRLSCAASGF NLYTSQMHWVRQAPGKGLEWVALVY PGYYVTSYADSVKGRFTISADTSKN TAYLQMNSLRAEDTAVYYCSRGAYY YSSAMDYWGQGTLVTVSS | 144 |
| ILDTAGHEEY (SEQ ID NO: 2) | HLA-A1 | H/K/N RAS Q61H_A1_cl4 | DIQMTQSPSSLSASVGDRVTITCRA SQDVNTAVAWYQQKPGKAPKLLIYS ASFLYSGVPSRFSGSRSGTDFTLTI SSLQPEDFATYYCQQYDYYPFTFGQ GTKVEIKRTGGGSGGGGSGGGASEV QLVESGGGLVQPGGSLRLSCAASGF NVFGYAIHWVRQAPGKGLEWVAEVY PGYDVTSYADSVKGRFTISADTSKN TAYLQMNSLRAEDTAVYYCSRYSWA GAFDYWGQGTLVTVSS | 145 |
| ILDTAGHEEY (SEQ ID NO: 2) | HLA-A1 | H/K/N RAS Q61H_A1_cl5 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSSYSPWTFGQ GTKVEIKRTGGGSGGGGSGGGASEV QLVESGGGLVQPGGSLRLSCAASGF NISPWDMHWVRQAPGKGLEWVAQLY PSSGYTNYADSVKGRFTISADTSKN TAYLQMNSLRAEDTAVYYCSRSVYW SLDYWGQGTLVTVSS | 146 |
| ILDTAGHEEY (SEQ ID NO: 2) | HLA-A1 | H/K/N RAS Q61H_A1_cl8 | DIQMTQSPSSLSASVGDRVTITCRA SQDVNTAVAWYQQKPGKAPKLLIYS ASFLYSGVPSRFSGSRSGTDFTLTI | 147 |

TABLE 3-continued

MANAbody scFv sequences.

| Target Peptide(s) | Target HLA Allele | scFv clone name | scFv sequence | SEQ ID NO: |
|---|---|---|---|---|
| | | | SSLQPEDFATYYCQQSFSTPITFGQ GTKVEIKRTGGGSGGGGSGGGASEV QLVESGGGLVQPGGSLRLSCAASGF NISEYLMHWVRQAPGKGLEWVALLP PGLSYTNYADSVKGRFTISADTSKN TAYLQMNSLRAEDTAVYYCSRYGYY AFDYWGQGTLVTVSS | |
| ILDTAGHEEY (SEQ ID NO: 2) | HLA-A1 | H/K/N RAS Q61H_A1_cl9 | DIQMTQSPSSLSASVGDRVTITCRA SQDVNTAVAWYQQKPGKAPKLLIYS ASFLYSGVPSRFSGSRSGTDFTLTI SSLQPEDFATYYCQQGEYSPLTFGQ GTKVEIKRTGGGSGGGGSGGGASEV QLVESGGGLVQPGGSLRLSCAASGF NVFESAMHWVRQAPGKGLEWVAWVY GSYDYTYYADSVKGRFTISADTSKN TAYLQMNSLRAEDTAVYYCSRSFAY FQAMDYWGQGTLVTVSS | 148 |
| ILDTAGHEEY (SEQ ID NO: 2) | HLA-A1 | H/K/N RAS Q61H_A1_ cl10 | DIQMTQSPSSLSASVGDRVTITCRA SQDVNTAVAWYQQKPGKAPKLLIYS ASFLYSGVPSRFSGSRSGTDFTLTI SSLQPEDFATYYCQQTYYTPVTFGQ GTKVEIKRTGGGSGGGGSGGGASEV QLVESGGGLVQPGGSLRLSCAASGF NISHYVMHWVRQAPGKGLEWVADFY PHSDSTYYADSVKGRFTISADTSKN TAYLQMNSLRAEDTAVYYCSRYQSY SFDYWGQGTLVTVSS | 149 |

3) H/K/N RAS Q61L(55-64)-A1

| Target Peptide(s) | Target HLA Allele | scFv clone name | scFv sequence | SEQ ID NO: |
|---|---|---|---|---|
| ILDTAGLEEY (SEQ ID NO: 3) | HLA-A1 | H/K/N RAS Q61L_A1_cl1 | DIQMTQSPSSLSASVGDRVTITCRA SQDVNTAVAWYQQKPGKAPKLLIYS ASFLYSGVPSRFSGSRSGTDFTLTI SSLQPEDFATYYCQQASRQPYTFGQ GTKVEIKRTGGGSGGGGSGGGASEV QLVESGGGLVQPGGSLRLSCAASGF NFSESGMHWVRQAPGKGLEWVAHFS GDSGYTYYADSVKGRFTISADTSKN TAYLQMNSLRAEDTAVYYCSRYMYY SGYFDYWGQGTLVTVSS | 150 |
| ILDTAGLEEY (SEQ ID NO: 3) | HLA-A1 | H/K/N RAS Q61L_A1_ cl2 (L2) | DIQMTQSPSSLSASVGDRVTITCRA SQDVNTAVAWYQQKPGKAPKLLIYS ASFLYSGVPSRFSGSRSGTDFTLTI SSLQPEDFATYYCQQAVSYPWTFGQ GTKVEIKRTGGGSGGGGSGGGASEV QLVESGGGLVQPGGSLRLSCAASGF NISSSGIHWVRQAPGKGLEWVAMVY GGSGYTNYADSVKGRFTISADTSKN TAYLQMNSLRAEDTAVYYCSRWAHY SAYMDYWGQGTLVTVSS | 151 |
| ILDTAGLEEY (SEQ ID NO: 3) | HLA-A1 | H/K/N RAS Q61L_A1_cl3 | DIQMTQSPSSLSASVGDRVTITCRA SQDVNTAVAWYQQKPGKAPKLLIYS ASFLYSGVPSRFSGSRSGTDFTLTI SSLQPEDFATYYCQQTSSYPITFGQ GTKVEIKRTGGGSGGGGSGGGASEV QLVESGGGLVQPGGSLRLSCAASGF NIYWYGMHWVRQAPGKGLEWVAQVY PWSGFTYYADSVKGRFTISADTSKN TAYLQMNSLRAEDTAVYYCSRDYYS YSLDYWGQGTLVTVSS | 152 |
| ILDTAGLEEY (SEQ ID NO: 3) | HLA-A1 | H/K/N RAS Q61L_A1_cl4 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSWYSPSTFGQ GTKVEIKRTGGGSGGGGSGGGASEV QLVESGGGLVQPGGSLRLSCAASGF NISASGMHWVRQAPGKGLEWVAWIW GGSSYTYYADSVKGRFTISADTSKN | 153 |

TABLE 3-continued

MANAbody scFv sequences.

| Target Peptide(s) | Target HLA Allele | scFv clone name | scFv sequence | SEQ ID NO: |
|---|---|---|---|---|
| | | | TAYLQMNSLRAEDTAVYYCSRGQYL SYMDYWGQGTLVTVSS | |
| ILDTAGLEEY (SEQ ID NO: 3) | HLA-A1 | H/K/N RAS Q61L_A1_cl5 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSYYAPITFGQ GTKVEIKRTGGGSGGGGSGGGASEV QLVESGGGLVQPGGSLRLSCAASGF NFSYYGMHWVRQAPGKGLEWVAWIY PFSGYTNYADSVKGRFTISADTSKN TAYLQMNSLRAEDTAVYYCSREYYS RAFDYWGQGTLVTVSS | 154 |
| ILDTAGLEEY (SEQ ID NO: 3) | HLA-A1 | H/K/N RAS Q61L_A1_cl6 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSYYSPWTFGQ GTKVEIKRTGGGSGGGGSGGGASEV QLVESGGGLVQPGGSLRLSCAASGF NISYSNIHWVRQAPGKGLEWVAMIY GTRGGTYYADSVKGRFTISADTSKN TAYLQMNSLRAEDTAVYYCSRYYSY AMDYWGQGTLVTVSS | 155 |
| ILDTAGLEEY (SEQ ID NO: 3) | HLA-A1 | H/K/N RAS Q61L_A1_cl7 | DIQMTQSPSSLSASVGDRVTITCRA SQDVNTAVAWYQQKPGKAPKLLIYS ASFLYSGVPSRFSGSRSGTDFTLTI SSLQPEDFATYYCQQAYYPPWTFGQ GTKVEIKRTGGGSGGGGSGGGASEV QLVESGGGLVQPGGSLRLSCAASGF NVSRWAMHWVRQAPGKGLEWVARVY PSGYLTYYADSVKGRFTISADTSKN TAYLQMNSLRAEDTAVYYCSRNMQS YMDYWGQGTLVTVSS | 156 |
| ILDTAGLEEY (SEQ ID NO: 3) | HLA-A1 | H/K/N RAS Q61L_A1_cl8 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSYSSGPVTFG QGTKVEIKRTGGGSGGGGSGGGASE VQLVESGGGLVQPGGSLRLSCAASG FNFSYGGIHWVRQAPGKGLEWVAMI YPLTGYTNYADSVKGRFTISADTSK NTAYLQMNSLRAEDTAVYYCSRDYY YSVDVWGQGTLVTVSS | 157 |
| ILDTAGLEEY (SEQ ID NO: 3) | HLA-A1 | H/K/N RAS Q61L_A1_cl9 | DIQMTQSPSSLSASVGDRVTITCRA SQDVNTAVAWYQQKPGKAPKLLIYS ASFLYSGVPSRFSGSRSGTDFTLTI SSLQPEDFATYYCQQTYYYPFTFGQ GTKVEIKRTGGGSGGGGSGGGASEV QLVESGGGLVQPGGSLRLSCAASGF NLYAWGMHWVRQAPGKGLEWVALVY GGWGSTSYADSVKGRFTISADTSKN TAYLQMNSLRAEDTAVYYCSRAGSS KMSAGAFDYWGQGTLVTVSS | 158 |
| ILDTAGLEEY (SEQ ID NO: 3) | HLA-A1 | H/K/N RAS Q61L_A1_cl10 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSYYPYYPWTF GQGTKVEIKRTGGGSGGGGSGGGAS EVQLVESGGGLVQPGGSLRLSCAAS GFNVSHSAMHWVRQAPGKGLEWVAT VHPDWGNTYYADSVKGRFTISADTS KNTAYLQMNSLRAEDTAVYYCSRWQ QYYYSFDYWGQGTLVTVSS | 159 |
| ILDTAGLEEY (SEQ ID NO: 3) | HLA-A1 | H/K/N RAS Q61L_A1_cl11 | DIQMTQSPSSLSASVGDRVTITCRA SQDVNTAVAWYQQKPGKAPKLLIYS ASFLYSGVPSRFSGSRSGTDFTLTI SSLQPEDFATYYCQQYDRPITFGQG TKVEIKRTGGGSGGGGSGGGASEVQ | 160 |

TABLE 3-continued

| | | | | |
|---|---|---|---|---|
| | | | MANAbody scFv sequences. | |
| Target Peptide(s) | Target HLA Allele | scFv clone name | scFv sequence | SEQ ID NO: |
| | | | LVESGGGLVQPGGSLRLSCAASGFN IYYEAMHWVRQAPGKGLEWVAQIYP WNDYTYYADSVKGRFTISADTSKNT AYLQMNSLRAEDTAVYYCSRNYYAA TMDYWGQGTLVTVSS | |
| | | 4) H/K/N RAS Q61R(55-64)-A1 | | |
| ILDTAGREEY (SEQ ID NO: 4) | HLA-A1 | H/R/N RAS Q61R_A1_cl1 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSYTSPLTFGQ GTKVEIKRTGGGSGGGGSGGGASEV QLVESGGGLVQPGGSLRLSCAASGF NIYYGVMHWVRQAPGKGLEWVAMIY PDSSWTYYADSVKGRFTISADTSKN TAYLQMNSLRAEDTAVYYCSRDQDF HYMNYYLSYALDYWGQGTLVTVSS | 161 |
| ILDTAGREEY (SEQ ID NO: 4) | HLA-A1 | H/R/N RAS Q61R_A1_cl2 | DIQMTQSPSSLSASVGDRVTITCRA SQDVNTAVAWYQQKPGKAPKLLIYS ASFLYSGVPSRFSGSRSGTDFTLTI SSLQPEDFATYYCQQYWYYPITFG QGTKVEIKRTGGGSGGGGSGGGASE VQLVESGGGLVQPGGSLRLSCAASG FNIYSYDMHWVRQAPGKGLEWVAIS PGGSYTYYADSVKGRFTISADTSKN TAYLQMNSLRAEDTAVYYCSRSAFT GYFDVWGQGTLVTVSS | 162 |
| ILDTAGREEY (SEQ ID NO: 4) | HLA-A1 | H/R/N RAS Q61R_A1_cl3 | DIQMTQSPSSLSASVGDRVTITCRA SQDVNTAVAWYQQKPGKAPKLLIYS ASFLYSGVPSRFSGSRSGTDFTLTI SSLQPEDFATYYCQQSYYAPITFGQ GTKVEIKRTGGGSGGGGSGGGASEV QLVESGGGLVQPGGSLRLSCAASGF NVQWSHMHWVRQAPGKGLEWVARLS PPSGYTNYADSVKGRFTISADTSKN TAYLQMNSLRAEDTAVYYCSRLILS KGGYGWAMDYWGQGTLVTVSS | 163 |
| ILDTAGREEY (SEQ ID NO: 4) | HLA-A1 | H/R/N RAS Q61R_A1_cl5 | DIQMTQSPSSLSASVGDRVTITCRA SQDVNTAVAWYQQKPGKAPKLLIYS ASFLYSGVPSRFSGSRSGTDFTLTI SSLQPEDFATYYCQQYYLYQPITFG QGTKVEIKRTGGGSGGGGSGGGASE VQLVESGGGLVQPGGSLRLSCAASG FNIGMYTMHWVRQAPGKGLEWVALV YPDSGYTNYADSVKGRFTISADTSK NTAYLQMNSLRAEDTAVYYCSRYTW QSMDYWGQGTLVTVSS | 164 |
| ILDTAGREEY (SEQ ID NO: 4) | HLA-A1 | H/R/N RAS Q61R_A1_cl6 (R6) | DIQMTQSPSSLSASVGDRVTITCRA SQDVNTAVAWYQQKPGKAPKLLIYS ASFLYSGVPSRFSGSRSGTDFTLTI SSLQPEDFATYYCQQYSNYPLTFGQ GTKVEIKRTGGGSGGGGSGGGASEV QLVESGGGLVQPGGSLRLSCAASGF NVFYGSMHWVRQAPGKGLEWVAFIG PDSTYTYYADSVKGRFTISADTSKN T AYLQMNSLRAEDTAVYYCSRDLGSA YAMDYWGQGTLVTVSSDIQMTQSPS SLSASVGDRVTITCRASQDVNTAVA WYQQKPGKAPKLLIYSASFLYSGVP SRFSGSRSGTDFTLTISSLQPEDFA TYYCQQYASDPITFGQGTKVEIKRT GGGSGGGGSGGGASEVQLVESGGGL VQPGGSLRLSCAASGFNLDYGWMHW | 165 |
| ILDTAGREEY (SEQ ID NO: 4) | HLA-A1 | H/R/N RAS Q61R_A1_cl7 | VRQAPGKGLEWVAWVPGSDYTDYA DSVKGRFTISADTSKNTAYLQMNSL RAEDTAVYYCSRFHYTAFDVWGQGT | 166 |

TABLE 3-continued

MANAbody scFv sequences.

| Target Peptide(s) | Target HLA Allele | scFv clone name | scFv sequence | SEQ ID NO: |
|---|---|---|---|---|
| | | | LVTVSSDIQMTQSPSSLSASVGDRV TITCRASQDVNTAVAWYQQKPGKAP | |
| ILDTAGREEY (SEQ ID NO: 4) | HLA-A1 | H/R/N RAS Q61R_A1_cl13 | KLLIYS ASFLYSGVPSRFSGSRSGTDFTLTI SSLQPEDFATYYCQQYSYDPITFGQ GTKVEIKRTGGGSGGGGSGGGASEV QLVESGGGLVQPGGSLRLSCAASGF NFSYSAMHWVRQAPGKGLEWVADVV PDGDWTYYADSVKGRFTISADTSKN TAYLQMNSLRAEDTAVYYCSRGWYA LDYWGQGTLVTVSS | 167 |
| ILDTAGREEY (SEQ ID NO: 4) | HLA-A1 | H/R/N RAS Q61R_A1_cl18 | DIQMTQSPSSLSASVGDRVTITCRA SQDVNTAVAWYQQKPGKAPKLLIYS ASFLYSGVPSRFSGSRSGTDFTLTI SSLQPEDFATYYCQQYIYDPVTFGQ GTKVEIKRTGGGSGGGGSGGGASEV QLVESGGGLVQPGGSLRLSCAASGF NVDWAWMHWVRQAPGKGLEWVAWVV GGSDYTYYADSVKGRFTISADTSKN TAYLQMNSLRAEDTAVYYCSRSYYY AFDYWGQGTLVTVSS | 168 |
| ILDTAGREEY (SEQ ID NO: 4) | HLA-A1 | H/R/N RAS Q61R_A1_cl19 | DIQMTQSPSSLSASVGDRVTITCRA SQDVNTAVAWYQQKPGKAPKLLIYS ASFLYSGVPSRFSGSRSGTDFTLTI SSLQPEDFATYYCQQLMYDPITFGQ GTKVEIKRTGGGSGGGGSGGGASEV QLVESGGGLVQPGGSLRLSCAASGF NFGTYWMHWVRQAPGKGLEWVAWFL PDYDYTLYADSVKGRFTISADTSKN TAYLQMNSLRAEDTAVYYCSRHGEY AFDYWGQGTLVTVSS | 169 |

Figure 1:
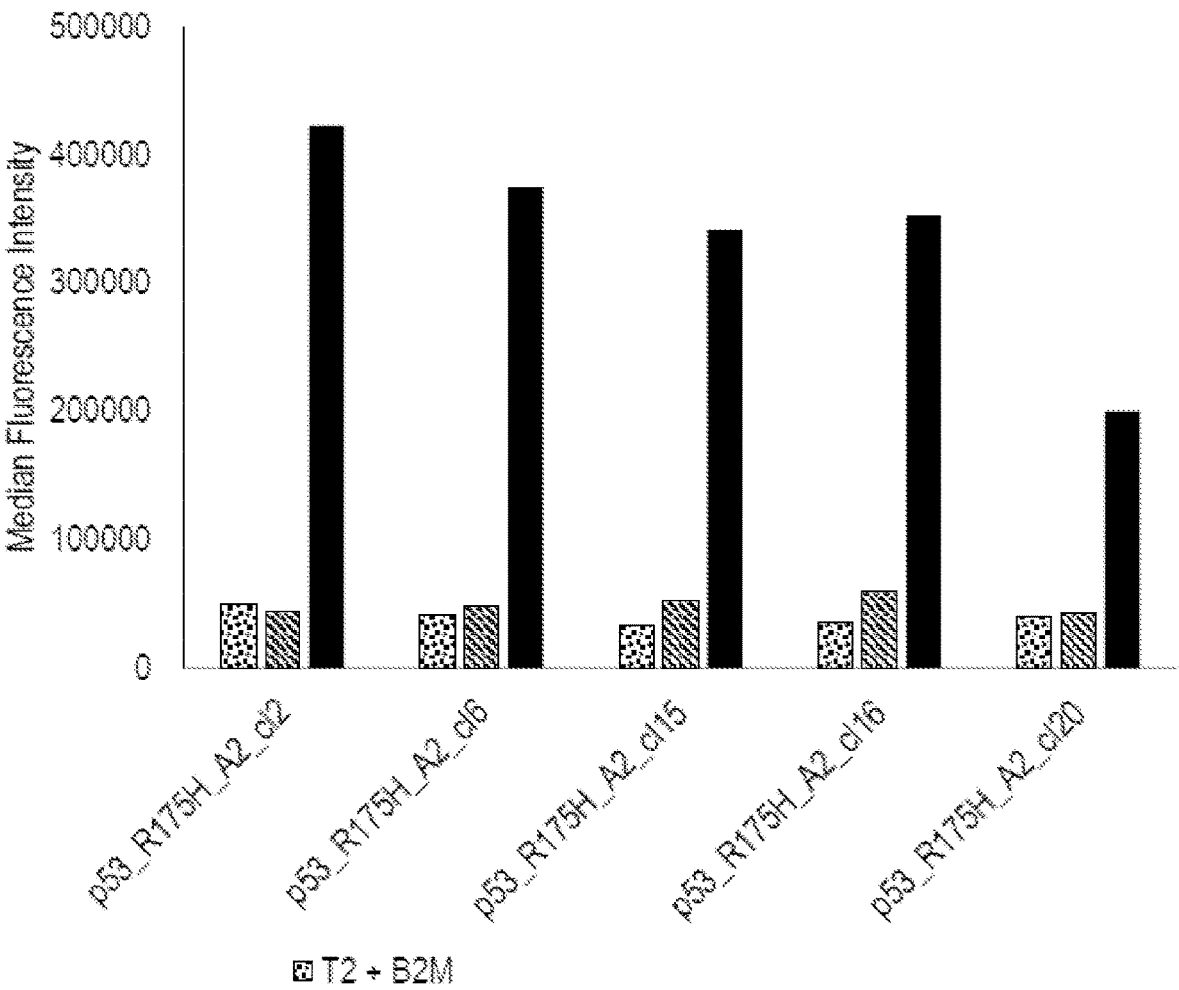
FIG. 1 contains a graph showing flow cytometry on peptide-pulsed A2+ cells. T2 cells were peptide-pulsed overnight at 37° C. in serum-free media with beta-2 microglobulin (β2M) protein only, or β2M with a p53 WT(168-176) peptide (HMTEVVRRC; SEQ ID NO:135), or p53 R175H(168-176) peptide (HMTEVVRHC; SEQ ID NO:1). Cells were stained with 50 μL of phage supernatant per 50 μL of cells, washed and stained with rabbit anti-M13 antibody, then washed and stained with anti-Rabbit-PE antibody. Cells were stained with a live/dead Near-infrared (IR) dye, washed, and analyzed by an iQue Screener (IntelliCyt, Albuquerque, NM).
Figure 2:
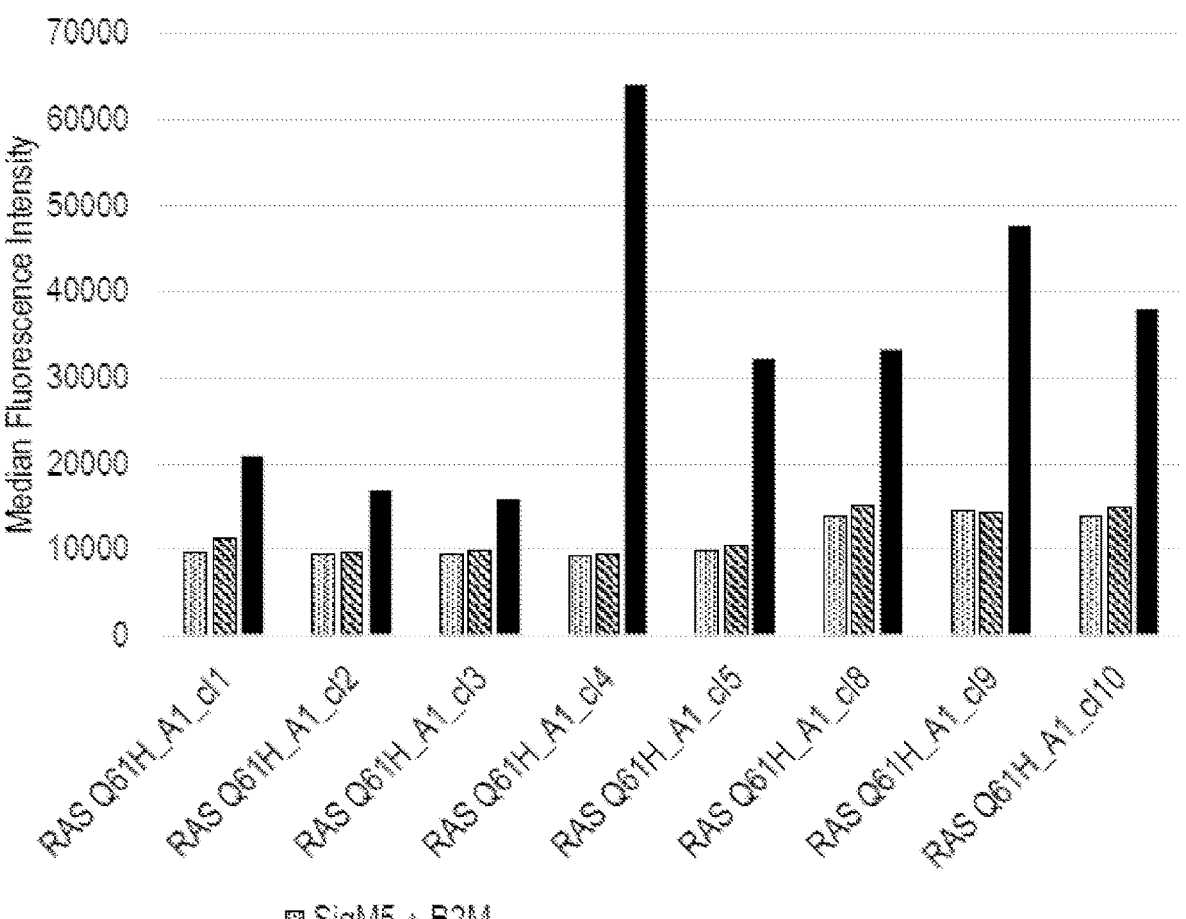
FIG. 2 contains a graph showing flow cytometry on peptide-pulsed A1+ cells. SigM5 cells were peptide-pulsed overnight at 37° C. in serum-free media with β2M only, β2M with the H/K/N RAS WT(55-64) peptide (ILDTAGQEEY; SEQ ID NO:136), β2M with a H/K/N RAS mutant Q61H(55-64) peptide (ILDTAGHEEY; SEQ ID NO:2). Cells were stained with 50 μL of phage supernatant per 50 μL of cells, washed and stained with rabbit anti-M13 antibody, then washed and stained with anti-Rabbit-PE antibody. Cells were stained with a live/dead Near-IR dye, washed, and analyzed by an iQue Screener (IntelliCyt, Albuquerque, NM).
Figure 3:
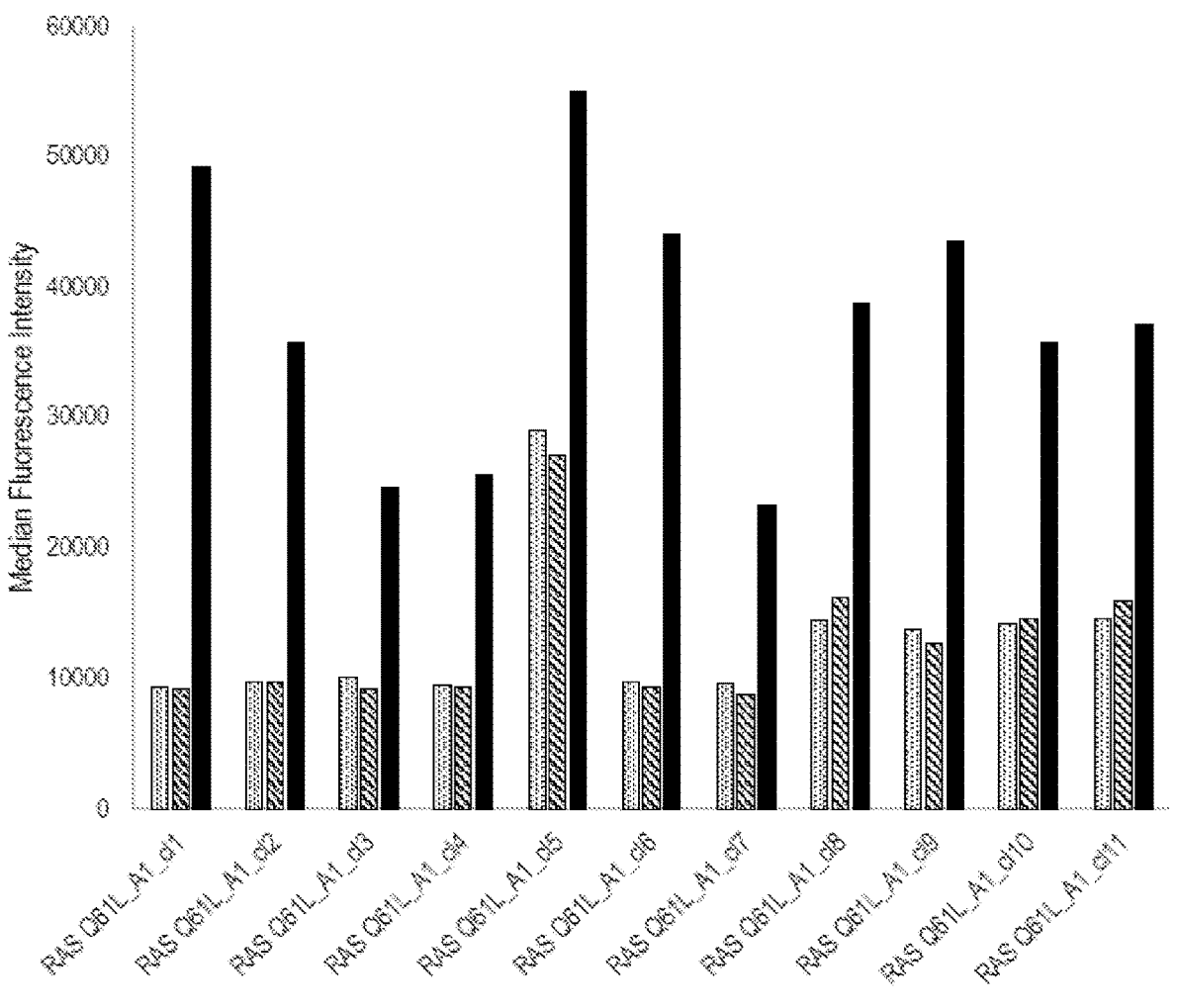
FIG. 3 contains a graph showing flow cytometry on peptide-pulsed A1+ cells. SigM5 cells were peptide-pulsed overnight at 37° C. in serum-free media with β2M only, β2M with the H/K/N RAS WT(55-64) peptide (ILD-TAGQEEY; SEQ ID NO:136), β2M with a H/K/N RAS mutant Q61L(55-64) peptide (ILDTAGLEEY; SEQ ID NO:3). Cells were stained with 50 μL of phage supernatant per 50 μL of cells, washed and stained with rabbit anti-M13 antibody, then washed and stained with anti-Rabbit-PE antibody. Cells were stained with a live/dead Near-IR dye, washed, and analyzed by an iQue Screener (IntelliCyt, Albuquerque, NM).
Figure 4:
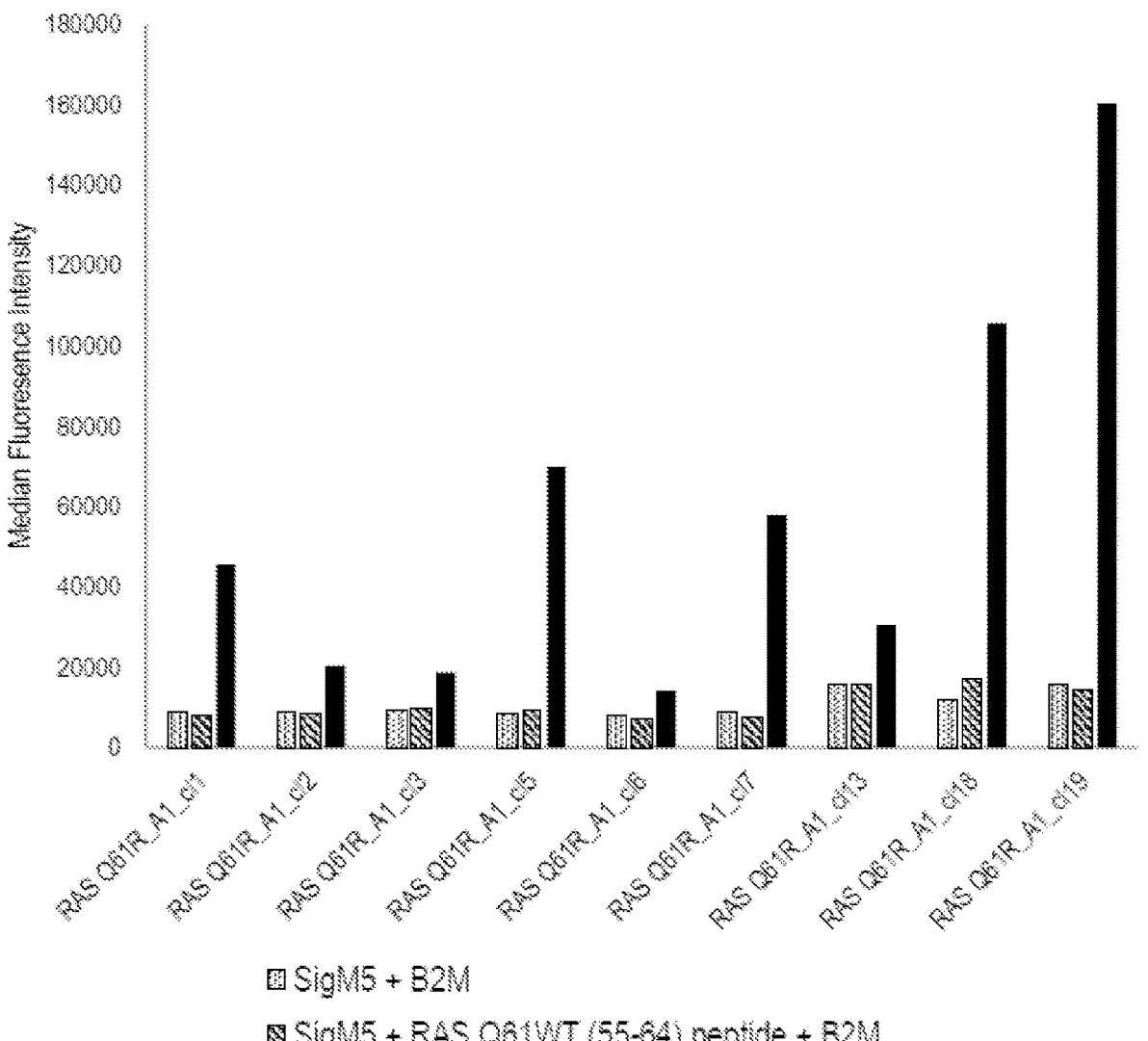
FIG. 4 contains a graph showing flow cytometry on peptide-pulsed A1+ cells. SigM5 cells were peptide-pulsed overnight at 37° C. in serum-free media with β2M only, β2M with the H/K/N RAS WT(55-64) peptide (ILD-TAGQEEY; SEQ ID NO:136), β2M with a H/K/N RAS mutant Q61R(55-64) peptide (ILDTAGREEY; SEQ ID NO:4). Cells were stained with 50 μL of phage supernatant per 50 μL of cells, washed and stained with rabbit anti-M13 antibody, then washed and stained with anti-Rabbit-PE antibody. Cells were stained with a live/dead Near-IR dye, washed, and analyzed by an iQue Screener (IntelliCyt, Albuquerque, NM).

Flow cytometry data for scFvs that specifically recognized a p53 peptide containing the R175H mutation in complex with HLA-A2 (HMTEVVRHC; SEQ ID NO: 1) are shown in FIG. 1. The scFvs specifically stained the HLA allele-matched cell lines when these cells are pulsed with the mutant peptide, but not the WT peptide or not pulsed with peptide at all. Flow cytometry data for scFvs specific for H/K/N RAS Q61H, Q61L, and Q61R peptides are shown in FIGS. 2-4.

To demonstrate that MANAbody clones can be utilized as a therapeutic modality, selected MANAbody clones were engineered into bispecific antibodies having one antibody-fragment binding to a mutant peptide presented in the context of HLA and having one antibody-fragment binding to a CD3 protein on the T cell surface (Table 4). The bispecific antibodies are referred to as single-chain diabody (scDb) hereafter. Specifically, bispecific antibodies targeting a mutant p53 R175H peptide presented in the context of HLA-A2 and CD3 were engineered, and bispecific antibodies targeting mutant H/K/N RAS Q61H, Q61L, and Q61R peptides presented in the context of HLA-A1 and CD3 were engineered.

Figure 5:
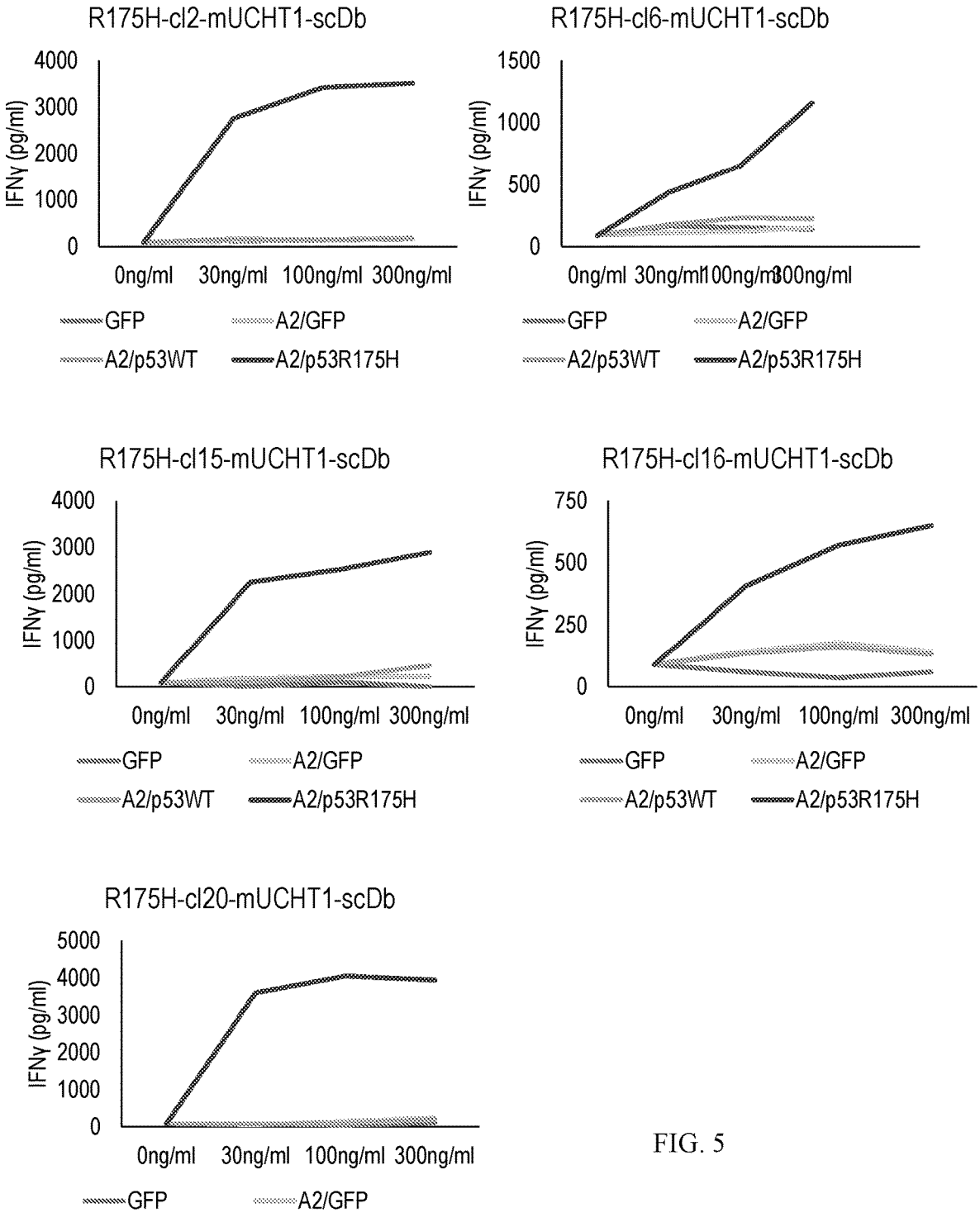
FIG. 5 contains graphs showing that scDbs can induce mutation-specific T-cell cytokine release. p53 R175H(168-176)-A2 cl.2, cl.6, cl.15, cl.16, and cl.20 scDbs, containing the anti-CD3 clone UCHT1, were incubated at the specified concentrations with T cells and COS-7 cells co-transfected with plasmids encoding various combinations of HLA-A2, p53(WT), p53(R175H), and GFP for 20 hours at 37° C. Following co-culture, conditioned media was collected and assayed for secreted IFNγ by ELISA.
Figure 6:
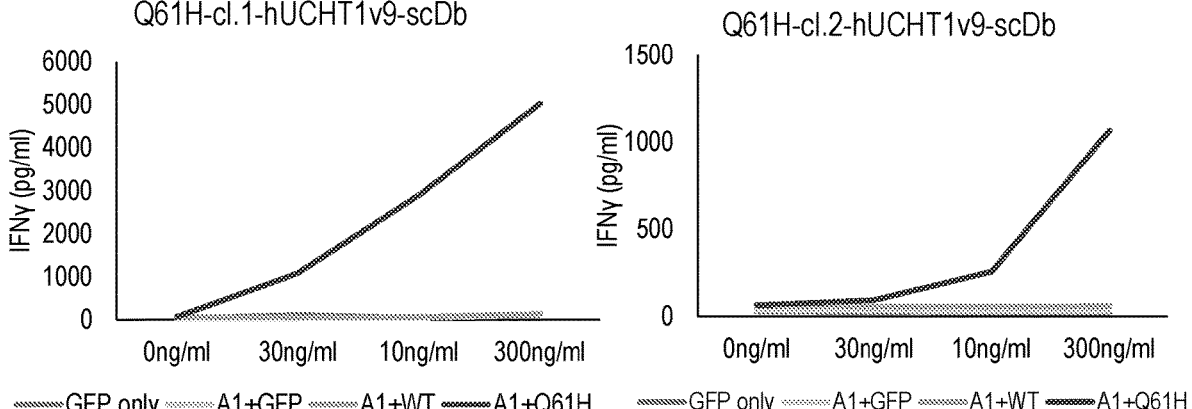
FIG. 6 contains graphs showing that scDbs can induce mutation-specific T-cell cytokine release. H/K/N RAS Q61H (55-64)-A1 cl.1, cl.2, and cl.4 scDbs, containing the anti-CD3 clone hUCHT1v9, were incubated at the specified concentrations with T cells and COS-7 cells co-transfected with plasmids encoding various combinations of HLA-A1, KRAS(WT), KRAS(Q61H), and GFP for 20 hours at 37° C. Following co-culture, conditioned media was collected and assayed for secreted IFNγ by ELISA.
Figure 6:
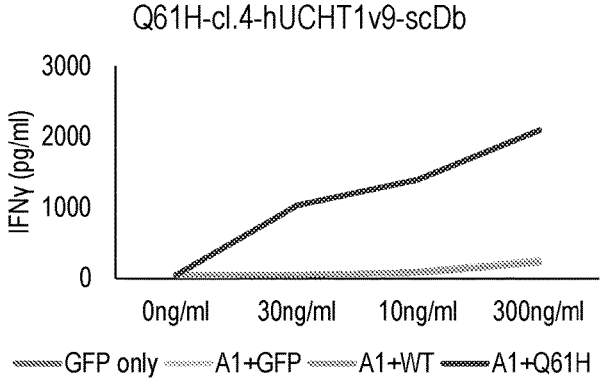
Figure 7:
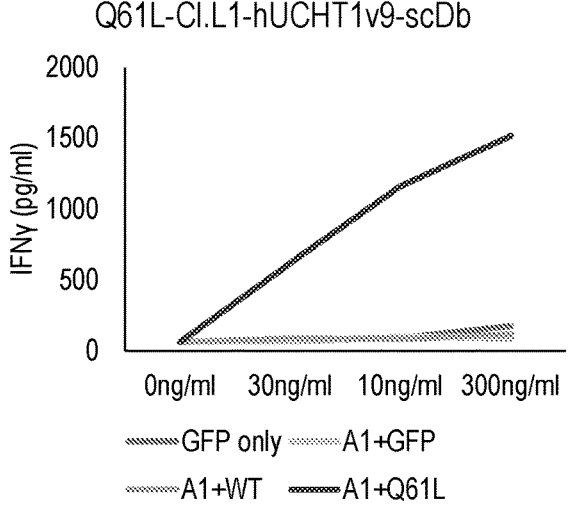
FIG. 7 contains graphs showing that scDbs can induce mutation-specific T-cell cytokine release. H/K/N RAS Q61L (55-64)-A1 cl.1, cl.2, cl.9, and cl.13 scDbs, containing the anti-CD3 clone hUCHT1v9, were incubated at the specified concentrations with T cells and COS-7 cells co-transfected with plasmids encoding various combinations of HLA-A1, KRAS(WT), KRAS(Q61L), and GFP for 20 hours at 37° C. Following co-culture, conditioned media was collected and assayed for secreted IFNγ by ELISA.
Figure 7:
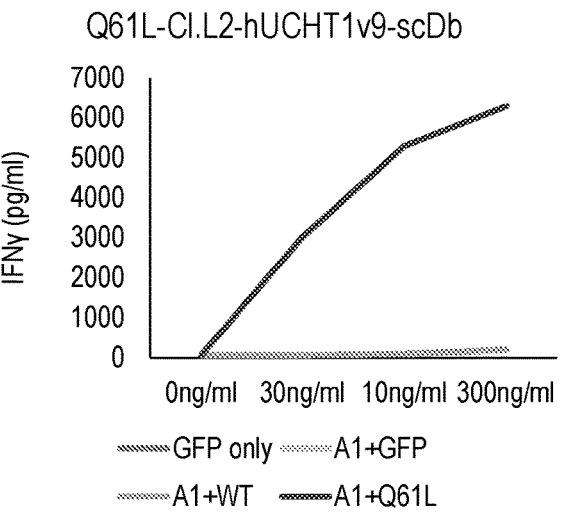
Figure 7:
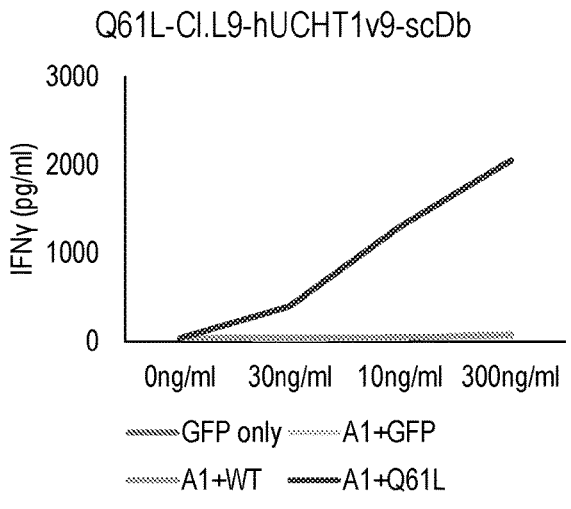
Figure 7:
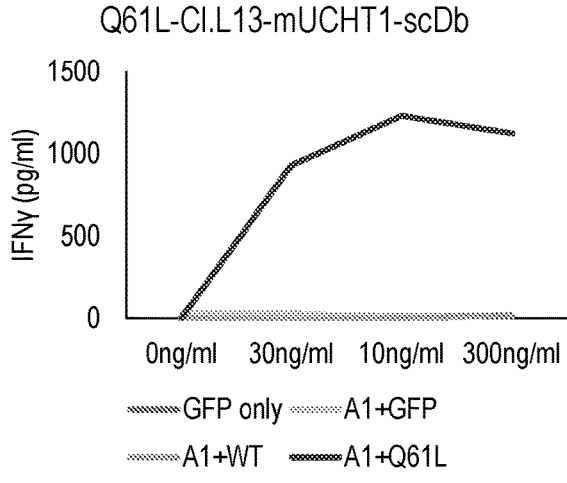
Figure 8:
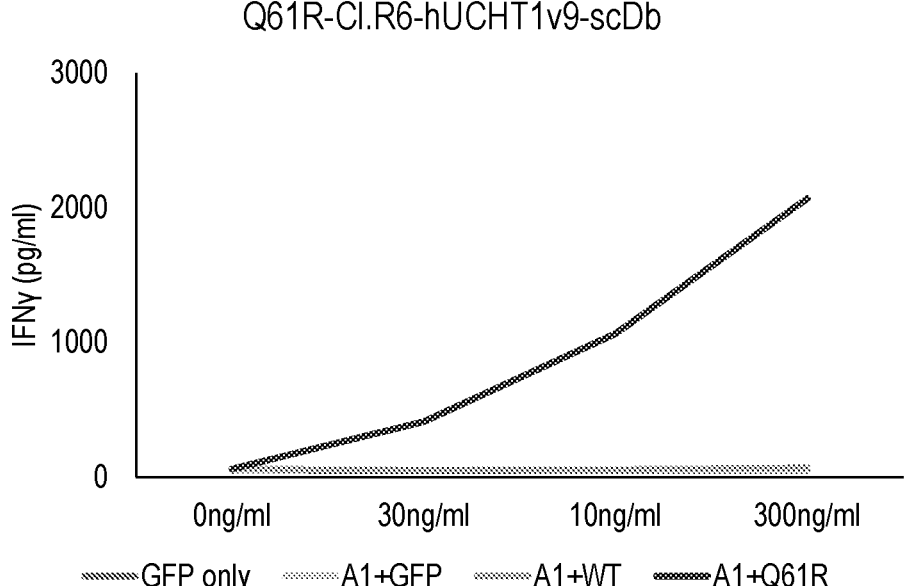
FIG. 8 contains a graph showing scDb can induce mutation-specific T-cell cytokine release. H/K/N RAS Q61R(55-64)-A1 cl.6 scDb, containing the anti-CD3 clone hUCHT1v9, was incubated at the specified concentrations with T cells and COS-7 cells co-transfected with plasmids encoding various combinations of HLA-A1, KRAS(WT), KRAS(Q61R), and GFP for 20 hours at 37° C. Following co-culture, conditioned media was collected and assayed for secreted IFNγ by ELISA.

Representative scDb co-culture results are shown in FIG. 5 for five p53 R175H HLA-A2 MANAbody scFv clones combined with anti-CD3 scFv. T cells were co-cultured with COS-7 cells co-transfected with plasmids encoding HLA-A2, full-length p53 variants, and/or GFP in the presence of the specified concentration of scDb. As a read out of T cell activation by cognate antigen on target cells, the release of IFNγ in the co-culture media supernatant was measured by ELISA. Only when COS-7 cells were co-transfected with HLA-A2 and mutant p53 R175H plasmids was there significant T cell release of IFNγ over background, with the level of IFNγ dependent on the concentration of scDb included in the well. T cells co-cultured with COS-7 cells co-transfected with HLA-A2 and WT p53 released only background levels of IFNγ. Representative scDb co-culture results are shown in FIGS. 6-8 for H/K/N RAS Q61H, Q61L, and Q61R HLA-A1 MANAbody scFv clones combined with an anti-CD3 clone into a scDb. In these co-cultures, only when COS-7 cells were co-transfected with HLA-A1 and mutant full-length KRAS Q61H, Q61L, or Q61R plasmids was there significant T cell release of IFNγ over background. T cells co-cultured with COS-7 cells co-transfected with HLA-A1 and WT KRAS released only background levels of IFNγ, similar to the levels of IFNγ seen in no scDb wells.

Figure 9A:
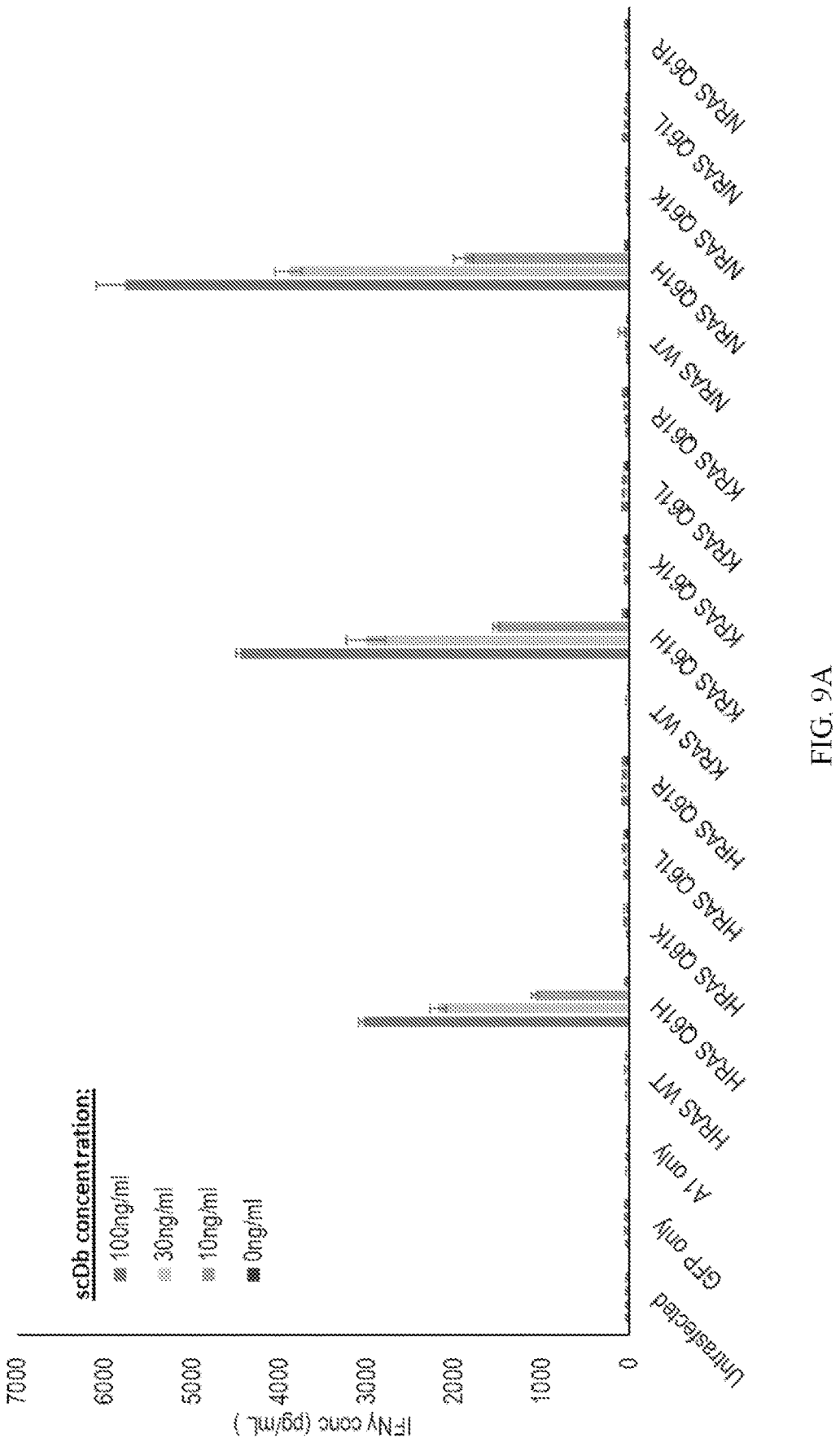
FIGS. 9A-9C contain graphs showing scDbs can react against Q61H, Q61L, and Q61R mutations in all 3 RAS isoforms, namely HRAS, KRAS, and NRAS.
Figure 9B:
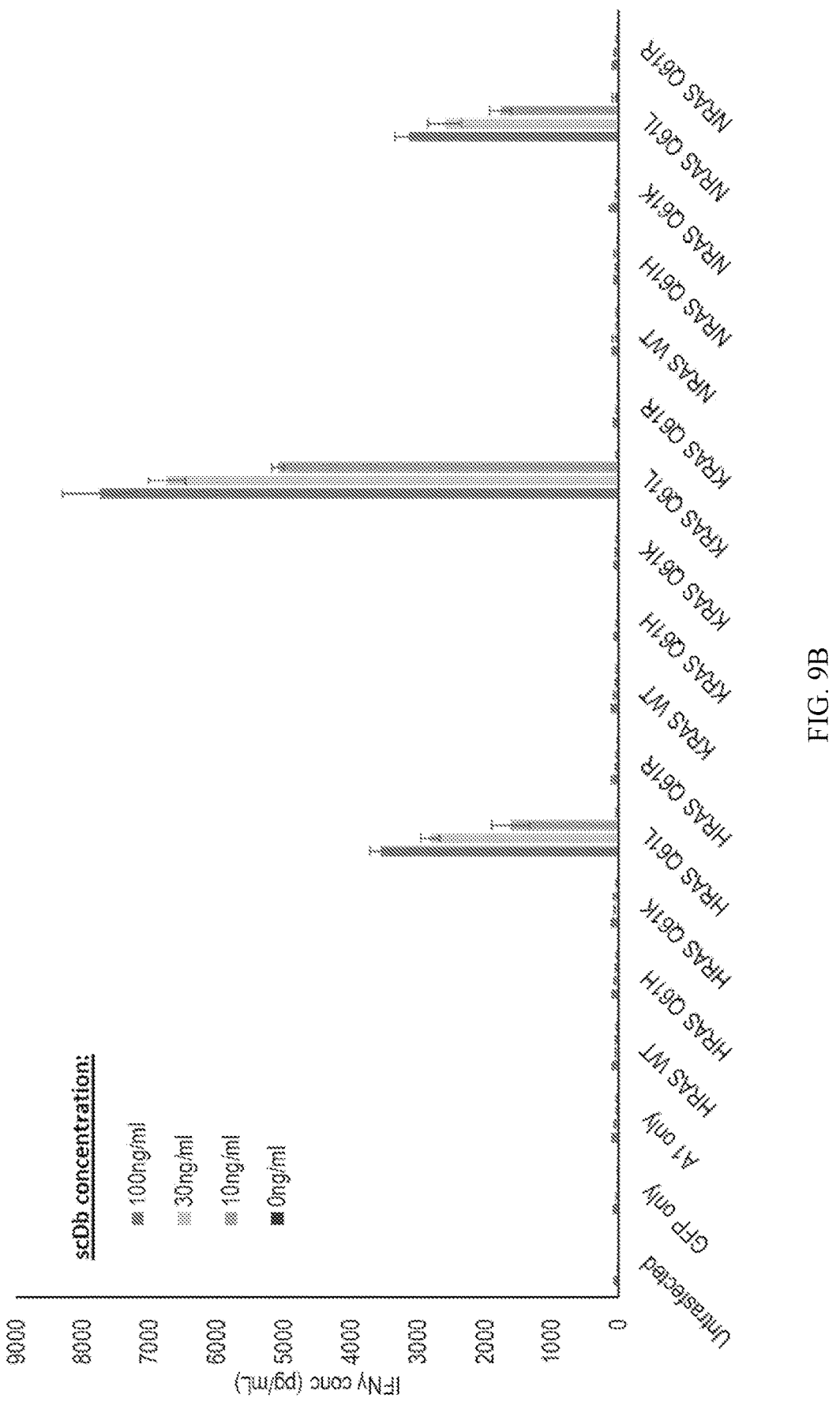
Figure 9C:
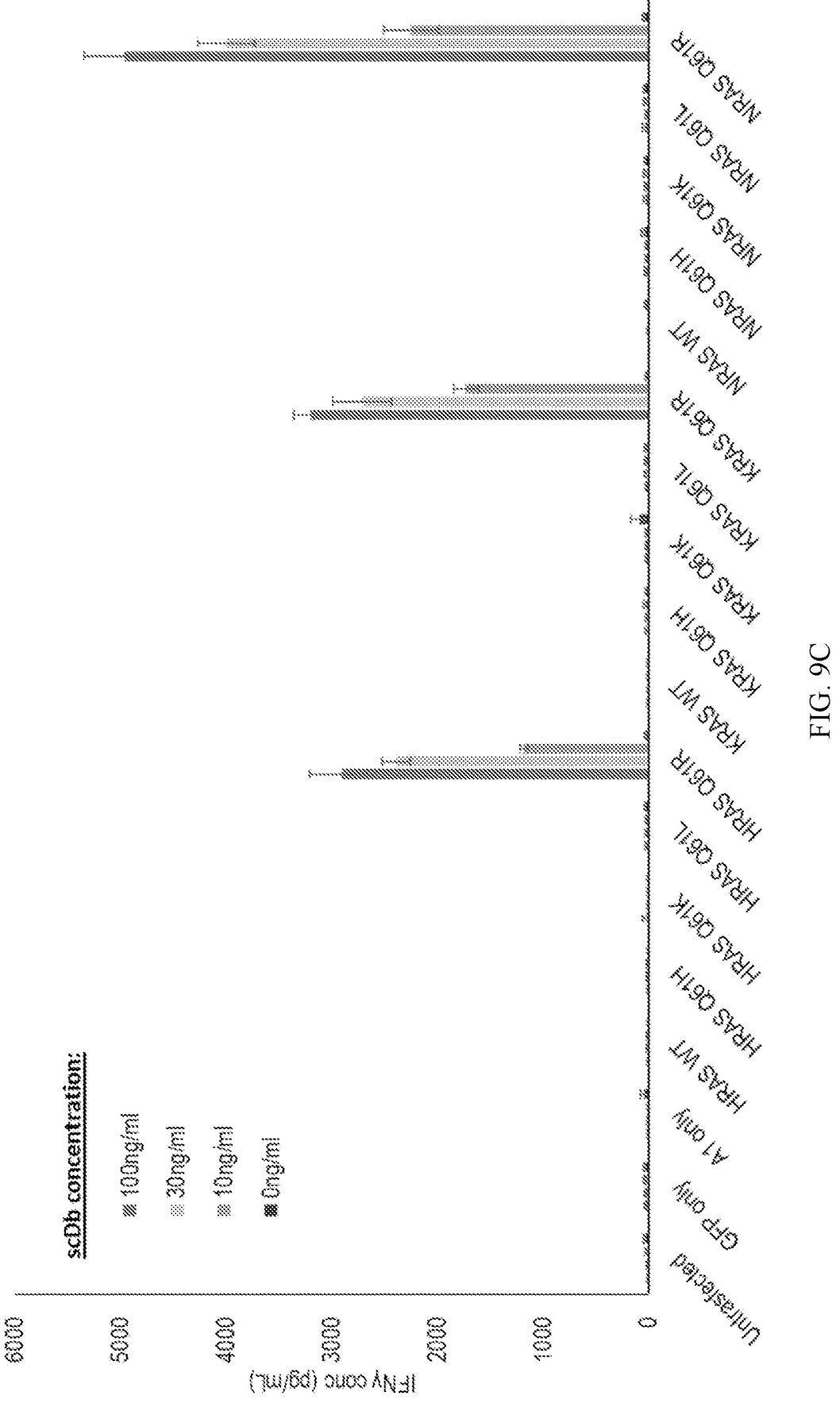

To evaluate whether the H/K/N RAS Q61H, Q61L, and Q61R scDbs can react against all 3 RAS isoforms with the cognate Q61 mutations, COS-7 cells were transfected with HLA-A1 and plasmids encoding for full-length HRAS, KRAS, or NRAS that are WT, or harbored Q61H, Q61K, Q61L, or Q61R mutation. The transfected COS-7 cells were then co-cultured with T cells and representative H/K/N RAS Q61H, Q61L, and Q61R scDbs. FIG. 9a shows that the H/K/N RAS Q61H scDb only induced IFNγ in the presence of COS-7 cells co-transfected with HLA-A1 and the Q61H mutant HRAS, KRAS, or NRAS. Likewise, H/K/N RAS Q61L scDb only induced IFNγ in the presence of COS-7 cells co-transfected with HLA-A1 and the Q61L mutant HRAS, KRAS, or NRAS (FIG. 9b) and H/K/N RAS Q61R scDb only induced IFNγ in the presence of COS-7 cells co-transfected with HLA-A1 and the Q61R mutant HRAS, KRAS, or NRAS (FIG. 9c).

Figure 10:
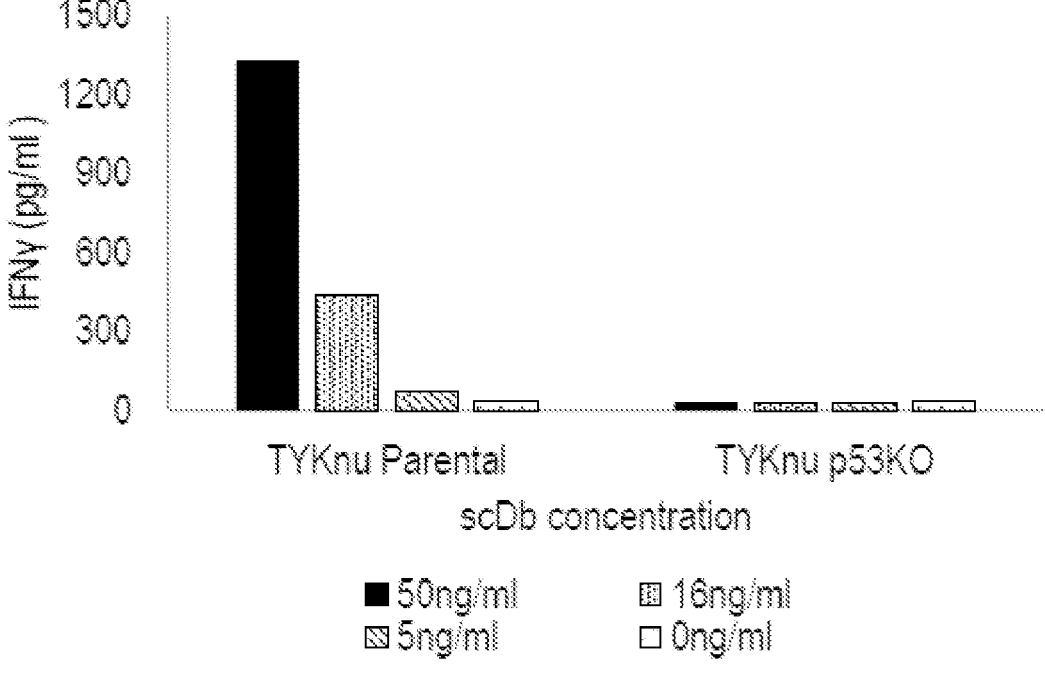
FIG. 10 contains graphs showing scDb can induce mutation-specific T-cell cytokine release against tumor cell line. p53 R175H(168-176)-A2 cl.2 UCHT1 scDb was incubated at the specified concentrations with T cells and either with parental TYKnu or p53 knockout (KO) TYKnu for 20 hours at 37° C. Following co-culture, conditioned media was collected and assayed for secreted IFNγ by ELISA.
Figure 11:
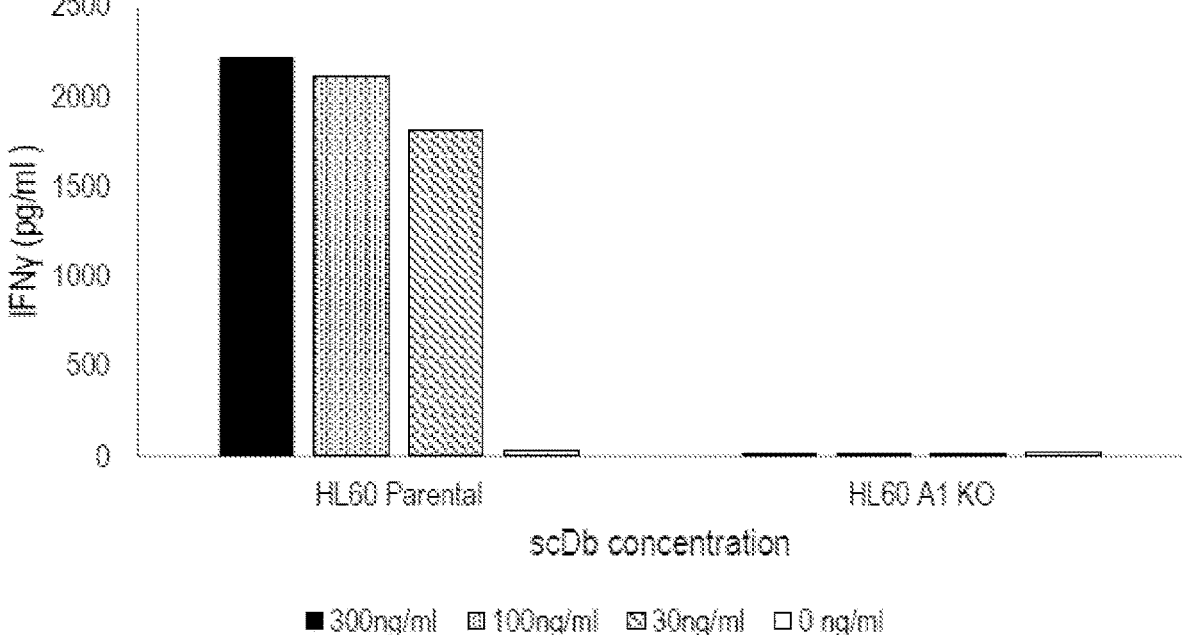
FIG. 11 contains graphs showing scDb can induce mutation-specific T-cell cytokine release against tumor cell line. H/K/N RAS Q61L(55-64)-A1 cl.2 UCHT1 scDb was incubated at the specified concentrations with T cells and either with parental HL-60 or HLA-A1 KO HL-60 for 20 hours at 37° C. Following co-culture, conditioned media was collected and assayed for secreted IFNγ by ELISA.

To evaluate the ability of MANAbody clones to recognize tumor cells, tumor cell lines with endogenous cognate HLA and mutations were co-cultured with T cells and scDbs. An endogenous p53 R175H HLA-A2 positive cell line TYKnu, along with its isogenic p53 knockout control, was cultured with T cells and p53 R175H HLA-A2 scDb. IFNγ release was only induced against the parental TYKnu cell line but not the p53 knockout TYKnu (FIG. 10). An endogenous NRAS Q61L HLA-A1 positive cell line HL-60, along with its isogenic HLA-A1 knockout control, was cultured with T cells and H/K/N RAS Q61L HLA-A1 scDb. IFNγ release was only seen against the parental HL-60 cell line but not the HLA-A1 knockout HL-60 (FIG. 11). Together, these findings suggest that bispecific antibodies containing MANAbody clones can target tumor cells expressing MANAs presented in the context of HLA molecules.

Figure 12:
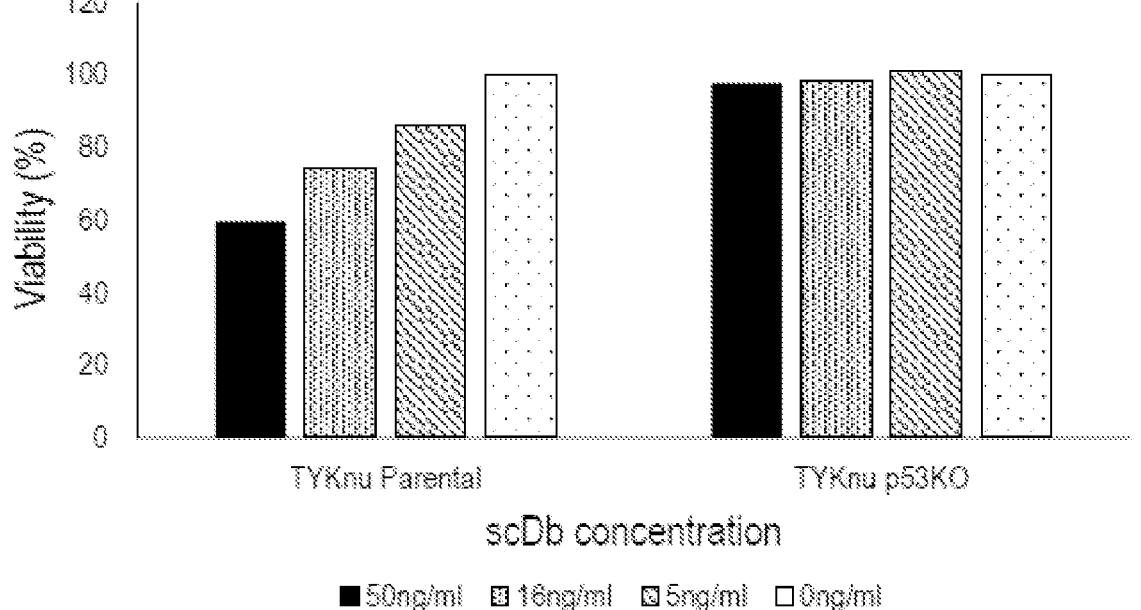
FIG. 12 shows that a MANAbody clone converted into a scDb can specifically kill tumor cells. p53 R175H(168-176)-A2 cl.2 UCHT1 scDb was incubated at the specified concentrations with T cells and either with parental TYKnu or p53 KO TYKnu for 20 hours at 37° C. Following co-culture, CellTiter-Glo was used to assay viable cells in each well. Percent target cell viability was calculated by subtracting the value from T cell only wells and normalizing to the value from target cell only wells.
Figure 13:
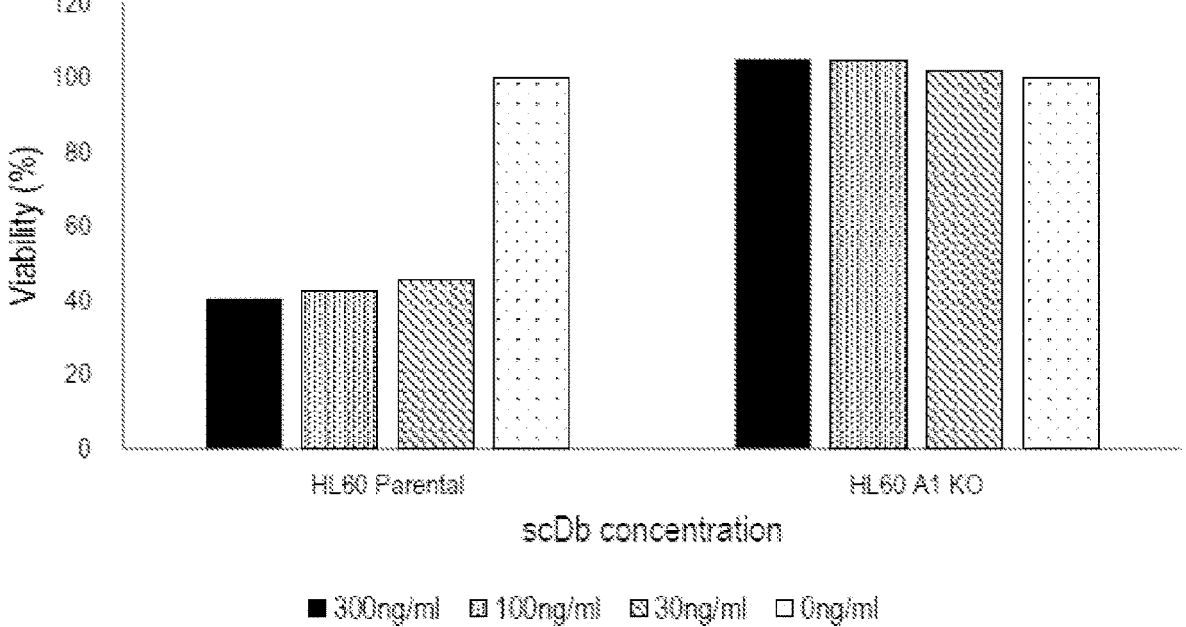
FIG. 13 shows that a MANAbody clone converted into a scDb can specifically kill tumor cells. H/K/N RAS Q61L (55-64)-A1 cl.2 UCHT1 scDb was incubated at the specified concentrations with T cells and either with parental HL-60 or HLA-A1 KO HL-60 for 20 hours at 37° C. Following co-culture, CellTiter-Glo was used to assay viable cells in each well. Percent target cell viability was calculated by subtracting the value from T cell only wells and normalizing to the value from target cell only wells.

To evaluate the efficacy of using MANAbody clones as a therapeutic modality, target cell viability of p53 R175H HLA-A2 and H/K/N RAS Q61L HLA-A1 scDb co-cultures was assayed using Promega's CellTiter-Glo reagent. CellTiter-Glo measures ATP concentration in a well, which is proportional to the number of viable cells. Percent target cell viability was measured by subtracting the CellTiter-Glo value from T cell only wells and normalizing to target cell only wells. Only when parental TYKnu cells were incubated with T cells in the presence of the p53 R175H HLA-A2 scDb, was there significant target cell death (FIG. 12). No target cell death was observed among the TYKnu p53 knockout wells. Similarly, only when parental HL-60 cells were incubated with T cells in the presence of the H/K/N RAS Q61L HLA-A1 scDb, was there significant target cell death (FIG. 13). No target cell death was observed among the HL-60 HLA-A1 knockout wells.

Together, these findings demonstrate that MANAbodies can be used to redirect and activate T cells to kill tumor cells expressing particular mutant protein and HLA allele pairs (e.g., p53 R175H with HLA-A2 and H/K/N RAS Q61L with HLA-A1).

TABLE 4

| Anti-human CD3 scFv sequences | | |
|---|---|---|
| Clone Name | Clone scFv Sequence | SEQ ID NO: |
| humanized UCHT1 (hUCHT1v9) | DIQMTQSPSSLSASVGDRVT ITCRASQDIRNYLNWYQQKP GKAPKLLIYYTSRLESGVPS RFSGSGSGTDYTLTISSLQP EDFATYYCQQGNTLPWTFGQ GTKVEIKGGGGSGGGGSGGG GSEVQLVESGGGLVQPGGSL RLSCAASGYSFTGYTMNWVR QAPGKGLEWVALINPYKGVS TYNQKFKDRFTISVDKSKNT AYLQMNSLRAEDTAVYYCAR SGYYGDSDWYFDVWGQGTLV TVSS | 170 |
| murine UCHT1 (mUCHT1) | DIQMTQTTSSLSASLGDRVT ISCRASQDIRNYLNWYQQKP DGTVKLLIYYTSRLHSGVPS KFSGSGSGTDYSLTISNLEQ EDIATYFCQQGNTLPWTFAG GTKLEIKGGGGSGGGGSGGG | 171 |

TABLE 4-continued

| Anti-human CD3 scFv sequences | | |
|---|---|---|
| Clone Name | Clone scFv Sequence | SEQ ID NO: |
| | GSEVQLQQSGPELVKPGASM KISCKASGYSFTGYTMNWVK QSHGKNLEWMGLINPYKGVS TYNQKFKDKATLTVDKSSST AYMELLSLTSEDSAVYYCAR SGYYGDSDWYFDVWGAGTTV TVSS | |
| diL2K | DIVLTQSPATLSLSPGERAT LSCRASQSVSYMNWYQQKPG KAPKRWIYDTSKVASGVPAR FSGSGSGTDYSLTINSLEAE DAATYYCQQWSSNPLTFGGG TKVEIKGGGGSGGGGSGGGG SDVQLVQSGAEVKKPGASVK VSCKASGYTFTRYTMHWVRQ APGQGLEWIGYINPSRGYTN YADSVKGRFTITTDKSTSTA YMELSSLRSEDTATYYCARY YDDHYCLDYWGQGTTVTVSS | 172 |
| hXR32 | QAVVTQEPSLTVSPGGTVTL TCRSSTGAVTTSNYANWVQQ KPGQAPRGLIGGTNKRAPWT PARFSGSLLGGKAALTITGA QAEDEADYYCALWYSNLWVF GGGTKLTVLGGGGSGGGGSG GGGSEVQLVESGGGLVQPGG SLRLSCAASGFTFNTYAMNW VRQAPGKGLEWVARIRSKYN NYATYYADSVKDRFTISRDD SKNSLYLQMNSLKTEDTAVY YCVRHGNFGNSYVSWFAYWG QGTLVTVSS | 173 |
| L2K-07/ TR66 | DIQLTQSPAIMSASPGEKVT MTCRASSSVSYMNWYQQKSG TSPKRWIYDTSKVASGVPYR FSGSGSGTSYSLTISSMEAE DAATYYCQQWSSNPLTFGAG TKLELKGGGGSGGGGSGGGG SDIKLQQSGAELARPGASVK MSCKTSGYTFTRYTMHWVKQ RPGQGLEWIGYINPSRGYTN YNQKFKDKATLTTDKSSSTA YMQLSSLTSEDSAVYYCARY YDDHYCLDYWGQGTTLTVSS | 174 |
| OKT3 | QIVLTQSPAIMSASPGEKVT MTCSASSSVSYMNWYQQKSG TSPKRWIYDTSKLASGVPAH FRGSGSGTSYSLTISGMEAE DAATYYCQQWSSNPFTFGSG TKLEINGGGGSGGGGSGGGG SQVQLQQSGAELARPGASVK MSCKASGYTFTRYTMHWVKQ RPGQGLEWIGYINPSRGYTN YNQKFKDKATLTTDKSSSTA YMQLSSLTSEDSAVYYCARY YDDHYCLDYWGQGTTLTVSS | 175 |
| PSMA-CD3 | QTVVTQEPSLTVSPGGTVTL TCGSSTGAVTSGNYPNWVQQ KPGQAPRGLIGGTKFLAPGT PARFSGSLLGGKAALTLSGV QPEDEAEYYCVLWYSNRWVF GGGTKLTVLGGGGSGGGGSG GGGSEVQLVESGGGLVQPGG SLKLSCAASGFTFNKYAMNW VRQAPGKGLEWVARIRSKYN NYATYYADSVKDRFTISRDD SKNTAYLQMNNLKTEDTAVY YCVRHGNFGNSYISYWAYWG QGTLVTVSS | 176 |

TABLE 4-continued

Anti-human CD3 scFv sequences

| Clone Name | Clone scFv Sequence | SEQ ID NO: |
|---|---|---|
| 28F11 | EIVLTQSPATLSLSPGERAT LSCRASQSVSSYLAWYQQKP GQAPRLLIYDASNRATGIPA RFSGSGSGTDFTLTISSLEP EDFAVYYCQQRSNWPPLTFG GGTKVEIKGGGGSGGGGSGG GGSQVQLVESGGGVVQPGRS LRLSCAASGFKFSGYGMHWV RQAPGKGLEWVAVIWYDGSK KYYVDSVKGRFTISRDNSKN TLYLQMNSLRAEDTAVYYCA RQMGYWHFDLWGRGTLVTVS S | 177 |
| 27H5-VL1 | EIVLTQSPRTLSLSPGERAT LSCRASQSVSSYLAWYQQK PGQAPRLLIYDASSRATGIP DRFSGSGSGTDFTLTISRLD PEDFAVYYCQQYGSSPITFG QGTRLEIKGGGGSGGGGSGG GGSQVQLVESGGGVVQPGRS LRLSCAASGFTFRSYGMHWV RQAPGKGLEWVAIIWYDGSK KNYADSVKGRFTISRDNSKN TLYLQMNSLRAEDTAVYYCA RGTGYNWFDPWGQGTLVTVS S | 178 |
| 27H5-VL2 | DILMTQSPSSLSASVGDRVT ITCRASQGISSALAWYQQKP GKAPKLLIYYASSLQSGVPS RFSGSGSGTDYTLTISSLQP EDFATYYCQQYYSTLTFGGG TKVEIKGGGGSGGGGSGGGG SQVQLVESGGGVVQPGRSLR LSCAASGFTFRSYGMHWVRQ APGKGLEWVAIIWYDGSKKN YADSVKGRFTISRDNSKNTL YLQMNSLRAEDTAVYYCARG TGYNWFDPWGQGTLVTVSS | 179 |
| 23F10 | EIVLTQSPATLSLSPGERAT LSCRASQSVSSYLAWYQQKP GQAPRLLIYDASNRATGIPA RFSGSGSGTDFTLTISSLEP EDFAVYYCQQRSNWPPLTFG GGTKVEIKGGGGSGGGGSGG GGSQVQLVQSGGGVVQSGRS LRLSCAASGFKFSGYGMHWV RQAPGKGLEWVAVIWYDGSK KYYVDSVKGRFTISRDNSKN TLYLQMNSLRGEDTAVYYCA RQMGYWHFDLWGRGTLVTVS S | 180 |
| 15C3-VL1 | EIVLTQSPATLSLSPGERAT LSCRASQSVSSYLAWYQQKP GQAPRLLIYDASNRATGIPA RFSGSGSGTDFTLTISSLEP EDFAVYYCQQRSNWPWTFGQ GTKVEIKGGGGSGGGGSGGG GSQVQLVQSGGGVVQPGRSL RLSCVASGFTFSSYGMHWVR QAPGKGLEWVAAIWYNGRKQ DYADSVKGRFTISRDNSKNT LYLQMNSLRAEDTAVYYCTR GTGYNWFDPWGQGTLVTVSS | 181 |
| 15C3-VL2 | AIQLTQSPSSLSASVGDRVT ITCRASQGISSALAWYQQKP GKAPKLLIYDASSLESGVPS RFSGSGSGTDFTLTISSLQP EDFATYYCQQFNSYPITFGQ | 182 |

TABLE 4-continued

Anti-human CD3 scFv sequences

| Clone Name | Clone scFv Sequence | SEQ ID NO: |
|---|---|---|
|  | GTRLEIKGGGGSGGGGSGGG GSQVQLVQSGGGVVQPGRSL RLSCVASGFTFSSYGMHWVR QAPGKGLEWVAAIWYNGRKQ DYADSVKGRFTISRDNSKNT LYLQMNSLRAEDTAVYYCTR GTGYNWFDPWGQGTLVTVSS |  |
| hu12F6 | QIVLSQSPAILSASPGEKVT MTCRASSSVSYMHWYQQKPG SSPKPWIYATSNLASGVPAR FSGSGSGTSYSLTISRVEAE DAATYYCQQWSSNPPTFGGG TKLETKRGGGGSGGGGSGGG GSQVQLQQSGAELARPGASV KMSCKASGYTFTSYTMHWVK QRPGQGLEWIGYINPSSGYT KYNQKFKDKATLTADKSSST AYMQLSSLTSEDSAVYYCAR WQDYDVYFDYWGQGTTLTVS S | 183 |

TABLE 5

Anti-human CD16a scFv sequences

| Clone Name | Clone scFv Sequence | SEQ ID NO: |
|---|---|---|
| 3G8 | DIVLTQSPASLAVSLGQRATISCKA SQSVDFDGDSFMNWYQQKPGQPPKL LIYTTSNLESGIPARFSASGSGTDF TLNIHPVEEEDTATYYCQQSNEDPY TFGGGTKLELKGGGGSGGGGSGGGG SQVTLKESGPGILQPSQTLSLTCSF SGFSLRTSGMGVGWIRQPSGKGLEW LAHIWWDDDKRYNPALKSRLTISKD TSSNQVFLKIASVDTADTATYYCAQ INPAWFAYWGQGTLVTVSA | 185 |
| Humanized 3G8 clone Mu 3 | DIVLTQSPDSLAVSLGERATINCKA SQSVDFDGDSFMNWYQQKPGQPPKL LIYTTSNLESGVPDRFSGSGSGTDF TLTIRPLQAEDVAVYYCQQSNEDPY TFGQGTKLEIKGGGGSGGGGSGGGG SQVTLKESGPALVKPTQTLTLTCTF SGFSLSTSGMGVGWIRQPPGKALEW LAHIWWDDDKRYNPALKSRLTISKD TSKNQVVLTMTNMDPVDTATYYCAQ INPAWFAYWGQGTLVTVSS | 186 |
| muA9 | DIELTQESALTTSPGETVTLTCRSN TGTVTTSNYANWVQEKPDHLFTGLI GHTNNRAPGVPARFSGSLIGDKAAL TITGAQTEDEAIYFCALWYNNHWVF GGGTKLEIKGGGGSGGGGSGGGGSE VQLQESGAELVRPGTSVKISCKASG YTFTNYWLGWVKQRPGHGLEWIGDI YPGGGYTNYNEKFKGKATVTADTSS RTAYVQVRSLTSEDSAVYFCARSAS WYFDVWGQGTTVTVSS | 187 |
| huA9 | DIELTQSPSSLSASVGDRVTITCRS NTGTVTTSNYASWYQQKPGKAPGGL IGHTNNRAPGVPSRFSGSLSGADAT LTISSLKPEDLATYYCALWYNHWVF GQGTKLEIKGGGGSGGGGSGGGGSE VQLQESGGGLVQPGDSLRLSCAASG FTFSNYWLGWIRQAPGKGPEWVGDI YPGGGYTNYNEKFKGRFTISADTSK | 188 |

TABLE 5-continued

Anti-human CD16a scFv sequences

| Clone Name | Clone scFv Sequence | SEQ ID NO: |
|---|---|---|
| | NIAYLQVNSLRAEDTAVYYCARSAS WYFDVWGQGTLVTVSS | |
| LSIV21 | SYVLTQPSSVSVAPGQTATISCGGH NIGSKNVHWYQQRPGQSPVLVIYQD NKRPSGIPERFSGSNSGNTATLTIS GTQAMDEADYYCQVWDNYSVLFGGG TKLTVLGGGGSGGGGSGGGGSQVQL VQSGAEVKKPGESLKVSCKASGYTF TSYYMHWVRQAPGQGLEWMGIINPS GGSTSYAQKFQGRVTMTRDTSTSTV YMELSSLRSEDTAVYYCARGSAYYY DFADYWGQGTLVTVSS | 189 |

Materials and Methods

Cells and Cell Lines.

RPMI-6666 cells (ATCC, Manassas, VA) were cultured in RPMI-1640 (ATCC) with 20% FBS (GE Hyclone, Logan, Utah, USA), and 1% penicillin streptomycin (Life Technologies). T2 cells (ATCC) and TYKnu (JCRB, Japan) were cultured in RPMI-1640 (ATCC) with 10% FBS (GE Hyclone), and 1% penicillin streptomycin (Thermo Fisher). SigM5 cells (DSMZ, Brunswick, Germany) and HL-60 cells (ATCC) were cultured in Iscove's MDM (ATCC) with 20% FBS (GE Hyclone), and 1% penicillin streptomycin (Thermo Fisher). COS-7 cells (ATCC) was cultured in McCoy's 5A (Modified) Medium (Thermo Fisher) with 10% FBS (GE Hyclone), and 1% penicillin streptomycin (Thermo Fisher). COS-7 cells (ATCC, CRL-1651™) were cultured in DMEM (high glucose, pyruvate; Thermo Fisher) with 10% FBS (GE Hyclone), and 1% Penicillin-Streptomycin (Thermo Fisher). 293FT cells (Thermo Fisher) were cultured in high-glucose D-MEM (Thermo Fisher), with 10% FBS (GE Hyclone), 0.1 mM MEM Non-Essential Amino Acids (NEAA, Thermo Fisher), 6 mM L-glutamine (Thermo Fisher), 1 mM MEM Sodium Pyruvate (Thermo Fisher), 500 µg/ml geneticin (Thermo Fisher), and 1% Penicillin-Streptomycin (Thermo Fisher). All cell lines were maintained at 37° C. under 5% $CO_2$.

PBMCs were obtained by Ficoll-Paque PLUS (GE Healthcare) gradient centrifugation of whole blood from healthy volunteer donors. To activate and expand T cells, PBMCs were cultured with 15 ng/ml OKT3 (BioLegend, San Diego, CA), 100 IU/mL recombinant human interleukin-2 (Aldesleukin, Prometheus Therapeutics and Diagnostics, San Diego, CA), and 5 ng/ml recombinant human interleukin-7 (BioLegend, San Diego, CA) in RPMI-1640 (ATCC) with 10% FBS (GE Hyclone), 1% Penicillin-Streptomycin (Life Technologies) at 37° C. under 5% $CO_2$ for 3 days. After 3 days, the expanded T cells were kept in the same cytokine-containing media without OKT3.

Phage Display Library Construction.

Oligonucleotides were synthesized by GeneArt (Thermo Fisher Scientific) using trinucleotide mutagenesis (TRIM) technology. The oligonucleotides were incorporated into the pADL-10b phagemid (Antibody Design Labs, San Diego, CA). This phagemid contains an F1 origin, a transcriptional repressor to limit uninduced expression, a lac operator, and a lac repressor. The scFv was synthesized with a pelB periplasmic secretion signal and was subcloned downstream of the lac operator. A FLAG (DYKDDDDK; SEQ ID NO:190) epitope tag was placed immediately downstream of the variable heavy chain, which was followed in frame by the full-length M13 pIII coat protein sequence.

Ten ng of the ligation product was mixed on ice with 10 µL of electrocompetent SS320 cells (Lucigen, Middleton, WI) and 14 µL of double-distilled water. This mixture was electroporated (200 ohms, 25 microFarads, 1.8 kV) using a Gene Pulser electroporation system (Bio-Rad, Hercules, CA) and allowed to recover in Recovery Media (Lucigen) for 45 minutes at 37° C. Cells transformed with 60 ng of ligation product were pooled and plated on a 24-cm×24-cm plate containing 2×YT medium supplemented with carbenicillin (100 µg/mL) and 2% glucose. Cells were grown at 37° C. for 6 hours and placed at 4° C. overnight. To determine the transformation efficiency for each series of electroporations, aliquots were taken and titered by serial dilution. Cells grown on plates were scraped into 850 mL of 2×YT medium with carbenicillin (100 µg/mL) plus 2% glucose for a final $OD_{600}$ of 5-15. Two mL of the 850 mL culture were taken and diluted ~1:200 to reach a final $OD_{600}$ of 0.05-0.07. To the remaining culture, 150 mL of sterile glycerol were added before snap freezing to produce glycerol stocks. The diluted bacteria were grown to an $OD_{600}$ of 0.3-0.5, infected with M13K07 Helper phage at an MOI of 4 (Antibody Design Labs) and shaken at 37° C. for 1 hour. The culture was centrifuged and the cells were resuspended in 2×YT medium with carbenicllin (100 µg/mL), kanamycin (50 µg/mL), and IPTG (50 mM, Thermo Fisher) and grown overnight at 30° C. for phage production. The following morning, the bacterial culture was aliquoted into 50 mL Falcon tubes and pelleted twice at high speed to obtain clarified supernatant. The phage-laden supernatant was precipitated on ice for 40 minutes with a 20% PEG-8000/2.5M NaCl solution at a 4:1 ratio of PEG/NaCl:supernatent. After precipitation, phage was centrifuged at 12,000 g for 40 minutes and resuspended in 1×TBS, 2 mM EDTA, and 1× Complete Protease Inhibitor Cocktail (Sigma-Aldrich, St. Louis, MO). Phages from multiple tubes were pooled and re-precipitated. The total number of transformants obtained was determined to be $3.6×10^{10}$. The library was aliquoted and stored in 15% glycerol at −80° C.

Next-Generation Sequencing of the Complete Phage Library.

DNA from the libraries was amplified using primers that flank the CDR-H3 region. The sequences at the 5'-ends of these primers incorporated molecular barcodes to facilitate unambiguous enumeration of distinct phage sequences. The protocols for PCR-amplification and sequencing are described by Kinde et al. (2011 *PNAS.* 108:9530-35). Sequences processed and translated using a custom SQL database and both the nucleotide sequences and amino acid translations were analyzed using Microsoft Excel.

Peptides and HLA-Monomers.

Mutant and WT peptides (listed in Table 1) were predicted to bind to HLA alleles using NetMHC version 4.0. All peptides were synthesized at a purity of >90% by Peptide 2.0 (Chantilly, VA). Peptides were resuspended in DMSO or DMF at 10 mg/mL and stored at −20° C. HLA monomers were synthesized by refolding recombinant HLA with peptide and beta-2 microglobulin, purified by gel-filtration, and biotinylated (Fred Hutchinson Immune Monitoring Lab, Seattle, WA). Monomers were confirmed to be folded prior to selection by performing an ELISA using W6/32 antibody (BioLegend, San Diego, CA).

Selection for Phage Binding to Mutant Peptide-HLA Monomers.

scFv-bearing phage clones specific to the mutant pHLA complexes were identified similar to methods described elsewhere (see, e.g., Skora et al, 2015 *PNAS*.112:9967-72). The panning schema involved an enrichment phase, a competition phase, and a final selection phase.

The phage display library stored at –20° C. in 15% glycerol, were regrown within a week of starting the panning process. A colony of phage-competent SS320 cells (Lucigen, Middleton, WI) was inoculated in a 37° C. overnight culture of 2×YT medium (Sigma-Aldrich, St. Louis, MO) supplemented with tetracycline (20 µg/mL), and the next day grown to 2 L of mid-log phase ($OD_{600}$ of 0.3-0.5) bacteria. Bacteria were infected with the phage library at an MOI of 0.5 and M13K07 Helper phage (Antibody Design Labs, San Diego, CA) at an MOI of 4 along with the addition of 2% (W/V) glucose (Sigma-Aldrich, St. Louis, MO) and allowed to shake for 1 hour at 37° C. The culture was centrifuged and the cells were resuspended in 2×YT medium with carbenicillin (100 µg/mL), kanamycin (50 µg/mL), and 50 µM IPTG and subsequently shaken and grown overnight at 30° C. for phage production. The following morning, the bacterial culture was aliquoted into 50 mL Falcon tubes and pelleted twice at high speed to obtain clarified supernatant. The phage-laden supernatant was precipitated on ice for 40 minutes with a 20% PEG-8000/2.5M NaCl solution at a 1:4 ratio of PEG/NaCl:supernatant. After precipitation, phage was centrifuged at 12,000×g for 40 minutes and resuspended in 1 mL of 1×TBS with 2 mM EDTA, 0.1% sodium azide, and 1×Complete Protease Inhibitor Cocktail (Sigma-Aldrich, St. Louis, MO).

Biotinylated pHLA monomer complexes were conjugated to M-280 streptavidin magnetic Dynabeads (Life Technologies, Carlsbad, CA). The biotinylated pHLA were incubated with either 25 µL of Dynabeads beads per 1 µg of pHLA in blocking buffer (PBS, 0.5% BSA, 2 mM EDTA, and 0.1% sodium azide) for 1 hour at room temperature (RT). After the initial incubation, the complexes were washed and resuspended in 100 µL of blocking buffer.

During the enrichment phase (Round 1), approximately $2×10^{13}$ phage, representing ~500-fold coverage of the library, were negatively selected for 1 hour at RT with a mixture of 1 mL unconjugated washed Dynabeads, 1 mg free streptavidin protein (RayBiotech, Norcross, GA) to remove any phage recognizing either the unconjugated Dynabead and streptavidin. After negative selection, beads were isolated with a DynaMag-2 magnet (Life Technologies, Carlsbad, CA) and the supernatant containing unbound phage was transferred for positive selection for 1 hour at RT against the 1 µg of mutant pHLA conjugated to Dynabeads. Prior to elution, beads were washed 10 times with 1 mL of TBST (1×TBS with 0.5% Tween-20). Phage were eluted by resuspending the beads in 1 mL of 0.2 M glycine, pH 2.2. After a 10 minutes incubation, the solution was neutralized by the addition of 150 µL of 1 M Tris, pH 9.0. Neutralized phages were used to infect 10 mL cultures of mid-log-phase SS320s, with the addition of M13K07 helper phage (MOI of 4) and 2% glucose. Bacteria were then incubated as previously described and the phages were precipitated the next morning with PEG/NaCl.

During the selection phase (Rounds 2-5), phage from the previous round was subjected to negative selection against HLA-matched cell lines without the mutations of interest, corresponding WT pHLA monomer conjugated to Dynabeads, unrelated pHLA monomerconjugated to Danybeads, and free streptavidin. After negative selection, beads were isolated with a DynaMag-2 magnet and unbound phage was transferred for positive selection. This was performed by incubating phage with 1 µg (Round 2), 0.5 µg (Rounds 3, 4), or 0.25 µg (Round 5) mutant pHLA conjugated to the magnetic Dynabeads. Prior to elution, beads were washed 10 times in 1 mL TBST. Phage were eluted from magnetic Dynabeads and used to infect mid-log phase SS320 cells as described above.

Flow Cytometry.

Monoclonal phage flow cytometry staining was performed by selecting individual colonies of SS320 cells transformed with a limiting dilution of phage obtained from the final selection round. Individual colonies were inoculated into 200 µl of 2×YT medium containing 100 µg/mL carbenicillin and 2% glucose and grown for three hours at 37° C. The cells were then infected with $1.6×10^7$ M13K07 helper phage and incubated for 1 hour at 37° C. with shaking. The cells were pelleted, resuspended in 300 µL of 2×YT medium containing carbenicillin (100 µg/mL), kanamycin (50 µg/mL), and 50 µM IPTG, and grown overnight at 30° C. for phage production. Cells were pelleted and the phage-laden supernatant was used for staining.

For peptide pulsing, HLA-matched cells were washed once with PBS and once with serum-free RPMI-1640 before incubation at $10^6$ cells per mL in serum-free RPMI-1640 containing 50 µg/mL peptide and 10 µg/mL human beta-2 microglobulin (ProSpec, East Brunswick, NJ) overnight at 37° C. The pulsed cells were pelleted, washed once in cold staining buffer (PBS containing 0.5% BSA, 2 mM EDTA, and 0.1% sodium azide), and resuspended in 50 µL of stain buffer. Phage staining was performed on ice with 50 µL monoclonal phage supernatant for 1 hour, followed by one 800 µL wash in cold staining buffer. Cells were then stained with 1 µg of rabbit anti-M13 antibody (Novus Biologics, Centennial, CO) in 100 µL total volume on ice for 1 hour and washed once with 800 µL of cold staining buffer. Cells were then stained with 5 µL anti-rabbit-PE (Biolegend) on ice for 1 hour in 100 µL total volume, followed by incubation with 200 µL LIVE/DEAD Fixable Near-IR Dead Cell Stain (Thermo Fisher) for 10 minutes at room temperature per manufacturer's instructions. Cells were washed once in 800 µL of staining buffer. Stained cells were analyzed using an iQue Screener (IntelliCyt, Albuquerque, NM).

Bispecific Antibody Production.

gBLOCKs encoding bispecific antibodies were ordered from IDT (Skokie, IL). gBLOCKs were cloned into the pcDNA3.4 plasmid (Thermo Fisher) by NEBuilder HiFi DNA Assembly (New England Biolabs, Ipswich, MA) following the manufacturer's protocol. 293FT cells (Thermo Fisher) were transfected with the bispecific antibody pcDNA3.4 plasmids using Lipofectamine 3000 (Life Technologies) per the manufacturer's instructions in a T75 flask. Following a 5-8 day incubation, media was harvested and centrifuged at 500 g for 10 minutes at 4° C. Bispecific antibody protein was purified using a Clontech Capturem™ His-Tagged Purification Mixiprep Kit (Takara Bio, Mountain View, CA) per manufacturer's instructions. Bispecific antibody protein was desalted into PBS using Zeba spin 7 k MWCO desalting columns per the manufacturer's instructions. Bispecific antibody concentration was quantified using Mini-PROTEAN® TGX Stain-Free™ Precast Gels (Biorad, Hercules, CA) using a standard curve of protein of known concentration. Stain-free gels were imaged using the ChemiDoc XRS+ Imager (Biorad).

Bispecific Antibody Co-Culture Assay.

COS-7 cells were transfected with various combinations of pcDNA3.1 or pcDNA3.4 (Life Technologies) plasmids encoding HLA-A2, HLA-A1, p53(WT, R175H), HRAS (WT, Q61H, Q61K, Q61L, Q61R), KRAS(WT, Q61H, Q61K, Q61L, Q61R), NRAS(WT, Q61H, Q61K, Q61L, Q61R) with Lipofectamine 3000 (Life Technologies) per manufacturer's instructions in a T75 flask. A total of 50,000 T cells were combined with transfected 50,000 COS-7 cells, 25,000 TYKnu cells, or 25,000 HL-60 cells and the specified concentration of bispecific antibody in a 96-well plate, and the co-culture was allowed to incubate for 20 hours at 37° C. under 5% $CO_2$. Following co-culture, conditioned media was collected and assayed for secreted IFNγ by Quantikine® ELISA (R&D Systems, Minneapolis, MN). Alternatively, following coculture, target cell viability was measured using CellTiter-Glo (Promega, Madison, WI) per the manufacturer's instructions.

CRISPR Cell Line Engineering.

The Alt-R CRISPR system (Integrated DNA Technologies, IDT) was used to modify the p53 of the TYKnu cell line and the HLA allele of HL-60 cell line. Alt-R® CRISPR Cas9 crRNAs (IDT) targeting TP53 exon 3 (CCCCGGAC-GATATTGAACAA; SEQ ID NO:191), and HLA-A exon 2 (CAGACTGACCGAGCGAACCT; SEQ ID NO:192) as well as Alt-R® CRISPR-Cas9 tracrRNA (IDT) were resuspended at 100 μM with Nuclease-Free Duplex Buffer (IDT). The crRNAs and tracrRNA were duplexed at a 1:1 molar ratio for 5 minutes at 95° C. according to the manufacturer's instructions. The duplexed RNA was allowed to cool to room temperature prior to mixing with Cas9 Nuclease (IDT) at a 1.2:1 molar ratio for 15 minutes. To knock out p53 of TYKnu cells, 40 μmols of the Cas9 RNP complexed with p53 gRNA were mixed with 200,000 TYKnu cells in 20 μL of OptiMEM. This mixture was loaded into a 0.1 cm cuvette (Biorad) and electroporated at 120V and 16 ms using an ECM 2001 (BTX). To knock out the HLA-A alleles in HL-60 cells, 40 pmols of the Cas9 RNP complexed with HLA-1 gRNA were mixed with 200,000 HL-60 cells in 20 μL of OptiMEM. This mixture was loaded into a 0.1 cm cuvette (Biorad) and electroporated at 150V and 16 ms using an ECM 2001 (BTX). After electroporation, cells were immediately transferred to complete growth medium and cultured for 10 days, changing media and passaging as needed.

p53 and HLA-A modified polyclonal pools were plated at a density of 0.5 cells per well in 96 well plates and cultured for 2 weeks. Single colonies were harvested and plated into 2 replicate 96-well plates. Genomic DNA was harvested from one of the plates using the Quick-DNA™ 96 Kit (Zymo Research, Irvine, CA), PCR amplified using Q5@ Hot Start High-Fidleity 2× Master Mix (New England Biolabs), and Sanger sequenced (Genewiz, South Plainfield, NJ) to select for clones with the desired modifications.

Example 2: Targeting a Neoantigen Derived from a Common TP53 Mutation

TP53 is the most commonly mutated cancer driver gene, but despite extensive efforts, no drug targeting mutant TP53 has been approved for treatment of the large number of patients whose tumor contain p53 mutations. This Example describes the identification of an antibody highly specific to the most common TP53 mutation (R175H) in complex with a common HLA-A allele on the cell surface. For example, this Example describes the identification of a TCRm antibody specific to the HLA-A*02:01-restricted $p53^{R175H}$ neoantigen, the structural basis of its specificity, and its conversion to a bispecific antibody that can lyse cancer cells in a fashion dependent on the presence of the neoantigen.

Such an immunotherapeutic agent that targets a common TP53 mutation can be used to target cancers containing other tumor suppressor gene mutations.

Results

The $p53^{R175H}$ Neoantigen is Presented on the Surface of Cancer Cells

The $p53^{R175H}$ (aa 168-176, HMTEVVRHC; SEQ ID NO:1) and $p53^{WT}$(HMTEVVRRC; SEQ ID NO:135) peptides were predicted on the NetMHCpan 4.0 server to bind HLA-A*02:01 at 5177.6 nM (rank 9.6%) and 7121.5 nM (11.6%), respectively. To provide experimental evidence of and to quantify such presentation, peptides eluted from HLA molecules were analyzed in four different cell culture systems using a mass spectrometry (MS)-based method. First, the human HLA-A*02:01 and either $p53^{R175H}$ or $p53^{WT}$ were co-expressed in monkey COS-7 cells. MS analysis of the peptides immunopurified with an anti-HLA antibody detected the $p53^{R175H}$ peptide at approximately 1500 copies per cell (FIG. 20, Table 6). Though relatively abundant $p53^{R175H}$ peptide was detected, the $p53^{WT}$ peptide was not observed. Second, MS analysis was performed on three human cancer cell lines, KMS26, TYK-nu, and KLE, all of which harbor $p53^{R175H}$ mutations and carry an HLA-A*02: 01 allele. The $p53^{R175H}$ peptide was detected on all three cell lines, and, as expected, at much lower levels than in the COS-7 cells in which the mutant TP53 and HLA genes were exogenously introduced (FIG. 20, Table 6). Based on comparisons with heavy isotope labeled controls, it was estimated that there were 2.4, 1.3, and 1.5 copies of cell-surface $p53^{R175H}$/HLA-A*02:01 complexes on the cell surfaces of KMS26, TYK-nu, and KLE cell lines, respectively (Table 6).

TABLE 6

Quantitative assessment of the $p53^{R175H}$ neoantigen peptide. The amount of $p53^{R175H}$ neoantigen peptide (HMTEVVRHC; SEQ ID NO: 1) present in COS-7 cells transfected with HLA-A*02:01 and $p53^{R175H}$ or $p53^{WT}$, as well as cells lines that endogenously express HLA-A*02:01 and $p53^{R175H}$, were quantified using mass spectrometry.

| Cell line | HLA and p53 status | No. cells (millions) used for analysis | Abundance (femtomole) | Copy no./ cell |
|---|---|---|---|---|
| COS-7 | Exogenous HLA-A* 02:01/$p53^{R175H}$ | 224.0 | 156 | 1587.3 |
| COS-7 | Exogenous HLA-A* 02:01/$p53^{WT}$ | 224.0 | Not detectable | Not detectable |
| KMS26 | Endogenous HLA-A* 02:01/$p53^{R175H}$ | 157.0 | 0.48 | 2.4 |
| KLE | Endogenous HLA-A* 02:01/$p53^{R175H}$ | 92.4 | 0.18 | 1.5 |
| TYK-nu | Endogenous HLA-A* 02:01/$p53^{R175H}$ | 168.3 | 0.28 | 1.3 |

Identification of scFv-Expressing Phage Clones Specific for the HLA-A*02:01-Restricted $p53^{R175H}$ Peptide and Conversion to scDb Format To identify TCR-mimic single-chain variable fragments (scFvs) selectively targeting mutant pHLA complexes, an scFv-displaying phage library was screened with an estimated complexity >1×10^{10}. Positive selection against HLA-A*02:01 pHLA monomers containing the $p53^{R175H}$ peptide were combined with negative selection against pHLA monomers containing the $p53^{WT}$ and irrelevant peptides. Selected phage clones were amplified and assessed for binding to T2 cells presenting the mutant or wild-type (WT) peptide via flow cytometry (FIG. 21).

Figure 14:
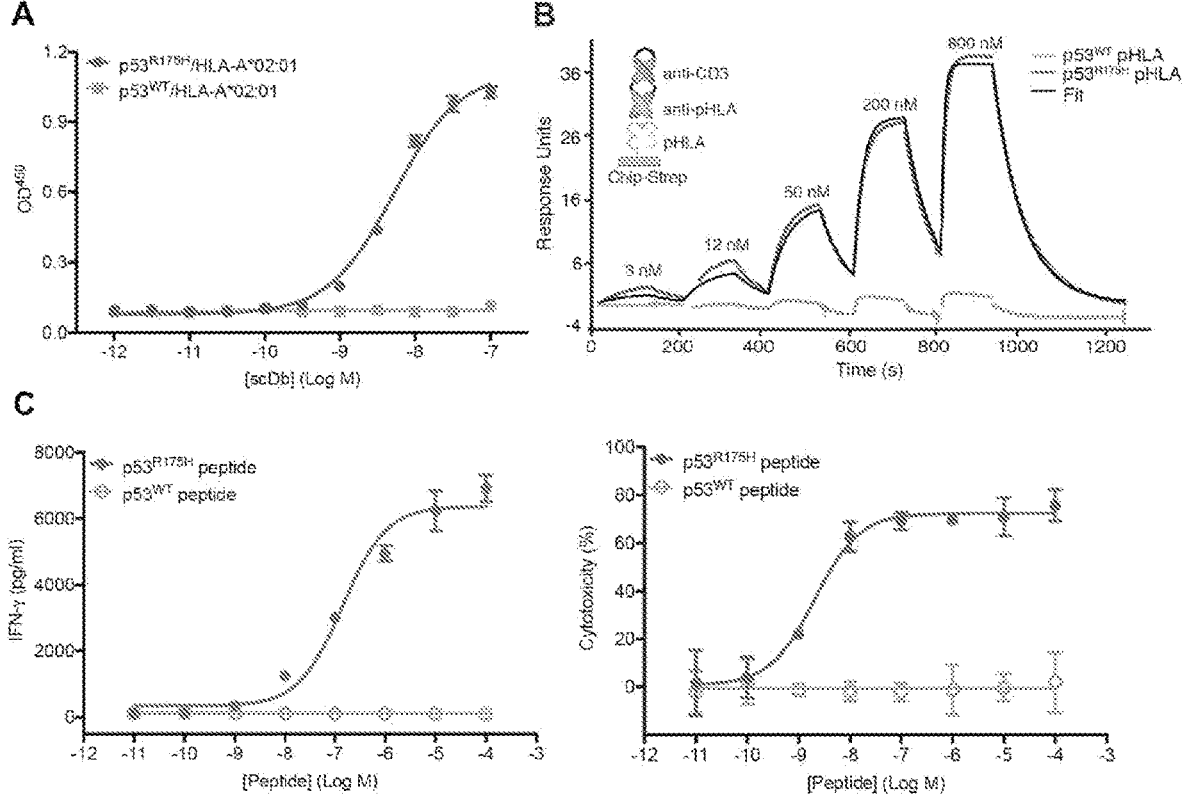
FIGS. 14A-14C show biological and biophysical characteristics of scFv clone H2. (A) H2-scDb binding to immobilized p53$^{R175H}$/HLA-A*02:01 (red) or p53$^{WT}$/HLA-A*02:01 (gray) pHLA was assessed by ELISA. Data shown represent mean±SD of three technical replicates. (B) H2-scDb binding to p53$^{R175H}$/HLA-A*02:01 was measured by single-cycle kinetics using SPR. H2-scDb was loaded at increasing concentrations, from 3, 12, 50, 200 to 800 nM. The blank- and reference-subtracted binding is shown for p53$^{R175H}$/HLA-A*02:01 (red) and p53$^{WT}$/HLA-A*02:01 (gray). H2-scDb binds to the p53$^{R175H}$/HLA-A*02:01 pHLA with a one-to-one binding kinetics at a $K_D$ of 86 nM (fitted line in black). There was negligible $p53^{WT}$/HLA-A*02:01 binding. (C) T2 cells pulsed with $p53^{R175H}$ or $p53^{WT}$ peptide was co-incubated with H2-scDb and T cells at an effector:target (E:T) ratio of 2:1. IFN-γ release was measured by ELISA (left) and cell lysis was evaluated by the CellTiter-Glo assay (right). Data indicate mean±SD of three technical replicates and are representative of three independent experiments.

Twenty-three phage clones with median fluorescence intensity (MFI) ratios of $p53^{R175H}$ to $p53^{WT}>4$ were then converted to T cell-retargeting bispecific antibodies (FIG. 21). This was achieved through linking each individual scFv to an anti-CD3 scFv (UCHT1) in a single-chain diabody (scDb) format (FIG. 22). The scDb format was chosen after evaluating several previously described bispecific antibody formats, such as bispecific T-cell engager (BiTE), dual-affinity re-targeting antibody (DART), and diabody in pilot experiments. The ability of scDbs to activate T cells was assessed by interferon-7 (IFN-7) release after co-incubation with COS-7 cells overexpressing HLA-A*02:01 and either full-length $p53^{R175H}$ or $p53^{WT}$ proteins. Two scDb clones, named H2-scDb and H20-scDb and derived from phage clones H2 and H20, respectively, showed the most potent and specific T-cell activation in the presence of $p53^{R175H}$/HLA-A*02:01 (FIG. 23). The specificity of these scDbs was further evaluated by titration enzyme-linked immunosorbent assay (ELISA). Both H2 and H20 bound to $p53^{R175H}$/HLA-A*02:01 at low concentrations, as expected. At high concentrations, H20-scDb also bound to $p53^{WT}$/HLA-A*02:01, while H2-scDb did not bind to the wild type pHLA complex even at very high concentrations of the scDb (FIG. 1A, FIG. 24). H2-scDb was therefore chosen for further analysis. As assessed by surface plasmon resonance (SPR), the H2-scDb bound to $p53^{R175H}$/HLA-A*02:01 with a $K_D=86$ nM, a $k_{on}$ of $1.76\times10^5$ $M^{-1}$ $s^{-1}$, and a $k_{off}$ of $1.48\times10^{-2}$ $s^{-1}$ (FIG. 14B). The $k_{on}$ of $1.76\times10^5$ $M^{-1}$ $s^{-1}$ suggested a lack of conformational change of the $p53^{R175H}$/HLA-A*02:01 upon binding. No detectable binding of the H2-scDb to $p53^{WT}$/HLA-A*02:01 was observed in the SPR experiments (FIG. 14B).

Next, it was examined whether anti-CD3 arms of the scDb other than the original UCHT1, could influence the ability of H2 to induce T-cell activation. The H2 scFv was linked to a panel of commonly used anti-CD3E scFvs, including UCHT1, hUCHT1v9, OKT3, TR66, and hXR32. It was found that, among the anti-CD3 scFvs tested, UCHT1 activated T cells at the lowest $p53^{R175H}$ peptide concentration when linked to the H2 scFv (FIG. 25), and used this particular bispecific antibody for further experiments.

H2-scDb Specifically Recognizes Cancer Cells Expressing the $p53^{R175H}$ Neoantigen It was next evaluated the ability of H2-scDb to recognize cancer cell lines harboring the $p53^{R175H}$ mutations and expressing various levels of HLA-A*02:01. H2-scDb elicited T-cell responses in a dose-dependent manner when T cells were co-cultured with three lines that expressed moderate to high levels of HLA-A*02:01 (FIG. 15A). This activation was noted even at very low (sub-nanomolar) concentrations of the bispecific antibody. The T-cell responses were polyfunctional, as indicated by the release of cytotoxic granule proteins granzyme B and perforin, cytotoxicity, and the production of cytokines IFN-7, tumor necrosis factor α (TNF-α), interleukin-2 (IL-2), and others (FIG. 15B, FIG. 26). Clustering of T cells around tumor cells, leading to their lysis in the presence of H2-scDb, was also visualized by real-time live-cell imaging (FIG. 15C). The specificity of the bispecific antibody for both the $p53^{R175H}$ peptide and HLA-A*02:01 was evident from the observation that much lower levels of IFN-γ were induced by cells harboring a $p53^{R175H}$ mutation but low levels of expression of HLA-A*02:01 (AU565 or SK-BR3) or by cells without $p53^{R175H}$ but relatively high levels of HLA-A*02:01 expression (FIG. 15A, FIG. 27).

Figure 16:
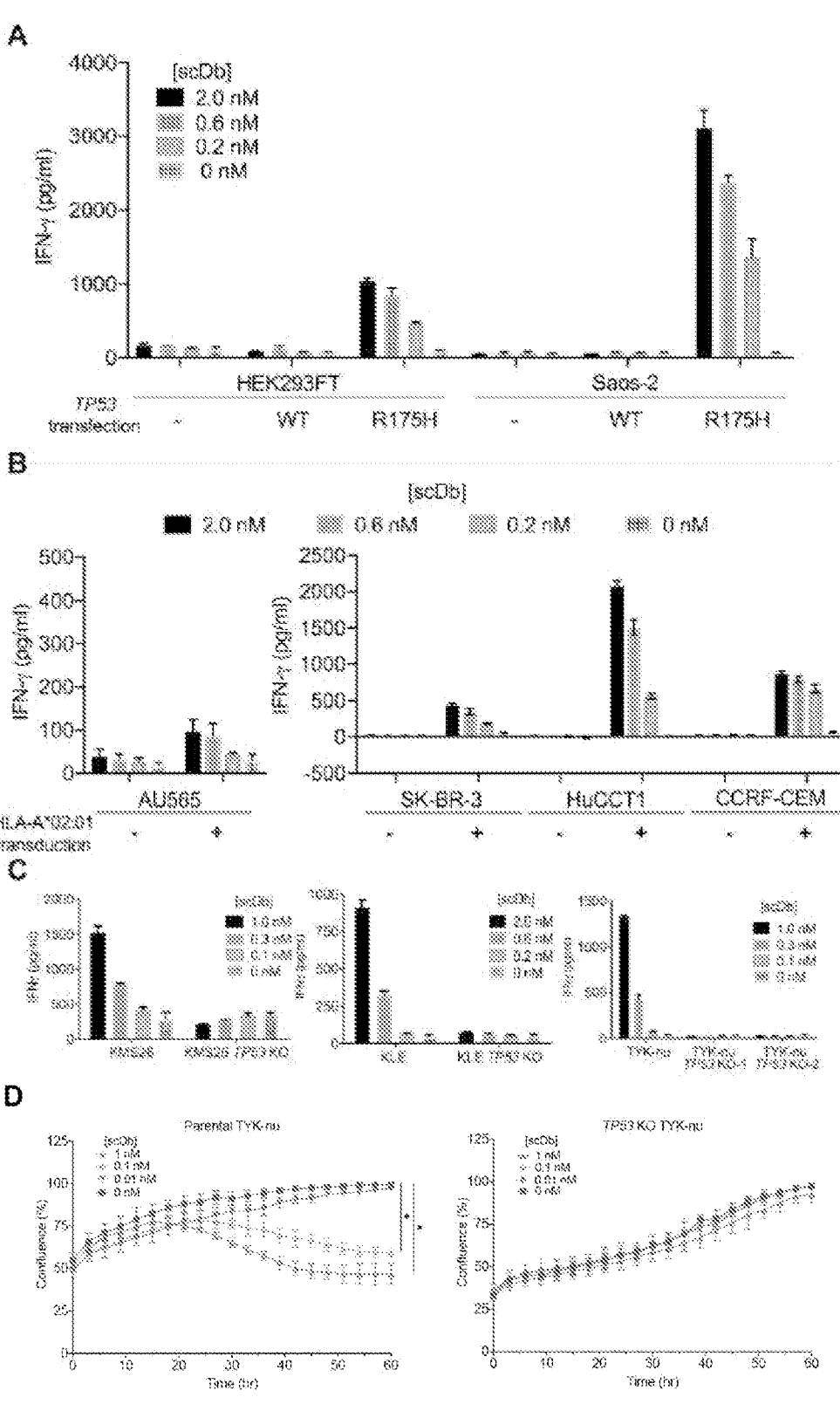
Figure 17:
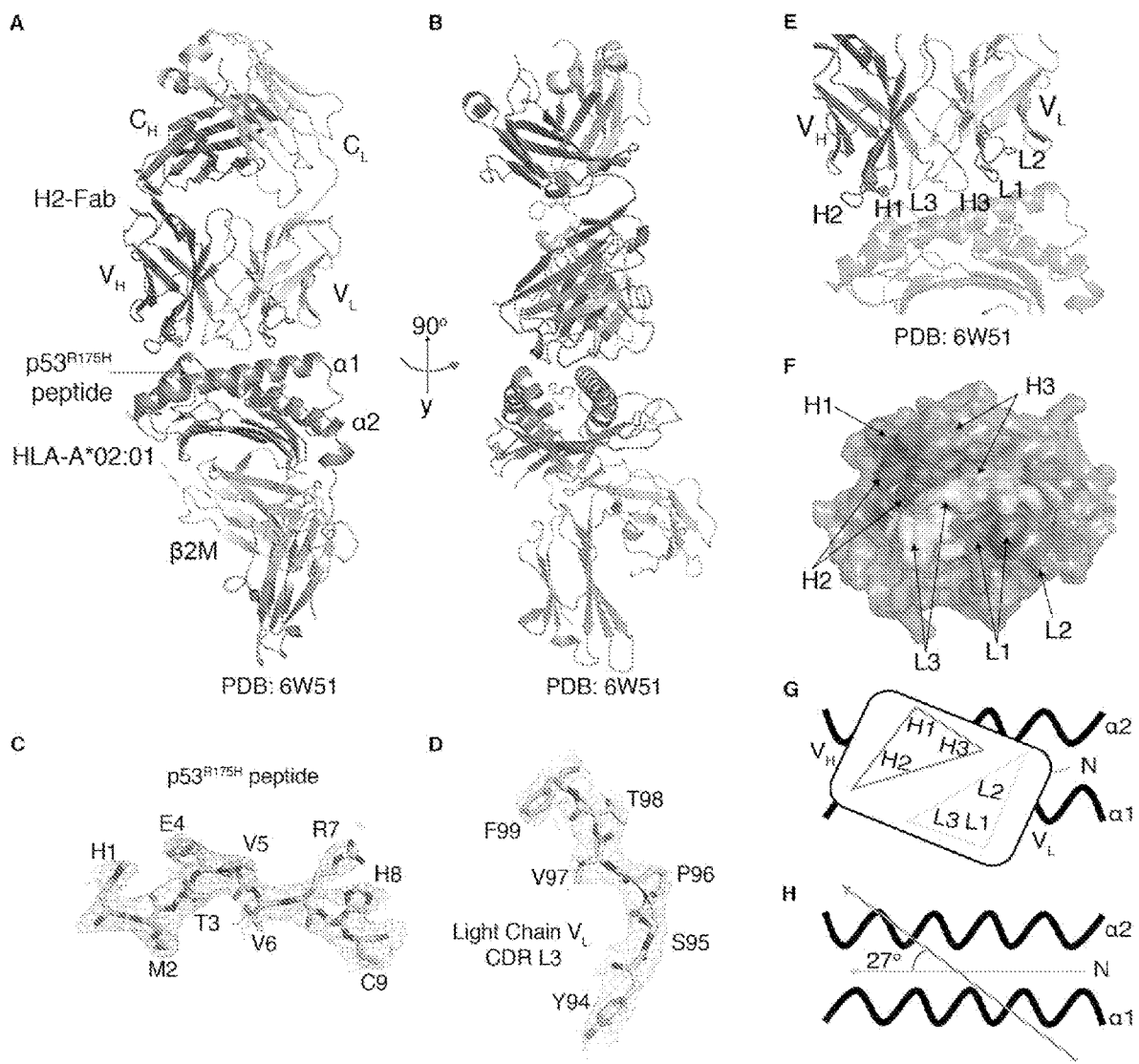

It was further validated the specificity of H2-scDb using nine pairs of isogenic cell lines that differed with respect to HLA-A*02:01 expression or $p53^{R175H}$ mutation. First, human HEK293FT (TP53$^{WT}$/HLA-A*02:01) or Saos-2 (TP53$^{null}$/HLA-A*02:01) cells were transfected with plasmids expressing either full-length $p53^{R175H}$ or $p53^{WT}$. H2-scDb induced robust T-cell activation when co-cultured with both cell lines overexpressing $p53^{R175H}$ but not with $p53^{WT}$-overexpressing or parental cells (FIG. 16A). Second, HLA-A*02:01-encoding retrovirus were transduced into four cell lines (AU565, SK-BR-3, HuCCT1, CCRF-CEM) that harbored the $p53^{R175H}$ mutation but had low levels of HLA-A*02:01 expression (FIG. 28). Exogenous expression of HLA-A*02:01 in all four lines conferred T-cell activation by H2-scDb (FIG. 16B). Third, TP53 was genetically disrupted in KMS26, TYK-nu, and KLE cancer cell lines that carry endogenous $p53^{R175H}$ using a CRISPR-based technology (FIG. 29A). T-cell activation, as assessed by IFN-γ secretion, was reduced to control levels when TP53 was knocked out in all three cell lines (FIG. 16C). The cytotoxicity mediated by H2-scDb was similarly mitigated by TP53 knock-out (KO) in these cells (FIG. 16D, FIG. 29B).

Overall Structure of the H2-Fab-$p53^{R175H}$/HLA-A *02:01 Ternary Complex

To understand the structural basis for the high specificity of the H2 clone for $p53^{R175H}$/HLA-A*02:01, the H2 fragment antigen-binding (H2-Fab)-$p53^{R175H}$/HLA-A*02:01 complex was purified (FIG. 30) and its crystal structure was determined by molecular replacement and refined to 3.5 Å resolution (PDB ID 6W51, Table 7). There were four H2-Fab and four $p53^{R175H}$/HLA-A*02:01 per asymmetric unit (FIG. 17A, B). All four H2-Fab were firmly positioned on the $p53^{R175H}$/HLA-A*02:01, without evidence of rocking with a root-mean-square deviation (rmsd) of 0.45 to 0.51 Å. The total buried surface area of the H2-Fab-$p53^{R175H}$/HLA-A*02:01 interface was 1173 Å$^2$, with roughly equal contributions from the heavy and light chains (644 Å$^2$ and 529 Å$^2$, respectively, Table 8). Although the entire structure was refined to a resolution of 3.5 Å, particularly clear electron densities were observed for the $p53^{R175H}$ neoantigen, the CDRs of the H2-Fab, and the HLA-A*02:01 (FIG. 17C, D).

TABLE 7

| X-ray Crystallography data collection and refinement statistics. | |
| --- | --- |
| Space group | P 1 2$_1$ 1 |
| Cell constants | |
| a, b, c (Å) | 113.29, 123.89, 137.07 |
| α, β, γ (°) | 90.00, 100.38, 90.00 |
| Resolution (Å) | 49.21-3.50 |
| | 49.17-3.50 |
| Number of reflections | 104482 |
| Number of unique reflections | 43734 |
| % Data completeness | 99.3 (49.21-3.50) |
| (in resolution range) | 99.4 (49.17-3.50) |
| R$_{merge}$ | 0.25 |
| CC$_{1/2}$ (%) | 0.938 |
| $<I/\sigma(I)>$ | 1.31 (at 3.48Å) |
| R, R$_{free}$ | 0.216, 0.267 |
| | 0.221, 0.272 |
| R$_{free}$ test set | 2349 reflections (5.01%) |
| Wilson B-factor (Å$^2$) | 61.6 |
| Anisotropy | 0.581 |
| L-test for twinning | $<|L|> = 0.38$, $<L^2> =$ |
| | 0.21 |
| F$_o$, F$_c$ correlation | 0.90 |
| Total number of atoms | 25900 |
| Average B, all atoms (Å$^2$) | 69.0 |

Binding of the $p53^{R175H}$ Peptide to HLA-A*02:01

Figure 18:
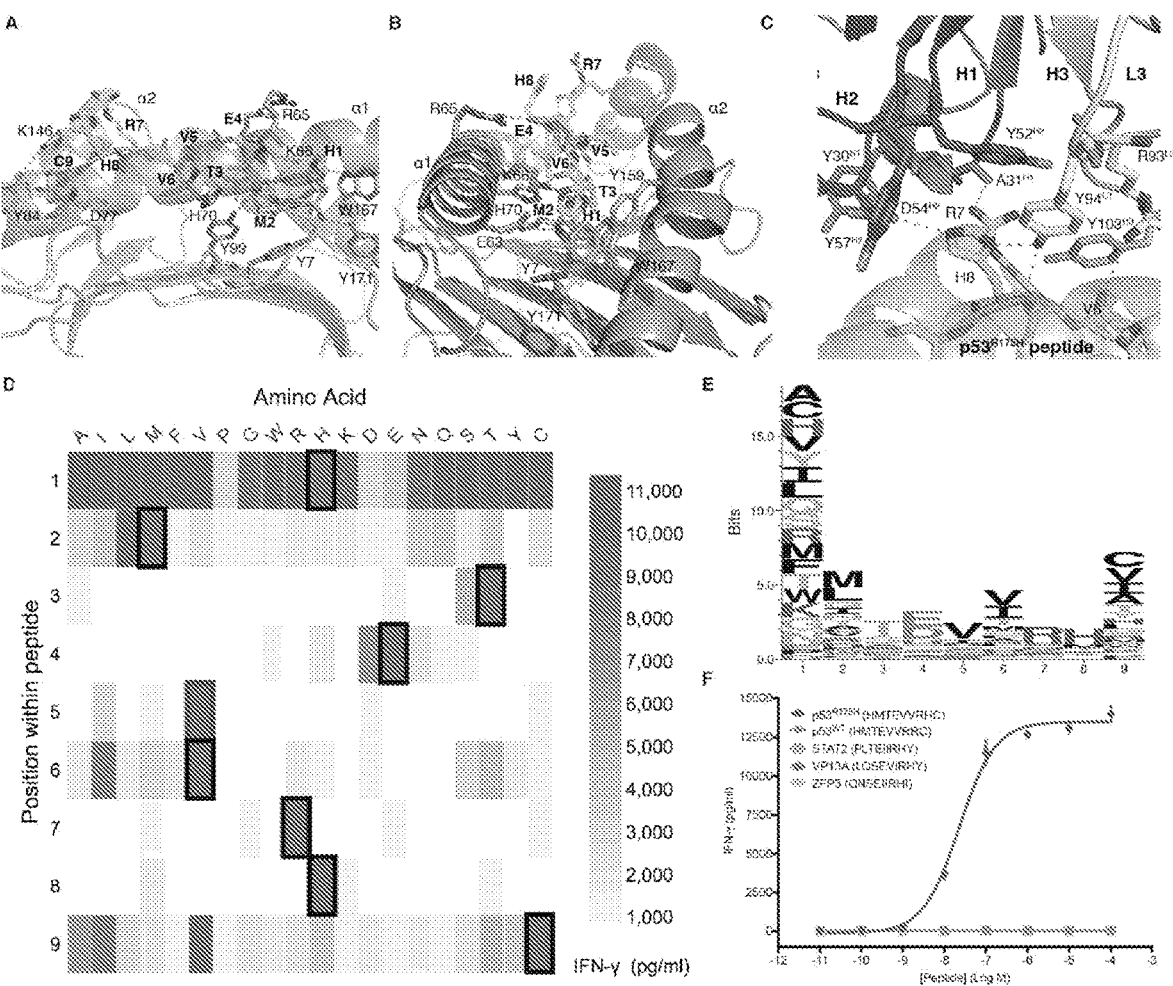
Figure 31:
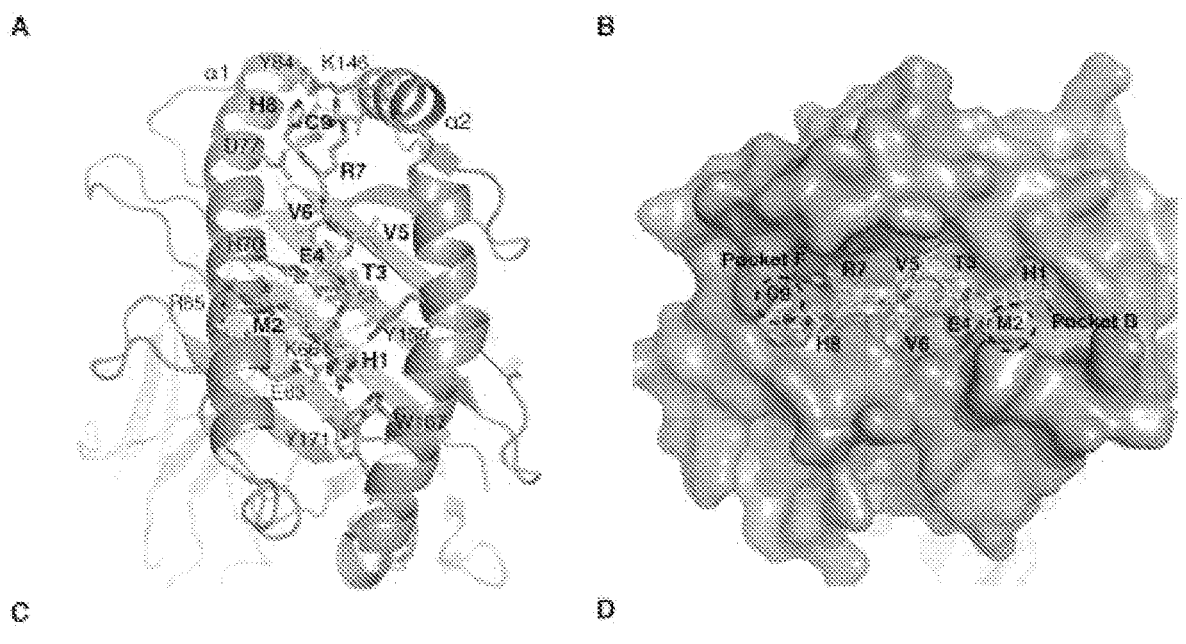
Figure 31:
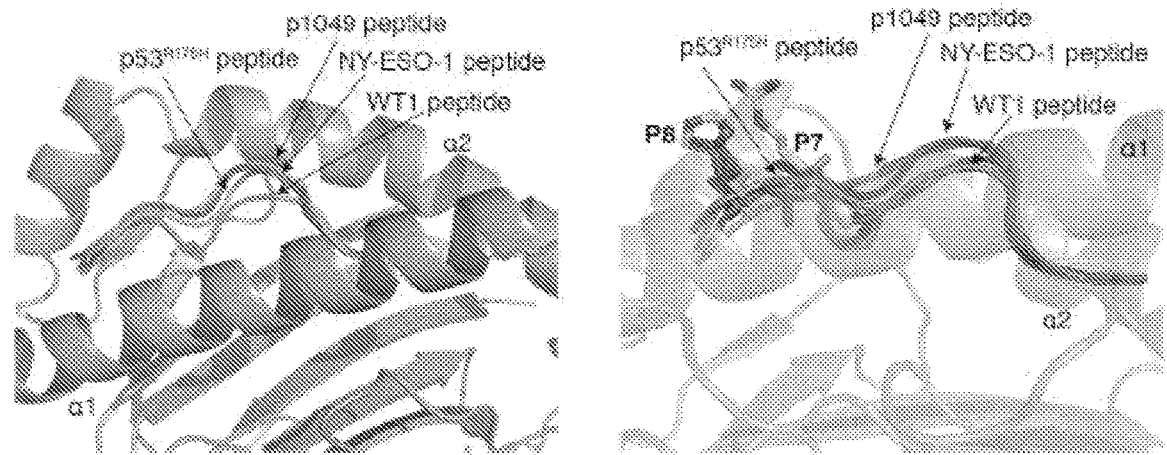

The $p53^{R175H}$ neoantigen occupies the binding cleft α1-α2 of HLA-A*02:01, burying a solvent accessible surface area of 870 Å², slightly larger than other peptide/HLA-A*02:01 complexes (FIG. 18A, B, FIG. 31A) and with the C-terminal arginine at position 7 (P7, Arg7, Arg174 in p53) and histidine at position 8 (P8, His8, His175 in mutant p53) pointing up, out of the groove. In contrast, the N-terminus of the peptide is situated deep within the peptide binding cleft, anchored by multiple residues in the HLA-A*02:01 (FIG. 18A, B, FIG. 31A). The anchor residues of the peptide, a methionine at position 2 (P2, Met2, Met169 in p53) and a cysteine residue at position 9 (P9) (FIG. 31B), departed from the canonical anchor residues-leucine at P2 and valine or leucine at P9. Peptides that bind to HLA-A*02:01 through either a methionine at P2 or a cysteine at P9 have been reported, but not both. Based on alignments with structures of other HLA-A*02:01 peptides in complex with TCR or TCRm, the unconventional anchoring of p53$^{R175H}$ did not result in drastic peptide conformational change or positioning (FIG. 31C, D).

Structural Basis for the Recognition of p53$^{R175H}$ HLA-A*02:01 by the H2-Fab

The recognition of the HLA-A*02:01 by the H2-Fab was mediated by all six CDRs. There were a total of 79 contacts between the H2-Fab CDRs and the α1 and α2 of HLA-A*02:01, with the light chain contributing to 61% of those contacts. The H2-Fab buried a solvent accessible surface area of 818 Å² within the HLA, of which 427 Å² were contributed by the light chain and 391 Å² by the heavy chain (Table 8). In contrast, only four of the six H2-Fab CDRs (H1, H2, H3 and L3) interacted with the p53$^{R175H}$ peptide. Overall, the H2-Fab made 36 contacts with the p53$^{R175H}$ neoantigen, including five hydrogen bonds and numerous van der Waals interactions. Importantly, His175 at P8 made 47% of all direct contacts with the H2-Fab. The CDR-H1, H2, and H3 of the heavy chain and CDR-L3 of the light chain formed a cage-like configuration around the C-terminus of the p53$^{R175H}$ peptide, trapping Arg174 at P7 and His175 at P8 into position by providing a stable interaction (FIG. 18C). The imidazole side chain of His175 at P8 was anchored by a hydrogen bonding network with Asp54 (CDR-H2) and Tyr94 (CDR-L3) (FIG. 18C, FIG. 32). Tyr52 (CDR-H2) acted as a ceiling and capped the cage-like structure around His8 by forming π-π interactions (FIG. 18C, FIG. 32).

TABLE 8

Structural comparison of H2-Fab-p53$^{R175H}$/HLA-A*02:01 with various TCR and Fab antibody-pHLA. Total bonds were calculated using a 4 Å cutoff which includes both hydrogen bonds and van der Waals. PDB, Protein Data Bank; BSA, buried surface area; α, TCRα chain; β, TCRβ chain; H, V$_H$ domain; L, V$_L$ domain; pep, HLA presented peptide.

| | H2-Fab | MAGE-A3 TCR | NY-ESO-1 Fab (3M4E4) | ESK-1 Fab |
|---|---|---|---|---|
| Affinity (K$_D$) | 86 nM | 7.1 nM | 95 nM | 13.2 nM |
| PDB | 6W51 | 5BRZ | 3HAE | 4WUU |
| Angle of rotation (°) | 27° | 57° | 134° | 112° |
| Total bonds | 115 | 114 | 167 | 183 |
| Peptide bonds | 4, 5, 6, | 1, 4, 5, | 1, 2, 4, 5, | 1, 4 |
| (bold ≥ 10) | 7, 8 | 7, 8 | 6, 7, 8, 9 | |
| Peptide bonds | 36 (31%) | 16 (14%) | 89 (53%) | 19 (10%) |
| Bonds from β/H | 21 | 10 | 47 | 10 |
| Bonds from α/L | 15 | 6 | 42 | 9 |
| HLA bonds | 79 | 98 | 78 | 164 |
| Bonds from β/H | 31 | 20 | 47 | 130 |
| Bonds from α/L | 48 | 78 | 31 | 34 |
| HLA ≥ 5 bonds | 61, 65, | 66, 154, | 65, 66, 72, 73 | 58, 62, 63, 65, |
| (bold ≥ 10) | 72, 80, | 155, 157, | | 66, 155, 161, |

TABLE 8-continued

Structural comparison of H2-Fab-p53$^{R175H}$/HLA-A*02:01 with various TCR and Fab antibody-pHLA. Total bonds were calculated using a 4 Å cutoff which includes both hydrogen bonds and van der Waals. PDB, Protein Data Bank; BSA, buried surface area; α, TCRα chain; β, TCRβ chain; H, V$_H$ domain; L, V$_L$ domain; pep, HLA presented peptide.

| | H2-Fab | MAGE-A3 TCR | NY-ESO-1 Fab (3M4E4) | ESK-1 Fab |
|---|---|---|---|---|
| | 146, 155 | 158, 163 | | 162, 166, 167, 169, 170 |
| BSA | | | | |
| BSA total | 1173 | 1027 | 1366 | 1084 |
| BSA β/H pep | 253 | 158 | 256 | 72 |
| BSA α/L pep | 102 | 112 | 260 | 93 |
| BSA β/H HLA | 391 | 247 | 523 | 601 |
| BSA α/L HLA | 427 | 510 | 327 | 318 |

Figure 33:
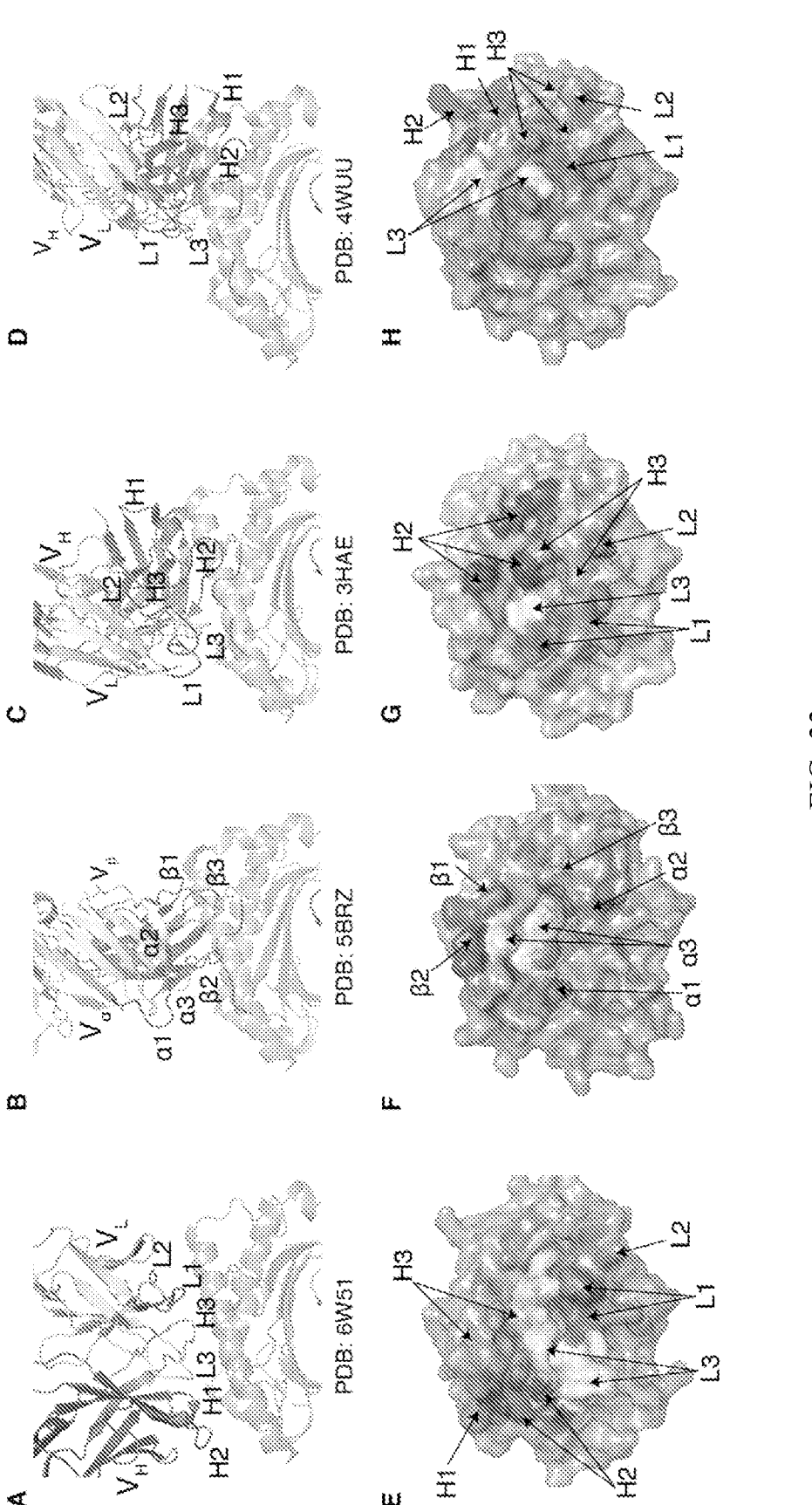
Figure 33:
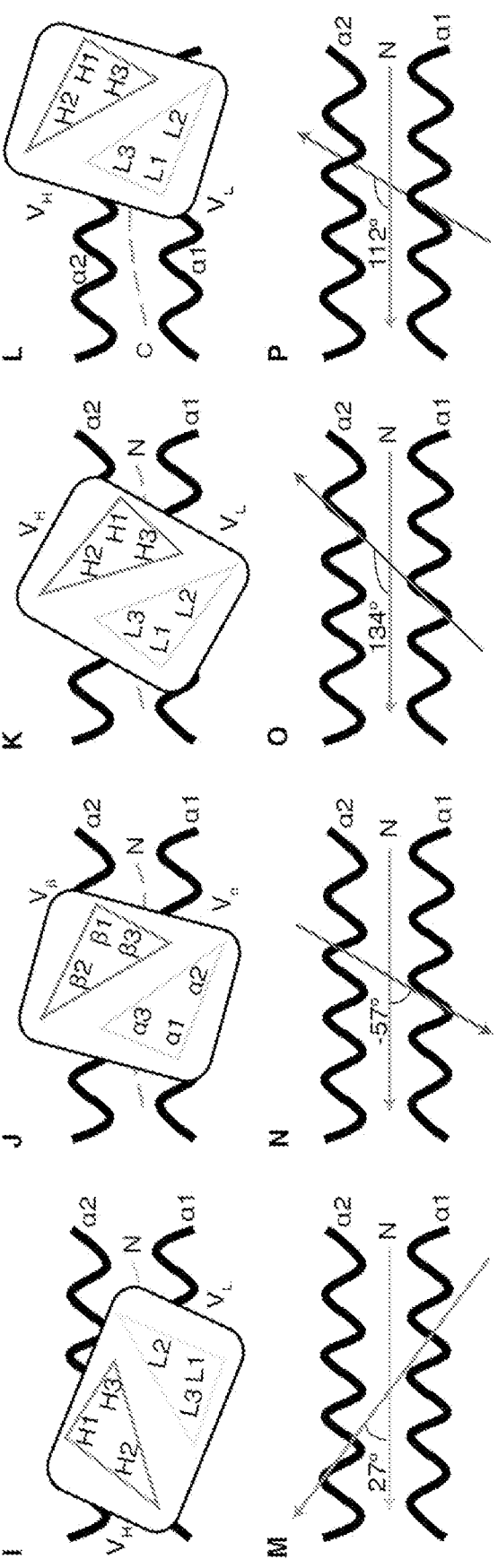

Viewed from the axis of the C-terminus to the N-terminus of the p53$^{R175H}$ peptide, the CDRs were arranged in the order H2, H1, L3, H3, L1, L2 (FIG. 17E, F, G). Interestingly, the axis of the H2-Fab was nearly parallel to the axis of the peptide within the HLA groove with a binding angle of 27° (FIG. 17G, H). This orientation was quite different from that of most previously described TCRs or TCRm antibodies to pHLA complexes, in which the axes are diagonal (FIG. 33).

Assessing Candidate Cross-Reactive Peptides

One of the major challenges confronting new immunotherapeutic antibodies is off-target binding, which can result in toxicity to normal cells. Several powerful approaches to profile TCR and TCRm specificity have been developed to address this important issue. Scanning mutagenesis was employed to identify peptides in the human proteome to which H2-scDb might cross-react. A peptide library was generated by systemically substituting amino acids at each position of the target p53$^{R175H}$ peptide (HMTEVVRHC; SEQ ID NO:1) with each of the remaining 19 common amino acids. T2 cells loaded with each of the 171 variant peptides were then used to assess T-cell activation by measuring IFN-γ release following incubation with H2-scDb (FIG. 18D). In congruence with the X-ray structural analysis, any changes in P8, where the mutant histidine residue lies, and any change in P7, which is encased with P8 by the CDR loops, abolished recognition of the peptide. Importantly, peptides with substitutions at these positions retained their ability to bind to HLA-A*02:01 (FIG. 34), but not to the H2-scDb. Other non-anchor residues at positions 3-6 also highly favored the parental amino acids present in the target peptide. This recognition pattern is illustrated as a Seq2Logo graph (FIG. 18E).

Figure 36:
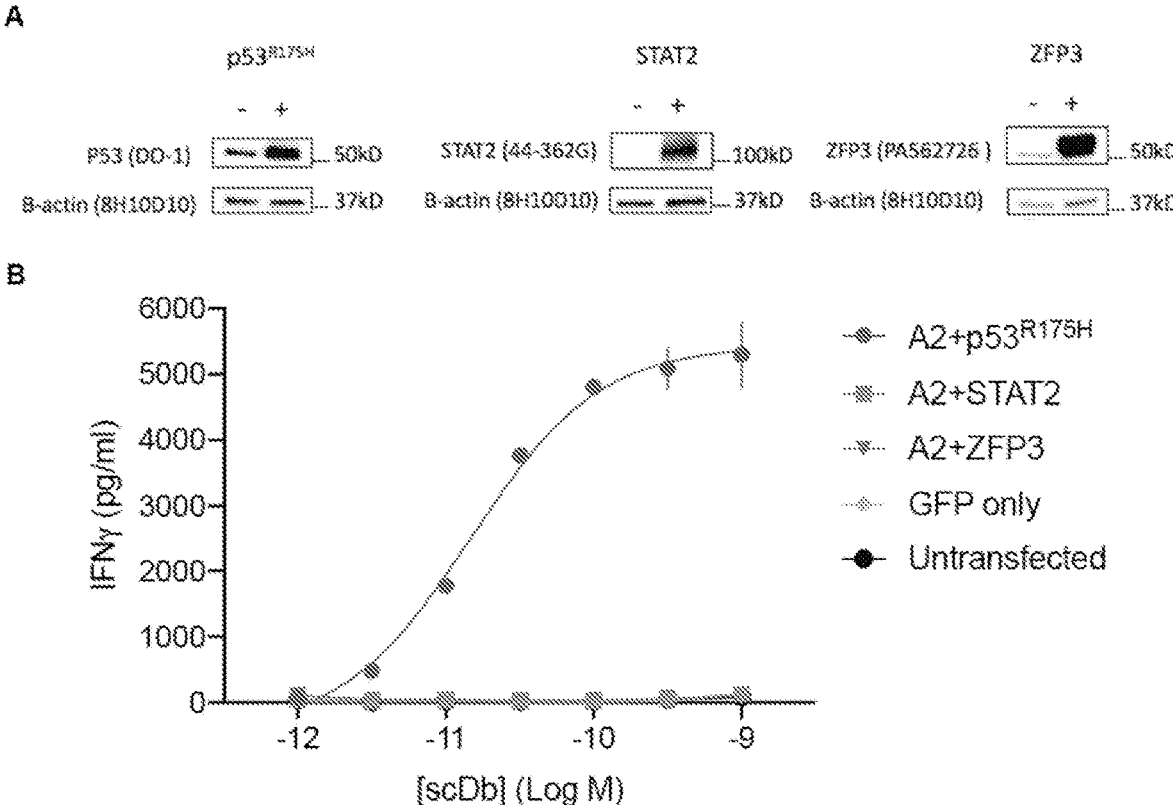

Next, a nonamer binding motif, x-[AILMVNQTC]-[ST]-[DE]-[IV]-[IMVST]-R-H-[AILVGHSTYC] (SEQ ID NO:197), was generated using 20% target peptide reactivity as a cutoff for permissive amino acids at each position (FIG. 35). A search of this motif in the UnitProtPK human protein database using ScanProsite yielded 3 homologous peptides from STAT2 (PLTEIIRHY; SEQ ID NO:185), VP13A (LQSEVIRHY; SEQ ID NO:186), and ZFP3 (QNSEIIRHI; SEQ ID NO:187) (Table 9). None of these 3 peptides were predicted to be potent binders of HLA-A*02:01 by NetMHCpan 4.0 (% rank all >2.0) and had lower predicted binding affinity than the parental p53$^{R175H}$ peptide (Table 9). However, to experimentally exclude the possibility of cross-reactivity, T2 cells were pulsed with each of these peptides. H2-scDb activated T cells only in the presence of T2 pulsed with the p53$^{R175H}$ peptide (FIG. 18F). Additionally, COS-7 cells were co-transfected with expression plasmids for HLA-A*02:01 and STAT2 or ZFP3; full-length VP13A was not tested due to its large size (3000 aa). Again, no T-cell activation was detected in the co-culture assay with COS-7 cells expressing the two proteins containing the candidate cross-reactive peptides (FIG. 36).

TABLE 9

Putative cross-reactive peptides identified through peptide scanning. A binding motif of H2-scDb was determined by positional scanning of the p53$^{R175H}$ HMTEVVRHC (SEQ ID NO: 1) peptide. Three peptides that conformed to this motif in the UniProtPK human protein database were identified using ScanProsite. NetMHCPan4.0 was used to predict the binding affinity and % rank of these peptides to HLA-A*02:01. The parental p53$^{R175H}$ target peptide is listed for comparison.

| UniProt ID | Name | Peptide position | Se-quence | SEQ ID NO | HLA-A*02:01 Affinity (nM) | % Rank |
|---|---|---|---|---|---|---|
| NA | p53$^{R175H}$ | 168-176 | HMTEVVRHC | 1 | 5177.6 | 9.7 |
| P52630 | STAT2 | 640-648 | PLTEIRHY | 185 | 32385.4 | 46.8 |
| Q96RL7 | VP13A | 2840-2848 | LQSEVIRHY | 186 | 21897.4 | 27.6 |
| Q96NJ6 | ZFP3 | 348-356 | QNSEIIRHI | 187 | 31174.4 | 43.9 |

Antitumor Activity of the H2-scDb In Vivo

To determine whether H2-scDb could control tumor growth in vivo, KMS26 cells were engrafted into NOD-SCID-Il2rg$^{-/-}$ (NSG) mice through intravenous injection, establishing widespread, actively growing cancer cells throughout the body. Two models were used to assess the effects of the H2-scDb in combination with human T cells. In an early treatment model, mice were randomized based on luminescence quantification of tumor burden and H2-scDb was subsequently administered through intraperitoneal infusion pumps at 0.3 mg/kg/day, starting one day after tumor inoculation. An irrelevant isotype scDb was administered in parallel as control. H2-scDb markedly suppressed the growth of parental KMS26 cells (FIG. 19A). In contrast, the H2-scDb had no effect on KMS26 cells in which the TP53 gene had been disrupted using CRISPR (FIG. 19B). In the second model, mice were randomized 6 days after tumor inoculation. The H2-scDb was administered at two doses (0.15 and 0.3 mg/kg/day). Both doses resulted in major tumor regressions and were well tolerated as assessed by the absence of significant changes in body weight (FIG. 19C, FIG. 37).

Taken together, these results demonstrate that—can be used to target p53, the most common mutation of the most commonly mutated tumor suppressor gene in human cancers, and, as such, can specifically target cancer cells harboring the mutation.

Materials and Methods

Cell Lines and Primary T Cells

COS-7, T2 (174×CEM.T2), Raji, HH, AU565, SK-BR-3, KLE, HCT116, SW480, NCI-H441, Saos-2, and CCRF-CEM cells were purchased from American Type Culture Collection (ATCC, Manassas, VA). KMS26, TYK-nu, and HuCCT1 were purchased from Japanese Collection of Research Bioresources Cell Bank (JCRB, Osaka, Japan). SigM5 was obtained from DSMZ (Braunschweig, Germany). HEK293FT was obtained from Invitrogen (Thermo Fisher Scientific, Waltham, MA). T2, Raji, Jurkat, HH, AU565, NCI-H441, TOV-112D, CCRF-CEM, KMS26, TYK-nu, and HuCCT1 were cultured in RPMI-1640 (ATCC, 30-2001) with 10% FBS (GE Healthcare, SH30070.03) and 1% Penicillin-Streptomycin (Thermo Fisher Scientific, 15140163). COS-7, SK-BR-3, HCT116, SW480, and Saos-2 were culture in McCoy's 5A modified media (Thermo Fisher Scientific, 16600108) with 10% FBS and 1% Penicillin-Streptomycin. SigM5 was cultured in IMDM (Thermo Fisher Scientific, 12440061) with 20% FBS and 1% Penicillin-Streptomycin. HEK293FT was cultured in DMEM (high glucose, pyruvate, Thermo Fisher Scientific, 11995065) with 10% FBS, additional 2 mM Gluta-MAX (Thermo Fisher Scientific, 35050061), 0.1 mM MEM non-essential amino acids (Thermo Fisher Scientific, 11140050), 1% Penicillin-Streptomycin, and 500 μg/mL Geneticin (Thermo Fisher Scientific, 10131027). PBMCs were isolated from leukapheresis samples (Stem Cell Technologies, Vancouver, BC) by standard density gradient centrifugation with Ficoll Paque Plus (GE Healthcare, 17-1440-03). T cells were expanded from PBMCs with addition of the anti-human CD3 antibody (OKT3, BioLegend, San Diego, 317347) at 15 ng/mL for three days. T cells were cultured in RPMI-1640 with 10% FBS, 1% Penicillin-Streptomycin, 100 IU/mL recombinant human IL-2 (aldesleukin, Prometheus Therapeutics and Diagnostics, San Diego, CA), and 5 ng/mL recombinant human IL-7 (BioLegend, 581908). All cells were grown at 37° C. in 5% $CO_2$ with humidification.

Detection of Neoantigen Peptide

HLA-A*02:01-restricted p53$^{R175H}$ peptide was directly detected and quantified in COS-7 cells transfected with HLA-A*02:01 and p53R175H and in human cancer cell lines expressing HLA-A*02:01 and p53$^{R175H}$ through MANA-SRM. In particular, the dual-reduction approach described in MANA-SRM was critical for this detection because a cystine and a methionine coexist in the p53$^{R175H}$ peptide. 100 femtomole heavy-isotope labeled peptide HMTEVVRHC (SEQ ID NO:1; New England Peptide Inc, Gardner, MA) were spiked into each sample before the assay. The MANA-SRM assays were performed at Complete Omics (Baltimore, MD).

Phage Display Library Construction

The scFv-bearing phage library was described elsewhere (see, e.g., Miller et al., *J. Biol. Chem.* 294:19322-19334 (2019); and Skora et al., *Proc. Natl. Acad. Sci. U.S.A* 112:9967-9972 (2015)). Oligonucleotides were synthesized by GeneArt (Thermo Fisher Scientific) using trinucleotide mutagenesis (TRIM) technology to diversify complementarity-determining region (CDR)-L2, CDR-L3, CDR-H1, CDR-H2, and CDR-H3. A FLAG (DYKDDDDK; SEQ ID NO:190) epitope tag was placed immediately downstream of the scFv, which was followed in frame by the full-length M13 pIII coat protein sequence. The total number of transformants obtained was determined to be 3.6×10$^{10}$.

Peptides and Monomers

All peptides were synthesized at a purity of >90% by Peptide 2.0 (Chantilly, VA) or ELIM Biopharm (Hayward, CA), except for the positional scanning library, where crude peptides were used. Peptides were resuspended in dimethylformamide at 10 mg/mL and stored at −20° C. Peptide-HLA monomers were synthesized by refolding recombinant HLA with peptide and β2 microglobulin (β2M), purified by gel-filtration, and biotinylated (Fred Hutchinson Immune Monitoring Lab, Seattle, WA). Monomers were confirmed to be folded prior to selection by performing an ELISA using W6/32 antibody (BioLegend, 311402), which recognizes only folded HLA.

Selection of Mutant pHLA Specific Phage Clone

Phage clones bearing scFvs specific to $p53^{R175H}$/HLA-A*02:01 pHLA were identified using an approach described elsewhere (Skora et al., *Proc. Natl. Acad. Sci. U.S.A* 112: 9967-9972 (2015)). Biotinylated HLA-A*02:01 pHLA monomer complexes were conjugated to 25 µL of M-280 streptavidin magnetic Dynabeads (Thermo Fisher Scientific, 11206D) per 1 µg of pHLA. During the enrichment phase (Round 1), approximately $4\times10^{13}$ phage, representing ~1000-fold coverage of the library, were negatively selected with a mixture of unconjugated Dynabeads and free streptavidin protein (RayBiotech, Norcross, GA, 228-11469). After negative selection, supernatant containing unbound phage was transferred for positive selection using 1 µg of $p53^{R175H}$/HLA-A*02:01 pHLA. Beads were then washed and phage was eluted to infect mid-log-phage SS320 bacteria, with the addition of M13K07 helper phage (MOI of 4). Bacteria were then grown overnight at 30° C. for phage production and the phage was precipitated the next morning with PEG/NaCl.

During the selection phase (Rounds 2-5), phage from the previous round was subjected to two stages of negative selection: 1) against cell lines without $p53^{R175H}$/HLA-A*02:01 (RPMI-6666, Jurkat, Raji, SigM5, HH, T2, and NCI-H441) and 2) against $p53^{WT}$/HLA-A*02:01 pHLA, unrelated HLA-A*02:01 pHLA, and free streptavidin. For negative selection using cell lines, phage was incubated with a total number of $5\times10^6$-$1\times10^7$ of cells at 4° C. overnight. After negative selection, beads were isolated and unbound phage was transferred for positive selection by incubating with 1 µg (Round 2), 0.5 µg (Round 3), or 0.25 µg (Round 4, 5) of $p53^{R175H}$/HLA-A*02:01 pHLA. Phage was then eluted and amplified by infecting SS320 as described above.

After five rounds of selection, SS320 cells were infected with a limiting dilution of the enriched phage. A total of 190 individual colonies of SS320 were picked and phage DNA was PCR amplified by primers flanking the CDRs (Forward: GGCCATGGCAGATATTCAGA (SEQ ID NO:198), Reverse: CCGGGCCTTTATCATCATC (SEQ ID NO:199)) using Q5 Hot Start High-Fidelity 2× Master Mix (New England BioLabs, M0494L) and Sanger sequenced by GENEWIZ (South Plainfield, NJ). Sequences flanking the CDRs were trimmed using DNA Baser Sequence Assembler v4 (Arges, Romania) and the sequences spanning the CDRs were clustered using the CD-HIT Suite. Colonies containing unique phage clones were selected and grown overnight in 400 µL of media in deep 96-well plates (Thermo Fisher Scientific, 278743) with the addition of M13K07 helper phage. Bacteria were pelleted the next day and the phage-laden supernatants were used for downstream analysis.

Peptide Pulsing

For peptide pulsing, T2 cells were washed with serum-free RPMI-1640 media before incubation at $5\times10^5$-$1\times10^6$ cells per mL in serum-free RPMI-1640 containing specified concentration of peptide for 2 hours at 37° C. For experiments assessed by flow cytometry, 10 µg/mL human β2M (ProSpec, East Brunswick, NJ, PRO-337) was added with the peptides and is specified in the figure legend of such experiments.

Flow Cytometry

Phage staining of peptide-pulsed T2 cells was performed with 50 µL phage supernatant on ice for 1 hour, followed by staining with 1 µg of rabbit anti-M13 antibody (Novus Biologicals, NB100-1633), and anti-rabbit-PE (BioLegend, 406421). HLA-A*02 staining was performed by staining cells with fluorescently labeled anti-human HLA-A*02 (BB7.2, BioLegend, 343308) or mouse isotype IgG2b, K (BioLegend), 402206). Stained cells were analyzed using an LSRII flow cytometer (Becton Dickinson, Mansfield, MA) or an iQue Screener (IntelliCyt, Albuquerque, NM).

ELISAs

Streptavidin-coated, 96-well plates (R&D Systems, Minneapolis, MN, CP004) were coated with 50 ng of biotinylated HLA-A*02:01 pHLA monomers in 50 µL of blocking buffer (PBS with 0.5% BSA, 2 mM EDTA, and 0.1% sodium azide) at 4° C. overnight. Plates were washed with 1×TBST (TBS+0.05% Tween-20) using a BioTek 405 TS plate washer (BioTek, Winooski, VT). Serial dilutions of single chain diabodies (scDbs) were incubated on the plate for 1 hour at RT, washed then incubated with 1 µg/mL recombinant protein L (Thermo Fisher Scientific, 77679) for 1 hour at RT, washed, then incubated with anti-protein L HRP (1:10000, Abcam, ab63506) for 1 hour at RT. Plates were washed, 50 µL of 3,3',5,5'-Tetramethylbenzidine (TMB) substrate (BioLegend, San Diego, CA, 4211101) was added to each well, and the reaction was quenched with 50 µl 2N sulfuric acid (Thermo Fisher Scientific). Absorbance at 450 nm was measured with a Synergy H1 Multi-Mode Reader (BioTek).

Bispecific Antibody Production

Single chain diabodies (scDbs) were produced by cloning gBlocks (IDT, Coralville, Iowa) encoding each of the variants in the format of, from N- to C-terminus: IL-2 signal sequence, anti-pHLA variable light chain ($V_L$), GGGGS linker (SEQ ID NO:200), anti-CD3 variable heavy chain ($V_H$), $(GGGGS)_3$ linker (SEQ ID NO:201), anti-CD3 $V_L$, GGGGS linker (SEQ ID NO:200), anti-pHLA $V_H$, and 6×HIS tag into linearized pcDNA3.4 vector (Thermo Fisher Scientific, A14697). The proteins were expressed by the Eukaryotic Tissue Culture Core Facility of Johns Hopkins University. Briefly, 1 mg of plasmid DNA was transfected with PEI at a ratio of 1:3 into 1 L of FreeStyle 293-F cells at a density of 2-2.5×10⁶ cells per mL and incubated at 37° C. Five days after transfection, culture media was collected and filtered through a 0.22-µm unit. The scDbs were purified using HisPur Ni-NTA Resin (Thermo Fisher Scientific, 88222) and desalted into PBS pH 7.4 or 20 mM Tris pH 9.0, 150 mM NaCl using 7 k MWCO Zeba Spin desalting columns (Thermo Fisher Scientific, 89890). Proteins were quantified using a 4-15% Mini-PROTEAN TGX gel (Bio-Rad, Hercules, CA, 4568085) and/or nanodrop (Thermo Fisher Scientific). Proteins were stored at 4° C. for short term storage or snap frozen with the addition of 7% glycerol and stored at −80° C. for long term storage. Alternatively, the scDb protein was produced by GeneArt (Thermo Fisher Scientific) in Expi293s, purified with a HisTrap column (GE Healthcare, 17-5255-01) followed by size exclusion chromatography with a HiLoad Superdex 200 26/600 column (GE Healthcare, 28989335).

Surface Plasmon Resonance Affinity Measurements of $p53^{R175H}$ HLA-A *02:01 to H2-scDb Biotinylated $p53^{R175H}$/HLA-A*02:01, $p53^{WT}$/HLA-A*02:01, and H2-scDb binding experiments were performed at 25° C. using a Biacore T200 SPR instrument (GE Healthcare). Approximately 100-110 response units (RU) of biotinylated $p53^{R175H}$/HLA-A*02:01 and $p53^{WT}$/HLA-A*02:01 were captured in flow cells (Fc) 2 and 4, respectively, using a streptavidin chip. Single-cycle kinetics were performed by injecting increasing concentrations (3, 12, 50, 200 to 800 nM) of purified clone H2-scDb flowed over Fc 1-4. Binding responses for kinetic analysis were both blank- and reference-subtracted. Both binding curves were fit with a 1:1 binding model using Biacore Insight evaluation software.

CRISPR-Mediated Knockout of TP53

The Alt-R CRISPR system (IDT) was used to knock out the TP53 gene from KMS26, TYK-nu, and KLE cell lines. CRISPR Cas9 crRNAs targeting TP53 exon 3 (p53-5: CCCCGGACGATATTGAACAA (SEQ ID NO:191) or p53-6: CCCCTTGCCGTCCCAAGCAA (SEQ ID NO:202)) as well as CRISPR-Cas9 tracrRNA were resuspended at 100 µM with Nuclease-Free Duplex Buffer. The crRNAs and tracrRNA were duplexed at a 1:1 molar ratio for 5 minutes at 95° C. The duplexed RNA was allowed to cool to room temperature prior to mixing with Cas9 Nuclease at a 1.2:1 molar ratio for 15 minutes. A total of 40 µmols of the Cas9 RNP complexed with TP53 gRNA were mixed with 200,000 cells in 20 µL of OptiMEM. This mixture was loaded into a 0.1 cm cuvette (Bio-Rad, 1652089) and electroporated at 120 V and 16 ms using an ECM 2001 (BTX, Holliston, MA). Cells were immediately transferred to complete growth medium and cultured for 7 days. Single cell clones were established by limiting dilution and genomic DNA was harvested using a Quick-DNA 96 Kit (Zymo Research, Irvine, CA, D3012). A region flanking the CRISPR cut site was PCR amplified (forward primer: GCTGCCCTGGTAGGTTTTCT (SEQ ID NO:203), reverse primer: GAGACCTGTGGGAAGCGAAA (SEQ ID NO:204)) and Sanger Sequenced to select for clones with the desired TP53 status.

Immunoblotting Analysis

Cells were lysed in cold RIPA buffer (Thermo Fisher Scientific, 89901) supplemented with protease inhibitor cocktail (Thermo Fisher Scientific, 87785). Protein concentration was determined using a BCA assay (Thermo Fisher Scientific, 23227). Equal amounts of total protein (20-50 µg) were loaded in each lane of a 4-15% Mini-PROTEAN TGX gel (Bio-Rad, 4568085) and transferred to polyvinylidene difluoride membranes after electrophoresis. The membranes were incubated with appropriate primary antibodies (p53 [DO-1], 1:1000, Santa Cruz, sc-126; STAT2, 1:1000, Thermo Fisher Scientific, 44-362G; ZFP3, 1:1000, Thermo Fisher Scientific, PA5-62726; 3-actin [13E5], 1:1000, Cell Signaling Technology, 5125S; β-actin [8H10D10], 1:1000, Cell Signaling Technology, 3700S) and species-specific HRP-conjugated secondary antibodies (1:5000-10000). Signal was detected by a ChemiDoc MP chemiluminescence system (Bio-Rad).

Transfection of Cell Lines gBlocks (IDT) encoding HLA and target proteins were cloned into pcDNA3.1 or pcDNA3.4 vectors (Thermo Fisher Scientific, V79020, A14697). COS-7, Saos-2, and HEK293FT cells were transfected at 70-80% confluency using Lipofectamine 3000 (Thermo Fisher Scientific, L3000015) and incubated at 37° C. overnight. A total of 15 µg and 30 µg plasmid (1:1 ratio of HLA plasmid/target protein plasmid in co-transfections) was used for T25 and T75 flasks, respectively.

Viral Transduction of Cell Lines

HLA-A*02:01-encoding retrovirus was produced using the MSCV retroviral expression system (Clontech, Mountain View, CA, 634401). In brief, a gBlock encoding HLA-A*02:01-T2A-GFP (IDT) was cloned into the pMSCVpuro retroviral vector by HiFi DNA assembly (New England Biolabs, Ipswich, MA, E2621L). The pMSCVpuro-HLA-A*02:01-T2A-GFP plasmid was then co-transfected with a pVSV-G envelope vector into the GP2-293 packaging cell line. Viral supernatant was harvested 48 hours after transfection and concentrated 20-fold using Retro-X Concentrator (Clontech, 631456). RediFect Red-Fluc-GFP lentivirus particles (Perkin Elmer, Waltham, MA, CLS960003) was used for generating luciferase-expressing cell lines.

For transduction, non-tissue culture-treated 48-well plates were coated with 200 µL of 10 µg/mL RetroNectin (Clontech, T100B) per well overnight at 4° C. and blocked with 10% FBS for 1 hour at RT. Viral particles and $2 \times 10^5$ target cells were added to each well in a total volume of 500 µL cell culture media and spun at 2000×g for 1 hour then incubated at 37° C. Selection with 1 µg/mL puromycin (Thermo Fisher Scientific, A1113803) began three days later. Transduced cells were sorted based on presence of GFP using FACSAria Fusion (BD Biosciences, San Jose, CA) 10-14 days after transduction.

In Vitro scDb Co-Incubation Assays

To each well of a 96-well flat-bottom plate, the following components were combined in a final volume of 100 µL RPMI-1640 with 10% FBS, 1% Penicillin-Streptomycin, and 100 IU/mL IL-2: bispecific antibody diluted to the specified concentration, $5 \times 10^4$ human T cells, and $1\text{-}5 \times 10^4$ target cells (COS-7, T2, or other tumor cell lines). The effector to target cell ratio is specified in the figure legend for each experiment. The co-culture plate was incubated for 20 hours at 37° C. and conditioned media was assayed for cytokine and cytotoxic granule protein secretion using the Human IFN-γ Quantikine Kit (R&D Systems, Minneapolis, MN, SIF50), Human IFN-γ Flex Set Cytometric Bead Array (BD, 558269), or the MILLIPLEX Luminex assays (Millipore Sigma, HSTCMAG28SPMX13, HCD8MAG-15K) read on the Bioplex 200 platform (Bio-Rad). Cytotoxicity was assayed by CellTiter-Glo Luminescent Cell Viability Assay (Promega, Madison, WI, G7571) or Bio-Glo Luciferase Assay (Promega, G7941) per manufacturer's instructions. For CellTiter-Glo assays, percent cytotoxicity was calculated by subtracting the luminescence signal from the average of the T cell only wells and normalizing to the no scDb condition: 1−(scDb well−T cell only)/(no scDb well−T cell only)×100. For Bio-Glo assays, percent cytotoxicity was calculated by normalizing luminescence signal to the no scDb condition: 1−(scDb well)/(no scDb well)×100.

Real-Time Live-Cell Imaging

A total of $1 \times 10^4$ CellTracker Green CMFDA (Thermo Fisher Scientific, C7025)-labeled target cells were plated in each well of a 96-well flat bottom plate and allowed to attach for 8 hours before adding T cells and scDb at the indicated E:T ratio and concentrations, respectively. Each condition was plated in triplicate. Plates were imaged every 3 hours using the IncuCyte ZOOM Live-Cell analysis system (Essen Bioscience, Ann Arbor, MI) for a total of 60 hours. Four images per well at 10× zoom were collected at each time point. Cell confluence in each well was quantified using the phase contrast channel.

Expression, purification and refolding of p53$^{R175H}$ HLA-A*02:01

Plasmids for HLA-A*02:01 and β2M were received from the NIH Tetramer Facility (Atlanta, GA) and separately transformed into BL21(DE3) cells. Each was expressed in inclusion bodies using auto-induction media as described elsewhere (Skora et al., Proc. Natl. Acad. Sci. U.S.A 112: 9967-9972 (2015); Martayan et al., The Journal of Immunology 182:3609-3617 (2009); and Huang et al., Bioinformatics 26:680-682 (2010)). Purification of the HLA-A*02:01 and β2M inclusion bodies was achieved with a series of detergent washes followed by solubilization with 8 M urea. Refolding of the HLA-A*02:01, β2M, and mutant p53$^{R175H}$ peptide was performed as described elsewhere (Myszka, *J. Mol. Recognit.* 12:279-284 (1999)). Briefly, HLA-A*02:01 and β2M inclusion bodies were combined in a refolding buffer containing 100 mM Tris pH 8.3, 400 mM L-arginine, 2 mM EDTA, 5 mM reduced glutathione, 0.5 mM oxidized glutathione, 2 mM PMSF, and 30 mg of the mutant $p53^{R175H}$ peptide (amino acid 168-176, HMTEVVRHC (SEQ ID NO:1)) dissolved in 1 mL of DMSO. The resultant solution was stirred at 4° C. for 2 days, with two further additions of HLA-A*02:01 inclusion bodies on day 2, concentrated to 10 mL and purified by size exclusion chromatography on a HiLoad 26/60 Superdex 75 Prep grade column (GE Healthcare, 28989334). For incubation with the H2-Fab, purified pHLA-A*02:01 was concentrated to ~1-3 mg/mL and stored at −80° C. until use.

Production of the H2-Fab Antibody Fragment

The light chain (LC) and heavy chain (HC) variable region sequences of H2 scFv were grafted, linked with the respective constant region sequences of human IgG1 and separately cloned into a pcDNA3.4 vector (Thermo Fisher Scientific, A14697). Both chains were preceded by a mouse IgKVIII signal peptide. Before large-scale expression of full-length antibody, optimization of the LC:HC DNA ratio for transfection was performed to determine optimal recombinant protein yields. For a 1 L expression, a total of 50 μg of purified plasmids (1:1 LC:HC ratio) were transfected with PEI at a ratio of 1:3 into Freestyle 293-F cells at a density of $2\text{-}2.5 \times 10^6$ cells per mL and incubated at 37° C. for 7 days. The media was harvested via centrifugation, filtered through a 0.22-μm unit and the full-length antibody was purified via protein A affinity chromatography on a HiTrap MabSelect™ SuRe™ column (GE Healthcare, 29-0491-04). Full-length antibody was eluted using a linear gradient of 0-100 mM sodium citrate, pH 3.5. The protein A fractions containing pure H2 antibody were pooled, quantified by SDS-PAGE gel electrophoresis and dialyzed into 20 mM sodium phosphate buffer, pH 7.0, 10 mM EDTA.

For generation of H2-Fab fragments, ~1-3 mg of full-length antibody was mixed with 0.5 mL of a 50% Immobilized Papain slurry (Thermo Fisher Scientific, 20341) pre-activated with digestion buffer (20 mM sodium phosphate buffer, pH 7.0, 10 mM EDTA) containing 20 mM cysteine-HCl. The mixture was incubated at 37° C. overnight with constant shaking at 200 rpm. The H2 antibody digest was separated from the immobilized resin by a gravity resin separator and washed with 10 mM Tris-HCl, pH 7.5. Newly generated H2-Fab fragments were further purified by cation-exchange chromatography using a Mono-S column (GE Healthcare, 17516801) and eluted using a linear gradient of 0-500 mM NaCl.

The H2-Fab fragments were concentrated, mixed with equimolar $p53^{R175H}$/HLA-A*02:01 and incubated at 4° C. overnight. The H2-Fab-$p53^{R175H}$/HLA-A*02:01 mixture was evaluated by size exclusion chromatography on a Superdex™ 200 Increase 10/300 column (GE Healthcare, 28990944). The fractions of ~98% pure pHLA-A*02:01-H2-Fab complex were pooled, concentrated to 12.6 mg/mL and exchanged into a buffer containing 25 mM HEPES, pH 7.0, 200 mM NaCl.

Crystallization, Data Collection and Structure Determination

Crystals of the ternary complex H2-Fab-$p53^{R175H}$/HLA-A*02:01 were grown in hanging drop by vapor diffusion in drops set up with a TTP mosquito robot with a reservoir solution of 0.2 M ammonium chloride and 20% (w/v) PEG 3350 MME. Crystals were flash-frozen in mother liquor. Data were collected at National Synchrotron Light Source-II at beamlines 17-ID-1(AMX) on a DECTRIS Eiger X 9M detector and 17-ID-2 (FMX) on a DECTRIS Eiger X 16M detector. Datasets were indexed, integrated and scaled using fastdp, XDS, and aimless. Monoclinic crystals of H2-Fab-$p53^{R175H}$/HLA-A*02:01 diffracted to 3.5 Å. The structure for the H2-Fab-$p53^{R175H}$/HLA-A*02:01 complex was determined by molecular replacement with PHASER using PDB ID 6O4Y (11) and 6UJ9 as the search models. The data was refined to a final resolution of 3.5 Å using iterative rounds of refinement with REFMAC5 and manual rebuilding in Coot. Structures were validated using Coot and PDB Deposition tools. The model has 94.11% of the residues in preferred and allowed regions according to Ramachandran statistics (Table 7). Figures were rendered in PyMOL (v2.2.3, Schrödinger, LLC, New York, NY). Buried areas were calculated with PDBePISA. The angle that determines the relative orientation between the pHLA and the Fab/TCR was calculated by the dot product of the vector defined by the position of the alpha carbon of the P1-P9 of the peptide and the vector defined by the disulfide bonds in the $V_H$ and $V_L$ domains.

Mouse Xenograft Model

Female NOD.Cg-Prkdc$^{scid}$II2rg$^{tm1Wjl}$/SzJ (NSG) mice at 6-10 weeks were acquired from the Jackson Laboratory (Bar Harbor, ME, 005557) and treated in compliance with the institutional Animal Care and Use Committee approved protocol. In the early treatment model, mice were inoculated intravenously with $1 \times 10^6$ luciferase-expressing KMS26 or KMS26-TP53 KO cells and $1 \times 10^7$ in vitro expanded human T cells via lateral tail vein injection on day 0. On day 1, mice were randomized based on luminescence quantification using the IVIS imaging system and Living Image software (Perkin Elmer) to ensure similar pretreatment tumor burden. After randomization, two-week micro-osmotic pumps (ALZET, Cupertino, CA, 1002) filled with H2-scDb or isotype control scDb (scFv against an irrelevant pHLA linked with UCHT1scFv) that had been primed in 1 mL PBS overnight at 37° C. were placed intraperitoneally using sterile surgical technique. Tumor growth was serially monitored by bioluminescent imaging. In the established tumor model, mice were inoculated with $3.5 \times 10^5$ luciferase-expressing KMS26 cells and $1 \times 10^7$ human T cells via lateral tail vein injection on day 0. On day 6, H2-scDb or isotype control scDb was administered similarly as in the early treatment model.

Statistical Analysis

Data are presented as means±SD. Statistical analyses were carried out using specific tests indicated in the figure legend. A P value of <0.05 was used to denote statistical significance. All analyses were performed using Prism version 8.0 (GraphPad, San Diego, CA).

Example 3: Bispecific Antibodies Targeting Mutant RAS Neoantigens

Mutations in the RAS oncogenes occur in multiple cancers and new approaches to target these mutations have been the subject of intense research for decades. Most of these efforts have been focused on conventional small molecule drugs rather than antibody-based therapies because the RAS proteins are intracellular.

This Example identifies scFvs specific for peptides derived from two recurrent RAS mutations, G12V and Q61H/L/R, which are presented on cancer cells in the context of two common human leukocyte antigen alleles, HLA-A3 and HLA-A1, respectively. The scFvs did not recognize the peptides derived from the wildtype (WT) form of RAS proteins or other related peptides. Given their extremely low antigen density on cancer cells, a very sensitive immunotherapeutic agent was developed to kill cells harboring RAS gene mutations. Single chain diabodies (scDbs) specific for peptides derived from G12V or Q61H/L/R were capable of inducing T cell activation and killing of target cancer cells expressing endogenous levels of the mutant RAS proteins and cognate HLA alleles.

Results

MANAs Derived from Clinically Relevant RAS Gene Mutations

In silico predictions suggested that the 10-mer peptide from codons 5 to 14 (KLVVVGAVGV, "G12V[5-14]"; SEQ ID NO:209), in which the underlined valine residue (V) represents the G12V mutation, would bind to HLA-A*02:01 (henceforth referred to as HLA-A2) (see, e.g., Skora et al., *Proc Natl Acad Sci USA* 112:9967-9972 (2015); and Andreatta, *Bioinformatics* 32:511-517 (2016)). A MANA-body (called D10) that bound to this pHLA-A2 complex and did not bind to the wildtype (WT) counterpart, with selective binding demonstrated using pHLA complexes attached to artificial surfaces as well as using cells pulsed with mutant peptides, was previously reported (Skora et al., *Proc Natl Acad Sci USA* 112:9967-9972 (2015)). However, it could not be demonstrated that the D10 MANAbody could bind to cells that expressed endogenous levels of the mutant KRAS gene or even to cells that overexpressed an exogenous mutant KRAS gene. It was hypothesized that despite the predictions of the in silico algorithms, the KRAS protein was not processed to the G12V[5-14] peptide and transported to the cell surface. There is indeed precedent for such in silico predictions to be inaccurate (Schmidt et al., *J Biol Chem* 292:11840-11849 (2017)). To evaluate this possibility, a highly-sensitive mass spectrometry (MS)-based approach (MANA-SRM) was developed to analyze HLA-bound peptides. Human HLA-A2 and full-length human KRAS containing G12V were expressed in SV40 virus-immortalized monkey kidney COS-7 cells and HLA-bound peptides were immunopurified. MS analysis of eluted peptides showed that the G12V[5-14] peptide could not be detected, even when the mutant KRAS gene was overexpressed (Table 10). It was concluded that this peptide was not processed and presented on PLA-A2+ cells harboring a KRAS G12V mutant gene.

TABLE 10

MANA-SRM quantification. Mutation-associated Neoantigen (MANA) peptides per cell were quantified using the mass-spectrometry based method MANA-SRM. COS-7 cells were co-transfected with plasmids encoding HLA alleles and full-length KRAS variants. To assess endogenous expression of MANAs, cell lines bearing HLA alleles and RAS variants of interest were analyzed.

| Cell Line | Transfection Condition | Endogenous HLA alleles | Predicted binding peptide by NetMHCv4.0 | SEQ ID NO: | Predicted Affinity by NetMHCv4.0 (nM) | Detected Copy Number Per Cell |
|---|---|---|---|---|---|---|
| COS-7 | HLA-A2 + KRAS G12V | N/A | KLVVVGAVGV | 209 | 300.18 | N/A |
| COS-7 | HLA-A3 + KRAS G12V | N/A | VVGAVGVGK | 206 | 277.44 | 24 |
| | | | VVVGAVGVGK | 205 | 396.16 | 102 |
| COS-7 | HLA-A2 + KRAS G12V | N/A | N/A | | N/A | N/A |
| COS-7 | HLA-A1 + KRAS Q61H | N/A | ILDTAGHEEY | 2 | 185.91 | 583 |
| COS-7 | HLA-A2 + KRAS Q61H | N/A | N/A | | N/A | N/A |
| COS-7 | HLA-A1 + KRAS Q61L | N/A | ILDTAGLEEY | 3 | 66.03 | 512 |
| COS-7 | HLA-A2 + KRAS Q61L | N/A | N/A | | N/A | N/A |
| COS-7 | HLA-AI + KRAS Q61R | N/A | ILDTAGREEY | 4 | 322.23 | 127 |
| NCI-H441 | N/A | A*02:01, A*03:01 | VVVGAVGVGK | 205 | 396.16 | 9 |
| CFPAC-1 | N/A | A*02:01, A*03:01 | VVVGAVGVGK | 205 | 396.16 | 3 |
| RD | N/A | A*01:01, A*01:01 | ILDTAGHEEY | 2 | 185.91 | 8 |
| HL-60 | N/A | A*01:01, A*01:01 | ILDTAGLEEY | 3 | 66.03 | 4 |
| Hs 940.T | N/A | A*01:01, A*01:01 | ILDTAGREEY | 4 | 322.23 | 1 |

Figure 45:
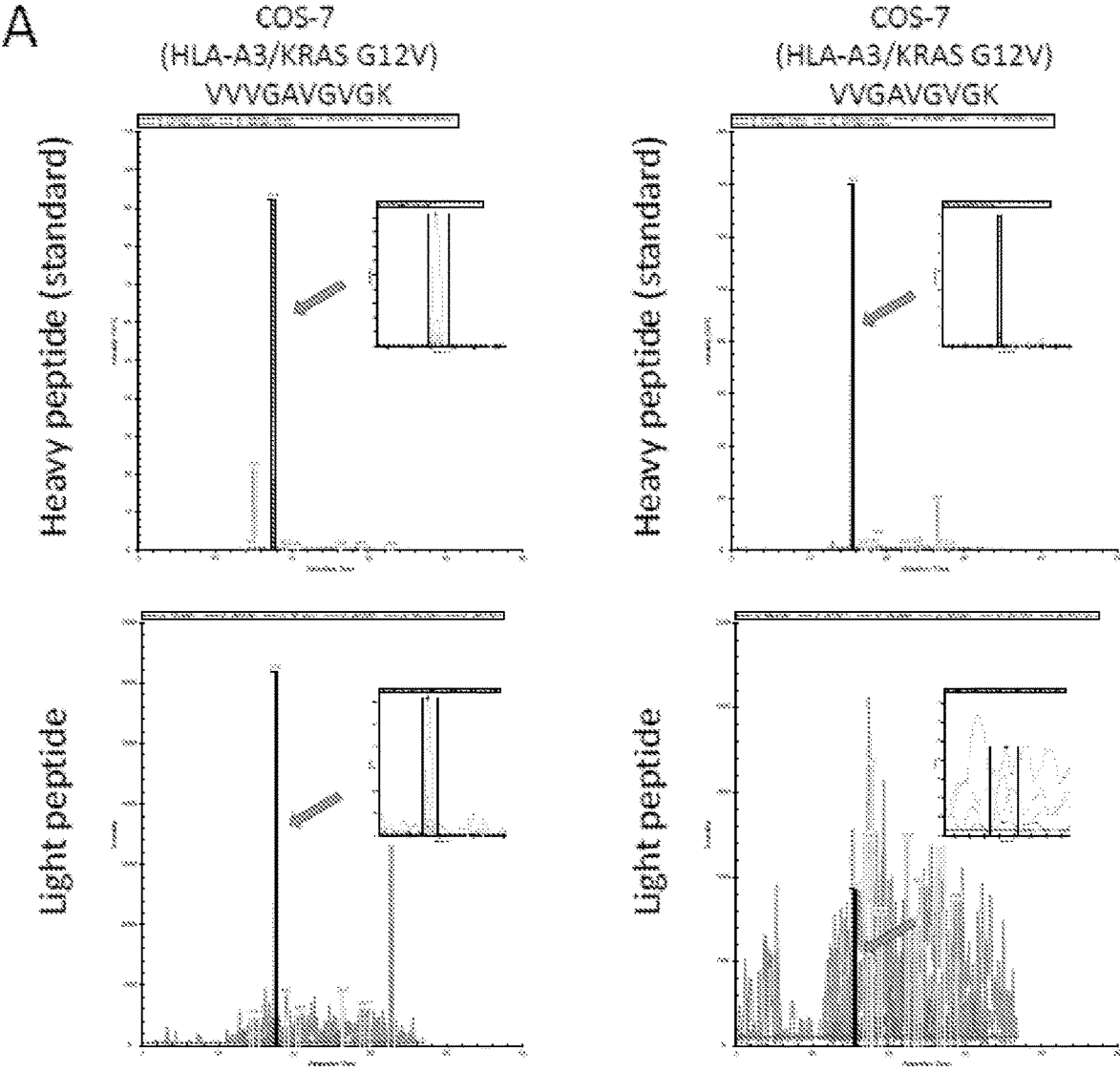
Figure 45:
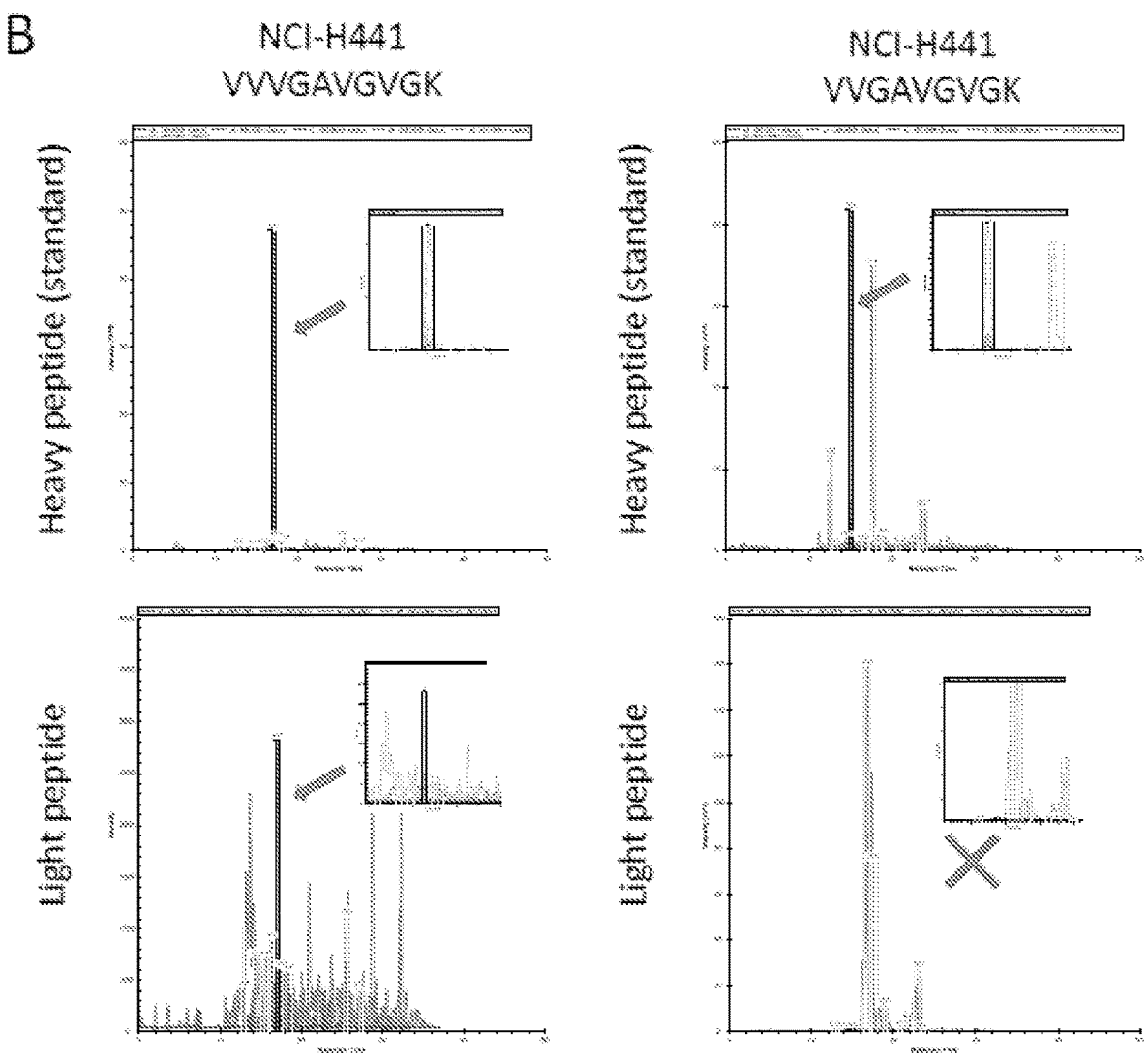
Figure 45:
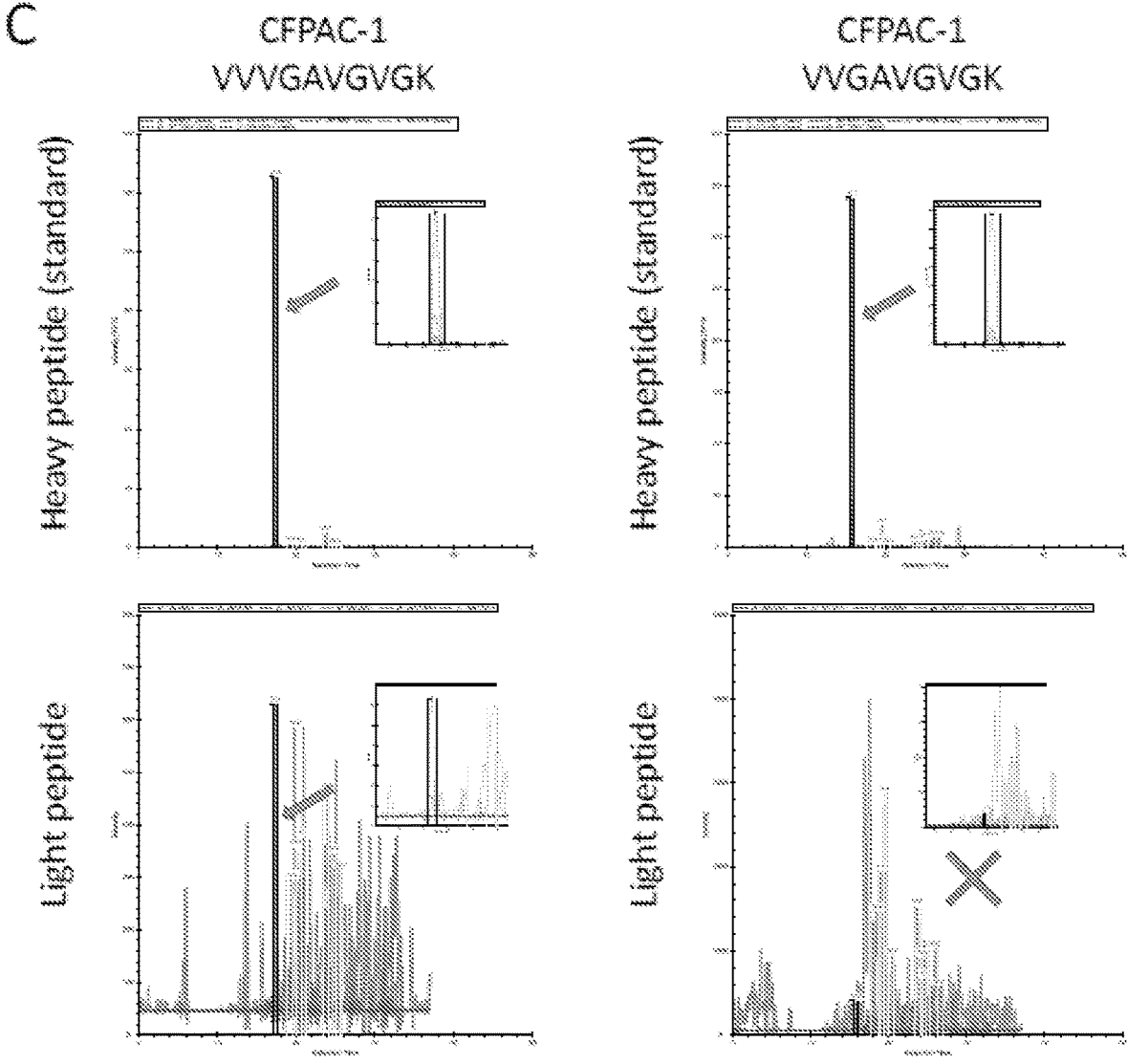

Thus, attention was to two peptides, a 9-mer (VVGAVGVGK; SEQ ID NO:206) from codons 8 to 16 ("G12V[8-16]") and a 10-mer (VVVGAVGVGK; SEQ ID NO:205) from codons 7 to 16 ("G12V[7-16]"), containing the RAS G12V mutation that were predicted by NetMHCv4.0 to bind HLA-A*03:01 (henceforth referred to as HLA-A3) with high affinity (Andreatta, *Bioinformatics* 32:511-517 (2016)). HLA-A3 is one of the most common HLA-A alleles. MANA-SRM was used to confirm the in silico predictions that these peptide complexes would be displayed on the cell surface before screening for MANA-bodies. Human HLA-A3 and full-length human KRAS G12V were expressed in COS-7 cells, then immunopurified with an anti-human HLA antibody. MS analysis of peptides eluted from the captured peptide-HLA complexes detected the G12V[7-16] peptide at 102 copies per cell and the G12V[8-16] peptide at considerably lower levels (24 copies per cell) (FIG. 45A, Table 10). Importantly, when COS-7 cells were transfected with HLA-A2 and KRAS G12V as a negative control, neither of these peptides were detected (Table 10). MANA-SRM analysis was then performed on two human cancer cell lines, the lung adenocarcinoma line NCI-H441 and the pancreatic ductal adenocarcinoma line CFPAC-1, both expressing endogenous levels of HLA-A3 and harboring the KRAS G12V mutation. The CFPAC-1 and NCI-H441 lines presented on average 3 and 9 copies per cell, respectively, of the G12V[7-16] peptide (FIGS. 45, B and C, Table 10), and the G12V[8-16] peptide was not detected. Given the higher abundance of the 10-mer G12V [7-16](henceforth referred to as "G12V") peptide, efforts were focused on targeting this MANA.

Another commonly mutated residue in RAS genes is the glutamine at codon 61. RAS codon 61 mutations are found in a wide variety of cancers, including melanomas, multiple myelomas, thyroid, and bladder cancers. Using NetMHCv4.0, it was predicted that a 10-mer RAS peptide (codons 55 to 64) could bind with high affinity to HLA-A*01:01 (henceforth referred to as HLA-A1), another common HLA-A allele (Maiers et al., *Hum Immunol* 68:779-788 (2007)). This peptide (ILDTAGQEEY; SEQ ID NO:136) as well as the flanking amino acids are conserved across all three RAS proteins. Using MANA-SRM, cell surface expression of 10-mer peptides from codons 55 to 64 containing the Q61H, Q61L, and Q61R mutations (ILD-TAGHEEY (SEQ ID NO:2), ILDTAGLEEY (SEQ ID NO:3), and ILDTAGREEY (SEQ ID NO:4), respectively) were previously evaluated, and in the transfected COS-7 overexpression system, an average of 583, 512, and 127 copies of the Q61H, Q61L, and Q61R peptides per cell were found (Wang et al., *Cancer Immunol Res* 7:1748-1754 (2019)). These peptides were also identified to be presented on cell lines expressing endogenous levels of Q61 mutant RAS proteins, notably with four copies of the Q61L peptide per cell found in the acute promyelocytic leukemia cell line HL-60 (Table 10).

Together, these data show that G12V and Q61 mutant RAS proteins can be processed into peptides that are presented on the surface of cancer cell lines, albeit at antigen densities below what is considered the minimum required for recognition by conventional antibody-based immunotherapeutic agents.

Identification of scFv-Expressing Phage Clones Targeting HLA-Restricted RAS Mutant Peptides To develop MANAbodies targeting the above-named RAS peptides, a second phage library displaying scFvs was built. This library was designed based on principles described elsewhere (Skora et al., *Proc Natl Acad Sci USA*

Figure 46:
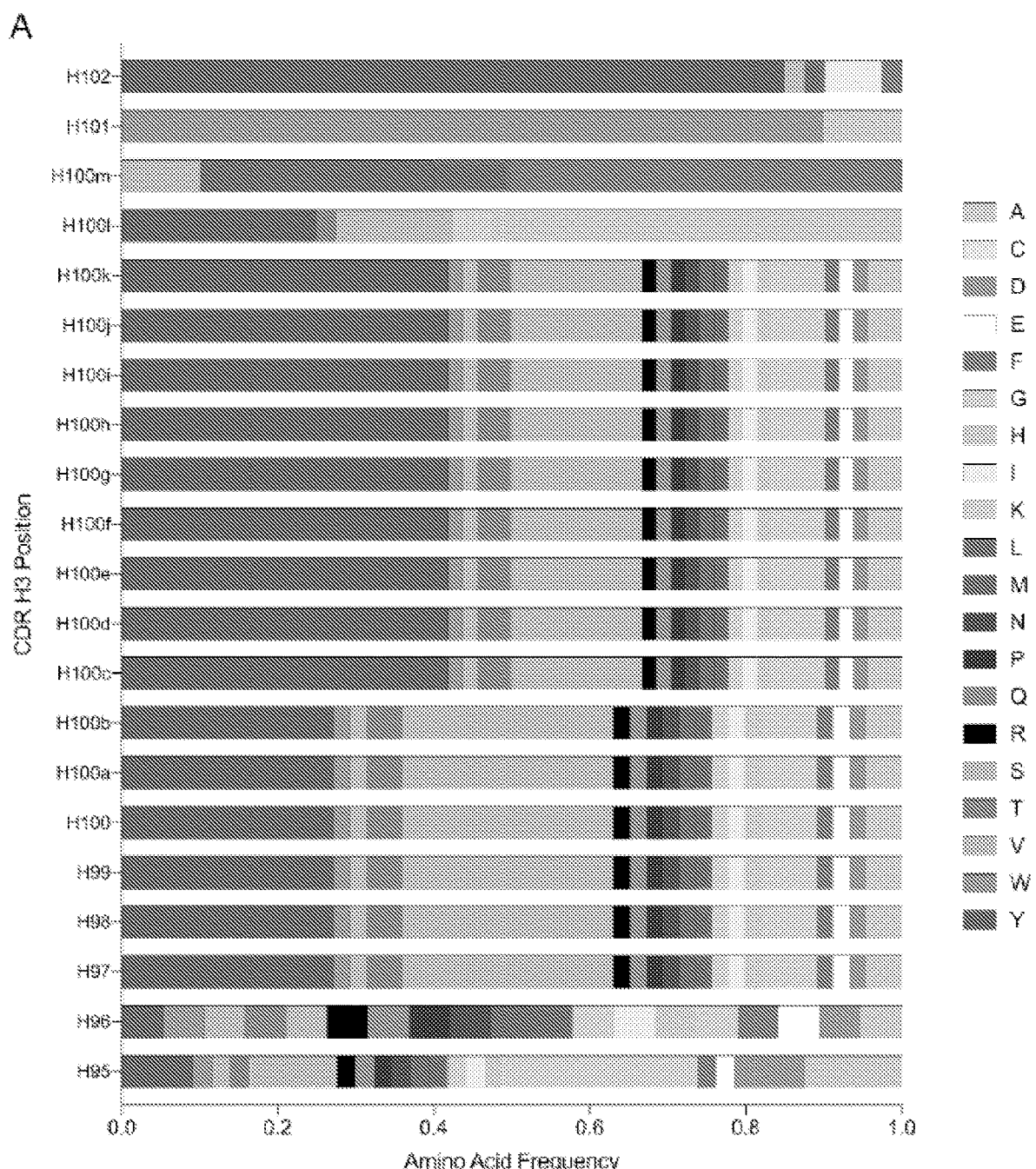
Figure 46:
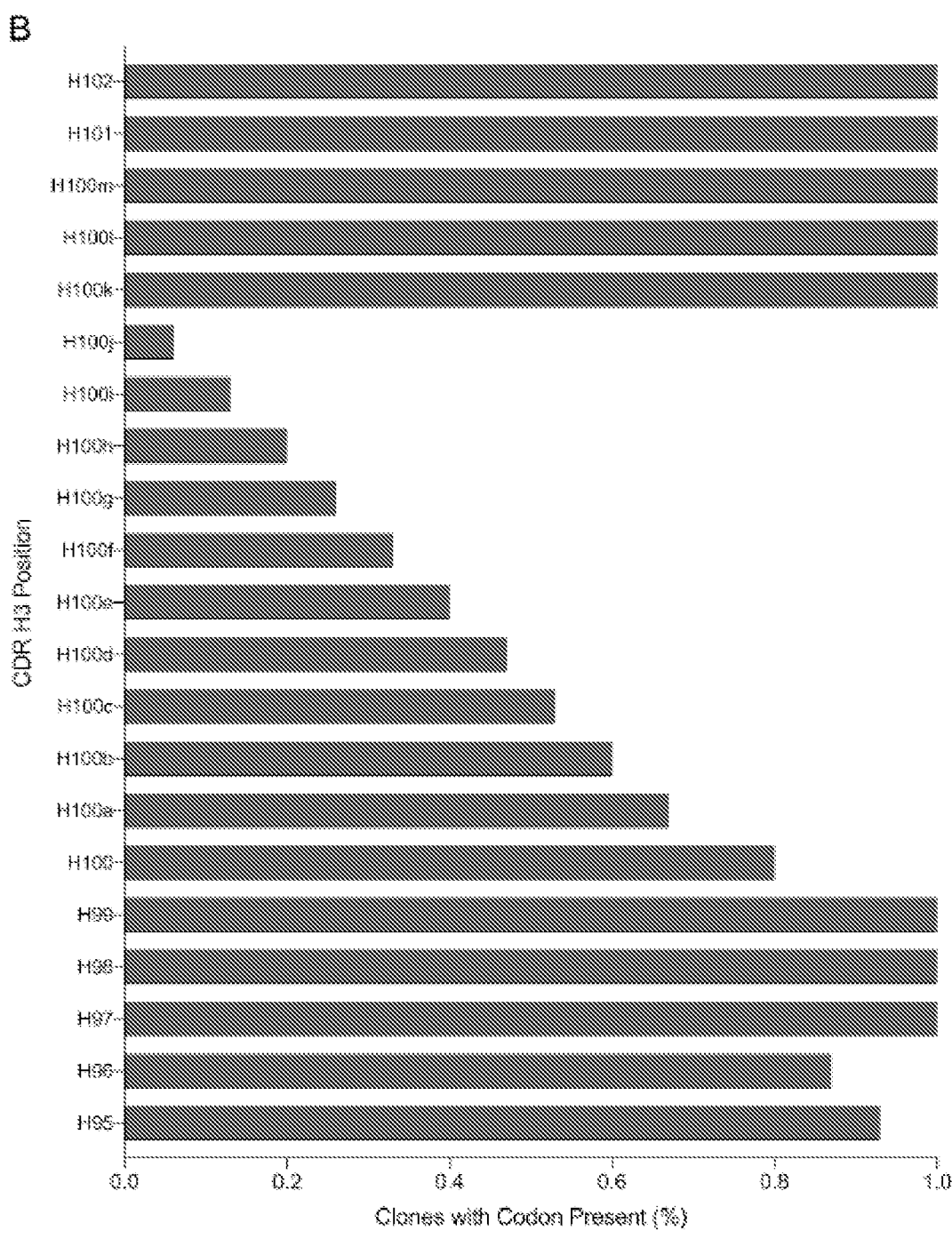
Figure 46:
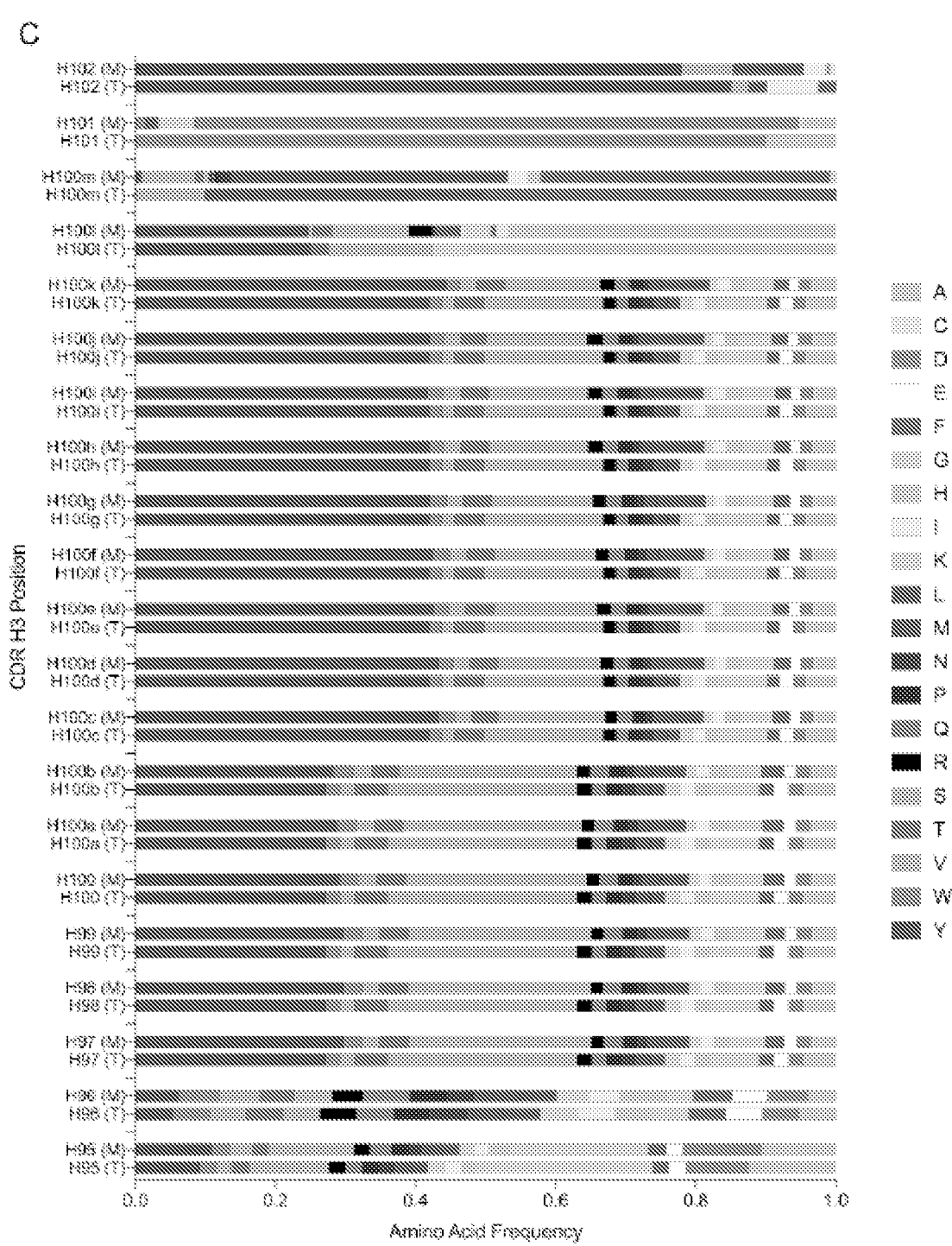

112:9967-9972 (2015)), but with important modifications. In particular, precursor library DNA was synthesized using trinucleotide mutagenesis (TRIM) technology, permitting fine tuning of the amino acid diversity at particular codons considered most critical for antigen binding. Diversity was introduced in five of the six complementarity-determining regions (CDRs), with the most amino acid diversity as well as length diversity incorporated into the third CDR of the heavy chain (CDR-H3) (FIGS. 46, A and B). The completed library was estimated to contain ~3.6×10^{10} unique clones. As a quality control step, a portion of the library was subjected to massively parallel sequencing of the heavy chain CDR3 region, demonstrating that the expected and actual amino acid diversity were in excellent alignment (FIG. 46C).

Figure 47:
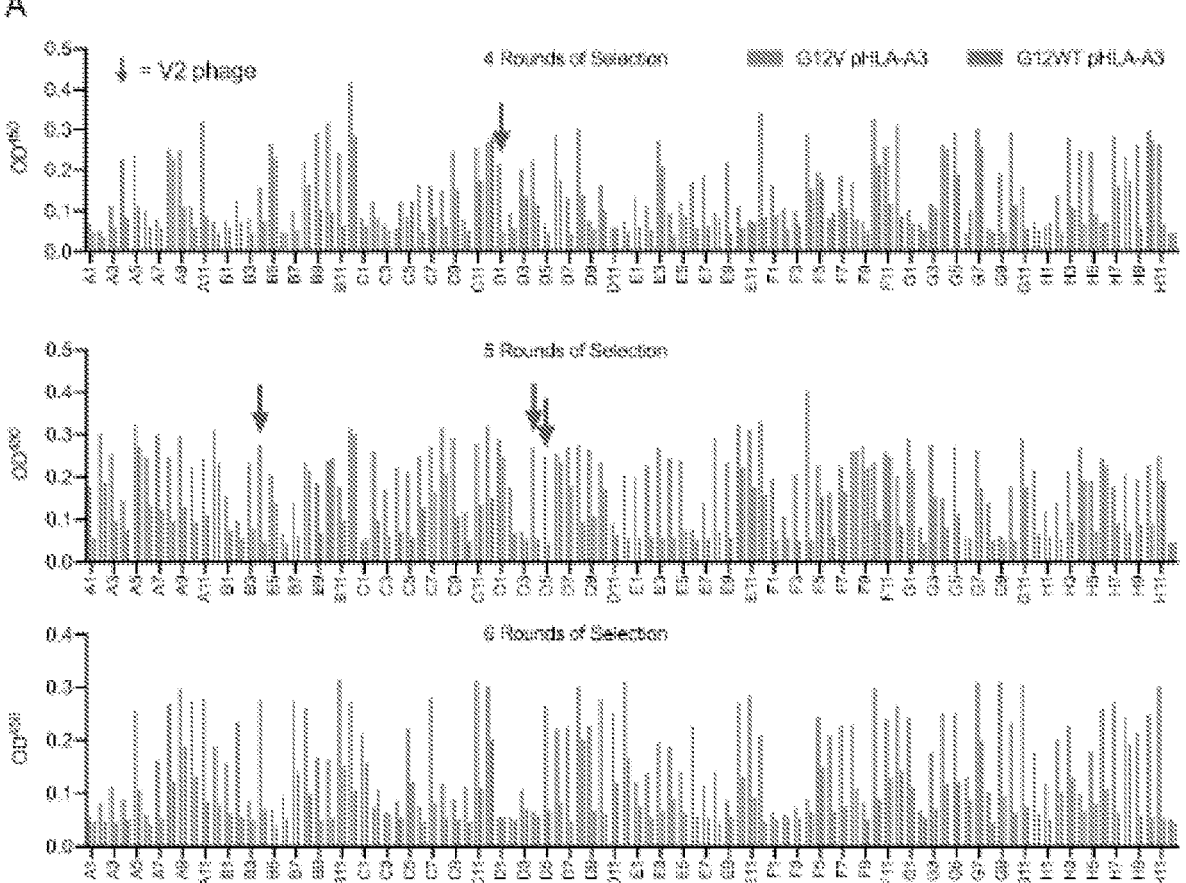
Figure 47:
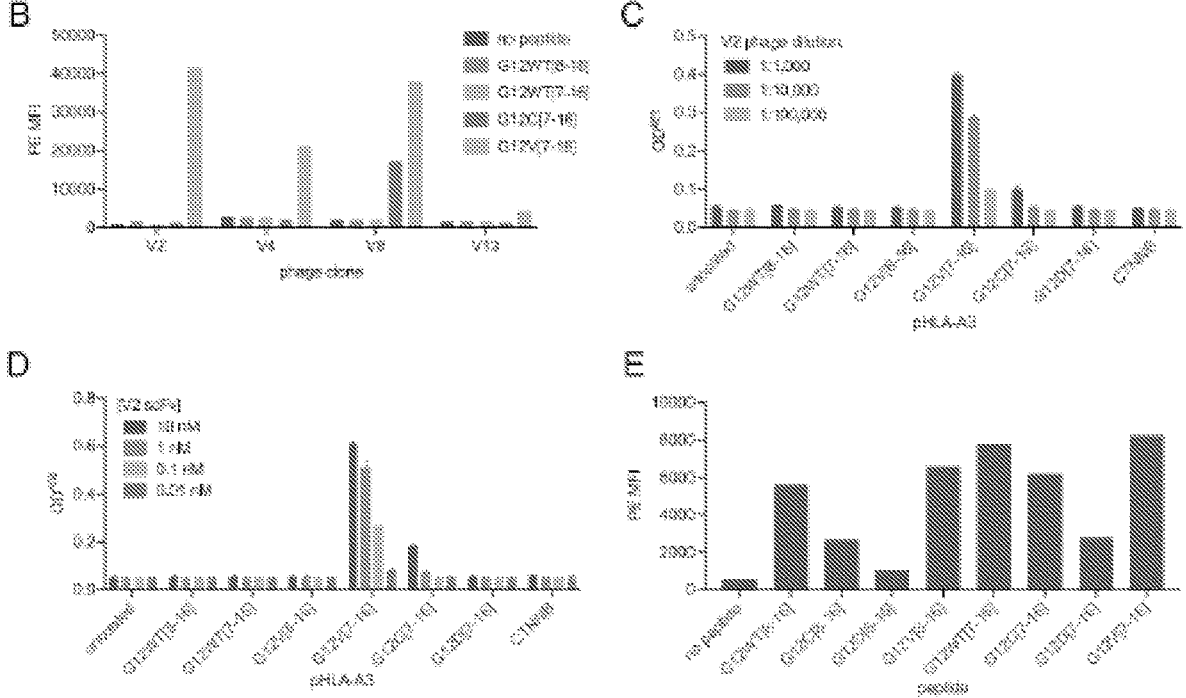

For the RAS G12V HLA-A3 MANA target, HLA-A3 and beta-2-microglobulin were folded together with the chemically synthesized G12V peptide or its WT [7-16] (G12WT) counterpart to form pHLA complexes (Table 11). These pHLA-A3 were then used to screen the phage display library described above. The screening process consisted of four to six rounds of phage selection, similar to the scheme described previously, with key differences outlined in the Materials and Methods. Over the course of this selection, phage were negatively selected against soluble streptavidin, streptavidin magnetic beads, denatured HLA-A3, unrelated pHLA-A3, and G12WT pHLA-A3 and positively selected against the G12V pHLA-A3. Following the screening process, individual phage clones were amplified and subjected to enzyme-linked immunosorbent assay (ELISA) to assess their binding specificity (FIG. 47A). While multiple clones initially appeared to be promising on ELISAs with plaste-bound pHLA complexes, one phage clone (V2) stood out upon subsequent flow cytometry assays on cells displaying these complexes (FIG. 47B, Table 12). The V2 phage had substantially greater binding to G12V pHLA-A3 compared to other pLA-A3, including those formed with LA-A3 folded with the G12WT peptide, the G12C or G12D variant, or an unrelated CTNNB peptide (FIG. 47C, Table 11). V2 phage also failed to detectably interact with VLA-A3 folded with the G12V[8-16] or G12WT[8-16] peptides (FIG. 47C, Table 11).

TABLE 11

Peptides for pHLA complexes. Peptides used for pHLA complexes were predicted to bind to the HLA allele of interest using NetMHCv4.0.

| Peptide Name | Sequence | SEQ ID NO | HLA-A allele | NetMHCv4.0 predicted HLA affinity (nM) |
|---|---|---|---|---|
| KRAS G12WT [8-16] | VVGAGGVGK | 208 | HLA-A* 03:01 | 277.44 |
| KRAS G12WT [7-16] | VVVGAGGVGK | 207 | HLA-A* 03:01 | 396.16 |
| KRAS G12C [8-16] | VVGACGVGK | 210 | HLA-A* 03:01 | 221.43 |
| KRAS G12C [7-16] | VVVGACGVGK | 211 | HLA-A* 03:01 | 375.53 |
| KRAS G12D [8-16] | VVGADGVGK | 212 | HLA-A* 03:01 | 1172.08 |
| KRAS G12D [7-16] | VVVGADGVGK | 213 | HLA-A* 03:01 | 938.8 |
| KRAS G12V [8-16] | VVGAVGVGK | 206 | HLA-A* 03:01 | 202.62 |

TABLE 11-continued

Peptides for pHLA complexes. Peptides used
for pHLA complexes were predicted to bind to
the HLA allele of interest using NetMHCv4.0.

| Peptide Name | Sequence | SEQ ID NO | HLA-A allele | NetMHCv4.0 predicted HLA affinity (nM) |
|---|---|---|---|---|
| KRAS G12V [7-16] | VVVGAVGVGK | 205 | HLA-A* 03:01 | 341.99 |
| CTNNB | TTAPSLSGK | 214 | HLA-A* 03:01 | 43.24 |
| RAS Q61WT [55-64] | ILDTAGQEEY | 136 | HLA-A* 01:01 | 86.69 |
| RAS Q61H [55-64] | ILDTAGHEEY | 2 | HLA-A* 01:01 | 185.91 |

TABLE 11-continued

Peptides for pHLA complexes. Peptides used
for pHLA complexes were predicted to bind to
the HLA allele of interest using NetMHCv4.0.

| Peptide Name | Sequence | SEQ ID NO | HLA-A allele | NetMHCv4.0 predicted HLA affinity (nM) |
|---|---|---|---|---|
| RAS Q61K [55-64] | ILDTAGKEEY | 215 | HLA-A* 01:01 | 324.9 |
| RAS Q61L [55-64] | ILDTAGLEEY | 3 | HLA-A* 01:01 | 66.03 |
| RAS Q61R [55-64] | ILDTAGREEY | 4 | HLA-A* 01:01 | 322.23 |
| CMV | YSEHPTFTSQY | 216 | HLA-A* 01:01 | 12.72 |

TABLE 12 scFv sequences. Amino Acid (AA) sequences of anti-CD3 scFvs
used for bispecific antibody construction. Affinities of
select anti-CD3 clones were gathered from the literature.

| scFv name | antigen | Affinity (nM) | variable light chain (AA) | SEQ ID NO | variable heavy chain (AA) | SEQ ID NO |
|---|---|---|---|---|---|---|
| V2 | RAS G12V [7-16] pHLA-A3 | 8.7 | DIQMTQSPSSLSASVGDRVTITCRAS QDVNTAVAWYQQKPGKAPKLLIYSA SFLYSGVPSRFSGSRSGTDFTLTISS LQPEDFATYYCQQSYYYFRPITFGQG TKVEIK | 699 | EVQLVESGGGLVQPGGSLRLSCAASGF NLSYSDIHWVRQAPGKGLEWVAVVMP DSGHTNYADSVKGRFTISADTSKNTAY LQMNSLRAEDTAVYYCSRATNIPVYAF DYWGQGTLVTVSS | 700 |
| H1 | RAS Q61H [55-64] pHLA-A1 | not determined | DIQMTQSPSSLSASVGDRVTITCRAS QDVNTAVAWYQQKPGKAPKLLIYSA SFLYSGVPSRFSGSRSGTDFTLTISS LQPEDFATYYCQQVIYYPFTFGQGT KVEIK | 701 | EVQLVESGGGLVQPGGSLRLSCAASGF NLYSYAIHWVRQAPGKGLEWVALLYP DYGVTSYADSVKGRFTISADTSKNTAY LQMNSLRAEDTAVYYCSRYRSYEYSVS SYSYSAMDYWGQGTLVTVSS | 702 |
| L2 | RAS Q61L [55-64] pHLA-A1 | 65 | DIQMTQSPSSLSASVGDRVTITCRAS QDVNTAVAWYQQKPGKAPKLLIYSA SFLYSGVPSRFSGSRSGTDFTLTISS LQPEDFATYYCQQAVSYPWTFGQGT KVEIK | 703 | EVQLVESGGGLVQPGGSLRLSCAASGF NISSSGIHWVRQAPGKGLEWVAMVYG GSGYTNYADSVKGRFTISADTSKNTAY LQMNSLRAEDTAVYYCSRWAHYSAY MDYWGQGTLVTVSS | 704 |
| R6 | RAS Q61R [55-64] pHLA-A1 | not determined | DIQMTQSPSSLSASVGDRVTITCRAS QDVNTAVAWYQQKPGKAPKLLIYSA SFLYSGVPSRFSGSRSGTDFTLTISS LQPEDFATYYCQQYSNYPLTFGQGT KVEIK | 705 | EVQLVESGGGLVQPGGSLRLSCAASGF NVFYGSMHWVRQAPGKGLEWVAFIGP DSTYTYYADSVKGRFTISADTSKNTAY LQMNSLRAEDTAVYYCSRDLGSAYAM DYWGQGTLVTVSS | 706 |
| UCHT1 "U" | human CD3 | 1.4-2.2 | DIQMTQTTSSLSASLGDRVTISCRAS QDIRNYLNWYQQKPDGTVKLLIYYT SRLHSGVPSKFSGSGSGTDYSLTISN LEQEDIATYFCQQGNTLPWTFAGGTK LEIK | 707 | EVQLQQSGPELVKPGASMKISCKASGY SFTGYTMNWVKQSHGKNLEWMGLINP YKGVSTYNQKFKDKATLTVDKSSSTAY MELLSLTSEDSAVYYCARSGYYGDSD WYFDVWGAGTTVTVSS | 708 |
| UCHT1.v9 "U2" | human CD3 | 2.5-4.7 | DIQMTQSPSSLSASVGDRVTITCRAS QDIRNYLNWYQQKPGKAPKLLIYYTS RLESGVPSRFSGSGSGTDYTLTISSL QPEDFATYYCQQGNTLPWTFGQGTK VEIK | 709 | EVQLVESGGGLVQPGGSLRLSCAASGY SFTGYTMNWVRQAPGKGLEWVALINP YKGVSTYNQKFKDRFTISVDKSKNTAY LQMNSLRAEDTAVYYCARSGYYGDSD WYFDVWGQGTLVTVSS | 710 |
| diL2K | human CD3 | 87 | DIVLTQSPATLSLSPGERATLSCRAS QSVSYMNWYQQKPGKAPKRWIYDTS KVASGVPARFSGSGSGTDYSLTINSL EAEDAATYYCQQWSSNPLTFGGGTK VEIK | 711 | DVQLVQSGAEVKKPGASVKVSCKASG YTFTRYTMHWVRQAPGQGLEWIGYIN PSRGYTNYADSVKGRFTITTDKSTSTAY MELSSLRSEDTATYYCARYYDDHYCL DYWGQGTTVTVSS | 712 |
| hXR32 | human CD3 | 3.6-6.1 | QAVVTQEPSLTVSPGGTVTLTCRSST GAVTTSNYANWVQQKPGQAPRGLI | 713 | EVQLVESGGGLVQPGGSLRLSCAASGF TFNTYAMNWVRQAPGKGLEWVARIRS | 714 |

TABLE 12-continued scFv sequences. Amino Acid (AA) sequences of anti-CD3 scFvs
used for bispecific antibody construction. Affinities of
select anti-CD3 clones were gathered from the literature.

| scFv name | antigen | Affinity (nM) | variable light chain (AA) | SEQ ID NO | variable heavy chain (AA) | SEQ ID NO |
|---|---|---|---|---|---|---|
| | | | GGTNKRAPWTPARFSGSLLGGKAAL TITGAQAEDEADYYCALWYSNLWV FGGGTKLTVL | | KYNNYATYYADSVKDRFTISRDDSKNS LYLQMNSLKTEDTAVYYCVRHGNFGN SYVSWFAYWGQGTLVTVSS | |
| L2K | human CD3 | — | DIQLTQSPAIMSASPGEKVTMTCRAS SSVSYMNWYQQKSGTSPKRWIYDTS KVASGVPYRFSGSGSGTSYSLTISSM EAEDAATYYCQQWSSNPLTFGAGTK LELK | 715 | DIKLQQSGAELARPGASVKMSCKTSGY TFTRYTMHWVKQRPGQGLEWIGYINPS RGYTNYNQKFKDKATLTTDKSSSTAY MQLSSLTSEDSAVYYCARYYDDHYCL DYWGQGTTLTVSS | 716 |
| OKT3 | human CD3 | 1.2-1.5 | QIVLTQSPAIMSASPGEKVTMTCSAS SSVSYMNWYQQKSGTSPKRWIYDTS KLASGVPAHFRGSGSGTSYSLTISGM EAEDAATYYCQQWSSNPFTFGSGTK LEIN | 717 | QVQLQQSGAELARPGASVKMSCKASG YTFTRYTMHWVKQRPGQGLEWIGYIN PSRGYTNYNQKFKDKATLTTDKSSSTA YMQLSSLTSEDSAVYYCARYYDDHYC LDYWGQGTTLTVSS | 718 |
| 28F11 | human CD3 | — | EIVLTQSPATLSLSPGERATLSCRASQ SVSSYLAWYQQKPGQAPRLLIYDAS NRATGIPARFSGSGSGTDFTLTISSLE PEDFAVYYCQQRSNWPPLTFGGGTK VEIK | 719 | QVQLVESGGGVVQPGRSLRLSCAASGF KFSGYGMHWVRQAPGKGLEWVAVIW YDGSKKYYVDSVKGRFTISRDNSKNTL YLQMNSLRAEDTAVYYCARQMGYWH FDLWGRGTLVTVSS | 720 |
| 27H5-VL1 | human CD3 | — | EIVLTQSPRTLSLSPGERATLSCRASQ SVSSSYLAWYQQKPGQAPRLLIYGA SSRATGIPDRFSGSGSGTDFTLTISRL DPEDFAVYYCQQYGSSPITFGQGTRL EIK | 721 | QVQLVESGGGVVQPGRSLRLSCAASGF TFRSYGMHWVRQAPGKGLEWVAIIWY DGSKKNYADSVKGRFTISRDNSKNTLY LQMNSLRAEDTAVYYCARGTGYNWFD PWGQGTLVTVSS | 722 |
| 23F10 | human CD3 | — | EIVLTQSPATLSLSPGERATLSCRASQ SVSSYLAWYQQKPGQAPRLLIYDAS NRATGIPARFSGSGSGTDFTLTISSLE PEDFAVYYCQQRSNWPPLTFGGGTK VEIK | 719 | QVQLVQSGGGVVQSGRSLRLSCAASGF KFSGYGMHWVRQAPGKGLEWVAVIW YDGSKKYYVDSVKGRFTISRDNSKNTL YLQMNSLRGEDTAVYYCARQMGYWH FDLWGRGTLVTVSS | 723 |
| 15C3-VL1 | human CD3 | — | EIVLTQSPATLSLSPGERATLSCRASQ SVSSYLAWYQQKPGQAPRLLIYDAS NRATGIPARFSGSGSGTDFTLTISSLE PEDFAVYYCQQRSNWPWTFGQGTK VEIK | 724 | QVQLVQSGGGVVQPGRSLRLSCVASGF TFSSYGMHWVRQAPGKGLEWVAAIW YNGRKQDYADSVKGRFTISRDNSKNTL YLQMNSLRAEDTAVYYCTRGTGYNWF DPWGQGTLVTVSS | 725 |
| 15C3-VL2 | human CD3 | — | AIQLTQSPSSLSASVGDRVTITCRASQ GISSALAWYQQKPGKAPKLLIYDASS LESGVPSRFSGSGSGTDFTLTISSLQP EDFATYYCQQFNSYPITFGQGTRLEI K | 726 | QVQLVQSGGGVVQPGRSLRLSCVASGF TFSSYGMHWVRQAPGKGLEWVAAIW YNGRKQDYADSVKGRFTISRDNSKNTL YLQMNSLRAEDTAVYYCTRGTGYNWF DPWGQGTLVTVSS | 725 |
| hu12F6 | human CD3 | — | QIVLSQSPAILSASPGEKVTMTCRASS SVSYMHWYQQKPGSSPKPWIYATSN LASGVPARFSGSGSGTSYSLTISRVE AEDAATYYCQQWSSNPPTFGGGTKL ETKR | 727 | QVQLQQSGAELARPGASVKMSCKASG YTFTSYTMHWVKQRPGQGLEWIGYINP SSGYTKYNQKFKDKATLTADKSSSTAY MQLSSLTSEDSAVYYCARWQDYDVYF DYWGQGTTLTVSS | 728 |

The scFv component of the phage was then expressed and purified in bacteria for further characterization. The recombinant V2 scFv retained the same binding profile as its phage counterpart (FIG. 47D), with only minimal binding to the WT pHLA complex at the highest concentration tested (FIG. 38A). TAP-deficient T2 cells modified to express HLA-A3 (T2A3) were pulsed with the G12V peptide or a variety of control peptides, and the cells were assessed for binding to V2 scFv or HLA-A3-specific monoclonal antibodies. Flow cytometric analysis showed remarkably specific binding of V2 scFv to G12V peptide pulsed T2A3 cells compared to cells pulsed with the G12WT, G12C, or G12D RAS peptides (FIG. 38B, FIG. 47E). As in the ELISA assay, the V2 scFv was unable to detectably bind to cells pulsed with 9-mer [8-16] peptides, whether mutant or WT. Surface plasmon resonance (SPR) binding analysis of the V2 scFv demonstrated a $K_D$ value of 8.7 nM for G12V pHLA-A3, while no appreciable binding to G12WT pHLA-A3 was identified (FIG. 38C).

Figure 38:
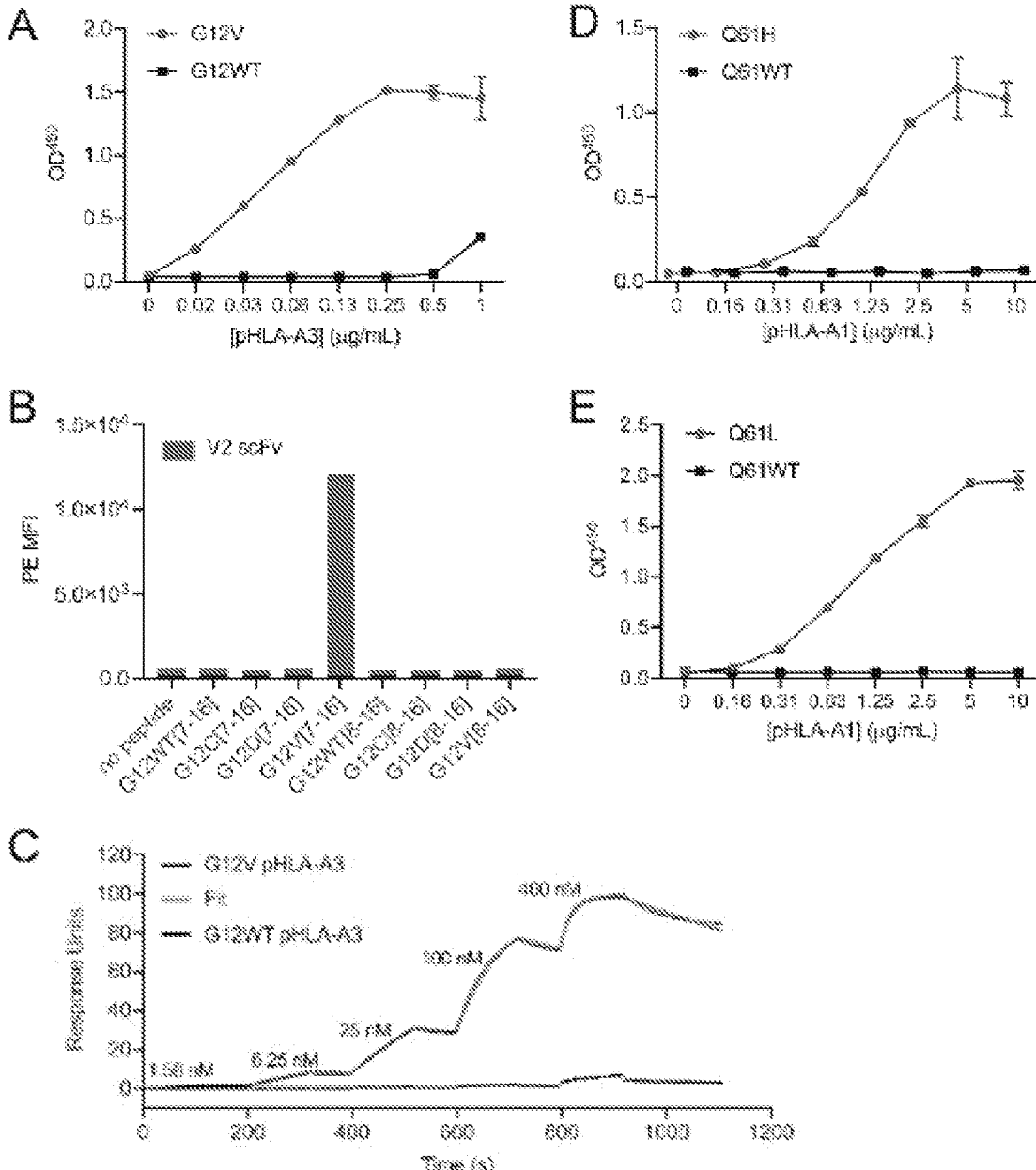
Figure 38:
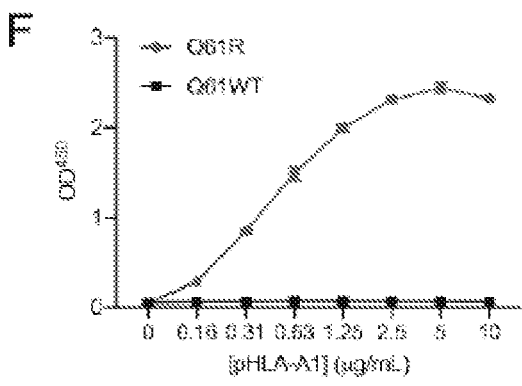
Figure 38:
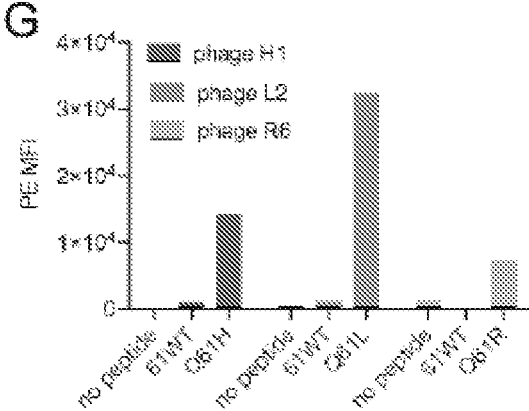
Figure 38:
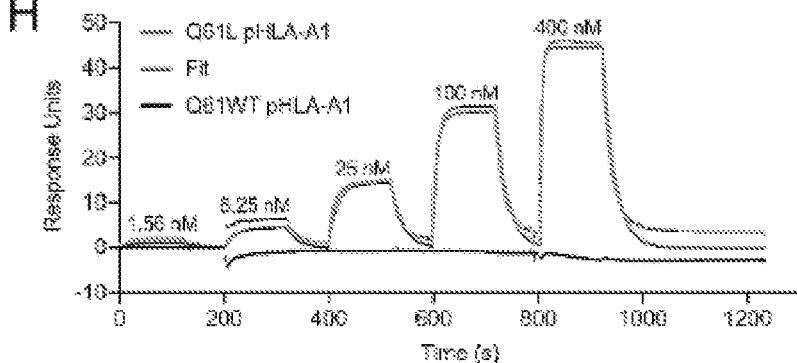
Figure 48:
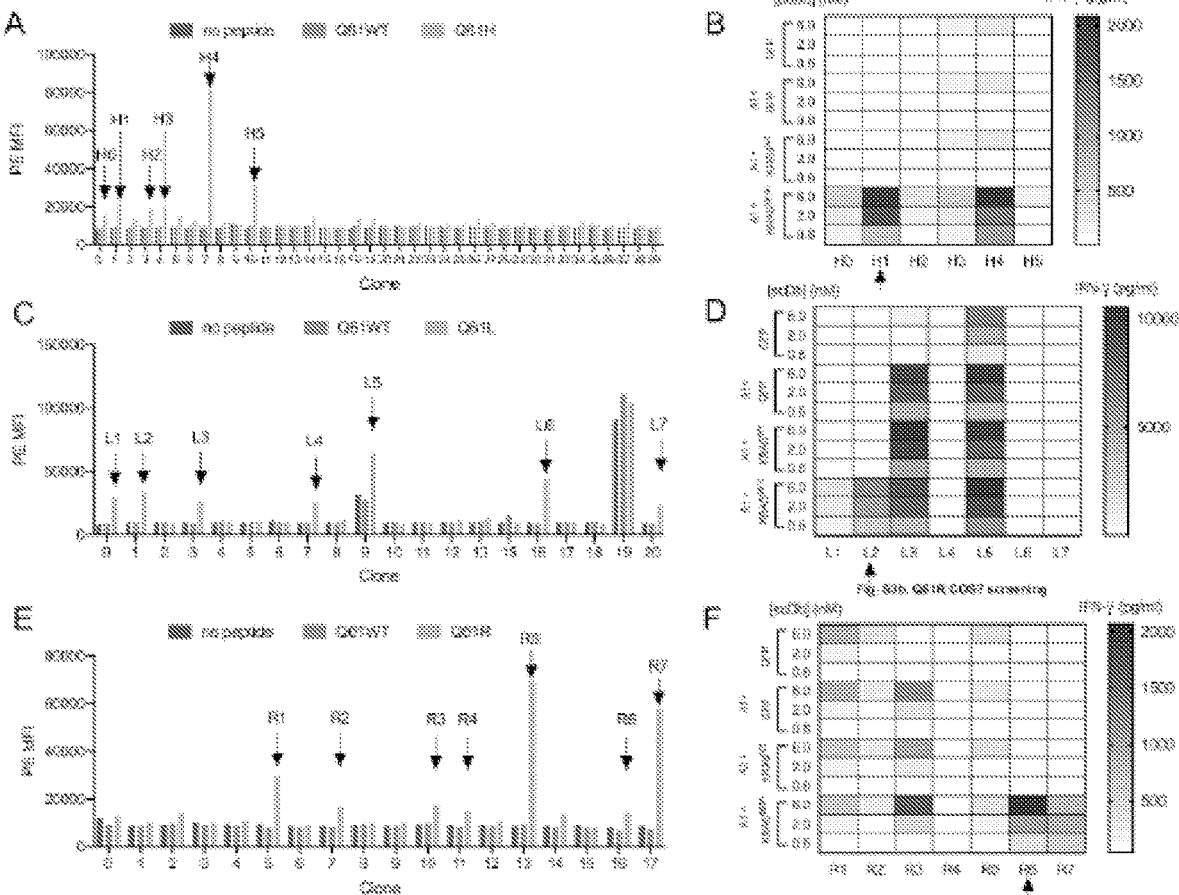

A similar screening procedure was used for RAS Q61H, Q61L, and Q61R pHLA-A1 MANA targets (see Materials and Methods). Using phage staining and T cell-based assays, one phage clone was identified displaying high specificity for each of the three targets: clone H1 for Q61H, clone L2 for Q61L, and clone R6 for Q61R (FIG. 48, A to F and Table 12). These clones bound to their cognate mutant pHLA with no detectable binding to the RAS Q61WT pHLA-A1 (FIG. 38, D to F). To further assess binding to pHLA complexes on the cell surface, the HLA-A1+ acute myeloid leukemia line SigM5 was pulsed with cognate peptides or controls. All three clones specifically bound to the expected pHLA complexes derived from mutant RAS genes (FIG. 38G). Given the efficient presentation of the Q61L peptide on transfected COS-7 cells (27) and its higher level of binding to peptide-pulsed SigM5 cells, most subsequent experiments focused on Q61L clone L2. SPR analysis of the L2 clone revealed a $K_D$ of 65 nM for Q61L pHLA-A1 and no appreciable binding to Q61WT pHLA-A1 (FIG. 38H).

T Cell-Engaging Bispecific Antibodies can Recognize Mutant RAS-Derived pHLA Complexes A variety of T cell-engaging bispecific antibody formats have been developed for targeting T cells to specific ligands. However, there are little data available on whether any of these formats can recognize targets when they are presented on the cell surface at low densities. To inform this point, six bispecific formats were evaluated: diabodies, single chain diabodies (scDbs), bispecific T cell engagers (BiTEs), dual affinity retargeting molecules (DARTs), bivalent scFv-Fcs, and trivalent scFv-Fcs (FIG. 49A). The scFv-Fcs were heterodimerized via the Knob-Into-Hole method. The V2 scFv was used as the pHLA-targeting moiety and different anti-CD3 antibodies were used for engaging T cells (Tables 12 and 13). In several of the formats, different configurations of the heavy ("H") and light ("L") chains of the V2 and anti-CD3 scFvs were tested (FIG. 49B).

TABLE 13

V2 bispecific antibody sequences. Amino acid sequences of the G12V pHL A-A3-targeting V2 bispecific antibodies tested.
The anti-CD3 clone UCHT1 is referred to as "U" and anti-CD3 clone UCHT1.v9 is referred to as "U2". The bivalent scFv-Fc was the product of co-expression of V2-FcHole and an anti-CD3-FcKnob. The trivalent scFv-Fc was the product of co-expression of V2-FcHole and an V2-FcKnob-anti-CD3.

| Bispecific Antibody | Sequence | SEQ ID NO |
|---|---|---|
| | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSEVQLVESGGGLVQPGG SLRLSCAASGYSFTGYTMNWVRQAP GKGLEWVALINPYKGVSTYNQKFKD RFTISVDKSKNTAYLQMNSLRAEDT AVYYCARSGYYGDSDWYFDVWGQGT LVTVSSGGGGSGGGGSGGGGSDIQM TQSPSSLSASVGDRVTITCRASQDI RNYLNWYQQKPGKAPKLLIYYTSRL ESGVPSRFSGSGSGTDYTLTISSLQ PEDFATYYCQQGNTLPWTFGQGTKV EIKGGGGSEVQLVESGGGLVQPGGS LRLSCAASGFNLSYSDIHWVRQAPG KGLEWVAVVMPDSGHTNYADSVKGR FTISADTSKNTAYLQMNSLRAEDTA VYYCSRATNIPVYAFDYWGQGTLVT VSSHHHHHH | 217 |
| V2-U-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSEVQLQQSGPELVKPGA SMKISCKASGYSFTGYTMNWVKQSH GKNLEWMGLINPYKGVSTYNQKFKD KATLTVDKSSSTAYMELLSLTSEDS AVYYCARSGYYGDSDWYFDVWGAGT | 218 |

TABLE 13-continued

V2 bispecific antibody sequences. Amino acid sequences of the G12V pHL A-A3-targeting V2 bispecific antibodies tested.
The anti-CD3 clone UCHT1 is referred to as "U" and anti-CD3 clone UCHT1.v9 is referred to as "U2". The bivalent scFv-Fc was the product of co-expression of V2-FcHole and an anti-CD3-FcKnob. The trivalent scFv-Fc was the product of co-expression of V2-FcHole and an V2-FcKnob-anti-CD3.

| Bispecific Antibody | Sequence | SEQ ID NO |
|---|---|---|
| | TVTVSSGGGGSGGGGSGGGGSDIQM TQTTSSLSASLGDRVTISCRASQDI RNYLNWYQQKPDGTVKLLIYYTSRL HSGVPSKFSGSGSGTDYSLTISNLE QEDIATYFCQQGNTLPWTFAGGTKL EIKGGGGSEVQLVESGGGLVQPGGS LRLSCAASGFNLSYSDIHWVRQAPG KGLEWVAVVMPDSGHTNYADSVKGR FTISADTSKNTAYLQMNSLRAEDTA VYYCSRATNIPVYAFDYWGQGTLVT VSSHHHHHH | |
| U2-V2-LHLH-scDb | MYRMQLLSCIALSLALVTNSDIQMT QSPSSLSASVGDRVTITCRASQDIR NYLNWYQQKPGKAPKLLIYYTSRLE SGVPSRFSGSGSGTDYTLTISSLQP EDFATYYCQQGNTLPWTFGQGTKVE IKGGGGSEVQLVESGGGLVQPGGSL RLSCAASGFNLSYSDIHWVRQAPGK GLEWVAVVMPDSGHTNYADSVKGRF TISADTSKNTAYLQMNSLRAEDTAV YYCSRATNIPVYAFDYWGQGTLVTV SSGGGGSGGGGSGGGGSDIQMTQSP SSLSASVGDRVTITCRASQDVNTAV AWYQQKPGKAPKLLIYSASFLYSGV PSRFSGSRSGTDFTLTISSLQPEDF ATYYCQQSYYYFRPITFGQGTKVEI KGGGGSEVQLVESGGGLVQPGGSLR LSCAASGYSFTGYTMNWVRQAPGKG LEWVALINPYKGVSTYNQKFKDRFT ISVDKSKNTAYLQMNSLRAEDTAVY YCARSGYYGDSDWYFDVWGQGTLVT VSSHHHHHH | 219 |
| U-V2-LHLH-scDb | MYRMQLLSCIALSLALVTNSDIQMT QTTSSLSASLGDRVTISCRASQDIR NYLNWYQQKPDGTVKLLIYYTSRLH SGVPSKFSGSGSGTDYSLTISNLEQ EDIATYFCQQGNTLPWTFAGGTKLE IKGGGGSEVQLVESGGGLVQPGGSL RLSCAASGFNLSYSDIHWVRQAPGK GLEWVAVVMPDSGHTNYADSVKGRF TISADTSKNTAYLQMNSLRAEDTAV YYCSRATNIPVYAFDYWGQGTLVTV SSGGGGSGGGGSGGGGSDIQMTQSP SSLSASVGDRVTITCRASQDVNTAV AWYQQKPGKAPKLLIYSASFLYSGV PSRFSGSRSGTDFTLTISSLQPEDF ATYYCQQSYYYFRPITFGQGTKVEI KGGGGSEVQLQQSGPELVKPGASMK ISCKASGYSFTGYTMNWVKQSHGKN LEWMGLINPYKGVSTYNQKFKDKAT LTVDKSSSTAYMELLSLTSEDSAVY YCARSGYYGDSDWYFDVWGAGTTVT VSSHHHHHH | 220 |
| V2-U2-HLHL-scDb | MYRMQLLSCIALSLALVTNSEVQLV ESGGGLVQPGGSLRLSCAASGFNLS YSDIHWVRQAPGKGLEWVAVVMPDS GHTNYADSVKGRFTISADTSKNTAY LQMNSLRAEDTAVYYCSRATNIPVY AFDYWGQGTLVTVSSGGGGSDIQMT QSPSSLSASVGDRVTITCRASQDIR NYLNWYQQKPGKAPKLLIYYTSRLE SGVPSRFSGSGSGTDYTLTISSLQP | 221 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | EDFATYYCQQGNTLPWTFGQGTKVE IKGGGGSGGGGSGGGGSEVQLVESG GGLVQPGGSLRLSCAASGYSFTGYT MNWVRQAPGKGLEWVALINPYKGVS TYNQKFKDRFTISVDKSKNTAYLQM NSLRAEDTAVYYCARSGYYGDSDWY FDVWGQGTLVTVSSGGGGSDIQMTQ SPSSLSASVGDRVTITCRASQDVNT AVAWYQQKPGKAPKLLIYSASFLYS GVPSRFSGSRSGTDFTLTISSLQPE DFATYYCQQSYYYFRPITFGQGTKV EIKHHHHHH | |
| V2-U-HLHL-scDb | MYRMQLLSCIALSLALVTNSEVQLV ESGGGLVQPGGSLRLSCAASGFNLS YSDIHWVRQAPGKGLEWVAVVMPDS GHTNYADSVKGRFTISADTSKNTAY LQMNSLRAEDTAVYYCSRATNIPVY AFDYWGQGTLVTVSSGGGGSDIQMT QTTSSLSASLGDRVTISCRASQDIR NYLNWYQQKPDGTVKLLIYYTSRLH SGVPSKFSGSGSGTDYSLTISNLEQ EDIATYFCQQGNTLPWTFAGGTKLE IKGGGGSGGGGSGGGGSEVQLQQSG PELVKPGASMKISCKASGYSFTGYT MNWVKQSHGKNLEWMGLINPYKGVS TYNQKFKDKATLTVDKSSSTAYMEL LSLTSEDSAVYYCARSGYYGDSDWY FDVWGAGTTVTVSSGGGGSDIQMTQ SPSSLSASVGDRVTITCRASQDVNT AVAWYQQKPGKAPKLLIYSASFLYS GVPSRFSGSRSGTDFTLTISSLQPE DFATYYCQQSYYYFRPITFGQGTKV EIKHHHHHH | 222 |
| U2-V2-HLHL-scDb | MYRMQLLSCIALSLALVTNSEVQLV ESGGGLVQPGGSLRLSCAASGYSFT GYTMNWVRQAPGKGLEWVALINPYK GVSTYNQKFKDRFTISVDKSKNTAY LQMNSLRAEDTAVYYCARSGYYGDS DWYFDVWGQGTLVTVSSGGGGSDIQ MTQSPSSLSASVGDRVTITCRASQD VNTAVAWYQQKPGKAPKLLIYSASF LYSGVPSRFSGSRSGTDFTLTISSL QPEDFATYYCQQSYYYFRPITFGQG TKVEIKGGGGSGGGGSGGGGSEVQL VESGGGLVQPGGSLRLSCAASGFNL SYSDIHWVRQAPGKGLEWVAVVMPD SGHTNYADSVKGRFTISADTSKNTA YLQMNSLRAEDTAVYYCSRATNIPV YAFDYWGQGTLVTVSSGGGGSDIQM TQSPSSLSASVGDRVTITCRASQDI RNYLNWYQQKPGKAPKLLIYYTSRL ESGVPSRFSGSGSGTDYTLTISSLQ PEDFATYYCQQGNTLPWTFGQGTKV EIKHHHHHH | 223 |
| U-V2-HLHL-scDb | MYRMQLLSCIALSLALVTNSEVQLQ QSGPELVKPGASMKISCKASGYSFT GYTMNWVKQSHGKNLEWMGLINPYK GVSTYNQKFKDKATLTVDKSSSTAY MELLSLTSEDSAVYYCARSGYYGDS DWYFDVWGAGTTVTVSSGGGGSDIQ MTQSPSSLSASVGDRVTITCRASQD VNTAVAWYQQKPGKAPKLLIYSASF | 224 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | LYSGVPSRFSGSRSGTDFTLTISSL QPEDFATYYCQQSYYYFRPITFGQG TKVEIKGGGGSGGGGSGGGGSEVQL VESGGGLVQPGGSLRLSCAASGFNL SYSDIHWVRQAPGKGLEWVAVVMPD SGHTNYADSVKGRFTISADTSKNTA YLQMNSLRAEDTAVYYCSRATNIPV YAFDYWGQGTLVTVSSGGGGSDIQM TQTTSSLSASLGDRVTISCRASQDI RNYLNWYQQKPDGTVKLLIYYTSRL HSGVPSKFSGSGSGTDYSLTISNLE QEDIATYFCQQGNTLPWTFAGGTKL EIKHHHHHH | |
| V2-diL2K-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSDVQLVQSGAEVKKPGA SVKVSCKASGYTFTRYTMHWVRQAP GQGLEWIGYINPSRGYTNYADSVKG RFTITTDKSTSTAYMELSSLRSEDT ATYYCARYYDDHYCLDYWGQGTTVT VSSGGGGSGGGGSGGGGSDIVLTQS PATLSLSPGERATLSCRASQSVSYM NWYQQKPGKAPKRWIYDTSKVASGV PARFSGSGSGTDYSLTINSLEAEDA ATYYCQQWSSNPLTFGGGTKVEIKG GGGSEVQLVESGGGLVQPGGSLRLS CAASGFNLSYSDIHWVRQAPGKGLE WVAVVMPDSGHTNYADSVKGRFTIS ADTSKNTAYLQMNSLRAEDTAVYYC SRATNIPVYAFDYWGQGTLVTVSSH HHHHH | 225 |
| V2-hXR32-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSEVQLVESGGGLVQPGG SLRLSCAASGFTNTYAMNWVRQAP GKGLEWVARIRSKYNNYATYYADSV KDRFTISRDDSKNSLYLQMNSLKTE DTAVYYCVRHGNFGNSYVSWFAYWG QGTLVTVSSGGGGSGGGGSGGGGSQ AVVTQEPSLTVSPGGTVTLTCRSST GAVTTSNYANWVQQKPGQAPRGLIG GTNKRAPWTPARFSGSLLGGKAALT ITGAQAEDEADYYCALWYSNLWVFG GGTKLTVLGGGGSEVQLVESGGGLV QPGGSLRLSCAASGFNLSYSDIHWV RQAPGKGLEWVAVVMPDSGHTNYAD SVKGRFTISADTSKNTAYLQMNSLR AEDTAVYYCSRATNIPVYAFDYWGQ GTLVTVSSHHHHHH | 226 |
| V2-L2K-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSDIKLQQSGAELARPGA SVKMSCKTSGYTFTRYTMHWVKQRP | 227 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | GQGLEWIGYINPSRGYTNYNQKFKD KATLTTDKSSSTAYMQLSSLTSEDS AVYYCARYYDDHYCLDYWGQTTLT VSSGGGGSGGGGSGGGGSDIQLTQS PAIMSASPGEKVTMTCRASSSVSYM NWYQQKSGTSPKRWIYDTSKVASGV PYRFSGSGSGTSYSLTISSMEAEDA ATYYCQQWSSNPLTFGAGTKLELKG GGGGSEVQLVESGGGLVQPGGSLRLS CAASGFNLSYSDIHWVRQAPGKGLE WVAVVMPDSGHTNYADSVKGRFTIS ADTSKNTAYLQMNSLRAEDTAVYYC SRATNIPVYAFDYWGQGTLVTVSSH HHHHH | |
| V2-OKT3-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSQVQLQQSGAELARPGA SVKMSCKASGYTFTRYTMHWVKQRP GQGLEWIGYINPSRGYTNYNQKFKD KATLTTDKSSSTAYMQLSSLTSEDS AVYYCARYYDDHYCLDYWGQTTLT VSSGGGGSGGGGSGGGGSQIVLTQS PAIMSASPGEKVTMTCSASSSVSYM NWYQQKSGTSPKRWIYDTSKLASGV PAHFRGSGSGTSYSLTISGMEAEDA ATYYCQQWSSNPFTFGSGTKLEING GGGSEVQLVESGGGLVQPGGSLRLS CAASGFNLSYSDIHWVRQAPGKGLE WVAVVMPDSGHTNYADSVKGRFTIS ADTSKNTAYLQMNSLRAEDTAVYYC SRATNIPVYAFDYWGQGTLVTVSSH HHHH | 228 |
| V2-28F11-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSQVQLVESGGGVVQPGR SLRLSCAASGFKFSGYGMHWVRQAP GKGLEWVAVIWYDGSKKYYVDSVKG RFTISRDNSKNTLYLQMNSLRAEDT AVYYCARQMGYWHFDLWGRGTLVTV SSGGGGSGGGGSGGGGSEIVLTQSP ATLSLSPGERATLSCRASQSVSSYL AWYQQKPGQAPRLLIYDASNRATGI PARFSGSGSGTDFTLTISSLEPEDF AVYYCQQRSNWPPLTFGGGTKVEIK GGGGSEVQLVESGGGLVQPGGSLRL SCAASGFNLSYSDIHWVRQAPGKGL EWVAVVMPDSGHTNYADSVKGRFTI SADTSKNTAYLQMNSLRAEDTAVYY CSRATNIPVYAFDYWGQGTLVTVSS HHHHHH | 229 |
| V2-27H5VL1-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSQVQLVESGGGVVQPGR | 230 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | SLRLSCAASGFTFRSYGMHWVRQAP GKGLEWVAIIWYDGSKKNYADSVKG RFTISRDNSKNTLYLQMNSLRAEDT AVYYCARGTGYNWFDPWGQGTLVTV SSGGGGSGGGGSGGGGSEIVLTQSP RTLSLSPGERATLSCRASQSVSSSY LAWYQQKPGQAPRLLIYGASSRATG IPDRFSGSGSGTDFTLTISRLDPED FAVYYCQQYGSSPITFGQGTRLEIK GGGGSEVQLVESGGGLVQPGGSLRL SCAASGFNLSYSDIHWVRQAPGKGL EWVAVVMPDSGHTNYADSVKGRFTI SADTSKNTAYLQMNSLRAEDTAVYY CSRATNIPVYAFDYWGQGTLVTVSS HHHHHH | |
| V2-23F10-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSQVQLVQSGGGVVQSGR SLRLSCAASGFKFSGYGMHWVRQAP GKGLEWVAVIWYDGSKKYYVDSVKG RFTISRDNSKNTLYLQMNSLRGEDT AVYYCARQMGYWHFDLWGRGTLVTV SSGGGGSGGGGSGGGGSEIVLTQSP ATLSLSPGERATLSCRASQSVSSYL AWYQQKPGQAPRLLIYDASNRATGI PARFSGSGSGTDFTLTISSLEPEDF AVYYCQQRSNWPPLTFGGGTKVEIK GGGGSEVQLVESGGGLVQPGGSLRL SCAASGFNLSYSDIHWVRQAPGKGL EWVAVVMPDSGHTNYADSVKGRFTI SADTSKNTAYLQMNSLRAEDTAVYY CSRATNIPVYAFDYWGQGTLVTVSS HHHHHH | 231 |
| V2-15C3VL1-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSQVQLVQSGGGVVQPGR SLRLSCVASGFTFSSYGMHWVRQAP GKGLEWVAAIWYNGRKQDYADSVKG RFTISRDNSKNTLYLQMNSLRAEDT AVYYCTRGTGYNWFDPWGQGTLVTV SSGGGGSGGGGSGGGGSEIVLTQSP ATLSLSPGERATLSCRASQSVSSYL AWYQQKPGQAPRLLIYDASNRATGI PARFSGSGSGTDFTLTISSLEPEDF AVYYCQQRSNWPWTFGQGTKVEIKG GGGGSEVQLVESGGGLVQPGGSLRLS CAASGFNLSYSDIHWVRQAPGKGLE WVAVVMPDSGHTNYADSVKGRFTIS ADTSKNTAYLQMNSLRAEDTAVYYC SRATNIPVYAFDYWGQGTLVTVSSH HHHHH | 232 |
| V2-15C3VL2-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK | 233 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | VEIKGGGGSQVQLVQSGGGVVQPGR SLRLSCVASGFTFSSYGMHWVRQAP GKGLEWVAAIWYNGRKQDYADSVKG RFTISRDNSKNTLYLQMNSLRAEDT AVYYCTRGTGYNWFDPWGQGTLVTV SSGGGGSGGGGSGGGGSAIQLTQSP SSLSASVGDRVTITCRASQGISSAL AWYQQKPGKAPKLLIYDASSLESGV PSRFSGSGSGTDFTLTISSLQPEDF ATYYCQQFNSYPITFGQGTRLEIKG GGGSEVQLVESGGGLVQPGGSLRLS CAASGFNLSYSDIHWVRQAPGKGLE WVAVVMPDSGHTNYADSVKGRFTIS ADTSKNTAYLQMNSLRAEDTAVYYC SRATNIPVYAFDYWGQGTLVTVSSH HHHHH | |
| V2-U212F6-LHLH-scDb | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSQVQLQQSGAELARPGA SVKMSCKASGYTFTSYTMHWVKQRP GQGLEWIGYINPSSGYTKYNQKFKD KATLTADKSSSTAYMQLSSLTSEDS AVYYCARWQDYDVYFDYWGQGTTLT VSSGGGGSGGGGSGGGGSQIVLSQS PAILSASPGEKVTMTCRASSSVSYM HWYQQKPGSSPKPWIYATSNLASGV PARFSGSGSGTSYSLTISRVEAEDA ATYYCQQWSSNPPTFGGGTKLETKR GGGGSEVQLVESGGGLVQPGGSLRL SCAASGFNLSYSDIHWVRQAPGKGL EWVAVVMPDSGHTNYADSVKGRFTI SADTSKNTAYLQMNSLRAEDTAVYY CSRATNIPVYAFDYWGQGTLVTVSS HHHHHH | 234 |
| V2-U2-LHHL-BITE | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSEVQLVE SGGGLVQPGGSLRLSCAASGYSFTG YTMNWVRQAPGKGLEWVALINPYKG VSTYNQKFKDRFTISVDKSKNTAYL QMNSLRAEDTAVYYCARSGYYGDSD WYFDVWGQGTLVTVSSGGGGSGGGG SGGGGSDIQMTQSPSSLSASVGDRV TITCRASQDIRNYLNWYQQKPGKAP KLLIYYTSRLESGVPSRFSGSGSGT DYTLTISSLQPEDFATYYCQQGNTL PWTFGQGTKVEIKHHHHHH | 235 |
| V2-U-LHHL-BITE | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP | 236 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSEVQLQQ SGPELVKPGASMKISCKASGYSFTG YTMNWVKQSHGKNLEWMGLINPYKG VSTYNQKFKDKATLTVDKSSSTAYM ELLSLTSEDSAVYYCARSGYYGDSD WYFDVWGAGTTVTVSSGGGGSGGGG SGGGGSDIQMTQTTSSLSASLGDRV TISCRASQDIRNYLNWYQQKPDGTV KLLIYYTSRLHSGVPSKFSGSGSGT DYSLTISNLEQEDIATYFCQQGNTL PWTFAGGTKLEIKHHHHHH | |
| V2-diL2K-LHHL-BITE | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSDVQLVQ SGAEVKKPGASVKVSCKASGYTFTR YTMHWVRQAPGQGLEWIGYINPSRG YTNYADSVKGRFTITTDKSTSTAYM ELSSLRSEDTATYYCARYYDDHYCL DYWGQGTTVTVSSGGGGSGGGGSGG GGSDIVLTQSPATLSLSPGERATLS CRASQSVSYMNWYQQKPGKAPKRWI YDTSKVASGVPARFSGSGSGTDYSL TINSLEAEDAATYYCQQWSSNPLTF GGGTKVEIKHHHHHH | 237 |
| V2-hXR32-LHHL-BITE | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSEVQLVE SGGGLVQPGGSLRLSCAASGFTFNT YAMNWVRQAPGKGLEWVARIRSKYN NYATYYADSVKDRFTISRDDSKNSL YLQMNSLKTEDTAVYYCVRHGNFGN SYVSWFAYWGQGTLVTVSSGGGGSG GGGSGGGGSQAVVTQEPSLTVSPGG TVTLTCRSSTGAVTTSNYANWVQQK PGQAPRGLIGGTNKRAPWTPARFSG SLLGGKAALTITGAQAEDEADYYCA LWYSNLWVFGGGTKLTVLHHHHHH | 238 |
| V2-OKT3-LHHL-BITE | MYRMQLLSCIALSLALVTNSDIQMT QSPSSLSASVGDRVTITCRASQDVN TAVAWYQQKPGKAPKLLIYSASFLY | 239 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSQVQLQQ SGAELARPGASVKMSCKASGYTFTR YTMHWVKQRPGQGLEWIGYINPSRG YTNYNQKFKDKATLTTDKSSSTAYM QLSSLTSEDSAVYYCARYYDDHYCL DYWGQGTLTVSSGGGGSGGGGSGG GGSQIVLTQSPAIMSASPGEKVTMT CSASSSVSYMNWYQQKSGTSPKRWI YDTSKLASGVPAHFRGSGSGTSYSL TISGMEAEDAATYYCQQWSSNPFTF GSGTKLEINHHHHHH | |
| V2-U2-LHLH-BITE | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSDIQMTQ SPSSLSASVGDRVTITCRASQDIRN YLNWYQQKPGKAPKLLIYYTSRLES GVPSRFSGSGSGTDYTLTISSLQPE DFATYYCQQGNTLPWTFGQGTKVEI KGGGGSGGGGSGGGGSEVQLVESGG GLVQPGGSLRLSCAASGYSFTGYTM NWVRQAPGKGLEWVALINPYKGVST YNQKFKDRFTISVDKSKNTAYLQMN SLRAEDTAVYYCARSGYYGDSDWYF DVWGQGTLVTVSSHHHHHH | 240 |
| V2-U-LHLH-BITE | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSDIQMTQ TTSSLSASLGDRVTISCRASQDIRN YLNWYQQKPDGTVKLLIYYTSRLHS GVPSKFSGSGSGTDYSLTISNLEQE DIATYFCQQGNTLPWTFAGGTKLEI KGGGGSGGGGSGGGGSEVQLQQSGP ELVKPGASMKISCKASGYSFTGYTM NWVKQSHGKNLEWMGLINPYKGVST YNQKFKDKATLTVDKSSSTAYMELL SLTSEDSAVYYCARSGYYGDSDWYF DVWGAGTTVTVSSHHHHHH | 241 |
| V2-diL2K-LHLH-BITE | MYRMQLLSCIALSLALVTNSDIQMT QSPSSLSASVGDRVTITCRASQDVN | 242 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSDIVLTQ SPATLSLSPGERATLSCRASQSVSY MNWYQQKPGKAPKRWIYDTSKVASG VPARFSGSGSGTDYSLTINSLEAED AATYYCQQWSSNPLTFGGGTKVEIK GGGGSGGGGSGGGGSDVQLVQSGAE VKKPGASVKVSCKASGYTFTRYTMH WVRQAPGQGLEWIGYINPSRGYTNY ADSVKGRFTITTDKSTSTAYMELSS LRSEDTATYYCARYYDDHYCLDYWG QGTTVTVSSHHHHHH | |
| V2-hXR32-LHLH-BITE | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSQAVVTQ EPSLTVSPGGTVTLTCRSSTGAVTT SNYANWVQQKPGQAPRGLIGGTNKR APWTPARFSGSLLGGKAALTITGAQ AEDEADYYCALWYSNLWVFGGGTKL TVLGGGGSGGGGSGGGGSEVQLVES GGGLVQPGGSLRLSCAASGFTFNTY AMNWVRQAPGKGLEWVARIRSKYNN YATYYADSVKDRFTISRDDSKNSLY LQMNSLKTEDTAVYYCVRHGNFGNS YVSWFAYWGQGTLVTVSSHHHHHH | 243 |
| V2-OKT3-LHLH-BITE | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSQIVLTQ SPAIMSASPGEKVTMTCSASSSVSY MNWYQQKSGTSPKRWIYDTSKLASG VPAHFRGSGSGTSYSLTISGMEAED AATYYCQQWSSNPFTFGSGTKLEIN GGGGSGGGGSGGGGSQVQLQQSGAE LARPGASVKMSCKASGYTFTRYTMH WVKQRPGQGLEWIGYINPSRGYTNY NQKFKDKATLTTDKSSSTAYMQLSS LTSEDSAVYYCARYYDDHYCLDYWG QGTTLTVSSHHHHHH | 244 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| V2-U2-LH-LH-DART | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGSGGGGEVQLVESGGGLVQ PGGSLRLSCAASGYSFTGYTMNWVR QAPGKGLEWVALINPYKGVSTYNQK FKDRFTISVDKSKNTAYLQMNSLRA EDTAVYYCARSGYYGDSDWYFDVWG QGTLVTVSSGGCGGGEVAALEKEVA ALEKEVAALEKEVAALEKEGRGSLL TCGDVEENPGPMYRMQLLSCIALSL ALVTNSDIQMTQSPSSLSASVGDRV TITCRASQDIRNYLNWYQQKPGKAP KLLIYYTSRLESGVPSRFSGSGSGT DYTLTISSLQPEDFATYYCQQGNTL PWTFGQGTKVEIKGGGSGGGGEVQL VESGGGLVQPGGSLRLSCAASGFNL SYSDIHWVRQAPGKGLEWVAVVMPD SGHTNYADSVKGRFTISADTSKNTA YLQMNSLRAEDTAVYYCSRATNIPV YAFDYWGQGTLVTVSSGGCGGGKVA ALKEKVAALKEKVAALKEKVAALKE HHHHHH | 245 |
| V2-U-LH-LH-DART | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGSGGGGEVQLQQSGPELVK PGASMKISCKASGYSFTGYTMNWVK QSHGKNLEWMGLINPYKGVSTYNQK FKDKATLTVDKSSSTAYMELLSLTS EDSAVYYCARSGYYGDSDWYFDVWG AGTTVTVSSGGCGGGEVAALEKEVA ALEKEVAALEKEVAALEKEGRGSLL TCGDVEENPGPMYRMQLLSCIALSL ALVTNSDIQMTQTTSSLSASLGDRV TISCRASQDIRNYLNWYQQKPDGTV KLLIYYTSRLHSGVPSKFSGSGSGT DYSLTISNLEQEDIATYFCQQGNTL PWTFAGGTKLEIKGGGSGGGGEVQL VESGGGLVQPGGSLRLSCAASGFNL SYSDIHWVRQAPGKGLEWVAVVMPD SGHTNYADSVKGRFTISADTSKNTA YLQMNSLRAEDTAVYYCSRATNIPV YAFDYWGQGTLVTVSSGGCGGGKVA ALKEKVAALKEKVAALKEKVAALKE HHHHHH | 246 |
| V2-diL2K-LH-LH-DART | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGSGGGGDVQLVQSGAEVKK PGASVKVSCKASGYTFTRYTMHWVR QAPGQGLEWIGYINPSRGYTNYADS VKGRFTITTDKSTSTAYMELSSLRS EDTATYYCARYYDDHYCLDYWGQGT TVTVSSGGCGGGEVAALEKEVAALE KEVAALEKEVAALEKEGRGSLLTCG | 247 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | DVEENPGPMYRMQLLSCIALSLALV TNSDIVLTQSPATLSLSPGERATLS CRASQSVSYMNWYQQKPGKAPKRWI YDTSKVASGVPARFSGSGSGTDYSL TINSLEAEDAATYYCQQWSSNPLTF GGGTKVEIKGGGSGGGGEVQLVESG GGLVQPGGSLRLSCAASGFNLSYSD IHWVRQAPGKGLEWVAVVMPDSGHT NYADSVKGRFTISADTSKNTAYLQM NSLRAEDTAVYYCSRATNIPVYAFD YWGQGTLVTVSSGGCGGGKVAALKE KVAALKEKVAALKEKVAALKEHHHH HH | |
| V2-hXR32-LH-LH-DART | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGSGGGGEVQLVESGGGLVQ PGGSLRLSCAASGFTFNTYAMNWVR QAPGKGLEWVARIRSKYNNYATYYA DSVKDRFTISRDDSKNSLYLQMNSL KTEDTAVYYCVRHGNFGNSYVSWFA YWGQGTLVTVSSGGCGGGEVAALEK EVAALEKEVAALEKEVAALEKEGRG SLLTCGDVEENPGPMYRMQLLSCIA LSLALVTNSQAVVTQEPSLTVSPGG TVTLTCRSSTGAVTTSNYANWVQQK PGQAPRGLIGGTNKRAPWTPARFSG SLLGGKAALTITGAQAEDEADYYCA LWYSNLWVFGGGTKLTVLGGGSGGG GEVQLVESGGGLVQPGGSLRLSCAA SGFNLSYSDIHWVRQAPGKGLEWVA VVMPDSGHTNYADSVKGRFTISADT SKNTAYLQMNSLRAEDTAVYYCSRA TNIPVYAFDYWGQGTLVTVSSGGCG GGKVAALKEKVAALKEKVAALKEKV AALKEHHHHHH | 248 |
| V2-OKT3-LH-LH-DART | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGSGGGGQVQLQQSGAELAR PGASVKMSCKASGYTFTRYTMHWVK QRPGQGLEWIGYINPSRGYTNYNQK FKDKATLTTDKSSSTAYMQLSSLTS EDSAVYYCARYYDDHYCLDYWGQGT TLTVSSGGCGGGEVAALEKEVAALE KEVAALEKEGRGSLLTCG DVEENPGPMYRMQLLSCIALSLALV TNSQIVLTQSPAIMSASPGEKVTMT CSASSSVSYMNWYQQKSGTSPKRWI YDTSKLASGVPAHFRGSGSGTSYSL TISGMEAEDAATYYCQQWSSNPFTF GSGTKLEINGGGSGGGGEVQLVESG GGLVQPGGSLRLSCAASGFNLSYSD IHWVRQAPGKGLEWVAVVMPDSGHT NYADSVKGRFTISADTSKNTAYLQM NSLRAEDTAVYYCSRATNIPVYAFD YWGQGTLVTVSSGGCGGGKVAALKE KVAALKEKVAALKEKVAALKEHHHH HH | 249 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| V2-U2-LH-LH-diabody | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSEVQLVESGGGLVQPGG SLRLSCAASGYSFTGYTMNWVRQAP GKGLEWVALINPYKGVSTYNQKFKD RFTISVDKSKNTAYLQMNSLRAEDT AVYYCARSGYYGDSDWYFDVWGQGT LVTVSSEGRGSLLTCGDVEENPGPM YRMQLLSCIALSLALVTNSDIQMTQ SPSSLSASVGDRVTITCRASQDIRN YLNWYQQKPGKAPKLLIYYTSRLES GVPSRFSGSGSGTDYTLTISSLQPE DFATYYCQQGNTLPWTFGQGTKVEI KGGGGSEVQLVESGGGLVQPGGSLR LSCAASGFNLSYSDIHWVRQAPGKG LEWVAVVMPDSGHTNYADSVKGRFT ISADTSKNTAYLQMNSLRAEDTAVY YCSRATNIPVYAFDYWGQGTLVTVS SHHHHHH | 250 |
| V2-U-LH-LH-diabody | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSEVQLQQSGPELVKPGA SMKISCKASGYSFTGYTMNWVKQSH GKNLEWMGLINPYKGVSTYNQKFKD KATLTVDKSSSTAYMELLSLTSEDS AVYYCARSGYYGDSDWYFDVWGAGT TVTVSSEGRGSLLTCGDVEENPGPM YRMQLLSCIALSLALVTNSDIQMTQ TTSSLSASLGDRVTISCRASQDIRN YLNWYQQKPDGTVKLLIYYTSRLHS GVPSKFSGSGSGTDYSLTISNLEQE DIATYFCQQGNTLPWTFAGGTKLEI KGGGGSEVQLVESGGGLVQPGGSLR LSCAASGFNLSYSDIHWVRQAPGKG LEWVAVVMPDSGHTNYADSVKGRFT ISADTSKNTAYLQMNSLRAEDTAVY YCSRATNIPVYAFDYWGQGTLVTVS SHHHHHH | 251 |
| V2-diL2K-LH-LH-diabody | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSDVQLVQSGAEVKKPGA SVKVSCKASGYTFTRYTMHWVRQAP GQGLEWIGYINPSRGYTNYADSVKG RFTITTDKSTSTAYMELSSLRSEDT ATYYCARYYDDHYCLDYWGQGTTVT VSSEGRGSLLTCGDVEENPGPMYRM QLLSCIALSLALVTNSDIVLTQSPA TLSLSPGERATLSCRASQSVSYMNW YQQKPGKAPKRWIYDTSKVASGVPA RFSGSGSGTDYSLTINSLEAEDAAT YYCQQWSSNPLTFGGGTKVEIKGGG GSEVQLVESGGGLVQPGGSLRLSCA ASGFNLSYSDIHWVRQAPGKGLEWV | 252 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | AVVMPDSGHTNYADSVKGRFTISAD TSKNTAYLQMNSLRAEDTAVYYCSR ATNIPVYAFDYWGQGTLVTVSSHHH HHH | |
| V2-hXR32-LH-LH-diabody | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSEVQLVESGGGLVQPGG SLRLSCAASGFTFNTYAMNWVRQAP GKGLEWVARIRSKYNNYATYYADSV KDRFTISRDDSKNSLYLQMNSLKTE DTAVYYCVRHGNFGNSYVSWFAYWG QGTLVTVSSEGRGSLLTCGDVEENP GPMYRMQLLSCIALSLALVTNSQAV VTQEPSLTVSPGGTVTLTCRSSTGA VTTSNYANWVQQKPGQAPRGLIGGT NKRAPWTPARFSGSLLGGKAALTIT GAQAEDEADYYCALWYSNLWVFGGG TKLTVLGGGGSEVQLVESGGGLVQP GGSLRLSCAASGFNLSYSDIHWVRQ APGKGLEWVAVVMPDSGHTNYADSV KGRFTISADTSKNTAYLQMNSLRAE DTAVYYCSRATNIPVYAFDYWGQGT LVTVSSHHHHHH | 253 |
| V2-OKT3-LH-LH-diabody | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSQVQLQQSGAELARPGA SVKMSCKASGYTFTRYTMHWVKQRP GQGLEWIGYINPSRGYTNYNQKFKD KATLTTDKSSSTAYMQLSSLTSEDS AVYYCARYYDDHYCLDYWGQGTTLT VSSEGRGSLLTCGDVEENPGPMYRM QLLSCIALSLALVTNSQIVLTQSPA IMSASPGEKVTMTCSASSSVSYMNW YQQKSGTSPKRWIYDTSKLASGVPA HFRGSGSGTSYSLTISGMEAEDAAT YYCQQWSSNPFTFGSGTKLEINGGG GSEVQLVESGGGLVQPGGSLRLSCA ASGFNLSYSDIHWVRQAPGKGLEWV AVVMPDSGHTNYADSVKGRFTISAD TSKNTAYLQMNSLRAEDTAVYYCSR ATNIPVYAFDYWGQGTLVTVSSHHH HHH | 254 |
| V2-FcHole | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSEPKSSD KTHTCPPCPAPELLGGPSVFLFPPK PKDTLMISRTPEVTCVVVDVSHEDP EVKFNWYVDGVEVHNAKTKPREEQY | 255 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | ASTYRVVSVLTVLHQDWLNGKEYKC KVSNKALPAPIAKTISKAKGQPREP QVCTLPPSREEMTKNQVSLSCAVKG FYPSDIAVEWESNGQPENNYKTTPP VLDSDGSFFLVSKLTVDKSRWQQGN VFSCSVMHEALHNHYTQKSLSLSPG KHHHHHH | |
| U2-FcKnob | MYRMQLLSCIALSLALVTNSDIQMT QSPSSLSASVGDRVTITCRASQDIR NYLNWYQQKPGKAPKLLIYYTSRLE SGVPSRFSGSGSGTDYTLTISSLQP EDFATYYCQQGNTLPWTFGQGTKVE IKGGGGSGGGGSGGGGSEVQLVESG GGLVQPGGSLRLSCAASGYSFTGYT MNWVRQAPGKGLEWVALINPYKGVS TYNQKFKDRFTISVDKSKNTAYLQM NSLRAEDTAVYYCARSGYYGDSDWY FDVWGQGTLVTVSSGGGGSEPKSSD KTHTCPPCPAPELLGGPSVFLFPPK PKDTLMISRTPEVTCVVVDVSHEDP EVKFNWYVDGVEVHNAKTKPREEQY ASTYRVVSVLTVLHQDWLNGKEYKC KVSNKALPAPIAKTISKAKGQPREP QVYTLPPCREEMTKNQVSLWCLVKG FYPSDIAVEWESNGQPENNYKTTPP VLDSDGSFFLYSKLTVDKSRWQQGN VFSCSVMHEALHNHYTQKSLSLSPG K | 256 |
| U-FcKnob | MYRMQLLSCIALSLALVTNSDIQMT QTTSSLSASLGDRVTISCRASQDIR NYLNWYQQKPDGTVKLLIYYTSRLH SGVPSKFSGSGSGTDYSLTISNLEQ EDIATYFCQQGNTLPWTFAGGTKLE IKGGGGSGGGGSGGGGSEVQLQQSG PELVKPGASMKISCKASGYSFTGYT MNWVKQSHGKNLEWMGLINPYKGVS TYNQKFKDKATLTVDKSSSTAYMEL LSLTSEDSAVYYCARSGYYGDSDWY FDVWGAGTTVTVSSGGGGSEPKSSD KTHTCPPCPAPELLGGPSVFLFPPK PKDTLMISRTPEVTCVVVDVSHEDP EVKFNWYVDGVEVHNAKTKPREEQY ASTYRVVSVLTVLHQDWLNGKEYKC KVSNKALPAPIAKTISKAKGQPREP QVYTLPPCREEMTKNQVSLWCLVKG FYPSDIAVEWESNGQPENNYKTTPP VLDSDGSFFLYSKLTVDKSRWQQGN VFSCSVMHEALHNHYTQKSLSLSPG K | 257 |
| V2-FcKnob-U2 | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSEPKSSD KTHTCPPCPAPELLGGPSVFLFPPK PKDTLMISRTPEVTCVVVDVSHEDP | 258 |

TABLE 13-continued

V2 bispecific antibody sequences. Amino acid
sequences of the G12V pHL A-A3-targeting V2
bispecific antibodies tested.
The anti-CD3 clone UCHT1 is referred to as
"U" and anti-CD3 clone UCHT1.v9 is referred
to as "U2". The bivalent scFv-Fc was the
product of co-expression of V2-FcHole and
an anti-CD3-FcKnob. The trivalent scFv-Fc
was the product of co-expression of V2-
FcHole and an V2-FcKnob-anti-CD3.

| Bispecific Antibody | Sequence | SEQ ID NO |
|---|---|---|
| | EVKFNWYVDGVEVHNAKTKPREEQY ASTYRVVSVLTVLHQDWLNGKEYKC KVSNKALPAPIAKTISKAKGQPREP QVYTLPPCREEMTKNQVSLWCLVKG FYPSDIAVEWESNGQPENNYKTTPP VLDSDGSFFLYSKLTVDKSRWQQGN VFSCSVMHEALHNHYTQKSLSLSPG KASGGGSGGGSEVQLVESGGGLVQP GGSLRLSCAASGYSFTGYTMNWVRQ APGKGLEWVALINPYKGVSTYNQKF KDRFTISVDKSKNTAYLQMNSLRAE DTAVYYCARSGYYGDSDWYFDVWGQ GTLVTVSSGGGGSGGGGSGGGGSDI QMTQSPSSLSASVGDRVTITCRASQ DIRNYLNWYQQKPGKAPKLLIYYTS RLESGVPSRFSGSGSGTDYTLTISS LQPEDFATYYCQQGNTLPWTFGQGT KVEIK | |
| V2-FcKnob-U | MYRMQLLSCIALSLALVTNSDIQMT QSPSSLSASVGDRVTITCRASQDVN TAVAWYQQKPGKAPKLLIYSASFLY SGVPSRFSGSRSGTDFTLTISSLQP EDFATYYCQQSYYYFRPITFGQGTK VEIKGGGGSGGGSGGGGSEVQLVE SGGGLVQPGGSLRLSCAASGFNLSY SDIHWVRQAPGKGLEWVAVVMPDSG HTNYADSVKGRFTISADTSKNTAYL QMNSLRAEDTAVYYCSRATNIPVYA FDYWGQGTLVTVSSGGGGSEPKSSD KTHTCPPCPAPELLGGPSVFLFPPK PKDTLMISRTPEVTCVVVDVSHEDP EVKFNWYVDGVEVHNAKTKPREEQY ASTYRVVSVLTVLHQDWLNGKEYKC KVSNKALPAPIAKTISKAKGQPREP QVYTLPPCREEMTKNQVSLWCLVKG FYPSDIAVEWESNGQPENNYKTTPP VLDSDGSFFLYSKLTVDKSRWQQGN VFSCSVMHEALHNHYTQKSLSLSPG KASGGGSGGGSEVQLQQSGPELVKP GASMKISCKASGYSFTGYTMNWVKQ SHGKNLEWMGLINPYKGVSTYNQKF KDKATLTVDKSSSTAYMELLSLTSE DSAVYYCARSGYYGDSDWYFDVWGA GTTVTVSSGGGGSGGGGSGGGGSDI QMTQTTSSLSASLGDRVTISCRASQ DIRNYLNWYQQKPDGTVKLLIYYTS RLHSGVPSKFSGSGSGTDYSLTISN LEQEDIATYFCQQGNTLPWTFAGGT KLEIK | 259 |

Figure 49:
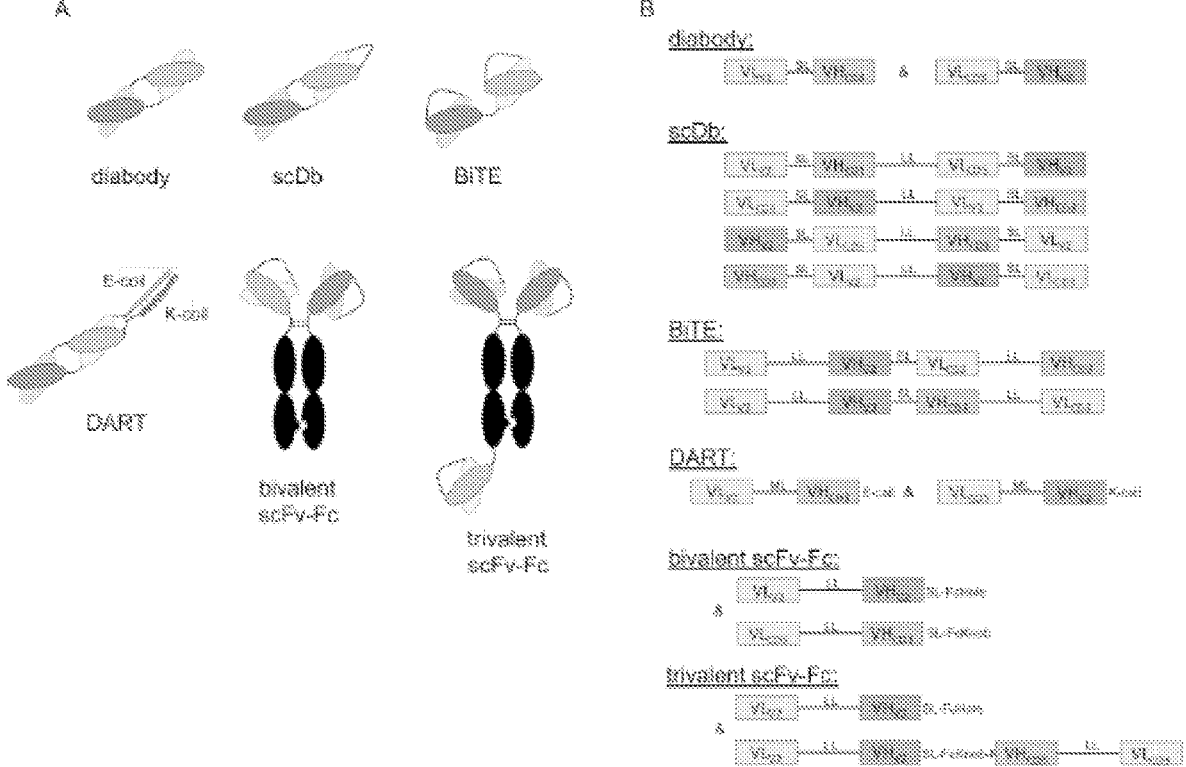

In sum, 42 recombinant proteins were expressed in HEK293 cells to identify the most effective format and configuration (FIGS. 49, A and B). Binding to G12V pHLA-A3 and recombinant CD3ε/δ protein (FIG. 49C) were assessed by ELISAs at various bispecific protein concentrations. While a few formats exhibited weak binding to one or both antigens, most had similar performance characteristics upon ELISA (FIG. 49C). To further compare the formats, T2A3 cells were pulsed with two concentrations of the G12V peptide and co-cultured with T cells and each of the V2 bispecific proteins at two concentrations, followed by measurement of IFNγ release to assess T cell activation (FIG. 49D). Despite their similar performance in ELISA assays, the ability of the bispecific formats to recognize the G12V peptide at low antigen densities on cells was highly variable. scDbs generally performed better than other formats, particularly at lower concentration of antibodies. Switching the order of the heavy and light variable domains in the analogous proteins ("LHLH" to "HLHL") abolished their ability to activate T cells, despite these formats showing equivalent functionality on ELISA (FIG. 49). Similarly, while the bivalent scFv-Fc and trivalent scFv-Fc performed particularly well in the ELISAs, they consistently performed poorly when assessed in peptide-pulsed cells.

Figure 50:
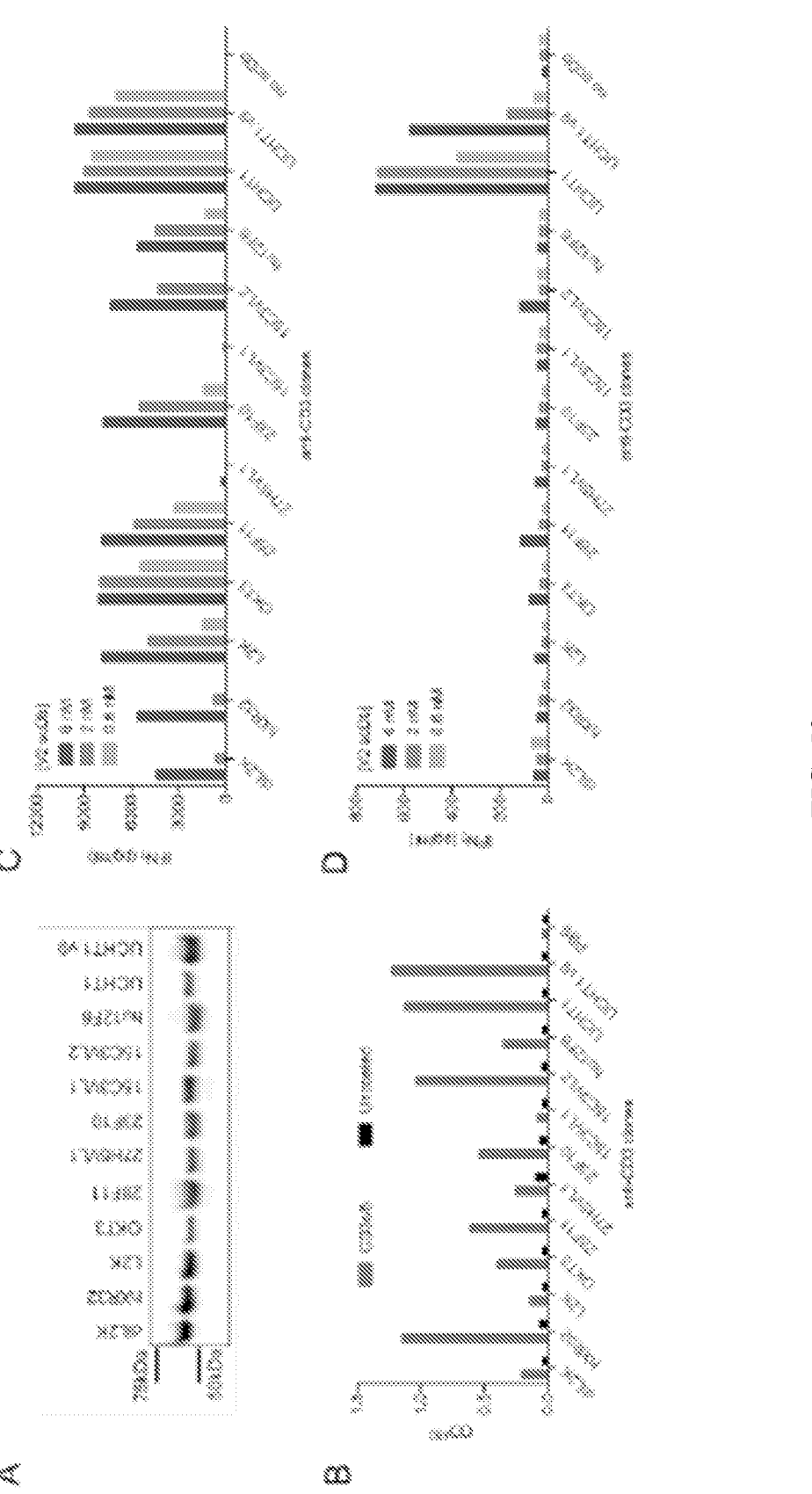

In the initial tests of formats and configurations, five different anti-CD3 scFvs were used. Based on the results indicating that the scDb performed best, seven additional anti-CD3 clones were tested (Tables 12 and 13). A total of twelve V2 scDbs were expressed, purified (FIG. 50A), and then tested with ELISA for their ability to bind the CD3ε/δ protein (FIG. 50B). Two target cell lines were used to further assess these V2 scDbs. The first was KRAS G12V and HLA-A3 co-transfected COS-7 and the second was the lung cancer cell line NCI-H441, which expressed endogenous HLA-A3 and mutant KRAS G12V. In a co-culture experiment with the COS-7 overexpression system, ten of the scDbs activated T cells as shown by substantial IFNγ release (FIG. 50C). However, with NCI-H441 cells, only the scDbs containing the UCHT1 ("U") and UCHT1.v9 ("U2") anti-CD3 clones activated T cells (FIG. 50D), with the UCHT1-based scDb (FIG. 39A) performing particularly well. Both scDbs (hereafter referred to as V2-U and V2-U2, respectively) (Tables 12 and 13) retained the remarkable specificity of V2 phage toward G12V pHLA-A3, as they failed to interact with pHLA-A3 folded with the other RAS peptides or an unrelated CTNNB peptide (FIG. 39B, FIG. 51A). They also bound to the CD3ε/δ heterodimer (FIG. 2B, FIG. 51A). Both scDbs could simultaneously interact with G12V pHLA-A3 and CD3ε/δ heterodimer, as shown by a "sandwich" ELISA (FIG. 51B), suggesting that the proteins were folded and functioned properly. Given all these data on relative expression, ELISA, and cellular reactivity, the V2-U scDb (N-terminus-L$_{V2}$-H$_U$-L$_U$-H$_{V2}$-C-terminus) was chosen as a focus (FIG. 39A) for most further studies, though V2-U2 was also used for select assays.

Figure 39:
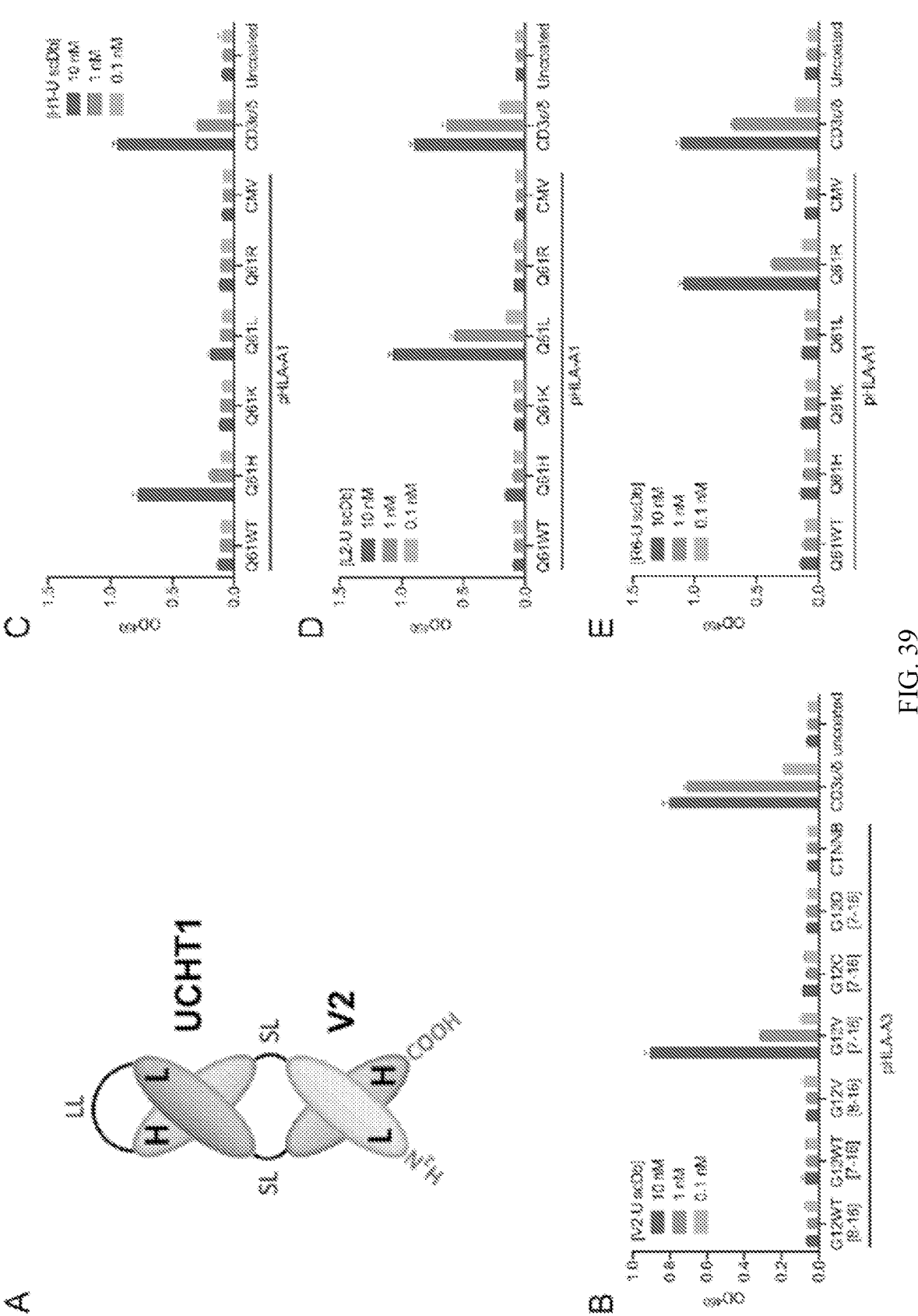
Figure 40:
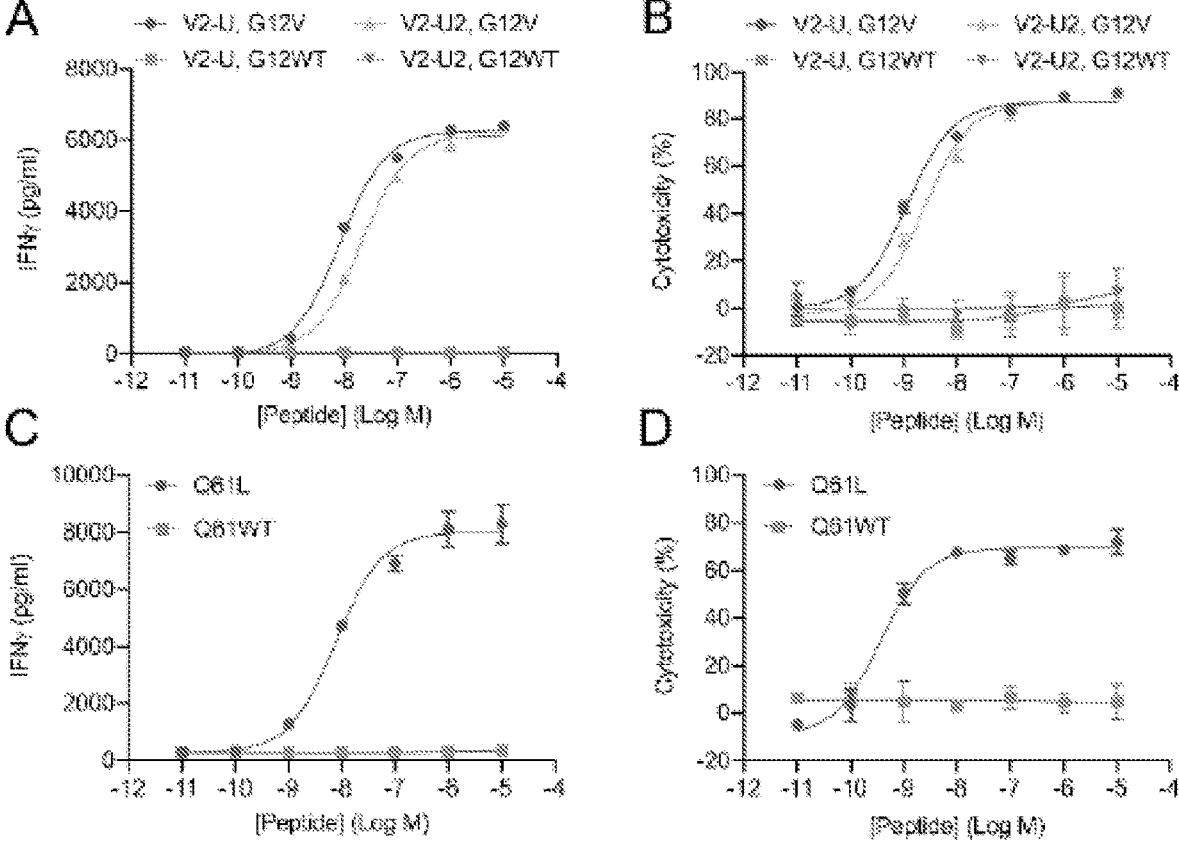
Figure 51:
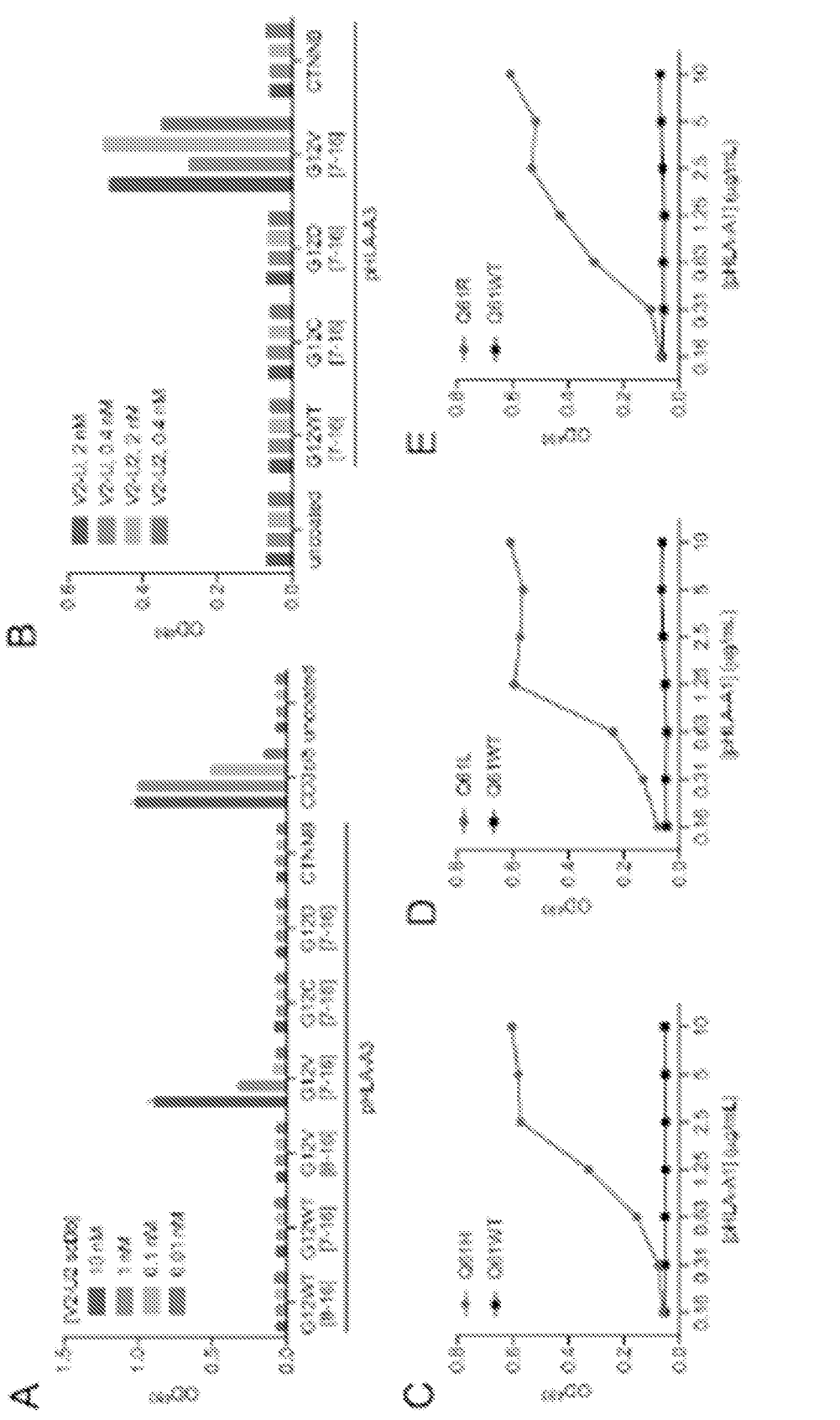

Based off of this work with the G12V clone V2, the Q61 scFv clones H1, L2, and R6 were grafted into the optimized scDb format to generate H1-U, L2-U, and R6-U scDbs. All three scDbs retained binding to their cognate mutant-derived Q61 pHLA-A1 and recombinant CD3ε/δ on ELISA and none exhibited appreciable binding to the Q61WT pHLA or to other control pHLA including an unrelated CMV pHLA (FIG. 39, C to E and FIG. 51, C to E, Table 11). This result showed that the format and configuration chosen on the basis of the RAS G12V scFv was generalizable, and applicable to three other scFvs with varying amino acid sequences and independent targets.

scDbs Recognize Cells Pulsed with Low Nanomolar Concentrations of Exogenous Peptides To assess the minimal concentration of target antigen required for activating T cells, T2A3 cells were pulsed with G12V or G12WT peptides and then co-cultured with healthy donor T cells in the presence of the V2-U scDb. T cells were activated at G12V peptide concentrations as low as 1 nM, as evidenced by IFNγ and TNFα secretion (FIG. 40A, FIG. 52A). Furthermore, even at low peptide concentrations, the scDb mediated antigen-dependent lysis of the peptide-pulsed T2A3 cells (FIG. 40B). There was no appreciable background cytokine secretion or cell killing when cells were pulsed with the G12WT peptide. Similarly, specific activation was seen with the V2-U2 scDb (FIGS. 40, A and B).

Figure 52:
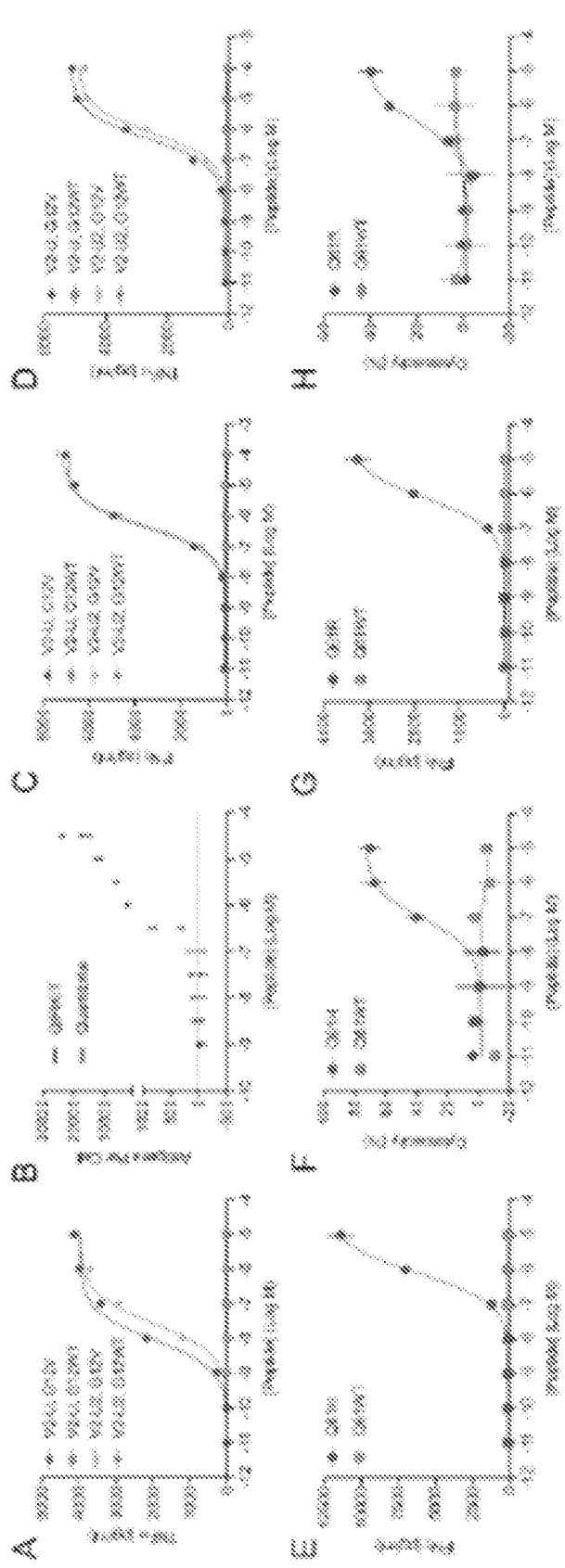
Figure 52:
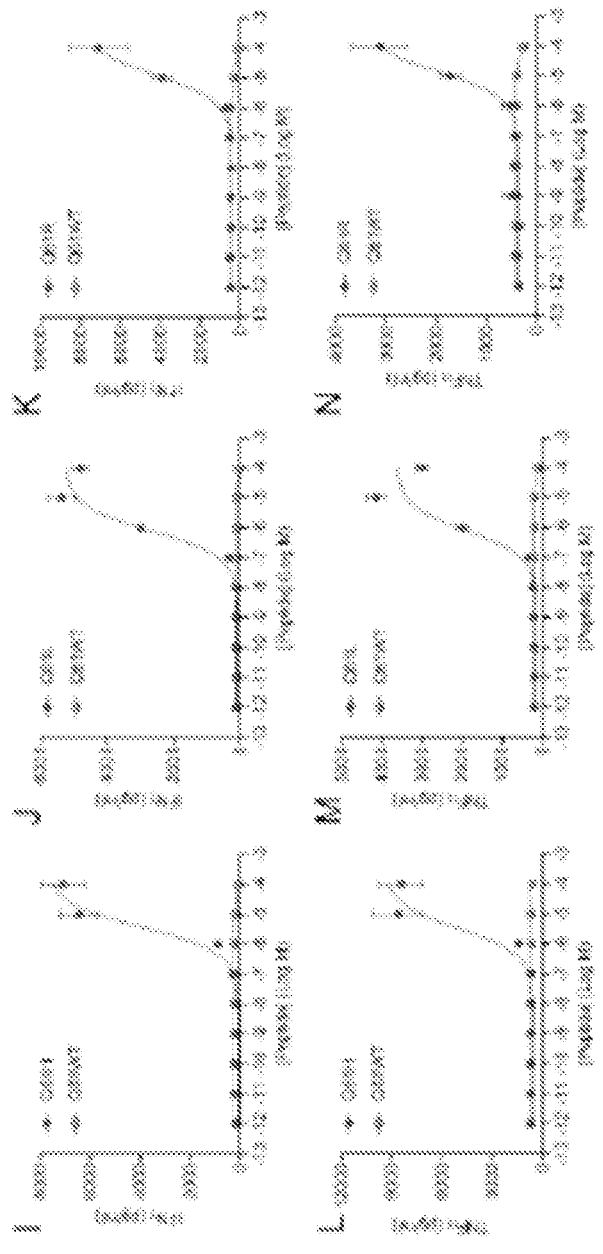

To determine the approximate antigen density on peptide-pulsed T2A3 cells, the cells were stained with the V2 scFv and assessed by flow cytometry. Antigen density was determined using QIFIKIT and Quantibrite Beads, which allowed quantitative determination of the number of cell surface antigenic molecules (FIG. 52B). It was found that cells pulsed with 320 nM of G12V peptide expressed 300 to 800 antigenic molecules per cell. This flow cytometric method did not have the sensitivity required to detect cells pulsed with <320 nM of G12V peptide. However, 300-fold lower concentrations of pulsed G12V peptide could activate T cells (FIG. 40B). Though there may not be a linear relationship between the concentration of the pulsed peptide and the number of peptide antigens displayed on the cell surface, these results suggest that the number of antigenic molecules per cell recognized by the V2-U scDb is far less than 300. An analogous peptide-pulsing experiment was performed with HLA-A3+ monocyte-derived immature dendritic cells (iDCs) to present the peptide and assayed for T cell secretion of IFNγ and TNFα. Both V2-U and V2-U2 scDbs were able to activate T cells when the iDCs were pulsed with G12V peptide at low nanomolar range (FIGS. 52, C and D).

Similar experiments were performed on the RAS Q61 targeting scDbs using peptide-pulsed SigM5 cells and iDCs. The L2-U scDb elicited T cell activation as shown by IFNγ secretion and SigM5 cytotoxicity when the target cells were pulsed with the Q61L peptide at concentrations as low as 1 nM, without cross-reactivity to the Q61WT peptide (FIGS. 40, C and D). While the H1-U and R6-U scDbs also showed no significant Q61WT peptide cross-reactivity, it required 100-fold more peptide (100 nM) for them to activate T cells (FIG. 52, E to H). Likewise, the L2-U scDb could activate T cells in the presence of iDCs at lower peptide concentrations than could the H1-U and R6-U scDbs (FIG. 52, I to N).

scDbs Recognize COS-7 Cells Overexpressing HLA and Mutant RAS Genes

Figure 53:
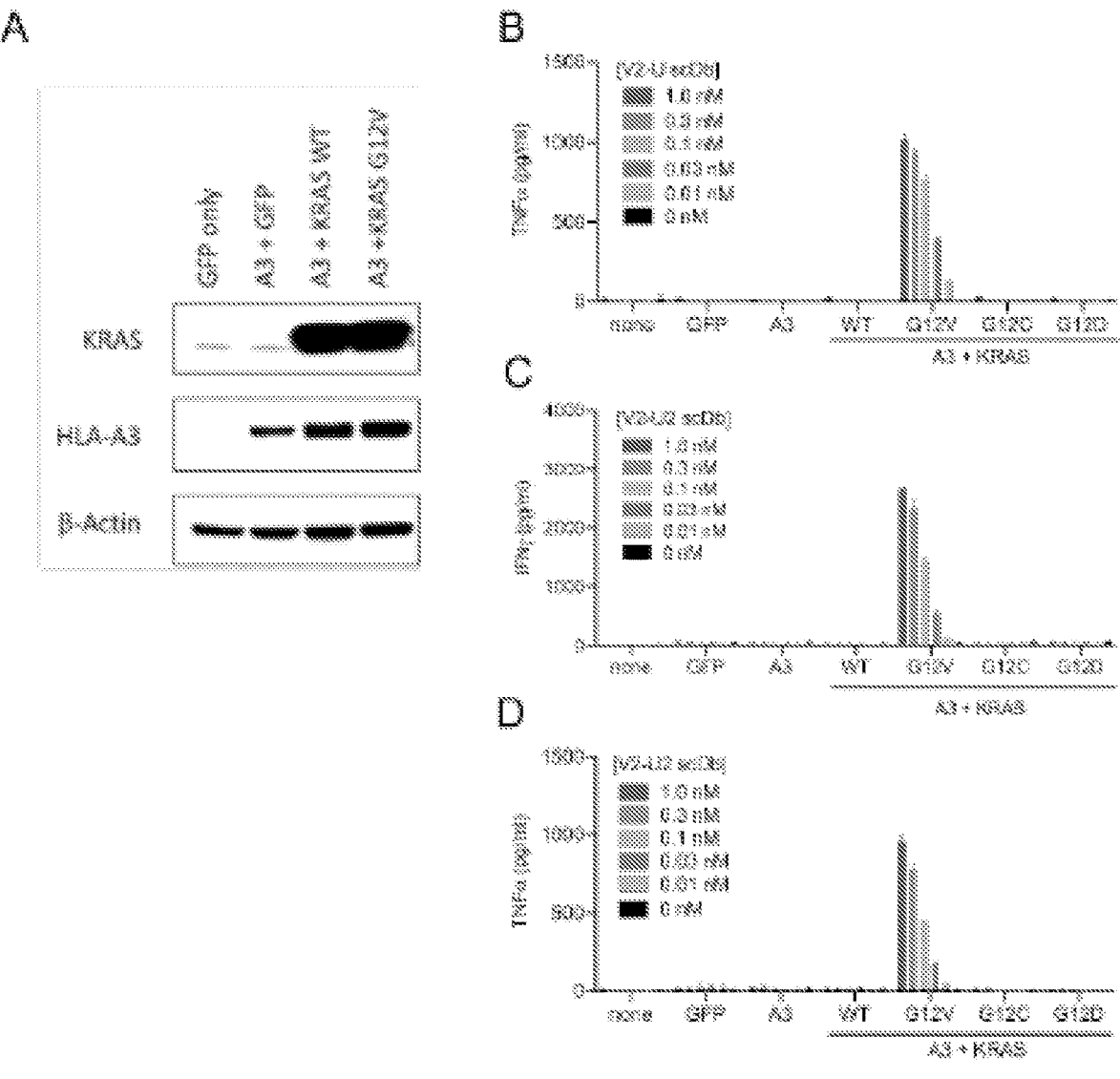

COS-7 cells were co-transfected with plasmids encoding HLA-A3 and either mutant or WT full-length KRAS (FIG. 53A), then co-cultured with T cells. As noted in the first section of the results, the COS-7 cells expressed ~100 copies of the G12V pHLA complex per cell. Addition of the V2-U scDb resulted in secretion of both IFNγ and TNFα from T cells in a dose-dependent manner only in the presence of COS-7 cells co-transfected with plasmids encoding HLA-A3 and KRAS G12V (FIG. 41A, FIG. 53B). As little as 10 μM of the V2-U scDb could activate T cells in this experiment (FIG. 41A, FIG. 53B). A similar activation of T cells by transfected COS-7 cells was observed in the presence of 30 μM of the V2-U2 scDb (FIGS. 53, C and D). The secretion of both IFNγ and TNFα was highly specific as the target cells expressing HLA-A3 and WT, G12C, or G12D KRAS did not trigger secretion of these cytokines (FIG. 41A, FIG. 53, B to D).

Figure 41:
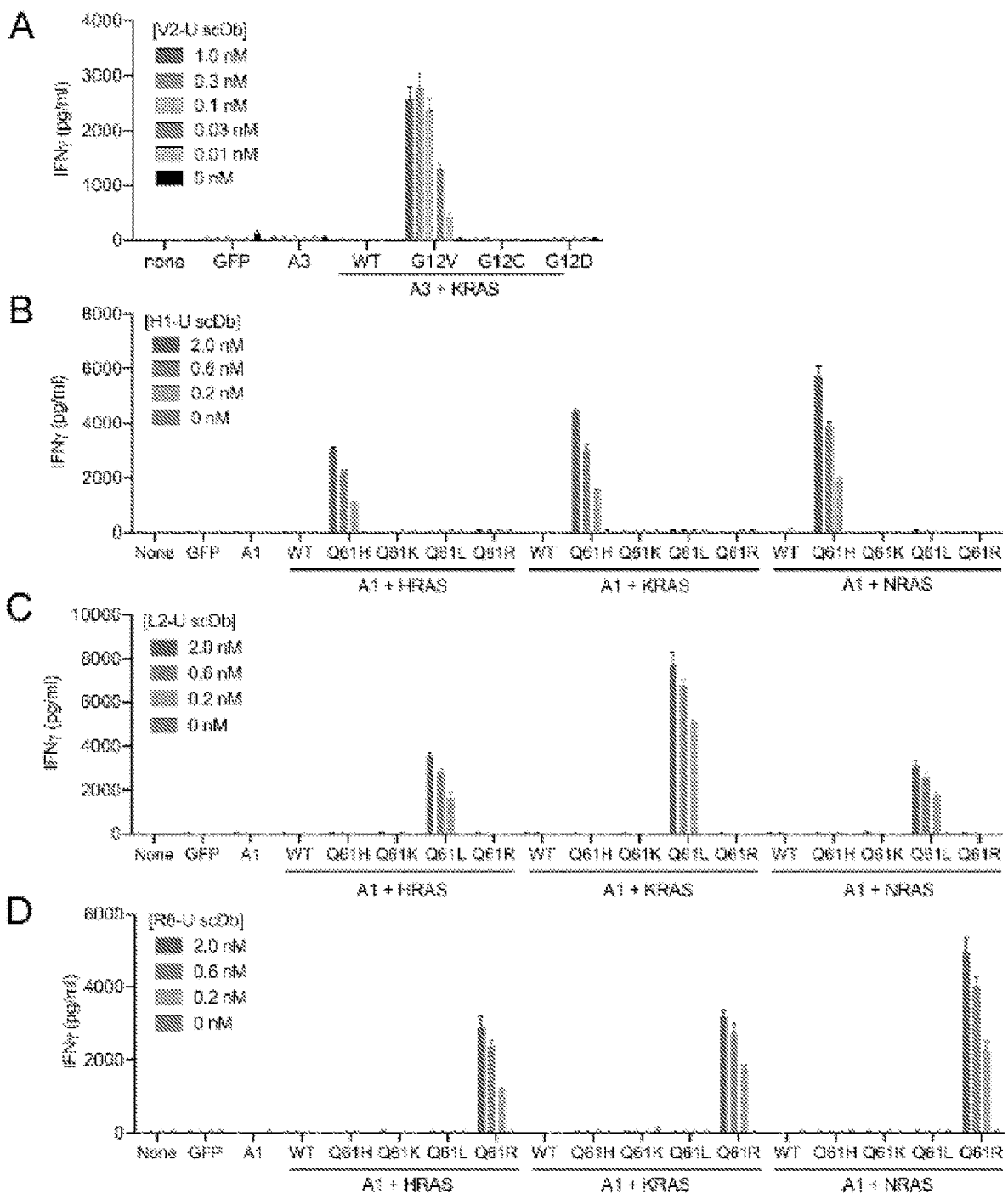
Figure 42:
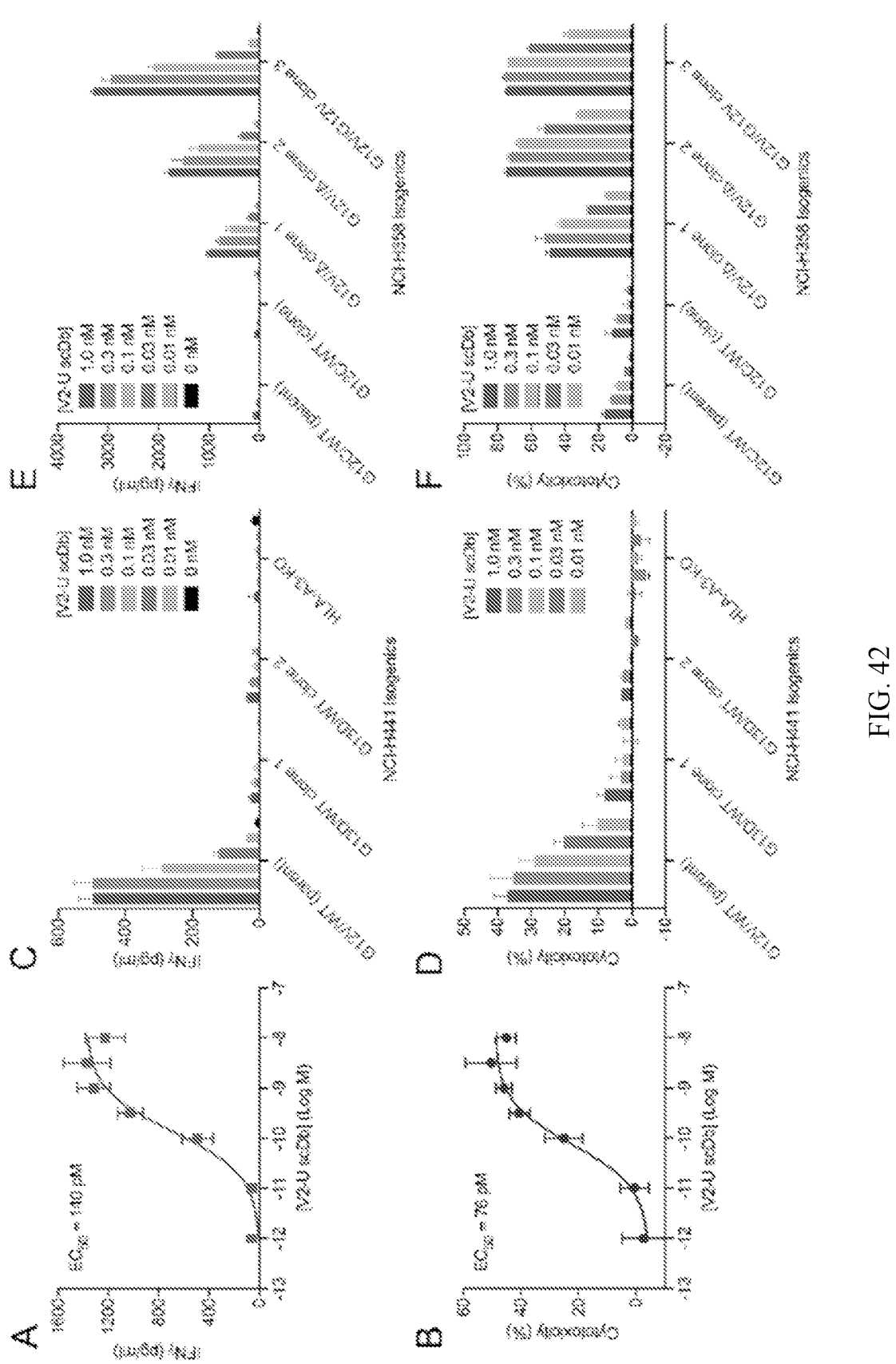
Figure 56:
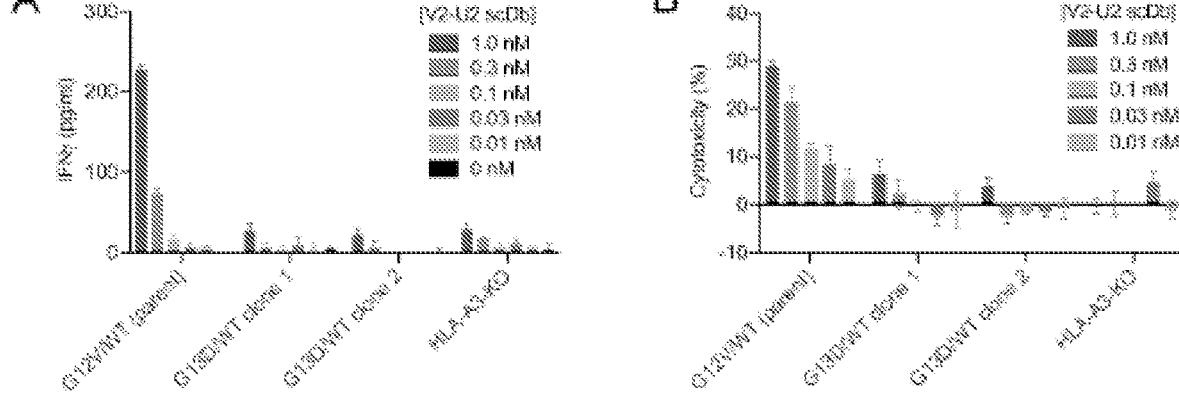

Analogous experiments were performed with the mutant RAS Q61-targeting H1-U, L2-U, and R6-U scDbs. COS-7 cells were co-transfected with plasmids encoding HLA-A1 and full-length WT or mutant HRAS, KRAS, or NRAS to assess whether each scDb was capable of recognizing the cognate mutant peptides derived from each of the RAS proteins. Each scDb elicited T cell responses highly specific for the COS-7 cells expressing the RAS gene with the Q61 mutation of interest, regardless of the RAS gene assessed (FIG. 41, B to D). Subnanomolar concentrations of the scDbs were sufficient to activate T cells when co-cultured with COS-7 cells harboring Q61 mutations in any of the three genes. Moreover, no activation of T cells was observed when co-cultured with COS-7 cells expressing HRAS, KRAS, or NRAS genes that were WT or contained the non-cognate Q61 mutations (FIG. 41, B to D).

scDbs Activate T Cells when Exposed to Cancer Cells Harboring Endogenous Mutant RAS Genes As noted above, the NCI-H441 cancer cell line presents only ~9 copies of mutant-derived KRAS G12V pHLA complexes per cell (Table 10). Despite this extremely low level of the target peptide, T cells could be activated by NCI-H441 cells in the presence of the V2-U scDb, as evidenced by the secretion of IFNγ and cytotoxicity (FIGS. 42, A and B). The potency of V2-U was high, with $EC_{50}$ of 140 µM and 76 µM for IFNγ secretion and cytotoxicity, respectively (FIGS. 42, A and B). To rigorously assess the specificity of the V2-U scDb, the HLA-A3 allele was disrupted in NCI-H441 cells by CRISPR-based technologies and the knock-out (KO) was confirmed via flow cytometry (FIG. 54). KO of the HLA-A3 allele eliminated the ability of the V2-U scDb to elicit IFNγ secretion or cytotoxicity by T cells upon exposure to the target NCI-H441 cells (FIGS. 42, C and D). CRISPR-based technologies were then used to replace ("knock-in" [KI]) KRAS G12V with KRAS G13D in parental NCI-H441 cells containing their endogenous HLA-A3 allele (FIG. 55). G12V was replaced with G13D, rather than knocking out the G12V allele, to maintain viability of the cells, which require mutant KRAS genes. Two independent NCI-H441 clones with the KRAS G13D substitution were tested, and both substantially abrogated the ability of T cells to be activated by V2-U scDb in the presence of NCI-H441 cells (FIGS. 42, C and D). Similarly, specific activation of T cells co-cultured with NCI-H441 cells was observed with the V2-U2 scDb, but as expected, the potency of the V2-U2 scDb was not as great as the V2-U scDb (FIG. 56). In all the experiments with endogenous levels of HLA-A3 and G12V alleles (FIGS. 42, A and C, FIG. 56A), IFNγ secretion from T cells was considerably lower than that in T cells activated by the transfected COS-7 cells (FIG. 41A, FIG. 539C), consistent with greater numbers of the pHLA complexes on the transfected COS-7 cells. Even so, the scDbs were able to induce efficient NCI-H441 target cell lysis through T cell activation in a KRAS G12V and HLA-dependent fashion (FIGS. 42, B and D, FIG. 56B). Moreover, other markers of T cell activation (TNFα, IL-2, granzyme B, and perforin) were released in a dose-dependent manner, demonstrating that the V2-U scDb was capable of inducing a poly-functional T cell response against cells expressing very low levels of antigen (FIG. 57).

Figure 58:
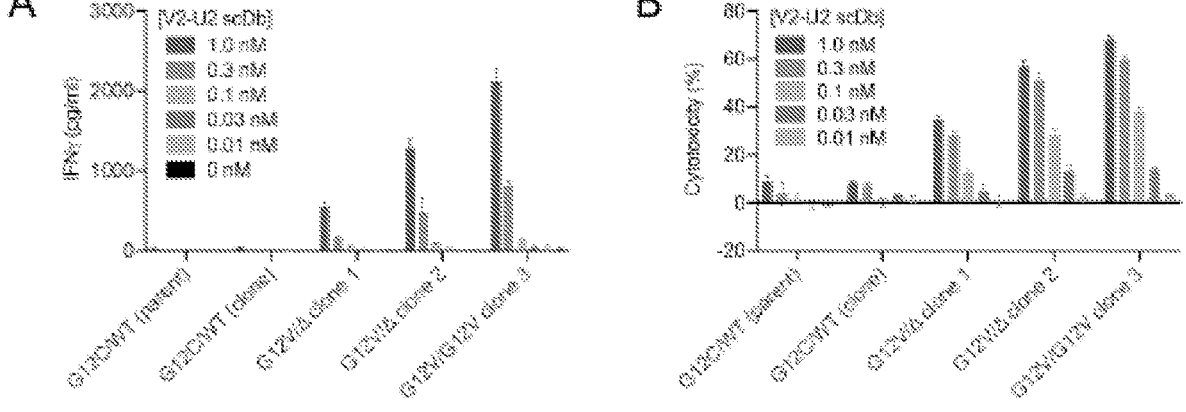

To further assess the specificity of the V2-U scDb, a second cell line, NCI-H358, was used. This lung cancer cell line contains the HLA-A3 allele and a KRAS G12C mutation. Using CRISPR, the G12V mutation was introduced in the KRAS locus in three independent clones (FIG. 55). All three G12V clones were able to induce cytokine secretion from T cells in the presence of the V2-U scDb, while parental cells or a clone retaining the G12C allele were not (FIG. 42E). Cytotoxicity to the G12V clones was also much greater, especially at subnanomolar scDb concentrations, than to isogenic NCI-H358 cells without the G12V allele (FIG. 42F). Similarly, specific cytokine secretion and cytotoxicity was observed upon co-culture of these cells with T cells in the presence of V2-U2 scDb (FIG. 58). All NCI-H358 variants expressed approximately the same level of HLA-A3 (FIG. 54).

Figure 59:
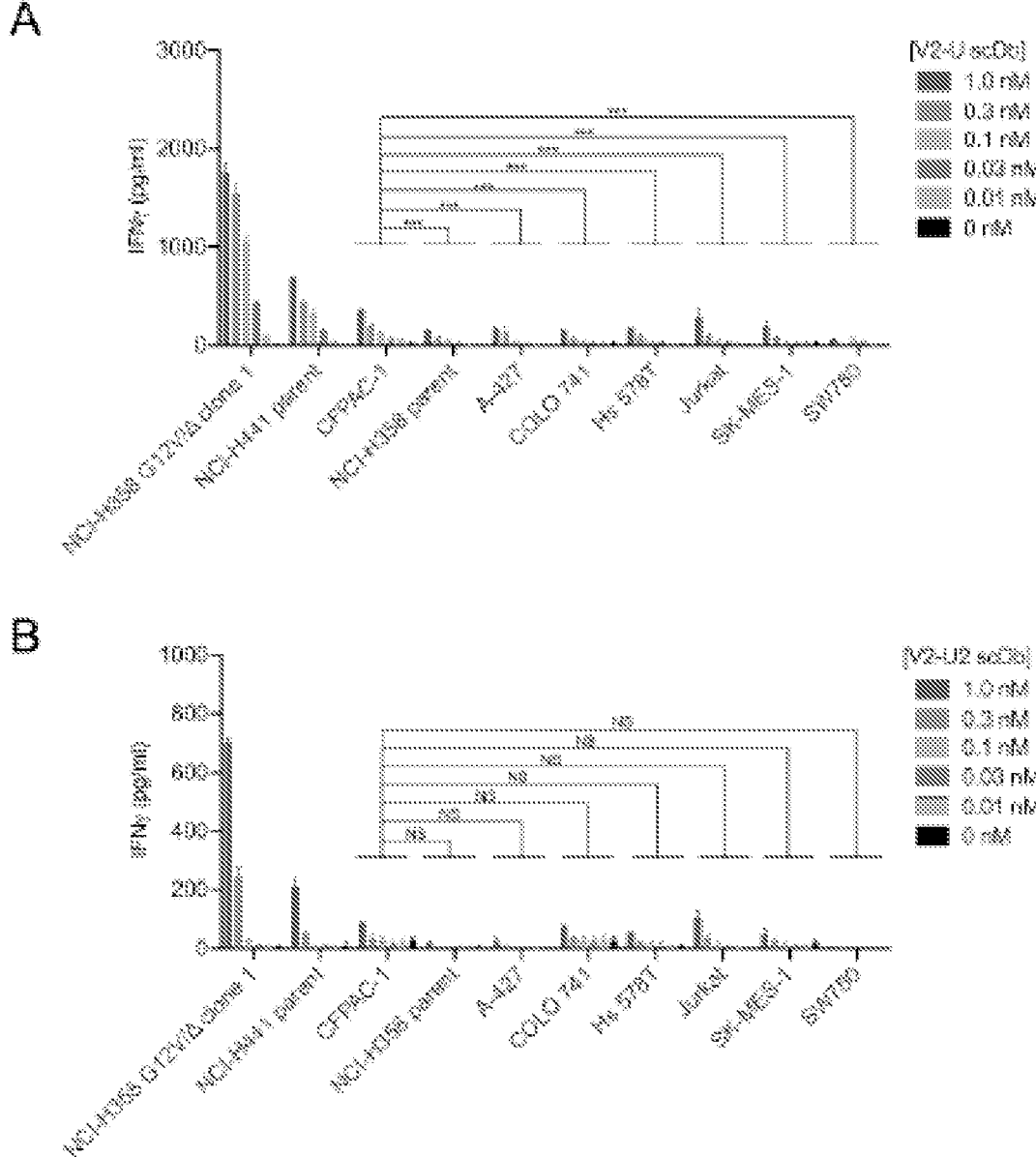

IFNγ secretion in co-cultures of T cells with several other HLA-A3+ cancer cell lines without RAS G12V mutations was assessed. These lines included A-427 (lung adenocarcinoma), COLO 741 (melanoma), Hs 578T (breast invasive ductal carcinoma), Jurkat (acute T cell leukemia), SK-MES-1 (lung squamous cell carcinoma), and SW780 (bladder transitional cell carcinoma). CFPAC-1, the KRAS G12V and HLA-A3+ pancreatic adenocarcinoma cell line that presents an average of only ~3 copies of the G12V peptide per cell were also assessed (Table 10). Expression of HLA-A3 in all these cell lines was confirmed via flow cytometry (FIG. 54). Neither V2-U nor V2-U2 scDb resulted in appreciable IFNγ release from T cells co-cultured with the cancer cell lines without the KRAS G12V mutation (FIG. 59). V2-U scDb induced a low but significantly higher level of IFNγ release with CFPAC-1 cells (FIG. 59A); however, there was no statistically significant difference when V2-U2 was used (FIG. 59B).

Figure 43:
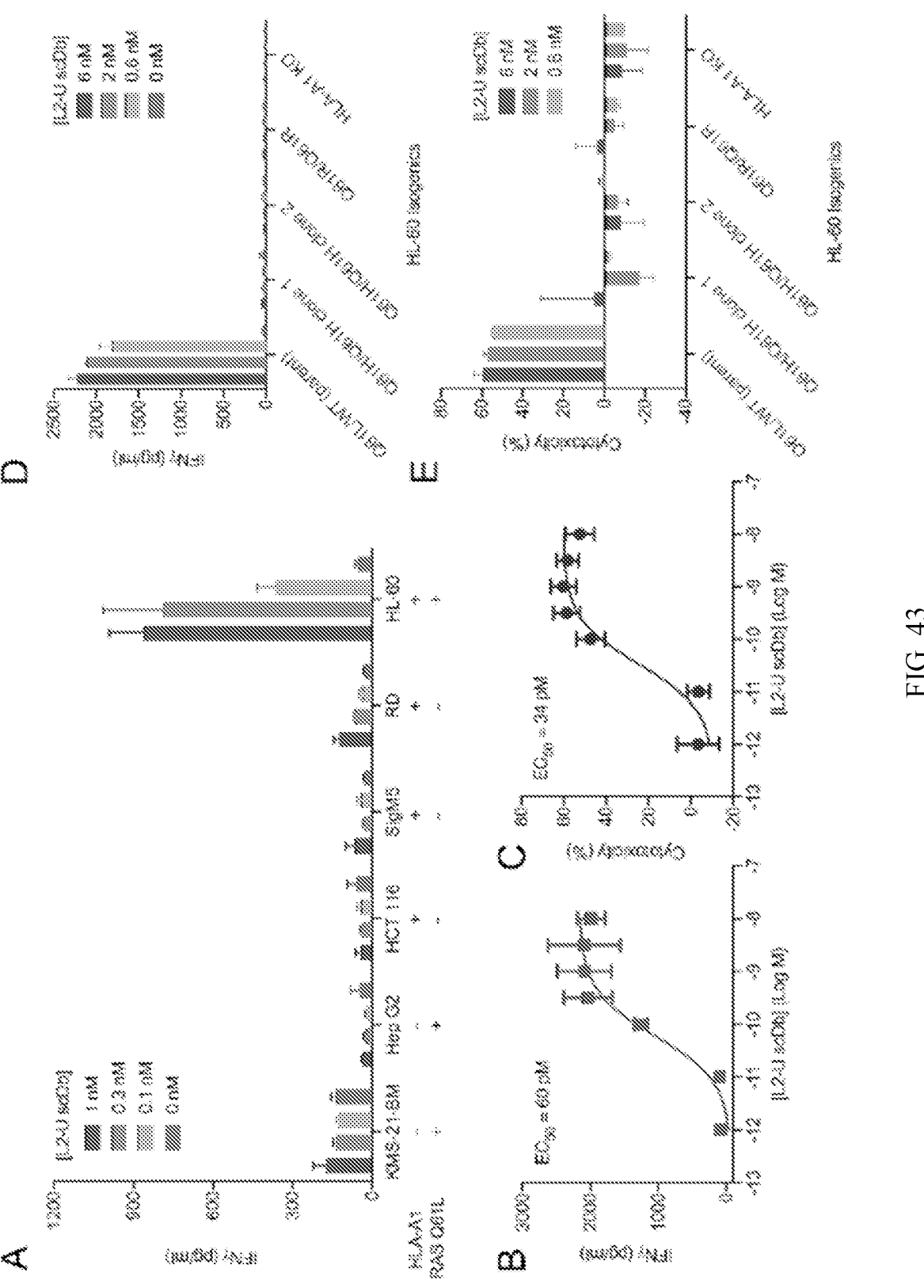

To study the ability of the L2-U scDb to induce T cell activation, co-culture with a panel of cell lines that differed in RAS mutation status and HLA-A1 expression were employed (FIG. 43A, FIG. 60). Substantial dose-dependent IFNγ secretion by T cells was only observed with the one cell line (HL-60) containing both HLA-A1 and RAS Q61L alleles (FIG. 43A). As noted above, HL-60 presents an average of four Q61L pHLA complexes per cell. In a titration experiment, the L2-U scDb was able to induce IFNγ release from T cells with an $EC_{50}$ of 60 µM (FIG. 43B) and HL-60 cell death with an $EC_{50}$ of 34 µM (FIG. 43C), despite the very low level of Q61L peptides per cell. Other markers of T cell activation were similarly released in a dose-dependent manner, showing that the L2-U scDb, like the V2-U scDb, was capable of inducing a poly-functional T cell response (FIG. 61). To assess the specificity of the L2-U scDb antigenic determinants in HL-60 cells, NRAS Q61H-KI, Q61R-KI, and HLA-A1-KO variants of these cells were generated (FIG. 55). These experiments confirmed that IFNγ secretion (FIG. 43D) and target cell cytotoxicity (FIG. 43E) were dependent on the co-presence of NRAS Q61L and HLA-A1 genes in HL-60 cells.

Assessing Potential Cross Reactivity to Other Putative HLA-A1 and HLA-A3-Binding Peptides To investigate whether the V2 scFv could bind to similar peptides derived from other proteins, a protein BLAST (BLASTp) search of the human RefSeq proteome was performed with the amino acid sequences of the G12V peptide or its G12WT, G12C, or G12D counterparts. Thirty-two proteins containing similar peptides were identified through this search. Of these, NetMHC v4.0 predicted that 17 peptides had strong or weak binding of HLA-A3 (Table 14). Each of these 17 peptides were synthesized and used to pulse T2A3 cells. While the majority of these peptides bind to HLA-A3, as assessed by GAP.A3 antibody staining, V2 phage only recognized the peptide IIVGAIGVGK ("Blast2"; SEQ ID NO:260), a peptide derived from the protein Rab-7b (FIG. 62A, Table 14).

TABLE 14

RAS G12 BLAST peptides. BLASTp was used to query the human RefSeq proteome for peptides similar to the G12V, G12WT, G12C, and G12D [7-16] peptides. These similar peptides were extended with the flanking amino acids from the source protein to produce the full peptide sequence. These peptides were analyzed by NetMHCv4.0 for predicted weak and strong binders to HLA*A03:01. These predicted binders are listed as BLAST peptides.

| Source Protein | Full Peptide Sequence | SEQ ID NO | BLAST Peptide (predicted HLA*03:01 binding peptide) | SEQ ID NO | Predicted HLA-A*03:01 Affinity | BLAST Peptide Name |
|---|---|---|---|---|---|---|
| RAS-related protein Rab-7b isoform a [Homo sapiens] | LIIVGAIGVGKT | 261 | IVGAIGVGK | 262 | 187.94 | Blast1 |
| | | | IIVGAIGVGK | 260 | 215.14 | Blast2 |
| PREDICTED: multidrug resistance-associated protein 6 isoform X1 [Homo sapiens] | LAVVGPVGAGK | 263 | VVGPVGAGK | 264 | 324.7 | Blast3 |
| | | | AVVGPVGAGK | 265 | 149.9 | Blast4 |
| PREDICTED: protein TANC1 isoform X2 [Homo sapiens] | VVVGNVGFGK | 266 | VVGNVGFGK | 267 | 167.47 | Blast5 |
| | | | VVVGNVGFGK | 266 | 264.35 | Blast6 |
| GTPase ERas precursor [Homo sapiens] | VVVGASGVGK | 268 | VVGASGVGK | 269 | 216.26 | Blast7 |
| | | | VVVGASGVGK | 268 | 355.27 | Blast8 |
| PREDICTED: mitochondrial Rho GTPase 2 isoform X1 [Homo sapiens] | KVVGARGVGK | 270 | VVGARGVGK | 271 | 140.14 | Blast9 |
| | | | KVVGARGVGK | 270 | 80.98 | Blast10 |
| glycogen debranching enzyme isoform 1 [Homo sapiens] | LGSVQLCGVGKFPSL | 272 | SVQLCGVGK | 273 | 576.87 | Blast11 |
| mitogen-activated protein kinase kinase kinase MLT isoform 1 [Homo sapiens] | SRNVVIAADGVLKI | 274 | VIAADGVLK | 275 | 127.74 | Blast12 |
| | | | VVIAADGVLK | 276 | 157.48 | Blast13 |
| RAS-related protein M-Ras isoform 1 precursor [Homo sapiens] | VVVGDGGVGK | 277 | VVVGDGGVGK | 277 | 718.71 | Blast14 |
| inactive hydroxysteroid dehydrogenase-like protein 1 isoform a [Homo sapiens] | WAVVSGATDGIGK | 278 | VSGATDGIGK | 279 | 954.98 | Blast15 |
| 60S acidic ribosomal protein P0 [Homo sapiens] | KCFIVGADNVGSK | 280 | IVGADNVGSK | 281 | 505.97 | Blast16 |
| rho-related GTP-binding protein RhoJ precursor [Homo sapiens] | KCVVVGDGAVGKT | 282 | VVVGDGAVGK | 283 | 468.81 | Blast17 |
| OTU domain-containing protein 5 isoform a [Homo sapiens] | VVVGVGGAVGVG | 284 | none | | | |
| PREDICTED: traB domain-containing protein isoform X1 [Homo sapiens] | VVVGVVGMGHVP | 285 | none | | | |
| PREDICTED: multidrug resistance-associated protein 6 isoform X1 [Homo sapiens] | AGEKVGIVGRTGAG | 286 | none | | | |
| multidrug resistance-associated protein 4 isoform 1 [Homo sapiens] | LQVVGVVSVAVAVIP | 287 | none | | | |
| MAGUK p55 subfamily member 7 [Homo sapiens] | RLVVLVGPVGVGLNE | 288 | none | | | |
| CD151 antigen [Homo sapiens] | LRVIGAVGIGIAC | 289 | none | | | |
| PREDICTED: protein TANC1 isoform X2 [Homo sapiens] | AENRGAVVVGNVG | 290 | none | | | |
| trimethylguanosine synthase isoform 1 [Homo sapiens] | DVVVDAFCGVGG | 291 | none | | | |
| keratin, type II cytoskeletal 5 [Homo sapiens] | VSLAGACGVGGYGS | 292 | none | | | |
| PREDICTED: uncharacterized protein LOC105376341 [Homo sapiens] | HSLPGACGVGPPRA | 293 | none | | | |
| disks large homolog 5 [Homo sapiens] | ETEVGPCGVGEAS | 294 | none | | | |

TABLE 14-continued

RAS G12 BLAST peptides. BLASTp was used to query the human RefSeq proteome for peptides
similar to the G12V, G12WT, G12C, and G12D [7-16] peptides. These similar peptides were
extended with the flanking amino acids from the source protein to produce the full
peptide sequence. These peptides were analyzed by NetMHCv4.0 for predicted weak and
strong binders to HLA*A03:01. These predicted binders are listed as BLAST peptides.

| Source Protein | Full Peptide Sequence | SEQ ID NO | BLAST Peptide (predicted HLA*03:01 binding peptide) | SEQ ID NO | Predicted HLA-A*03:01 Affinity | BLAST Peptide Name |
|---|---|---|---|---|---|---|
| solute carrier family 22 member 17 isoform a [Homo sapiens] | TLGLVGPCGVGGA | 295 | none | | | |
| solute carrier family 22 member 17 isoform a [Homo sapiens] | LQHVVLAACALLC | 296 | none | | | |
| rho GTPase-activating protein 5 isoform a [Homo sapiens] | EKDKGNCGVGKS | 297 | none | | | |
| olfactory receptor 9I1 [Homo sapiens] | WSLVVGAYVCGVSG | 298 | none | | | |
| receptor-type tyrosine-protein phosphatase beta isoform a [Homo sapiens] | KVVVGSCNRTIQN | 299 | none | | | |
| WD repeat-containing protein 90 [Homo sapiens] | SDSGALLCGVGKDH | 300 | none | | | |
| ribokinase isoform 1 [Homo sapiens] | VVVVGSCMTDLVS | 301 | none | | | |
| dedicator of cytokinesis protein 3 [Homo sapiens] | QQVVGACKPCSDPN | 302 | none | | | |
| PREDICTED: fibroin heavy chain-like isoform X2 [Homo sapiens] | GVDAGVGADVGTGVD | 303 | none | | | |
| translation initiation factor eIF-2B subunit alpha [Homo sapiens] | DLVIVGAEGVVENG | 304 | none | | | |
| PREDICTED: mitochondrial Rho GTPase 2 isoform X1 [Homo sapiens] | LCEVGTDGLLATSL | 305 | none | | | |
| methylthioribose-1-phosphate isomerase isoform 1 [Homo sapiens] | AVVVGADRVVANG | 306 | none | | | |
| collagen alpha-1 (XVIII) chain isoform 3 preproprotein [Homo sapiens] | KGEVGADGVPGFPGL | 307 | none | | | |
| collagen alpha-1 (XVIII) chain isoform 3 preproprotein [Homo sapiens] | GDPGKDGVGQPGLP | 308 | none | | | |
| protocadherin gamma-A3 isoform 1 precursor [Homo sapiens] | SHFVGADGVRAFL | 309 | none | | | |

Figure 62:
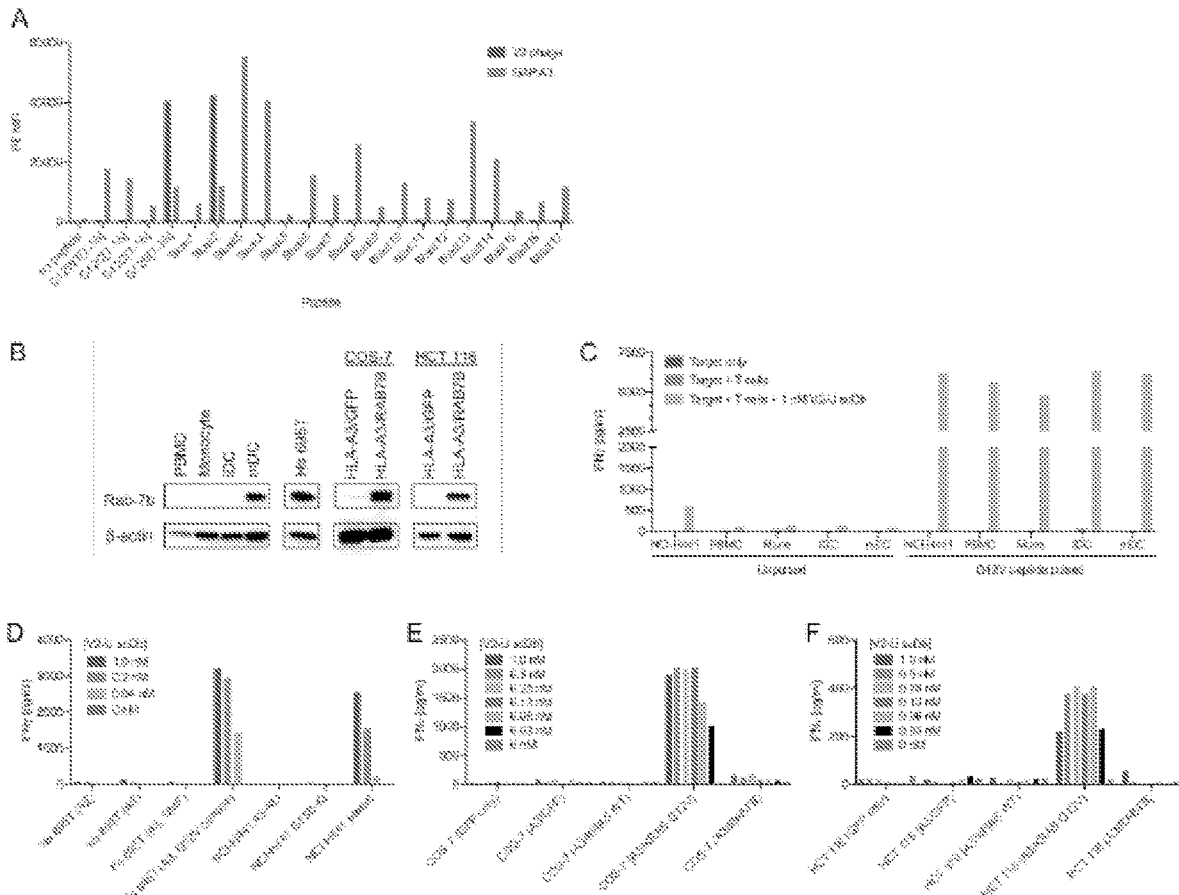

Rab-7b is a RAS-related protein expressed in monocytic cells and keratinocytes. To investigate whether this peptide represents an authentic alternative target and thus could cause off-target toxicity of the V2-U scDb, T cells first co-cultured with peripheral blood mononuclear cells (PBMC), monocytes, iDCs, and mature dendritic cells (mDC) prepared from an HLA-A3+ donor (FIGS. 62, B and C). None of these cells were able to activate T cells significantly above background as assessed by IFNγ secretion in the presence of the V2-U scDb (FIG. 62C). Importantly, these cells have the ability to activate T cells when pulsed with the G12V peptide (FIG. 62C). Next, V2-U scDb was tested against a skin derived cell line, Hs 695T, which highly expresses Rab-7b (FIG. 62B). As these cells do not express the HLA-A3 allele, they were transfected with either HLA-A3 or HLA-A2 and co-cultured with T cells. Despite high levels of expression of endogenous Rab-7b, Hs 695T cells did not activate T cells in the presence of V2-U scDb.

(FIG. 62D). As a positive control, the same experiment was performed after pulsing Hs 695 T cells with the G12V peptide, and under these circumstances, robust activation of T cells was achieved (FIG. 62D).

As a final assessment of the potential cross-reactivity with the Rab-7b peptide, plasmids encoding full length Rab-7b, KRAS WT, or KRAS G12V, in combination with HLA-A3, were transfected into COS-7. Cells overexpressing the mutant KRAS induced robust T cell activation in the presence of V2-U scDb (FIG. 62E), whereas COS-7 cells expressing control proteins, KRAS WT and Rab-7b, showed only marginal, non-dose dependent activation of the same T cells (FIGS. 62, B and E). This experiment was repeated in HCT 116 cells transfected with the same genes and again found that T cells were activated by KRAS in a mutant-dependent fashion but no activation was observed in Rab-7b-expressing cells (FIGS. 62, B and F).

Figure 44:
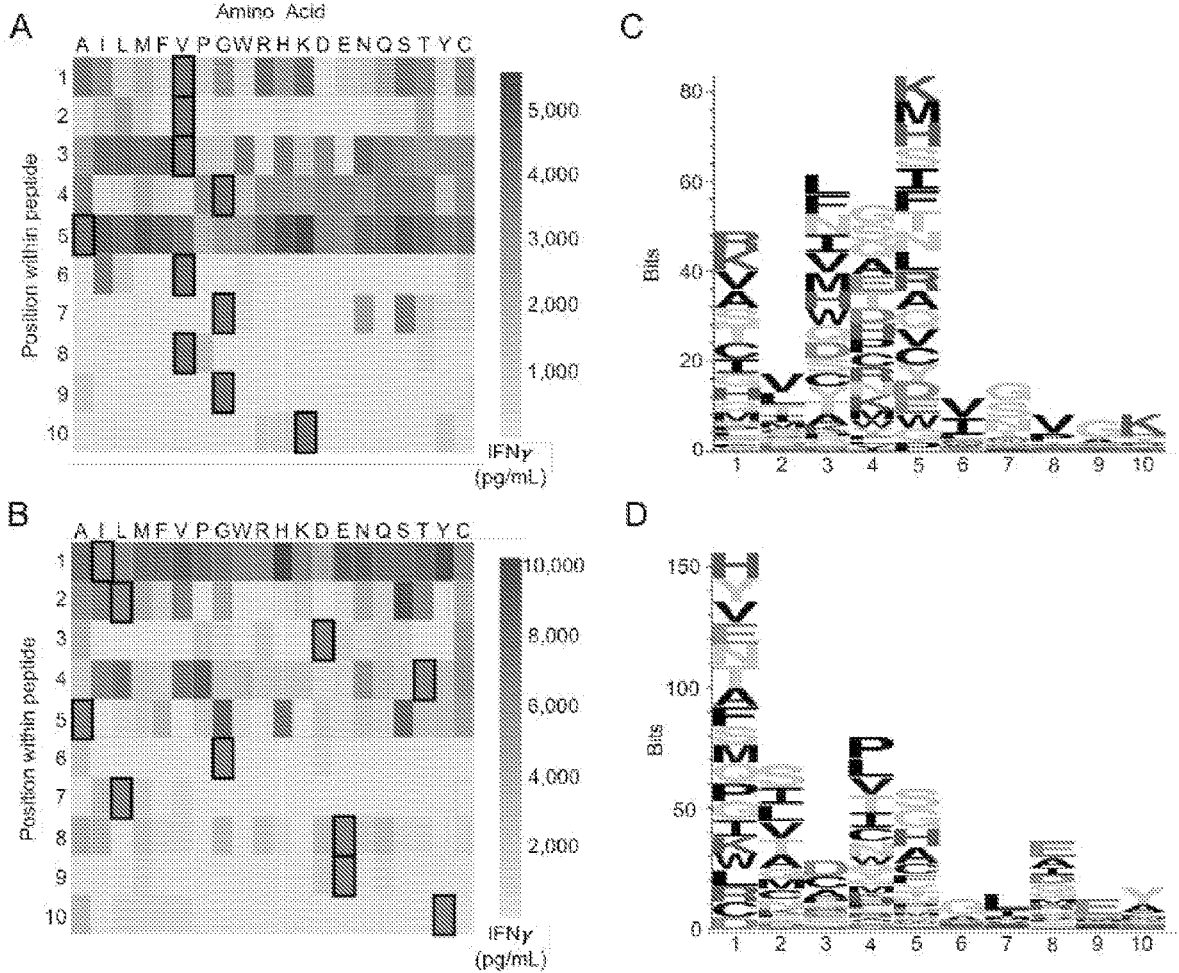
Figure 63:
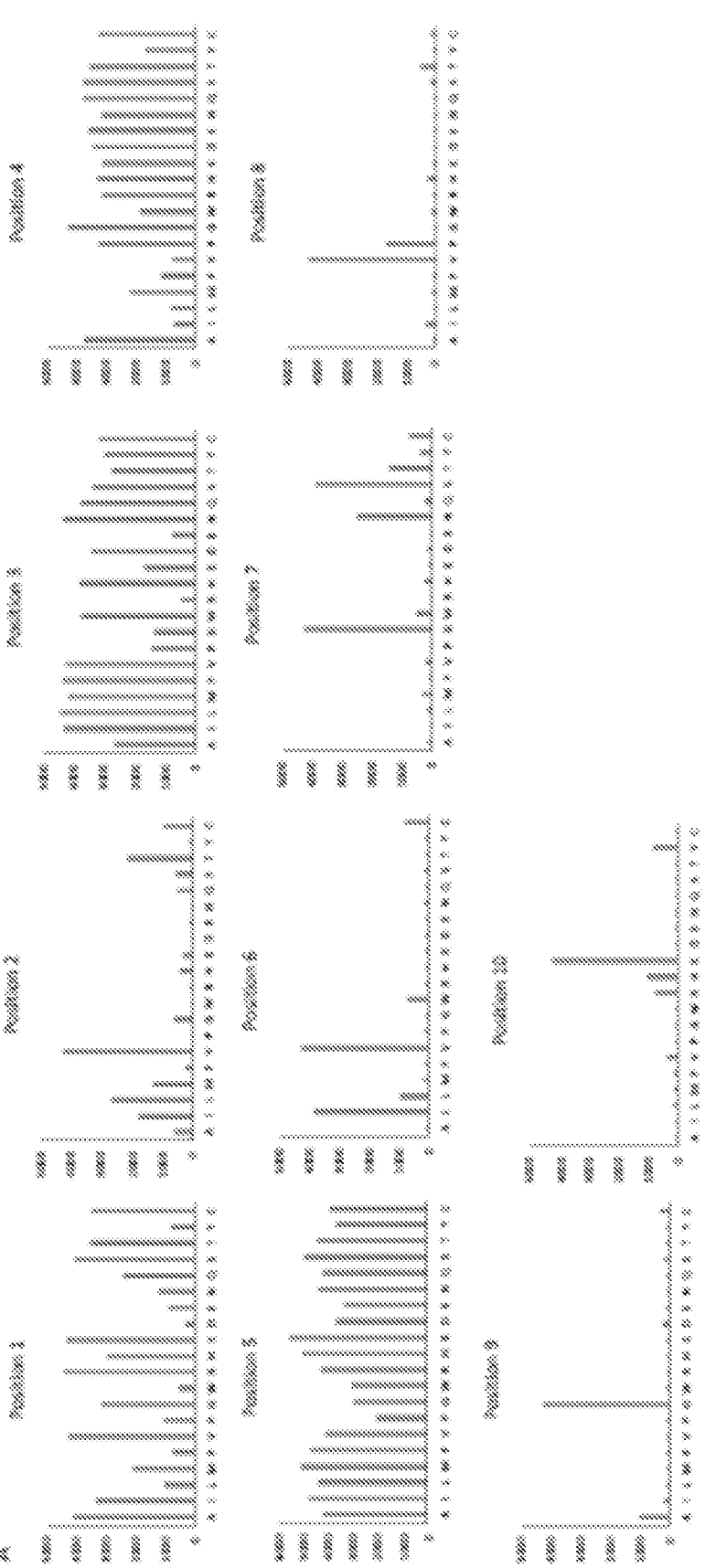
Figure 63:
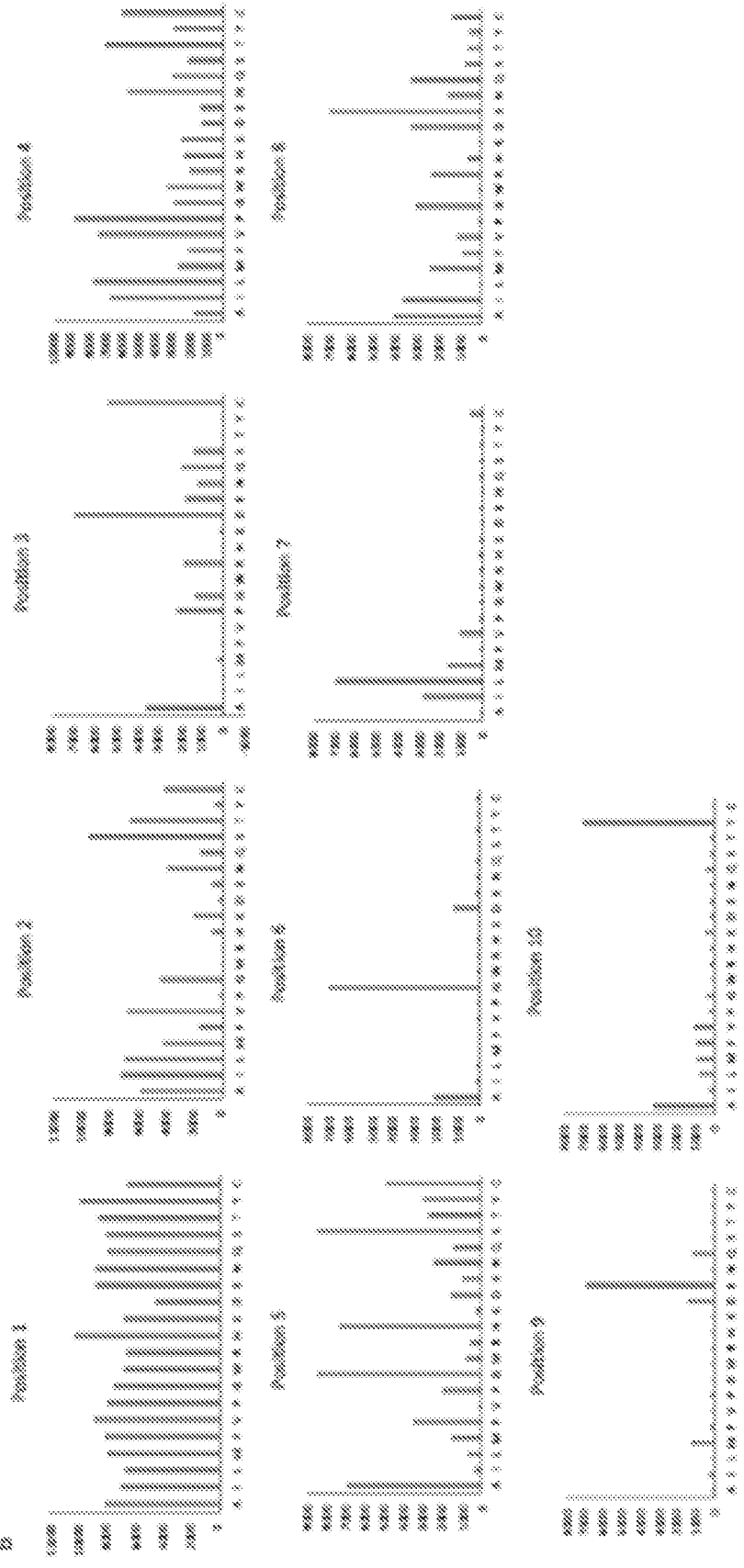
Figure 63:
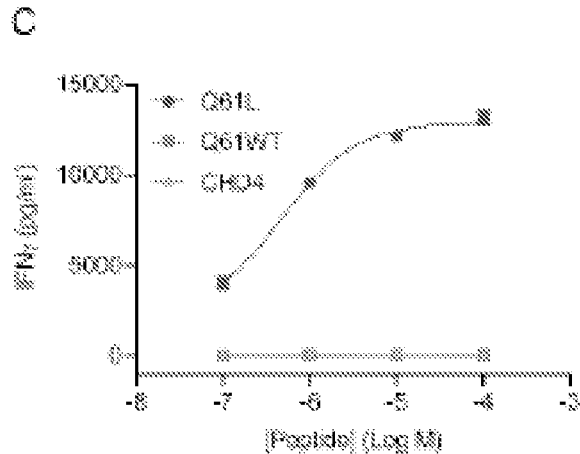

To further assay for potential cross-reactivity of the V2-U and L2-U scDbs, their binding to libraries of positional scanning variant peptides was evaluated. The library of peptides was generated by systematically substituting each amino acid of the original peptides with the other 19 amino acids. This resulted in 190 variants for each of the G12V and Q61L peptides for the V2 and L2 scDbs. The variant peptides were pulsed on to T2A3 cells (for V2-U scDb) or SigM5 cells (for L2-U scDb) and co-cultured with T cells. Recognition of the variant peptides was evaluated through IFNγ release (FIGS. 44, A and B, FIGS. 63, A and B). For both scDbs, amino acid positions in the C-terminal half of the peptides, where the mutant residue resided, demonstrated greater specificity. Most changes of amino acids at these positions abolished recognition by the scDbs. On the other hand, amino acids at the N-terminus of the peptides could in many cases be substituted without substantially changing interaction with the scDbs. These recognition patterns are also illustrated as Seq2Logo graphs (FIGS. 44, C and D). Next, using a 20% cognate peptide reactivity as a cutoff for permissive amino acids at each position, decamer binding motifs were generated for each candidate target peptide (Materials and Methods). A search of these motifs in the UniProtKB human protein database using ScanProsite yielded 162 peptides (including Rab-7b IIV-GAIGVGK (SEQ ID NO:260)) that could potentially bind to V2 and 232 peptides that could potentially bind to L2 (Tables 15 and 16). Comparing these peptides to an extensive database of peptides actually presented by HLA as assessed by mass spectrometry, it was found that none of the 162 peptides and only one of the 232 peptides were known to be presented by the cognate HLA. However, when this one peptide (DTELQGMNEY (SEQ ID NO:310), from chromodomain-helicase-DNA-binding protein 4 [CHD4]) was pulsed on SigM5 cells, which was then co-cultured with T cells and L2-U scDb, it did not elicit IFNγ release (FIG. 63C), demonstrating that L2-U scDb did not bind the CHD4 peptide.

TABLE 15

Human peptides matching the V2 binding motif. Using a 20% cognate peptide reactivity as a cutoff for permissive amino acids at each position based on the results of the peptide library analysis, a decamer binding motif for V2 was generated. These motifs were searched in the UniProtKB human protein database using ScanProsite to identify peptides matching the motif.

| UniProt Accession Number (Entry Name) | Start position | End position | Peptide Sequence | SEQ ID NO |
|---|---|---|---|---|
| sp\|Q8N412\|STPG2_HUMAN | 115 | 124 | ACDSTLGPAY | 311 |
| sp\|Q05469\|LIPS_HUMAN | 351 | 360 | ALGRLLGVAH | 312 |
| sp\|O43151\|TET3_HUMAN | 1188 | 1197 | ALHNSLSPAY | 313 |
| sp\|P14550\|AK1A1_HUMAN | 59 | 68 | ALKEDVGPGK | 314 |
| sp\|Q7RTX9\|MOT14_HUMAN | 207 | 216 | ALMRPLSPGK | 315 |
| sp\|P78363\|ABCA4_HUMAN | 1626 | 1635 | ALVSFLNVAH | 316 |
| sp\|Q6PIV7\|S2534_HUMAN | 266 | 275 | ALYKGLGPAY | 317 |
| sp\|P28838\|AMPL_HUMAN | 244 | 253 | AMGSFLSVAK | 318 |
| sp\|P17302\|CXA1_HUMAN | 249 | 258 | ATSGALSPAK | 319 |
| sp\|O15197\|EPHB6_HUMAN | 545 | 554 | ATVTQLSPGH | 320 |
| sp\|Q96JB1\|DYH8_HUMAN | 200 | 209 | AVINVLNVAH | 321 |
| sp\|P14550\|AK1A1_HUMAN | 32 | 41 | AVKYALSVGY | 322 |
| sp\|Q8N104\|D106A_HUMAN | 9 | 18 | AVLFFLTPAK | 323 |
| sp\|Q86WI1\|PKHL1_HUMAN | 1294 | 1303 | CLLPKLSPGK | 324 |
| sp\|Q9Y6T7\|DGKB_HUMAN | 261 | 270 | CLNMLIGVGK | 325 |
| sp\|Q8IXW5\|RPAP2_HUMAN | 77 | 86 | ECGRFITPAH | 326 |
| sp\|Q8WWQ8\|STAB2_HUMAN | 1866 | 1875 | ELLFDLGVAY | 327 |
| sp\|Q9H3U7\|SMOC2_HUMAN | 408 | 417 | ELMGCLGVAK | 328 |
| sp\|Q16653\|MOG_HUMAN | 50 | 59 | ELPCRISPGK | 329 |
| sp\|O75366\|AVIL_HUMAN | 771 | 780 | ELPEDVNPAK | 330 |
| sp\|Q5VUG0\|SMBT2_HUMAN | 550 | 559 | ELPQSVGPGK | 331 |
| sp\|Q8IWI9\|MGAP_HUMAN | 2357 | 2366 | ELSEEINVAH | 332 |
| sp\|Q8NGI7\|O10V1_HUMAN | 270 | 279 | EMGRVVSVAY | 333 |

TABLE 15-continued

Human peptides matching the V2 binding motif. Using a
20% cognate peptide reactivity as a cutoff for
permissive amino acids at each position based on the
results of the peptide library analysis, a decamer
binding motif for V2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|A7E2V4\|ZSWM8_HUMAN | 1738 | 1747 | ETLQRLSPAH | 334 |
| sp\|Q9HB07\|MYG1_HUMAN | 114 | 123 | ETMSSLSPGK | 335 |
| sp\|Q9NRY4\|RHG35_HUMAN | 441 | 450 | ETSPFITPGK | 336 |
| sp\|Q01094\|E2F1_HUMAN | 301 | 310 | ETVGGISPGK | 337 |
| sp\|Q8NEB7\|ACRBP_HUMAN | 513 | 522 | ETYSALSPGK | 338 |
| sp\|P36382\|CXA5_HUMAN | 322 | 331 | EVPNGVSPGH | 339 |
| sp\|P07942\|LAMB1_HUMAN | 1429 | 1438 | GCGGLVTVAH | 340 |
| sp\|O15353\|FOXN1_HUMAN | 343 | 352 | GCLWALNPAK | 341 |
| sp\|Q9C0H6\|KLHL4_HUMAN | 295 | 304 | GCTELLNVAH | 342 |
| sp\|Q14332\|FZD2_HUMAN | 285 | 294 | GCYTMVSVAY | 343 |
| sp\|Q9ULJ3\|ZBT21_HUMAN | 3 | 12 | GLLHYINPAH | 344 |
| sp\|Q96Q06\|PLIN4_HUMAN | 689 | 698 | GLMGAVNVAK | 345 |
| sp\|Q96Q06\|PLIN4_HUMAN | 161 | 170 | GLTGAVNVAK | 346 |
| sp\|Q96Q06\|PLIN4_HUMAN | 491 | 500 | GLTGAVNVAK | 346 |
| sp\|Q96Q06\|PLIN4_HUMAN | 590 | 599 | GLVGAVNVAK | 347 |
| sp\|Q9BT76\|UPK3B_HUMAN | 67 | 76 | GTPTPVSVAH | 348 |
| sp\|Q9BW71\|HIRP3_HUMAN | 119 | 128 | GVAAEVSPAK | 349 |
| sp\|Q95460\|HMR1_HUMAN | 40 | 49 | GVPEFISVGY | 350 |
| sp\|Q96Q06\|PLIN4_HUMAN | 920 | 929 | GVTGAVNVAK | 351 |
| sp\|Q96Q06\|PLIN4_HUMAN | 953 | 962 | GVTGAVNVAK | 351 |
| sp\|Q96Q06\|PLIN4_HUMAN | 524 | 533 | GVTSAVNVAK | 352 |
| sp\|Q96Q06\|PLIN4_HUMAN | 623 | 632 | GVTSAVNVAK | 352 |
| sp\|Q96Q06\|PLIN4_HUMAN | 656 | 665 | GVTSAVNVAK | 352 |
| sp\|Q8N594\|MPND_HUMAN | 130 | 139 | HCKKLVNPAK | 353 |
| sp\|Q3B8N5\|PROX2_HUMAN | 435 | 444 | HIQEGLNPGH | 354 |
| sp\|P51003\|PAPOA_HUMAN | 311 | 320 | HLMPIITPAY | 355 |
| sp\|Q9NRJ5\|PAPOB_HUMAN | 311 | 320 | HLMPIITPAY | 355 |
| sp\|Q9BWT3\|PAPOG_HUMAN | 310 | 319 | HLMPIITPAY | 355 |
| sp\|Q02040\|AK17A_HUMAN | 451 | 460 | HTHDELGVAH | 356 |
| sp\|O60384\|ZN861_HUMAN | 40 | 49 | HVCGEVGVGY | 357 |
| sp\|O94915\|FRYL_HUMAN | 426 | 435 | IIFDLLSVGK | 358 |
| sp\|Q96AH8\|RAB7B_HUMAN | 12 | 21 | IIVGAIGVGK | 260 |
| sp\|Q8N109\|KI2LA_HUMAN | 80 | 89 | ILMGPVTPAH | 359 |
| sp\|Q8NHK3\|KI2LB_HUMAN | 80 | 89 | ILMGPVTPAH | 359 |
| sp\|Q68DQ2\|CRBG3_HUMAN | 2098 | 2107 | ILSSEVSPGH | 360 |

TABLE 15-continued

Human peptides matching the V2 binding motif. Using a
20% cognate peptide reactivity as a cutoff for
permissive amino acids at each position based on the
results of the peptide library analysis, a decamer
binding motif for V2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp|Q92621|NU205_HUMAN | 475 | 484 | IMGSYLGVAH | 361 |
| sp|Q99550|MPP9_HUMAN | 974 | 983 | IMLTPVTVAY | 362 |
| sp|Q9Y3R5|DOP2_HUMAN | 1355 | 1364 | IMMQLVSVAK | 363 |
| sp|Q9P2P6|STAR9_HUMAN | 356 | 365 | IMVATVSPAH | 364 |
| sp|A8TX70|CO6A5_HUMAN | 946 | 955 | ITIFAVGVGK | 365 |
| sp|O00370|LORF2_HUMAN | 983 | 992 | ITIQDIGVGK | 366 |
| sp|O00339|MATN2_HUMAN | 787 | 796 | ITMYAVGVGK | 367 |
| sp|O95460|MATN4_HUMAN | 518 | 527 | IVMYAVGVGK | 378 |
| sp|Q9BZG1|RAB34_HUMAN | 56 | 65 | IVVGDLSVGK | 369 |
| sp|O60645|EXOC3_HUMAN | 733 | 742 | IVVPSLNVAK | 370 |
| sp|P19838|NFKB1_HUMAN | 85 | 94 | KICNYVGPAK | 371 |
| sp|Q8TE73|DYH5_HUMAN | 2739 | 2748 | KIFGVIGVGH | 372 |
| sp|Q5PT55|NTCP5_HUMAN | 68 | 77 | KILQMVNVAK | 373 |
| sp|P43004|EAA2_HUMAN | 148 | 157 | KLKKQLGPGK | 374 |
| sp|Q96Q15|SMG1_HUMAN | 2054 | 2063 | KLKTPLNPAK | 375 |
| sp|Q8N1V2|CFA52_HUMAN | 237 | 246 | KLLTDVGPAK | 376 |
| sp|Q14204|DYHC1_HUMAN | 447 | 456 | KMVWRINPAH | 377 |
| sp|O00206|TLR4_HUMAN | 150 | 159 | KTLKELNVAH | 378 |
| sp|Q8WTR2|DUS19_HUMAN | 91 | 100 | KVTHILNVAY | 379 |
| sp|Q9BRR8|GPTC1_HUMAN | 143 | 152 | LLDDLITPAK | 380 |
| sp|Q9NP78|ABCB9_HUMAN | 61 | 70 | LLGATIGVAK | 381 |
| sp|Q8N4A0|GALT4_HUMAN | 13 | 22 | LLLAFLTVAY | 382 |
| sp|Q86VR7|VS10L_HUMAN | 456 | 465 | LLLPAVGPGH | 383 |
| sp|Q9P2N4|ATS9_HUMAN | 849 | 858 | LLLQVLSVGK | 384 |
| sp|Q15155|NOMO1_HUMAN | 21 | 30 | LLLSGVGPAH | 385 |
| sp|Q5JPE7|NOMO2_HUMAN | 21 | 30 | LLLSGVGPAH | 385 |
| sp|P69849|NOMO3_HUMAN | 21 | 30 | LLLSGVGPAH | 385 |
| sp|Q8TCY9|URGCP_HUMAN | 278 | 287 | LLNAVLSPGH | 386 |
| sp|Q9UQL6|HDAC5_HUMAN | 854 | 863 | LLQQKLNVGK | 387 |
| sp|Q8TDG4|HELQ_HUMAN | 294 | 303 | LLSEEINVAK | 388 |
| sp|Q9NX45|SOLH2_HUMAN | 22 | 31 | LLVGDVTVGY | 389 |
| sp|Q99698|LYST_HUMAN | 2747 | 2756 | LLVHILSPAH | 390 |
| sp|Q9Y3R4|NEUR2_HUMAN | 142 | 151 | LTDAAIGPAY | 391 |
| sp|Q8TE58|ATS15_HUMAN | 779 | 788 | LTVEVLSVGK | 392 |

TABLE 15-continued

Human peptides matching the V2 binding motif. Using a
20% cognate peptide reactivity as a cutoff for
permissive amino acids at each position based on the
results of the peptide library analysis, a decamer
binding motif for V2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|P57729\|RAB38_HUMAN | 13 | 22 | LVIGDLGVGK | 393 |
| sp\|Q13637\|RAB32_HUMAN | 29 | 38 | LVIGELGVGK | 394 |
| sp\|Q9UN74\|PCDA4_HUMAN | 580 | 589 | LVPWSVGVGH | 395 |
| sp\|Q9Y2L1\|RRP44_HUMAN | 667 | 676 | MLLANISVAK | 396 |
| sp\|Q9BXL7\|CAR11_HUMAN | 32 | 41 | MLSRYINPAK | 397 |
| sp\|O76082\|S22A5_HUMAN | 349 | 358 | MLWMTISVGY | 398 |
| sp\|Q8NA54\|IQUB_HUMAN | 318 | 327 | MTDKLVTPGK | 399 |
| sp\|Q6ZMS4\|ZN852_HUMAN | 494 | 503 | NLMNVLSVGK | 400 |
| sp\|Q4VNC0\|AT135_HUMAN | 722 | 731 | NLQTAITVAK | 401 |
| sp\|Q9Y4K4\|M4K5_HUMAN | 562 | 571 | NTLMSLSVGK | 402 |
| sp\|Q99502\|EYA1_HUMAN | 451 | 460 | NVGGLLGPAK | 403 |
| sp\|O95677\|EYA4_HUMAN | 498 | 507 | NVGGLLGPAK | 403 |
| sp\|Q9ULU8\|CAPS1_HUMAN | 868 | 877 | NVGRLITPAK | 404 |
| sp\|P98155\|VLDLR_HUMAN | 314 | 323 | NVNQCLGPGK | 405 |
| sp\|Q9NP78\|ABCB9_HUMAN | 524 | 533 | NVSFSLSPGK | 406 |
| sp\|Q00688\|FKBP3_HUMAN | 161 | 170 | PLSFKVGVGK | 407 |
| sp\|Q9NS98\|SEM3G_HUMAN | 141 | 150 | PTCALITVGH | 408 |
| sp\|Q6UXF1\|TM108_HUMAN | 266 | 275 | PTTTSLGPAK | 409 |
| sp\|Q9BRQ3\|NUD22_HUMAN | 20 | 29 | QIQAELSPAH | 410 |
| sp\|Q96B70\|LENG9_HUMAN | 443 | 452 | QLHPHLTVAK | 411 |
| sp\|Q96CT2\|KLH29_HUMAN | 294 | 303 | QMLRTIGVGK | 412 |
| sp\|Q07157\|ZO1_HUMAN | 1515 | 1524 | QTQKTVTPAY | 413 |
| sp\|Q13702\|RAPSN_HUMAN | 285 | 294 | QVQALLGVAK | 414 |
| sp\|Q9BWT7\|CAR10_HUMAN | 37 | 46 | RLARALNPAK | 415 |
| sp\|P56975\|NRG3_HUMAN | 501 | 510 | RLGGIVGPAY | 416 |
| sp\|Q03001\|DYST_HUMAN | 546 | 555 | RLTPSVTPAY | 417 |
| sp\|Q13769\|THOC5_HUMAN | 518 | 527 | RLVKWVTVAH | 418 |
| sp\|Q96PU9\|ODF3A_HUMAN | 78 | 87 | RTGKDLGPAY | 418 |
| sp\|O75192\|PX11A_HUMAN | 230 | 239 | SIAGMITVAY | 420 |
| sp\|O60284\|ST18_HUMAN | 23 | 32 | SLIQELSVAY | 421 |
| sp\|Q12797\|ASPH_HUMAN | 455 | 464 | SLKNDLGVGY | 422 |
| sp\|Q9P0R6\|GSKIP_HUMAN | 109 | 118 | SLLDTLSPAY | 423 |
| sp\|Q8NDA8\|MROH1_HUMAN | 168 | 177 | SLLPVLGVAK | 424 |
| sp\|Q96LD8\|SENP8_HUMAN | 185 | 194 | SLLQLLTPAY | 425 |
| sp\|Q8N1T3\|MYO1H_HUMAN | 992 | 1001 | SLQFFISPGK | 426 |

US 12,674,002 B2

121

122

TABLE 15-continued

Human peptides matching the V2 binding motif. Using a
20% cognate peptide reactivity as a cutoff for
permissive amino acids at each position based on the
results of the peptide library analysis, a decamer
binding motif for V2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|Q9UKZ4\|TEN1_HUMAN | 1923 | 1932 | SLQTMLSVGY | 427 |
| sp\|Q15911\|ZFHX3_HUMAN | 353 | 362 | STANLIGPGH | 428 |
| sp\|Q86X29\|LSR_HUMAN | 326 | 335 | STYAHLSPAK | 429 |
| sp\|A2RUS2\|DEND3_HUMAN | 728 | 737 | SVKTNLGVGK | 430 |
| sp\|Q13330\|MTA1_HUMAN | 558 | 567 | SVLSSLTPAK | 431 |
| sp\|Q15788\|NCOA1_HUMAN | 389 | 398 | SVNPSISPAH | 432 |
| sp\|P98168\|ZXDA_HUMAN | 743 | 752 | SVSELLTPAK | 434 |
| sp\|Q6V0I7\|FAT4_HUMAN | 2206 | 2215 | SVTGAITVAK | 435 |
| sp\|P21912\|SDHB_HUMAN | 252 | 261 | TCPKGLNPGK | 436 |
| sp\|Q9Y6D6\|BIG1_HUMAN | 1025 | 1034 | TIKTLITVAH | 437 |
| sp\|Q9Y6D5\|BIG2_HUMAN | 970 | 979 | TIKTLITVAH | 437 |
| sp\|P27816\|MAP4_HUMAN | 565 | 574 | TLANNVTPAK | 438 |
| sp\|Q9Y251\|HPSE_HUMAN | 82 | 91 | TLARGLSPAY | 439 |
| sp\|Q96T83\|SL9A7_HUMAN | 154 | 163 | TLKGEISPGK | 440 |
| sp\|Q6P1M9\|ARMX5_HUMAN | 332 | 341 | TMIMGISPAY | 441 |
| sp\|Q17RG1\|KCD19_HUMAN | 264 | 273 | TTCSPLSPGK | 442 |
| sp\|O94851\|MICA2_HUMAN | 945 | 954 | TVHPQLTVGK | 443 |
| sp\|P28332\|ADH6_HUMAN | 151 | 160 | TVIKEISVAK | 444 |
| sp\|Q14973\|NTCP_HUMAN | 203 | 212 | TVLSAINVGK | 445 |
| sp\|O15014\|ZN609_HUMAN | 716 | 725 | TVNPALTPAK | 446 |
| sp\|Q9BSJ5\|CQ080_HUMAN | 588 | 597 | TVPPCIGVAK | 447 |
| sp\|P11766\|ADHX_HUMAN | 150 | 159 | TVVADISVAK | 448 |
| sp\|Q9UPT5\|EXOC7_HUMAN | 321 | 330 | VCAADISPGH | 449 |
| sp\|Q8IV61\|GRP3_HUMAN | 221 | 230 | VITKFINVAK | 450 |
| sp\|P27695\|APEX1_HUMAN | 206 | 215 | VLCGDLNVAH | 451 |
| sp\|P01266\|THYG_HUMAN | 1156 | 1165 | VLSRRVSPGY | 452 |
| sp\|Q96DY7\|MTBP_HUMAN | 633 | 642 | VLTPELSPGK | 453 |
| sp\|Q13423\|NNTM_HUMAN | 1040 | 1049 | VMKRSLGVGY | 454 |
| sp\|P10809\|CH60_HUMAN | 73 | 82 | VTKDGVTVAK | 455 |
| sp\|O43598\|DNPH1_HUMAN | 94 | 103 | VTQPSLGVGY | 456 |
| sp\|Q15772\|SPEG_HUMAN | 2927 | 2936 | VTVQSLSPAK | 457 |
| sp\|P49281\|NRAM2_HUMAN | 509 | 518 | VVAAVVSVAY | 458 |
| sp\|Q9NYS0\|KBRS1_HUMAN | 8 | 17 | VVCGLLSVGK | 459 |

TABLE 15-continued

Human peptides matching the V2 binding motif. Using a
20% cognate peptide reactivity as a cutoff for
permissive amino acids at each position based on the
results of the peptide library analysis, a decamer
binding motif for V2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|O15091\|MRPP3_HUMAN | 406 | 415 | VVIDGLNVAK | 460 |
| sp\|Q8N441\|FGRL1_HUMAN | 115 | 124 | VVLDDISPGK | 461 |

TABLE 16

Human peptides matching the L2 binding motif. Using
a 20% cognate peptide reactivity as a cutoff for
permissive amino acids at each position based on the
results of the peptide library analysis, a decamer
binding motif for L2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|O15018\|PDZD2_HUMAN | 2787 | 2796 | AAEQAGIIEA | 462 |
| sp\|P23276\|KELL_HUMAN | 598 | 607 | ACDNHALQEA | 463 |
| sp\|Q9P2V4\|LRIT1_HUMAN | 121 | 130 | AFPWAALRDA | 464 |
| sp\|Q9NVI7\|ATD3A_HUMAN | 135 | 144 | AGECCALQEY | 465 |
| sp\|P15884\|ITF2_HUMAN | 651 | 660 | AGPHPGMGDA | 466 |
| sp\|A0JNW5\|UH1BL_HUMAN | 1438 | 1447 | AKAKMALAEA | 467 |
| sp\|O75533\|SF3B1_HUMAN | 706 | 715 | ALAIAALAEA | 468 |
| sp\|P20711\|DDC_HUMAN | 216 | 225 | AMRASALQEA | 469 |
| sp\|Q86Y56\|DAAF5_HUMAN | 592 | 601 | AQSGPALGEA | 470 |
| sp\|P14679\|TYRO_HUMAN | 348 | 357 | ASPLTGIADA | 471 |
| sp\|Q92508\|PIEZ1_HUMAN | 164 | 173 | ASPTAGLQEA | 472 |
| sp\|Q9NVR2\|INT10_HUMAN | 500 | 509 | ATCHFALGEY | 473 |
| sp\|Q8NFY4\|SEM6D_HUMAN | 369 | 378 | CCAKHGLAEA | 474 |
| sp\|Q9UGU0\|TCF20_HUMAN | 1869 | 1878 | CGRLYGLQEA | 475 |
| sp\|Q14674\|ESPL1_HUMAN | 647 | 656 | CSALDAIREA | 476 |
| sp\|Q8IZJ3\|CPMD8_HUMAN | 1420 | 1429 | CVALQALAEY | 477 |
| sp\|Q86X53\|ERIC1_HUMAN | 359 | 368 | DAASAALADA | 478 |
| sp\|P35443\|TSP4_HUMAN | 497 | 506 | DADRDGIGDA | 479 |
| sp\|Q99459\|CDC5L_HUMAN | 519 | 528 | DARKQAIRDA | 480 |
| sp\|Q14674\|ESPL1_HUMAN | 206 | 215 | DASGHGLNEA | 481 |
| sp\|P35442\|TSP2_HUMAN | 730 | 739 | DFDKDGIGDA | 482 |
| sp\|Q6F5E8\|CARL2_HUMAN | 615 | 624 | DISGNAMGDA | 483 |
| sp\|Q49MG5\|MAP9_HUMAN | 594 | 603 | DKDKQAINEY | 484 |
| sp\|Q63HN8\|RN213_HUMAN | 2947 | 2956 | DKEFFGLRDY | 485 |

TABLE 16-continued

Human peptides matching the L2 binding motif. Using
a 20% cognate peptide reactivity as a cutoff for
permissive amino acids at each position based on the
results of the peptide library analysis, a decamer
binding motif for L2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|P04035\|HMDH_HUMAN | 115 | 124 | DKELTGLNEA | 486 |
| sp\|Q8IWE5\|PKHM2_HUMAN | 976 | 985 | DLPHTAIQEA | 487 |
| sp\|Q9C0D3\|ZY11B_HUMAN | 4 | 13 | DQAGAAMEEA | 488 |
| sp\|P49747\|COMP_HUMAN | 397 | 406 | DSDGDGIGDA | 489 |
| sp\|P21283\|VATC1_HUMAN | 343 | 352 | DSSAAAIIDA | 490 |
| sp\|Q14839\|CHD4_HUMAN | 1267 | 1276 | DTELQGMNEY | 310 |
| sp\|Q7Z3K3\|POGZ_HUMAN | 706 | 715 | DTPPSALQEA | 491 |
| sp\|Q14686\|NCOA6_HUMAN | 934 | 943 | DTRPAGLEEA | 492 |
| sp\|P49747\|COMP_HUMAN | 302 | 311 | DVDRDGIGDA | 493 |
| sp\|P42684\|ABL2_HUMAN | 83 | 92 | DVEPQALNEA | 494 |
| sp\|O43633\|CHM2A_HUMAN | 199 | 208 | EAAASALADA | 495 |
| sp\|Q8TE73\|DYH5_HUMAN | 3285 | 3294 | EAAKPALEEA | 496 |
| sp\|Q96JB1\|DYH8_HUMAN | 3149 | 3158 | EAAKPALEEA | 496 |
| sp\|Q14CN2\|CLCA4_HUMAN | 463 | 472 | EAQNNGLIDA | 497 |
| sp\|Q969T3\|SNX21_HUMAN | 344 | 353 | EARLQALQEA | 498 |
| sp\|Q13415\|ORC1_HUMAN | 784 | 793 | EFRRSGLEEA | 499 |
| sp\|Q96FB5\|RRNAD_HUMAN | 316 | 325 | EGACHALEEY | 500 |
| sp\|P07711\|CATL1_HUMAN | 176 | 185 | EGCNGGLMDY | 501 |
| sp\|P51649\|SSDH_HUMAN | 515 | 524 | EGSKYGIDEY | 502 |
| sp\|P30876\|RPB2_HUMAN | 555 | 564 | EISPAAIADA | 503 |
| sp\|QOVDF9\|HSP7E_HUMAN | 149 | 158 | EKQKNALGEA | 504 |
| sp\|Q96S94\|CCNL2_HUMAN | 299 | 308 | EKRKHAIEEA | 505 |
| sp\|P10589\|COT1_HUMAN | 346 | 355 | EKSQCALEEY | 506 |
| sp\|P24468\|COT2_HUMAN | 339 | 348 | EKSQCALEEY | 506 |
| sp\|Q9P2L0\|WDR35_HUMAN | 800 | 809 | EQANNAIGDY | 507 |
| sp\|Q8NF91\|SYNE1_HUMAN | 991 | 1000 | EQEQQGLQEA | 508 |
| sp\|Q7Z5Q1\|CPEB2_HUMAN | 385 | 394 | ESSVQALIDA | 509 |
| sp\|Q8NE35\|CPEB3_HUMAN | 494 | 503 | ESSVQALIDA | 509 |
| sp\|Q17RY0\|CPEB4_HUMAN | 525 | 534 | ESSVQALIDA | 509 |
| sp\|Q9UGU0\|TCF20_HUMAN | 1217 | 1226 | ETDGHGLAEA | 510 |
| sp\|Q9BVI0\|PHF20_HUMAN | 858 | 867 | ETRGSALDDA | 511 |
| sp\|Q96IS3\|RAX2_HUMAN | 155 | 164 | FADGFALEEA | 512 |
| sp\|Q86YC2\|PALB2_HUMAN | 1016 | 1025 | FAEVQGMQEA | 513 |
| sp\|Q17RP2\|TIGD6_HUMAN | 491 | 500 | FGQLNGIDEY | 514 |
| sp\|Q9HBE1\|PATZ1_HUMAN | 280 | 289 | FGSPGGLREA | 515 |

TABLE 16-continued

Human peptides matching the L2 binding motif. Using
a 20% cognate peptide reactivity as a cutoff for
permissive amino acids at each position based on the
results of the peptide library analysis, a decamer
binding motif for L2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|Q53GS7\|GLE1_HUMAN | 538 | 547 | FKEGMALEDY | 516 |
| sp\|Q8N998\|CCD89_HUMAN | 39 | 48 | FKELDGLREA | 517 |
| sp\|Q9Y5W7\|SNX14_HUMAN | 217 | 226 | FLQQAALEEY | 518 |
| sp\|Q9C0E2\|XPO4_HUMAN | 68 | 77 | FQAATAIMEA | 519 |
| sp\|Q5T011\|SZT2_HUMAN | 2376 | 2385 | GAARQALADA | 520 |
| sp\|A6NGH8\|ANR61_HUMAN | 191 | 200 | GADVNAINEA | 521 |
| sp\|Q8IX07\|FOG1_HUMAN | 807 | 816 | GAPAPALADY | 522 |
| sp\|Q9Y275\|TN13B_HUMAN | 96 | 105 | GAPKAGLEEA | 523 |
| sp\|Q02080\|MEF2B_HUMAN | 151 | 160 | GCDPSGLGEA | 524 |
| sp\|O15357\|SHIP2_HUMAN | 1190 | 1199 | GGRASGLGEA | 525 |
| sp\|P00742\|FA10_HUMAN | 99 | 108 | GKCKDGLGEY | 526 |
| sp\|Q9UJX5\|APC4_HUMAN | 380 | 389 | GLDAAGIEEA | 527 |
| sp\|Q5SRE5\|NU188_HUMAN | 891 | 900 | GNDAAAIRDA | 528 |
| sp\|Q8N7H1\|CL061_HUMAN | 114 | 123 | GNSRSALQEA | 529 |
| sp\|O94761\|RECQ4_HUMAN | 1113 | 1122 | GQEPGGMEDA | 530 |
| sp\|Q8IYF1\|ELOA2_HUMAN | 291 | 300 | GQRVPALEEA | 531 |
| sp\|Q9NR16\|C163B_HUMAN | 1290 | 1299 | GSALAALRDA | 532 |
| sp\|O94921\|CDK14_HUMAN | 173 | 182 | GTPFTAIREA | 533 |
| sp\|Q96JH8\|RADIL_HUMAN | 194 | 203 | GTPTPALGDA | 534 |
| sp\|O94933\|SLIK3_HUMAN | 781 | 790 | GTQPPGMGEA | 535 |
| sp\|Q96Q40\|CDK15_HUMAN | 141 | 150 | GVPFTAIREA | 536 |
| sp\|Q9ULL4\|PLXB3_HUMAN | 1278 | 1287 | HKSKQALRDY | 537 |
| sp\|Q92539\|LPIN2_HUMAN | 363 | 372 | HLPNAALAEA | 538 |
| sp\|O95613\|PCNT_HUMAN | 1152 | 1161 | HSERGALQDA | 539 |
| sp\|Q9BQS2\|SYT15_HUMAN | 112 | 121 | HTSSGGLGDA | 540 |
| sp\|P78562\|PHEX_HUMAN | 644 | 653 | IADNGGLREA | 541 |
| sp\|Q68CZ6\|HAUS3_HUMAN | 71 | 80 | ILEGAALDEA | 542 |
| sp\|P05120\|PAI2_HUMAN | 323 | 332 | ILRSMGMEDA | 543 |
| sp\|Q96PC5\|MIA2_HUMAN | 41 | 50 | INRVSAMRDY | 544 |
| sp\|Q8NF91\|SYNE1_HUMAN | 654 | 663 | IQQHTAMNDA | 545 |
| sp\|Q93073\|SBP2L_HUMAN | 746 | 755 | IQSKGGLDEA | 546 |
| sp\|Q9H9A5\|CNO10_HUMAN | 204 | 213 | KAESGALIEA | 547 |
| sp\|P46821\|MAP1B_HUMAN | 1217 | 1226 | KFSRSALRDA | 548 |
| sp\|P24071\|FCAR_HUMAN | 46 | 55 | KIQCQAIREA | 549 |

TABLE 16-continued

Human peptides matching the L2 binding motif. Using
a 20% cognate peptide reactivity as a cutoff for
permissive amino acids at each position based on the
results of the peptide library analysis, a decamer
binding motif for L2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|A0AUZ9\|KAL1L_HUMAN | 964 | 973 | KKQSDGMEEY | 550 |
| sp\|Q96CP6\|ASTRA_HUMAN | 513 | 522 | KNSWSGIEDY | 551 |
| sp\|Q8IY33\|MILK2_HUMAN | 457 | 466 | KQALSALEEA | 552 |
| sp\|Q9BXF6\|RFIP5_HUMAN | 506 | 515 | KSSWFGLREA | 553 |
| sp\|Q86WX3\|AROS_HUMAN | 54 | 63 | KVPKSALDEY | 554 |
| sp\|P23610\|HAP40_HUMAN | 178 | 187 | LAALQALGEA | 555 |
| sp\|Q9H8S5\|CNTD2_HUMAN | 59 | 68 | LARPPGLEEA | 556 |
| sp\|A6NK58\|LIPT2_HUMAN | 126 | 135 | LCELQGLQDA | 557 |
| sp\|Q13946\|PDE7A_HUMAN | 177 | 186 | LFSLHGLIEY | 558 |
| sp\|Q6ZW49\|PAXI1_HUMAN | 607 | 616 | LGCVFAIADY | 559 |
| sp\|Q12882\|DPYD_HUMAN | 67 | 76 | LGERGALREA | 560 |
| sp\|A3KFT3\|OR2M5_HUMAN | 151 | 160 | LGSMDAIIDA | 561 |
| sp\|Q6P0Q8\|MAST2_HUMAN | 1583 | 1592 | LGSPQAIEEA | 562 |
| sp\|Q96R28\|OR2M2_HUMAN | 151 | 160 | LGSTDGIIDA | 563 |
| sp\|Q8NG81\|OR2M7_HUMAN | 151 | 160 | LGSTDGIIDA | 563 |
| sp\|Q96AY4\|TTC28_HUMAN | 1680 | 1689 | LKASAALGEA | 564 |
| sp\|Q9UID3\|VPS51_HUMAN | 385 | 394 | LLAAAGLADA | 565 |
| sp\|A6NKF1\|SAC31_HUMAN | 327 | 336 | LLALDGLREA | 566 |
| sp\|Q6ZQQ6\|WDR87_HUMAN | 485 | 494 | LLCSYGMDDY | 567 |
| sp\|Q99727\|TIMP4_HUMAN | 20 | 29 | LLRPPGLGEA | 568 |
| sp\|Q5TF39\|MFS4B_HUMAN | 428 | 437 | LLSSSGLNEY | 569 |
| sp\|P45379\|TNNT2_HUMAN | 109 | 118 | LNELQALIEA | 570 |
| sp\|P34897\|GLYM_HUMAN | 197 | 206 | LNPKTGLIDY | 571 |
| sp\|O75461\|E2F6_HUMAN | 147 | 156 | LSDLSAMEDA | 572 |
| sp\|Q8N393\|ZN786_HUMAN | 770 | 779 | LSQLFAMIEA | 573 |
| sp\|O95620\|DUS4L_HUMAN | 301 | 310 | LSSTSAIIDY | 574 |
| sp\|P01303\|NPY_HUMAN | 19 | 28 | LVCLGALAEA | 575 |
| sp\|Q9NU02\|ANKE1_HUMAN | 577 | 586 | LVESGALIDA | 576 |
| sp\|P0C1H6\|H2BFM_HUMAN | 1 | 10 | MAAASAMAEA | 577 |
| sp\|Q9H2Z4\|NKX24_HUMAN | 163 | 172 | MGSLTGIADA | 578 |
| sp\|Q9BVS5\|TR61B_HUMAN | 210 | 219 | MLRRPALEDY | 579 |
| sp\|Q9BRK5\|CAB45_HUMAN | 310 | 319 | MNEYNALNEA | 580 |
| sp\|O43681\|ASNA_HUMAN | 136 | 145 | MSAFPGIDEA | 581 |
| sp\|P48200\|IREB2_HUMAN | 96 | 105 | MVDFAAMREA | 582 |
| sp\|Q8IZY2\|ABCA7_HUMAN | 1703 | 1712 | MVRNQAMADA | 583 |

TABLE 16-continued

Human peptides matching the L2 binding motif. Using
a 20% cognate peptide reactivity as a cutoff for
permissive amino acids at each position based on the
results of the peptide library analysis, a decamer
binding motif for L2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|A6NIE6\|RN3P2_HUMAN | 233 | 242 | NASRQGIEDA | 584 |
| sp\|Q9NYV6\|RRN3_HUMAN | 257 | 266 | NASRQGIEDA | 584 |
| sp\|Q8WZ42\|TITIN_HUMAN | 21672 | 21681 | NFRISAINDA | 585 |
| sp\|Q96A65\|EXOC4_HUMAN | 818 | 827 | NKDISAIEEA | 586 |
| sp\|O95359\|TACC2_HUMAN | 991 | 1000 | NKSQQALADA | 587 |
| sp\|O43895\|XPP2_HUMAN | 201 | 210 | NQPIYALQEA | 588 |
| sp\|O14647\|CHD2_HUMAN | 1179 | 1188 | NSCVSAMQEY | 589 |
| sp\|P53597\|SUCA_HUMAN | 123 | 132 | PFAAAAINEA | 590 |
| sp\|Q96EP1\|CHFR_HUMAN | 451 | 460 | PGAPQALGDA | 591 |
| sp\|O15067\|PUR4_HUMAN | 775 | 784 | PGEGAALADA | 592 |
| sp\|Q5M9Q1\|NKAPL_HUMAN | 302 | 311 | PGEGAAMAEY | 593 |
| sp\|Q8N5F7\|NKAP_HUMAN | 315 | 324 | PGEGAAMAEY | 593 |
| sp\|Q9H0D2\|ZN541_HUMAN | 462 | 471 | PGPGGGLEDA | 594 |
| sp\|Q9HBR0\|S38AA_HUMAN | 561 | 570 | PGQAQALEEA | 595 |
| sp\|Q01955\|CO4A3_HUMAN | 1203 | 1212 | PGRKGAMGDA | 596 |
| sp\|Q9Y4K3\|TRAF6_HUMAN | 71 | 80 | PICLMALREA | 597 |
| sp\|Q5VWJ9\|SNX30_HUMAN | 239 | 248 | PLEFAAIGDY | 598 |
| sp\|Q63HN8\|RN213_HUMAN | 173 | 182 | PLQAQALGEA | 599 |
| sp\|P0C2L3\|F163B_HUMAN | 146 | 155 | PNRLSAMREA | 600 |
| sp\|Q9NSE4\|SYIM_HUMAN | 247 | 256 | PSSRTALAEA | 601 |
| sp\|Q9H7M6\|ZSWM4_HUMAN | 242 | 251 | PTAGAGIEDA | 602 |
| sp\|O00159\|MYO1C_HUMAN | 834 | 843 | PTPPP ALREA | 603 |
| sp\|Q9P1Y6\|PHRF1_HUMAN | 1217 | 1226 | PTRLPALGEA | 604 |
| sp\|Q96RL7\|VP13A_HUMAN | 1176 | 1185 | QAAKQALAEA | 605 |
| sp\|Q9Y623\|MYH4_HUMAN | 896 | 905 | QAEADALADA | 606 |
| sp\|Q8TF72\|SHRM3_HUMAN | 1080 | 1089 | QFQQSALADY | 607 |
| sp\|Q8N205\|SYNE4_HUMAN | 282 | 291 | QGRGQGLEEA | 608 |
| sp\|Q6ZR54\|YN009_HUMAN | 171 | 180 | QGSLAALGEA | 609 |
| sp\|Q8N7Z5\|ANR31_HUMAN | 1252 | 1261 | QKQKSALDEA | 610 |
| sp\|Q4G0P3\|HYDIN_HUMAN | 2481 | 2490 | QLPPAGMEEA | 611 |
| sp\|O95479\|G6PE_HUMAN | 127 | 136 | QLQHAGLREA | 612 |
| sp\|Q6WRI0\|IGS10_HUMAN | 697 | 706 | QLRTSALMEA | 613 |
| sp\|Q9HAV4\|XPO5_HUMAN | 642 | 651 | QMEKCALMEA | 614 |
| sp\|Q9H254\|SPTN4_HUMAN | 1600 | 1609 | QSAWAGLREA | 615 |

TABLE 16-continued

Human peptides matching the L2 binding motif. Using
a 20% cognate peptide reactivity as a cutoff for
permissive amino acids at each position based on the
results of the peptide library analysis, a decamer
binding motif for L2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|A8K7I4\|CLCA1_HUMAN | 462 | 471 | QVQNNGLIDA | 616 |
| sp\|Q8WZ42\|TITIN_HUMAN | 9235 | 9244 | QVRKAGMNDA | 617 |
| sp\|Q9P225\|DYH2_HUMAN | 83 | 92 | RAALTGLADA | 618 |
| sp\|P57082\|TBX4_HUMAN | 15 | 24 | RAPGPALGEA | 619 |
| sp\|O96024\|B3GT4_HUMAN | 91 | 100 | RASWGGLREA | 620 |
| sp\|Q8IUA7\|ABCA9_HUMAN | 768 | 777 | RCSNQGIEDY | 621 |
| sp\|Q7Z3C6\|ATG9A_HUMAN | 231 | 240 | RFRLPGLGEA | 622 |
| sp\|Q8WUT4\|LRRN4_HUMAN | 184 | 193 | RGAQGGIAEA | 623 |
| sp\|Q8IUL8\|CILP2_HUMAN | 966 | 975 | RGQLYGLRDA | 624 |
| sp\|O43157\|PLXB1_HUMAN | 1513 | 1522 | RKSKQALRDY | 625 |
| sp\|Q5TH69\|BIG3_HUMAN | 1605 | 1614 | RLACCALQDA | 626 |
| sp\|Q9C0G6\|DYH6_HUMAN | 1294 | 1303 | RLCKAAIADY | 627 |
| sp\|Q9Y6D6\|BIG1_HUMAN | 208 | 217 | RMENQALQEA | 628 |
| sp\|P30679\|GNA15_HUMAN | 186 | 195 | RMPTTGINEY | 629 |
| sp\|Q96NK8\|NDF6_HUMAN | 104 | 113 | RNRMHGLNDA | 630 |
| sp\|O75154\|RFIP3_HUMAN | 645 | 654 | RSSSMGLQEY | 631 |
| sp\|Q9HD90\|NDF4_HUMAN | 97 | 106 | RTRMHGLNDA | 632 |
| sp\|Q96RL1\|UIMC1_HUMAN | 650 | 659 | RVPSPGMEEA | 633 |
| sp\|P29992\|GNA11_HUMAN | 183 | 192 | RVPTTGIIEY | 634 |
| sp\|O95837\|GNA14_HUMAN | 179 | 188 | RVPTTGIIEY | 634 |
| sp\|P50148\|GNAQ_HUMAN | 183 | 192 | RVPTTGIIEY | 634 |
| sp\|P84243\|H33_HUMAN | 87 | 96 | SAAIGALQEA | 635 |
| sp\|P0DPK5\|H3X_HUMAN | 87 | 96 | SAAIGALQEA | 635 |
| sp\|P0DPK2\|H3Y_HUMAN | 87 | 96 | SAAIGALQEA | 635 |
| sp\|Q6NXT2\|H3C_HUMAN | 86 | 95 | SAAVGALQEA | 636 |
| sp\|Q96JG9\|ZN469_HUMAN | 3262 | 3271 | SASATALADA | 637 |
| sp\|Q2NKX8\|ERC6L_HUMAN | 922 | 931 | SASHSALQDA | 638 |
| sp\|P54750\|PDE1A_HUMAN | 161 | 170 | SFDVFALNEA | 639 |
| sp\|Q8WXE1\|ATRIP_HUMAN | 369 | 378 | SFSLSALREA | 640 |
| sp\|P39059\|COFA1_HUMAN | 243 | 252 | SGETSGLQEA | 641 |
| sp\|Q9ULT8\|HECD1_HUMAN | 372 | 381 | SKDTD ALIDA | 642 |
| sp\|Q96H22\|CENPN_HUMAN | 308 | 317 | SLAPAGIADA | 643 |
| sp\|Q6ZS7\|RIPR1_HUMAN | 1005 | 1014 | SLRQPGLAEA | 644 |
| sp\|P15172\|MYOD1_HUMAN | 204 | 213 | SNCSDGMMDY | 645 |
| sp\|Q16695\|H31T_HUMAN | 87 | 96 | SSAVMALQEA | 646 |

TABLE 16-continued

Human peptides matching the L2 binding motif. Using
a 20% cognate peptide reactivity as a cutoff for
permissive amino acids at each position based on the
results of the peptide library analysis, a decamer
binding motif for L2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|P68431\|H31_HUMAN | 87 | 96 | SSAVMALQEA | 646 |
| sp\|Q71DI3\|H32_HUMAN | 87 | 96 | SSAVMALQEA | 646 |
| sp\|O95428\|PPN_HUMAN | 391 | 400 | SSDGAGIQEA | 647 |
| sp\|Q96BP3\|PPWD1_HUMAN | 240 | 249 | SSDKSGMIEY | 648 |
| sp\|Q9BR61\|ACBD6_HUMAN | 105 | 114 | SSPSQAMQEY | 649 |
| sp\|O75694\|NU155_HUMAN | 13 | 22 | STSAAALQEA | 650 |
| sp\|O00750\|P3C2B_HUMAN | 225 | 234 | SVDYDGINDA | 651 |
| sp\|Q9HCU0\|CD248_HUMAN | 665 | 674 | TAAPTALGEA | 652 |
| sp\|Q9NSE4\|SYIM_HUMAN | 393 | 402 | TAPAHGMEDY | 653 |
| sp\|P37837\|TALDO_HUMAN | 28 | 37 | TGDFHAIDEY | 654 |
| sp\|O15050\|TRNK1_HUMAN | 1979 | 1988 | TGQLSGIAEA | 655 |
| sp\|Q9H0X9\|OSBL5_HUMAN | 667 | 676 | TQEKFALEEA | 656 |
| sp\|Q58EX7\|PKHG4_HUMAN | 885 | 894 | TQELSALREA | 657 |
| sp\|A6NMB9\|FIGL2_HUMAN | 535 | 544 | TSRPAALDEA | 658 |
| sp\|Q7Z6P3\|RAB44_HUMAN | 133 | 142 | TTSFPALEEA | 659 |
| sp\|Q9BTD8\|RBM42_HUMAN | 253 | 262 | VAAAAGLEEA | 660 |
| sp\|Q6ZVN8\|RGMC_HUMAN | 375 | 384 | VAAQAALEDA | 661 |
| sp\|Q6UXB0\|F131A_HUMAN | 171 | 180 | VAEQFAIAEA | 662 |
| sp\|Q9C026\|TRIM9_HUMAN | 317 | 326 | VAQCDALIDA | 663 |
| sp\|O95450\|ATS2_HUMAN | 158 | 167 | VGDVAGLAEA | 664 |
| sp\|Q99437\|VATO_HUMAN | 158 | 167 | VGSGAALADA | 665 |
| sp\|Q9BXW9\|FACD2_HUMAN | 680 | 689 | VKALYGLEEY | 666 |
| sp\|Q8IVU9\|CBCO1_HUMAN | 59 | 68 | VKQANAIIDY | 667 |
| sp\|Q9UIV8\|SPB13_HUMAN | 299 | 308 | VLAAMGMGDA | 668 |
| sp\|Q13342\|SP140_HUMAN | 248 | 257 | VLESNGMIDA | 669 |
| sp\|Q9BZJ7\|GPR62_HUMAN | 39 | 48 | VLRTPGLRDA | 670 |
| sp\|O94967\|WDR47_HUMAN | 118 | 127 | VQCLHALEEY | 671 |
| sp\|Q9UBC5\|MYO1A_HUMAN | 232 | 241 | VSRVDGMDDA | 672 |
| sp\|Q8NCK7\|MOT11_HUMAN | 282 | 291 | VVAVAAMGDA | 673 |
| sp\|P21399\|ACOC_HUMAN | 94 | 103 | VVDFAAMRDA | 674 |
| sp\|Q9NTG1\|PKDRE_HUMAN | 782 | 791 | WQANQALQEY | 675 |
| sp\|Q9NUU6\|OTULL_HUMAN | 210 | 219 | WTEFNGIRDY | 676 |
| sp\|Q8N239\|KLH34_HUMAN | 405 | 414 | WTEVPAMREA | 678 |

TABLE 16-continued

Human peptides matching the L2 binding motif. Using
a 20% cognate peptide reactivity as a cutoff for
permissive amino acids at each position based on the
results of the peptide library analysis, a decamer
binding motif for L2 was generated. These motifs were
searched in the UniProtKB human protein database using
ScanProsite to identify peptides matching the motif.

| UniProt Accession Number (Entry Name) | Start position | End position | Peptide Sequence | SEQ ID NO |
|---|---|---|---|---|
| sp\|Q9BXL5\|HEMGN_HUMAN | 371 | 380 | YQEIPGLEEY | 679 |
| sp\|Q9Y646\|CBPQ_HUMAN | 213 | 222 | YSPHTGIQEY | 680 |

Evaluation of scDbs in Mouse Models

Figure 65:
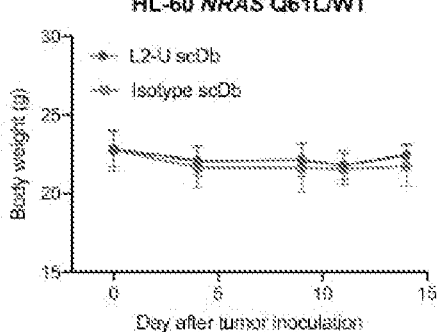
Figure 65:
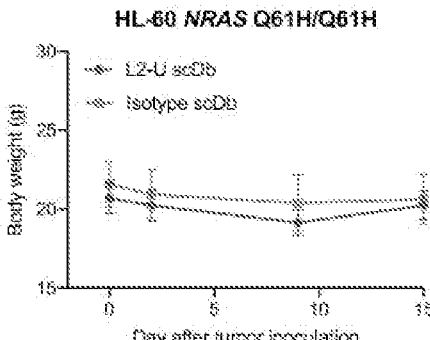

To determine whether the L2-U scDb could control tumor growth in vivo, HL-60 leukemia cells (NRAS Q61L/WT) and human T cells were intravenously injected into NSG mice to establish widespread leukemic infiltrates. As controls, HL-60 cells engineered to harbor Q61H instead of Q61L/WT alleles were used in a separate group of mice. Bioluminescence established tumor uptake, and mice were randomized to receive the L2-U scDb or a control scDb through intraperitoneal 14-day infusion pumps. The L2-U scDb slowed the growth of the Q61L leukemic cells (FIG. 64C), but not the HL-60 Q61H cells (FIG. 64D). Though the tumor growth retardation was significant ($p<0.05$, multiple t-tests with Bonferroni-Dunn correction), the effect size was modest. Therapeutic effects were not assessed at later time points because of the lifetime of the pumps. No substantial changes in body weight were noted in any of the V2-U or L2-U scDb treated mice (FIG. 65).

Together these results demonstrate that highly specific bispecific antibodies can be generated against pHLA complexes resulting from common mutations occurring in cancer cells. The format and configuration of the bispecific antibodies developed here are highly specific and sensitive scDbs against protein products containing mutations occurring in cancer cells.

Materials and Methods

Study Design

The objective of this study was to generate therapeutic agents that target common mutations in RAS genes. This was accomplished by using phage display to identify scFvs specific to MANAs that had been confirmed to be presented via mass spectrometry. These scFvs were grafted into an optimized bispecific antibody format, the scDb. The scDbs were then shown to mediate MANA-specific T cell activation and target cell cytotoxicity in overexpression and endogenous-level expression model systems. All data presented were representative of data collected during this study. All experiments were performed in triplicate with three technical replicates unless otherwise noted. All experiments were performed in a way to minimize confounding variables, such as plate layout effects.

Plasmids

Plasmids encoding KRAS (isoform B), HRAS (isoform 1), and NRAS variants (WT and mutant) and HLA class I alleles A*01:01 and A*03:01 were synthesized and cloned into pcDNA3.1 by GeneArt (Thermo Fisher Scientific, Waltham, MA) or synthesized into gBlocks (IDT, Coralville, Iowa) and assembled into pcDNA3.4 using NEBuilder® HiFi DNA Assembly Cloning Kit (NEB, Ipswich, MA).

Cell Lines and Primary Cells

All cells were grown at 37° C. under 5% C02. HEK293F cells (Thermo Fisher Scientific) were cultured in FreeStyle Expression media. T2A3 cells (a kind gift from Eric Lutz and Elizabeth Jaffee, JHU) were cultured in RPMI-1640 (ATCC, Manassas, VA) with 10% HyClone FBS (GE Healthcare, Chicago, IL), 1% Penicillin-Streptomycin (Thermo Fisher Scientific), 500 µg/mL Geneticin (Thermo Fisher Scientific), and 1× Non-Essential Amino Acids (Thermo Fisher Scientific). COS-7, NCI-H441, CFPAC-1, NCI-H358, and HCT 116 cells (all from ATCC, Manassas, VA) were cultured in McCoy's 5A (Modified) (Thermo Fisher Scientific) with 10% HyClone FBS and 1% Penicillin-Streptomycin. Jurkat (Clone E6-1, ATCC), COLO 741 (Sigma-Aldrich, St. Louis, MO), and SW780 (ATCC) cells were cultured in RPMI-1640 with 10% HyClone FBS and 1% Penicillin-Streptomycin. KMS-21-BM (JCRB Cell Bank, Osaka, Japan) cells were cultured in RPMI-1640 with 20% HyClone FBS and 1% Penicillin-Streptomycin. A-427, Hep G2, Hs 695T, SK-MES-1 (all from ATCC) cells were cultured in Eagle's Minimum Essential Medium (ATCC) with 10% HyClone FBS and 1% Penicillin-Streptomycin. SigM5 (DSMZ) and HL-60 (ATCC) cells were cultured in Iscove's Modified Dulbecco's Medium (ATCC) with 20% HyClone FBS and 1% Penicillin-Streptomycin. RD (ATCC) cells were cultured in Dulbecco's Modified Eagle's Medium (ATCC) with 10% HyClone FBS and 1% Penicillin-Streptomycin. Hs 578T (ATCC) cells were cultured in Dulbecco's Modified Eagle's Medium (ATCC) with 10% HyClone FBS, 1% Penicillin-Streptomycin, and 0.01 mg/ml bovine insulin (Sigma-Aldrich).

Peripheral blood cells were obtained from healthy volunteer donors or purchased as leukapheresis samples (Stem Cell Technologies, Vancouver, BC). PMBCs were purified by density gradient centrifugation with Ficoll Paque Plus (GE Healthcare). T cells were expanded from PBMCs with addition of the anti-human CD3 antibody (clone OKT3, BioLegend, San Diego, CA) at 15 ng/mL, or with Human T-Activator CD3/CD28 Dynabeads (Thermo Fisher Scientific) at a 1:5 bead:cell ratio for three days, after which beads were removed with a magnet and the medium was changed. T cells were cultured in RPMI-1640 with 10% HyClone FBS, 1% Penicillin-Streptomycin, 100 IU/mL recombinant human IL-2 (aldesleukin, Prometheus Therapeutics and Diagnostics, San Diego, CA), and 5 ng/mL recombinant human IL-7 (BioLegend). The culture medium was changed every 3-4 days and cells were maintained at ~1 million cells/mL.

To generate dendritic cells, monocytes were negatively isolated from PBMCs using microbeads (Miltenyi) and cultured in Mo-DC differentiation media (Miltenyi) for 5 days to induce differentiation into immature dendritic cells. To generate mature dendritic cells, immature dendritic cells were cultured with 0.5 mg/mL CD40 ligand oligomer (Enzo) in Mo-DC differentiation media for 2 more days.

Phage Display Library Construction

All cloning was modeled in SnapGene (GSL Biotech LLC, San Diego, CA). Oligonucleotides were synthesized by GeneArt (Thermo Fisher Scientific) using trinucleotide mutagenesis (TRIM) technology. The oligonucleotides were incorporated into the pADL-10b phagemid (Antibody Design Labs, San Diego, CA) (FIG. 66).

Ten ng of the ligation product was mixed on ice with 10 μL of electrocompetent SS320 cells (Lucigen, Middleton, WI) and 14 μL of double-distilled water. This mixture was electroporated (200 ohms, 25 microFarads, 1.8 kV) using a Gene Pulser electroporation system (Bio-Rad, Hercules, CA) and allowed to recover in Recovery Media (Lucigen) for 45 minutes at 37° C. Cells transformed with 60 ng of ligation product were pooled and plated on a 24-cm×24-cm plate containing 2×YT medium supplemented with carbenicillin (100 μg/mL) and 2% glucose. Cells were grown at 37° C. for 6 hours and placed at 4° C. overnight. To determine the transformation efficiency for each series of electroporations, aliquots were titered by serial dilution. Cells grown on plates were scraped into 850 mL of 2×YT medium with carbenicillin (100 μg/mL) plus 2% glucose for a final $OD_{600}$ of 5-15. Two mL of the 850 mL culture were taken and diluted ~1:200 to reach a final $OD_{600}$ of 0.05-0.07. To the remaining culture, 150 mL of sterile glycerol was added before snap freezing to produce glycerol stocks. The diluted bacteria were grown to an $OD_{600}$ of 0.3-0.5, transduced with M13K07 helper phage at an MOI of 4 (Antibody Design Labs) and shaken at 37° C. for 1 hour. The culture was centrifuged and the cells were re-suspended in 2×YT medium with carbenicllin (100 μg/mL), kanamycin (50 μg/mL), and IPTG (50 mM, Thermo Fisher Scientific) and grown overnight at 30° C. for phage production. The following morning, the bacterial culture was aliquoted into 50 mL Falcon tubes and pelleted twice at high speed to obtain clarified supernatant. The phage-laden supernatant was precipitated on ice for 40 minutes with a 20% PEG-8000/2.5 M NaCl solution at a 1:4 ratio of PEG/NaCl:supernatant. After precipitation, phage were centrifuged at 12,000 g for 40 minutes and re-suspended in 1×TBS (25 mM Tris-HCl, 150 mM NaCl, pH 7.5) containing 2 mM EDTA. Phage from multiple tubes were pooled and re-precipitated to achieve a higher concentration. Final phage were re-suspended in 1×TBS, 2 mM EDTA, and 1× Complete Protease Inhibitor Cocktail (Sigma-Aldrich, St. Louis, MO). The total number of transformants obtained was determined to be $3.6×10^{10}$. The library was aliquoted and stored in 15% glycerol at −80° C. and in 50% glycerol at −20° C.

DNA from the library was amplified using the following primers (Forward: CGACGTAAAACGACGGCCAGTNNNNNNNNNNNN NNCGTGCAGAGGATACAGC AGTG (SEQ ID NO:681), Reverse: CACACAGGAAACAGCTATGAC-CATGCTAACGGTAACCAGGGTGCCCTG (SEQ ID NO:682)) which flank the CDR-H3 region. (All oligonucleotide sequences listed in this manuscript begin with the most 5' nucleotide.) The sequences at the 5'-ends of these primers incorporated molecular barcodes to facilitate unambiguous enumeration of distinct phage sequences as well as universal primer sites. The protocols for PCR-amplification and sequencing were described elsewhere (Kinde et al., *Proc Natl Acad Sci USA* 108:9530-9535 (2011)). Sequences were processed and translated using a custom SQL database and both the nucleotide sequences and amino acid translations were assessed.

Peptides and pHLAs

Peptides (Table 11) were synthesized at a purity of >90% by Peptide 2.0 (Chantilly, VA) or ELIM Biopharm (Hayward, CA), with the exception of the crude peptides that were used for the positional scanning library. Peptides were re-suspended in DMF at 10 mg/mL and stored at −80° C. pHLAs were synthesized by refolding recombinant HLA-A*01:01 (HLA-A1) or HLA-A*03:01 (HLA-A3) with peptide and beta-2 microglobulin, purified by gel-filtration, and biotinylated (Fred Hutchinson Immune Monitoring Lab, Seattle, WA; or Baylor MHC Tetramer Production Lab, Houston, TX). These pHLA were confirmed to be folded prior to selection via ELISA using the W6/32 antibody (BioLegend, San Diego, CA), which recognizes only folded HLA. Blast peptides (Table 14) were synthesized as described above, re-suspended in DMF at 10 mg/mL and stored at −80° C. Cognate peptide reactivity search of the UniProtKB human protein database using ScanProsite was performed using binding motifs with a 20% parental peptide IFNγ value as a cutoff. The V2 motif was {FWDY}-[ILMVTC]-{RE}-{ILV}-x-[ILV]-[GNST]-[VP]-[AG]-[HKY] (SEQ ID NO:683). The L2 motif was x-{PWRHDEY}-[APRDEQSC]-{DE}-[AMFPGHDNQSTYC]-[AG]-[ILM]-[AIMGRDENQ]-[DE]-[AY] (SEQ ID NO:684).

Selection of Mutant pHLA-Specific Phage Clones scFv-bearing phage specific to the RAS G12V[7-16] "G12V" pHLA-A3 and RAS Q61H, Q61L, Q61R, referred to collectively as "Q61X", in pHLA-A1 were identified using methods similar to those described elsewhere (Skora et al., *Proc Natl Acad Sci USA* 112:9967-9972 (2015); and Miller et al., *J Biol Chem* 294:19322-19334 (2019)). The phage display library was regrown within a week of starting the selection process. A colony of phage-competent SS320 cells (Lucigen, Middleton, WI) was inoculated in 2×YT medium (Sigma-Aldrich, St. Louis, MO) supplemented with tetracycline (20 μg/mL) and cultured at 37° C. overnight, then grown to 2 L of mid-log phase ($OD_{600}$ of 0.3-0.5) bacteria. Bacteria were transduced with the phage library at an MOI of 0.5 and M13K07 helper phage (Antibody Design Labs, San Diego, CA) at an MOI of 4 along with the addition of 2% (W/V) glucose (Sigma-Aldrich, St. Louis, MO) and shaken, not stirred, for 1 hour at 37° C. The cells were pelleted and re-suspended in 2×YT medium with carbenicillin (100 μg/mL), kanamycin (50 μg/mL), and 50 μM IPTG and subsequently shaken and grown overnight at 30° C. for phage production. The following morning, the bacterial culture was aliquoted into 50 mL Falcon tubes and pelleted twice by centrifugation at 12,000×g to obtain clarified supernatant. The phage-laden supernatant was precipitated on ice for 40 minutes with a 20% PEG-8000/2.5 M NaCl solution at a 1:4 ratio of PEG/NaCl:supernatant. After precipitation, phage were pelleted by centrifugation at 12,000×g for 40 minutes and re-suspended in 1 mL of 1×TBS with 2 mM EDTA, 0.1% sodium azide, and 1× Complete Protease Inhibitor Cocktail (Sigma-Aldrich, St. Louis, MO).

For the G12V pHLA-A3 target MANA, the selection scheme involved an enrichment phase (one round), a competition phase (up to three rounds), and a final selection phase (two rounds). The biotinylated pHLA were incubated with 25 μL of M-280 streptavidin Dynabeads (Invitrogen, Thermo Fisher Scientific) or 100 μL of streptavidin-coated agarose beads (Novagen EMD Millipore, Burlington, MA) per 1 μg of pHLA in blocking buffer (phosphate-buffered saline or PBS, 0.5% BSA, 0.1% sodium azide) for 1 hour at room temperature (RT). After the initial incubation, the complexes were washed and re-suspended in 100 μL of blocking buffer. During the enrichment phase (Round 1), approximately $4 \times 10^{12}$ phage, representing ~100-fold coverage of the library, were negatively selected overnight at 4° C. against 500 μL unconjugated washed Dynabeads, 500 μg free streptavidin protein (RayBiotech, Norcross, GA), and 3 μg heat-denatured, allele-matched HLA conjugated to Dynabeads. This step was designed to remove phage recognizing Dynabeads, streptavidin or denatured HLA-A3. After negative selection, beads were isolated with a DynaMag-2 magnet (Life Technologies, Carlsbad, CA) and the supernatant containing unbound phage was used for positive selection by incubation with 0.5 μg G12V pHLA-A3 conjugated to Dynabeads for 1 hour at RT. The beads were washed 10 times with 1×TBS with 0.5% Tween-20 using the DynaMag-2 magnet, and the phage were eluted from the beads by re-suspension in 1 mL of 0.2 M glycine, pH 2.2. After a 10-minute incubation, the solution was pH-neutralized by the addition of 150 μL of 1 M Tris, pH 9.0. The neutralized solution was used to transduce 10 mL cultures of mid-log-phase SS320s to which M13K07 helper phage (MOI of 4) and 2% glucose was added. Bacteria were then incubated as described above and the phage precipitated the next morning with PEG/NaCl.

During the competitive phase (Rounds 2-4), the amount of input phage used in each round was decreased to 5%, 1%, and 0.1% of the total precipitated phage from the previous round, respectively. These phage were subjected to negative selection against 1 μg heat-denatured HLA-A3, 1 μg total of unrelated pHLA-A3, and 20 μg free streptavidin for 1 hour at RT. After negative selection, beads were isolated with a DynaMag-2 magnet and the unbound phage were used for positive selection. This was accomplished by simultaneously co-incubating phage with 0.5 μg G12V pHLA-A3 conjugated to the magnetic Dynabeads and corresponding 1 μg G12WT pHLA-A3 conjugated to streptavidin-coated agarose beads as competitor. Prior to elution, beads were washed 10 times in 1 mL 1×TBS with 0.5% Tween-20. Phage were eluted from magnetic Dynabeads and used to transduce mid-log phase SS320 cells as described above.

During the final selection phase, phage resulting from rounds 2, 3, and 4 were separately subjected to additional, more stringent rounds of selection. 0.1% of the precipitated phage from these rounds underwent two negative selections against 0.5 μg G12WT pHLA-A3, followed by a positive selection against 0.5 μg of G12V pHLA-A3. The beads were washed 10 times in 1 mL 1×TBS with 0.5% Tween-20, and phage were eluted and used to transduce mid-log phase SS320 cells as described above. The final selection steps described above was repeated a second time, thus the phage underwent a total of four to six total rounds of negative/positive selection.

scFv-bearing phage specific to RAS Q61X-HLA-A1 MANA targets were selected as described above with the following differences. The Q61X pHLA-A1 panning scheme involved one round of enrichment and four rounds of more stringent selection. In the enrichment round, ~2.6× $10^{13}$ phage, representing ~720-fold coverage of the library, were negatively selected against 1 mL unconjugated washed Dynabeads and 1 mg free streptavidin protein. This was followed by positive selection of the unbound phage using 2 μg of the mutant Q61X pHLA-A1. For the four subsequent selection rounds, 10%, 1%, 0.1%, and 0.02% of the phage from the previous round were used as input for panning, respectively. In each of these rounds, phage were negatively selected using 2 μg Q61WT pHLA-A1, 2 μg unrelated pHLA-A1, and $5 \times 10^8$ cells from HLA-A1+ cell lines lacking the RAS mutation of interest. Unbound phage were used for positive selection with 1 μg, 0.5 μg, 0.5 μg, and 0.25 μg Q61X pHLA-A1 in the four sequential rounds, respectively.

To obtain monoclonal phage, individual colonies of SS320 cells transduced with a limiting dilution of phage were inoculated into 200 μL of 2×YT medium containing 100 μg/mL carbenicillin and 2% glucose and grown for 3 hours at 37° C. The cells were then transduced with $1.6 \times 10^7$ M13K07 helper phage and incubated for 1 hour at 37° C. with shaking. The cells were pelleted, re-suspended in 300 μL of 2×YT medium containing carbenicillin (100 μg/mL), kanamycin (50 μg/mL), and 50 μM IPTG, and grown overnight at 30° C. for phage production. Cells were pelleted and the phage-laden supernatant was used for downstream analysis.

PCR and Sanger Sequencing

Monoclonal phage DNA was PCR amplified using 1 μL of monoclonal phage supernatant in a reaction with primers flanking the CDRs (Forward: GGCCATGGCAGATAT-TCAGA (SEQ ID NO:198), Reverse: CCGGGCCTTTAT-CATCATC (SEQ ID NO:199)) and Q5 Hot Start High-Fidelity 2× Master Mix (New England BioLabs). The PCR product was Sanger-sequenced by Genewiz (South Plainfield, NJ). Sequences flanking the CDRs were trimmed using DNA Baser Sequence Assembler v4 (Arges, Romania) and the sequences spanning the CDRs were clustered using the CD-HIT Suite. Colonies containing unique phage clones were selected for further assays.

ELISAs

Streptavidin-coated, 96-well plates (R&D Systems, Minneapolis, MN) were coated with 50 ng of biotinylated pHLA-A3 or pHLA-A1 (unless otherwise specified) or 25 ng of biotinylated recombinant heterodimeric CD3/6ε/δ (Abcam, Cambridge, MA) in 50 μL of blocking buffer (PBS with 0.5% BSA, 2 mM EDTA, and 0.1% sodium azide) at 4° C. overnight. Plates were washed with 1×TBST (1×TBS+ 0.05% Tween-20) using a BioTek 405 TS plate washer (BioTek, Winooski, VT).

The phage clones resulting from the RAS G12V pHLA-A3 panning were characterized via monoclonal ELISA, where individual monoclonal phage clones were separately interrogated for their binding to G12V pHLA-A3 and G12WT pHLA-A3 via ELISA. 50 μL of phage supernatant was added to washed streptavidin ELISA plates coated with either G12V or G12WT pHLA-A3. Plates were incubated for 2 hours at RT and then washed 6 times. The bound phage were then incubated with 50 μL of rabbit anti-fd/M13 bacteriophage antibody (Novus Biologicals, Abingdon, UK) diluted 1:3000 in 1×TBST for 1 hour at RT, followed by washing and incubation with 50 μL of goat anti-rabbit HRP (Thermo Fisher Scientific) diluted 1:10,000 in 1×TBST for 1 hour at RT. After washing, 50 μL of 3,3',5,5'-tetramethylbenzidine (TMB) substrate (BioLegend) was added to each well and the reaction was quenched with 1 N sulfuric acid (Fisher Scientific, Thermo Fisher Scientific). Absorbance at 450 nm was measured with a Synergy H1 Multi-Mode Reader (BioTek).

ELISA with purified scFvs, scDbs, and other bispecific antibody formats was performed essentially as above, with serial dilutions of the recombinant protein of interest incubated for 1 hour at RT, followed by incubation with 1 μg/mL recombinant protein L (Pierce, Thermo Fisher) for 1 hour at RT, followed by incubation with anti-protein L HRP (Abcam). Plates were washed, exposed, and read as described above. pHLA titration ELISAs assessing the binding of the scFvs (at a fixed concentration) to the mutant and WT pHLA (at varying concentrations) were performed by AxioMx Inc (Abcam).

Sandwich ELISAs were performed by coating biotinylated pHLA-A3 on a streptavidin plate and incubating with scDbs as described above, followed by incubation with recombinant heterodimeric CD3ε/δ protein containing a human Fc domain at 1 µg/mL for 1 hour at RT, followed by detection with anti-human Fc HRP (Abcam) at 1:10,000 for 1 hour at RT. Plates were washed, exposed, and read as described above.

Flow Cytometry

For peptide pulsing of cells, cells were washed once with PBS and once with RPMI-1640 containing 1% Penicillin-Streptomycin without serum. The cells were then incubated at $5\times10^5$-$1\times10^6$ cells per mL in serum-free RPMI-1640 containing 50 µg/mL or specified concentration of peptide and 10 µg/mL human beta-2 microglobulin (ProSpec, East Brunswick, NJ) for 4 hours at 37° C. Prior to staining, cells were spun and re-suspended in cold stain buffer (PBS containing 0.5% BSA, 2 mM EDTA, and 0.1% sodium azide).

The phage clones resulting from the RAS Q61X pHLA-A1 selection were characterized via flow cytometry, where individual monoclonal phage clones were separately interrogated for their binding to mutant Q61X and Q61WT peptide-pulsed SigM5 cells. Monoclonal phage were grown and sequenced as described above. Phage supernatant from representative wells of each unique clone was selected for flow cytometry analysis. In each well of a deep 96-well 2 mL plate, 50 µL of monoclonal phage was incubated with $2.5\times10^5$ peptide-pulsed SigM5 cells in 50 µL of stain buffer. Plates were incubated on ice for 1 hour, followed by washing with 1 mL of stain buffer. Cells were then stained with 1 µg of rabbit anti-M13 antibody (Novus Biologicals), washed, stained with anti-rabbit-PE (BioLegend), incubated with an additional 100 µL of LIVE/DEAD Fixable Near-IR dye diluted 1:1000 in PBS for 10 minutes at RT in the dark, followed by washing in stain buffer before analysis. Stained cells were analyzed using an Intellicyt iQue3 flow cytometer (Sartorius, Gottingen, Germany).

Peptide-pulsed T2A3 phage staining assays were performed by incubating $5\times10^5$-$1\times10^6$ cells with $1\times10^{10}$ phage in 100 µL stain buffer on ice for 1 hour, followed by one wash in stain buffer. Cells were then stained with 1 µg of rabbit anti-M13 antibody (Novus Biologicals), washed, stained with anti-rabbit-PE (BioLegend), incubated with an additional 500 µL of LIVE/DEAD Fixable Near-IR dye diluted 1:1000 in PBS for 10 minutes at RT in the dark, and washed in stain buffer before analysis. V2 scFv staining was performed using 0.33 µg of V2 scFv premixed with 1 µg anti-FLAG-PE antibody (BioLegend) overnight at 4° C. followed by incubation with peptide-pulsed T2A3 cells as described above. Anti-HLA-A3 staining was performed by staining $5\times10^5$ cells with 0.125 µg clone GAP.A3-PE (eBioscience, Thermo Fisher Scientific) or mouse isotype IgG2a-PE (BioLegend). Anti-HLA-A1 staining was performed by staining $5\times10^5$ cells with 0.5 µg anti-HLA-A1/A11/A26 antibody clone 8.L.101 (Abcam) or mouse isotype IgM (Thermo Fisher) followed by 0.25 µg anti-mouse-PE (BioLegend). Stained cells were analyzed using an LSRII flow cytometer (Becton Dickinson, Mansfield, MA).

Quantification of cell surface-bound G12V peptide was performed using two commercial kits: PE Quantibrite Beads (BD, Franklin Lakes, NJ) and QIFIKIT (Agilent, Santa Clara, CA). For Quantibrite-based quantification, peptide-pulsed T2A3s were stained with 0.5 µg V2 scFv preconjugated to 1.5 µg clone L5 anti-FLAG-PE (BioLegend), followed by flow cytometry and quantification according to the manufacturer's instructions. For QIFIKIT-based quantification, peptide-pulsed T2A3s were stained with 0.5 µg V2 scFv preconjugated to 1.5 µg clone M2 anti-FLAG (Sigma Aldrich), followed by staining with anti-mouse-PE (BioLegend), flow cytometry and quantification according to the manufacturer's instructions.

Recombinant scFv and Bispecific Antibody Production

Recombinant scFv proteins were produced and purified by AxioMx Inc (Abcam). In brief, the V2, H1, L2, and R6 scFv sequences were subcloned into a vector containing a periplasmic localization sequence, and C-terminal Flag and His tags. ScFvs were expressed in *E. coli* and purified via nickel chromatography.

Bispecific antibodies were produced after subcloning gBlocks (IDT, Coralville, IA) encoding each of the variants with an IL-2 signal sequence and C-terminal 6×HIS tag into the pcDNA3.4 vector (Thermo Fisher Scientific). Bispecific antibodies were produced by the Eukaryotic Tissue Culture Core Facility of Johns Hopkins University. In brief, 1 mg of plasmid was transfected using polyethylenimine (PEI) into HEK293F cells which were then grown as suspension culture at a density of $2\times10^6$ cells/mL in FreeStyle 293 expression media (Thermo Fisher Scientific) at 37° C., 170 rpm, and 5% C02. Protein was expressed for 5 days, after which cells were harvested by centrifugation, and the resulting supernatant filtered using a 0.22 µm filter. To each 1 L of supernatant, 2 mL of Ni-NTA His-Bind (Millipore Sigma) resin slurry was added and allowed to incubate at 4° C. overnight on an orbital shaker. The supernatant containing the slurry was passed through a centrifuge column (Pierce, Thermo Fisher Scientific), whereby the slurry was washed with 20 mM imidazole in PBS, and eluted in 50 mM, 100 mM, and 250 mM imidazole fractions. Protein fractions were run on mini-PROTEAN TGX stain-free gels (Bio-Rad, Hercules, California) and appropriate fractions were combined for desalting into PBS, pH 7.4 or 20 mM Tris, 150 mM NaCl, pH 9 using 7 k MWCO Zeba Spin desalting columns (Thermo Fisher Scientific). Proteins were quantified via stain free gel and BCA protein assay (Pierce, Thermo Fisher Scientific). For scDb western blots, protein was transferred from the stain-free gel to a Trans-Blot Turbo Mini 0.2 µm PVDF membrane (Bio-Rad) using the Trans-Blot Turbo Transfer System (Bio-Rad). Membrane was blocked with blocking buffer (5% Bio-Rad Blotting-Grade Blocker in 1×TBST) on an orbital shaker (VWR) for 1 hour at RT, followed by incubation with anti-6×His tag antibody clone ab9108 at 1:1000 in blocking buffer at 4° C. overnight, washing in 1×TBST, and incubation with anti-rabbit-HRP (Thermo Fisher Scientific) at 1:10,000 in blocking buffer for 1 hour at RT. Membrane was washed in 1×TBST followed by ddH$_2$O, then imaged using SuperSignal West Pico PLUS Chemiluminescent Substrate (Thermo Fisher Scientific) on a ChemiDoc XRS+ imager (Bio-Rad). Proteins were stored at 4° C. for short term storage or snap frozen with the addition of 7% glycerol and stored at −80° C. for long term storage. Alternatively, the V2-U scDb and L2-U scDb proteins were produced by GeneArt in Expi293s, purified with a HisTrap column followed by size exclusion chromatography using a HiLoad Superdex 200 26/600 column.

SPR

RAS G12V pHLA-A3, G12WT pHLA-A3, and V2 scFv binding experiments were performed at 25° C. using a Biacore T200 SPR instrument (GE Healthcare, Chicago, IL). Approximately 130-140 response units (RU) of biotinylated pHLA-A3 were captured in flow cells (Fc) 2 and 4, respectively, using a streptavidin chip. Single-cycle kinetics were performed by injecting increasing concentrations (1.56, 6.25, 25, 100, 400 nM) of purified V2 scFv flowed over Fc 1-4. Binding responses for kinetic analysis were both blank and reference subtracted. Both binding curves were fit with a 1:1 binding model using Biacore Insight evaluation software. Measurements for L2-U scDb were done similarly, using biotinylated Q61L pHLA-A1 and Q61WT pHLA-A1.

pHLA Immunoprecipitation and Mass Spectrometry pHLA immunoprecipitation and mass spectrometry were performed as described elsewhere (Wang et al., *Cancer Immunol Res* 7:1748-1754 (2019)). Briefly, COS-7 cells seeded into 24.5×24.5 cm$^2$ plates were transfected at 95% confluency using Lipofectamine 3000 Reagent (Thermo Fisher Scientific). For each plate, 125 µg of plasmids (50 µg of HLA plasmid and 75 µg of mutant or WT protein plasmid) were mixed with 200 µL of Lipofectamine P3000 in 6 mL of Opti-MEM (Thermo Fisher Scientific). In a separate tube, 200 µL of Lipofectamine 3000 Reagent was mixed with 6 mL of Opti-MEM. The contents of the two tubes were mixed and allowed to complex for 10 minutes. Medium bathing cells were removed and 50 mL of fresh complete medium was added followed by the Lipofectamine-DNA mixture. Cells were harvested 48 hours post-transfection. The transfection efficiency of COS-7 was >90% as assessed by GFP+ cell fraction on flow cytometry (BD LSRII).

Cells (transfected or untransfected) were grown to near confluency in 24.5×24.5 cm$^2$ plates. Cultured cells were washed with PBS two times, followed by another wash with PBS pre-chilled at 4° C. containing 1× protease inhibitor. Cells were scraped and collected in a 500-mL centrifuge bottle. The bottle was centrifuged at 1,000 g for 5 minutes and the supernatant discarded. Cell pellets were snap frozen in liquid nitrogen and stored at –80° C. for future experiments.

Neoantigen-expressing cells were processed as described elsewhere (Wang et al., *Cancer Immunol Res* 7:1748-1754 (2019)). In brief, a total of 500 million cells were lysed and pHLA complexes were immunoprecipitated using Protein G Dynal Magnetic Beads (Thermo Fisher Scientific) pre-conjugated with anti-human HLA-A, B, C antibody clone W6/32 (Bio-X-Cell). After elution, dissociation, and filtration, peptides were lyophilized before further analysis. HPLC fractionation and a Dual-Reduction procedure were then performed (Wang et al., *Cancer Immunol Res* 7:1748-1754 (2019)). Controls for detection of the RAS G12V [7-16] and [8-16] peptides were established using AQUA™ heavy isotope labeled peptides of the same sequence (Sigma-Aldrich). These AQUA peptides were added to the cell lysates in every experiment. Transition parameters were manually examined and curated to exclude ions with excessive noise due to co-elution with impurities. Absolute copy numbers of peptides presented on the cell surface were calculated based on the MANA-SRM quantification using the AQUA™ heavy isotope labeled peptides and the recovery ratios of the pipeline, as described elsewhere (Wang et al., *Cancer Immunol Res* 7:1748-1754 (2019)).

CRISPR on Cell Lines

The Alt-R CRISPR system (Integrated DNA Technologies, IDT) was used to modify the HLA alleles, the KRAS mutation status of the NCI-H358 and NCI-H441 cell lines, and the NRAS mutation status of the HL-60 cell line. Alt-R® CRISPR Cas9 crRNAs (IDT) and Alt-R® CRISPR- Cas9 tracrRNA (IDT) were re-suspended at 100 µM with Nuclease-Free Duplex Buffer (IDT). The crRNAs and tracrRNA were mixed at a 1:1 molar ratio and denatured for 5 minutes at 95° C., followed by slow cooling to room temperature to duplex prior to mixing with Cas9 Nuclease (IDT) at a 1.2:1 molar ratio for 15 minutes. To knock out the HLA-A3 allele in NCI-H441 cells, 40 pmoles of the Cas9 ribonucleoprotein (RNP) containing tracrRNA/HLA-A crRNA (GCTGCGACGTGGGGTCGGAC; SEQ ID NO:685) duplex were mixed with 2×10$^5$ NCI-H441 cells in 20 µL of OptiMEM. This mixture was loaded into a 0.1 cm cuvette (Bio Rad) and electroporated at 150 V for 10 ms using an ECM 2001 (BTX). HLA-A1 was similarly knocked out in HL-60 cells by mixing Cas9 RNP containing tracrRNA/HLA-A1 crRNA (CA-GACTGACCGAGCGAACCTG; SEQ ID NO:686) duplex with 5×10$^5$ HL-60 cells, and electroporated at 120V for 16 ms. Cells were immediately transferred to complete growth medium and cultured for 10 days.

To change ("KI") the KRAS mutation status of NCI-H358 from G12C/WT to G12V and NCI-H441 from G12V/WT to G13D/WT, Cas9 RNPs were co-electroporated with single-strand DNA homology directed repair templates. The G12V repair template was ATTAGCTGTATCGT-CAAGGCACTCTTGCCTACGC-CAACGGCGCCGACAACGACG AGTTTATATTCAGT-CATTTTCAGCAGGCCTTATAA (SEQ ID NO:687) for KRAS-G12V crRNA (AATGACTGAATATAAACTTG; SEQ ID NO:688). The G13D repair template was AACAA-GATTTACCTCTATTGTTGGATCATATTCGTC-CACAAAATGATTCTGAATT AGCTGTATCGT-CAAGGCACTCTTGCCTACGTCACCAGCTCCAACTAC-CACAAGTT TATATTCAGTCATTTTC (SEQ ID NO:689) for KRAS-G13D-1 crRNA (CTTGTGGTAGTTG-GAGCTGT; SEQ ID NO:690). Both repair templates were obtained as Ultramer® Oligos from IDT. To improve rates of homology directed repair, NCI-H441 cells were pre-treated with 200 ng/mL of nocodazole (Sigma Aldrich) and 1 µM of SCR7 pyrazine (Sigma Aldrich) for 17 hours prior to electroporation. The electroporation mixture contained 40 pmoles of Cas9 RNP, 20 pmoles of repair template, and 2×10$^5$ cells in 20 µL of OptiMEM. NCI-H441 cells were electroporated at 150 V for 10 ms, while NCI-H358 cells were electroporated at 120 V for 16 ms. Both cell types were transferred to complete growth media containing 1 µM SCR7 for 72 hours following electroporation. Cells were grown in culture for 5 to 10 more days before use.

The NRAS mutation status in HL-60 was modified similarly. 5×10$^5$ HL-60 cells were co-electroporated at 120 V for 16 ms with Cas9 RNPs containing tracrRNA/NRAS crRNA (CCTCATGTATTGGTCTCTCATGG; SEQ ID NO:691) duplex and either the repair template for Q61H (AAACCTGTTTGTTGGACATACTGGATA-CAGCTGGACATGAGGAATATTCTGCAA TGAGA-GACCAATACATGAGGACAGGCGAAGGCTTCCT; SEQ ID NO:692) or Q61R (AAACCTGTTTGTTGGACAT-ACTGGATACAGCTGGAAGAGAGGAATATTCTGCAA TGAGAGACCAATACAT-GAGGACAGGCGAAGGCTTCCT; SEQ ID NO:693).

HLA-A and RAS modified polyclonal pools were plated at a density of 0.5 to 2 cells per well in 96 well plates and cultured for 3 weeks. Single colonies were transferred into 2 or 3 replica 96-well plates. For HLA-A modified NCI-H441 cells, two replica plates were used. One plate was used to stain cells with the HLA-A3 specific antibody GAP.A3-PE and the other with anti-HLA-A2 specific antibody BB7.2-PE (BioLegend). Comparison of the staining allowed identification of clones with only the HLA-A3 allele knocked out, as NCI-H441 normally expresses both HLA-A2 and HLA-A3. HL-60 cells were stained with anti-HLA-A1 (clone 8.L.101) to select clones with HLA-A1 knocked out. For the RAS modified cells, genomic DNA was harvested from one of the plates using the Quick-DNA™ 96 Kit (Zymo Research), PCR amplified using Q5@ Hot Start High-Fidelity 2× Master Mix (New England BioLabs), and Sanger sequenced to identify clones with the desired RAS mutation status. Targeted next generation sequencing was performed to confirm the mutation status of selected clones.

Co-Cultures

COS-7 cells were plated in a T25 flask and transfected at 70% confluency. For each flask, 10 μg of plasmid DNA (1:1 ratio of HLA plasmid:RAS plasmid, or control plasmid DNA, was mixed with 20 μL of P3000 Reagent in 250 μL of Opti-MEM (Thermo Fisher Scientific). In a separate tube, 20 μL of Lipofectamine 3000 Reagent was mixed with 250 μL of Opti-MEM. The contents of the two tubes were mixed and allowed to complex for 10 minutes at room temperature. Existing medium on pre-plated COS-7 cells was removed and fresh medium was added followed by the Lipofectamine-DNA mixture. Cells were harvested 24 hour post-transfection for co-culture after washing once with PBS, adding 1 mL 0.05% trypsin (Thermo Fisher Scientific) and incubation at 37° C. for 5-10 minutes. Trypsin was quenched with serum-containing media and cells were counted. The co-culture was set up in 96-well flat-bottom tissue culture treated plates. To each well, the following components were combined: 50 μL of antibody diluted to the desired concentration in complete RPMI-1640 with a final IL-2 concentration of 100 IU/mL, $1\times10^4$ COS-7s in 100 μL complete RPMI-1640, $5\times10^4$ human T cells in 50 μL complete RPMI-1640. The co-cultures were incubated for 24 hours at 37° C. The resultant supernatant was assayed for cytokines using a Human IFNγ Quantikine and Human TNFα Quantikine ELISA Kits (both R&D Systems Bio-techne, Minneapolis, MN) according to the manufacturer's instructions.

For co-cultures with pulsed cells, cells were peptide-pulsed in a 96-well plate by combining the specified number of target cells in 50 μL of serum-free RPMI-1640 media (for T2A3, SigM5, Hs 695T) or serum-containing RPMI-1640 media (for PBMCs, monocytes, iDCs, mDCs) with 50 μL of serially diluted peptide in serum-free RPMI-1640 media. Cells were incubated for 4 hours at 37° C., after which $5\times10^4$ human T cells and antibodies were added in an additional 100 μL of serum-containing RPMI-1640 medium, with a final IL-2 concentration of 100 IU/mL. The co-cultures were incubated for 24 hours at 37° C., the cells pelleted by centrifugation at 500 g, and the cell-free supernatant was assayed for cytokines as described above. Cell viability was assayed by CellTiter-Glo Luminescent Cell Viability Assay (Promega, Madison, WI) according to the manufacturer's instructions. Cytotoxicity was calculated by taking the luciferase signal of a given well, subtracting the luciferase signal of the T cell only wells, and normalizing to the luciferase signal of the wells without scDb.

Co-cultures with other target cell lines were set up similarly, with target cells and human T cells combined as specified in the figure legends. For Luminex assays, IFNγ, IL-2, TNFα, granzyme B, and perforin were measured using MILLIPLEX panels (MilliporeSigma, Burlington, MA).

Western Blots

COS-7 cells were transfected as above and harvested after 24 hours. Cells were pelleted, snap frozen, and re-suspended in radioimmunoprecipitation assay (RIPA) buffer (Thermo Fisher Scientific). 25 μg of cell lysate or approximately 0.5-1.5 μg of recombinant protein was run on mini-PRO-TEAN TGX stain-free gels (Bio-Rad, Hercules, California). Protein was transferred from the stain-free gel to a Trans-Blot Turbo Mini 0.2 μm PVDF membrane (Bio-Rad) using the Trans-Blot Turbo Transfer System (Bio-Rad). Membrane was blocked with blocking buffer (5% Bio-Rad Blotting-Grade Blocker Bio-Rad in 1×TBST) on an orbital shaker (VWR) for 1 hour at RT. All antibody incubations were also performed using this blocking buffer. All incubations with primary antibodies were done at 4° C. overnight (except for β-Actin as noted below). All incubations with secondary antibodies were done for 1 hour at RT. All washes were performed with 1×TBST. KRAS was detected with mouse monoclonal antibody (mAb) F234 (Santa Cruz Biotechnology, Dallas, TX, at 1:500), followed by anti-mouse-HRP (Thermo Fisher Scientific, at 1:10 k). HLA-A3 was detected with mouse mAb 7g7h8 (Abcam, at 1:500), followed by anti-mouse-HRP (Thermo Fisher Scientific, at 1:10 k). Rab-7b was detected with rabbit anti-Rab7b mAb ab193360 (Abcam, at 1:500), followed by anti-rabbit-HRP (Thermo Fisher Scientific, at 1:10 k). β-Actin was detected with rabbit mAb 13E5 conjugated to HRP (Cell Signaling Technology, Danvers, MA, at 1:3000) for 1 hour at RT. Recombinant proteins with 6×HIS tags were detected with anti-6× HIS tag rabbit polyclonal antibody ab9108 (Abcam, 1:1000), followed by anti-rabbit-HRP (Thermo Fisher Scientific, at 1:10 k). Prior to imaging, the membranes were washed with ddH$_2$O, then imaged using SuperSignal West Pico PLUS Chemiluminescent Substrate (Thermo Fisher Scientific) on a ChemiDoc XRS+ imager (Bio-Rad).

Viral Transduction of Cell Lines

To generate luciferase-expressing NCI-H358 and HL-60 cell lines for in vivo experiments, NCI-H358 and HL-60 cells were transduced with RediFect Red-Fluc-GFP lentiviral particles (Perkin Elmer, Waltham, MA). Non-tissue culture-treated 48-well plates were coated with 250 μL of 20 μg/mL RetroNectin (Clontech) per well for 2 hours at RT, then blocked with 10% FBS for 1 hour at RT. Viral particles and $2\times10^5$ target cells were added to each well in a total volume of 275 μL of cell culture media and subjected to centrifugation at 1200×g for 1 hour at 20° C. Cell culture volumes were brought up to 500 μL with complete media. Cells were then incubated at 37° C. for 3 days before exchanging media. Transduced cells were sorted based on the presence of GFP using FACSAria Fusion (BD Biosciences) 18 days after transduction.

Mouse Xenograft Model

Female NOD.Cg-Prkdc$^{scid}$Il2rg$^{tmlWjl}$/SzJ (NSG) mice at 6-10 weeks were acquired from the Johns Hopkins Sidney Kimmel Comprehensive Cancer Center Animal Resources Core and treated in compliance with a research protocol approved by the Johns Hopkins University Animal Care and Use Committee. Mice were maintained on an irradiated Uniprim rodent diet (Envigo, Indianapolis, IN). Littermate controls were used for all experiments.

For the NCI-H358 intrasplenic model, $5\times10^5$ luciferase-expressing NCI-H358 cells (CRISPR KRAS G12V-KI clone 1) or isogenic parental NCI-H358 clone (KRAS G12C/WT) were inoculated into mouse spleens on day zero using sterile surgical techniques. Intraoperatively, two-week micro-osmotic pumps (model 1002, ALZET, Cupertino, CA) filled with V2-U scDb or isotype control (L2-U scDb) were placed intraperitoneally. Successful tumor inoculation was ensured by bioluminescence imaging one day later, followed by intravenous injection of $1\times10^7$ human T cells via lateral tail vein. Bioluminescent imaging (IVIS imaging system) was performed using RediJect D-luciferin Ultra (Perkin Elmer)

according to the manufacturer's instructions (Perkin Elmer). Image analysis was performed using Living Image software. Individual luminescence measurements were normalized to the average fluorescence of the injection marker dye ($745^{ex}$/$800^{em}$) in the thoracic region.

For the HL-60 leukemia cell model, mice were inoculated intravenously with $1 \times 10^7$ human T cells and $5 \times 10^5$ luciferase-expressing parental HL-60 (NRAS WT/Q61L) or isogenic control HL-60 (NRAS Q61H/Q61H) via lateral tail vein injection. On day 1, mice were randomized based on luminescence to ensure similar pretreatment tumor burden. Two-week micro-osmotic pumps filled with L2-U scDb or isotype control scDb (V2-U scDb) that had been primed in 1 mL PBS overnight at 37° C. were then placed intraperitoneally using sterile surgical techniques. Tumor growth was serially monitored by bioluminescent imaging.

Statistics

Statistical analyses were performed with Prism 8 (GraphPad Software, La Jolla, CA). Unless otherwise indicated, error bars represent the standard deviation of three technical replicates that were independently assembled. Error bars smaller than the symbols used to represent the mean of these replicates are not shown. Percent cytotoxicity of target cells for in vitro experiments was calculated as described above. For in vivo experiments, statistical significance was performed with an unpaired, two-tailed t-test with Bonferroni-Dunn correction for multiple comparisons.

Example 4: Targeting a Neoantigen Derived from a Common TP53 Mutation

This Example describes an immunotherapeutic agent that targets a common TP53 mutation. Results from Example 2 were reanalyzed with additional samples and included in the following.

Results

The $p53^{R175H}$ Neoantigen is Presented on the Surface of Cancer Cells

The $p53^{R175H}$ (aa 168-176, HMTEVVRHC; SEQ ID NO:1) and $p53^{WT}$(HMTEVVRRC; SEQ ID NO:135) peptides were predicted on the NetMHCpan 4.0 server to bind HLA-A*02:01 at 5177.6 nM (rank 9.7%) and 7121.5 nM (11.6%), respectively. To provide experimental evidence of, and to quantify such presentation, peptides eluted from HLA molecules were analyzed in four different cell culture systems using a mass spectrometry (MS)-based method. First, the human HLA-A*02:01 and either full-length $p53^{R175H}$ or $p53^{WT}$ were co-expressed in monkey COS-7 cells. MS analysis of the peptides immunopurified with an anti-HLA antibody detected the $p53^{R175H}$ peptide at approximately 700 copies per cell (FIG. 73A, Table 17). Though relatively abundant amounts of the $p53^{R175H}$ peptide were detected in pHLA complexes, the $p53^{WT}$ peptide was not observed in pHLA complexes in transfected cells, despite equivalent amounts of $p53^{WT}$ and $p53^{R175H}$ total protein expression as assessed by Western blotting (FIG. 73B). Second, MS analysis was performed on three human cancer cell lines, KMS26, TYK-nu, and KLE, all of which harbor the $p53^{R175H}$ mutation and carry an HLA-A*02:01 allele. The $p53^{R175H}$ peptide was detected on all three cell lines, and at much lower levels than in the COS-7 cells in which the mutant TP53 and HLA genes were exogenously introduced (FIG. 73C, Table 17). Based on comparisons with heavy isotope labeled controls, it was estimated that there were 2.4, 1.3, and 1.5 copies of cell-surface $p53^{R175H}$/HLA-A*02:01 complexes on the cell surfaces of KMS26, TYK-nu, and KLE cell lines, respectively (Table 17).

TABLE 17

Quantitative assessment of the $p53^{R175H}$ neoantigen peptide. The amount of $p53^{R175H}$ neoantigen peptide (HMTEVVRHC) present in COS-7 cells transfected with HLA-A*02:01 and $p53^{R175H}$ or $p53^{WT}$, as well as cells lines that endogenously express HLA-A*02:01 and $p53^{R175H}$, were quantified using mass spectrometry. *Corrected for peptide recovery (all cell lines) and transfection efficiency (COS-7).

| Cell line | HLA and p53 status | No. cells (millions) used for analysis | Abundance (femtomole) | Copy no./ cell* |
|---|---|---|---|---|
| COS-7 | Exogenous HLA-A* 02:01/$p53^{R175H}$ | 375.0 | 32.43 | 703.5 |
| COS-7 | Exogenous HLA-A* 02:01/$p53^{WT}$ | 375.0 | Not detectable | Not detectable |
| KMS26 | Endogenous HLA-A* 02:01/$p53^{R175H}$ | 157.0 | 0.48 | 2.4 |
| KLE | Endogenous HLA-A* 02:01/$p53^{R175H}$ | 92.4 | 0.18 | 1.5 |
| TYK-nu | Endogenous HLA-A* 02:01/$p53^{R175H}$ | 168.3 | 0.28 | 1.3 |

Figure 74:
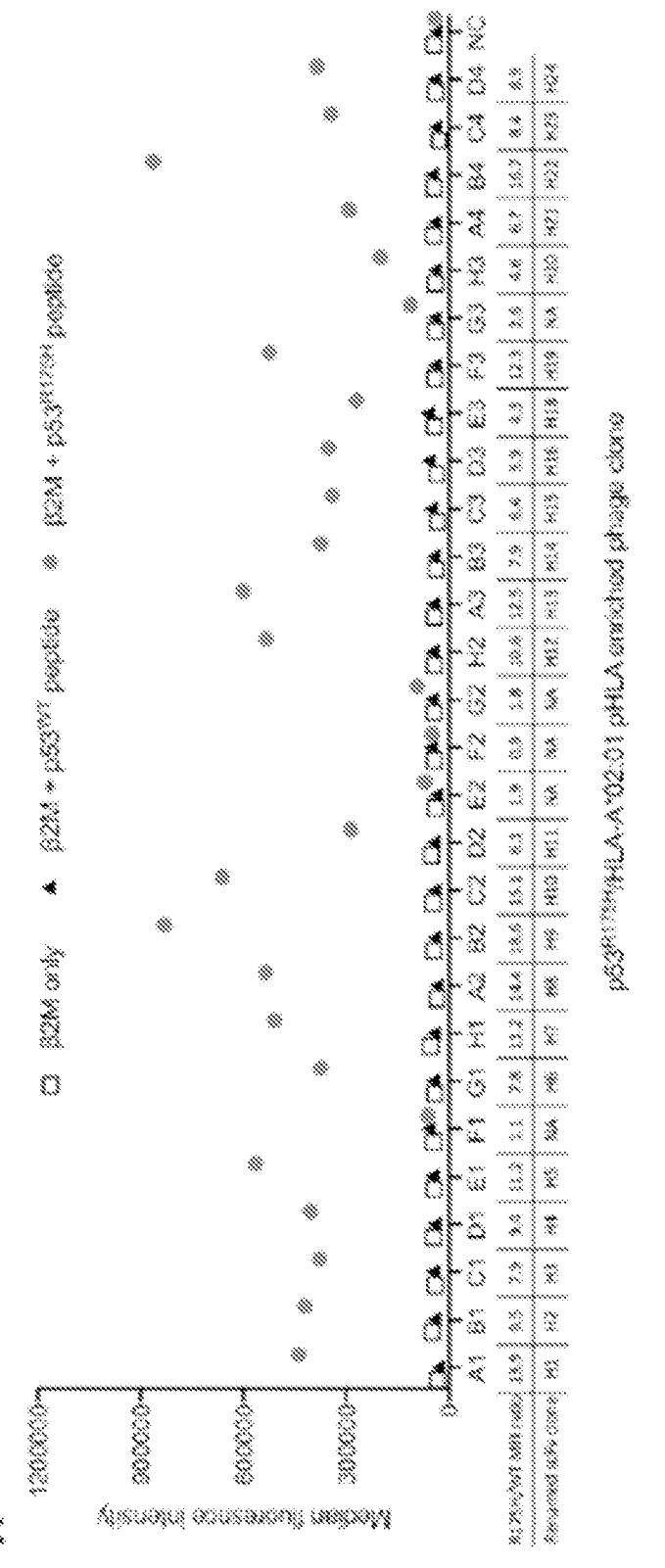
Figure 74:
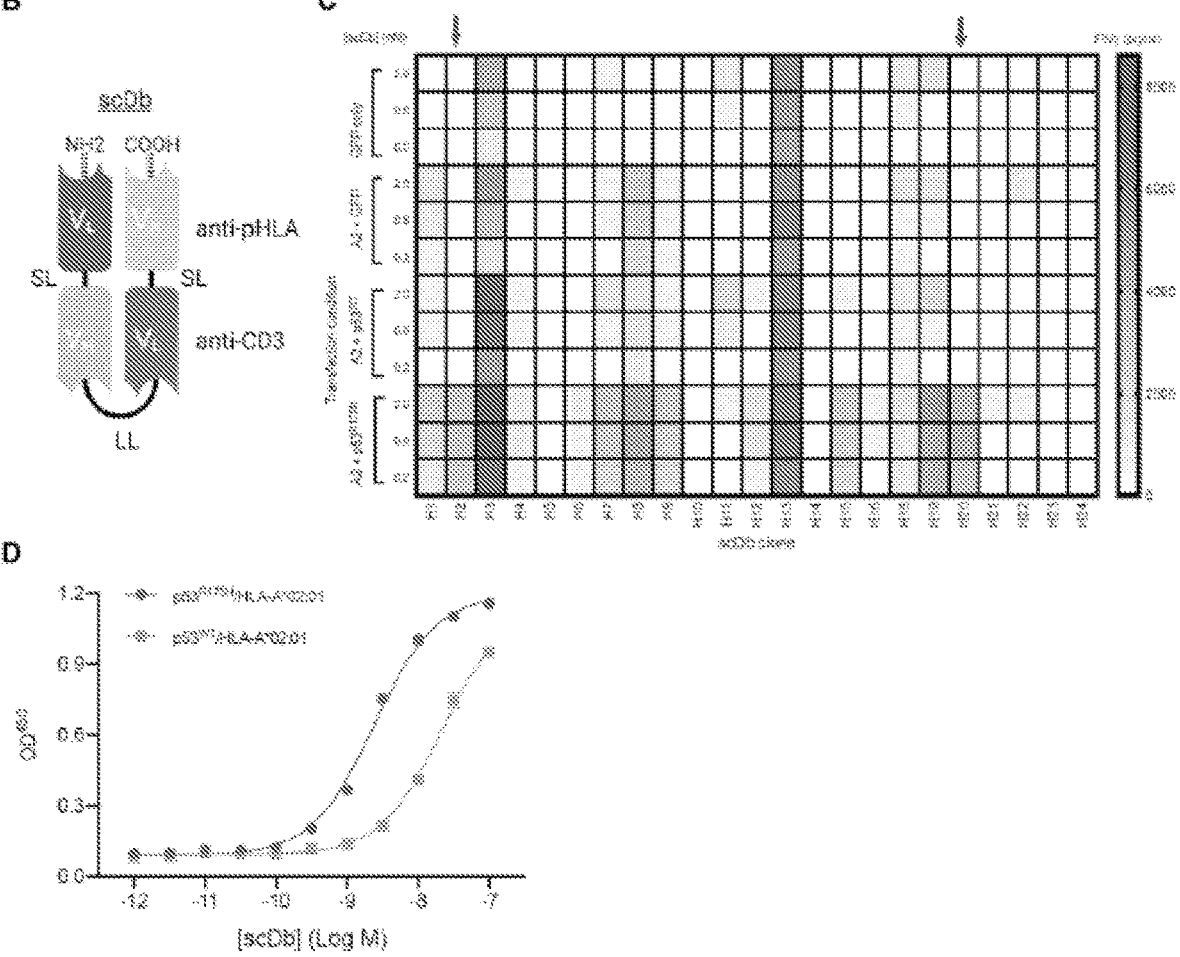

Identification of scFv-Expressing Phage Clones Specific for the HLA-A*02:01-Restricted $p53^{R175H}$ Peptide and Conversion to scDb Format To identify TCRm single-chain variable fragments (scFvs) selectively targeting mutant pHLA complexes, an scFv-displaying phage library was screened with an estimated complexity $>1 \times 10^{10}$. Positive selection against HLA-A*02:01 pHLA monomers containing the $p53^{R175H}$ peptide were combined with negative selection against pHLA monomers containing the $p53^{WT}$ and irrelevant peptides. Selected phage clones were amplified and assessed for binding to T2 cells presenting the mutant or wild-type (WT) peptide via flow cytometry (FIG. 74A).

Twenty-three phage clones with median fluorescence intensity (MFI) ratios of $p53^{R175H}$ to $p53^{WT} > 4$ were then converted to T cell-retargeting bispecific antibodies. This was achieved through linking each individual scFv to an anti-CD3E scFv (UCHT1) in a single-chain diabody (scDb) format (FIG. 74B). The scDb format was chosen after evaluating several previously described bispecific antibody formats, such as bispecific T-cell engager (BiTE), dual-affinity re-targeting antibody (DART), and diabody in pilot experiments assessing protein expression and in vitro T cell activation. The ability of scDbs to activate T cells was assessed by interferon-7 (IFN-7) release after co-incubation with COS-7 cells overexpressing HLA-A*02:01 and either full-length p53R175H or $p53^{WT}$ proteins. Two scDb clones, named H2-scDb and H20-scDb and derived from phage clones H2 and H20, respectively, showed the most potent and specific T-cell activation in the presence of $p53^{R175H}$/HLA-A*02:01 (FIG. 74C, Table 18). The specificity of these scDbs was further evaluated by titration enzyme-linked immunosorbent assay (ELISA). Both H2- and H20-scDb bound to $p53^{R175H}$/HLA-A*02:01 at low concentrations. At high concentrations, H20-scDb also bound to $p53^{WT}$/HLA-A*02:01, while H2-scDb did not bind to the WT pHLA complex even at very high concentrations of the scDb (FIG. 67A, FIG. 74D). H2-scDb was therefore chosen for further analysis. As assessed by surface plasmon resonance (SPR), the H2-scDb bound to $p53^{R175H}$/HLA-A*02:01 with a $K_D = 86$ nM, a $k_{on}$ of $1.76 \times 10^5$ M$^{-1}$ s$^{-1}$, and a $k_{off}$ of $1.48 \times 10^{-2}$ s$^{-1}$ (FIG. 67B). The $k_{on}$ of $1.76 \times 10^5$ M$^{-1}$ s$^{-1}$ suggested a lack of overall conformational change of the $p53^{R175H}$/HLA-A*02:01 upon binding. No detectable binding of the H2-scDb to $p53^{WT}$/HLA-A*02:01 was observed in the SPR experiments (FIG. 67B).

TABLE 18

| | | | | |
|---|---|---|---|---|
| | | SEQ | | SEQ |
| scFv | VL | ID NO | VH | ID NO |
| H2 | DIQMTQSPSSLSASVGDRVTITCRASQDVNT AVAWYQQKPGKAPKLLIYSAYFLYSGVPSRF SGSRSGTDFTLTISSLQPEDFATYYCQQYSRY SPVTFGQGTKVEIK | 729 | EVQLVESGGGLVQPGGSLRLSCAASGFN VYASGMHWVRQAPGKGLEWVAKIYPDS DYTYYADSVKGRFTISADTSKNTAYLQM NSLRAEDTAVYYCSRDSSFYYVYAMDY WGQGTLVTVSS | 730 |
| H20 | DIQMTQSPSSLSASVGDRVTITCRASQDVNT AVAWYQQKPGKAPKLLIYSASFLYSGVPSRF SGSRSGTDFTLTISSLQPEDFATYYCQQSNAY PITFGQGTKVEIK | 731 | EVQLVESGGGLVQPGGSLRLSCAASGFN LNSYYMHWVRQAPGKGLEWVAMIIPGY GYTNYADSVKGRFTISADTSKNTAYLQM NSLRAEDTAVYYCSRSYYMYMDYWGQ GTLVTVSS | 732 |

Figure 75:
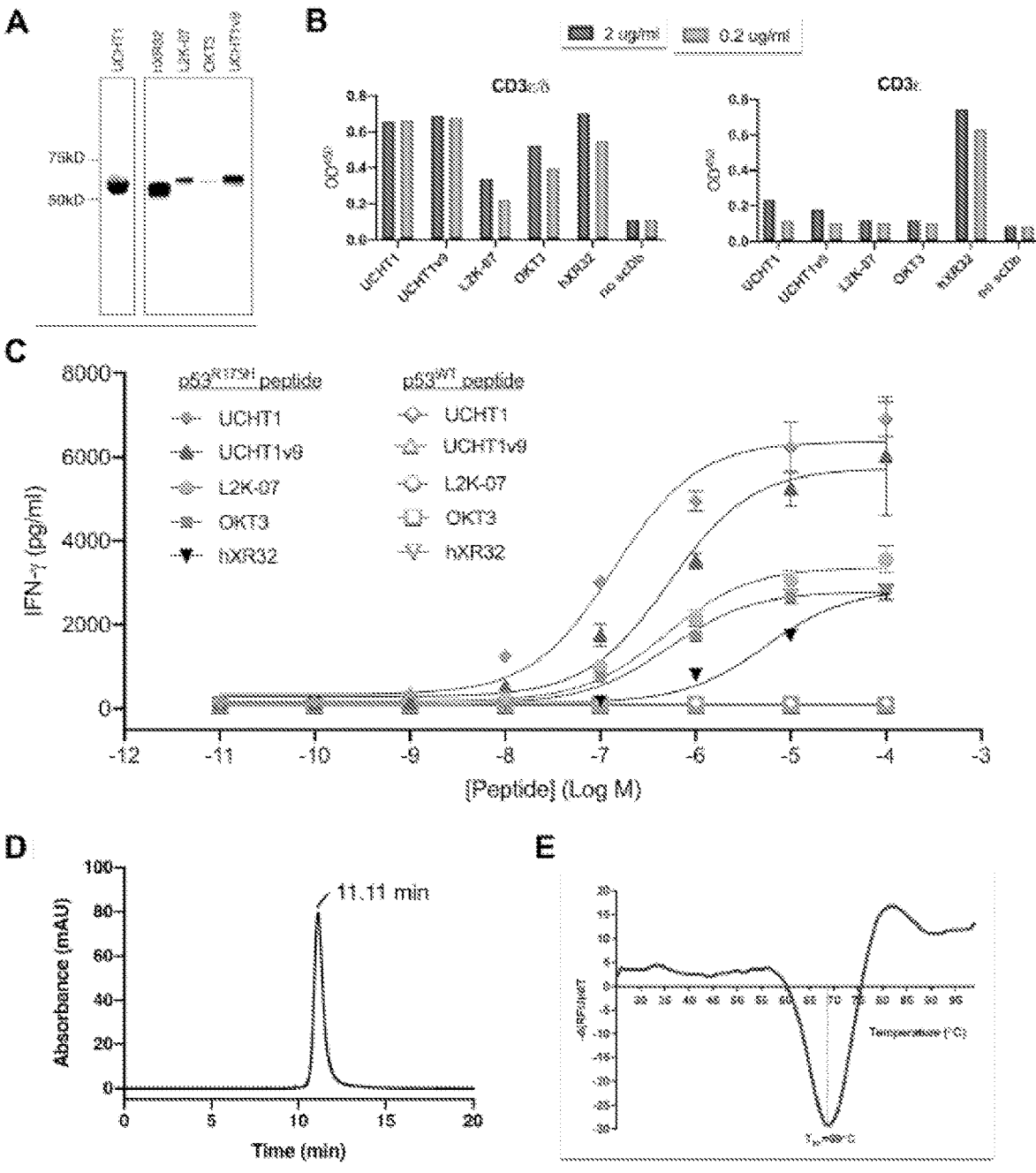

Next, it was examined whether anti-CD3 arms of the scDb other than the original UCHT1, could influence the ability of H2 to induce T-cell activation. The H2-scFv was linked to a panel of commonly used anti-CD3E scFvs, including UCHT1, UCHT1v9, L2K-07, OKT3, and hXR32 (FIG. 75A, B). It was found that, among the anti-CD3E scFvs tested, UCHT1, which has the highest reported affinity (Table 19), activated T cells at the lowest p53$^{R175H}$ peptide concentration when linked to the H2-scFv (FIG. 75C, FIG. 67C). H2-UCHT1-scDb (hereafter H2-scDb) was thus used for further experiments. Thermal stability of H2-scDb as measured by differential scanning fluorimetry showed a single melting temperature ($T_m$) at 69° C., suggesting it being a stable molecule (FIG. 75D, E).

TABLE 19

Reported affinity of the anti-human CD3ε scFvs used in the study.

| anti-CD3$_ε$ scFv clone | Reported affinity ($K_D$, nM) | Format in which affinity was measured |
|---|---|---|
| UCHT1 | 1.8 | Full-length antibody |
| UCHT1v9 | 4.7 | Full-length bispecific antibody |
| L2K-07 | 110 | BiTE |
| OKT3 | 2730 | Fab |
| hXR32 | 21.2 | Fc-bearing DART |

Figure 68:
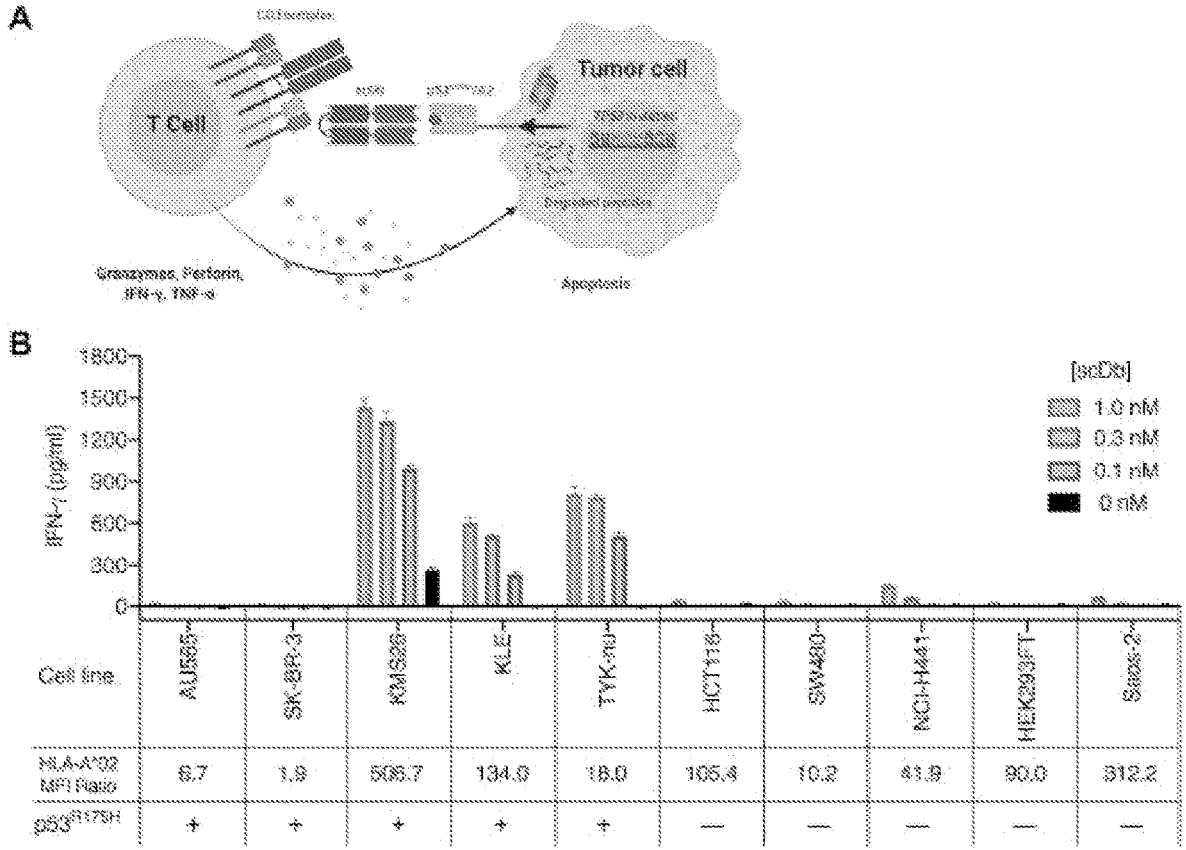
Figure 68:
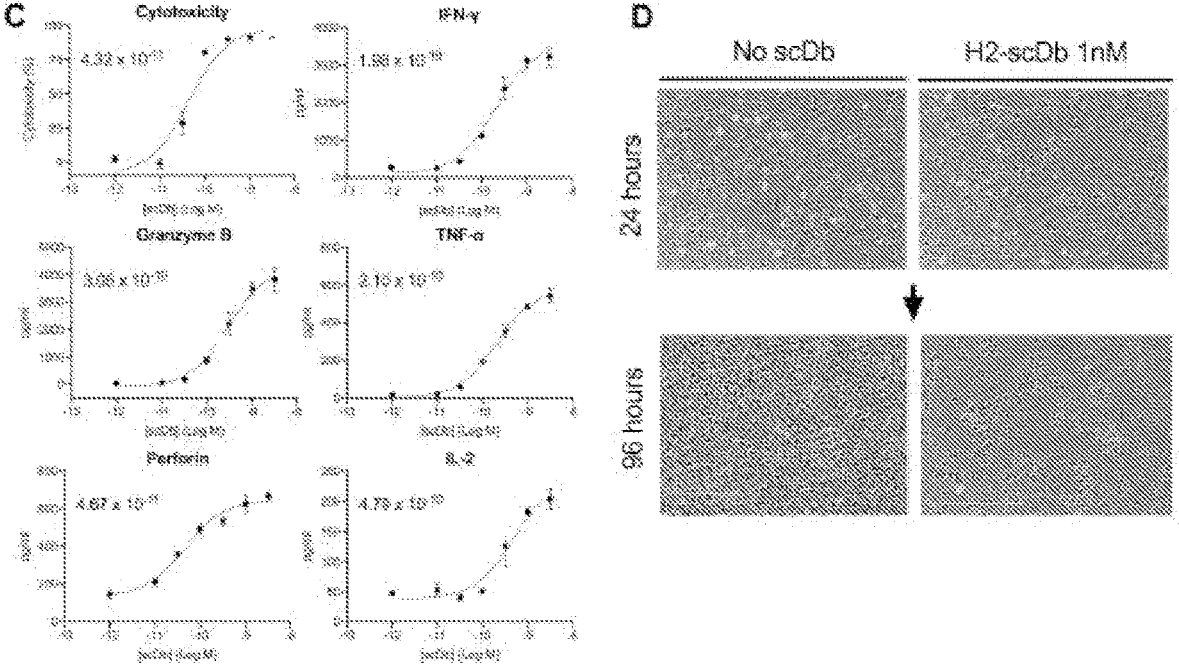
Figure 76:
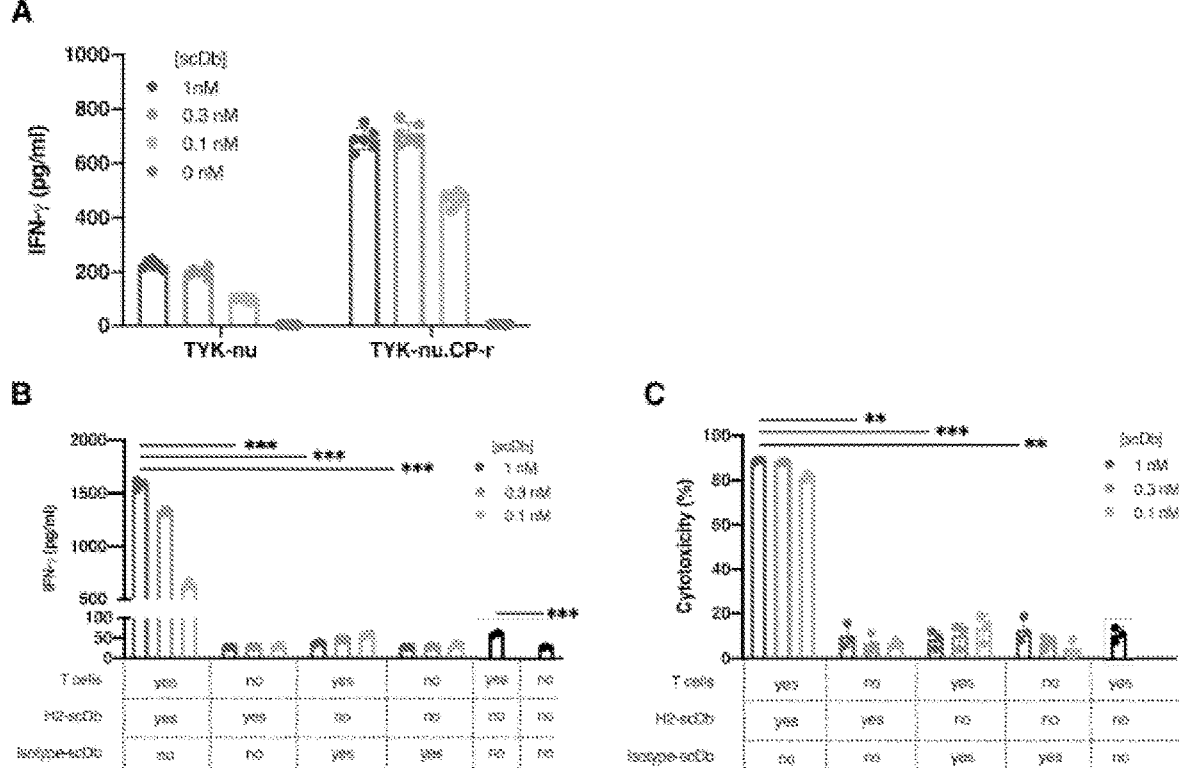
Figure 76:
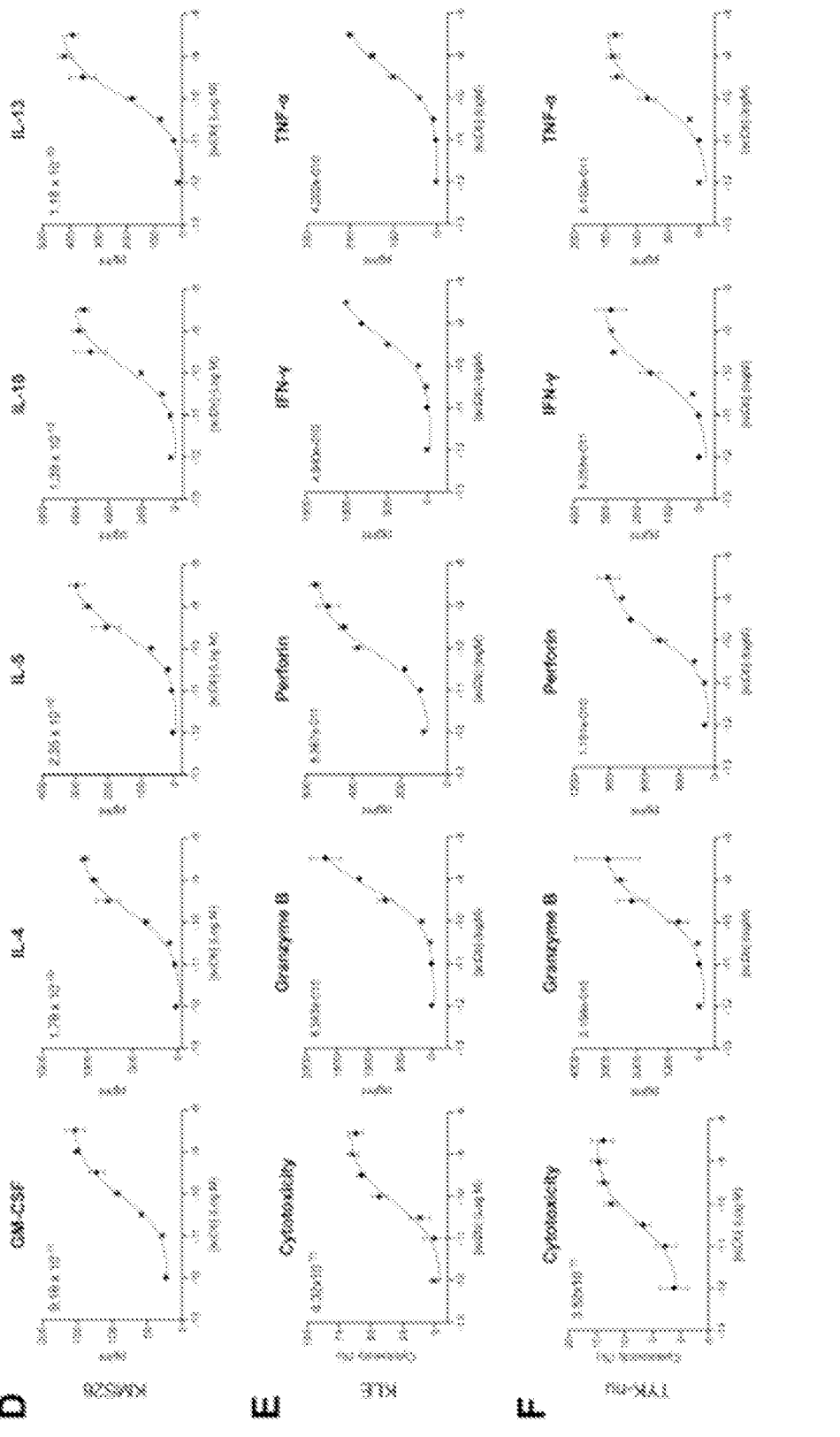

H2-scDb Specifically Recognizes Cancer Cells Expressing the p53$^{R175H}$ Neoantigen The ability of H2-scDb to recognize cancer cell lines expressing various levels of HLA-A*02:01 and having different p53 mutation status was next evaluated. H2-scDb elicited T-cell responses in a dose-dependent manner when T cells were co-cultured with three cell lines that expressed moderate to high levels of HLA-A*02:01 and harboring p53$^{R175H}$ (KMS26, KLE, TYK-nu, as well as the cisplatin-resistant variant of TYK-nu) (FIG. 68A, B, FIG. 76A). This activation was noted even at very low (sub-nanomolar) concentrations of the bispecific antibody and the reactivity was strictly T cell and H2-scDb-dependent (FIG. 76B, C). The T-cell responses were polyfunctional, as indicated by the release of cytotoxic granule proteins granzyme B and perforin, cytotoxicity, and the production of cytokines IFN-γ, tumor necrosis factor α (TNF-α), interleukin-2 (IL-2), and others (FIG. 68C, FIG. 76D-F). Clustering of T cells around tumor cells, leading to their lysis in the presence of H2-scDb, was also visualized by real-time live-cell imaging (FIG. 68D). The specificity of the bispecific antibody for both the p53$^{R175H}$ peptide and HLA-A*02:01 was evident from the observation that much lower levels of IFN-γ were induced by cells harboring a p53$^{R175H}$ mutation but low levels of expression of HLA-A*02:01 (AU565 or SK-BR3) or by cells without p53$^{R175H}$ but relatively high levels of HLA-A*02:01 expression (FIG. 68B, FIG. 77A).

Figure 69:
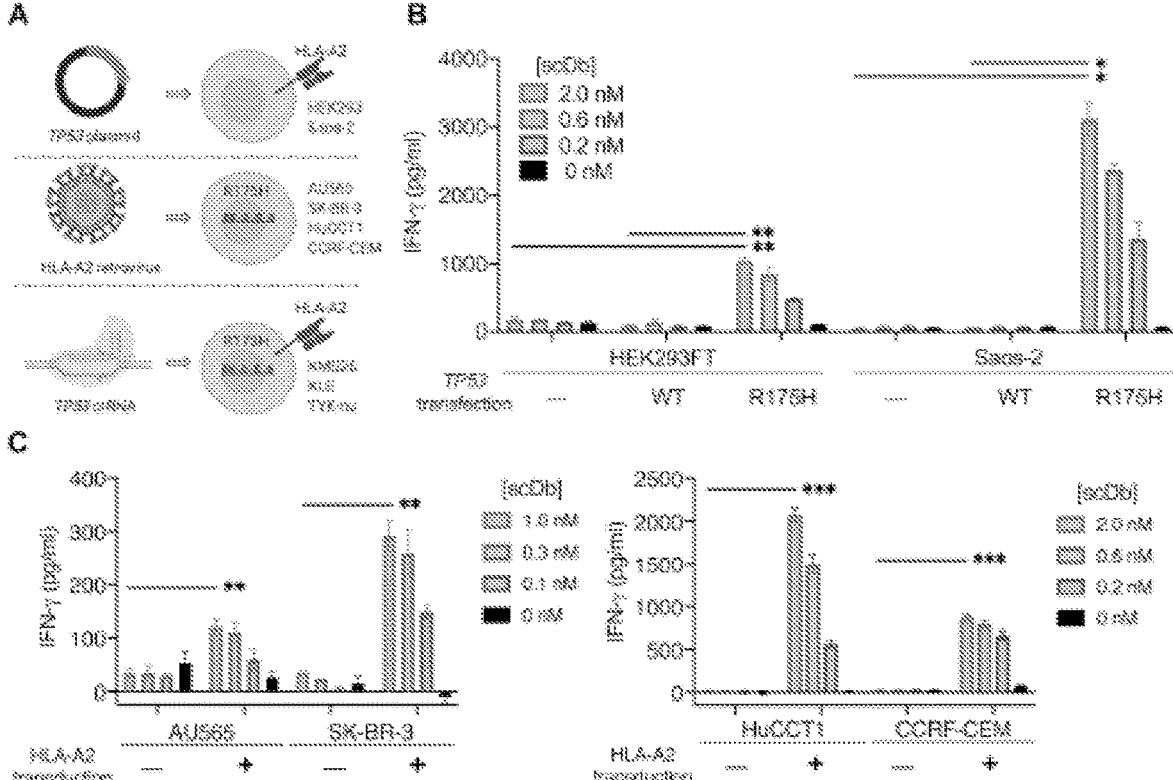
Figure 69:
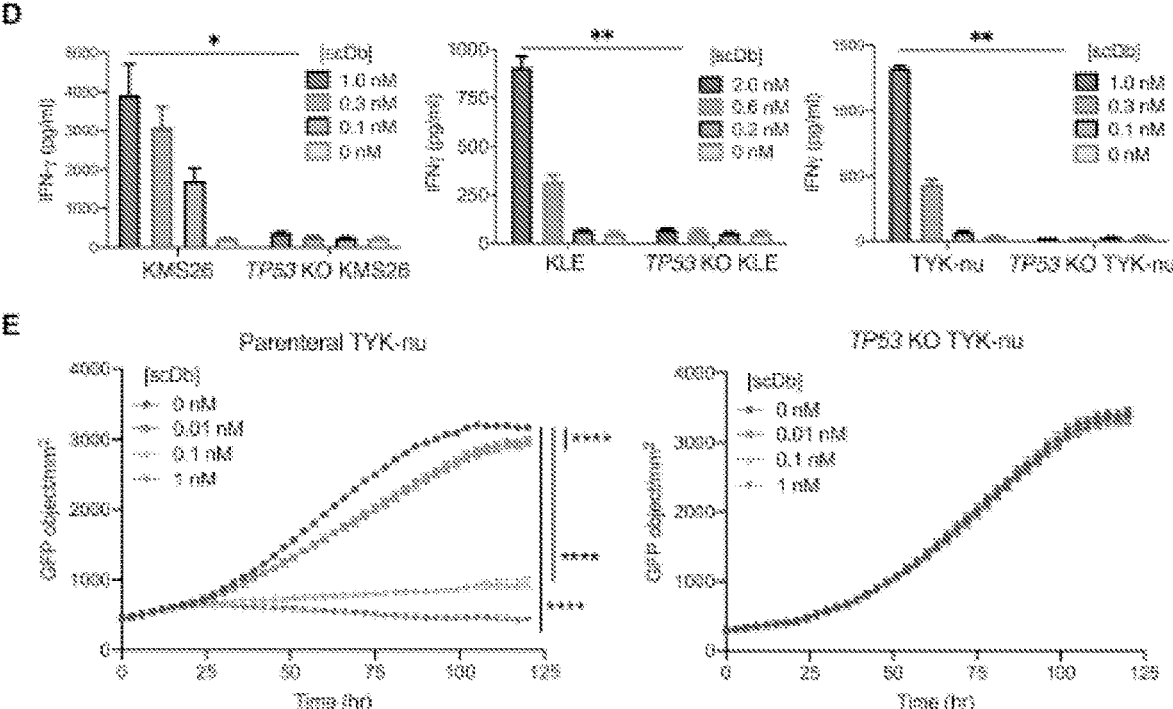

The specificity of H2-scDb was validated using nine pairs of isogenic cell lines that differed with respect to HLA-A*02:01 expression or p53$^{R175H}$ mutation (FIG. 69A). First, human HEK293FT (TP53$^{WT}$/HLA-A*02:01) or Saos-2 (TP53$^{null}$/HLA-A*02:01) cells were transfected with plasmids expressing either full-length p53$^{R175H}$ or p53$^{WT}$. H2-scDb induced robust T-cell activation when co-cultured with both cell lines overexpressing p53$^{R175H}$ but not with p53$^{WT}$-overexpressing or parental cells (FIG. 69B). Second, HLA-A*02:01-encoding retrovirus was transduced into four cell lines (AU565, SK-BR-3, HuCCT1, CCRF-CEM) that harbored the p53$^{R175H}$ mutation but had low levels of HLA-A*02:01 expression (FIG. 77B). Exogenous expression of HLA-A*02:01 in all four lines conferred T-cell activation by H2-scDb (FIG. 69C). Third, TP53 in KMS26, TYK-nu, and KLE cancer cell lines that carry endogenous p53$^{R175H}$ were genetically disrupted using a CRISPR-based technology (FIG. 78A). T-cell activation, as assessed by IFN-γ secretion, was reduced to control levels when TP53 was knocked out in all three cell lines (FIG. 69D). The cytotoxicity mediated by H2-scDb was similarly mitigated by TP53 knock-out (KO) in these cells (FIG. 69E, FIG. 78B).

Overall Structure of the H2-Fab-p53$^{R175H}$/HLA-A *02:01 Ternary Complex

Figure 70:
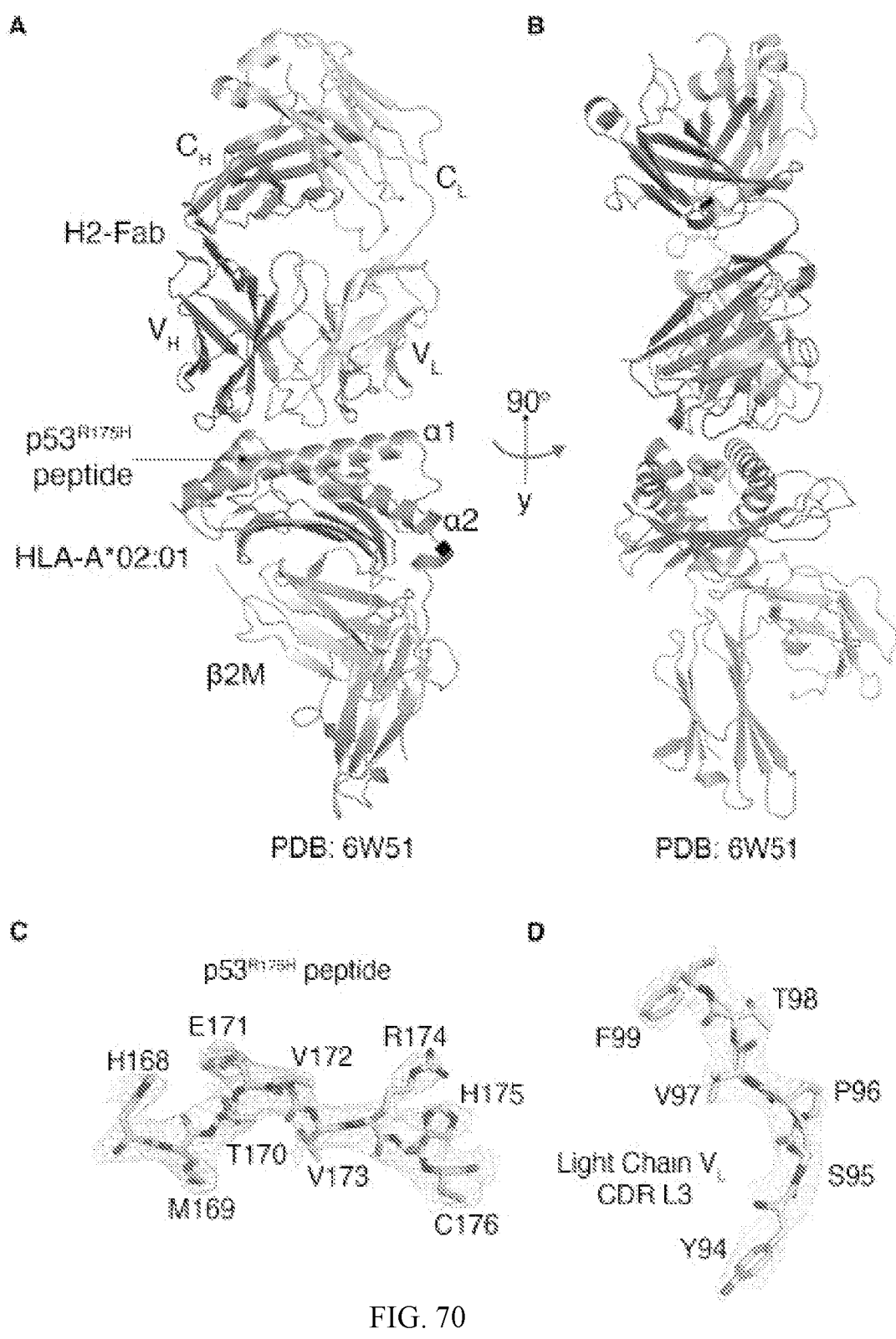
Figure 70:
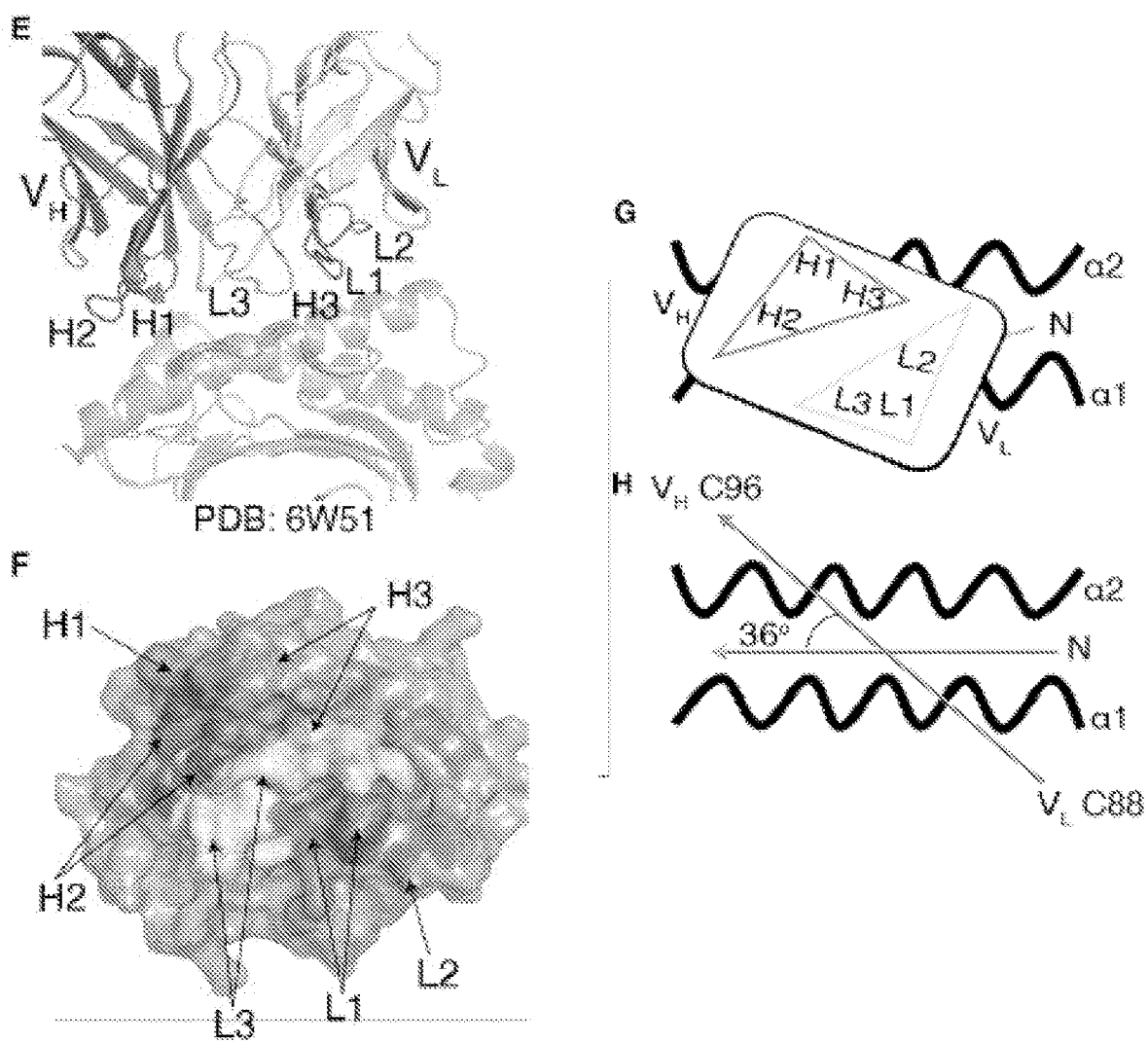
Figure 79:
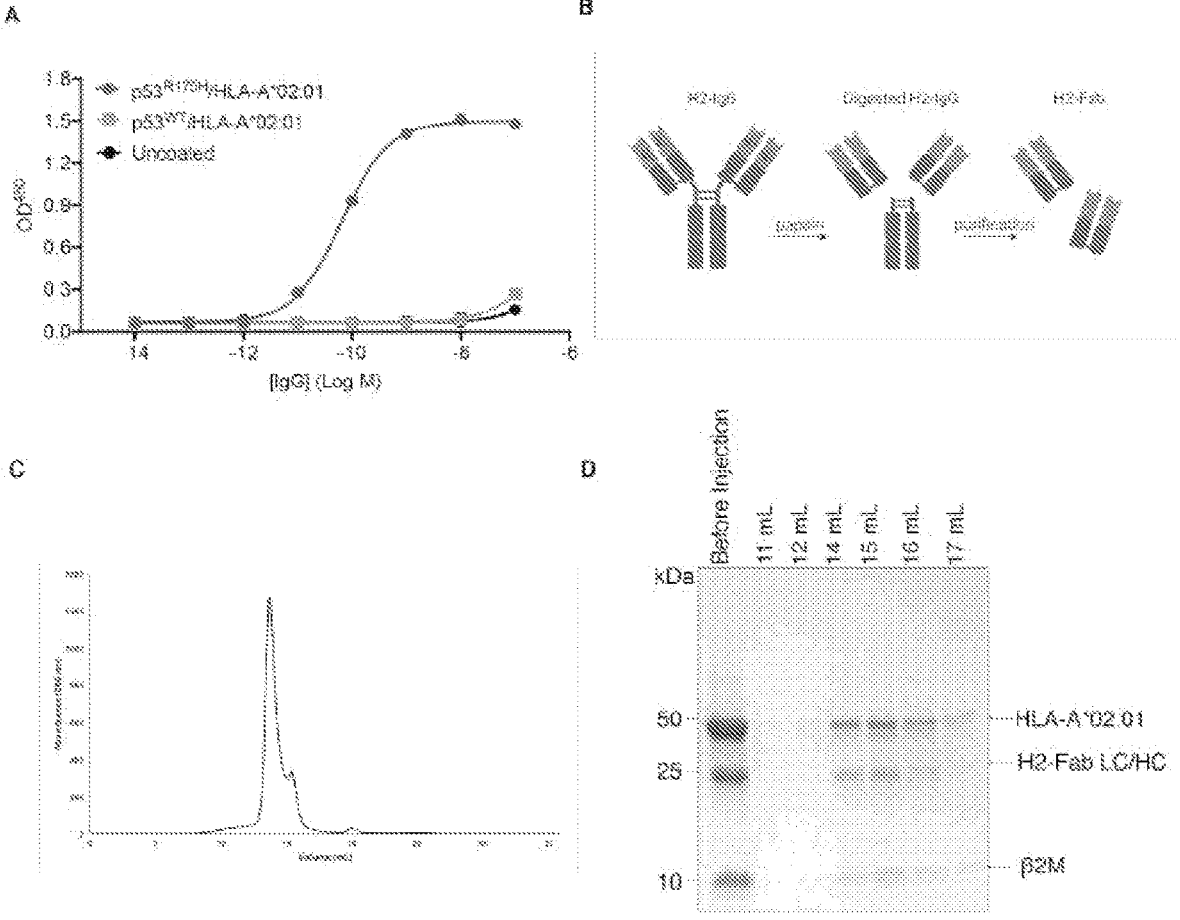

To understand the structural basis for the high specificity of the H2 clone for p53$^{R175H}$/HLA-A*02:01, H2 was converted into full-length IgG (H2-IgG) and confirmed that binding specificity was preserved in this format (FIG. 79A). The H2-IgG was then digested into an antigen-binding fragment (H2-Fab) with papain (FIG. 79B). The H2-Fab-p53$^{R175H}$/HLA-A*02:01 complex was purified (FIG. 79C, D) and its crystal structure was determined by molecular replacement and refined to 3.5 Å resolution (PDB ID 6W51, Table 20). There were four H2-Fab and four p53$^{R175H}$/HLA-A*02:01 per asymmetric unit (FIG. 70A, B). All four H2-Fab were firmly positioned on the p53$^{R175H}$/HLA-A*02:01 with a pairwise root-mean-square deviation (rmsd) range of 0.27 to 0.45 Å for 382 to 419 $C^{alpha}$ carbon's, as calculated by PyMOL (Table 21). The total buried surface area of the H2-Fab-p53$^{R175H}$/HLA-A*02:01 interface was 1173 Å$^2$, with roughly equal contributions from heavy and light chains (644 Å$^2$ and 529 Å$^2$, respectively, Table 22). Although the entire structure was refined to a resolution of 3.5 Å, particularly clear electron densities were observed for the p53$^{R175H}$ neoantigen, the complementarity-determining regions (CDRs) of the H2-Fab, and the HLA-A*02:01 (FIG. 70C, D).

TABLE 20

X-ray Crystallography data collection and refinement statistics.

| | p53$^{R175H}$/HLA-A* 02:01-Fab H2 (PDB ID 6W51) |
|---|---|
| Data Collection | |
| Diffraction source | NSLS-II X17-ID-2 |
| Wavelength (Å) | 0.979321 |
| Temperature (K) | 100 |
| Detector | Dectris EIGER X 16M |
| Space group | P12₁1 |
| a, b, c (Å) | 113.3, 123.7, 136.9 |
| α, β, γ (°) | 90, 100.4, 90 |
| Resolution range (Å) | 30.37-3.53 (3.66-3.53) |
| Total no. of reflections | 104,474 (9,774) |
| No. of unique reflections | 43,734 (4,273) |
| Completeness (%) | 95.3 (89.2) |
| Redundancy | 2.4 (2.3) |
| <I/σ(I)> | 3.6 (1.4) |
| R$_{merge}$ | 0.25 (0.76) |
| Rmeas | 0.29 (0.89) |
| Rpim | 0.18 (0.58) |
| CC$_{1/2}$ | 0.94 (0.54) |
| Refinement | |
| Resolution range (Å) | 30.38-3.53 (3.62-3.53) |
| No. of reflections, working set | 41,530 |
| R$_{work}$/R$_{free}$ | 0.20/0.28 (0.30/0.35) |
| No. of non-H atoms | |
| MHC (HLA-A*02:01 + β2m) | 3,078 |
| p53$^{R175H}$ peptide | 75 |
| Fab H2 Heavy Chain | 1,667 |
| Fab H2 Light Chain | 1,652 |
| Total of non-H atoms | 6,472 |
| R.m.s. deviations | |
| Bonds (Å) | 0.009 |
| Angles (°) | 1.66 |
| Wilson B-factor (Å²) | 62 |
| Average B factors (Å²) | |
| MHC (HLA-A*02:01 + β2m) | 74 |
| p53$^{R175H}$ peptide | 56 |
| Fab H2 Heavy Chain | 59 |
| Fab H2 Light Chain | 63 |
| Total average B factor | 63 |
| Ramachandran (%) | |
| Favorable | 95.2 |
| Allowed | 3.8 |
| Outlier | 1.0 |

*Values in parentheses are for highest-resolution shell. All atoms refer to non-H atoms.

TABLE 21

Pairwise rmsd of the four H2-Fab in the asymmetric unit. The root-mean square deviation (rmsd) and number of C$^{alpha}$ carbons were calculated by PyMOL (v2.2.3, Schrödinger, LLC, New York, NY). For chain reference see PDB ID 6W51.

| | Chains M, N (Å/#C$^{alpha}$) | Chains S, T (Å/#C$^{alpha}$) | Chains Q, R (Å/#C$^{alpha}$) |
|---|---|---|---|
| Chains O, P | 0.32/382 | 0.36/414 | 0.42/413 |
| Chains Q, R | 0.45/419 | 0.27/386 | 0 |
| Chains S, T | 0.34/408 | 0 | — |

TABLE 22

Structural comparison of H2-Fab-p53$^{R175H}$/HLA-A*02:01 with various TCR and Fab antibody-pHLA. Total bonds were calculated using a 4 Å cutoff which includes both hydrogen bonds and van der Waals interactions as calculated using CONTACTS in the CCP4 suite. PDB, Protein Data Bank; BSA, buried surface area; α, TCRα chain; β, TCRβ chain; H, V$_H$ domain; L, V$_L$ domain; pep, HLA presented peptide.

| | H2-Fab | MAGE-A3 TCR | NY-ESO-1 Fab (3M4E4) | ESK-1 Fab |
|---|---|---|---|---|
| Affinity (K$_D$) | 86 nM | 7.1 nM | 95 nM | 13.2 nM |
| PDB | 6W51 | 5BRZ | 3HAE | 4WUU |
| Angle of rotation (°) | 36° | 57° | 138° | 122° |
| Total bonds | 115 | 114 | 167 | 183 |
| Peptide bonds (bold ≥ 10) | 4, 5, 6, 7, 8 | 1, 4, 5, 7, 8 | 1, 2, 4, 5, 6, 7, 8, 9 | 1, 4 |
| Peptide bonds | 36 (31%) | 16 (14%) | 89 (53%) | 19 (10%) |
| Bonds from β/H | 21 | 10 | 47 | 10 |
| Bonds from α/L | 15 | 6 | 42 | 9 |
| HLA bonds | 79 | 98 | 78 | 164 |
| Bonds from β/H | 31 | 20 | 47 | 130 |
| Bonds from α/L | 48 | 78 | 31 | 34 |
| HLA ≥ 5 bonds (bold ≥ 10) | 61, 65, 72, 80, 146, 155 | 66, 154, 155, 157, 158, 163 | 65, 66, 72, 73 | 58, 62, 63, 65, 66, 155, 161, 162, 166, 167, 169, 170 |
| BSA | | | | |
| BSA total | 1173 | 1027 | 1366 | 1084 |
| BSA β/H pep | 253 | 158 | 256 | 72 |
| BSA α/L pep | 102 | 112 | 260 | 93 |
| BSA β/H HLA | 391 | 247 | 523 | 601 |
| BSA α/L HLA | 427 | 510 | 327 | 318 |

Binding of the p53$^{R175H}$ Peptide to HLA-A*02:01

Figure 71:
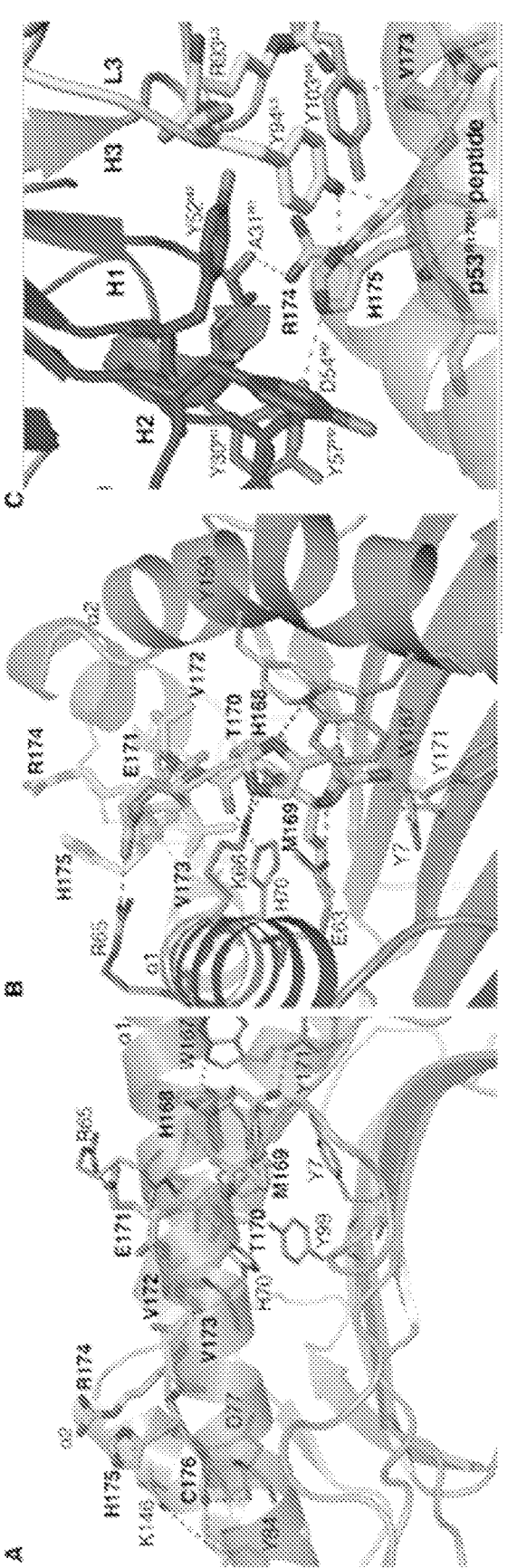
Figure 71:
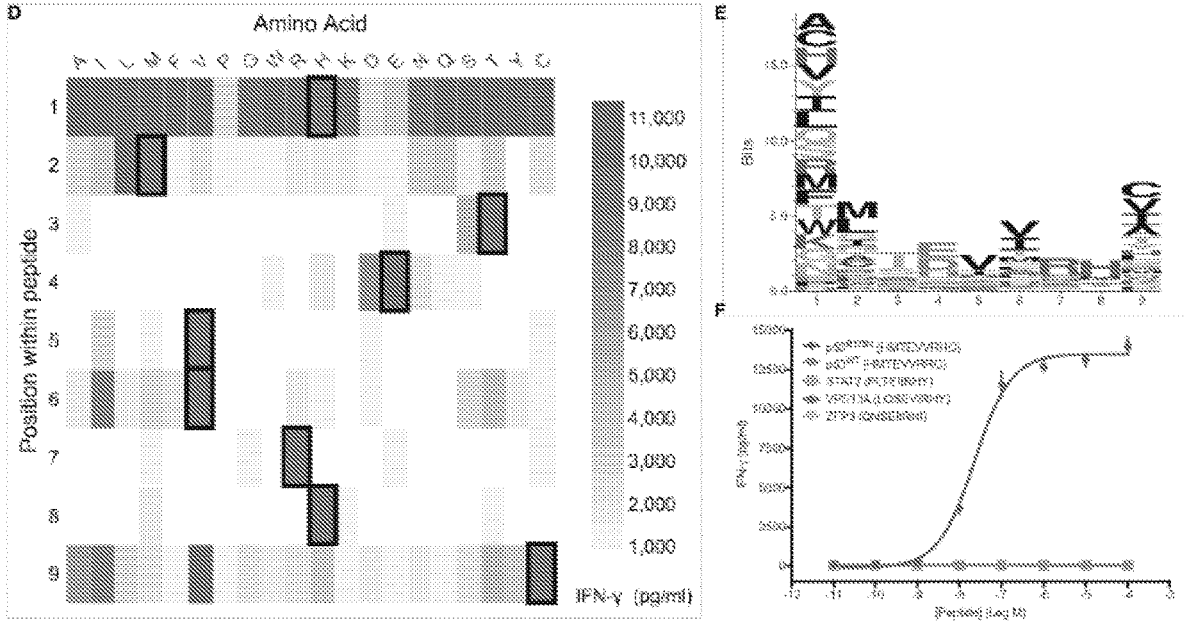
Figure 80:
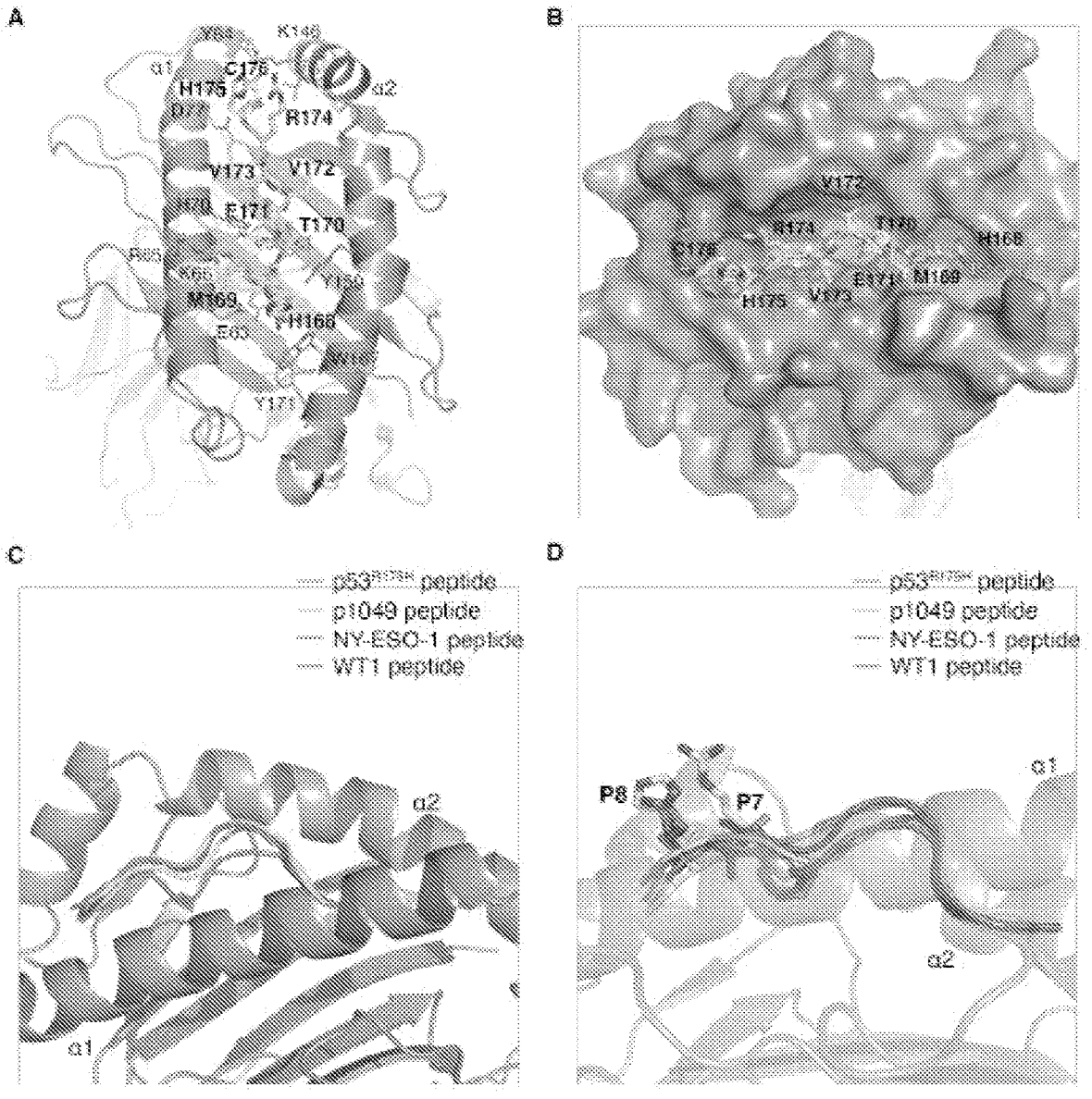

The p53$^{R175H}$ peptide (HMTEVVRHC; SEQ ID NO:1) occupied the binding cleft al-α2 of HLA-A*02:01, burying a solvent accessible surface area of 870 Å$^2$, slightly larger than other peptide/HLA-A*02:01 complexes (FIG. 71A, B, FIG. 80A) and with the C-terminal arginine at position 7 (Arg174) and mutant histidine at position 8 (His175) pointing up, out of the groove. In contrast, the N-terminus of the peptide is situated deep within the peptide binding cleft, anchored by multiple residues in the HLA-A*02:01 (FIG. 71A, B, FIG. 80A). The anchor residues of the peptide, a methionine at position 2 (P2. Met169) and a cysteine residue at position 9 (P9, Cys176) (FIG. 80B), departed from the canonical anchor residues-leucine at P2 and valine or leucine at P9. Peptides that bind to HLA-A*02:01 through either a methionine at P2 or a cysteine at P9 have been reported, but not both (Webb et al., *J. Biol. Chem.* 279: 23438-23446 (2004); and Ataie et al., *J. Mol. Biol.* 428:194-205 (2016)). Based on alignments with structures of other HLA-A*02:01 peptides in complex with TCR or TCRm, the unconventional anchoring of p53$^{R175H}$ did not result in drastic peptide conformational change or positioning (FIG. 80C, D).

Structural Basis for the Recognition of p53$^{R175H}$ HLA-A*02:01 by the H2-Fab

The recognition of the HLA-A*02:01 by the H2-Fab was mediated by all six CDRs. There were a total of 79 contacts, with a cutoff of 4 Å, between the H2-Fab CDRs and the α1 and α2 of HLA-A*02:01, with the light chain contributing to 61% of those contacts (Table 22). The H2-Fab buried a solvent accessible surface area of 818 Å$^2$ within the HLA, of which 427 Å$^2$ were contributed by the light chain and 391 Å$^2$ by the heavy chain (Table 22). In contrast, only four of the six H2-Fab CDRs (H1, H2, H3 and L3) interacted with the p53$^{R175H}$ peptide. Overall, the H2-Fab made 36 contacts with the p53$^{R175H}$ neoantigen, including five hydrogen bonds and numerous van der Waals interactions. His175 made 47% of all direct contacts with the H2-Fab. The CDR-H1, H2, and H3 of the heavy chain and CDR-L3 of the light chain formed a cage-like configuration around the C-terminus of the p53$^{R175H}$ peptide, trapping Arg174 and His175 into position by providing a stable interaction (FIG. 71C). The imidazole side chain of His175 was anchored by a hydrogen bonding network with Asp54 (CDR-H2) and Tyr94 (CDR-L3) (FIG. 71C, FIG. 81). Tyr52 (CDR-H2) acted as a ceiling and capped the cage-like structure around His175 by forming π-π interactions (FIG. 71C, FIG. 81).

Figure 82:
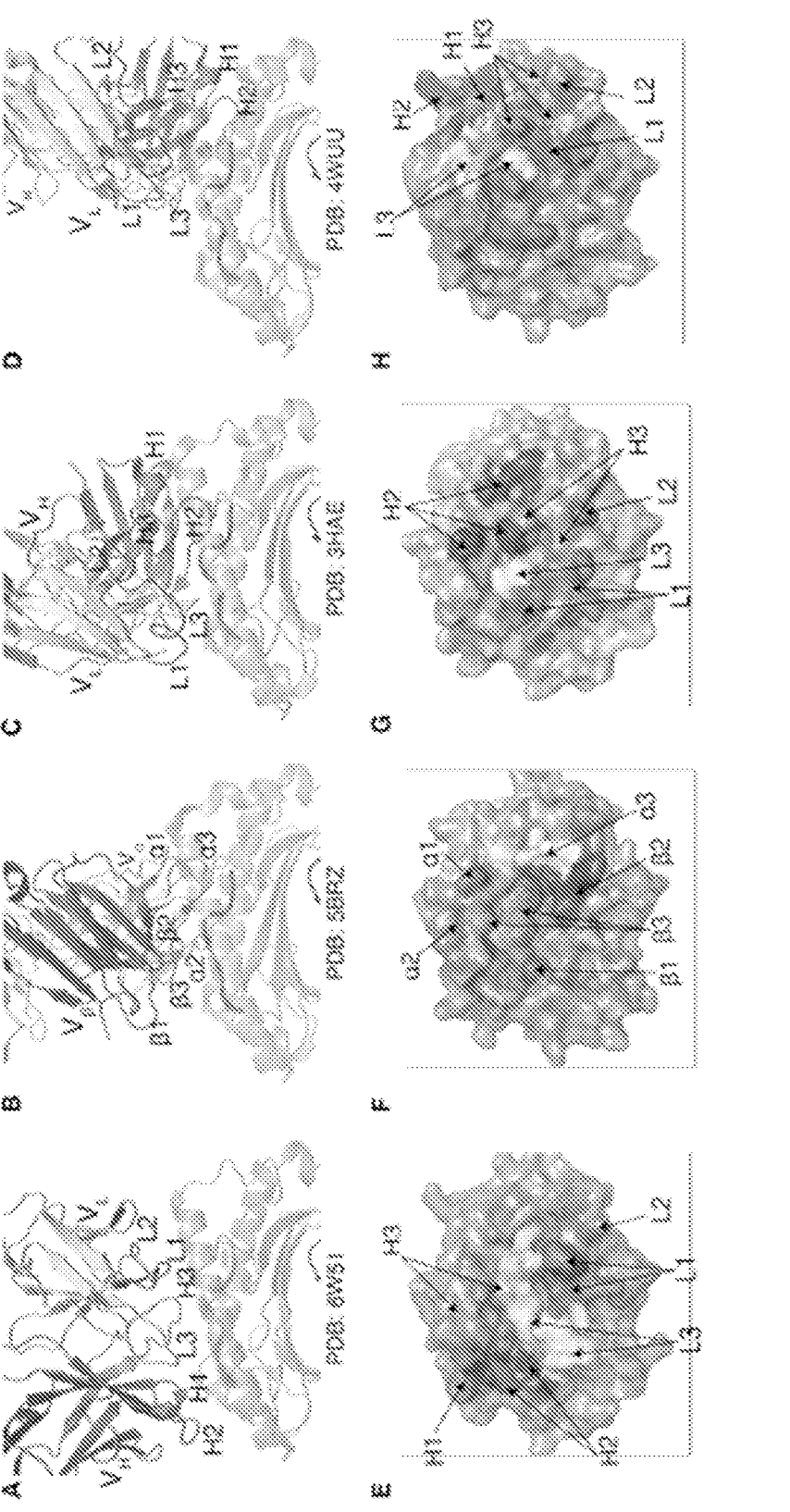
Figure 82:
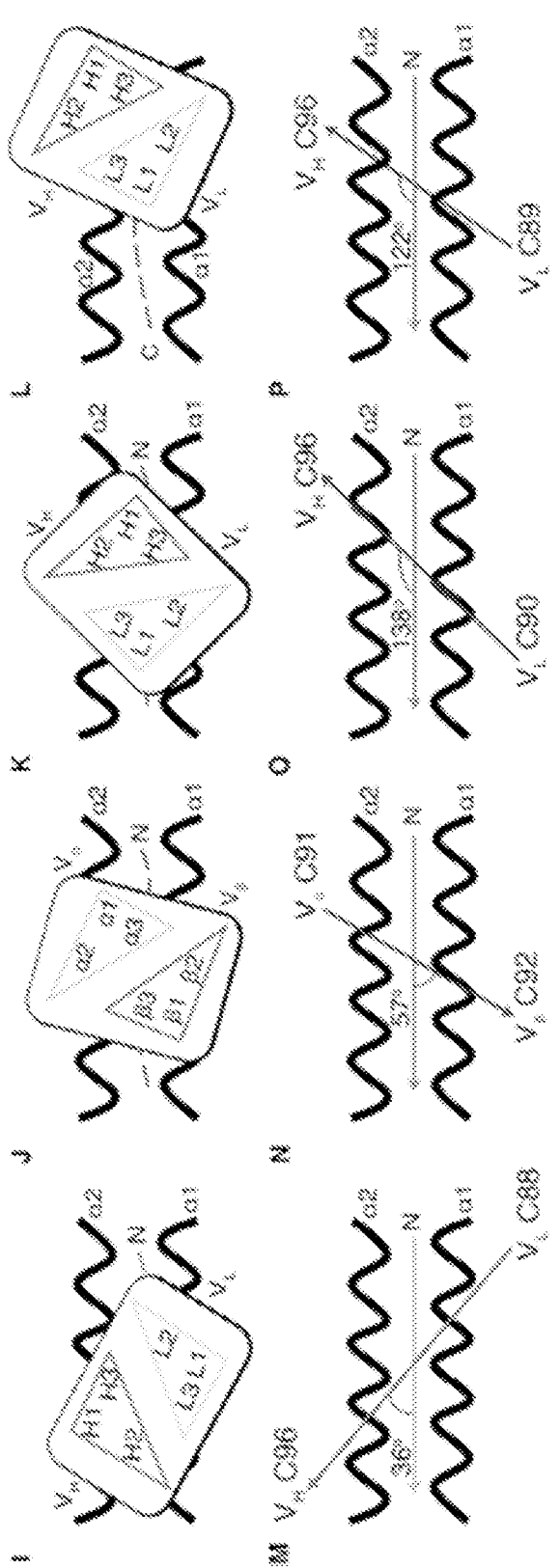

Viewed from the axis of the C-terminus to the N-terminus of the p53$^{R175H}$ peptide, the CDRs were arranged in the order H2, H1, L3, H3, L1, L2 (FIG. 70E, F, G). The docking angle of the H2-Fab to the peptide within the HLA groove is 36° (FIG. 70G, H). This orientation angle was quite different from that of most previously described TCRs or TCRm antibodies to pHLA complexes, in which the axis of the peptide is almost perpendicular to the axis defined between the disulfide bonds of the V$_L$/α to V$_H$/β chains (FIG. 82).

Assessing Candidate Cross-Reactive Peptides

One of the major challenges confronting new immuno-therapeutic antibodies is off-target binding, which can result in toxicity to normal cells. Scanning mutagenesis was employed to identify peptides in the human proteome to which H2-scDb might cross-react. A peptide library was generated by systemically substituting amino acids at each position of the target p53$^{R175H}$ peptide (HMTEVVRHC; SEQ ID NO:1) with each of the remaining 19 common amino acids. T2 cells loaded with each of the 171 variant peptides were then used to assess T-cell activation by measuring IFN-γ release following incubation with T cells and H2-scDb (FIG. 71D). In congruence with the X-ray structural analysis, any changes in P8, where the mutant histidine residue lies, and any change in P7, which is encased with P8 by the CDR loops, abolished recognition of the peptide. Peptides with substitutions at these positions retained their ability to bind to HLA-A*02:01 (FIG. 83A), but not to the H2-scDb. Other non-anchor residues at positions 3-6 also highly favored the parental amino acids present in the target peptide. This recognition pattern is illustrated as a Seq2Logo graph (FIG. 71E).

Figure 83:
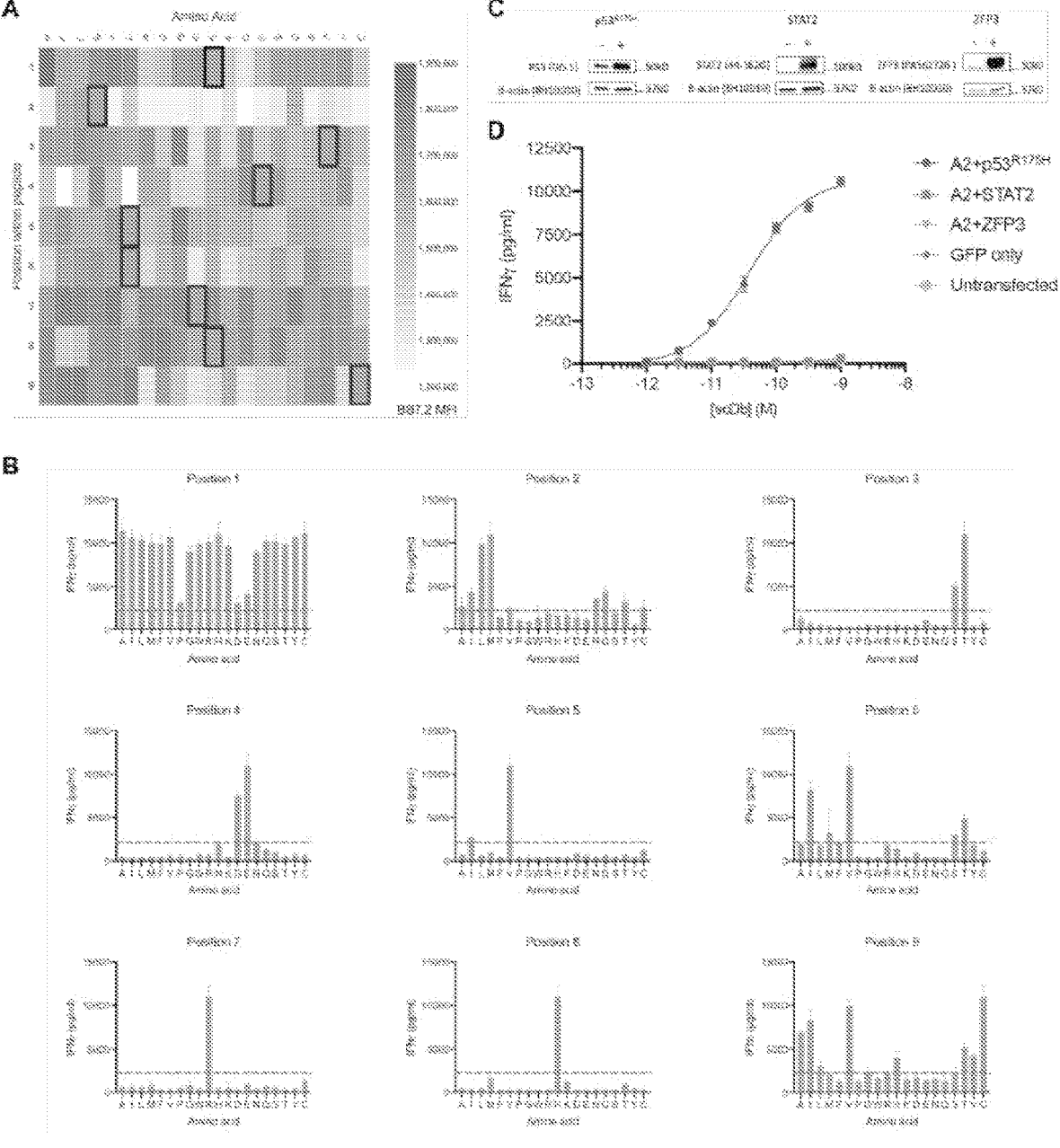

Next, a nonamer binding motif, x-[AILMVNQTC]-[ST]-[DE]-[IV]-[IMVST]-R-H-[AILVGHSTYC] (SEQ ID NO:197), was generated using 20% target peptide reactivity as a cutoff for permissive amino acids at each position (FIG. 83B). A search of this motif in the UniProtKB human protein database using ScanProsite yielded 3 homologous peptides from STAT2 (PLTEIIRHY; SEQ ID NO:185), VPS13A (LQSEVIRHY; SEQ ID NO: 186), and ZFP3 (QNSEIIRHI; SEQ ID NO:187) (Table 9). None of these 3 peptides were predicted to be potent binders of HLA-A*02:01 by NetMHCpan 4.0 (% rank all >2.0) and had lower predicted binding affinity than the parental p53$^{R175H}$ peptide (Table 9). However, to experimentally exclude the possibility of cross-reactivity, T2 cells were pulsed with each of these peptides. H2-scDb activated T cells only in the presence of T2 pulsed with the p53$^{R175H}$ peptide (FIG. 71F). Additionally, COS-7 cells were co-transfected with expression plasmids for HLA-A*02:01 and full-length STAT2 or ZFP3; VPS13A was not tested due to its large size (>3000 aa). Again, no T-cell activation was detected in the co-culture assay with COS-7 cells expressing the two proteins containing the candidate cross-reactive peptides (FIG. 83C, D).

Antitumor Activity of the H2-scDb In Vivo

Figure 84:
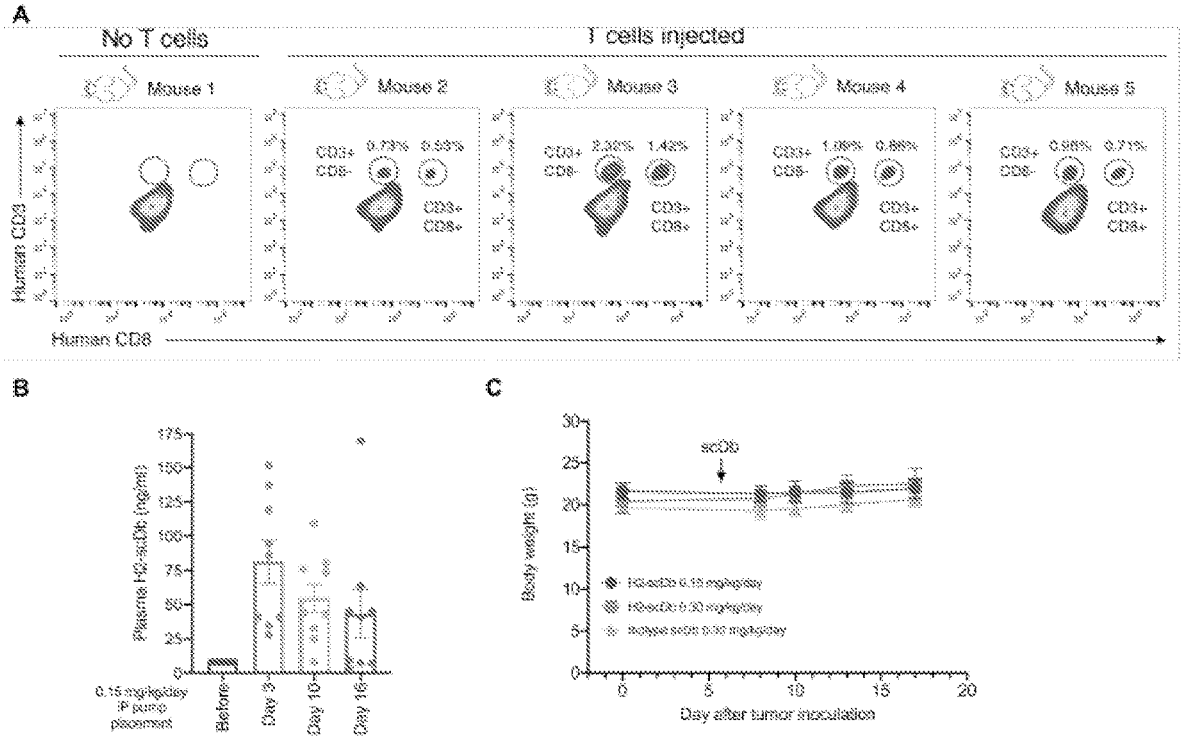
Figure 84:
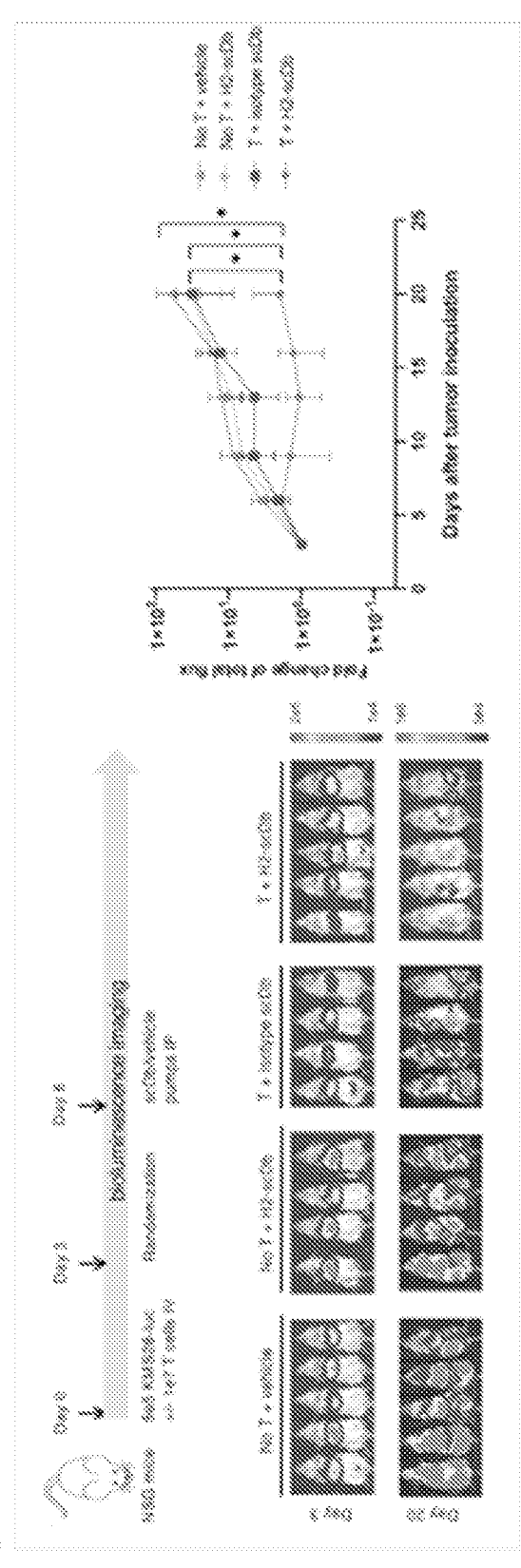

To determine whether H2-scDb could control tumor growth in vivo, KMS26 multiple myeloma cells were engrafted into NOD-SCID-Il2rg$^{-/-}$ (NSG) mice through intravenous injection, establishing widespread, actively growing cancers throughout the body. Two models were used to assess the effects of the H2-scDb in combination with human T cells engrafted in these mice (FIG. 84A). In an early treatment model, mice were randomized based on luminescence quantification of tumor burden and H2-scDb was subsequently administered through continuous intraperitoneal infusion pumps at 0.3 mg/kg/day, starting one day after tumor inoculation. The pumps were able to maintain significant plasma concentrations of scDb for two weeks (FIG. 84B). An irrelevant isotype scDb was administered to mice in parallel as control. H2-scDb markedly suppressed the growth of parental KMS26 tumors (FIG. 72A). In contrast, the H2-scDb had no effect on KMS26 tumors in which the TP53 gene had been disrupted using CRISPR (FIG. 72A). In the second model, mice were randomized 6 days after tumor inoculation. The H2-scDb was administered at two doses (0.15 and 0.3 mg/kg/day). Both doses resulted in major tumor regressions and were well-tolerated as assessed by the absence of significant changes in body weight (FIG. 72B, FIG. 84C). No treatment effect of H2-scDb was observed in the absence of human T cells, supporting the T cell-dependent nature of H2-scDb (FIG. 84D).

Together these results demonstrate that highly specific bispecific antibodies can be generated against pHLA complexes resulting from common mutations occurring in cancer cells. The format and configuration of the bispecific antibodies developed here are highly specific and sensitive scDbs against protein products containing mutations occurring in cancer cells.

Materials and Methods

Cell Lines and Primary T Cells

COS-7, RPMI 6666, T2 (174×CEM.T2), Raji, HH, AU565, SK-BR-3, KLE, HCT116, SW480, NCI-H441, Saos-2, and CCRF-CEM cells were purchased from American Type Culture Collection (ATCC, Manassas, VA). KMS26, TYK-nu, and HuCCT1 were purchased from Japanese Collection of Research Bioresources Cell Bank (JCRB, Osaka, Japan). SigM5 was obtained from DSMZ (Braunschweig, Germany). HEK293FT was obtained from Invitrogen (Thermo Fisher Scientific, Waltham, MA). T2, Raji, Jurkat, HH, AU565, NCI-H441, TOV-112D, CCRF-CEM, KMS26, TYK-nu, TYK-nu.CP-r and HuCCT1 were cultured in RPMI-1640 (ATCC, 30-2001) with 10% FBS (GE Healthcare, SH30070.03) and 1% Penicillin-Streptomycin (Thermo Fisher Scientific, 15140163). RPMI 6666 was cultured in RPMI-1640 with 20% FBS and 1% Penicillin-Streptomycin. COS-7, SK-BR-3, HCT116, SW480, and Saos-2 were cultured in McCoy's 5A modified media (Thermo Fisher Scientific, 16600108) with 10% FBS and 1% Penicillin-Streptomycin. SigM5 was cultured in IMDM (Thermo Fisher Scientific, 12440061) with 20% FBS and 1% Penicillin-Streptomycin. HEK293FT was cultured in DMEM (high glucose, pyruvate, Thermo Fisher Scientific, 11995065) with 10% FBS, additional 2 mM GlutaMAX (Thermo Fisher Scientific, 35050061), 0.1 mM MEM non-essential amino acids (Thermo Fisher Scientific, 11140050), 1% Penicillin-Streptomycin, and 500 µg/mL Geneticin (Thermo Fisher Scientific, 10131027). PBMCs were isolated from leukapheresis samples (Stem Cell Technologies, Vancouver, BC) by standard density gradient centrifugation with Ficoll Paque Plus (GE Healthcare, 17-1440-03). T cells were expanded from PBMCs with addition of the anti-human CD3 antibody (OKT3, BioLegend, San Diego, 317347) at 15 ng/mL for three days. T cells were cultured in RPMI-1640 with 10% FBS, 1% Penicillin-Streptomycin, 100 IU/mL recombinant human IL-2 (aldesleukin, Prometheus Therapeutics and Diagnostics, San Diego, CA), and 5 ng/mL recombinant human IL-7 (BioLegend, 581908). In general, T cells from at least two different donors were tested in in vitro assays. All cells were grown at 37° C. in 5% C02 with humidification.

Detection of Neoantigen Peptide

HLA-A*02:01 restricted p53$^{R175H}$ peptide was directly detected and quantified in human cancer cells carrying p53$^{R175H}$ mutations through MANA-SRM in COS-7 cells transfected with HLA-A*02:01 and p53$^{R175H}$ and in human cancer cells carrying p53$^{R175H}$ mutations and expressing HLA-A*02:01. In particular, the dual-reduction approach described in MANA-SRM was critical for this detection because a cysteine and a methionine coexist in the p53$^{R175H}$ peptide. One hundred femtomole heavy-isotope labeled p53$^{R175H}$ peptide HMTEVVRHC (SEQ ID NO:1) and p53$^{WT}$ peptide HMTEVVRRC (SEQ ID NO:135; New England Peptide Inc, Gardner, MA) were spiked into each sample before the assay. The MANA-SRM assays were performed at Complete Omics Inc. (Baltimore, Maryland).

Peptides and Monomers

All peptides were synthesized at a purity of >90% by Peptide 2.0 (Chantilly, VA) or ELIM Biopharm (Hayward, CA), except for the positional scanning library, where crude peptides were used. Peptides were resuspended in dimethylformamide at 10 mg/mL and stored at −20° C. Biotinylated pHLA monomers were synthesized by Fred Hutchinson Cancer Research Center Immune Monitoring Lab (Seattle, WA). Monomers were confirmed to be folded prior to selection by performing an ELISA using W6/32 antibody (BioLegend, 311402), which recognizes only folded HLA.

Phage Display Library Construction

The scFv-bearing phage library used in this study has been described elsewhere (see, e.g., Miller et al., *J. Biol. Chem.* 294:19322-19334 (2019)). Briefly, oligonucleotides were synthesized by GeneArt (Thermo Fisher Scientific) using trinucleotide mutagenesis (TRIM) technology to diversify complementarity-determining region (CDR)-L2, CDR-L3, CDR-H1, CDR-H2, and CDR-H3. A FLAG (DYKDDDDK; SEQ ID NO:190) epitope tag was placed immediately downstream of the scFv, which was followed in-frame by the full-length M13 pIII coat protein sequence. The total number of transformants obtained was determined to be 3.6×10$^{10}$.

Selection of Mutant pHLA Specific Phage Clone

Phage clones bearing scFvs specific to p53$^{R175H}$/HLA-A*02:01 pHLA were identified using an approach described elsewhere (see, e.g., Skora et al, 2015 *PNAS.* 112:9967-72). One g of biotinylated HLA-A*02:01 pHLA monomer complexes were conjugated to 25 μL of M-280 streptavidin magnetic Dynabeads (Thermo Fisher Scientific, 11206D). During the enrichment phase (Round 1), phages were negatively selected with a mixture of unconjugated Dynabeads and free streptavidin protein (RayBiotech, Norcross, GA, 228-11469). After negative selection, supernatant containing unbound phages were transferred for positive selection using 1 μg of p53$^{R175H}$/HLA-A*02:01 pHLA. Beads were then washed and phages were eluted to infect mid-log-phase SS320 bacteria, with the addition of M13K07 helper phages (multiplicity of infection of 4). Bacteria were then grown overnight at 30° C. for phage production and the phages were precipitated the next morning with PEG/NaCl.

During the selection phase (Rounds 2-5), phages from the previous round were subjected to two stages of negative selection: 1) against cell lines without p53$^{R175H}$/HLA-A*02:01 (RPMI 6666, Jurkat, Raji, SigM5, HH, T2, and NCI-H441) and 2) against p53$^{WT}$/HLA-A*02:01 pHLA, unrelated HLA-A*02:01 pHLA, and free streptavidin. For negative selection using cell lines, phages were incubated with a total number of 0.5-1×10$^7$ of cells at 4° C. overnight. After negative selection, beads were isolated and unbound phages were transferred for positive selection by incubating with 1 μg (Round 2), 0.5 μg (Round 3), or 0.25 μg (Round 4, 5) of p53$^{R175H}$/HLA-A*02:01 pHLA. Phages were then eluted and amplified by infecting SS320 as described above.

After five rounds of selection, SS320 cells were infected with a limiting dilution of the enriched phages. A total of 190 individual colonies of SS320 were picked and phage DNA was PCR amplified by primers flanking the CDRs (Forward: GGCCATGGCAGATATTCAGA (SEQ ID NO:198), Reverse: CCGGGCCTTTATCATCATC (SEQ ID NO:199)) using Q5 Hot Start High-Fidelity 2× Master Mix (New England BioLabs, M0494L) and Sanger sequenced by GENEWIZ (South Plainfield, NJ). Sequences flanking the CDRs were trimmed using DNA Baser Sequence Assembler v4 (Arges, Romania) and the sequences spanning the CDRs were clustered using the CD-HIT Suite. Colonies containing unique phage clones were selected and grown overnight in 400 μL of media in deep 96-well plates (Thermo Fisher Scientific, 278743) with the addition of M13K07 helper phages. Bacteria were pelleted the next day and the phage-laden supernatants were used for downstream analysis.

Peptide Pulsing

For peptide pulsing, T2 cells were washed with serum-free RPMI-1640 media before incubation at 0.5-1×10$^6$ cells per mL in serum-free RPMI-1640 containing peptides at the specified concentration of 2 hours at 37° C. For experiments assessed using flow cytometry, human β2M (ProSpec, East Brunswick, NJ, PRO-337) at 10 μg/mL was added with the peptides and specified in the figure legends of such experiments.

Flow Cytometry

Phage staining of peptide-pulsed T2 cells was performed with 50 μL phage supernatant on ice for 1 hour, followed by staining with 1 μg of rabbit anti-M13 antibody (Novus Biologicals, NB100-1633), and anti-rabbit-PE (BioLegend, 406421). HLA-A*02 staining was performed by staining cells with fluorescently labeled anti-human HLA-A*02 (BB7.2, BioLegend, 343308) or mouse isotype IgG2b, K (BioLegend, 402206). Stained cells were analyzed using an LSRII flow cytometer (Becton Dickinson, Mansfield, MA) or an iQue Screener (IntelliCyt, Albuquerque, NM).

ELISAs

Streptavidin-coated, 96-well plates (R&D Systems, Minneapolis, MN, CP004) were coated with 50 ng of biotinylated HLA-A*02:01 pHLA monomers in 50 μL of blocking buffer (PBS with 0.5% BSA, 2 mM EDTA, and 0.1% sodium azide) or 25 ng of recombinant human CD3/6 (Acro Biosystems, DE, CDD-H52W4) at 4° C. overnight. Plates were washed with 1×TBST (TBS+0.05% Tween-20) using a BioTek 405 TS plate washer (BioTek, Winooski, VT). Serial dilutions of scDb or IgG was incubated on the plate for 1 hour at RT and washed. For scDbs, the plate was then incubated with 1 μg/mL recombinant protein L (Thermo Fisher Scientific, 77679) for 1 hour at RT, washed, followed by incubation with anti-protein L HRP (1:10000, Abcam, ab63506) for 1 hour at RT. For IgG, the plate was incubated with anti-human IgG HRP (1:1000, Thermo Fisher Scientific 62-8420) for 1 hour at RT. Plates were washed, 50 µL of 3,3',5,5'-Tetramethylbenzidine (TMB) substrate (BioLegend, 4211101) was added to each well, and the reaction was quenched with 50 µl 2N sulfuric acid (Thermo Fisher Scientific). Absorbance at 450 nm was measured with a Synergy H1 Multi-Mode Reader (BioTek).

scDb Production scDbs were produced by cloning gBlocks (IDT, Coralville, Iowa) encoding each of the variants in the format (from N- to C-terminus): IL-2 signal sequence, anti-pHLA variable light chain ($V_L$), GGGGS (SEQ ID NO:200) short linker, anti-CD3 variable heavy chain ($V_H$), (GGGGS)$_3$ (SEQ ID NO:201) long linker, anti-CD3 $V_L$, GGGGS (SEQ ID NO:200) short linker, anti-pHLA $V_H$, and 6×HIS tag into linearized pcDNA3.4 vector (Thermo Fisher Scientific, A14697). The proteins were expressed by the Eukaryotic Tissue Culture Core Facility of Johns Hopkins University. Briefly, 1 mg of plasmid DNA was transfected with polyethylenimine (PEI) at a ratio of 1:3 into 1 L of FreeStyle 293-F cells at a concentration of 2-2.5×10$^6$ cells per mL and the transfected cells incubated at 37° C. Five days after transfection, culture media was collected and filtered through a 0.22-µm unit. The scDbs were purified using HisPur Ni-NTA Resin (Thermo Fisher Scientific, 88222) and desalted into PBS pH 7.4 or 20 mM Tris pH 9.0, 150 mM NaCl using 7 k MWCO Zeba Spin desalting columns (Thermo Fisher Scientific, 89890). Proteins were quantified using a 4-15% Mini-PROTEAN TGX gel (Bio-Rad, Hercules, CA, 4568085) and/or NanoDrop (Thermo Fisher Scientific). Alternatively, the scDb proteins were produced by GeneArt (Thermo Fisher Scientific) in Expi293s, purified with a HisTrap column (GE Healthcare, 17-5255-01) followed by size exclusion chromatography with a HiLoad Superdex 200 26/600 column (GE Healthcare, 28989335). Analytic chromatography was performed using TSKgel G3000SWxl column (TOSOH Bioscience, Tokyo, Japan) using a running buffer of 50 mM sodium phosphate and 300 mM sodium chloride at pH 7, at a flow rate of 1.0 mL/minute.

Surface Plasmon Resonance Affinity Measurements of p53$^{R175H}$/HLA-A*02:01 and H2-scDb Interaction Biotinylated p53$^{R175H}$/HLA-A*02:01, p53$^{WT}$/HLA-A*02:01, and H2-scDb binding experiments were performed at 25° C. using a Biacore T200 SPR instrument (GE Healthcare). Approximately 100-110 response units (RU) of biotinylated p53$^{R175H}$/HLA-A*02:01 and p53$^{WT}$/HLA-A*02:01 were captured in flow cells (Fc) 2 and 4, respectively, using a streptavidin chip. Single-cycle kinetics were performed by injecting increasing concentrations (3, 12, 50, 200, and 800 nM) of purified H2-scDb which was flowed over Fc 1-4. Binding responses for kinetic analysis were both blank- and reference-subtracted. Both binding curves were fit with a 1:1 binding model using Biacore Insight evaluation software.

Differential Scanning Fluorimetry

Thermal stability of the H2-scDb was evaluated by a differential scanning fluorimetry (DSF) assay which monitor the fluorescence of a dye that binds to the hydrophobic region of a protein as it becomes exposed upon temperature induced denaturation. Reaction mixture (20 µL) was set up in a white low-profile 96-well, unskirted polymerase chain reaction plate (BioRad, MLL9651) by mixing 2 µL of purified H2-scDb at a concentration of 1 mg/mL (final concentration ~2 µg) with 2 µL of 50×SYPRO orange dye (Invitrogen, S6650, 5× final concentration) in PBS, pH 7.4. The plate was sealed with an optical transparent film and centrifuged for 1,000×g for 30 seconds. Thermal scanning was performed from 25 to 100° C. (1° C./minute temperature gradient) using a CFX9 Connect real-time polymerase chain reaction instrument (BioRad). Protein unfolding/melting temperature $T_m$ was calculated from the maximum value of the negative first derivative of the melt curve using CFX Manager software (BioRad).

CRISPR-Mediated Knockout of TP53

The Alt-R CRISPR system (IDT) was used to knock out the TP53 gene from KMS26, TYK-nu, and KLE cell lines. CRISPR-Cas9 crRNAs targeting TP53 exon 3 (p53-5: CCCCGGACGATATTGAACAA (SEQ ID NO:191) or p53-6: CCCCTTGCCGTCCCAAGCAA (SEQ ID NO:202)) as well as CRISPR-Cas9 tracrRNA were resuspended at 100 µM with Nuclease-Free Duplex Buffer. The crRNAs and tracrRNA were duplexed at a 1:1 molar ratio for 5 minutes at 95° C. followed by cooling down slowly to RT according to the manufacturer's instructions. The duplexed RNA was then mixed with Cas9 Nuclease at a 1.2:1 molar ratio for 15 minutes. A total of 40 µmols of the Cas9 RNP complexed with TP53 gRNA were mixed with 2×10$^5$ cells in 20 µL of OptiMEM. This mixture was loaded into a 0.1 cm cuvette (Bio-Rad, 1652089) and electroporated at 120V and 16 ms using an ECM 2001 (BTX, Holliston, MA). Cells were transferred to complete growth medium and cultured for 7 days. Single cell clones were established by limiting dilution and genomic DNA was harvested using a Quick-DNA 96 Kit (Zymo Research, Irvine, CA, D3012). A region flanking the CRISPR cut site was PCR amplified (forward primer: GCTGCCCTGGTAGGTTTTCT (SEQ ID NO:203), reverse primer: GAGACCTGTGGGAAGCGAAA (SEQ ID NO:204)) and Sanger sequenced to select for clones with the desired TP53 status.

Immunoblotting Analysis

Cells were lysed in cold RIPA buffer (Thermo Fisher Scientific, 89901) supplemented with protease inhibitor cocktail (Thermo Fisher Scientific, 87785). Protein concentration was determined using a BCA assay (Thermo Fisher Scientific, 23227). Equal amounts of total protein (20-50 µg) were loaded in each lane of a 4-15% Mini-PROTEAN TGX gel (Bio-Rad, 4568085) and transferred to polyvinylidene difluoride membranes after electrophoresis. The membranes were incubated with appropriate primary antibodies (anti-6×His tag, 1:2000, Abcam, ab9108; p53 [DO-1], 1:1000, Santa Cruz, sc-126; STAT2, 1:1000, Thermo Fisher Scientific, 44-362G; ZFP3, 1:1000, Thermo Fisher Scientific, PA5-62726; β-actin [13E5], 1:1000, Cell Signaling Technology, 5125S; β-actin [8H10D10], 1:1000, Cell Signaling Technology, 3700S) and species-specific HRP-conjugated secondary antibodies (1:5000-10000). Signal was detected by a ChemiDoc MP chemiluminescence system (Bio-Rad).

Transfection of Cell Lines gBlocks (IDT) encoding HLA and target proteins were cloned into pcDNA3.1 or pcDNA3.4 vectors (Thermo Fisher Scientific, V79020, A14697). COS-7, HEK293FT, and Saos-2 cells were transfected at 70-80% confluency using Lipofectamine 3000 (Thermo Fisher Scientific, L3000015) and incubated at 37° C. overnight. A total of 15 µg and 30 µg plasmid (1:1 ratio of HLA plasmid/target protein plasmid in co-transfections) was used for T25 and T75 flasks, respectively.

Viral Transduction of Cell Lines

HLA-A*02:01-encoding retrovirus was produced using the MSCV retroviral expression system (Clontech, Mountain View, CA, 634401). In brief, a gBlock encoding HLA-A*02:01-T2A-GFP (IDT) was cloned into the pMSCVpuro retroviral vector by HiFi DNA assembly (New England Biolabs, Ipswich, MA, E2621L). The pMSCVpuro-HLA-A*02:01-T2A-GFP plasmid was then co-transfected with a pVSV-G envelope vector into the GP2-293 packaging cell line. Viral supernatant was harvested 48 hours after transfection and concentrated 20-fold using Retro-X Concentrator (Clontech, 631456). RediFect Red-Fluc-GFP lentivirus particles (Perkin Elmer, Waltham, MA, CLS960003) was used for generating luciferase-expressing cell lines. NucLight green lentivirus (Essen Bioscience, Ann Arbor, MI, 4624) was used to generate TYK-nu cell lines with nuclear GFP expression.

For transduction, non-tissue culture-treated 48-well plates were coated with 200 μL of 10 μg/mL RetroNectin (Clontech, T100B) per well overnight at 4° C. and blocked with 10% FBS for 1 hour at RT. Viral particles and $2 \times 10^5$ target cells were added to each well in a total volume of 500 μL cell culture media and spun at 2000×g for 1 hour then incubated at 37° C. Selection with 1 μg/mL puromycin (Thermo Fisher Scientific, A1113803) began three days later. Transduced cells were sorted based on presence of GFP using FACSAria Fusion (BD Biosciences, San Jose, CA) 10-14 days after transduction.

In Vitro scDb Co-Incubation Assays

To each well of a 96-well flat-bottom plate, the following components were combined in a final volume of 100 μL RPMI-1640 with 10% FBS, 1% Penicillin-Streptomycin, and 100 IU/mL IL-2: scDb diluted to the specified concentration, $5 \times 10^4$ human T cells, and $1-5 \times 10^4$ target cells (COS-7, T2, or other tumor cell lines). The effector to target cell ratio is specified in the figure legend for each experiment. The co-culture plate was incubated for 20 hour at 37° C. and conditioned media was assayed for cytokine and cytotoxic granule protein secretion using the Human IFN-γ Quantikine Kit (R&D Systems, Minneapolis, MN, SIF50), Human IFN-γ Flex Set Cytometric Bead Array (BD, 558269), or the MILLIPLEX Luminex assays (Millipore Sigma, HSTCMAG28SPMX13, HCD8MAG-15K) read on the Bioplex 200 platform (Bio-Rad). Cytotoxicity was assayed by CellTiter-Glo Luminescent Cell Viability Assay (Promega, Madison, WI, G7571), Bio-Glo Luciferase Assay (Promega, G7941), or Steady-Glo Luciferase Assay (Promega, E2510) per manufacturer's instructions. For CellTiter-Glo assays, percent cytotoxicity was calculated by subtracting the luminescence signal from the average of the T cell only wells and normalizing to the no scDb condition: 1−(scDb well−T cell only)/(no scDb well−T cell only)×100. For Bio-Glo assays, percent cytotoxicity was calculated by normalizing luminescence signal to the no scDb condition: 1−(scDb well)/(no scDb well)×100.

Real-Time Live-Cell Imaging

A total of $1 \times 10^4$ NucLight Green-labeled target cells were plated in each well of a 96-well flat bottom plate and allowed to attach for 4 hours before adding $2 \times 10^4$ T cells and scDb at the indicated concentrations. Each condition was plated in triplicate. Plates were imaged every 6 hours using the IncuCyte ZOOM Live-Cell analysis system (Essen Bioscience) for a total of 120 hours. Four images per well at 10× zoom were collected at each time point. The number of GFP positive objects per $mm^2$ in each well was quantified using the green fluorescence channel.

Expression, purification and refolding of p53$^{R175H}$ HLA-A*02:01

Plasmids for HLA-A*02:01 and β2M were received from the NIH Tetramer Facility (Atlanta, GA) and separately transformed into BL21(DE3) cells. Each was expressed in inclusion bodies using auto-induction media. Purification of the HLA-A*02:01 and β2M inclusion bodies was achieved with a series of detergent washes followed by solubilization with 8 M urea. Refolding of the HLA-A*02:01, β2M, and mutant p53$^{R175H}$ peptide was performed. Briefly, solubilized HLA-A*02:01 and β2M were combined in a refolding buffer containing 100 mM Tris pH 8.3, 400 mM L-arginine, 2 mM EDTA, 5 mM reduced glutathione, 0.5 mM oxidized glutathione, 2 mM PMSF, and 30 mg of the mutant p53$^{R175H}$peptide (aa 168-176, HMTEVVRHC; SEQ ID NO:1) dissolved in 1 mL of DMSO. The resultant solution was stirred at 4° C. for 2 days, with two further additions of HLA-A*02:01 on day 2, concentrated to 10 mL and purified by size exclusion chromatography on a HiLoad 26/60 Superdex 75 Prep grade column (GE Healthcare, 28989334). For incubation with the H2-Fab, purified pHLA-A*02:01 was concentrated to ~1-3 mg/mL and stored at −80° C. until use.

Production of the H2-Fab Antibody Fragment

The light chain (LC) and heavy chain (HC) variable region sequences of H2 scFv were grafted onto the respective constant chains of trastuzumab and separately cloned into a pcDNA3.4 vector (Thermo Fisher Scientific, A14697). Both chains were preceded by a mouse IgKVIII signal peptide. Before large-scale expression of full-length antibody, optimization of the LC:HC DNA ratio for transfection was performed to determine optimal recombinant protein yields. For a 1 L expression, a total of 50 μg of purified plasmids (1:1 LC:HC ratio) were transfected with PEI at a ratio of 1:3 into Freestyle 293-F cells at a concentration of $2-2.5 \times 10^6$ cells per mL and incubated at 37° C. for 7 days. The media was harvested via centrifugation, filtered through a 0.22-μm unit and the full-length antibody was purified via protein A affinity chromatography on a HiTrap MabSelect™ SuRe™ column (GE Healthcare, 29-0491-04). Full-length antibody was eluted using a linear gradient of 0-100 mM sodium citrate, pH 3.5. The protein A fractions containing pure H2 antibody were pooled, quantified by SDS-PAGE gel electrophoresis and dialyzed into 20 mM sodium phosphate buffer, pH 7.0, 10 mM EDTA.

For generation of H2-Fab fragments, ~1-3 mg of full-length antibody was mixed with 0.5 mL of a 50% Immobilized Papain slurry (Thermo Fisher Scientific, 20341) pre-activated with digestion buffer (20 mM sodium phosphate buffer, pH 7.0, 10 mM EDTA) containing 20 mM cysteine-HCl. The mixture was incubated at 37° C. overnight with constant shaking at 200 rpm. The H2 antibody digest was separated from the immobilized resin by a gravity resin separator and washed with 10 mM Tris-HCl, pH 7.5. Newly generated H2-Fab fragments were further purified by cation-exchange chromatography using a Mono-S column (GE Healthcare, 17516801) and eluted using a linear gradient of 0-500 mM NaCl.

The H2-Fab fragments were concentrated, mixed with equimolar p53$^{R175H}$/HLA-A*02:01 and incubated at 4° C. overnight. The H2-Fab-p53$^{R175H}$/HLA-A*02:01 mixture was evaluated by size exclusion chromatography on a Superdex™ 200 Increase 10/300 column (GE Healthcare, 28990944). The fractions of ~98% pure pHLA-A*02:01-H2-Fab complex were pooled, concentrated to 12.6 mg/mL and exchanged into a buffer containing 25 mM HEPES, pH 7.0, 200 mM NaCl.

Crystallization, Data Collection and Structure Determination

Crystals of the ternary complex H2-Fab-p53$^{R175H}$/HLA-A*02:01 were grown by vapor diffusion in hanging drops set up with a TTP mosquito robot with a reservoir solution of 0.2 M ammonium chloride and 20% (w/v) PEG 3350 MME. Crystals were flash-cooled in mother liquor. Data were collected at National Synchrotron Light Source-II at beamlines 17-ID-1(AMX) on a Dectris EIGER X 16M detector. The dataset was indexed, integrated and scaled using fastdp, XDS, and aimless. Monoclinic crystals of H2-Fab-p53$^{R175H}$/HLA-A*02:01 diffracted to 3.5 Å. The structure for the H2-Fab-p53$^{R175H}$/HLA-A*02:01 complex was determined by molecular replacement with PHASER using PDB ID 6O4Y and 6UJ9 as the search models. The data were refined to a final resolution of 3.5 Å using iterative rounds of refinement with REFMAC5 and manual rebuilding in Coot. Structures were validated using Coot and PDB Deposition tools. The model has 95.2% of the residues in preferred and 3.8% in allowed regions according to Ramachandran statistics (Table 20). Figures were rendered in PyMOL (v2.2.3, Schrödinger, LLC, New York, NY). Buried areas were calculated with PDBePISA. The docking angle that determines the relative orientation between the pHLA and the Fab/TCR was calculated by the web server TCR3d.

Mouse Xenograft Model

Female NOD.Cg-Prkdc$^{scid}$Il2rg$^{tm1Wjl}$/SzJ (NSG) mice at 6-10 weeks were acquired from the Jackson Laboratory (Bar Harbor, Maine, 005557) and treated in compliance with the institutional Animal Care and Use Committee approved protocol. In the early treatment model, mice were inoculated intravenously with 1×10$^6$ luciferase-expressing KMS26 or KMS26-TP53 KO cells and 1×10$^7$ in vitro expanded human T cells via lateral tail vein injection on day 0. On day 1, mice were randomized based on luminescence quantification using the IVIS imaging system and Living Image software (Perkin Elmer) to ensure similar pretreatment tumor burden. Prior to imaging, mice received intraperitoneal injection of luciferin (150 μl, RediJect D-Luciferin Ultra Bioluminescent Substrate, PerkinElmer, 770505) were anesthetized using inhaled isoflurane in an induction chamber for 5 minutes. After randomization, two-week micro-osmotic pumps (ALZET, Cupertino, CA, 1002) filled with H2-scDb, isotype control scDb (scFv against an irrelevant pHLA linked with UCHT1 scFv), or vehicle only that had been primed in 1 mL PBS overnight at 37° C. were placed intraperitoneally using sterile surgical technique. Tumor growth was serially monitored by bioluminescent imaging. In the established tumor model, mice were inoculated with 3.5×10$^5$ or 5×10$^5$ luciferase-expressing KMS26 cells and 1×10$^7$ human T cells via lateral tail vein injection on day 0. On day 6, H2-scDb or isotype control scDb was administered similarly as in the early treatment model.

For mouse blood-based analysis, 200 μL blood was collected in EDTA-treated microvettes (Sarstedt, Nümbrecht, Germany, 20.1278.100) by cheek bleed, followed by centrifugation at 1000×g for 3 minutes. Plasma was collected and stored at −80° C. until analysis. The blood cell pellet was resuspended with 100 μL PBS, followed by two 5-minute incubations with 1 mL ACK lysis buffer (Thermo Fisher Scientific, A1049201) with one PBS wash in between, and resuspended in flow stain buffer with TruStain FcX (anti-mouse CD16/32) antibody (BioLegend, 101320) and cell-surface staining antibodies. For scDb quantification, plasma was thawed and incubated in biotinylated recombinant human CD3ε/δ coated streptavidin plate and detected as described in "ELISA."

Statistical Analysis

Data are presented as means±SD unless otherwise specified. Statistical analyses were carried out using specific tests indicated in the figure legends. A P value of <0.05 was used to denote statistical significance. All analyses were performed using Prism version 8.0 (GraphPad, San Diego, CA). In all figures, NS, P>0.05; * P<0.05;  P<0.01; *P<0.001, **** P<0.0001.

Example 5: Exemplary Bispecific Molecules Targeting a TP53 Mutation

TABLE 23

Amino acid sequences of bispecific molecules targeting a TP53 mutation

| | Sequence | SEQ ID NO |
|---|---|---|
| H2-UCHT1-scDb | DIQMTQSPSSLSASVGDRVTITCRASQDVNTAVAWYQQKPGK APKLLIYSAYFLYSGVPSRFSGSRSGTDFTLTISSLQPEDFATY YCQQYSRYSPVTFGQGTKVEIKGGGGSEVQLQQSGPELVKPG ASMKISCKASGYSFTGYTMNWVKQSHGKNLEWMGLINPYK GVSTYNQKFKDKATLTVDKSSSTAYMELLSLTSEDSAVYYCA RSGYYGDSDWYFDVWGAGTTVTVSSGGGGSGGGGSGGGGS DIQMTQTTSSLSASLGDRVTISCRASQDIRNYLNWYQQKPDG TVKLLIYYTSRLHSGVPSKFSGSGSGTDYSLTISNLEQEDIATY FCQQGNTLPWTFAGGTKLEIKGGGGSEVQLVESGGGLVQPG GSLRLSCAASGFNVYASGMHWVRQAPGKGLEWVAKIYPDSD YTYYADSVKGRFTISADTSKNTAYLQMNSLRAEDTAVYYCS RDSSFYYVYAMDYWGQGTLVTVSS | 733 |
| H20-UCHT1-scDb | DIQMTQSPSSLSASVGDRVTITCRASQDVNTAVAWYQQKPGK APKLLIYSASFLYSGVPSRFSGSRSGTDFTLTISSLQPEDFATYY CQQSNAYPITFGQGTKVEIKGGGGSEVQLQQSGPELVKPGAS MKISCKASGYSFTGYTMNWVKQSHGKNLEWMGLINPYKGV STYNQKFKDKATLTVDKSSSTAYMELLSLTSEDSAVYYCARS GYYGDSDWYFDVWGAGTTVTVSSGGGGSGGGGSGGGGSDI QMTQTTSSLSASLGDRVTISCRASQDIRNYLNWYQQKPDGTV KLLIYYTSRLHSGVPSKFSGSGSGTDYSLTISNLEQEDIATYFC QQGNTLPWTFAGGTKLEIKGGGGSEVQLVESGGGLVQPGGS LRLSCAASGFNLNSYYMHWVRQAPGKGLEWVAMIIPGYGYT NYADSVKGRFTISADTSKNTAYLQMNSLRAEDTAVYYCSRS YYMYMDYWGQGTLVTVSS | 734 |
| H2-UCHT1-tandem scFvs | DIQMTQSPSSLSASVGDRVTITCRASQDVNTAVAWYQQKPGK APKLLIYSAYFLYSGVPSRFSGSRSGTDFTLTISSLQPEDFATY YCQQYSRYSPVTFGQGTKVEIKGGGGSGGGGSGGGGSEVQL VESGGGLVQPGGSLRLSCAASGFNVYASGMHWVRQAPGKG LEWVAKIYPDSDYTYYADSVKGRFTISADTSKNTAYLQMNSL | 735 |

TABLE 23-continued

Amino acid sequences of bispecific molecules targeting a TP53 mutation

| | Sequence | SEQ ID NO |
|---|---|---|
| | RAEDTAVYYCSRDSSFYYVYAMDYWGQGTLVTVSSGGGGS<br>EVQLQQSGPELVKPGASMKISCKASGYSFTGYTMNWVKQSH<br>GKNLEWMGLINPYKGVSTYNQKFKDKATLTVDKSSSTAYME<br>LLSLTSEDSAVYYCARSGYYGDSDWYFDVWGAGTTVTVSSG<br>GGGSGGGGSGGGGSDIQMTQTTSSLSASLGDRVTISCRASQDI<br>RNYLNWYQQKPDGTVKLLIYYTSRLHSGVPSKFSGSGSGTDY<br>SLTISNLEQEDIATYFCQQGNTLPWTFAGGTKLEIK | |
| H2-UCHT1-scDb-<br>bispecific single-<br>chain Fc | DIQMTQSPSSLSASVGDRVTITCRASQDVNTAVAWYQQKPGK<br>APKLLIYSAYFLYSGVPSRFSGSRSGTDFTLTISSLQPEDFATY<br>YCQQYSRYSPVTFGQGTKVEIKGGGGSEVQLQQSGPELVKPG<br>ASMKISCKASGYSFTGYTMNWVKQSHGKNLEWMGLINPYK<br>GVSTYNQKFKDKATLTVDKSSSTAYMELLSLTSEDSAVYYCA<br>RSGYYGDSDWYFDVWGAGTTVTVSSGGGGSGGGGSGGGGS<br>DIQMTQTTSSLSASLGDRVTISCRASQDIRNYLNWYQQKPDG<br>TVKLLIYYTSRLHSGVPSKFSGSGSGTDYSLTISNLEQEDIATY<br>FCQQGNTLPWTFAGGTKLEIKGGGGSEVQLVESGGGLVQPG<br>GSLRLSCAASGFNVYASGMHWVRQAPGKGLEWVAKIYPDSD<br>YTTYYADSVKGRFTISADTSKNTAYLQMNSLRAEDTAVYYCS<br>RDSSFYYVYAMDYWGQGTLVTVSSGGGGDKTHTCPPCPAPE<br>LLGGPSVFLFPPKPKDTLMISRTPEVTCVVVDVSHEDPEVKFN<br>WYVDGVEVHNAKTKPCEEQYGSTYRCVSVLTVLHQDWLNG<br>KEYKCKVSNKALPAPIEKTISKAKGQPREPQVYTLPPSREEMT<br>KNQVSLTCLVKGFYPSDIAVEWESNGQPENNYKTTPPVLDSD<br>GSFFLYSKLTVDKSRWQQGNVFSCSVMHEALHNHYTQKSLS<br>LSPGKGGGGSGGGGSGGGGSGGGGSGGGGSGGGGSDKTHTC<br>PPCPAPELLGGPSVFLFPPKPKDTLMISRTPEVTCVVVDVSHE<br>DPEVKFNWYVDGVEVHNAKTKPCEEQYGSTYRCVSVLTVLH<br>QDWLNGKEYKCKVSNKALPAPIEKTISKAKGQPREPQVYTLP<br>PSREEMTKNQVSLTCLVKGFYPSDIAVEWESNGQPENNYKTT<br>PPVLDSDGSFFLYSKLTVDKSRWQQGNVFSCSVMHEALHNH<br>YTQKSLSLSPGK | 736 |
| H2-UCHT1-<br>tandem scFvs<br>single-chain Fc | DIQMTQSPSSLSASVGDRVTITCRASQDVNTAVAWYQQKPGK<br>APKLLIYSAYFLYSGVPSRFSGSRSGTDFTLTISSLQPEDFATY<br>YCQQYSRYSPVTFGQGTKVEIKGGGGSGGGGSGGGGSEVQL<br>VESGGGLVQPGGSLRLSCAASGFNVYASGMHWVRQAPGKG<br>LEWVAKIYPDSDYTTYYADSVKGRFTISADTSKNTAYLQMNSL<br>RAEDTAVYYCSRDSSFYYVYAMDYWGQGTLVTVSSGGGGS<br>EVQLQQSGPELVKPGASMKISCKASGYSFTGYTMNWVKQSH<br>GKNLEWMGLINPYKGVSTYNQKFKDKATLTVDKSSSTAYME<br>LLSLTSEDSAVYYCARSGYYGDSDWYFDVWGAGTTVTVSSG<br>GGGSGGGGSGGGGSDIQMTQTTSSLSASLGDRVTISCRASQDI<br>RNYLNWYQQKPDGTVKLLIYYTSRLHSGVPSKFSGSGSGTDY<br>SLTISNLEQEDIATYFCQQGNTLPWTFAGGTKLEIKGGGGDKT<br>HTCPPCPAPELLGGPSVFLFPPKPKDTLMISRTPEVTCVVVDVS<br>HEDPEVKFNWYVDGVEVHNAKTKPCEEQYGSTYRCVSVLTV<br>LHQDWLNGKEYKCKVSNKALPAPIEKTISKAKGQPREPQVYT<br>LPPSREEMTKNQVSLTCLVKGFYPSDIAVEWESNGQPENNYK<br>TTPPVLDSDGSFFLYSKLTVDKSRWQQGNVFSCSVMHEALHN<br>HYTQKSLSLSPGKGGGGSGGGGSGGGGSGGGGSGGGGSGGG<br>GSDKTHTCPPCPAPELLGGPSVFLFPPKPKDTLMISRTPEVTCV<br>VVDVSHEDPEVKFNWYVDGVEVHNAKTKPCEEQYGSTYRC<br>VSVLTVLHQDWLNGKEYKCKVSNKALPAPIEKTISKAKGQPR<br>EPQVYTLPPSREEMTKNQVSLTCLVKGFYPSDIAVEWESNGQ<br>PENNYKTTPPVLDSDGSFFLYSKLTVDKSRWQQGNVFSCSVM<br>HEALHNHYTQKSLSLSPGK | 737 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A molecule comprising an antigen-binding domain comprising a variable heavy chain and a variable light chain that can bind to a peptide-HLA complex, wherein said peptide is a modified p53 peptide comprising the amino acid sequence set forth in SEQ ID NO:1, wherein the antigen-binding domain comprises a CDR-VL1, a CDR-VL2, a CDR-VL3, a CDR-VH1, a CDR-VH2, and a CDR-VH3 as set forth in one of the groups below:

(i) the CDR-VL1 set forth in SEQ ID NO:5, the CDR-VL2 having the amino acid sequence SAY or SAS, the CDR-VL3 set forth in SEQ ID NO:6, the CDR-VH1 set forth in SEQ ID NO: 11, the CDR-VH2 set forth in SEQ ID NO:16, and the CDR-VH3 set forth in SEQ ID NO: 21;

(ii) the CDR-VL 1 set forth in SEQ ID NO:5, the CDR-VL2 having the amino acid sequence SAY or SAS, the CDR-VL3 set forth in SEQ ID NO:7, the CDR-VH1 set forth in SEQ ID NO: 12, the CDR-VH2 set forth in SEQ ID NO: 17, and the CDR-VH3 set forth in SEQ ID NO: 22;

(iii) the CDR-VL 1 set forth in SEQ ID NO:5, the CDR-VL2 having the amino acid sequence SAY or SAS, the CDR-VL3 set forth in SEQ ID NO:8, the CDR-VH1 set forth in SEQ ID NO: 13, the CDR-VH2 set forth in SEQ ID NO: 18, and the CDR-VH3 set forth in SEQ ID NO: 23;

(iv) the CDR-VL1 set forth in SEQ ID NO:5, the CDR-VL2 having the amino acid sequence SAY or SAS, the CDR-VL3 set forth in SEQ ID NO:9, the CDR-VH1 set forth in SEQ ID NO: 14, the CDR-VH2 set forth in SEQ ID NO: 19, and the CDR-VH3 set forth in SEQ ID NO: 24; and (v) the CDR-VL 1 set forth in SEQ ID NO:5, the CDR-VL2 having the amino acid sequence SAY or SAS, the CDR-VL3 set forth in SEQ ID NO:10, the CDR-VH1 set forth in SEQ ID NO:15, the CDR-VH2 set forth in SEQ ID NO:20, and the CDR-VH3 set forth in SEQ ID NO: 25.

2. The molecule of claim 1, wherein said antigen binding domain comprises an amino acid sequence having at least 90% identity to the amino acid sequence set forth in SEQ ID NO:137, SEQ ID NO:138, SEQ ID NO:139, SEQ ID NO:140, or SEQ ID NO:141.

3. The molecule of claim 1, wherein said molecule is selected from the group consisting of an antibody, a single chain variable fragment (scFv), a chimeric antigen receptor (CAR), a tandem scFv, a bispecific T cell engager, a diabody, a single-chain diabody (scDb), an scFv-Fc, a bispecific antibody, and a dual-affinity re-targeting antibody.

4. The molecule of claim 1, wherein said molecule further comprises a second antigen-binding domain comprising a variable heavy chain and a variable light chain that binds to an effector cell receptor selected from the group consisting of CD3, CD28, CD4, CD8, CD16a, NKG2D, PD-1, CTLA-4, 4-1BB, OX40, ICOS, and CD27.

5. The molecule of claim 4, wherein said second antigen-binding domain binds to CD3, and wherein said second antigen-binding domain comprises the amino acid sequence selected from the group consisting of SEQ ID NO: 170, SEQ ID NO: 171, SEQ ID NO:172, SEQ ID NO:173, SEQ ID NO: 174, SEQ ID NO: 175, SEQ ID NO:176, SEQ ID NO: 177, SEQ ID NO: 178, SEQ ID NO: 179, SEQ ID NO: 180, SEQ ID NO:181, SEQ ID NO:182, and SEQ ID NO:183.

6. The molecule of claim 4, wherein the second antigen-binding domain binds CD3 and comprises the amino acid sequence selected from the group consisting of SEQ ID NO: 170, SEQ ID NO: 171, SEQ ID NO: 172, SEQ ID NO: 173, SEQ ID NO: 174, and SEQ ID NO: 175.

7. The molecule of claim 4, wherein said second antigen-binding domain binds CD16a and wherein said second antigen-binding domain comprises the amino acid sequence selected from the group consisting of SEQ ID NO: 185, SEQ ID NO: 186, SEQ ID NO: 187, SEQ ID NO:188, and SEQ ID NO: 189.

8. The molecule of claim 1, wherein said antigen binding domain comprises an amino acid sequence having at least 95% identity to the amino acid sequence set forth in SEQ ID NO: 137, SEQ ID NO:138, SEQ ID NO: 139, SEQ ID NO: 140, or SEQ ID NO: 141.

9. The molecule of claim 1, wherein said antigen binding domain comprises a VL having at least 95% identity to SEQ ID NO:729 and/or a VH having at least 95% identity to SEQ ID NO:730.

10. The molecule of claim 1, wherein said antigen binding domain comprises a VL comprising the amino acid sequence set forth in SEQ ID NO:729 and a VH comprising the amino acid sequence set forth in SEQ ID NO:730.

11. The molecule of claim 1, wherein the HLA of the peptide-HLA complex is HLA-A*02:01.

12. The molecule of claim 1, wherein the HLA of the peptide/HLA complex comprises an HLA allele alpha chain and a beta-2 microglobulin.

13. A method for treating a human having a cancer, said method comprising:

administering to said human the molecule of claim 1, wherein said cancer comprises cancer cells expressing a modified p53 peptide comprising the amino acid sequence of SEQ ID NO: 1 .

14. The method of claim 13, wherein said cancer is selected from the group consisting of Hodgkin's lymphoma, non-Hodgkin's lymphoma, acute myeloid leukemia, acute lymphoblastic leukemia, multiple myeloma, lung cancer, pancreatic cancer, gastric cancer, colorectal cancer, ovarian cancer, endometrial cancer, biliary tract cancer, liver cancer, breast cancer, prostate cancer, esophageal cancer, stomach cancer, kidney cancer, bone cancer, soft tissue cancer, head and neck cancer, glioblastoma multiforme, astrocytoma, thyroid cancer, germ cell tumor, and melanoma.

* * * * *